US011441159B2

(12) United States Patent
Noe et al.

(10) Patent No.: US 11,441,159 B2
(45) Date of Patent: Sep. 13, 2022

(54) CORN ELITE EVENT MZIR098

(71) Applicant: Syngenta Crop Protection AG, Basel (CH)

(72) Inventors: Andrew Noe, Clinton, IL (US); Jared Conville, Research Triangle Park, NC (US); Weining Gu, Research Triangle Park, NC (US); Yaping Jiang, Research Triangle Park, NC (US); Ryan William Carlin, Research Triangle Park, NC (US); Wenjin Yu, Research Triangle Park, NC (US); Volker Mittendorf, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 149 days.

(21) Appl. No.: 16/619,271

(22) PCT Filed: Jun. 13, 2018

(86) PCT No.: PCT/US2018/037189
§ 371 (c)(1),
(2) Date: Dec. 5, 2019

(87) PCT Pub. No.: WO2018/231890
PCT Pub. Date: Dec. 20, 2018

(65) Prior Publication Data

US 2020/0190533 A1 Jun. 18, 2020

Related U.S. Application Data

(60) Provisional application No. 62/519,993, filed on Jun. 15, 2017.

(51) Int. Cl.
*C12N 15/82* (2006.01)
*C12Q 1/6895* (2018.01)

(52) U.S. Cl.
CPC ..... *C12N 15/8286* (2013.01); *C12N 15/8274* (2013.01); *C12Q 1/6895* (2013.01); *C12Q 2600/13* (2013.01)

(58) Field of Classification Search
CPC .................................................. C12N 15/8286
See application file for complete search history.

(56) References Cited

U.S. PATENT DOCUMENTS

2005/0260603 A1 11/2005 Denise et al.

FOREIGN PATENT DOCUMENTS

WO 2016209360 A1 12/2016
WO 2017025454 A1 2/2017

OTHER PUBLICATIONS

Gen Bank Accession No. XR_006010930, submitted on Jun. 11, 2021.*
Nugraha et al, J. Trop. Conserv. Sci. (2015) 8:796-812.*
Request for an Extension of Determination of Nonregulated Status for Insect-Resistant and Herbicide-Tolerant MZIR098 Corn, Syngenta Seeds Inc., Submission Date Aug. 3, 2015; USDA Submission; available at https://www.aphis.usda.gov/brs/aphisdocs/15_21801p.pdf.*
Herbicide-tolerant and insect-protected corn event MZIR098 (Published by Government of Canada; available at https://www.canada.ca/en/health-canada/services/food-nutrition/genetically-modified-foods-other-novel-foods/approved-products/herbicide-tolerant-mzir098-corn.html; modified on Sep. 13, 2017.*
IPRP for International application No. PCT/US2018/037189 dated Dec. 17, 2019.
Extended ESR for EP188116765.4, mailed on Dec. 23, 2020.
Prins, Theo W et al.: "Novel TaqMan PCR screening methods for element cry3A and construct gat/T-pinll to support detection of both known and unknown GMOs", European Food Research and Technology, Springer Berlin Heidelberg, vol. 243, No. 3, Aug. 2, 2016, pp. 481-488, XP036152860, ISSN: 1438-2377, DOI: 10.1007/S00217-016-2761-6.
Bruce, E. Hibbard et al.: "Mortality Impact of Bt Transgenic Maize Roots Expressing eCry3.1Ab, mCry3A, and eCry3.1Ab Plus mCry3A on Western Corn Rootworm Larvae in the Field", Journal of Economic Entomology, vol. 14, No. 5, Oct. 1, 2011, pp. 1584-1591, XP55340937, US ISSN: 0022-0493, DOI10.1603/EC11186.
Davis et al., "Request for an extension of determination of nonregulated status for insect-resistant and herbicide-tolerant event Mzir098 Corn" Syngenta Seeds, Inc., Nov. 13, 2015 [online]. [Retrieved on Aug. 20, 2018] URL: https://www.aphis.usda.gov/brs/aphisdocs/15_21801p.pdf.
Genbank submission FN191699.1, Nov. 3, 2011 [online], [Retrieved on Sep. 3, 2018] URL https://www.ncbi.nlm.nih.gov/nucest/FN191699.1.
International Search Report for International Patent Application No. PCT/US2018/37189 dated Oct. 30, 2018.

* cited by examiner

*Primary Examiner* — Mykola V. Kovalenko
(74) *Attorney, Agent, or Firm* — Katherine Seguin

(57) ABSTRACT

A novel transgenic corn elite event designated MZIR098 is disclosed. The invention relates to DNA sequences of the recombinant constructs inserted into the corn genome and of genomic sequences flanking the insertion site that resulted in elite event MZIR098. The invention further relates to assays for detecting the presence of the DNA sequences of corn elite event MZIR098, to corn plants and corn seeds comprising the genotype thereof, and to methods for producing a corn plant by crossing a corn plant comprising the elite event MZIR098 genotype with itself or another corn variety.

1 Claim, 2 Drawing Sheets

Specification includes a Sequence Listing.

```
                         SEQUENCE LISTING


<160> NUMBER OF SEQ ID NOS: 71

<210> SEQ ID NO 1
<211> LENGTH: 20
<212> TYPE: DNA
<213> ORGANISM: Artificial Sequence
<220> FEATURE:
<223> OTHER INFORMATION: Zea mays, Agrobacterium tumefaciens

<400> SEQUENCE: 1

aacggagctg gtttaaactg                                               20


<210> SEQ ID NO 2
<211> LENGTH: 20
<212> TYPE: DNA
<213> ORGANISM: Artificial Sequence
<220> FEATURE:
<223> OTHER INFORMATION: Zea mays, Agrobacterium tumefaciens

<400> SEQUENCE: 2

caccacaata ccaggcccag                                               20


<210> SEQ ID NO 3
<211> LENGTH: 120
<212> TYPE: DNA
<213> ORGANISM: Artificial Sequence
<220> FEATURE:
<223> OTHER INFORMATION: Zea mays, Agrobacterium tumefaciens

<400> SEQUENCE: 3
```

```
gcaacaaaat atacgtgtgt gcgtcgagct gcatattcta gttgtaccgg cacggcagtc     60

gaacgatctc agacaccaaa ccgagatcca agtgacagcg aacggagctg gtttaaactg    120


<210> SEQ ID NO 4
<211> LENGTH: 120
<212> TYPE: DNA
<213> ORGANISM: Artificial Sequence
<220> FEATURE:
<223> OTHER INFORMATION: Zea mays, Agrobacterium tumefaciens

<400> SEQUENCE: 4

caccacaata ccaggcccag gcgcgaccgg ccgcagcgcg ccgacaagga accatgccgg     60

ttgcctaact aacggctgac tcgctcgatc gagcggagca tgcggacact gcagcaggtt    120


<210> SEQ ID NO 5
<211> LENGTH: 8487
<212> TYPE: DNA
<213> ORGANISM: Artificial Sequence
<220> FEATURE:
<223> OTHER INFORMATION: Derived from Zea mays, Agrobacterium
      tumefaciens, Cestrum Yellow Leaf Curl Virus, Bacillus
      thuringiensis, Cauliflower Mosaic Virus, and Streptomyces
      viridochromogenes

<400> SEQUENCE: 5

aacggagctg gtttaaactg gcactagcct aacggtgttg actaagtagg ccgcttccct     60

aattagctaa gggacccggg tcattgagcg gagaattaag ggagtcacgt tatgaccccc    120

gccgatgacg cgggacaagc cgttttacgt ttggaactga cagaaccgca acgaatattg    180

gcagacaaag tggcagacat actgtcccac aaatgaagat ggaatctgta aaagaaaacg    240

cgtgaaataa tgcgtctgac aaaggttagg tcggctgcct ttaatcaata ccaaagtggt    300

ccctaccacg atggaaaaac tgtgcagtcg gtttggcttt ttctgacgaa caaataagat    360

tcgtggccga caggtggggg tccaccatgt gaaggcatct tcagactcca ataatggagc    420

aatgacgtaa gggcttacga aataagtaag ggtagtttgg gaaatgtcca ctcacccgtc    480

agtctataaa tacttagccc ctccctcatt gttaagggag caaaatctca gagagatagt    540

cctagagaga gaaagagagc aagtagccta gaagtggatc caccatgact agtaacggcc    600

gccagtgtgc tggtattcgc ccttatgacg gccgacaaca acaccgaggc ctggacagca    660

gcaccaccaa ggacgtgatc cagaagggca tcagcgtggt gggcgacctg ctgggcgtgg    720

tgggcttccc cttcggcggc gccctggtga gcttctacac caacttcctg aacaccatct    780

ggcccagcga ggacccctgg aaggccttca tggagcaggt ggaggccctg atggaccaga    840

agatcgccga ctacgccaag aacaaggcac tggccgagct acagggcctc cagaacaacg    900

tggaggacta tgtgagcgcc ctgagcagct ggcagaagaa ccccgctgca ccgttccgca    960

acccccacag ccagggccgc atccgcgagc tgttcagcca ggccgagagc cacttccgca   1020

acagcatgcc cagcttcgcc atcagcggct acgaggtgct gttcctgacc acctacgccc   1080

aggccgccaa cacccacctg ttcctgctga aggacgccca aatctacgga gaggagtggg   1140

gctacgagaa ggaggacatc gccgagttct acaagcgcca gctgaagctg acccaggagt   1200

acaccgacca ctgcgtgaag tggtacaacg tgggtctaga caagctccgc ggcagcagct   1260

acgagagctg ggtgaacttc aaccgctacc gccgcgagat gaccctgacc gtgctggacc   1320

tgatcgccct gttccccctg tacgacgtgc gcctgtaccc caaggaggtg aagaccgagc   1380

tgacccgcga cgtgctgacc gaccccatcg tgggcgtgaa caacctgcgc ggctacggca   1440
```

```
ccaccttcag caacatcgag aactacatcc gcaagcccca cctgttcgac tacctgcacc   1500
gcatccagtt ccacacgcgt ttccagcccg gctactacgg caacgacagc ttcaactact   1560
ggagcggcaa ctacgtgagc acccgcccca gcatcggcag caacgacatc atcaccagcc   1620
ccttctacgg caacaagagc agcgagcccg tgcagaacct tgagttcaac ggcgagaagg   1680
tgtaccgcgc cgtggctaac accaacctgg ccgtgtggcc ctctgcagtg tacagcggcg   1740
tgaccaaggt ggagttcagc cagtacaacg accagaccga cgaggccagc acccagacct   1800
acgacagcaa gcgcaacgtg ggcgccgtga gctgggacag catcgaccag ctgccccccg   1860
agaccaccga cgagcccctg gagaagggct acagccacca gctgaactac gtgatgtgct   1920
tcctgatgca gggcagccgc ggcaccatcc ccgtgctgac ctggacccac aagagcgtcg   1980
acttcttcaa catgatcgac agcaagaaga tcacccagct gcccctgacc aagagcacca   2040
acctgggcag cggcaccagc gtggtgaagg gccccggctt caccggcggc gacatcctgc   2100
gccgcaccag ccccggccag atcagcaccc tgcgcgtgaa catcaccgcc cccctgagcc   2160
agcgctaccg cgtccgcatc cgctacgcca gcaccaccaa cctgcagttc cacaccagca   2220
tcgacggccg ccccatcaac cagggcaact tcagcgccac catgagcagc ggcagcaacc   2280
tgcagagcgg cagcttccgc accgtgggct tcaccacccc cttcaacttc agcaacggca   2340
gcagcgtgtt caccctgagc gcccacgtgt tcaacagcgg caacgaggtg tacatcgacc   2400
gcatcgagtt cgtgcccgcc gaggtgacct tcgaggccga gtacgacctg gagagggctc   2460
agaaggccgt gaacgagctg ttcaccagca gcaaccagat cggcctgaag accgacgtga   2520
ccgactacca catcgatcag gtgtaggagc tgagctcttc atatgacgat cgttcaaaca   2580
tttggcaata aagtttctta agattgaatc ctgttgccgg tcttgcgatg attatcatat   2640
aatttctgtt gaattacgtt aagcatgtaa taattaacat gtaatgcatg acgttattta   2700
tgagatgggt ttttatgatt agagtcccgc aattatacat ttaatacgcg atagaaaaca   2760
aaatatagcg cgcaaactag gataaattat cgcgcgcggt gtcatctatg ttactagatc   2820
gcggacccaa gcttgcatgc ctgcagtgca gcgtgacccg gtcgtgcccc tctctagaga   2880
taatgagcat tgcatgtcta agttataaaa aattaccaca tatttttttt gtcacacttg   2940
tttgaagtgc agtttatcta tctttataca tatatttaaa ctttactcta cgaataatat   3000
aatctatagt actacaataa tatcagtgtt ttagagaatc atataaatga acagttagac   3060
atggtctaaa ggacaattga gtattttgac aacaggactc tacagtttta tctttttagt   3120
gtgcatgtgt tctccttttt ttttgcaaat agcttcacct atataatact tcatccattt   3180
tattagtaca tccatttagg gtttagggtt aatggttttt atagactaat ttttttagta   3240
catctatttt attctatttt agcctctaaa ttaagaaaac taaaactcta ttttagtttt   3300
tttatttaat aatttagata taaaatagaa taaaataaag tgactaaaaa ttaaacaaat   3360
accctttaag aaattaaaaa aactaaggaa acatttttct tgtttcgagt agataatgcc   3420
agcctgttaa acgccgccga cgagtctaac ggacaccaac cagcgaacca gcagcgtcgc   3480
gtcgggccaa gcgaagcaga cggcacggca tctctgtcgc tgcctctgga cccctctcga   3540
gagttccgct ccaccgttgg acttgctccg ctgtcggcat ccagaaattg cgtggcggag   3600
cggcagacgt gagccggcac ggcaggcggc ctcctcctcc tctcacggca ccggcagcta   3660
cgggggattc ctttcccacc gctccttcgc tttcccttcc tcgcccgccg taataaatag   3720
acaccccctc cacaccctct ttccccaacc tcgtgttgtt cggagcgcac acacacacaa   3780
ccagatctcc cccaaatcca cccgtcggca cctccgcttc aaggtacgcc gctcgtcctc   3840
```

```
ccccccccc cctctctacc ttctctagat cggcgttccg gtccatagtt agggcccggt   3900
agttctactt ctgttcatgt ttgtgttaga tccgtgtttg tgttagatcc gtgctgttag   3960
cgttcgtaca cggatgcgac ctgtacgtca gacacgttct gattgctaac ttgccagtgt   4020
ttctctttgg ggaatcctgg gatggctcta gccgttccgc agacgggatc gatttcatga   4080
tttttttgt ttcgttgcat agggtttggt ttgccctttt cctttatttc aatatatgcc   4140
gtgcacttgt ttgtcgggtc atcttttcat gctttttttt gtcttggttg tgatgatgtg   4200
gtctggttgg gcggtcgttc tagatcggag tagaattctg tttcaaacta cctggtggat   4260
ttattaattt tggatctgta tgtgtgtgcc atacatattc atagttacga attgaagatg   4320
atggatggaa atatcgatct aggataggta tacatgttga tgcgggtttt actgatgcat   4380
atacagagat gctttttgtt cgcttggttg tgatgatgtg gtgtggttgg gcggtcgttc   4440
attcgttcta gatcggagta gaatactgtt tcaaactacc tggtgtattt attaattttg   4500
gaactgtatg tgtgtgtcat acatcttcat agttacgagt ttaagatgga tggaaatatc   4560
gatctaggat aggtatacat gttgatgtgg gttttactga tgcatataca tgatggcata   4620
tgcagcatct attcatatgc tctaaccttg agtacctatc tattataata aacaagtatg   4680
ttttataatt attttgatct tgatatactt ggatgatggc atatgcagca gctatatgtg   4740
gattttttta gccctgcctt catacgctat ttatttgctt ggtactgttt cttttgtcga   4800
tgctcaccct gttgtttggt gttacttctg cagggatcca ccatgacggc cgacaacaac   4860
accgaggccc tggacagcag caccaccaag gacgtgatcc agaagggcat cagcgtggtg   4920
ggcgacctgc tgggcgtggt gggcttcccc ttcggcggcg ccctggtgag cttctacacc   4980
aacttcctga acaccatctg gcccagcgag gacccctgga aggccttcat ggagcaggtg   5040
gaggccctga tggaccagaa gatcgccgac tacgccaaga acaaggcact ggccgagcta   5100
cagggcctcc agaacaacgt ggaggactat gtgagcgccc tgagcagctg gcagaagaac   5160
cccgctgcac cgttccgcaa cccccacagc cagggccgca tccgcgagct gttcagccag   5220
gccgagagcc acttccgcaa cagcatgccc agcttcgcca tcagcggcta cgaggtgctg   5280
ttcctgacca cctacgccca ggccgccaac acccacctgt tcctgctgaa ggacgcccaa   5340
atctacggag aggagtgggg ctacgagaag gaggacatcg ccgagttcta caagcgccag   5400
ctgaagctga cccaggagta caccgaccac tgcgtgaagt ggtacaacgt gggtctagac   5460
aagctccgcg gcagcagcta cgagagctgg gtgaacttca accgctaccg ccgcgagatg   5520
accctgaccg tgctggacct gatcgccctg ttcccccctgt acgacgtgcg cctgtacccc   5580
aaggaggtga agaccgagct gacccgcgac gtgctgaccg accccatcgt gggcgtgaac   5640
aacctgcgcg gctacggcac caccttcagc aacatcgaga actacatccg caagccccac   5700
ctgttcgact acctgcaccg catccagttc cacacgcgtt tccagcccgg ctactacggc   5760
aacgacagct tcaactactg gagcggcaac tacgtgagca cccgccccag catcggcagc   5820
aacgacatca tcaccagccc cttctacggc aacaagagca gcgagcccgt gcagaacctt   5880
gagttcaacg gcgagaaggt gtaccgcgcc gtggctaaca ccaacctggc cgtgtggccc   5940
tctgcagtgt acagcggcgt gaccaaggtg gagttcagcc agtacaacga ccagaccgac   6000
gaggccagca cccagaccta cgacagcaag cgcaacgtgg gcgccgtgag ctgggacagc   6060
atcgaccagc tgccccccga gaccaccgac gagcccctgg agaagggcta cagccaccag   6120
ctgaactacg tgatgtgctt cctgatgcag ggcagccgcg gcaccatccc cgtgctgacc   6180
```

-continued

```
tggacccaca agagcgtcga cttcttcaac atgatcgaca gcaagaagat cacccagctg   6240
cccctggtga aggcctacaa gctccagagc ggcgccagcg tggtggcagg cccccgcttc   6300
accggcggcg acatcatcca gtgcaccgag aacggcagcg ccgccaccat ctacgtgacc   6360
cccgacgtga gctacagcca gaagtaccgc gcccgcatcc actacgccag caccagccag   6420
atcaccttca ccctgagcct ggacggggcc cccttcaacc aatactactt cgacaagacc   6480
atcaacaagg gcgacaccct gacctacaac agcttcaacc tggccagctt cagcacccct   6540
ttcgagctga gcggcaacaa cctccagatc ggcgtgaccg gcctgagcgc cggcgacaag   6600
gtgtacatcg acaagatcga gttcatcccc gtgaactaga tctgaggggt accagctctt   6660
gacgacctgc taagatcgtt caaacatttg gcaataaagt ttcttaagat tgaatcctgt   6720
tgccggtctt gcgatgatta tcaatataat ttctgttgaa ttacgttaag catgtaataa   6780
ttaacatgta atgcatgacg ttatttatga gatgggtttt tatgattaga gtcccgcaat   6840
tatacattta atacgcgata gaaaacaaaa tatagcgcgc aaactaggat aaattatcgc   6900
gcgcggtgtc atctattgtt actagatcta attgacggac ccggcgcgcc atttaaatgg   6960
taccggtccg gcatgcatgc agggatccac atggagtcaa agattcaaat agaggaccta   7020
acagaactcg ccgtaaagac tggcgaacag ttcatacaga gtctcttacg actcaatgac   7080
aagaagaaaa tcttcgtcaa catggtggag cacgacacgc ttgtctactc caaaaatatc   7140
aaagatacag tctcagaaga ccaaagggca attgagactt ttcaacaaag ggtaatatcc   7200
ggaaacctcc tcggattcca ttgcccagct atctgtcact ttattgtgaa gatagtggaa   7260
aaggaaggtg gctcctacaa atgccatcat tgcgataaag gaaaggccat cgttgaagat   7320
gcctctgccg acagtggtcc caaagatgga cccccaccca cgaggagcat cgtggaaaaa   7380
gaagacgttc caaccacgtc ttcaaagcaa gtggattgat gtgatatctc cactgacgta   7440
agggatgacg cacaatccca ctatccttcg caagaccctt cctctatata aggaagttca   7500
tttcatttgg agaggacacg ctgaaatcac tagtccacca tgtctccgga gaggagacca   7560
gttgagatta ggccagctac agcagctgat atggccgcgg tttgtgatat cgttaaccat   7620
tacattgaga cgtctacagt gaactttagg acagagccac aaacaccaca agagtggatt   7680
gatgatctag agaggttgca agatagatac ccttggttgg ttgctgaggt tgagggtgtt   7740
gtggctggta ttgcttacgc tgggccctgg aaggctagga acgcttacga ttggacagtt   7800
gagagtactg tttacgtgtc acataggcat caaaggttgg gcctaggatc cacattgtac   7860
acacatttgc ttaagtctat ggaggcgcaa ggttttaagt ctgtggttgc tgttataggc   7920
cttccaaacg atccatctgt taggttgcat gaggctttgg gatacacagc gcggggtaca   7980
ttgcgcgcag ctggatacaa gcatggtgga tggcatgatg ttggtttttg gcaaagggat   8040
tttgagttgc cagctcctcc aaggccagtt aggccagtta cccagatctg aatagtgata   8100
tcggcgcctg ggtcgacctg cagatcgttc aaacatttgg caataaagtt tcttaagatt   8160
gaatcctgtt gccggtcttg cgatgattat catataattt ctgttgaatt acgttaagca   8220
tgtaataatt aacatgtaat gcatgacgtt atttatgaga tgggttttta tgattagagt   8280
cccgcaatta tacatttaat acgcgataga aaacaaaata tagcgcgcaa actaggataa   8340
attatcgcgc gcggtgtcat ctatgttact agatccgtag ccctgcagga aatttaccgg   8400
tgcccgggcg gccagcatgg ccgtatccgc aatgtgttat taagttgtct aagcgtcaat   8460
ttgtttacac cacaatacca ggcccag                                        8487
```

```
<210> SEQ ID NO 6
<211> LENGTH: 8687
<212> TYPE: DNA
<213> ORGANISM: Artificial Sequence
<220> FEATURE:
<223> OTHER INFORMATION: Derived from Zea mays, Agrobacterium
      tumefaciens, Cestrum Yellow Leaf Curl Virus, Bacillus
      thuringiensis, Cauliflower Mosaic Virus, and Streptomyces
      viridochromogenes

<400> SEQUENCE: 6

gcaacaaaat atacgtgtgt gcgtcgagct gcatattcta gttgtaccgg cacggcagtc     60

gaacgatctc agacaccaaa ccgagatcca agtgacagcg aacggagctg gtttaaactg    120

gcactagcct aacggtgttg actaagtagg ccgcttccct aattagctaa gggacccggg    180

tcattgagcg gagaattaag ggagtcacgt tatgaccccc gccgatgacg cgggacaagc    240

cgttttacgt ttggaactga cagaaccgca acgaatattg gcagacaaag tggcagacat    300

actgtcccac aaatgaagat ggaatctgta aaagaaaacg cgtgaaataa tgcgtctgac    360

aaaggttagg tcggctgcct ttaatcaata ccaaagtggt ccctaccacg atggaaaaac    420

tgtgcagtcg gtttggcttt ttctgacgaa caaataagat tcgtggccga caggtggggg    480

tccaccatgt gaaggcatct tcagactcca ataatggagc aatgacgtaa gggcttacga    540

aataagtaag ggtagtttgg gaaatgtcca ctcacccgtc agtctataaa tacttagccc    600

ctccctcatt gttaagggag caaaatctca gagagatagt cctagagaga gaaagagagc    660

aagtagccta gaagtggatc caccatgact agtaacggcc gccagtgtgc tggtattcgc    720

ccttatgacg gccgacaaca acaccgaggc ctggacagca gcaccaccaa ggacgtgatc    780

cagaagggca tcagcgtggt gggcgacctg ctgggcgtgg tgggcttccc cttcggcggc    840

gccctggtga gcttctacac caacttcctg aacaccatct ggcccagcga ggacccctgg    900

aaggccttca tggagcaggt ggaggccctg atggaccaga agatcgccga ctacgccaag    960

aacaaggcac tggccgagct acagggcctc cagaacaacg tggaggacta tgtgagcgcc   1020

ctgagcagct ggcagaagaa ccccgctgca ccgttccgca acccccacag ccagggccgc   1080

atccgcgagc tgttcagcca ggccgagagc cacttccgca acagcatgcc cagcttcgcc   1140

atcagcggct acgaggtgct gttcctgacc acctacgccc aggccgccaa cacccacctg   1200

ttcctgctga aggacgccca aatctacgga gaggagtggg gctacgagaa ggaggacatc   1260

gccgagttct acaagcgcca gctgaagctg acccaggagt acaccgacca ctgcgtgaag   1320

tggtacaacg tgggtctaga caagctccgc ggcagcagct acgagagctg ggtgaacttc   1380

aaccgctacc gccgcgagat gaccctgacc gtgctggacc tgatcgccct gttccccctg   1440

tacgacgtgc gcctgtaccc caaggaggtg aagaccgagc tgacccgcga cgtgctgacc   1500

gaccccatcg tgggcgtgaa caacctgcgc ggctacggca ccaccttcag caacatcgag   1560

aactacatcc gcaagcccca cctgttcgac tacctgcacc gcatccagtt ccacacgcgt   1620

ttccagcccg gctactacgg caacgacagc ttcaactact ggagcggcaa ctacgtgagc   1680

acccgcccca gcatcggcag caacgacatc atcaccagcc ccttctacgg caacaagagc   1740

agcgagcccg tgcagaacct tgagttcaac ggcgagaagg tgtaccgcgc cgtggctaac   1800

accaacctgg ccgtgtggcc ctctgcagtg tacagcggcg tgaccaaggt ggagttcagc   1860

cagtacaacg accagaccga cgaggccagc acccagacct acgacagcaa gcgcaacgtg   1920

ggcgccgtga gctgggacag catcgaccag ctgccccccg agaccaccga cgagcccctg   1980

gagaagggct acagccacca gctgaactac gtgatgtgct tcctgatgca gggcagccgc   2040
```

```
ggcaccatcc ccgtgctgac ctggacccac aagagcgtcg acttcttcaa catgatcgac   2100
agcaagaaga tcacccagct gcccctgacc aagagcacca acctgggcag cggcaccagc   2160
gtggtgaagg gccccggctt caccggcggc gacatcctgc gccgcaccag ccccggccag   2220
atcagcaccc tgcgcgtgaa catcaccgcc cccctgagcc agcgctaccg cgtccgcatc   2280
cgctacgcca gcaccaccaa cctgcagttc cacaccagca tcgacggccg ccccatcaac   2340
cagggcaact tcagcgccac catgagcagc ggcagcaacc tgcagagcgg cagcttccgc   2400
accgtgggct tcaccacccc cttcaacttc agcaacggca gcagcgtgtt caccctgagc   2460
gcccacgtgt tcaacagcgg caacgaggtg tacatcgacc gcatcgagtt cgtgcccgcc   2520
gaggtgacct tcgaggccga gtacgacctg gagagggctc agaaggccgt gaacgagctg   2580
ttcaccagca gcaaccagat cggcctgaag accgacgtga ccgactacca catcgatcag   2640
gtgtaggagc tgagctcttc atatgacgat cgttcaaaca tttggcaata aagtttctta   2700
agattgaatc ctgttgccgg tcttgcgatg attatcatat aatttctgtt gaattacgtt   2760
aagcatgtaa taattaacat gtaatgcatg acgttattta tgagatgggt ttttatgatt   2820
agagtcccgc aattatacat ttaatacgcg atagaaaaca aaatatagcg cgcaaactag   2880
gataaattat cgcgcgcggt gtcatctatg ttactagatc gcggacccaa gcttgcatgc   2940
ctgcagtgca gcgtgacccg gtcgtgcccc tctctagaga taatgagcat tgcatgtcta   3000
agttataaaa aattaccaca tatttttttt gtcacacttg tttgaagtgc agtttatcta   3060
tctttataca tatatttaaa ctttactcta cgaataatat aatctatagt actacaataa   3120
tatcagtgtt ttagagaatc atataaatga acagttagac atggtctaaa ggacaattga   3180
gtattttgac aacaggactc tacagtttta tctttttagt gtgcatgtgt tctccttttt   3240
ttttgcaaat agcttcacct atataatact tcatccattt tattagtaca tccatttagg   3300
gtttagggtt aatggttttt atagactaat ttttttagta catctatttt attctatttt   3360
agcctctaaa ttaagaaaac taaaactcta ttttagtttt tttatttaat aatttagata   3420
taaaatagaa taaaataaag tgactaaaaa ttaaacaaat accctttaag aaattaaaaa   3480
aactaaggaa acatttttct tgtttcgagt agataatgcc agcctgttaa acgccgccga   3540
cgagtctaac ggacaccaac cagcgaacca gcagcgtcgc gtcgggccaa gcgaagcaga   3600
cggcacggca tctctgtcgc tgcctctgga cccctctcga gagttccgct ccaccgttgg   3660
acttgctccg ctgtcggcat ccagaaattg cgtggcggag cggcagacgt gagccggcac   3720
ggcaggcggc ctcctcctcc tctcacggca ccggcagcta cgggggattc ctttcccacc   3780
gctccttcgc tttcccttcc tcgcccgccg taataaatag acacccccctc cacaccctct   3840
ttccccaacc tcgtgttgtt cggagcgcac acacacacaa ccagatctcc cccaaatcca   3900
cccgtcggca cctccgcttc aaggtacgcc gctcgtcctc cccccccccc cctctctacc   3960
ttctctagat cggcgttccg gtccatagtt agggcccggt agttctactt ctgttcatgt   4020
ttgtgttaga tccgtgtttg tgttagatcc gtgctgttag cgttcgtaca cggatgcgac   4080
ctgtacgtca gacacgttct gattgctaac ttgccagtgt ttctctttgg ggaatcctgg   4140
gatggctcta gccgttccgc agacgggatc gatttcatga ttttttttgt ttcgttgcat   4200
agggtttggt ttgccctttt cctttatttc aatatatgcc gtgcacttgt ttgtcgggtc   4260
atcttttcat gctttttttt gtcttggttg tgatgatgtg gtctggttgg gcggtcgttc   4320
tagatcggag tagaattctg tttcaaacta cctggtggat ttattaattt tggatctgta   4380
```

-continued

```
tgtgtgtgcc atacatattc atagttacga attgaagatg atggatggaa atatcgatct   4440

aggataggta tacatgttga tgcgggtttt actgatgcat atacagagat gctttttgtt   4500

cgcttggttg tgatgatgtg gtgtggttgg gcggtcgttc attcgttcta gatcggagta   4560

gaatactgtt tcaaactacc tggtgtattt attaattttg gaactgtatg tgtgtgtcat   4620

acatcttcat agttacgagt ttaagatgga tggaaatatc gatctaggat aggtatacat   4680

gttgatgtgg gttttactga tgcatataca tgatggcata tgcagcatct attcatatgc   4740

tctaaccttg agtacctatc tattataata aacaagtatg ttttataatt attttgatct   4800

tgatatactt ggatgatggc atatgcagca gctatatgtg gattttttta gccctgcctt   4860

catacgctat ttatttgctt ggtactgttt cttttgtcga tgctcaccct gttgtttggt   4920

gttacttctg cagggatcca ccatgacggc cgacaacaac accgaggccc tggacagcag   4980

caccaccaag gacgtgatcc agaagggcat cagcgtggtg ggcgacctgc tgggcgtggt   5040

gggcttcccc ttcggcggcg ccctggtgag cttctacacc aacttcctga acaccatctg   5100

gcccagcgag gacccctgga aggccttcat ggagcaggtg gaggccctga tggaccagaa   5160

gatcgccgac tacgccaaga acaaggcact ggccgagcta cagggcctcc agaacaacgt   5220

ggaggactat gtgagcgccc tgagcagctg gcagaagaac cccgctgcac cgttccgcaa   5280

cccccacagc cagggccgca tccgcgagct gttcagccag gccgagagcc acttccgcaa   5340

cagcatgccc agcttcgcca tcagcggcta cgaggtgctg ttcctgacca cctacgccca   5400

ggccgccaac acccacctgt tcctgctgaa ggacgcccaa atctacggag aggagtgggg   5460

ctacgagaag gaggacatcg ccgagttcta caagcgccag ctgaagctga cccaggagta   5520

caccgaccac tgcgtgaagt ggtacaacgt gggtctagac aagctccgcg gcagcagcta   5580

cgagagctgg gtgaacttca accgctaccg ccgcgagatg accctgaccg tgctggacct   5640

gatcgccctg ttcccccctgt acgacgtgcg cctgtacccc aaggaggtga agaccgagct   5700

gacccgcgac gtgctgaccg accccatcgt gggcgtgaac aacctgcgcg gctacggcac   5760

caccttcagc aacatcgaga actacatccg caagccccac ctgttcgact acctgcaccg   5820

catccagttc cacacgcgtt tccagcccgg ctactacggc aacgacagct tcaactactg   5880

gagcggcaac tacgtgagca cccgccccag catcggcagc aacgacatca tcaccagccc   5940

cttctacggc aacaagagca gcgagcccgt gcagaacctt gagttcaacg gcgagaaggt   6000

gtaccgcgcc gtggctaaca ccaacctggc cgtgtggccc tctgcagtgt acagcggcgt   6060

gaccaaggtg gagttcagcc agtacaacga ccagaccgac gaggccagca cccagaccta   6120

cgacagcaag cgcaacgtgg gcgccgtgag ctgggacagc atcgaccagc tgccccccga   6180

gaccaccgac gagcccctgg agaagggcta cagccaccag ctgaactacg tgatgtgctt   6240

cctgatgcag ggcagccgcg gcaccatccc cgtgctgacc tggacccaca agagcgtcga   6300

cttcttcaac atgatcgaca gcaagaagat cacccagctg cccctggtga aggcctacaa   6360

gctccagagc ggcgccagcg tggtggcagg cccccgcttc accggcggcg acatcatcca   6420

gtgcaccgag aacggcagcg ccgccaccat ctacgtgacc cccgacgtga gctacagcca   6480

gaagtaccgc gcccgcatcc actacgccag caccagccag atcaccttca ccctgagcct   6540

ggacggggcc ccttcaacc aatactactt cgacaagacc atcaacaagg gcgacaccct   6600

gacctacaac agcttcaacc tggccagctt cagcacccct ttcgagctga gcggcaacaa   6660

cctccagatc ggcgtgaccg gcctgagcgc cggcgacaag gtgtacatcg acaagatcga   6720

gttcatcccc gtgaactaga tctgaggggt accagctctt gacgacctgc taagatcgtt   6780
```

```
caaacatttg gcaataaagt ttcttaagat tgaatcctgt tgccggtctt gcgatgatta   6840
tcaatataat ttctgttgaa ttacgttaag catgtaataa ttaacatgta atgcatgacg   6900
ttatttatga gatgggtttt tatgattaga gtcccgcaat tatacattta atacgcgata   6960
gaaaacaaaa tatagcgcgc aaactaggat aaattatcgc gcgcggtgtc atctattgtt   7020
actagatcta attgacggac ccggcgcgcc atttaaatgg taccggtccg gcatgcatgc   7080
agggatccac atggagtcaa agattcaaat agaggaccta acagaactcg ccgtaaagac   7140
tggcgaacag ttcatacaga gtctcttacg actcaatgac aagaagaaaa tcttcgtcaa   7200
catggtggag cacgacacgc ttgtctactc caaaaatatc aaagatacag tctcagaaga   7260
ccaaagggca attgagactt ttcaacaaag ggtaatatcc ggaaacctcc tcggattcca   7320
ttgcccagct atctgtcact ttattgtgaa gatagtggaa aaggaaggtg gctcctacaa   7380
atgccatcat tgcgataaag gaaaggccat cgttgaagat gcctctgccg acagtggtcc   7440
caaagatgga cccccaccca cgaggagcat cgtggaaaaa gaagacgttc caaccacgtc   7500
ttcaaagcaa gtggattgat gtgatatctc cactgacgta agggatgacg cacaatccca   7560
ctatccttcg caagaccctt cctctatata aggaagttca tttcatttgg agaggacacg   7620
ctgaaatcac tagtccacca tgtctccgga gaggagacca gttgagatta ggccagctac   7680
agcagctgat atggccgcgg tttgtgatat cgttaaccat tacattgaga cgtctacagt   7740
gaactttagg acagagccac aaacaccaca agagtggatt gatgatctag agaggttgca   7800
agatagatac ccttggttgg ttgctgaggt tgagggtgtt gtggctggta ttgcttacgc   7860
tgggccctgg aaggctagga acgcttacga ttggacagtt gagagtactg tttacgtgtc   7920
acataggcat caaaggttgg gcctaggatc cacattgtac acacatttgc ttaagtctat   7980
ggaggcgcaa ggttttaagt ctgtggttgc tgttataggc cttccaaacg atccatctgt   8040
taggttgcat gaggctttgg gatacacagc gcggggtaca ttgcgcgcag ctggatacaa   8100
gcatggtgga tggcatgatg ttggtttttg gcaaagggat tttgagttgc cagctcctcc   8160
aaggccagtt aggccagtta cccagatctg aatagtgata tcggcgcctg ggtcgacctg   8220
cagatcgttc aaacatttgg caataaagtt tcttaagatt gaatcctgtt gccggtcttg   8280
cgatgattat catataattt ctgttgaatt acgttaagca tgtaataatt aacatgtaat   8340
gcatgacgtt atttatgaga tgggttttta tgattagagt cccgcaatta tacatttaat   8400
acgcgataga aaacaaaata tagcgcgcaa actaggataa attatcgcgc gcggtgtcat   8460
ctatgttact agatccgtag ccctgcagga aatttaccgg tgcccgggcg gccagcatgg   8520
ccgtatccgc aatgtgttat taagttgtct aagcgtcaat ttgtttacac cacaatacca   8580
ggcccaggcg cgaccggccg cagcgcgccg acaaggaacc atgccggttg cctaactaac   8640
ggctgactcg ctcgatcgag cggagcatgc ggacactgca gcaggtt                  8687
```

<210> SEQ ID NO 7
<211> LENGTH: 8467
<212> TYPE: DNA
<213> ORGANISM: Artificial Sequence
<220> FEATURE:
<223> OTHER INFORMATION: Derived from Zea mays, Agrobacterium tumefaciens, Cestrum Yellow Leaf Curl Virus, Bacillus thuringiensis, Cauliflower Mosaic Virus, Streptomyces viridochromogenes

<400> SEQUENCE: 7

```
gtttaaactg gcactagcct aacggtgttg actaagtagg ccgcttccct aattagctaa     60
```

```
gggacccggg tcattgagcg gagaattaag ggagtcacgt tatgaccccc gccgatgacg    120
cgggacaagc cgttttacgt ttggaactga cagaaccgca acgaatattg gcagacaaag    180
tggcagacat actgtcccac aaatgaagat ggaatctgta aagaaaaacg cgtgaaataa    240
tgcgtctgac aaaggttagg tcggctgcct ttaatcaata ccaaagtggt ccctaccacg    300
atggaaaaac tgtgcagtcg gtttggcttt ttctgacgaa caaataagat tcgtggccga    360
caggtggggg tccaccatgt gaaggcatct tcagactcca ataatggagc aatgacgtaa    420
gggcttacga aataagtaag ggtagtttgg gaaatgtcca ctcacccgtc agtctataaa    480
tacttagccc ctccctcatt gttaagggag caaaatctca gagagatagt cctagagaga    540
gaaagagagc aagtagccta gaagtggatc caccatgact agtaacggcc gccagtgtgc    600
tggtattcgc ccttatgacg gccgacaaca acaccgaggc ctggacagca gcaccaccaa    660
ggacgtgatc cagaagggca tcagcgtggt gggcgacctg ctgggcgtgg tgggcttccc    720
cttcggcggc gccctggtga gcttctacac caacttcctg aacaccatct ggcccagcga    780
ggacccctgg aaggccttca tggagcaggt ggaggccctg atggaccaga agatcgccga    840
ctacgccaag aacaaggcac tggccgagct acagggcctc cagaacaacg tggaggacta    900
tgtgagcgcc ctgagcagct ggcagaagaa ccccgctgca ccgttccgca acccccacag    960
ccagggccgc atccgcgagc tgttcagcca ggccgagagc cacttccgca acagcatgcc   1020
cagcttcgcc atcagcggct acgaggtgct gttcctgacc acctacgccc aggccgccaa   1080
cacccacctg ttcctgctga aggacgccca aatctacgga gaggagtggg gctacgagaa   1140
ggaggacatc gccgagttct acaagcgcca gctgaagctg acccaggagt acaccgacca   1200
ctgcgtgaag tggtacaacg tgggtctaga caagctccgc ggcagcagct acgagagctg   1260
ggtgaacttc aaccgctacc gccgcgagat gaccctgacc gtgctggacc tgatcgccct   1320
gttccccctg tacgacgtgc gcctgtaccc caaggaggtg aagaccgagc tgacccgcga   1380
cgtgctgacc gaccccatcg tgggcgtgaa caacctgcgc ggctacggca ccaccttcag   1440
caacatcgag aactacatcc gcaagcccca cctgttcgac tacctgcacc gcatccagtt   1500
ccacacgcgt ttccagcccg gctactacgg caacgacagc ttcaactact ggagcggcaa   1560
ctacgtgagc acccgcccca gcatcggcag caacgacatc atcaccagcc ccttctacgg   1620
caacaagagc agcgagcccg tgcagaacct tgagttcaac ggcgagaagg tgtaccgcgc   1680
cgtggctaac accaacctgg ccgtgtggcc ctctgcagtg tacagcggcg tgaccaaggt   1740
ggagttcagc cagtacaacg accagaccga cgaggccagc acccagacct acgacagcaa   1800
gcgcaacgtg ggcgccgtga gctgggacag catcgaccag ctgccccccg agaccaccga   1860
cgagcccctg gagaagggct acagccacca gctgaactac gtgatgtgct tcctgatgca   1920
gggcagccgc ggcaccatcc ccgtgctgac ctggacccac aagagcgtcg acttcttcaa   1980
catgatcgac agcaagaaga tcacccagct gcccctgacc aagagcacca acctgggcag   2040
cggcaccagc gtggtgaagg gccccggctt caccggcggc gacatcctgc gccgcaccag   2100
ccccggccag atcagcaccc tgcgcgtgaa catcaccgcc cccctgagcc agcgctaccg   2160
cgtccgcatc cgctacgcca gcaccaccaa cctgcagttc cacaccagca tcgacggccg   2220
ccccatcaac cagggcaact tcagcgccac catgagcagc ggcagcaacc tgcagagcgg   2280
cagcttccgc accgtgggct tcaccacccc cttcaacttc agcaacggca gcagcgtgtt   2340
caccctgagc gcccacgtgt tcaacagcgg caacgaggtg tacatcgacc gcatcgagtt   2400
```

```
cgtgcccgcc gaggtgacct tcgaggccga gtacgacctg gagagggctc agaaggccgt   2460
gaacgagctg ttcaccagca gcaaccagat cggcctgaag accgacgtga ccgactacca   2520
catcgatcag gtgtaggagc tgagctcttc atatgacgat cgttcaaaca tttggcaata   2580
aagtttctta agattgaatc ctgttgccgg tcttgcgatg attatcatat aatttctgtt   2640
gaattacgtt aagcatgtaa taattaacat gtaatgcatg acgttattta tgagatgggt   2700
ttttatgatt agagtcccgc aattatacat ttaatacgcg atagaaaaca aaatatagcg   2760
cgcaaactag gataaattat cgcgcgcggt gtcatctatg ttactagatc gcggacccaa   2820
gcttgcatgc ctgcagtgca gcgtgacccg gtcgtgcccc tctctagaga taatgagcat   2880
tgcatgtcta agttataaaa aattaccaca tatttttttt gtcacacttg tttgaagtgc   2940
agtttatcta tctttataca tatatttaaa ctttactcta cgaataatat aatctatagt   3000
actacaataa tatcagtgtt ttagagaatc atataaatga acagttagac atggtctaaa   3060
ggacaattga gtattttgac aacaggactc tacagtttta tctttttagt gtgcatgtgt   3120
tctccttttt ttttgcaaat agcttcacct atataatact tcatccattt tattagtaca   3180
tccatttagg gtttagggtt aatggttttt atagactaat ttttttagta catctatttt   3240
attctatttt agcctctaaa ttaagaaaac taaaactcta ttttagtttt tttatttaat   3300
aatttagata taaaatagaa taaaataaag tgactaaaaa ttaaacaaat accctttaag   3360
aaattaaaaa aactaaggaa acatttttct tgtttcgagt agataatgcc agcctgttaa   3420
acgccgccga cgagtctaac ggacaccaac cagcgaacca gcagcgtcgc gtcgggccaa   3480
gcgaagcaga cggcacggca tctctgtcgc tgcctctgga cccctctcga gagttccgct   3540
ccaccgttgg acttgctccg ctgtcggcat ccagaaattg cgtggcggag cggcagacgt   3600
gagccggcac ggcaggcggc ctcctcctcc tctcacggca ccggcagcta cgggggattc   3660
ctttcccacc gctccttcgc tttcccttcc tcgcccgccg taataaatag acaccccctc   3720
cacaccctct ttccccaacc tcgtgttgtt cggagcgcac acacacacaa ccagatctcc   3780
cccaaatcca cccgtcggca cctccgcttc aaggtacgcc gctcgtcctc cccccccccc   3840
cctctctacc ttctctagat cggcgttccg gtccatagtt agggcccggt agttctactt   3900
ctgttcatgt ttgtgttaga tccgtgtttg tgttagatcc gtgctgttag cgttcgtaca   3960
cggatgcgac ctgtacgtca gacacgttct gattgctaac ttgccagtgt ttctctttgg   4020
ggaatcctgg gatggctcta gccgttccgc agacgggatc gatttcatga ttttttttgt   4080
ttcgttgcat agggtttggt ttgccctttt cctttatttc aatatatgcc gtgcacttgt   4140
ttgtcgggtc atcttttcat gctttttttt gtcttggttg tgatgatgtg gtctggttgg   4200
gcggtcgttc tagatcggag tagaattctg tttcaaacta cctggtggat ttattaattt   4260
tggatctgta tgtgtgtgcc atacatattc atagttacga attgaagatg atggatggaa   4320
atatcgatct aggataggta tacatgttga tgcgggtttt actgatgcat atacagagat   4380
gctttttgtt cgcttggttg tgatgatgtg gtgtggttgg gcggtcgttc attcgttcta   4440
gatcggagta gaatactgtt tcaaactacc tggtgtattt attaattttg gaactgtatg   4500
tgtgtgtcat acatcttcat agttacgagt ttaagatgga tggaaatatc gatctaggat   4560
aggtatacat gttgatgtgg gttttactga tgcatataca tgatggcata tgcagcatct   4620
attcatatgc tctaaccttg agtacctatc tattataata aacaagtatg ttttataatt   4680
attttgatct tgatatactt ggatgatggc atatgcagca gctatatgtg gattttttta   4740
gccctgcctt catacgctat ttatttgctt ggtactgttt cttttgtcga tgctcaccct   4800
```

```
gttgtttggt gttacttctg cagggatcca ccatgacggc cgacaacaac accgaggccc   4860
tggacagcag caccaccaag gacgtgatcc agaagggcat cagcgtggtg ggcgacctgc   4920
tgggcgtggt gggcttcccc ttcggcggcg ccctggtgag cttctacacc aacttcctga   4980
acaccatctg gcccagcgag gacccctgga aggccttcat ggagcaggtg gaggccctga   5040
tggaccagaa gatcgccgac tacgccaaga acaaggcact ggccgagcta cagggcctcc   5100
agaacaacgt ggaggactat gtgagcgccc tgagcagctg gcagaagaac cccgctgcac   5160
cgttccgcaa cccccacagc cagggccgca tccgcgagct gttcagccag gccgagagcc   5220
acttccgcaa cagcatgccc agcttcgcca tcagcggcta cgaggtgctg ttcctgacca   5280
cctacgccca ggccgccaac acccacctgt tcctgctgaa ggacgcccaa atctacggag   5340
aggagtgggg ctacgagaag gaggacatcg ccgagttcta caagcgccag ctgaagctga   5400
cccaggagta caccgaccac tgcgtgaagt ggtacaacgt gggtctagac aagctccgcg   5460
gcagcagcta cgagagctgg gtgaacttca accgctaccg ccgcgagatg accctgaccg   5520
tgctggacct gatcgccctg ttccccctgt acgacgtgcg cctgtacccc aaggaggtga   5580
agaccgagct gacccgcgac gtgctgaccg accccatcgt gggcgtgaac aacctgcgcg   5640
gctacggcac caccttcagc aacatcgaga actacatccg caagccccac ctgttcgact   5700
acctgcaccg catccagttc cacacgcgtt tccagcccgg ctactacggc aacgacagct   5760
tcaactactg gagcggcaac tacgtgagca cccgccccag catcggcagc aacgacatca   5820
tcaccagccc cttctacggc aacaagagca gcgagcccgt gcagaacctt gagttcaacg   5880
gcgagaaggt gtaccgcgcc gtggctaaca ccaacctggc cgtgtggccc tctgcagtgt   5940
acagcggcgt gaccaaggtg gagttcagcc agtacaacga ccagaccgac gaggccagca   6000
cccagaccta cgacagcaag cgcaacgtgg gcgccgtgag ctgggacagc atcgaccagc   6060
tgccccccga gaccaccgac gagcccctgg agaagggcta cagccaccag ctgaactacg   6120
tgatgtgctt cctgatgcag ggcagccgcg gcaccatccc cgtgctgacc tggacccaca   6180
agagcgtcga cttcttcaac atgatcgaca gcaagaagat cacccagctg cccctggtga   6240
aggcctacaa gctccagagc ggcgccagcg tggtggcagg cccccgcttc accggcggcg   6300
acatcatcca gtgcaccgag aacggcagcg ccgccaccat ctacgtgacc cccgacgtga   6360
gctacagcca gaagtaccgc gcccgcatcc actacgccag caccagccag atcaccttca   6420
ccctgagcct ggacggggcc cccttcaacc aatactactt cgacaagacc atcaacaagg   6480
gcgacaccct gacctacaac agcttcaacc tggccagctt cagcacccct ttcgagctga   6540
gcggcaacaa cctccagatc ggcgtgaccg gcctgagcgc cggcgacaag gtgtacatcg   6600
acaagatcga gttcatcccc gtgaactaga tctgaggggt accagctctt gacgacctgc   6660
taagatcgtt caaacatttg gcaataaagt ttcttaagat tgaatcctgt tgccggtctt   6720
gcgatgatta tcaatataat ttctgttgaa ttacgttaag catgtaataa ttaacatgta   6780
atgcatgacg ttatttatga gatgggtttt tatgattaga gtcccgcaat tatacattta   6840
atacgcgata gaaaacaaaa tatagcgcgc aaactaggat aaattatcgc gcgcggtgtc   6900
atctattgtt actagatcta attgacggac ccggcgcgcc atttaaatgg taccggtccg   6960
gcatgcatgc agggatccac atggagtcaa agattcaaat agaggaccta acagaactcg   7020
ccgtaaagac tggcgaacag ttcatacaga gtctcttacg actcaatgac aagaagaaaa   7080
tcttcgtcaa catggtggag cacgacacgc ttgtctactc caaaaatatc aaagatacag   7140
```

```
tctcagaaga ccaaagggca attgagactt ttcaacaaag ggtaatatcc ggaaacctcc   7200
tcggattcca ttgcccagct atctgtcact ttattgtgaa gatagtggaa aaggaaggtg   7260
gctcctacaa atgccatcat tgcgataaag gaaaggccat cgttgaagat gcctctgccg   7320
acagtggtcc caaagatgga cccccaccca cgaggagcat cgtggaaaaa gaagacgttc   7380
caaccacgtc ttcaaagcaa gtggattgat gtgatatctc cactgacgta agggatgacg   7440
cacaatccca ctatccttcg caagaccctt cctctatata aggaagttca tttcatttgg   7500
agaggacacg ctgaaatcac tagtccacca tgtctccgga gaggagacca gttgagatta   7560
ggccagctac agcagctgat atggccgcgg tttgtgatat cgttaaccat tacattgaga   7620
cgtctacagt gaactttagg acagagccac aaacaccaca agagtggatt gatgatctag   7680
agaggttgca agatagatac ccttggttgg ttgctgaggt tgagggtgtt gtggctggta   7740
ttgcttacgc tgggccctgg aaggctagga acgcttacga ttggacagtt gagagtactg   7800
tttacgtgtc acataggcat caaaggttgg gcctaggatc cacattgtac acacatttgc   7860
ttaagtctat ggaggcgcaa ggttttaagt ctgtggttgc tgttataggc cttccaaacg   7920
atccatctgt taggttgcat gaggctttgg gatacacagc gcggggtaca ttgcgcgcag   7980
ctggatacaa gcatggtgga tggcatgatg ttggtttttg gcaaagggat tttgagttgc   8040
cagctcctcc aaggccagtt aggccagtta cccagatctg aatagtgata tcggcgcctg   8100
ggtcgacctg cagatcgttc aaacatttgg caataaagtt tcttaagatt gaatcctgtt   8160
gccggtcttg cgatgattat catataattt ctgttgaatt acgttaagca tgtaataatt   8220
aacatgtaat gcatgacgtt atttatgaga tgggttttta tgattagagt cccgcaatta   8280
tacatttaat acgcgataga aaacaaaata tagcgcgcaa actaggataa attatcgcgc   8340
gcggtgtcat ctatgttact agatccgtag ccctgcagga aatttaccgg tgcccgggcg   8400
gccagcatgg ccgtatccgc aatgtgttat taagttgtct aagcgtcaat ttgtttacac   8460
cacaata                                                             8467
```

<210> SEQ ID NO 8
<211> LENGTH: 1076
<212> TYPE: DNA
<213> ORGANISM: Zea mays

<400> SEQUENCE: 8

```
gtacgtttgg tgcacgtacc gatttggcca accccccaca accaaccgcc gttgcgttgc     60
gtccatcggc ctcgctcgca ccggcaccgc cgacatgagg tgggcgggcg ggcggctcca    120
ggtccaggtg gcgtcgtcgg ggtgatgcgc gccgacgtgg agacgtggcc ccttccttct    180
tctacgcaaa atcccccacc cacccaccca cccccatcca tccacacctc ctcttcctaa    240
tccggacgcg ggacgtcaat ttgcttgcca gcagcgacgg catcggccgc ccgccttgta    300
tctaatctaa ccccgtaatc attcacgcta acgacgcccg tggcggggtt agcgtaggca    360
gcggcccggc tggctgtggc tgtctctgtc tgcttggaag ttggaccacg gtgcggcgcg    420
taggggcccg gccagctggt gctgtcgtct gcccgctcgc gtggtcgcgt ttatttctcg    480
gtcggcgcgg gcaagcgctc ctctaccggg tccggatccg gacggtagct agagggcgca    540
gttgcaggtc ggtggccgag ggcgggcgag tcgtttacgt cgcggagaga tggatcggag    600
ttgggtgtgc aggtaggtag gtgtgcgccc gccccagcag acttcagata tctgggatga    660
cgtggggagt tctgttgggt ccgtccggcc cgccgtacgt agtacgccag ctcgctgctt    720
gtctgtacta gagtgaccag ccgagctcgc gacgggtact ggatgccggt ccgtaccggt    780
```

ggtaaacagc gcatgcagtg cagctagcta gatccagtac tagtatttag ctatatattc 840
gtcgtaccag atcagaggca gagctggtcc ccgcctcccc ggacaggtaa actgcttcca 900
tctgtttcca tcggaggcgg ccctggcgtg gcagtggcac tggctctggc agcctcgcca 960
tgcaacgcaa caaaatatac gtgtgtgcgt cgagctgcat attctagttg taccggcacg 1020
gcagtcgaac gatctcagac accaaaccga gatccaagtg acagcgaacg gagctg 1076

<210> SEQ ID NO 9
<211> LENGTH: 1075
<212> TYPE: DNA
<213> ORGANISM: Zea mays

<400> SEQUENCE: 9
ccaggcccag gcgcgaccgg ccgcagcgcg ccgacaagga accatgccgg ttgcctaact 60
aacggctgac tcgctcgatc gagcggagca tgcggacact gcagcaggtt gatagttcca 120
aggagcaata gctgagctag ccaagcctag ctgtacgatg tgttgacacc catgcatgtc 180
catgtccatg gggccggcct gtactgcgag tgcgcgacga tgctcctcag ctgcttgccc 240
gccctcaggg gcacgacgtt atcagtagcc tcggtccgtg aagcagggaa acgcgagccc 300
ttccacggct acgacctcaa ctccgatccg aataccacac accgatcgca acaacacatg 360
ttttccgttg atcgctagac gatgccaccg cccaggttat cttcagcttc gattccatgt 420
gtctgcgctg catgatgaaa aggttggggg gcctgcccgc ctggatccgt ttccgtgcat 480
gattagatgc agtgcagtgc aggccctgaa acttgctgct ttcttctcgc aattcgtcac 540
aggcacaggc ggccggccgg ccgcagtccg cttgtcgcct tgcccagcag agatgccacg 600
ggctgaccgg cgcggggatg gggaaggggc cggacggggg aacgggcccc cgatgacaag 660
cctcctgcag tcctgtcgat atgatgtgga gcaaaccagg acaggcgcca gcagatgagc 720
gcagagtggg cactctcttt gtgtgtgtgt gtgtggtcgt ggcatcttgc cgtcttgcat 780
ggatccatca tggtcggtgg ctggaccgtc ggagggcacc gcaccataga tagaggagca 840
ttgcattcac ggtatcacag aagaggctgc ccaggccggt ggtaaagcta ggtgacgagg 900
aaaatgttgc atggacaagt gctgcagaca tagagtcgtc ctcttacact cggcactttc 960
ggtgcaggtg ctgaggtgtt gacccggcga gaacgagcga gcgagggccc tcccccgacg 1020
cgtgcaagcg atcgagaaat aaacctgaat cgagaacggt tggtgctgct ggtcg 1075

<210> SEQ ID NO 10
<211> LENGTH: 23
<212> TYPE: DNA
<213> ORGANISM: Zea mays

<400> SEQUENCE: 10
atctcagaca ccaaaccgag atc 23

<210> SEQ ID NO 11
<211> LENGTH: 22
<212> TYPE: DNA
<213> ORGANISM: Agrobacterium tumefaciens

<400> SEQUENCE: 11
acaccgttag gctagtgcca gt 22

<210> SEQ ID NO 12
<211> LENGTH: 26
<212> TYPE: DNA

<213> ORGANISM: Artificial Sequence
<220> FEATURE:
<223> OTHER INFORMATION: Derived from Zea mays, Agrobacterium tumefaciens

<400> SEQUENCE: 12
caagtgacag cgaacggagc tggttt 26

<210> SEQ ID NO 13
<211> LENGTH: 73
<212> TYPE: DNA
<213> ORGANISM: Artificial Sequence
<220> FEATURE:
<223> OTHER INFORMATION: Derived from Zea mays, Agrobacterium tumefaciens

<400> SEQUENCE: 13
atctcagaca ccaaaccgag atccaagtga cagcgaacgg agctggttta aactggcact 60
agcctaacgg tgt 73

<210> SEQ ID NO 14
<211> LENGTH: 19
<212> TYPE: DNA
<213> ORGANISM: Zea mays

<400> SEQUENCE: 14
tccggacggt agctagagg 19

<210> SEQ ID NO 15
<211> LENGTH: 20
<212> TYPE: DNA
<213> ORGANISM: Zea mays

<400> SEQUENCE: 15
cgtttatttc tcggtcggcg 20

<210> SEQ ID NO 16
<211> LENGTH: 21
<212> TYPE: DNA
<213> ORGANISM: Zea mays

<400> SEQUENCE: 16
ttacgtcgcg gagagatgga t 21

<210> SEQ ID NO 17
<211> LENGTH: 27
<212> TYPE: DNA
<213> ORGANISM: Artificial Sequence
<220> FEATURE:
<223> OTHER INFORMATION: Derived from Cestrum Yellow Leaf Curl Virus

<400> SEQUENCE: 17
gtgagtggac atttcccaaa ctaccct 27

<210> SEQ ID NO 18
<211> LENGTH: 21
<212> TYPE: DNA
<213> ORGANISM: Artificial Sequence
<220> FEATURE:
<223> OTHER INFORMATION: Derived from Streptomyces viridochromogenes

<400> SEQUENCE: 18
caaggccagt taggccagtt a 21

<210> SEQ ID NO 19
<211> LENGTH: 19
<212> TYPE: DNA
<213> ORGANISM: Zea mays

<400> SEQUENCE: 19
gacatggaca tgcatgggt 19

<210> SEQ ID NO 20
<211> LENGTH: 25
<212> TYPE: DNA
<213> ORGANISM: Zea mays

<400> SEQUENCE: 20
ccacacacac acacacaaag agagt 25

<210> SEQ ID NO 21
<211> LENGTH: 22
<212> TYPE: DNA
<213> ORGANISM: Zea mays

<400> SEQUENCE: 21
gtggcatcgt ctagcgatca ac 22

<210> SEQ ID NO 22
<211> LENGTH: 22
<212> TYPE: DNA
<213> ORGANISM: Artificial Sequence
<220> FEATURE:
<223> OTHER INFORMATION: Derived from Agrobacterium tumefaciens

<400> SEQUENCE: 22
gtaggccgct tccctaatta gc 22

<210> SEQ ID NO 23
<211> LENGTH: 22
<212> TYPE: DNA
<213> ORGANISM: Artificial Sequence
<220> FEATURE:
<223> OTHER INFORMATION: Derived from Bacillus thuringiensis

<400> SEQUENCE: 23
cgctgatgcc cttctggatc ac 22

<210> SEQ ID NO 24
<211> LENGTH: 28
<212> TYPE: DNA
<213> ORGANISM: Artificial Sequence
<220> FEATURE:
<223> OTHER INFORMATION: Derived from Cestrum Yellow Leaf Curl Virus

<400> SEQUENCE: 24
gtagtttggg aaatgtccac tcacccgt 28

<210> SEQ ID NO 25
<211> LENGTH: 25
<212> TYPE: DNA
<213> ORGANISM: Artificial Sequence
<220> FEATURE:
<223> OTHER INFORMATION: Derived from Agrobacterium tumefaciens

<400> SEQUENCE: 25
accggcaaca ggattcaatc ttaag 25

<210> SEQ ID NO 26

<211> LENGTH: 20
<212> TYPE: DNA
<213> ORGANISM: Artificial Sequence
<220> FEATURE:
<223> OTHER INFORMATION: Derived from Bacillus thuringiensis

<400> SEQUENCE: 26
accagatcgg cctgaagacc 20

<210> SEQ ID NO 27
<211> LENGTH: 26
<212> TYPE: DNA
<213> ORGANISM: Artificial Sequence
<220> FEATURE:
<223> OTHER INFORMATION: Derived from Zea mays

<400> SEQUENCE: 27
cagaagtaga actaccgggc cctaac 26

<210> SEQ ID NO 28
<211> LENGTH: 19
<212> TYPE: DNA
<213> ORGANISM: Artificial Sequence
<220> FEATURE:
<223> OTHER INFORMATION: Derived from Zea mays

<400> SEQUENCE: 28
ggattccttt cccaccgct 19

<210> SEQ ID NO 29
<211> LENGTH: 21
<212> TYPE: DNA
<213> ORGANISM: Artificial Sequence
<220> FEATURE:
<223> OTHER INFORMATION: Derived from Bacillus thuringiensis

<400> SEQUENCE: 29
gctgggccag atggtgttca g 21

<210> SEQ ID NO 30
<211> LENGTH: 25
<212> TYPE: DNA
<213> ORGANISM: Artificial Sequence
<220> FEATURE:
<223> OTHER INFORMATION: Derived from Zea mays

<400> SEQUENCE: 30
gccctgcctt catacgctat ttatt 25

<210> SEQ ID NO 31
<211> LENGTH: 25
<212> TYPE: DNA
<213> ORGANISM: Artificial Sequence
<220> FEATURE:
<223> OTHER INFORMATION: Derived from Agrobacterium tumefaciens

<400> SEQUENCE: 31
accggcaaca ggattcaatc ttaag 25

<210> SEQ ID NO 32
<211> LENGTH: 23
<212> TYPE: DNA
<213> ORGANISM: Artificial Sequence
<220> FEATURE:
<223> OTHER INFORMATION: Derived from Bacillus thuringiensis

<400> SEQUENCE: 32

```
cagcaccagc cagatcacct tca                                            23


<210> SEQ ID NO 33
<211> LENGTH: 23
<212> TYPE: DNA
<213> ORGANISM: Artificial Sequence
<220> FEATURE:
<223> OTHER INFORMATION: Derived from Streptomyces viridochromogenes

<400> SEQUENCE: 33

ccacaacacc ctcaacctca gca                                            23


<210> SEQ ID NO 34
<211> LENGTH: 27
<212> TYPE: DNA
<213> ORGANISM: Artificial Sequence
<220> FEATURE:
<223> OTHER INFORMATION: Derived from Streptomyces viridochromogenes

<400> SEQUENCE: 34

acagtgaact ttaggacaga gccacaa                                        27


<210> SEQ ID NO 35
<211> LENGTH: 18
<212> TYPE: DNA
<213> ORGANISM: Artificial Sequence
<220> FEATURE:
<223> OTHER INFORMATION: Derived from Agrobacterium tumefaciens

<400> SEQUENCE: 35

cacattgcgg atacggcc                                                  18


<210> SEQ ID NO 36
<211> LENGTH: 19
<212> TYPE: DNA
<213> ORGANISM: Zea mays

<400> SEQUENCE: 36

gacatggaca tgcatgggt                                                 19


<210> SEQ ID NO 37
<211> LENGTH: 26
<212> TYPE: DNA
<213> ORGANISM: Artificial Sequence
<220> FEATURE:
<223> OTHER INFORMATION: Derived from Cauliflower Mosaic Virus

<400> SEQUENCE: 37

gacgtaaggg atgacgcaca atccca                                         26


<210> SEQ ID NO 38
<211> LENGTH: 20
<212> TYPE: DNA
<213> ORGANISM: Zea mays

<400> SEQUENCE: 38

ctggcgtggc agtggcactg                                                20


<210> SEQ ID NO 39
<211> LENGTH: 21
<212> TYPE: DNA
<213> ORGANISM: Artificial Sequence
<220> FEATURE:
<223> OTHER INFORMATION: Derived  from Bacillus thuringiensis
```

<400> SEQUENCE: 39
tgtcggccgt catggtggat c 21

<210> SEQ ID NO 40
<211> LENGTH: 23
<212> TYPE: DNA
<213> ORGANISM: Artificial Sequence
<220> FEATURE:
<223> OTHER INFORMATION: Derived from Zea mays

<400> SEQUENCE: 40
tctttgggga atcctgggat ggc 23

<210> SEQ ID NO 41
<211> LENGTH: 20
<212> TYPE: DNA
<213> ORGANISM: Zea mays

<400> SEQUENCE: 41
catggttcct tgtcggcgcg 20

<210> SEQ ID NO 42
<211> LENGTH: 29
<212> TYPE: DNA
<213> ORGANISM: Artificial Sequence
<220> FEATURE:
<223> OTHER INFORMATION: Derived from Agrobacterium tumefaciens

<400> SEQUENCE: 42
gtacgtttgg tgcacgtacc gatttggcc 29

<210> SEQ ID NO 43
<211> LENGTH: 28
<212> TYPE: DNA
<213> ORGANISM: Artificial Sequence
<220> FEATURE:
<223> OTHER INFORMATION: Derived from Agrobacterium tumefaciens

<400> SEQUENCE: 43
cgtgactccc ttaattctcc gctcaatg 28

<210> SEQ ID NO 44
<211> LENGTH: 30
<212> TYPE: DNA
<213> ORGANISM: Artificial Sequence
<220> FEATURE:
<223> OTHER INFORMATION: Derived from Agrobacterium tumefaciens

<400> SEQUENCE: 44
tgagatgggt ttttatgatt agagtcccgc 30

<210> SEQ ID NO 45
<211> LENGTH: 21
<212> TYPE: DNA
<213> ORGANISM: Zea mays

<400> SEQUENCE: 45
cgaccagcag caccaaccgt t 21

<210> SEQ ID NO 46
<211> LENGTH: 19
<212> TYPE: DNA
<213> ORGANISM: Artificial Sequence
<220> FEATURE:
<223> OTHER INFORMATION: Derived from Agrobacterium tumefaciens

<400> SEQUENCE: 46
gggggtcata acgtgactc 19

<210> SEQ ID NO 47
<211> LENGTH: 24
<212> TYPE: DNA
<213> ORGANISM: Artificial Sequence
<220> FEATURE:
<223> OTHER INFORMATION: Derived from Agrobacterium tumefaciens

<400> SEQUENCE: 47
gggggtcata acgtgactcc ctta 24

<210> SEQ ID NO 48
<211> LENGTH: 20
<212> TYPE: DNA
<213> ORGANISM: Artificial Sequence
<220> FEATURE:
<223> OTHER INFORMATION: Derived from Agrobacterium tumefaciens

<400> SEQUENCE: 48
ctcccttaat tctccgctca 20

<210> SEQ ID NO 49
<211> LENGTH: 19
<212> TYPE: DNA
<213> ORGANISM: Artificial Sequence
<220> FEATURE:
<223> OTHER INFORMATION: Derived from Agrobacterium tumefaciens

<400> SEQUENCE: 49
aattctccgc tcaatgacc 19

<210> SEQ ID NO 50
<211> LENGTH: 25
<212> TYPE: DNA
<213> ORGANISM: Artificial Sequence
<220> FEATURE:
<223> OTHER INFORMATION: Derived from Streptomyces viridochromogenes

<400> SEQUENCE: 50
acccagatct gaatagtgat atcgg 25

<210> SEQ ID NO 51
<211> LENGTH: 22
<212> TYPE: DNA
<213> ORGANISM: Artificial Sequence
<220> FEATURE:
<223> OTHER INFORMATION: Derived from Agrobacterium tumefaciens

<400> SEQUENCE: 51
ccgcaattat acatttaata cg 22

<210> SEQ ID NO 52
<211> LENGTH: 20
<212> TYPE: DNA
<213> ORGANISM: Artificial Sequence
<220> FEATURE:
<223> OTHER INFORMATION: Derived from Agrobacterium tumefaciens

<400> SEQUENCE: 52
gccctgcagg aaatttaccg 20

<210> SEQ ID NO 53

<211> LENGTH: 93
<212> TYPE: DNA
<213> ORGANISM: Artificial Sequence
<220> FEATURE:
<223> OTHER INFORMATION: Derived from Agrobacterium tumefaciens

<400> SEQUENCE: 53

```
tcattgagcg gagaattaag ggagtcacgt tatgaccccc gccgatgacg cgggacaagc     60

cgttttacgt ttggaactga cagaaccgca acg                                 93
```

<210> SEQ ID NO 54
<211> LENGTH: 397
<212> TYPE: DNA
<213> ORGANISM: Artificial Sequence
<220> FEATURE:
<223> OTHER INFORMATION: Derived from Cestrum Yellow Leaf Curl Virus

<400> SEQUENCE: 54

```
tggcagacaa agtggcagac atactgtccc acaaatgaag atggaatctg taaaagaaaa     60

cgcgtgaaat aatgcgtctg acaaaggtta ggtcggctgc ctttaatcaa taccaaagtg    120

gtccctacca cgatggaaaa actgtgcagt cggtttggct ttttctgacg aacaaataag    180

attcgtggcc gacaggtggg ggtccaccat gtgaaggcat cttcagactc caataatgga    240

gcaatgacgt aagggcttac gaaataagta agggtagttt gggaaatgtc cactcacccg    300

tcagtctata aatacttagc cctccctca ttgttaaggg agcaaaatct cagagagata     360

gtcctagaga gagaaagaga gcaagtagcc tagaagt                             397
```

<210> SEQ ID NO 55
<211> LENGTH: 1962
<212> TYPE: DNA
<213> ORGANISM: Artificial Sequence
<220> FEATURE:
<223> OTHER INFORMATION: Derived from Bacillus thuringiensis

<400> SEQUENCE: 55

```
atgactagta acggccgcca gtgtgctggt attcgccctt atgacggccg acaacaacac     60

cgaggcctgg acagcagcac caccaaggac gtgatccaga agggcatcag cgtggtgggc    120

gacctgctgg gcgtggtggg cttccccttc ggcggcgccc tggtgagctt ctacaccaac    180

ttcctgaaca ccatctggcc cagcgaggac ccctggaagg ccttcatgga gcaggtggag    240

gccctgatgg accagaagat cgccgactac gccaagaaca aggcactggc cgagctacag    300

ggcctccaga acaacgtgga ggactatgtg agcgccctga gcagctggca gaagaacccc    360

gctgcaccgt tccgcaaccc ccacagccag ggccgcatcc gcgagctgtt cagccaggcc    420

gagagccact tccgcaacag catgcccagc ttcgccatca gcggctacga ggtgctgttc    480

ctgaccacct acgcccaggc cgccaacacc cacctgttcc tgctgaagga cgcccaaatc    540

tacggagagg agtggggcta cgagaaggag gacatcgccg agttctacaa gcgccagctg    600

aagctgaccc aggagtacac cgaccactgc gtgaagtggt acaacgtggg tctagacaag    660

ctccgcggca gcagctacga gagctgggtg aacttcaacc gctaccgccg cgagatgacc    720

ctgaccgtgc tggacctgat cgccctgttc ccctgtacg acgtgcgcct gtaccccaag     780

gaggtgaaga ccgagctgac ccgcgacgtg ctgaccgacc ccatcgtggg cgtgaacaac    840

ctgcgcggct acggcaccac cttcagcaac atcgagaact acatccgcaa gccccacctg    900

ttcgactacc tgcaccgcat ccagttccac acgcgtttcc agcccggcta ctacggcaac    960

gacagcttca actactggag cggcaactac gtgagcaccc gccccagcat cggcagcaac   1020
```

```
gacatcatca ccagcccctt ctacggcaac aagagcagcg agcccgtgca gaaccttgag   1080

ttcaacggcg agaaggtgta ccgcgccgtg gctaacacca acctggccgt gtggccctct   1140

gcagtgtaca gcggcgtgac caaggtggag ttcagccagt acaacgacca gaccgacgag   1200

gccagcaccc agacctacga cagcaagcgc aacgtgggcg ccgtgagctg ggacagcatc   1260

gaccagctgc cccccgagac caccgacgag cccctggaga agggctacag ccaccagctg   1320

aactacgtga tgtgcttcct gatgcagggc agccgcggca ccatccccgt gctgacctgg   1380

acccacaaga gcgtcgactt cttcaacatg atcgacagca agaagatcac ccagctgccc   1440

ctgaccaaga gcaccaacct gggcagcggc accagcgtgg tgaagggccc cggcttcacc   1500

ggcggcgaca tcctgcgccg caccagcccc ggccagatca gcaccctgcg cgtgaacatc   1560

accgcccccc tgagccagcg ctaccgcgtc cgcatccgct acgccagcac caccaacctg   1620

cagttccaca ccagcatcga cggccgcccc atcaaccagg gcaacttcag cgccaccatg   1680

agcagcggca gcaacctgca gagcggcagc ttccgcaccg tgggcttcac cacccccttc   1740

aacttcagca acggcagcag cgtgttcacc ctgagcgccc acgtgttcaa cagcggcaac   1800

gaggtgtaca tcgaccgcat cgagttcgtg cccgccgagg tgaccttcga ggccgagtac   1860

gacctggaga gggctcagaa ggccgtgaac gagctgttca ccagcagcaa ccagatcggc   1920

ctgaagaccg acgtgaccga ctaccacatc gatcaggtgt ag                      1962
```

<210> SEQ ID NO 56
<211> LENGTH: 253
<212> TYPE: DNA
<213> ORGANISM: Artificial Sequence
<220> FEATURE:
<223> OTHER INFORMATION: Derived from Agrobacterium tumefaciens

<400> SEQUENCE: 56

```
gatcgttcaa acatttggca ataaagtttc ttaagattga atcctgttgc cggtcttgcg     60

atgattatca tataatttct gttgaattac gttaagcatg taataattaa catgtaatgc    120

atgacgttat ttatgagatg ggtttttatg attagagtcc cgcaattata catttaatac    180

gcgatagaaa acaaaatata gcgcgcaaac taggataaat tatcgcgcgc ggtgtcatct    240

atgttactag atc                                                       253
```

<210> SEQ ID NO 57
<211> LENGTH: 1993
<212> TYPE: DNA
<213> ORGANISM: Artificial Sequence
<220> FEATURE:
<223> OTHER INFORMATION: Derived from Zea mays

<400> SEQUENCE: 57

```
ctgcagtgca gcgtgacccg gtcgtgcccc tctctagaga taatgagcat tgcatgtcta     60

agttataaaa aattaccaca tatttttttt gtcacacttg tttgaagtgc agtttatcta    120

tctttataca tatatttaaa ctttactcta cgaataatat aatctatagt actacaataa    180

tatcagtgtt ttagagaatc atataaatga acagttagac atggtctaaa ggacaattga    240

gtattttgac aacaggactc tacagtttta tctttttagt gtgcatgtgt tctccttttt    300

ttttgcaaat agcttcacct atataatact tcatccattt tattagtaca tccatttagg    360

gtttagggtt aatggttttt atagactaat ttttttagta catctatttt attctatttt    420

agcctctaaa ttaagaaaac taaaactcta ttttagtttt tttatttaat aatttagata    480
```

```
taaaatagaa taaaataaag tgactaaaaa ttaaacaaat accctttaag aaattaaaaa    540

aactaaggaa acatttttct tgtttcgagt agataatgcc agcctgttaa acgccgccga    600

cgagtctaac ggacaccaac cagcgaacca gcagcgtcgc gtcgggccaa gcgaagcaga    660

cggcacggca tctctgtcgc tgcctctgga cccctctcga gagttccgct ccaccgttgg    720

acttgctccg ctgtcggcat ccagaaattg cgtggcggag cggcagacgt gagccggcac    780

ggcaggcggc ctcctcctcc tctcacggca ccggcagcta cgggggattc ctttcccacc    840

gctccttcgc tttcccttcc tcgcccgccg taataaatag acacccctc cacaccctct     900

ttccccaacc tcgtgttgtt cggagcgcac acacacacaa ccagatctcc cccaaatcca    960

cccgtcggca cctccgcttc aaggtacgcc gctcgtcctc cccccccccc cctctctacc   1020

ttctctagat cggcgttccg gtccatagtt agggcccggt agttctactt ctgttcatgt   1080

ttgtgttaga tccgtgtttg tgttagatcc gtgctgttag cgttcgtaca cggatgcgac   1140

ctgtacgtca gacacgttct gattgctaac ttgccagtgt ttctctttgg ggaatcctgg   1200

gatggctcta gccgttccgc agacgggatc gatttcatga ttttttttgt ttcgttgcat   1260

agggtttggt ttgccctttt cctttatttc aatatatgcc gtgcacttgt ttgtcgggtc   1320

atcttttcat gctttttttt gtcttggttg tgatgatgtg gtctggttgg gcggtcgttc   1380

tagatcggag tagaattctg tttcaaacta cctggtggat ttattaattt tggatctgta   1440

tgtgtgtgcc atacatattc atagttacga attgaagatg atggatggaa atatcgatct   1500

aggataggta tacatgttga tgcgggtttt actgatgcat atacagagat gctttttgtt   1560

cgcttggttg tgatgatgtg gtgtggttgg gcggtcgttc attcgttcta gatcggagta   1620

gaatactgtt tcaaactacc tggtgtattt attaattttg gaactgtatg tgtgtgtcat   1680

acatcttcat agttacgagt ttaagatgga tggaaatatc gatctaggat aggtatacat   1740

gttgatgtgg gttttactga tgcatataca tgatggcata tgcagcatct attcatatgc   1800

tctaaccttg agtacctatc tattataata aacaagtatg ttttataatt attttgatct   1860

tgatatactt ggatgatggc atatgcagca gctatatgtg gattttttta gccctgcctt   1920

catacgctat ttatttgctt ggtactgttt cttttgtcga tgctcaccct gttgtttggt   1980

gttacttctg cag                                                      1993
```

<210> SEQ ID NO 58
<211> LENGTH: 1797
<212> TYPE: DNA
<213> ORGANISM: Artificial Sequence
<220> FEATURE:
<223> OTHER INFORMATION: Derived from Bacillus thuringiensis

<400> SEQUENCE: 58

```
atgacggccg acaacaacac cgaggccctg gacagcagca ccaccaagga cgtgatccag     60

aagggcatca gcgtggtggg cgacctgctg ggcgtggtgg gcttcccctt cggcggcgcc    120

ctggtgagct tctacaccaa cttcctgaac accatctggc ccagcgagga cccctggaag    180

gccttcatgg agcaggtgga ggccctgatg gaccagaaga tcgccgacta cgccaagaac    240

aaggcactgg ccgagctaca gggcctccag aacaacgtgg aggactatgt gagcgccctg    300

agcagctggc agaagaaccc cgctgcaccg ttccgcaacc cccacagcca gggccgcatc    360

cgcgagctgt tcagccaggc cgagagccac ttccgcaaca gcatgcccag cttcgccatc    420

agcggctacg aggtgctgtt cctgaccacc tacgcccagg ccgccaacac ccacctgttc    480

ctgctgaagg acgcccaaat ctacggagag gagtggggct acgagaagga ggacatcgcc    540
```

```
gagttctaca agcgccagct gaagctgacc caggagtaca ccgaccactg cgtgaagtgg    600

tacaacgtgg gtctagacaa gctccgcggc agcagctacg agagctgggt gaacttcaac    660

cgctaccgcc gcgagatgac cctgaccgtg ctggacctga tcgccctgtt cccccctgtac   720

gacgtgcgcc tgtaccccaa ggaggtgaag accgagctga cccgcgacgt gctgaccgac    780

cccatcgtgg gcgtgaacaa cctgcgcggc tacggcacca ccttcagcaa catcgagaac    840

tacatccgca agccccacct gttcgactac ctgcaccgca tccagttcca cacgcgtttc    900

cagcccggct actacggcaa cgacagcttc aactactgga gcggcaacta cgtgagcacc    960

cgccccagca tcggcagcaa cgacatcatc accagcccct tctacggcaa caagagcagc   1020

gagcccgtgc agaaccttga gttcaacggc gagaaggtgt accgcgccgt ggctaacacc   1080

aacctggccg tgtggccctc tgcagtgtac agcggcgtga ccaaggtgga gttcagccag   1140

tacaacgacc agaccgacga ggccagcacc cagacctacg acagcaagcg caacgtgggc   1200

gccgtgagct gggacagcat cgaccagctg ccccccgaga ccaccgacga gcccctggag   1260

aagggctaca gccaccagct gaactacgtg atgtgcttcc tgatgcaggg cagccgcggc   1320

accatccccg tgctgacctg gacccacaag agcgtcgact tcttcaacat gatcgacagc   1380

aagaagatca cccagctgcc cctggtgaag gcctacaagc tccagagcgg cgccagcgtg   1440

gtggcaggcc cccgcttcac cggcggcgac atcatccagt gcaccgagaa cggcagcgcc   1500

gccaccatct acgtgacccc cgacgtgagc tacagccaga agtaccgcgc ccgcatccac   1560

tacgccagca ccagccagat caccttcacc ctgagcctgg acggggcccc cttcaaccaa   1620

tactacttcg acaagaccat caacaagggc gacaccctga cctacaacag cttcaacctg   1680

gccagcttca gcaccccttt cgagctgagc ggcaacaacc tccagatcgg cgtgaccggc   1740

ctgagcgccg gcgacaaggt gtacatcgac aagatcgagt tcatccccgt gaactag      1797
```

<210> SEQ ID NO 59
<211> LENGTH: 277
<212> TYPE: DNA
<213> ORGANISM: Artificial Sequence
<220> FEATURE:
<223> OTHER INFORMATION: Derived from Agrobacterium tumefaciens

<400> SEQUENCE: 59

```
ttgacgacct gctaagatcg ttcaaacatt tggcaataaa gtttcttaag attgaatcct     60

gttgccggtc ttgcgatgat tatcaatata atttctgttg aattacgtta agcatgtaat    120

aattaacatg taatgcatga cgttatttat gagatgggtt tttatgatta gagtcccgca    180

attatacatt taatacgcga tagaaaacaa aatatagcgc gcaaactagg ataaattatc    240

gcgcgcggtg tcatctattg ttactagatc taattga                              277
```

<210> SEQ ID NO 60
<211> LENGTH: 521
<212> TYPE: DNA
<213> ORGANISM: Artificial Sequence
<220> FEATURE:
<223> OTHER INFORMATION: Derived from Cauliflower Mosaic Virus

<400> SEQUENCE: 60

```
agtcaaagat tcaaatagag gacctaacag aactcgccgt aaagactggc gaacagttca     60

tacagagtct cttacgactc aatgacaaga agaaaatctt cgtcaacatg gtggagcacg    120

acacgcttgt ctactccaaa aatatcaaag atacagtctc agaagaccaa agggcaattg    180
```

```
agacttttca acaaagggta atatccggaa acctcctcgg attccattgc ccagctatct    240

gtcactttat tgtgaagata gtggaaaagg aaggtggctc ctacaaatgc catcattgcg    300

ataaaggaaa ggccatcgtt gaagatgcct ctgccgacag tggtcccaaa gatggacccc    360

cacccacgag gagcatcgtg gaaaaagaag acgttccaac cacgtcttca aagcaagtgg    420

attgatgtga tatctccact gacgtaaggg atgacgcaca atcccactat ccttcgcaag    480

acccttcctc tatataagga agttcatttc atttggagag g                        521


<210> SEQ ID NO 61
<211> LENGTH: 552
<212> TYPE: DNA
<213> ORGANISM: Artificial Sequence
<220> FEATURE:
<223> OTHER INFORMATION: Derived from Streptomyces viridochromogenes

<400> SEQUENCE: 61

atgtctccgg agaggagacc agttgagatt aggccagcta cagcagctga tatggccgcg     60

gtttgtgata tcgttaacca ttacattgag acgtctacag tgaactttag gacagagcca    120

caaacaccac aagagtggat tgatgatcta gagaggttgc aagatagata cccttggttg    180

gttgctgagg ttgagggtgt tgtggctggt attgcttacg ctgggccctg gaaggctagg    240

aacgcttacg attggacagt tgagagtact gtttacgtgt cacataggca tcaaaggttg    300

ggcctaggat ccacattgta cacacatttg cttaagtcta tggaggcgca aggttttaag    360

tctgtggttg ctgttatagg ccttccaaac gatccatctg ttaggttgca tgaggctttg    420

ggatacacag cgcggggtac attgcgcgca gctggataca agcatggtgg atggcatgat    480

gttggttttt ggcaaaggga ttttgagttg ccagctcctc caaggccagt taggccagtt    540

acccagatct ga                                                        552


<210> SEQ ID NO 62
<211> LENGTH: 2740
<212> TYPE: DNA
<213> ORGANISM: Artificial Sequence
<220> FEATURE:
<223> OTHER INFORMATION: Derived from Cestrum Yellow Leaf Curl Virus,
      Bacillus thuringiensis, and Agrobacterium tumefaciens

<400> SEQUENCE: 62

tcattgagcg gagaattaag ggagtcacgt tatgaccccc gccgatgacg cgggacaagc     60

cgttttacgt ttggaactga cagaaccgca acgaatattg gcagacaaag tggcagacat    120

actgtcccac aaatgaagat ggaatctgta aaagaaaacg cgtgaaataa tgcgtctgac    180

aaaggttagg tcggctgcct ttaatcaata ccaaagtggt ccctaccacg atggaaaaac    240

tgtgcagtcg gtttggcttt ttctgacgaa caaataagat tcgtggccga caggtggggg    300

tccaccatgt gaaggcatct tcagactcca ataatggagc aatgacgtaa gggcttacga    360

aataagtaag ggtagtttgg gaaatgtcca ctcacccgtc agtctataaa tacttagccc    420

ctccctcatt gttaagggag caaaatctca gagagatagt cctagagaga gaaagagagc    480

aagtagccta gaagtggatc caccatgact agtaacggcc gccagtgtgc tggtattcgc    540

ccttatgacg gccgacaaca acaccgaggc ctggacagca gcaccaccaa ggacgtgatc    600

cagaagggca tcagcgtggt gggcgacctg ctgggcgtgg tgggcttccc cttcggcggc    660

gccctggtga gcttctacac caacttcctg aacaccatct ggcccagcga ggacccctgg    720

aaggccttca tggagcaggt ggaggccctg atggaccaga agatcgccga ctacgccaag    780
```

```
aacaaggcac tggccgagct acagggcctc cagaacaacg tggaggacta tgtgagcgcc    840

ctgagcagct ggcagaagaa ccccgctgca ccgttccgca acccccacag ccagggccgc    900

atccgcgagc tgttcagcca ggccgagagc cacttccgca acagcatgcc cagcttcgcc    960

atcagcggct acgaggtgct gttcctgacc acctacgccc aggccgccaa cacccacctg   1020

ttcctgctga aggacgccca aatctacgga gaggagtggg gctacgagaa ggaggacatc   1080

gccgagttct acaagcgcca gctgaagctg acccaggagt acaccgacca ctgcgtgaag   1140

tggtacaacg tgggtctaga caagctccgc ggcagcagct acgagagctg ggtgaacttc   1200

aaccgctacc gccgcgagat gaccctgacc gtgctggacc tgatcgccct gttcccccctg   1260

tacgacgtgc gcctgtaccc caaggaggtg aagaccgagc tgacccgcga cgtgctgacc   1320

gaccccatcg tgggcgtgaa caacctgcgc ggctacggca ccaccttcag caacatcgag   1380

aactacatcc gcaagcccca cctgttcgac tacctgcacc gcatccagtt ccacacgcgt   1440

ttccagcccg gctactacgg caacgacagc ttcaactact ggagcggcaa ctacgtgagc   1500

acccgcccca gcatcggcag caacgacatc atcaccagcc ccttctacgg caacaagagc   1560

agcgagcccg tgcagaacct tgagttcaac ggcgagaagg tgtaccgcgc cgtggctaac   1620

accaacctgg ccgtgtggcc ctctgcagtg tacagcggcg tgaccaaggt ggagttcagc   1680

cagtacaacg accagaccga cgaggccagc acccagacct acgacagcaa gcgcaacgtg   1740

ggcgccgtga gctgggacag catcgaccag ctgcccccccg agaccaccga cgagcccctg   1800

gagaagggct acagccacca gctgaactac gtgatgtgct tcctgatgca gggcagccgc   1860

ggcaccatcc ccgtgctgac ctggacccac aagagcgtcg acttcttcaa catgatcgac   1920

agcaagaaga tcacccagct gcccctgacc aagagcacca acctgggcag cggcaccagc   1980

gtggtgaagg gccccggctt caccggcggc gacatcctgc gccgcaccag ccccggccag   2040

atcagcaccc tgcgcgtgaa catcaccgcc cccctgagcc agcgctaccg cgtccgcatc   2100

cgctacgcca gcaccaccaa cctgcagttc cacaccagca tcgacggccg ccccatcaac   2160

cagggcaact tcagcgccac catgagcagc ggcagcaacc tgcagagcgg cagcttccgc   2220

accgtgggct tcaccacccc cttcaacttc agcaacggca gcagcgtgtt caccctgagc   2280

gcccacgtgt tcaacagcgg caacgaggtg tacatcgacc gcatcgagtt cgtgcccgcc   2340

gaggtgacct tcgaggccga gtacgacctg gagagggctc agaaggccgt gaacgagctg   2400

ttcaccagca gcaaccagat cggcctgaag accgacgtga ccgactacca catcgatcag   2460

gtgtaggagc tgagctcttc atatgacgat cgttcaaaca tttggcaata aagtttctta   2520

agattgaatc ctgttgccgg tcttgcgatg attatcatat aatttctgtt gaattacgtt   2580

aagcatgtaa taattaacat gtaatgcatg acgttattta tgagatgggt ttttatgatt   2640

agagtcccgc aattatacat ttaatacgcg atagaaaaca aaatatagcg cgcaaactag   2700

gataaattat cgcgcgcggt gtcatctatg ttactagatc                         2740
```

<210> SEQ ID NO 63
<211> LENGTH: 4095
<212> TYPE: DNA
<213> ORGANISM: Artificial Sequence
<220> FEATURE:
<223> OTHER INFORMATION: Derived from Zea mays, Bacillus thuringiensis, and Agrobacterium tumefaciens

<400> SEQUENCE: 63

```
ctgcagtgca gcgtgacccg gtcgtgcccc tctctagaga taatgagcat tgcatgtcta     60
```

```
agttataaaa aattaccaca tattttttt gtcacacttg tttgaagtgc agtttatcta     120
tctttataca tatatttaaa ctttactcta cgaataatat aatctatagt actacaataa    180
tatcagtgtt ttagagaatc atataaatga acagttagac atggtctaaa ggacaattga    240
gtattttgac aacaggactc tacagtttta tctttttagt gtgcatgtgt tctccttttt    300
ttttgcaaat agcttcacct atataatact tcatccattt tattagtaca tccatttagg    360
gtttagggtt aatggttttt atagactaat ttttttagta catctatttt attctatttt    420
agcctctaaa ttaagaaaac taaaactcta ttttagtttt tttatttaat aatttagata    480
taaaatagaa taaaataaag tgactaaaaa ttaaacaaat accctttaag aaattaaaaa    540
aactaaggaa acatttttct tgtttcgagt agataatgcc agcctgttaa acgccgccga    600
cgagtctaac ggacaccaac cagcgaacca gcagcgtcgc gtcgggccaa gcgaagcaga    660
cggcacggca tctctgtcgc tgcctctgga cccctctcga gagttccgct ccaccgttgg    720
acttgctccg ctgtcggcat ccagaaattg cgtggcggag cggcagacgt gagccggcac    780
ggcaggcggc ctcctcctcc tctcacggca ccggcagcta cgggggattc ctttcccacc    840
gctccttcgc tttcccttcc tcgcccgccg taataaatag acacccccctc cacaccctct    900
ttccccaacc tcgtgttgtt cggagcgcac acacacacaa ccagatctcc cccaaatcca    960
cccgtcggca cctccgcttc aaggtacgcc gctcgtcctc cccccccccc cctctctacc   1020
ttctctagat cggcgttccg gtccatagtt agggcccggt agttctactt ctgttcatgt   1080
ttgtgttaga tccgtgtttg tgttagatcc gtgctgttag cgttcgtaca cggatgcgac   1140
ctgtacgtca gacacgttct gattgctaac ttgccagtgt ttctctttgg ggaatcctgg   1200
gatggctcta gccgttccgc agacgggatc gatttcatga ttttttttgt ttcgttgcat   1260
agggtttggt ttgccctttt cctttatttc aatatatgcc gtgcacttgt ttgtcgggtc   1320
atcttttcat gctttttttt gtcttggttg tgatgatgtg gtctggttgg gcggtcgttc   1380
tagatcggag tagaattctg tttcaaacta cctggtggat ttattaattt tggatctgta   1440
tgtgtgtgcc atacatattc atagttacga attgaagatg atggatggaa atatcgatct   1500
aggataggta tacatgttga tgcgggtttt actgatgcat atacagagat gctttttgtt   1560
cgcttggttg tgatgatgtg gtgtggttgg gcggtcgttc attcgttcta gatcggagta   1620
gaatactgtt tcaaactacc tggtgtattt attaattttg gaactgtatg tgtgtgtcat   1680
acatcttcat agttacgagt ttaagatgga tggaaatatc gatctaggat aggtatacat   1740
gttgatgtgg gttttactga tgcatataca tgatggcata tgcagcatct attcatatgc   1800
tctaaccttg agtacctatc tattataata aacaagtatg ttttataatt attttgatct   1860
tgatatactt ggatgatggc atatgcagca gctatatgtg gattttttta gccctgcctt   1920
catacgctat ttatttgctt ggtactgttt cttttgtcga tgctcaccct gttgtttggt   1980
gttacttctg cagggatcca ccatgacggc cgacaacaac accgaggccc tggacagcag   2040
caccaccaag gacgtgatcc agaagggcat cagcgtggtg ggcgacctgc tgggcgtggt   2100
gggcttcccc ttcggcggcg ccctggtgag cttctacacc aacttcctga acaccatctg   2160
gcccagcgag gacccctgga aggccttcat ggagcaggtg gaggccctga tggaccagaa   2220
gatcgccgac tacgccaaga acaaggcact ggccgagcta cagggcctcc agaacaacgt   2280
ggaggactat gtgagcgccc tgagcagctg gcagaagaac cccgctgcac cgttccgcaa   2340
cccccacagc cagggccgca tccgcgagct gttcagccag gccgagagcc acttccgcaa   2400
cagcatgccc agcttcgcca tcagcggcta cgaggtgctg ttcctgacca cctacgccca   2460
```

ggccgccaac acccacctgt tcctgctgaa ggacgcccaa atctacggag aggagtgggg 2520
ctacgagaag gaggacatcg ccgagttcta caagcgccag ctgaagctga cccaggagta 2580
caccgaccac tgcgtgaagt ggtacaacgt gggtctagac aagctccgcg gcagcagcta 2640
cgagagctgg gtgaacttca accgctaccg ccgcgagatg accctgaccg tgctggacct 2700
gatcgccctg ttcccccctgt acgacgtgcg cctgtacccc aaggaggtga agaccgagct 2760
gacccgcgac gtgctgaccg accccatcgt gggcgtgaac aacctgcgcg gctacggcac 2820
caccttcagc aacatcgaga actacatccg caagccccac ctgttcgact acctgcaccg 2880
catccagttc cacacgcgtt tccagcccgg ctactacggc aacgacagct tcaactactg 2940
gagcggcaac tacgtgagca cccgccccag catcggcagc aacgacatca tcaccagccc 3000
cttctacggc aacaagagca gcgagcccgt gcagaacctt gagttcaacg gcgagaaggt 3060
gtaccgcgcc gtggctaaca ccaacctggc cgtgtggccc tctgcagtgt acagcggcgt 3120
gaccaaggtg gagttcagcc agtacaacga ccagaccgac gaggccagca cccagaccta 3180
cgacagcaag cgcaacgtgg gcgccgtgag ctgggacagc atcgaccagc tgccccccga 3240
gaccaccgac gagcccctgg agaagggcta cagccaccag ctgaactacg tgatgtgctt 3300
cctgatgcag ggcagccgcg gcaccatccc cgtgctgacc tggacccaca agagcgtcga 3360
cttcttcaac atgatcgaca gcaagaagat cacccagctg cccctggtga aggcctacaa 3420
gctccagagc ggcgccagcg tggtggcagg cccccgcttc accggcggcg acatcatcca 3480
gtgcaccgag aacggcagcg ccgccaccat ctacgtgacc cccgacgtga gctacagcca 3540
gaagtaccgc gcccgcatcc actacgccag caccagccag atcaccttca ccctgagcct 3600
ggacggggcc cccttcaacc aatactactt cgacaagacc atcaacaagg gcgacaccct 3660
gacctacaac agcttcaacc tggccagctt cagcacccct ttcgagctga gcggcaacaa 3720
cctccagatc ggcgtgaccg gcctgagcgc cggcgacaag gtgtacatcg acaagatcga 3780
gttcatcccc gtgaactaga tctgaggggt accagctctt gacgacctgc taagatcgtt 3840
caaacatttg gcaataaagt ttcttaagat tgaatcctgt tgccggtctt gcgatgatta 3900
tcaatataat ttctgttgaa ttacgttaag catgtaataa ttaacatgta atgcatgacg 3960
ttatttatga gatgggtttt tatgattaga gtcccgcaat tatacattta atacgcgata 4020
gaaaacaaaa tatagcgcgc aaactaggat aaattatcgc gcgcggtgtc atctattgtt 4080
actagatcta attga 4095

<210> SEQ ID NO 64
<211> LENGTH: 1381
<212> TYPE: DNA
<213> ORGANISM: Artificial Sequence
<220> FEATURE:
<223> OTHER INFORMATION: Derived from Cauliflower Mosaic Virus, Streptomyces viridochromogenes, and Agrobacterium tumefaciens

<400> SEQUENCE: 64
agtcaaagat tcaaatagag gacctaacag aactcgccgt aaagactggc gaacagttca 60
tacagagtct cttacgactc aatgacaaga agaaaatctt cgtcaacatg gtggagcacg 120
acacgcttgt ctactccaaa aatatcaaag atacagtctc agaagaccaa agggcaattg 180
agacttttca acaaagggta atatccggaa acctcctcgg attccattgc ccagctatct 240
gtcactttat tgtgaagata gtggaaaagg aaggtggctc ctacaaatgc catcattgcg 300
ataaaggaaa ggccatcgtt gaagatgcct ctgccgacag tggtcccaaa gatggacccc 360
cacccacgag gagcatcgtg gaaaaagaag acgttccaac cacgtcttca aagcaagtgg 420
attgatgtga tatctccact gacgtaaggg atgacgcaca atcccactat ccttcgcaag 480
acccttcctc tatataagga agttcatttc atttggagag gacacgctga aatcactagt 540
ccaccatgtc tccggagagg agaccagttg agattaggcc agctacagca gctgatatgg 600
ccgcggtttg tgatatcgtt aaccattaca ttgagacgtc tacagtgaac tttaggacag 660
agccacaaac accacaagag tggattgatg atctagagag gttgcaagat agataccctt 720
ggttggttgc tgaggttgag ggtgttgtgg ctggtattgc ttacgctggg ccctggaagg 780
ctaggaacgc ttacgattgg acagttgaga gtactgttta cgtgtcacat aggcatcaaa 840
ggttgggcct aggatccaca ttgtacacac atttgcttaa gtctatggag gcgcaaggtt 900
ttaagtctgt ggttgctgtt ataggccttc caaacgatcc atctgttagg ttgcatgagg 960
ctttgggata cacagcgcgg ggtacattgc gcgcagctgg atacaagcat ggtggatggc 1020
atgatgttgg tttttggcaa agggattttg agttgccagc tcctccaagg ccagttaggc 1080
cagttaccca gatctgaata gtgatatcgg cgcctgggtc gacctgcaga tcgttcaaac 1140
atttggcaat aaagtttctt aagattgaat cctgttgccg gtcttgcgat gattatcata 1200
taatttctgt tgaattacgt taagcatgta ataattaaca tgtaatgcat gacgttattt 1260
atgagatggg tttttatgat tagagtcccg caattataca tttaatacgc gatagaaaac 1320
aaaatatagc gcgcaaacta ggataaatta tcgcgcgcgg tgtcatctat gttactagat 1380
c 1381

<210> SEQ ID NO 65
<211> LENGTH: 21
<212> TYPE: DNA
<213> ORGANISM: Zea mays

<400> SEQUENCE: 65
accaaaccga gatccaagtg a 21

<210> SEQ ID NO 66
<211> LENGTH: 16
<212> TYPE: DNA
<213> ORGANISM: Zea mays

<400> SEQUENCE: 66
gcgcgtcgac ctgcac 16

<210> SEQ ID NO 67
<211> LENGTH: 18
<212> TYPE: DNA
<213> ORGANISM: Zea mays

<400> SEQUENCE: 67
gcatggttcc ttgtcggc 18

<210> SEQ ID NO 68
<211> LENGTH: 23
<212> TYPE: DNA
<213> ORGANISM: Zea mays

<400> SEQUENCE: 68
ctagttgtac ctgcccccgc ctg 23

<210> SEQ ID NO 69

<211> LENGTH: 18
<212> TYPE: DNA
<213> ORGANISM: Zea mays

<400> SEQUENCE: 69
aacggagctg cccccgcc 18

<210> SEQ ID NO 70
<211> LENGTH: 172841
<212> TYPE: DNA
<213> ORGANISM: Zea mays
<220> FEATURE:
<221> NAME/KEY: misc_feature
<222> LOCATION: (1424)..(1523)
<223> OTHER INFORMATION: n is a, c, g, or t
<220> FEATURE:
<221> NAME/KEY: misc_feature
<222> LOCATION: (8718)..(8817)
<223> OTHER INFORMATION: n is a, c, g, or t
<220> FEATURE:
<221> NAME/KEY: misc_feature
<222> LOCATION: (9815)..(9914)
<223> OTHER INFORMATION: n is a, c, g, or t
<220> FEATURE:
<221> NAME/KEY: misc_feature
<222> LOCATION: (11286)..(11385)
<223> OTHER INFORMATION: n is a, c, g, or t
<220> FEATURE:
<221> NAME/KEY: misc_feature
<222> LOCATION: (35128)..(35227)
<223> OTHER INFORMATION: n is a, c, g, or t
<220> FEATURE:
<221> NAME/KEY: misc_feature
<222> LOCATION: (89878)..(89977)
<223> OTHER INFORMATION: n is a, c, g, or t
<220> FEATURE:
<221> NAME/KEY: misc_feature
<222> LOCATION: (105187)..(105286)
<223> OTHER INFORMATION: n is a, c, g, or t
<220> FEATURE:
<221> NAME/KEY: misc_feature
<222> LOCATION: (108813)..(108912)
<223> OTHER INFORMATION: n is a, c, g, or t
<220> FEATURE:
<221> NAME/KEY: misc_feature
<222> LOCATION: (119229)..(119328)
<223> OTHER INFORMATION: n is a, c, g, or t
<220> FEATURE:
<221> NAME/KEY: misc_feature
<222> LOCATION: (132486)..(132585)
<223> OTHER INFORMATION: n is a, c, g, or t
<220> FEATURE:
<221> NAME/KEY: misc_feature
<222> LOCATION: (134025)..(134124)
<223> OTHER INFORMATION: n is a, c, g, or t
<220> FEATURE:
<221> NAME/KEY: misc_feature
<222> LOCATION: (144520)..(144619)
<223> OTHER INFORMATION: n is a, c, g, or t
<220> FEATURE:
<221> NAME/KEY: misc_feature
<222> LOCATION: (147090)..(147189)
<223> OTHER INFORMATION: n is a, c, g, or t
<220> FEATURE:
<221> NAME/KEY: misc_feature
<222> LOCATION: (151745)..(151844)
<223> OTHER INFORMATION: n is a, c, g, or t
<220> FEATURE:
<221> NAME/KEY: misc_feature
<222> LOCATION: (169545)..(169644)
<223> OTHER INFORMATION: n is a, c, g, or t
<220> FEATURE:
<221> NAME/KEY: misc_feature
<222> LOCATION: (170871)..(170970)
<223> OTHER INFORMATION: n is a, c, g, or t

<400> SEQUENCE: 70

```
ctctcatgct atggaattgg caggccgttg ggcatgcgct taaagatatg gagactttat     60
atcatgggga acaagtgcca agtataacgg atcataagag tttatattca ctcaggaagg    120
atctcaacct taggcacgcc gttggttgga gcttattaag ggataatgat ttggagattc    180
actatcactg ggcaaggcaa atttggttgc agaagccttt gagtcgaaag gagcatgttc    240
attcagctat tgttgcccag ctacccgatg agattgttga ggatttcagg agacttaacc    300
tggggataga tgctcacgct taaggagtca ttattgatgt ggaacctacc ttggagcaag    360
aaaatccaca gaacgacaga ttggtgatgc caagatacaa gagatcaagg atcttattac    420
gaaaggtaga ggtccggaat ttacggaaga tgaacaagac acaatatggt tcaagggcag    480
gatatgtgtt cctggtattg aaagccttcg taagactatt ctaaaggaag cccataactt    540
ggattattct attcatcctg gtagtaccaa gatgtatcag gaattgaagc agaaatactg    600
gtggtatgga ttgaagagag atgtggctgc acatgtggct atgtgcgatg ggtgtcaaag    660
agttaaggcc taacaccaaa gaccagctgg actattacat ccactgaaga tacccaagtg    720
gaaggggaag aaattggtaa ggacttcatt actggattgc ctcgcacccc gtgtcacacc    780
cggctttaag gaacaaagcc aggtgcatct catacatgcg ccaagaagac aacatatata    840
ataacagagt gtatagagat aaatgtcgta aaacatcaga gtatttatta catagcggaa    900
gacttattaa aaaaataaaa gataaaagta aaacgaacta aggatcgtcg gcgccaatgt    960
caactgagaa acgccaccta gatcagatca tactcctcgc cttgtggctc ctcctgaacc   1020
acctgctctt ctcctgtggg gggggtgtga gacagcaagg gtgagctcac acatgatcat   1080
cgctcaacaa gttgtgggga ataatgtgac atgaactcac caaaggtgag agctcatgga   1140
gtgtaaggct tatcaaagag aatggttaaa gctgagcatt gcttttaagt agttggtcaa   1200
aattttatta gcagttacta agtgtaagta aataccaaac cttaaataaa gtaatagaac   1260
aaaattaata ataaacccat gcatatgcaa atgacaaaat tgaatttaag ttccataatt   1320
taaacatcag agagtcctga gctgctcatg accgtgagct cggctagtat accagtttta   1380
cactaatgca gaggttgtac ccttagacga atctctagat tcgnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnngtttggt tacattaatg cacatacaag taaagccaac   1560
atgatgcact taggttattt aggtgtcttt tgttaattat ttatttgttt aggtgagatg   1620
tccacatgaa atgctacata gggatgacac ccatatatgc gaaggaatat aatctttact   1680
cttaggtttt atttttacaa agtgggtgtt acaaatccta ccccccttaa aaataatctc   1740
gtcctcgaga tttaggaaga acgagggaaa aggtgaggaa aatctatgcg aagctcttct   1800
tctctttccc aagttgcttc atcttcaccg tggtgactcc attggacttt gcacatcttt   1860
accaccttat ttcttgtaac tcgagtcaaa gtatcctaaa tcttgatcgg gtattccgtg   1920
taagttaaat caccctgaac actaagctct tccattggta actgttcctc agggacacgg   1980
agccacttct tgagttgaga tacgtgaaac acattatgca catccgatag actagcaggt   2040
aactcaagtt ggtatgccat ctctccaact ctcctaaaga tcaagaatgg tccaatatag   2100
cgaggggaca atttgccctt aactttgaat ctcctcattc cacgcagtgg tgacaccttg   2160
agatacacat aatctccttc ttcaaattac agtggcctcc ttctattatc agcataactc   2220
ttttgcctgg tttgagccac tctcaaattc tctcgaatta tacggacttg ttcttctgct   2280
tcttgaatca attcaggccc aaagaactgt ctctctccag tctgatccca atacaaagga   2340
```

-continued

```
gtcctgcact tcctcccatg ctgaagggca catgctctca acatatcttc caaaacttga   2400
ttagtccttt cagtctgttc atcagtctga gggtgataag ccgtactaaa attcaacttc   2460
gtgctcatgt tctcatgaaa gcttctccaa aatcttgagg taaactgcga acctcgatca   2520
gacacgatct tctttggtac tccatgtaaa cacacaagcc gagccatata caactctgct   2580
agctgagaac ctttataagt agtcttgaca ggaataaagt gagccacttt agtcaatcta   2640
tccacaatca cccatatagc atcatatcct ttctgggtgc gaggcaatcc agtaatgaaa   2700
tccataccaa tctcttccca cttccactcg ggtatcttca gtgggtgcaa tagtccaact   2760
ggcctctggt gttcagcctt aactctttga catacatcac acatagccac atgtgcagcc   2820
acatctcttt tcaatccata ccaccaatac ttccgcttca aatcctgata catcttagta   2880
ctaccaggat gaatagaata atttgagtca tgggcctcct tcaatatagt ctcacgaagg   2940
ctttcaatat caggaacaca catcttgtcc ttgaaccata cagtgccttg ctcatcttcc   3000
gtaaattcca gaactcgacc ttcagtaatc agatccttaa tctctcgtat tttagcatca   3060
ccaatttgtc ctttacggat ttcttgctcc aaggtaggtt ccacatcaat agtaactcct   3120
tcagtgtgag caactatccc caggttaagt ctcctgaaat cctcaacaat ctcatcgggt   3180
agctgggcaa caacagctga atgaacatgc tcctttcgac tcaaggcatc tgcaaccaaa   3240
tttgccttgc tcgggtgata gtgaatctcc aaatcataat ccttaataag ctccaaccaa   3300
cggcgttgcc taaggttgag atccttctga gtgaatatat acttcagact cttatgatct   3360
gtgtatactt gacacttgat tcccataatg taatgtctcc aaatcttaag tgcatgcaca   3420
acggctgcca attccaagtc atgagtgggg tagttcaatt catgtctccg taattgtcga   3480
gaagcataag caatcacatg tccttcctgc atgaccacac atcctaagcc ttggccacat   3540
gcatcgcaat agatatcaaa tcctttctgt aggtccggca taaccaatac tggtggcgac   3600
attaacctct tcttcaatag atcaaagctg tcttgacact tctcgtccca cttaaattct   3660
tttcctttct ccaaaagcga agtcataggc ttggcaatct tagagaaccc ttcaataaat   3720
ctccgataat agcctgctaa tcccaagaaa ctccgaatct cagtcactgt agtgggtact   3780
ctccactcca ttatctcctt aactttagca ggatccactg atattcctcc atcagaaatg   3840
atatgtccaa gaaatggcac ctcgccaatc caaaactcgc atttggtaaa cttggtgtag   3900
agttgattat ctcttagctt ttgtagcacc aatctcagat gttcctcatg atcactatca   3960
ctcttggaat aaataagaat atcgtcgatg aatactacga cgagtctgtc caaatactcc   4020
ataaacacct tattcatcaa gttcataaaa taagctggtg cattggttaa tccaaacgac   4080
ataacagtaa actcatataa tccatatcga gtcgagaaag ccgtcttggg aatatccgat   4140
ggtctaatcc tcatctgatg gtaacccgat cggagatcaa tcttcgagaa tactctagca   4200
cctctcatct gattaaataa atccttaatg cggggtaatg gacacttgtc cttcacagtg   4260
acatcgttaa gggtcctata atccacgcac atcccttgcg atccatcttt cttctgtaca   4320
aaatagaact ggtgctccac aaggtgaaga actcggacga atgtacccat cctcttgtaa   4380
ttccgttaat tgcttcttaa gttcctttta gttcttctac ggacatcttg tatggccatt   4440
tagaaatagg ggcggttcca ggtaagagat caataacaaa ctcaacttct ctatcgggtg   4500
gcatccctgg taactcctct ggaaagacat ccggaaaatc tctaaccaca cggatgttgt   4560
cacccacaac ttctcatcta ctaagaacgc cactagtctg atggtggtag ttactgcaac   4620
ttcaacttca aatctttgtc ctttggaact ggtgagtgct acggttccct tagcacaatg   4680
tacaaagtgc ctttgccttt cttaaccatg acataccaag gatcaagcct atactgctct   4740
```

```
cttctaacag tatagggta gcccatttgg gtcaggaaca cagggtaaga aagaaaggat   4800
tatagacaag gcatgtaatt acgagtaatg ttactacggg ggatttatta gctaagtaga   4860
ttagtgtgtc acccactaaa gctaatacat taccttatgg tggtacatgc taagatgccc   4920
gtctatacta tttcaatcaa tcaaagaagc aaatcaggca ttgatcatca gaacaatcaa   4980
ccaacatttt taataaagaa aatagtttta attttgtctt aggcttccta cctcttaaaa   5040
atgtcatagg ggtagggact ccaaggtgtg aaatccatct tgtctaggag tagaaaaggt   5100
aagaatgata agagtagaac aatagaaggt gagacaagat caagatgaga tgagtataga   5160
atgagtcaga gtaaggtaag taggaaaggg tctgtccatt tctatctagg tttcgtccta   5220
cagtcaacat ttcctctgat accacttctg tcacacccgg ctttaaggaa caaagccagg   5280
tgcatctcat acatgcgcca agaagacaac atatataata acagagtgta tagagataaa   5340
tgtcgtaaaa catcagagta tttattacat agcggaagac ttattaaaaa aataaaagat   5400
aaaagtaaaa cgaactaagg atcgtcggcg ccaatgtcaa ctgagaaacg ccacctagat   5460
cagatcatac tcctcgcctt gtggctcctc ctgaaccacc tgctcttctc ctgtgggggg   5520
ggggtgtgag acagcaaggg tgagctcaca catgatcatc gctcaacaag ttgtggggaa   5580
taatgtgaca tgaactcacc aaaggtgaga gctcatggag tgtaaggctt atcaaagaga   5640
atggttaaag ctgagcattg cttttaagta gttggtcaaa attttattag cagttactaa   5700
gtgtaagtaa ataccaaacc ttaaataaag taatagaaca aaattaataa taaacccatg   5760
catatgcaaa tgacaaaatt gaatttaagt tccataattt aaacatcaga gagtcctgag   5820
ctgctcatga ccgtgagctc ggctagtata ccagttttac actctgcaga ggttgtaccc   5880
tttacccaca agtcatgcta cccatctgcc aaggggtcgc gaatcccata cacctctacc   5940
taggaagcgc ggcagggcaa cactacgagg cctttacaaa gttccactag cttccgaaaa   6000
cccgctacag tttataggaa gttccaatgc agggttcctg gctgaccgcc atcgcagcaa   6060
aatcaaccag ggacctccct tcattgacca ctcccctact gcccttgccc ctttcgggta   6120
aggtagtctt ccactagctt tcctaattaa tcagccaagg gcgtcccatt aaaccccttgt   6180
ggtggcacgt ggttctcaag ttaagctcta tgttccaatt aacattaatg atctcaacat   6240
gaacataaat agaataacaa aaagaattgg aacatagagg taataaatga ttatcccaaa   6300
accatgtaaa gcaatagcaa actacccaag tgattcaggg gtaaacaagg taatgagata   6360
aacaatctag ggtgacctat cggtcccat caaaattaac ctatgcatgg ataagtgata   6420
ttaaagaaca ttattgggta aaaagtggtc aagggcacaa cttgccttca atgagctcct   6480
gctcagctac ttcaacctgc tgctcaccag ggtcctcggt cacgggctct tctactcgcc   6540
acaatacaaa caagcacaat gcatatagag aaattaacat tacatcaaac atataaacaa   6600
aatacacagt aataatctac acattaaaat aaaattctag gaacaggaat cataattttt   6660
ggagttatag aatttaagtt atggattttc aaaggtttta tgtgctttaa ataggattaa   6720
gtgataaata aatttcttac tgttttcatg acataacaga ggctctaggt gataaagaat   6780
aaaattacaa aaatttagaa ggtggaatgg attattttga agttcatatg tattttctat   6840
gaattatcaa agttctagca attattttgt attaaaaagt aatttctata attaaataac   6900
tgaatttaaa gaactatgga ctgggcctca ttttctgcaa actacagggg tcttagagta   6960
agattcttaa gacacagtga acaacactgt gcggaccgcg ggtgatttcc ctaaaaacag   7020
aggggcctaa tcgctaaacc gacccgccga aggggtatcc ttcgaacccg agccgcccga   7080
```

```
tcgtcgaccg agggtcctga ttagatcaag accacacccg aaatggtatg taatactatg   7140
cgctggattg gcattcgacg gctaccagcg atccccacac tcatctaatc ctgaccaacc   7200
aacccgggat caacgaccag cacttcatcg ttcccaacac actgaccatg cgcggcggcg   7260
ccgcccagct aatcctacgg atgtgagcac ggcggcgaac tacggatctg tgatttggcg   7320
agctattccg aacgcggtga tgagcaatcg gtagtggaga ttacgacgaa ctcaatgggg   7380
gcaatcttac cggtggttga tcggtgtaga gagccgacga cggggtttgg cggcagtagc   7440
ggcctccgtc gagcaattat ggaggtccag ggcccttct cgtccagcga tgtgatgagc   7500
ggctccagtg gtgtcaggcg aaactccctg cactccaatt cggccacggg tggcgcggtg   7560
gtctgggaac aagtacggcg gctactttct ttcgcaatgg cgcacggtgg caatggggaa   7620
agggagagga aaggaggggg tcggtccgca gatatagaag gtgaggatca cgacgcgcag   7680
agttcggtca ggtcatgggc cagcgcagat tgtggcatgc gcggttgcgg cggcttagct   7740
ctgaactcgg cggagttagg cgacgacgcg cgggttccgc gtgccagaga tcgcgctcgg   7800
ggtggtcaac agttctcgcg acgcgcccgg ggtctttgta cccaggttga gggggcaaat   7860
ctcgacctga tcctccgatc aacgcggcgg ctgttacaac tacgcgcgcg attcatcggc   7920
gagtaaagcg gcggcgactt tggagacccg tttcacgcca gcggcaatca ggggaagatg   7980
accctggcaa cacgggtcca cttgtctgcg actggtgcgc acgcgcgaag tcttcctggc   8040
cagtaggccc acgttgtcag cggagccagc agcgcagcca tgctcccgcc tgggctgcgc   8100
ggaggggtaa tgcgaaactg ggccaaaagg ggtagccacg gcccaggtag gctttatctt   8160
tttttttctt ttttttatt ttcctttct tttatctttt aaatctctat ttgaattcaa    8220
atttttttgt tgtgaatttg tactcagaca aaagttgtaa cttaagagta ccaatttgaa   8280
aagttatatt tatttttata tagttttctt tacaaggtga tccctttctt ttccttgttc   8340
ttttatgtta tttccatttt tttaaattgt aaatgaggtc tttgaatccc aatttgggac   8400
acctttgtat ttctattgat atgattattg ttatcattaa atgcacatac aagtaaaagc   8460
caacatgatg cacttaggtt atttaggtgt cttttgttaa ttatttattt gtttaggtga   8520
gatgtccaca tgaaatgcta catagggatg acacccatat atgcgaagga atataatctt   8580
tactcttagg ttttattttt acaaagtggg tgttacaaat cctacccccc ttaaaaataa   8640
tctcgtcctc gagatttagg aagaacgagg gaaaaggtga ggaaaatcta tgcgaagctc   8700
ctccttctct tcccatgnnn nnnnnnnnnn nnnnnnnnnn nnnnnnnnnn nnnnnnnnnn   8760
nnnnnnnnnn nnnnnnnnnn nnnnnnnnnn nnnnnnnnnn nnnnnnnnnn nnnnnnnact   8820
aatctagaga ttcgttacct tacccgaaag gggcaagggc agtaggggag tggtcagtgt   8880
agggaggtcc ttggttgatt ttgctgcgat ggcggtcaga ccaagaaccc tgcattggaa   8940
cttcttataa actgtagcgg gttttcggaa gctagtggaa ctttgtaaag gcctcgtagt   9000
gttgccctgc cgcgcttcct aggtagaggt gtatgggatt cgcgacccct tggcagatgg   9060
gtagcatgac ttgtgggtaa agggtacaac ctctgcagag tgtaaaacta gtatactagc   9120
cgtgctcgcg gtcatgagcg gctcaggact ctctgatgtt taaattatgg aacttaaatt   9180
caattttgtc atttgcattg catgggtcta ttattaattt tgttcaatta ctttatctaa   9240
ggtttggtat tcacttgtac ttagtaactg ctaataaaat tttgaccaac tacttaaaag   9300
caatgctcag ctttaacccc tatcattgat tagccttaca catcacatga cctcacacct   9360
ttgtgagttt atgtccaccg gttccccaca acttgttgag ctatgatcat gtgtgagctc   9420
acccttgctg tctcacaccc ccccacagga gaagagcagg tggttcagga ggagccgcct   9480
```

```
aacactgagg agttcgatct gatctaggtg gcgtttccca gtcgacattg gcgccgacga   9540
tccttagttc gttttacttt tatcttttat tttgtaataa gtcttccgct atgtaataaa   9600
tactctgatg ttttatgaca tttatctcta tacactctgt tattatatat gttgtcttct   9660
tggcgcatgt atgagatgca cccggctttg ttccttaaag ccgggtgtga caaagagaga   9720
acccttctgg cccaactcct aatcctgtgt ccccttcccc atttctcctt ccacctccta   9780
agtctgagta taaggtacga atctctagat tcatnnnnnn nnnnnnnnnn nnnnnnnnnn   9840
nnnnnnnnnn nnnnnnnnnn nnnnnnnnnn nnnnnnnnnn nnnnnnnnnn nnnnnnnnnn   9900
nnnnnnnnnn nnnnagatct aggagattcg tcgtggagat acgacgaact caatgggggc   9960
aatcttaccg gggagccatg taagagccga cgacggggtt tggcggcaga agcggcctcc  10020
gtcgagcaat tatggaggtc caggggccct tctcgtccag cgatgtgatg agcggctcca  10080
gtggtgtcag gcgaaactcc ctgcactcca attcggccac gggtggcgcg gtggtctggg  10140
aacaagtacg gcggctactt tctttcgcaa tggcgcacgg tggcaatggg gaaagggaga  10200
ggaaaggagg gggtcggtcc gcagatatag aaggtgagga tcacgacgcg cagagttcgg  10260
tcaggtcatg ggccagcgca gattgtggca tgcgcggttg cggcggctta gctctgaact  10320
cggcggagtt aggcgacgac gcgcgggttc cgcgtgccag agatcgcgct cggggtggtc  10380
aacagttctc gcgacgcgcc cggggtcttt gtacccaggt tgagggggca aatctcgacc  10440
tgatcctccg atcaacgcgg cggctgttac aactacgcgc gcgattcatc ggcgagtaaa  10500
gcggcggcga ctttggagac ccgtttcacg ccagcggcaa tcaggggaag atgaccctgg  10560
caacacgggt ccacttgtct gcgactggtg cgcacgcgcg aagtcttcct ggccagtagg  10620
cccaccaggc aaatgcgcac agcccaaaag aacggattag accgtgtgcc gaccggtggg  10680
ccgttggtgc cagcctcttc cctctgcgcc gatggtgggg gccacattcc agatgcgcgt  10740
gctgtggcga cttgcaggcg ggcccaggtt gtcagttcct tccccttcgc cgtaacagaa  10800
ctcgcgttct ctacgccgcg tgactatcac ttccgccgag cccaggaccg ctctggattc  10860
tattgcagag atctcgccgt caccgccgcg ggtatcggat ggtcgttaca tcgtgtgccg  10920
acttatgcgg attggcctgg gcgcataagt agcgcgccgc tcggtatctt ggcccaccaa  10980
atgaacccct gcctcgcacc acagttgatt gtgtagcctc gtcggtggga gaactccgct  11040
gccgccgaag aaagctcgac ccatagccag tactagagag agaaagacgt gcgccaccgg  11100
gcggattaac gggtttccgc ggtcacctga gtaggggagt gggtgcggca tctgtcgccg  11160
ttgggcaccg cacccgtgcc ttccgtcccc gcctgcttgc agtgaccccg cgcatttttt  11220
tttcgcaact cgtgcgtgcc cgctcctgtc actcgcggtc gggtggacga aatctctagg  11280
attctnnnnn nnnnnnnnnn nnnnnnnnnn nnnnnnnnnn nnnnnnnnnn nnnnnnnnnn  11340
nnnnnnnnnn nnnnnnnnnn nnnnnnnnnn nnnnnnnnnn nnnnntccga ttctgatgaa  11400
tcagcttgat tcgtacacgt gccaccacaa gggtttaatg ggacgccctt ggaagacaaa  11460
ttaggaaagc tagtggaaga ctaccttacc cgaaaggggc aagggcagta ggggagtggt  11520
cagtgtaggg aggtccttgg ttgattttgc tgcgatggcg gtcagacaag aaccctgcat  11580
tggaacttct tataaactgt agcgggtttt cggaagctag tggaactttg taaaggcctc  11640
gtagtgttgc cctgccgcgc ttcctaggta gaggtgtatg ggattcacga ccccttggca  11700
gatgggtagc atgacttgtg ggtaaagggt acaacctctg cagagtgtaa aactagtata  11760
ctagccgtgc tcgcggtcat gagcggctca ggactctctg atgtttaaat tatggaactt  11820
```

```
aaattcaatt ttgtcatttg cattgcatgg gtctattatt aattttgttc aattacttta  11880
tctaaggttt ggtattcact tatacttagt aactgctaat aaaattttga ccaactactt  11940
aaaagcaatg ctcagcttta accctatca ttgattagcc ttacacatca catgacctca  12000
cacctttgtg agtttatgtc caccggttcc ccacaacttg ttgagctatg atcatgtgtg  12060
agctcaccct tgctgtctca caccccccca caggagaaga gcaggtggtt caggaggagc  12120
cgcctaacac tgaggagttc gatctgatct aggtggcgtt tcccagtcga cattggcgcc  12180
gacgatcctt agttcgtttt acttttatct tttattttgt aataagtctt ccgctatgta  12240
ataaatactc tgatgtttta tgacatttat ctctatacac tctgttatta tatatgttgt  12300
cttcttggcg catgtatgag atgcacccgg ctttgttcct taaagccggg tgtgacaaag  12360
agagaaccct tctggcccaa ctcctaatcc tgcggcccac ttccccattt tctcctttcc  12420
acctcctaag tctgagtata aggtttttaa cgctatcatg atatatagtc aatgtggcgg  12480
taaacaggag tgttggtgca ggagcgagaa gtacgtgggg gcgagcgcat gcaatagata  12540
ttaaacatgg ctattacaac gtgtacctca gtaccggtag ccatggatgc acatgctgac  12600
tctgcaacaa gtgtctgatg cacagaacac gggaggacga agcatgggct ggacctggac  12660
caggaccagg acggctcggc gtgcccctgt tgacgctgtt catcacgtac taacaacttt  12720
tcttctcggt acggatatat attctctcct attcctatcc aaagtttacg agttgcgctg  12780
caagcctgca tctgcattgt cagtacgtcc tagtcagtag ggacccaacc aagacaaggc  12840
aacattgtcc atcatcacct ttatttttgt tgacgccggc cttgacggca ttgcctagtg  12900
gccagctgtg gctacaaata aagagccatc tccacccacg gcaaatccaa atagtcatgc  12960
catgctagtt tcgacttact tgctctgtat taaggtcttg ttcagttatt tcaattccat  13020
ataaattaaa ttgtattaga ataaattaaa atattttta atttgctatg tattcaaatc  13080
ggttcaatat cattcattct acatggtttg tcgtccggga atactaaagt atcgtgtata  13140
tatatagtaa taactatcgt tgtcacttgt ctatcacccg tagctgtact gcaccacgcg  13200
ccgtggacta ggaaagtggg aagcctgatc cattcccctt gggtcacgga cttcataccg  13260
tcgtgcatat aatttccgac catttgttct aaaaataaac tcactcaatc aattaccaac  13320
ggaagactat gtgttttctt tatctagtac agtatgtgtt tttatattaa acaatacaga  13380
aaaaatgttt tttcctctat aactccgact atggggtgtt tggttagagg gactaaagat  13440
tagtttctag tttttagtct catttagtcc tttttttgcc aaacactagg attaaatata  13500
aactaaaatg atttagtctt tagtagggac taaaccatat taattccaca tttatcactc  13560
atttagttca attgtactaa tagtagtaga atgttaaagg tcattttagt tttcttataa  13620
gtcatttaat atattcttac tatttttagc ctctataacc aaacatgtta gagactaaac  13680
tttagtcttc taattaaact ttagtctcta gactaaagaa accaaacata gcctatattt  13740
tacctatgcg tagccgcgta ggtaacggcg aaagcatgat gacgatacac atacacaccg  13800
cccccggccg tggccgccac ctagcctgta tgtaccgtgt accatattcg taaggctatc  13860
cgcactcata ctactctaaa tttctacttt aaaaagaata ttttatcccc gtcagcaaga  13920
ttatctactc tataccacaa tcctctgcag tcatgtttac tctatatctc aactctatac  13980
caactaccac atattatatt actttttccc acttctcaac taccggttgt ccgcacccat  14040
accggctgtc actgggcccc acaccgacag ccccgtatat agagtgagag agtgcaagcg  14100
ctgaatatag agttttcggt gtcctctata catgtgcagt catcggtaca gtttaccgct  14160
gcagctcccg cgtccactgt aaaatcttag gggagctttt acagctcgcg actgcgacca  14220
```

```
gcctaaggcc gggagcacac tagtgctggg aaggccgaac cggacccgcc caagtccatt  14280
gtgtcttggg ccaagaagac ataaaagtag agttggacat tcgttttttt aaacttgggt  14340
tcggattttc ggttttaaaa aactttgatt tttctagaca ttagaaatcg atcgttttct  14400
ctaaaataaa aaaatcgaga agttcagttt cgatttctta ctttggtttt ggtttttggt  14460
aaaaaccgaa taccaaactt atactaagac aacacataca acaagtttac atgatagatt  14520
acacataatt ttcaaaagta aaaattatat aggtacaaat attcagagat acatcataca  14580
tcacatataa ataagtgaat aacaatttaa ttgattcaca catttagttc acataatcaa  14640
atagtcaaat tttagaattg ataaagtttg gtttttggtt ttttggtatt tcggttcggt  14700
atacagtaaa aaacgaactt ctgatataaa aaaccgaaac tgaaccgaac taccgaaatt  14760
tcgttttggt tcggtttaag gtaaaaatgt gcccacccct acctaaaaga aaagtttgag  14820
tcgtttcgtt gcctgtctaa agagtagaaa taatggtcaa ttccggtcct aaagtttgta  14880
gctatgttac aacaatataa attctgtacc ttactaaatc aaataaattt aaaaatcgat  14940
gtcgggttcc gatgggctag aacatagggc ccgacctagg cccgcattcg attcatatta  15000
ttttattgtg ggatgtgttt tacgcttcta tttttaggtc atgtgtgctg gcccaaacaa  15060
aaactaacac atattcctag cactaagcca cactgctagt gacaggcagg ggagcaaaca  15120
ctagtcgcgt gattggacgt ctgcacctgc ccattcagcc tctgtgtatg tgttgaccat  15180
gctgcgactc tcgtttggtt gcctgcttac acggcgccaa ggctgcaccc gcggctgcag  15240
cttaagcctg aaacatctct cctaattaca tgcacatata cgtaaggaac ggcctgtttc  15300
cagtggacca ggctcgcacg agtcagacca cacttacaca cccaacccat cagaggatat  15360
atcacgctcc aagaagcaag aagcagtcct ctcggtctct tggccgggca gggcgacagg  15420
cttgatgagg ccaacagtag acgggaggca tgagccggac accgcttttc cctatcttcc  15480
gtaggtgccg ttcggttgtt tgagattagt gcttatctaa tttatataaa ctttaattaa  15540
ctgaaataat tttttatgca atgtggtaca aaagaacaaa gacttaggtc ttgttcgttt  15600
gtgccggatt ggtgtgggtc gaaaagattt ctaattggat tgcttctcta atttatataa  15660
actttgattt gctggaacga tttcagttac aatccgacac aaacgaagaa ggccttaggg  15720
tgtgttcgtt tgttccggaa tcgtgaccta gaaccaatcc aaccaggaat gcttatctaa  15780
tttgtatagg ttttgatcac ctggaaccat tcctgcccca atcctaaaca aacgaacgca  15840
gccttaggtc ttttcgttta catcggatta catccggaat cgttccagtt aatcaaagtt  15900
tatataaatt agagaagcaa tccggttcgg aattgttccg acccaccaat ccgacgtaaa  15960
cgaacaagtc cttaatcagc acaaaaccag gtcggtcacg cacgggtact ggcgtactgc  16020
catgcaccaa acgctagtcg tagcgtagga aaaggaaaca gtggtcgtcg accagcagca  16080
ccaaccgttc tcgattcagg ctttttttctc gatcgcttgc ccgcgtcggc gggaggggcc  16140
tcgctcgctc gttcgccggg tcaacacctc agcacctgca ccgaaagtgc cgagtgtaag  16200
aggacgactc tgtgtgtttg ccgccatggc ccagcagcct ggctgcgctc tcaggctgca  16260
gttctcgtat ttgcgttggc ctgacttgat cgggagcctg gctgtccgcg tgcaagttta  16320
gtctctcagc ctggctccac agaaacgaga tgaaggtccg ttttctggga gcctggctgg  16380
tcgtggcgca aggattccac ggttaggtag ttttagtctt ctaacccggc tacatactgg  16440
gtgacaaaca ccagctcgtc tgagccagtc tctgagtctc atatgataca aatgcgcaaa  16500
tatagtaagt tgcggaagct gggacagact aatcttagcc tggaccagtt gaacgggccg  16560
```

```
aactagtcag gcacagggtc gcaaacacgc cctctctgtc tgcagcactt ggccatgcat  16620
cattttcctc gtcacctagc tttaccaccg gcctgggcag cctcttctgt gatatcgtga  16680
atgcaatgct cctctatcta tggtgcggtg ccctccgacg gtccagccac cgaccatgat  16740
ggatccatgc aagacggcaa gatgccacca cacacacaca cacacaaaga gagtgctgcc  16800
cactctgcgt tcatctgctg gcggctgtcc tggtttgctc cacatcatat cgacaggact  16860
gcaggaggct tgtcatgggg ggcccgttcc cccgtccggc ccctcccctc cccgcgccgg  16920
ccagcccgtg gcatggcatc tctgcgcaag gcgaccagcg gactgcggcc ggccggccgc  16980
ctgtgcctgt gacgatttgt cagaagaaaa cagcaatttt cagggcctgc actgcatcta  17040
atcatgcacg gaaacggatc caggcgggcg ggggcccaac cttttcatca tgcagaagac  17100
acatggaatc gaagctgaag atagcctggg cgagtgggcg gtggcttcta gcgatcaacg  17160
gaaaacatgt gttgggatca gtgtggtatt cggatcggag ttcaggtcgt aggtcgtagc  17220
cgtggaaggg ctcgcgctcc ctgcttcacg gaccgaggct actgataacg tcgtgcccct  17280
gagggcaagc agcgagacag cagctgagga gcatcgtcgc gcagtacagg ccccatggac  17340
atggacatgc atggcttggc tagctcagct attcctcctt tgaactatca acctgcagtg  17400
tccgtattat aggtgcctaa acggatggcc cggcccggcc cagcacgggc ccgttagatc  17460
cgacgaataa ttgggccgtg cccggctggc ccgcgtgccg cggcccaggc acggcacgcc  17520
ggcctggtag tcgtgctgag ccggcccgtt aactggtcac gttctcccat taaattaagg  17580
aaaatagcaa aaaactgtgt gtgtgtctag ctcagctatt gctccttgaa actatcaacc  17640
tgcattgtca gcattatagg tgcccaaacg ggtggcacag cccggcccag cacgggcccg  17700
ttaggcccga tagataatcg ggccatgctc ggccggcccg catgccatgg tagtcgtgcc  17760
aggccggccc gttaactggc cacgttctcc aattaaatca aggaaaatag caaaaaaaac  17820
tgtgtgtgag tgagaatttg aacccgcgac ctctctttac aaggctgaaa acattaacta  17880
aaagagacta atcaatagaa ctctagtaca tttgttgtaa atagcaaata taaaatgtaa  17940
atatatatac tatattttat aaaatagaaa atatatagtc gtgccgggcc gggccgggcc  18000
gcactgcgga ccaaggcagc ggcccaagca cagtacaatt ctcgtgctga acttggccca  18060
gcactattaa acgggtcgtg cttcggaccg gccccgttag gcacagtcta tttggccatt  18120
tatggtccgc atgctccgct cgatcgagct agtcagccag catggttcct tgtcggcgcg  18180
ctgcggccgg tcgcgcctgg gcctggcggc agctatgcag gccgtctggg ctgggcaggc  18240
gggggcagct ccgttcgccg tcacttggat ctcggtttgg tgtctgagat cgttcgacac  18300
ttgaactgcc tgccggtaca actagaatat gcagctcgac gcgcacacgt ataatcgttg  18360
cgttgcatgg cgaggcagcc agagccagtg ccagtgccac tgccacgcca gggccgcctc  18420
cgatggaaac agatggaagc agtttacctg tccggggagg cggggaccag ctatgcctct  18480
gatctggtac gacgaatata tagttaaaac tactagtact ggatctagct agctgaaatg  18540
cactgcatgc gctgtttacc accggtacgg tacggaccgg catccagtac ccgtcgcgag  18600
ctcggctggt cactctagta cagacaagca gcgagctggc gtactacgta cggcgggccg  18660
gacggaccca acagaactcc ccacgtcatc ccagatatct gaagtctgct ggggcgggcg  18720
cacacctacc tacctgcaca cccaactccg atccagctct ccgcgacgta tacgactcgc  18780
ccgccctcgg ccaccgacct gcagcaactg cgccctctag ctaccgtccg gatccggacc  18840
cggtagagga gcgcttgccc gcgccgaccg agaaataaac gcgaccacgc gagcgggcag  18900
acgacagcac cagctggccg ggcccctacg cgccgcaccg tggtccaact tccaagcaga  18960
```

```
cagagacagc cacagccagc cgggccgctg cctacgctaa ccccgccacg ggcgtcgtta  19020
gcgtgaatga ttacggggtt agattagata caaggcgggc ggccgatgcc gtcgctgctg  19080
gcaagcaaat tgacgtcccg cgtccggatt aggaagagga ggtgtggatg gatgggggtg  19140
ggtgggtggg tgggggattt tgcgtagaag aaggaagggg ccacgtctcc acgtcggcgc  19200
gcatcacccc gacgacgcca cctggacctg gagccgcccg cccgcccacc tcatgtcggc  19260
ggtgccggtg cgagcgaggc cgatggacgc aacgcaacgg cggttggttg tgggggggttg  19320
gccaaatcgg tacgtgcacc aaacgtacgg cgcctggaca tgtgcccgtg ccctgtttgt  19380
ctcgctctcc tcctccgccg gctgaaccta acaaacgacg gccaaagcac ccggtgagcc  19440
gatgaccacc tccaatcccg gcatccacca tccactacac catcgctgct gacctgcgcc  19500
gtaccagttg atcagagtga cggggttttt tttttctctt tccctgtcca ctcgtgtaat  19560
ctccaacaga gaagtactac cggcccgtac tactttcgtc tgcggataca gtgacgtttc  19620
tttgtcctgc acggctgcac agtgggtggt actgttgact gcgatgaaat caatatcgtt  19680
gacatgctgc ccatacgtgc cagatgccac tgttgtgcca agtaaaaaaa aactctgcgt  19740
gggacagaaa aatagggaat tagctagcta gctaggcgcg ttgatgtctt gaggaacatt  19800
agctaggacg tggcgactac agtagtggcc ggcatcgccg agtgcgaagg agagatgaaa  19860
cgagcaagga agaagaagat gagttggaca atcctatttg cactggccgg caccgccgca  19920
ccacacaggc tatagctcgg gggcgcgatc gacgttgagg caccactacc ggcgccctag  19980
ccgctagcta gcctacagct acatacaccg ctcgtactat aggactacaa cgttattgtc  20040
cacctatcga gctcgagcct cgtgcatgtg gtccaggtag ggcgaggtga aggccccgcc  20100
ggccgaccgc gccccagcga cacgtcgtgt ttgtccgtcc cccgtgctgc cctgccgccg  20160
ctggatccaa aaccccactg cccggtgtac gtacgacctg ccgccgacga cgacgagccg  20220
cgcgcttgct tgcttgcttg ctggcgctga tgattgggta ctactggcga tgccctggcg  20280
tctcgagagc agagcagcag gtctctcgta ggaaaccgac agctctcggc tttagatttg  20340
catgattttt tgggtttgga gtcgcgggca ggagaggagg aaagccgggc cagctattcc  20400
ccccgcagca aattatgcac gcgagcggcg cgcccgggtc ggtggcggca cctatctgcc  20460
ctgcccacct aaaaaagcac agcatggcgg caaggcaatt atcaggagcg tcgtcatgct  20520
gcgaccacgt tatttactta aaaaaaccac gcagcataaa aaaaaaagta gtcttggctg  20580
cggactgcgt agcttcaatc caaaccaaaa gtttcaaacg gcgaaaccac gcagcatcga  20640
ccaggttttt acttgtgtgg tgactgagtg gagcgacgac ggctccgtac ggaagcacgt  20700
actcctcgtc ccagatcatt ccaagaaaca tcgccgggcc cagacgccat tattccgtcc  20760
tccaacacac gtagccagag gtacgcacca cgttagggtc aatccgccac gcattctgtc  20820
ctgggaacta gtgaacgaaa cgtttagggt cagcagggca acggtgaggc gacaggtgtg  20880
cacatgggtt ggtgacgagc agggaggaga gcgagcgggt ggggtggggg tgcgttgtga  20940
ttgtgacaac cagatgctcg tatcgtatcc acgccaattt ggttcttgac attattgtct  21000
tcacctttct ttctagattg taaattgtcg ctgttcgtaa acccatccaa tgctgacgca  21060
attaaccagt gtgcccaaca ggtaagcttc ttcacgggat cgcttccgtg gctccgtcca  21120
cagctaggcc tgtgtacatc aattcacctt ttatattcta cgtggcagaa acctacctag  21180
gttcagcgca aaatttctgt agctcagatt ctaatgtaca cgtacgtccc cacccctctt  21240
tcctactaat ctctttttcc tctcgccatt tctctaccac aaccattacc tttccttctt  21300
```

-continued

```
tgtctcgttg ttatacagta gggtccctaa ccaagaaggt atggacaagc tgttagagct  21360
ccttagagta actctaatag ttctctaaac aactctctaa atcgtcttaa atttaataat  21420
taaacagaaa aaatggttct ctaaatagac ttgctaatta gttagttgct gtcaactcta  21480
tataatctct atatttggca actcgatagg agctccttaa atgcacctga cgtcaatttc  21540
ttcacactgg catgattatt ttttccattt tccacacagt gaggtagcaa ggtatagcaa  21600
gctcgttttc cactttctag cacagtgata tagctaggtc aaacacgttt ggcataagtt  21660
tctcctttac cgttggacct tactgtccca taggttgtgt cagcggacca tcactcctcc  21720
atatgtcatg tcgaccggcc tttttctctt ctgccctcga catcctctgc ttccaaccct  21780
accgtcagcc tgatctgata ggtgcagggc tgccaaagct agattgaaaa tcgaattact  21840
ccctaaatat gagcagctat cggagactat gttactttta ctttggatag ctattttgta  21900
acttgctaaa catgatttta tcaagctctt tttttataga actattggag ttgctttgtg  21960
gtagtaattt aacaaactac cagatcgttt tattactgat atgaaggaag acaagataaa  22020
agactataag ttagctatga aaaaaagatt gataaagcaa cttataaatt agaatataaa  22080
gaatcggtgc acgaggtagg agaggaagat gaggaggagg actagtagtt tatagttata  22140
ttaacgaatt gtgtattttt ttttggttta agccatgtac ttttaaattt taaatggatt  22200
atgtaatttt atttgcttaa ttatgtaatc aaatgtattt ttatttaaat aaaataatat  22260
gtttatgtca actataagta cgtaaaagaa aagttaacgt ggtgttgaga tgattgtaag  22320
atgagattga agactgtgcg ttagataact acgatatata agaggtgacg aaggttatat  22380
gactatggta gataattagg gtcgatataa gagaataata caacatagcc ggagatacgt  22440
acccgcagtt tggaaccagt catatatagt tagcccgttg gcagtggatg ggcaccggat  22500
gcaagttagc cggtggacct aacaatttgt gtgccggcgg tgagagctcc cttccaaaca  22560
gcacagcaca gtacaggggg tgtcgtcgac gccttccgcc caactcatcc ccccttcgac  22620
ccacaaaatc ccaatacaaa tactcgccca gcaaacagag agacagggaa gggaagccaa  22680
gaaaaccacg ccaccgccaa aagcagctgc agataccact gctgctgcgc ctgcctgcac  22740
agcccccagc aggagagaga gagagagaga aagaggggga ggcggcagcg gcagccagca  22800
aaggcggcgg cttgcggctt gagctgttga tgatgcaggg cgagtaccgg tcttccatcg  22860
aggagtcggc tgcggccgct gttgccgcag ccgcagccat ggctcctctg gcggccgcgg  22920
cggtgaagat ggaggcggag caggcggcga tggcggcgcc gcagctgggg gcggcgcacc  22980
agcagacgca gccgcggcgg cagtaccgcg gcgtgcgcat gcgcaagtgg ggcaagtggg  23040
tggcggagat ccgggagccg cacaagcgca cgcgcatctg gctggggtcc tacgccacgg  23100
ccgtggcggc ggcgcgcgcc tacgacacgg ccgtgttcta cctgcgcggg cggtcggcgc  23160
ggctcaactt ccccgaggag atcccctcgt tcgggctggc ggatggcgtg gacgtggggg  23220
agcacgcgcg cgacccggcc gccgccgccg ccggcggcgg cggcggctgc acgctgtccg  23280
cggcgtccat acggaagaag gccatcgagg tggggtcccg cgtggacgcg ctccagaccg  23340
gcatggtggt cccgccgccg caccaccgcg agcgccatag gcaccacaac cacctgccgc  23400
agctgcgggt gcacgcggag gagcagcagg aggaagagga gcagaagccg cagcggcctg  23460
cgtggagcgg gcgcgtcaag aacccggatc tgaaccgtgc gccgagcccc gagagctccg  23520
acgccgagtg acaagcgagc gagagagctg agcagcaggc accgcaaggc gaggttcaac  23580
gacgacgtcc gttatcggtt attcccaatc ccacgacgca gcatgccgtt gtcgtctccg  23640
tccgaccgtc cccacgtacg tacgtacgta cacgacgatc cagctgaccc ggccgcctgc  23700
```

```
ctatcctatc ctatccgtcc tcgacgaccg gatggtcggc gggcgggagg gcggtgcggc  23760
gagggttttg gccttttggg tacgttgtgg ataagcacga aggcagcagg ccagcagcag  23820
caggggcggc gtggcgggcg ggcaggcagg ggcagggcag gcggagacgg agggaggcgg  23880
ccacaagcgg cggtctttcc aaaatgtcaa aaaggacagc tgtaacagcg ataagaaaaa  23940
caagtcatca tcaccctctc tcactactag ttctactact agcagtatga ttattcgaat  24000
cggccttgct tgacagcgat taatatcttt gccgcctgag ttgcaccata aactaatctc  24060
cccccgccgc ccgctttggc atgatccagt tgtttcgttc cgtcggcatc gccccccgcc  24120
ttggcttggc ttaccaacgc agttagctgt cggctggtgc gcgaatccgc cgcgttaggt  24180
cggctggccc gcttcctcgt cacttcgttc gtgcgccggg cggccggcag ccagttagct  24240
gaggactgca tgggtgcaat catggaccag cctcccactg ccagctcatc gtggccagtc  24300
gctaacgcct aacgaaccgg gatagcggtc gccgagggtc agggtgggtg agcagtgccc  24360
ctgcctgctg ccggtgatgc tcgcgttgca tttgcatggg gcgatttggg taattgggtg  24420
ggtgttgtta ggccacccac cacatcggaa agggaaaagg gaagtgaagg caaaggcaac  24480
gggactacgg gagtcttagc gggcgcgcgt catcatgttt caacggcgct gtatgcgagc  24540
gctgcatatg agcatgacaa agtaccgtct gtgtagcttt gttagcagca gctcaacggc  24600
gcaggcactt gccccgatgc caaggcgact ggcagctgac cagctgtcgt gcgtgcgtgc  24660
gagatttcca tgggcctgcg agccatgggc ggcgcgcgaa ggcggaggac ggaggctagc  24720
gcgcgaacat gccggcagca gtaccgcgaa cgacgtggtc cggtccggag caacgacagc  24780
gaggcgggtt tcagttccag cacataaaat agtttagtac agtgacatgc tgtttcagtt  24840
cgagctacgg agctagtaat gatcatcaga atgtccgtac gatatgaatc gttcctccac  24900
cttttttttt tgaccggaga aacttcattt ctattacttg cataacagaa atacattgtt  24960
cgtaccagct atcacagcaa ccaaacatga aacacccaca caccaacctg attcaggtca  25020
aggacaacta tcaggcatag tccaaattca ctacatcaag caggaaagac attaaccaaa  25080
aggtggctgg caaaattttc ccgaccaaaa aaaaaaaagc gtagcaatac gaatcggcaa  25140
atgatctcgc gaaccatcga gtgaacatag aaacatgggg gatgtctctg acacgagcct  25200
ttgttcgggt ttcaggtctt cttcaatgcg gtgctcttgc agatggggca cacgttcttc  25260
accaccagcc attgcttgat gcagccagcg tggaagtcgt gcccgcagtc cagcttcccg  25320
aggtcgtctc catcagcgta ctcctcctgg acagggataa aaaggacata aggtaggtat  25380
atatattagc ctcgttcaac tgctaatttc attgctctat aaggtgacgc tgggacatgt  25440
tcataggcaa aaaggaatta aattcacagc agataacaga tactggtgta catgatttac  25500
atcgacaatg gaaatcctga ttaaatagac agttctatgc tacaggtttt gttgccagag  25560
ttgatgttat tttttattag ccaccctata aaaaaggtta acagtgttga gtatatttgg  25620
ccgttaggac attgtaatct cgtactgaca tatgtatccc gagaggcatc ttgccctcca  25680
accctctgaa ctaaatattt ttttccctga aaggttccgt gcaaattaaa cgcacgcatt  25740
atgcctagtc ctctacacta tcaccttaag ggcttgttcg tttgtgtcgg attggtgggt  25800
cggaataatt ccgagccgga ttgcttctat aatttatata aactttgatt aatcggaacg  25860
attccgggta caatccgatg taaacgaaca aggcctaagt agtctttttt agtgatccga  25920
tggaagtcat gctagagtcg gattgtaatt ctttcctgag acactaggaa ccaagatcaa  25980
tagcatggaa atctcaaggg atgagacaaa tattcttagt tctaccattt caaaccgtta  26040
```

```
atttgtagaa atccagagac ctaccagggt atgattctcc attggaggcc tagatggtat  26100
aagtagacaa gcttagcaac ttttagactt aacttgccct tctaatattt gtgggccaat  26160
ttagttaagt gctgcattgc tttgtacacg tgatgatggc ctaggtgacc taactgaggt  26220
gccgtttggt tcacgaaatg taacataaat ggcaacggta atgatttaca ctcgattacc  26280
atcggtaaca agtttgaata ggacggtatc aatttctagt gtggtattcg attacggttg  26340
gacttaaaca aacatggttt aacgttaccg attaccgttc acgctacaaa tatgtgaacc  26400
aaaaacacct gaatgcccaa ttcaatcatt caatgcgatt ggtgtatcta cctacggcaa  26460
aagaacaagc catgattctg agatgctcgg gagtatatga aatacctggc agatacaaca  26520
tggttcaggg tccaaagatg cttttagtgt ccaagatgaa aatttccttt gtttgagcaa  26580
ccttatcaca gcttcctcgc tgaggccagt gccgacattt cctattcttt cctcgagtgc  26640
taatagctcc tgaaagtagg gcaaccatct tagattagat tttagattcg caaaggtgca  26700
ggtaatgctt cactaaggaa cacaaacctc ataggacata ttgtcaatgt caaggcgcat  26760
gtccctgtgt ctatcgtgaa tgtcaacacc gccatagaag atagactgtt caagaataca  26820
tttggcgtaa gaaggaaata tatcaagtac tagcaggtaa aaactcaagg gcacccaaaa  26880
cttttgaatt cattcagttt tatttttct tcgtgctgta cactcatggg attcatgatt  26940
ttctatctac aagtactgaa ctttcagatt actagtttgc tacatgttga cccattaatt  27000
ttaagcaaat taaatataaa cctcctacca actaacaaat agtagttttg gactacagta  27060
gatcacagga ggcaattcat tgtcacttat atctgtgttt ctgttatatg cttaaactta  27120
tgcggtagtt gatattagtc cttagttttc tgctgacagc tgtaggtatg gtatgtttac  27180
gattatagtc atgtttttct tttcttacca tgctatttta aattggaatt ttaattacag  27240
ggtaacacag gctggcaggc ttaacacaat attatgctga agtacgattg tactaaccag  27300
ccaatcataa cttaaccacg tccagcaaaa aaaaagaaca atccacaaag aacaatttta  27360
cttttgttta ttttagtggc atgtcgatat aatggtagca aacagagtta aaaaaactca  27420
gatggacatt gctagtactg acctcaagcc ttacattctc ccctctatgg atcatttcaa  27480
gtgcattccg aatctgttga caagtaaact tggattgtca taagacaagg aaccatgcac  27540
ctttacatga tggtcacagt agttaacgca agcaagaaca agcaaggcta gggaacaaaa  27600
aggataaaat agtgcagtat tttgcataaa aacataaggt gaaacatatc attaaggttc  27660
aagtttctct ataacaatac tagtgaaaat atcttagaaa aaaagtaaaa gatacaacaa  27720
ccggcagtgt gataatatgt ggaaataaat gataaaaaaa tttcagtatt tcaagagttg  27780
caggggcatg aagaagcatg ctagatcaaa ttagggatta tgaagtgcac aaacaaaatg  27840
aaataaagca tttcgagtag agcagttcta ccaatttggt gtgggaatag aatagggtaa  27900
tttgcttaga taggcaaaca caaagatgac aaggataact gaaaacaagg ggggcctttg  27960
caagcataaa ttcataaatt agaggatgat ttagtgtaat ctttgctgcc acacaaaaaa  28020
cacctaataa tgatggactt ttatgtttcc aagtggatgc taaaaaccat ttttttgaac  28080
agaaccgatc atcttacctc cattaacctt cttccttctc taccccttgt tgataaagga  28140
acaccccaaa caccatcgcc ctggcgctcc aacagaaacc ccggccttaa gcgtgggggt  28200
tgatggccgc gaagtgctcc agatagccga ccaatctcct ataagaaaat aaaagatcaa  28260
atcgagaaga tgatcaaacc aaattttaag tatggcgtca cttgatattt tggtgggaag  28320
atgagcaatc aaactgaaaa ccaaaatcca aaaatagaga aaaccaaatg cgaaaaatgg  28380
aggaaaaaaa tacctctgat aaatttcgag gatggcgccg ggtgaggttt tggtgactga  28440
```

```
atcctgctgg cggattaaca gttgcactgt tattagctct tgatacagga ggaatacttc  28500
ctgatattgc agtgcctcgg acatcagaac tccaattaga tggttctggc agcaaacgtc  28560
tcgggtctac tacagacggg ggaactaaat cagagtagtt ggcaggcacc acattccttg  28620
taggagcctc ttgactacca agaattctgt tctccaaact gccagctctc gatgatgaag  28680
ctccatggcc agtgaaacgg tttgcagccg gtggcacact agaaacattc actggatgct  28740
ggtattgcaa gttgaggctg ctgaccacag gaataacctc ctgggtatca tcaaatgcac  28800
tttgaaaatg aggtggctga tgattccatg aattaggaag tctgatagca tttgaagagg  28860
gccatacact acagggagca atctgttgag acgtagtaat tcttgcccgg aaacttctct  28920
gcgaattccc agcattgttg acccctccat taaggtcata ggtaccggct gagagccctg  28980
cattagttcc atatcgtggg agttgatcat cgatagaact tggaaccggc aagcaattgg  29040
gtgaggacgg atttctgata ggtgcaggat tgtaacttga agaagcaatg ttatggaaag  29100
cattgtcgtt cctgtgggaa aaactagtgc tagcacctgc tgaactctgg ccattgggtc  29160
cttcaacatt ttttctcttg caggctagcc ggcgtccatc cagggaacta ccgggtcttt  29220
ggtcaatgct ttcttgcatc agtgaaaaat cacacaaagg gttttcacta gggttcaaag  29280
taaaagaatc tgcttgctct gcatctagta ggaaagtcct gtatgggtgt aatctcaggt  29340
cagttggctg agaatttaca acactacgat caccgccacc atagtgctca gggccctgag  29400
atgtacagtt aacatttgaa ctttgaccac atagatcgtt aacgttggcg ttaaggttga  29460
tatccacatc cagagaaatg ccattgtcag ctaccagtcg cctttcacca atcctcagac  29520
caccgccaat actaagatgc tctgttttgg cattgttaga gctgccactt gcacttgctt  29580
cgcctgattc ccagaaacca agaaatgtac catcttgctg tgtctcattc ccatatggca  29640
tggcagcatc actgtgattc atctgataac cttgaagatt ctgcgattct actgatccaa  29700
gaacattgtt ccaatatgac tgctgatcca tcacagggtt gcctgaacta gatgcaatgt  29760
cgaatccaaa aacatcagca aaatgctcca cagaattcct ctgtccttgc attgtgatga  29820
tccaaactag ggtagcgaga taacatcaat tggtctgttg ccttagcatc tctgatggtt  29880
cctcgttcca gtattttaaa ggacctgcca gttgtaagta acacatcaaa cattttgggc  29940
aacagagctg tgctccaact ttattggaac acaagaaaag gactgaaatg aacgggatat  30000
agaacggggc tacgctttat ctaggctatt ccttcaacat ttgccaccaa aatatgtcaa  30060
ctctacatac aaggaactgt tgtctgcact ccaaaaatat tgtaattcta ctctgggttg  30120
ttactctatg gaagcagctg cacctgtttt gctctcacac attactgtag taggcagcaa  30180
ctaatcaggg tattggcaac taatccgact gtaggaatct tggcattagg cgcatttggt  30240
gtggcgtacg cgtgcaccaa acttgatggt tcgggttgct gttgcgagca aaaagctgtg  30300
gtgatgcatg cattttaatg ggtgaagcaa agcacggtga atgtacaatg catgcgacct  30360
aaacagatgg accgcatgca ggatggggcc cgttgctcct gtggacgctc gctcacaatg  30420
tttttttct cttttgtatt tatttccctt ccctatcggt tttgcaaaag gtgaaaagga  30480
cgcagtaaaa gaagcaaaaa tataaaggga aaaggtggga gtagccatcc actatttcca  30540
agagaaggat cgattccctc tgcgatgacg aaaacgaaat acgggagcag ataagaggtt  30600
tttaactgaa ccaagaacac gcccagtaca tccatctatc tctgtaccgc gagcaaacga  30660
aagaaaaaag tgttttttt caaacatgga agttgggaat tttgcttcgg ggaagacaag  30720
aattattgac agcttaacga gagccgtacc aaggccgctc catgtacaag tactgtggat  30780
```

```
tgaaacgtga aggaatcagc gaggaaaaaa aacgcatatt tgcgaaggaa tcatggattg  30840
aaacaacaaa caagggattg tttcgctatg caaaatcaag agatataact agaaatacaa  30900
aaaaaggcag tttaacagag agatgcaaca aaccgtacca gaaactggcc cagagtttct  30960
gaacaactcg cgagaaccgc aatccaggca aaagaacagg ctccgttctg atttctcttc  31020
tttcctgtct cctgtttctc gatcctctcc tctccacgga gaggaagaga gagagaatca  31080
acccagcaga cggaggaaac aagaaccgat tggttgcgag agagagaggc aacagacaga  31140
tggagcggtg ggcaagacga gaggaaattc agatagaaag aggtggatcg gtggagtcgg  31200
tggggaagaa gaggaggaag agaatgggtg gaggaaattt tgtcaagagg gagagggaga  31260
aagacagggg aggaggaggg gtgtggtggt ggtgacagga ggtgggagag agaggtttgg  31320
ctgaattcgg gtttatttat ttctccctct tccccacatc caggcactca ctctctctct  31380
ctcttctagg cctttgcaag ggtccttttc ctccccacta ataaaaaccc cttaaatgcg  31440
cccccattag aattagcagg agtataagat cactagatgg acttgtgtaa aaacatataa  31500
agcaatgttt tatactacag gctatattct gtagactaga gtttaaaacg aagggtgggt  31560
tataaaataa ctgatgacct tattaataac ctgacctcac atgaaggacc aaaggttaga  31620
ggcctgtatc gtgttgtctt tcacatgacc tccctgcgcc tgacccattt ggttttggag  31680
ccttgcagtt gcagcagcag cactacgaca gcaaggccta tccttctctc tctcatcctt  31740
tgcatacact gcacttggac agcgcagcat caggatggat gatggctgct atgctcatgc  31800
tcatgagctc atcccttgca tcgcattgaa tttatctttt tcttttcttg tctcggagta  31860
gcatccttcg cattgaatac ctccgggtgt aacccaagtg ccatgagata gtagtagtag  31920
tatgtttagt tggatcgtgt gcagctagct gctgcacatt tgtcagctca tgagaaaaaa  31980
tcatgaaagc gagttgtttc agaacaagcc gcgcgccatt cattatatat gcatcaactc  32040
gtgagctgtg ctggagcctc tggtgatttt gtttttttcac ctgctaatca agcgtcattt  32100
cctggcaact aatcaagcgc gctgtatggg ctttggttgc cccagggcaa tggttgtcag  32160
gtgcttatat tctggcgggc ggcgatgctt aaaatgtgga ccgcacatca agtgccacca  32220
caaaataact tgccttgttc aagcagaaaa caggtcaaaa agaaagaaga tcacggaggc  32280
agtctgaacc caccacgtac gtacggtacc accaccattc tcgctgcgtt tcttcagttc  32340
ctttcgtgtt cccaccagcg acgtgtgagg tcgatcatgc gttcaactgc acaaacagca  32400
cggaaatgtt aggatttatg ggcttggccc aattaagtta ttcaaataaa tcccaggaaa  32460
atctcaaaag cccatataag tggatggcaa agggataggt ggaaccaata gcaccatatt  32520
gctagctctt gtggagtaga gctaacttaa atatggaagc cacactcact caccaagtca  32580
tggatgagag gagagagtgt ggagagccac acgcgcgcgc gcgctcgctc gcctggccgg  32640
gccgggccgg gccggggcgg ggcggggcgg ggcgaagggc gcacgacatg cgcgcgaatg  32700
gtccgccgaa atccggcccc tcgccttgcg ggggcgcggc taccttttgc cgtttgattt  32760
tttggtttct tggctgttac gcttatccta accgatccct ataaaatctc aactgattgc  32820
gagattttcg tgggcggata agcactgggg tcgcggactc ggccctataa aaggagcccg  32880
gcagccagcc tccaaataat cccagatccc agttcgcttt cgcctctctt catagctgag  32940
ccgcctttta gttcccttcg tcccgaccgc agaggtgcat ctgcgatcag gagagcaggt  33000
ctctggaacc cttcgtcttc tagatcctgc accgggagag ggcgaataag gtttttggga  33060
agcgtcttca cgcgactgct cgtgatcttc tgacatcgtc gacccagctg atcctggcgc  33120
gcgccaacaa tcagtaagtc taatcagtac gcatcatctg atttggcttt tatttcagtt  33180
```

```
cttctgattt ggtcatgatt tatattcgga atttaatttg gaatttgtct aattaatcaa  33240
caatccaaaa accttattgt agacaatttc ctagtttttc tatggctgct tttgccgacg  33300
cgctgaagcc agaaaagttt aatggtatgc actttaagag atggcaagtc aaggccacgc  33360
tctggcttac tgctatgaat gtcttccatg ttagtaaagg cagacctgag ggtccactga  33420
ctcctgaaca ggagaaagag tacgaccatg ccaatactat gttcacggga gccgttctta  33480
gcgcccttgt tgaccgtctg gttgatgcga atatgcagta cacagacggg aaacagttgt  33540
gggatgcact tactactaag tatggtgcat cagatgctgg cagtgacctg tatatcatgg  33600
agagctttca tgattataag atggttgata atcgctctat tgtagagcaa gctcatgaaa  33660
tacagtgtat agccaaggag ctcgaccacc ttaagatagt ccttcctgac cgatttgtgg  33720
ccggatgcat tattgcaaag ttgccttcta catggaggaa cttcgccaca gctctgaaac  33780
ataagagaca ggagatatca gttgaaaatc tgatagcgtc tctggatgtt gaggagaaag  33840
ctcgggctaa ggacacggga tctaaaggag gcgagggcca ctccagcgcc aacatggttc  33900
agaagaacca caacaagggc aaaggaaagc caaaatctaa caagcccaac aaaactacca  33960
acttcaagaa gaagaagaac aaggctgaat tgacatgttt cgcatgtggc gaggcgggtc  34020
attttgccaa ggattgtccc gatcgagcgg atcgccgtgg caaaaagggc aatgtcaaca  34080
cagtggtcgc tagcaatgag gaagacaaag ggtatggtaa tttacctttc atcttctcag  34140
tatttcaatc acctagctgg tggcttgata ctggtgctaa tgttcatgtg tgttctgaca  34200
tcaacttgtt ctcttcttat cagggcgccc gggattcttc cgtgctaatg gggaatgggt  34260
cacatgcttc tgttcatggc actggcacgg tggatctgaa gtttacttcg ggaaagatcg  34320
tgcagctgaa gaacgtgcat catgtccctt ctatacacaa gaatctcgtt agcggaaccc  34380
ttctatgtag agatgggttc aaggtagttt tagagtccaa taaattagtt gtgtccaagt  34440
ctggacaatt tattggtaaa ggctatgatt gcggaggctt gttccgcttt tctttgttag  34500
atttcaataa taagtctgtg aaccatattt gtgctaatgt tgatgatctt gcgagtattt  34560
ggcattctcg tttgtgtcat attaattttg gctctatgtc tcggcttgca accatgagtt  34620
taattccgaa tatcaccata gtcaaaggtt ctaagtgcca tagttgtgtg cagtcgaagc  34680
aacctcgaaa gcctcataag gctgctgagg agagacacct ggcaccacta gaactcatac  34740
attctgatct ttgtgagatg aatggtgtgt tgacaaaagg tggtaaaaga tacttcatga  34800
cattgattga tgatgcgtct agattttgct atgtatactt gctaaaaact aaagatgagg  34860
ctttagacta ctttaaaatc tataaggctg aagttgaaaa ccaactagag agaaagatca  34920
aacgtcttag atcagatcgt ggtggcgagt tctttcccaa agtctttgac gatttctgtg  34980
cagaacatgg cattattcat gagaggactc ctccctattc acccgagtca aacgggattg  35040
ctgaaaggaa aaaccgtacg ttgactgacc tggtgaatgc catgttagac acttgtggtt  35100
tatctaatgc atggtggggg gaggcagnnn nnnnnnnnnn nnnnnnnnnn nnnnnnnnnn  35160
nnnnnnnnnn nnnnnnnnnn nnnnnnnnnn nnnnnnnnnn nnnnnnnnnn nnnnnnnnnn  35220
nnnnnnntga catgtttcgg atgtggcgag gcgggtcatt ttgccaagga ttgtcccgat  35280
cgagcggatc gccgtggcaa aaagggcaat gtcaacacag tggtcgctag caatgaggaa  35340
gacaaagggt atggtaattt acctttcatc ttctcagtat ttcaatcacc tagctggtgg  35400
cttgatactg gtgctaatgt tcatgtgtgt tctgacatca acttgttctc ttcttatcag  35460
ggcgcccggg attcttccgt gctaatgggg aatgggtcac atgcttctgt tcatggcact  35520
```

```
ggcacggtgg atctgaagtt tacttcggga aagatcgtgc agctgaagaa cgtgcatcat  35580
gtcccttcta tacacaagaa tctcgttagc ggaacccttc tatgtagaga tgggttcaag  35640
gtagttttag agtccaataa gttagttgtg tccaagtctg gacaatttat tggtaaaggc  35700
tatgattgcg gaggcttgtt ccgcttttct ttgttagatt tcaataataa gtctgtgaac  35760
catatttgtg caaatgttga tgatcttgcg agtatttggc attctcgttt gtgtcatatt  35820
aattttggct ctatgtctcg gcttgcaacc atgagtttaa ttccgaatat caccatagtc  35880
aaaggttcta agtgccatag ttgtgtgcag tcgaagcaac ctcgaaagcc tcataaggct  35940
gctgaggaga gacacctggc accactagaa ctcatacatt ctgatctttg tgagatgaat  36000
ggtgtgttga caaaaggtgg taagagatac ttcatgacat tgattgatga tgcgtctaga  36060
ttttgctatg tatacttgct aaaaactaaa gatgaggctt tagactactt taaaatctat  36120
aaggctgagg ttgaaaacca actagagaga aagatcaaac gtcttagatc agatcgtggt  36180
ggcgagttct ttcccaaagt ctttgatgat ttctgtgcag aacatggcat tattcatgag  36240
aggactcctc cctattcacc cgagtcaaac gggattgctg aaaggaaaaa ccgtacgttg  36300
actgacctgg tgaatgccat gttagacact tgtggtttat ctaaggcatg gtggggggag  36360
gcagtcctga cttcatgtca tgttctgaat agaattccta tgggcaaaga agagaaaacc  36420
ccttatgaga agtgggttgg gagaaaacca tcactttcat acttgcgcac ttgggggtgc  36480
atggcgaaag tcaatgtacc aattaataaa aagcgcaagc ttggtccaag gacagtggat  36540
tgtgtctttc ttggatatgc ttcgtgtagc atagcatata gatttttagt agttaaatct  36600
gaagttcctg atgtgtatgt tgatactatt atggaatcac gtgatgctac tttctttgag  36660
catatatttc caatgaaaga cattcatagc aattctagat actcttctga gataattcct  36720
gaacataata cacctattga gagttttgaa cagccacatg aaattgtcct agaggaggat  36780
gacaatgatg ctcctaaaag gagcaagaga caaagggttg aaaaatcctt tggtaatgat  36840
ttcattgtgt accttgtgga cgatactcct actaccattg cagaagcatt tgcatctcca  36900
gatgcagatg attggaaaga agcagttcat aatgagatgg actctattct ttcaaatggt  36960
acgtgggaag tcactgatcg accctatgga tgcaaacccg tgggttgtaa gtgggtgttt  37020
aaaaagaagc tcaagcctga tggtacaatt gaaaagtaca aggctaggct tgtggctaaa  37080
ggctatactc agaaagaagg agaagacttc tttgatactt actcacctgt tgctagaatg  37140
accactattc gagtactact ttctttggct gcctcgtatg gtctccttgt tcatcagatg  37200
gatgtaaaga cagcttttct taatggagag ctggacgagg aaatctatat ggaacagcct  37260
gatggatttg tagtaaaggg tcaagaaagc aaggtgtgca agttattgaa atctttgtat  37320
ggtctgaagc aagcaccaaa gcagtggcat gagaagtttg acactactct aacgtctgca  37380
ggctttgcca ttaatgaggc agacaggtgt gtatattatc gctgtggtgg gggcgaagga  37440
gttatattgt gcttatatgt tgatgatata ttgatatttg gcacaaacat tgatgtgatc  37500
aatgaagtca agtcttttct atcaaagagt tttgatatga aagatctggg agaagctgat  37560
gtgattctaa acatcaagct gattaaggca gatggtggga ttactctctc gcaatctcac  37620
tatgttgaaa aggttttgaa gcgatttggc ttctctgagt gcaaaccttc tccaactcct  37680
tatgatccca gtgtgacact gcgaaagaac aagagaattg gtttagacca attgagatac  37740
tctcagattg tcggttcact catgtatctt gctggtgcaa caaggcccga tatctcgttt  37800
gctgtgagca aattgagtag gttcatgtca aaccccggga ctgatcattg gcatgcactt  37860
gagcgggtta tgcgctacct gcaaggtaca atgagttatg gaattcacta ttctggtcag  37920
```

```
catgcagtac ttgaaggata tagtgattcg aactggatat ctgatgcaga cgagctttat  37980
gccaccagtg gttatgtctt tactattggt ggaggtgcgg tatcatggag gtcatgcaag  38040
cagaccattt tgacgaggtc aaccatggaa gccgagctag ctgcacttga cacagcaacc  38100
gttgaggcag aatggttgcg tgaactcttg atggacttgc cggtggttga gaaaccaata  38160
ccagctatcc ttatgaactg tgacaatcag acagtgattg ctaaagtgac gagttctaag  38220
gataatggaa agtcatcaag acatgtcaaa agacgattga agtctgtcag aaagttgaga  38280
aactccggag ttataagtgt gacttatatt tcaacagata aaaatctggc agatcctttt  38340
accaagggac taccacgtaa tgtgatagaa atcgcatcga gagagatggg tatgagaccc  38400
gaataaagtt gccatggtgg aaacccagtc tatgtgatcg gagatcccgt gaattaggtc  38460
ctgggaagaa caagccattg gtgaactgag gagagtaact tttgaccctc tctaagtaaa  38520
gatgcaatac tctcaaatgc tgtaaggcag gttggctttg tgccttaatg tgttctgttg  38580
gcttgtatta gcgaagatgt tgtcctgcag aacattcttt gaaagaacac acctatatga  38640
gttagactgt ctaacgtcgc agtctatgag atctgggtga tctctagtaa actcatgaag  38700
agaccttgga gtacgacgta tatgctccac ccgagaaggg gactactggt agccaagtac  38760
tagtcatgac ttcaagtgaa acccattcac gcaaaacttg caattcaagg catagtccat  38820
tgtccaagtt gtgggttggt gtaacttgga gttctaggcg gaagttcaac ttaacagtct  38880
ctgctgaaaa actagtatat taaacagtag tgaacagtgg cgaaaactgc agatgggcat  38940
ttgagatctg gtgggggatt gttaggattt atgggcttgg cccaattaag ttattcaaat  39000
aaatcccagg aaaatctcaa aagcccatat aagtggatgg caaagggata ggtggaacca  39060
atagcaccat attgctagct cttgtggagt agagctaact taaatatgga agccacactc  39120
actcaccaag tcatggatga gaggagagag tgtggagagc cacacgcgcg cgcgcgctcg  39180
ctcgcctcgc ctggcctggc cgggccgggc cggggcgggg cggggcgggg cgaagggcgc  39240
gggcgcacga catgcgcgcg aatggtccgc cgaaatccgg cccctcgcct tgcgggggcg  39300
cggctacctt ttgccgtttg attttttggt ttcttggctg ttacgcttat cctaaccgat  39360
ccctataaaa tctcaactga ttgcgagatt ttcgtgggcg gataagcact ggggtcgcgg  39420
actcggccct ataaaaggag cccggcagcc agcctccaaa taatcccaga tcccagttcg  39480
ctttcgcctc tcttcatagc tgagccgcct tttagttccc ttcgtcccga ccgcagaggt  39540
gcatctgcga tcaggagagc aggtctccgg aacccttcgt cttctagatc ctgcaccggg  39600
agagggcgaa taaggttttt gggaagcgtc ttcacgcgac tgctcgtgat cttctgacat  39660
cgtcgaccca gctgatcctg gcgcgcgcca acaatcagta agtctaatca gtacgcatca  39720
tctgatttgg cttttatttc agttcttctg atttggtcat gatttatatt tggaatttaa  39780
tttggaattt gtctaattaa tcaacaggaa agacgctgct cgtcagccac gccgctcatg  39840
aagcaaagag gctgtttttt tcgcgcggtt ttcgggtaaa acgtcccgag cccgaggcct  39900
actccgctcc cgttgatgcg gatgcctgcg ctgcgctgcg ctgtcgatct ggcgcgtgct  39960
tcgctgcttt tctgaccggg actcgtgctc ctcgtccgtc cgtcctccct ccaccccggg  40020
ggccggggcg aatatacggc cggtggaagg atgcgccggc gatccgccat ggtctttacc  40080
ttttttcccc gttgttgcca ctttgggcta aattacgtaa agaacctcgc ctaaatgcgg  40140
tgccagcttt tttctttcac ctcacctcga tcgtcacctg ctctgctcgc tcaccaatca  40200
ctgaatggat gccttttttt tcttcttgat tttcttgttt cagtaagttc agacgaaagg  40260
```

gtttcctgct ctcccatatt atccagaata gtgtgtagta gcgccctcca ccactgtgtt 40320
atcctctgcc gctctgtgct gtgctagtgt gctgcctgtg catattaatt accttttgac 40380
cagttcttca gagagctggc tgagggtttg gatttgtctc tataattgtt gttggtgctg 40440
gctagtgatt actgtaaaag catatgcacc ggatcattcc tcctgcgtcc actgtgattt 40500
ggccccacac acacacacac acacgtcgac aacaaactca ctctcttatt attaatccgt 40560
ctcaacgagc caacatattc tgacagatgc acgctgtaac ctgcctggta aaaaagattg 40620
tttttttttc tttcaaaaga aaaattgcta gctggtggat acgcgctagc tatgggctgc 40680
tgctgctgcg cccatctgcc attcccttcc ctagcgggaa cgtaaagaag gtgagagcag 40740
taggcgagcg ggcactggct ggctagaatg cgatgcaaga gcgcagtgtt gtgttggtgt 40800
gccaccaata ccattgaaag gcaagaatcc tctcagcatc aacacaacaa gtgtataaaa 40860
cagggcacgc atgcttatct tcttcttctg ctttggctta ccggtcgtct cgtctgcttc 40920
gtactgctaa gactttaggt ggtgcatgat gcatggcttt acgtgccttg cctttcatcc 40980
accaagcatc atccagaaat cctgctgggg ttttccgtcg aggtagccgg ctacttctcc 41040
ctccgctcat acaaatagtg acacaggaag gccggcgaga ggagacgtca ggctctgcat 41100
cagacatgga cgcgcgctgc ctgcgtaaaa gctgcgtacc gtgtgaggcg tggacggacg 41160
gacaggacag tgtagggcgt gcattttggc gtctcgccgt tggacagttt ctggttcacc 41220
cattgactcc cgactcccga gccgcatggc aatttcttct acggagtaga ctattttagt 41280
agcactgtag cattgtctgc aaaagtcatg tgtcagcagt tattacacaa gtagcctgag 41340
tgcctgactg ctgggaccca ccgaccccag tttcaaactt cgaaccgtac ccaacccttg 41400
tcaaaagaga gaacttcaca cactgtaaca cagcgcctct gccggcgcat ggagcagcag 41460
ggtaaaaagt taatcagatt tatatattaa aagatactga tatttcttat actcactgtt 41520
tgtctaaaac atcgtttagt tttagtctat ttaacacacc gtttgcacac ggcggtacac 41580
ggtactacac ccgggttctt ttaatcaacc gttcatccca ttaaaataat cgtttcaccc 41640
tactaagcga ctgtttagcg tgaataatgg ttaggcatta ttaagttggt atgtttttc 41700 aaagaaaaac tttggtacaa agtttgtgtt cacatgactt catacaaaat tggtatgttt 41760 ttttttaaa aaaaaatttg gtatgttgct gctccctccg cccctcccgt gagccttttg 41820
gaccaagcaa tgcaggcgat ggcaagcaca ctgtaatcta ctaatctgaa agcgcctgtc 41880
acgggaatct cgctttacct gtggctgtgg gtgggcccgc tcatttccgc ggtgcgtgat 41940
cccacgcata tgcatgcatg catacacaac gggtcaactg agcaattact gctgcaactg 42000
accaccgcgg gtcgttcgac gacccagccg ttcagctttc ggccacgcgc ccaccgagca 42060
tgtcacagca cctgcaggcc cctttggacc agcagcctcg ctctgctgct ctggccacca 42120
accccgtcgc actcagccac tgccgtggag tggattcgcg gcggacccgt gccgtcccgt 42180
acagtccaga cggtgaccga cgatgtaaca gtaacagtct gcggacggcg ggcggttcga 42240
gctgcagctt gctcccccgg tccacggccc cgtgccgctg ctctgctctg ctcccgaaag 42300
ccgcttattg ggccgacgtt aaagttgcat cacgagcccg gtctgctagt agcatgccag 42360
tcgaagcggg aaggtcatgc agtgattgca ggctagcgtg cacactcaag gcggcgcccg 42420
cagactgcag actgtcgctg ccggcgcttc cgttgcggcc cgactcggcc gttgcttgcc 42480
tccaggctcc agcatccacg cacgagccat ggcccatggg ctacgtgccc acgtctgctt 42540
cccgatggct cattacacgt ctgggctata tggcctatgg gcttcttgcg tgtagacgtt 42600
ttgtttttta aaagtataaa acctctgttt ttttttgaaa gcgagtaaac agggccagag 42660

```
ctacaccaaa tctaataatg aattggaatt tacttaataa aatagactat ttgtcgtgaa  42720
aatttacatt ccaccgcttt ttcaaaagtt tagatataag gctatcttag attaggatga  42780
gagatgaaaa ttaattttat gttgaaccaa gatatttatc tactctacaa tttataacac  42840
gttcttcatt tgattcttct acagtagaat gttgccgcat aaatatcttt atcatatggt  42900
caatccatat tagattaatt gatctatgtc taaatcacga ttattcaaat gatctaagcg  42960
ggaaatgcac ttgctttatg actggtttgg aaggaattaa ggggctttcc ttccccctcg  43020
ggccttgttt ggttacaaaa ggatcgtagg agattgaaga ggattaaatc cttcttattt  43080
aattttaact agaaagggac tccctaacct tataagccct taatctcctt taattctact  43140
attactaaac cagaccatat tagtgaaaag attcatgata atgtcttgtt tggtgacaag  43200
gggattggat aggattaaag acaaaattag ttgattttct cctcaatccg tctcaattcc  43260
cttgtgacca aagaagccct aagtgttagt tttggagcca caaaactgga atggaattca  43320
atttctttc ggatttgtgg ctcccaaact agccctaagt gcgtcgaata caatgaaaaa  43380
ttagctcaga atcatcaacc gtctctacat gaatgaaaac gctggtagca actatctttt  43440
ttttttaca ttgccaactt gccatcttgt tgagcctctt tcaaatgcca caagcaaatc  43500
tgacctgacc cccacggttc ttgtaaagag gctgagctgt tttggaagac accagctttt  43560
gctaacctga cccccacggt tcttgtacac tggatggaaa cgcttccaga tcaaacctgt  43620
ctctcaagca acaccaccta aacaacggca aggagcaacg gcgtattgtt tccttgtgga  43680
cacatcacgc ataaaaggtt atccagtata caacgagtgt gtcgaggcgt gggcaacaac  43740
agtctgaaac gttttctcaa acgtagttta attataaaac taattatata gataaaaact  43800
aaataataat tagattacat ttaatattta taataaagat taaaactttc aatgtgacaa  43860
cgtattaaat tttggcctct ggaaccaaac acctaacagt gttcttgggt ttgatgtcag  43920
gacccactga gccgatgtcg gcctctacgc ctcatcacag cacgagcatg acgaggccct  43980
tctgcctttt gtaccgatgc tccggttgct gagagtgcat gcaagaactc agcacacggt  44040
gcgctattca ccaactgttt atagtttcct ttcttgaaaa aacaccgacc aaaagctctg  44100
gtttccgcac gcccagacgt tagagatgga atgtgcaata atagcagatg atgatgatga  44160
tatgactgaa cgaggaaaaa tggccaaaac gatgatgatt gatgaatggg atcgagctgc  44220
agagctttac tacattcgcg cacggtacaa gtgatctctt acttcgacga ccaataagag  44280
aaaaagtggg cggacgatga ggaggaggag gcccggttgg tgtcgcccac cgttgcctgc  44340
ggcgacggcc cgccatcggc gaagctcagc gccggcgggg ggtacgcggc caggacgccc  44400
aacggcggga gcttcctcat agccgacagc ggcggcgaga acccgccggc atccttctcg  44460
tcgtacgcgc acgcctcctc ctccgtgacc ccgtacggcg acgagcccgg cgtctcgaac  44520
ggcggcgtct ccccaccgcc ggcggccgcg gtctgccctc ggtcgtacac cgggttggag  44580
atgcacatga acgcgtcgcc gcacgccgag gtggctcccg acgagcccga gcgcgacggc  44640
ggcggcggcg accaccgcca cacggcgccc tccagcctgg ggatggcgac gaggaggtcc  44700
ttggtgctgg gcgcgtgcag gacgccgtgc gcgtagtaga agggcggcgt gccggcgaac  44760
gcctcgcgtg acgacgacgc ggcggcgtcg cgcgccgggg acggcggcgt cgccagcgcc  44820
aggccgagct tcgaccagga cgcctcggcg cggagccgcc ggcgccggag gtgcgcgcag  44880
atgaggtccg cgaggaggag cactaggatg gtgaggaaga tggccaggct gaacgccacc  44940
gtgacgctca ccgccaccgc cagcctcgac atgccgtcgg tgaacatggc ccgctggctc  45000
```

-continued

```
cgggcgccgg cctcacgaga ccgtggcgtg gcgtggcgag cggagcggtc gcggtgcaga  45060
gctgagtgtg aggagagagc aagtgtgcag gtgcaactgc aagctcaaca aacacaagtg  45120
gcgcggcaac gggccaacgg tgagcgactg cttgaggtcc catcagacga caaaatgccc  45180
ccctcccttg acattgattg actaattcac ccggtaatta acatcctcgg cacgctttcc  45240
gaggcgagct agttgttcca aaagctagag cacggcacga ttatcgtgtg ctttgtctga  45300
atgaaccagc agccacttgt cagtaagggt ggtaatggat tgtgatccat atggttcttc  45360
acaaaatgtc aaggccctaa ataaattata gttcaaaaat gactagaaat aaaacccgat  45420
cctaatccga tttgatcctt aaatcttata gtgcaaaatt tacagcccat tgtcagccct  45480
acttgtcagc ctctgagcct tcgcacagtg gcaaccgggt cctggcccgt gtggggtccc  45540
caatcatcac gagctcgcga gtgacagcca cttgtcagcc tctgagcctt ctcacagtgg  45600
caaccggtaa ttagtgatga gcttggcccg ctctctgctt ggccctgagg ccttgtctgc  45660
gtcaactaga aggtcaagtg tagtcaaacc acagtgaaat gagtgaaaca cctgtgtatg  45720
acagttttga gagtcgaggg actatttcta catgactgat gcaatctggc taatgtttga  45780
tctgaatcaa ctgtcgtcat tgagcttttt cgcgggcaat ctggttaatg caccctcagt  45840
gtaaccgcac atcgtgcttc tacatgcagg cacaacgcgc ctcctggtac ggtcgtggac  45900
gccgaggttg agggaggcca aggacattct tatactcggt tgaagaaggc ctgttctttc  45960
tgaaagctaa cactctgcag cgccgccttg tcatcgtgac atagcgtgca aagtttggtt  46020
ctcagatgtt tagcaaatgc gtatagattg acatattgta tagttgtacc agcctactag  46080
ggtagcgcgt gagcctgata gtatatatgc atgtacgtga ttttttagc gtgaatctca  46140
ctagtacaca gaaaaactat agtgacagtc ctaaaactgt tttcactggc gtttttcagt  46200
gccgtcagtg ctaggggcta gtgaaaatcg tcattttcca ttggcggtta ttcaacaacc  46260
accagtggaa atagcatttt cactggcggt tttcttaaac aaccaccagt aaaaatagca  46320
ttttcactgg cggttttatt aagaagctgg agttgttgcg agaggagcta ggattctctg  46380
ctgccaagag gcagtggtgg ttgagcactt gagctaggaa tcgagcgaga gtaggttttt  46440
gagatatatt accacatgta catgggtata ttcaaagtct gatgcaatga aatatgcaga  46500
tacactacac cgagcaaaaa aagctgaagt aaatgcggcc taggatcggg aacaacgggt  46560
ctcaaaagtt gaagcgagaa taccgagcga gagtaggttt ttgagatata ttaccacatg  46620
tacatgggta tattcaaagt ctgatgcaat gaaatatgca gatacactac accgagcaaa  46680
aaaagctgaa gtaaatgcgg cctaggatcg ggaacaacgg gtctcaaaag ttgaagcgag  46740
aataccgagc gagagtaggt ttttgagata tattaccaca tgtacatggg tatattcaaa  46800
gtctgatgca atgaaatatg cagatacact acaccgagca aaaaaagctg aagtaaatgc  46860
ggcctaggat cgggaacaac gggtctcaaa agttgaagcg agaataccga gcgagagtag  46920
tttttgaga tatattacca catgtacatg ggtatattca aagtctgatg caatgaaata  46980
tgcagataca ctacaccgag caaaaaaagc tgaagtaaat gcggcctagg atcgggaaca  47040
acgggtctca aaagttgaag cgagaatacc gagcgagagt agtttttgag atatattacc  47100
acatgtacat gggtatattc aaagtctgat gcaatgaaat atgcagatac actacaccga  47160
gcaaaaaaag ctgaagtaaa tgcggcctag gatcgggaac aacgggtctc aaaagttgaa  47220
gcgagaatac cgagcgagag tagtttttg agatatatta ccacatgtac atgggtatat  47280
tcaaagtctg atgcaatgaa atatgcagat acactacacc gagcaaaaaa agctgaagta  47340
aatgcggcct aggatcggga acaacgggtc tcaaaagttg aagcgagaat accgagcgag  47400
```

```
agtagttttt tgagatatat taccacatgt acatgggtat attcaaagtc tgatgcaatg  47460
aaatatgcag atacactaca ccgagcaaaa aaagctgaag taaatgcggc ctaggatcgg  47520
taacaacggg tctcaaaagt tgaagcgaga ataccgagtg ataataaaaa aatcgccgtt  47580
gccggggatc gaacccgggt cgtccgcgtg acaggcggaa atacttacca ctatactaca  47640
acgacttgga tgactgtaca atctacgacc atttctagaa gtagcggaat ggcacgaaga  47700
tttcagcata tgtaactata agggcatttt acaagttttc ggctccgaag acagggaccg  47760
attggtcttc gttcggttca gatttgatca tgaccgatct ggccggacta aaaaaataat  47820
cactaaataa tgtacaccct ctgcctaaaa ttaaaattcg ttttaggctt taaatagata  47880
tacgcagtaa ttaatgtatg tgttttgtat atctatctag atttatcgtc atacctttaa  47940
atatagacgt aaaaatcaag agctaaaacg aatagataat ggtaaatata gacacataaa  48000
ttaattattg tgtggacata ttaattaact aaaataaatt ttagttttgg acggagagag  48060
tatgttattg taacgctatt agaaaaaagg gggaacagtc acacatctca atacgtgaca  48120
attggttggt aacatggcat cctatccctg atcccatacc gaacatgtag cgttaaggaa  48180
cgtatctggt gttcaaaggg ttatgatgtt catgtgcata ttttaaatct ggtgcatcta  48240
ttttacattt aacagcagca ccaattttgt gaagcacccc ttccaccttc ctcccatgat  48300
ggaaggagtt tttcgtaaaa ttagctggtg ccgttgaatg catgatggat gcaccagatt  48360
taaaatatgc atatgaacat cgtacccctt tgagcaccag atacgttccc atttgagctc  48420
tcaagttgac ctatttgggc ctaacggctt aagtcatctg tcatgcttag cagccattaa  48480
actgtctaaa aatatataaa aagtgataaa atgcacacaa atcagcaaat tcagtgcagg  48540
taacagttgg ccagatgagt ttgtaggtat tctggggaac ttggtctttg ctagatggat  48600
tttattacag tccccatgtt tgaggatatc gggaccatat gaattccatg attagcataa  48660
tttctctatt cttctatgag actgagcata gaaaacagta tgccacctat cgattctttc  48720
tacctcttga atagaagtat ctaaatttct tctgattatt ggtaccattg tgattttttt  48780
agttggtggc agcatgcatc atcaaacctc gcaagctacg agcaacagga tgctcatgaa  48840
ttctttattt ccatccttga ccatatctcc atatccatga gaatataaag gatgaccaac  48900
aaaaatcgca tgcccaaggc atgcttctct ttttgctgtt ttctgaataa aaggccttca  48960
catatgacat atgttgcagt caactgaaat ctatatcgag tggctatata tattttatat  49020
tttgtttcta gactgcaagt tagtttgcta agttatgttt aaattaaggt aagattattt  49080
agcatgatcc actgaggaca gtctcatgcc cacgttaaga agatgggtct tctctggaaa  49140
ccgtggaatt cctgttggtt agacacctgt tggggacttg ttctcaaatg ctatgaatta  49200
agaacaaggc aacataaaat gttgaatatt aacatccttc gtccatgaaa caatattccc  49260
ttgaggataa tgaaccatgg acgaaggttc atgaagacat aattacgaag gttagatctc  49320
cgtaatcata ttctcatata aaataacata agataaagga tatgaaaaga taaacgagtc  49380
atgcacaaat attaaattta cttaatatat taaattattg aatacaatta tacctctgcc  49440
ttggcaaaga ttggtttccg aaagatgcga ttacaatagc cagaatgcgt gaacagtaaa  49500
ggaatactgt tcactattta taggcacagg acacagcctg tgaggaatta caattatgcc  49560
cctcataaaa gtttacaaca ttgacccaga cctttatgga ctaaaaggtc attccatcct  49620
taagtcggtt tgtaataccg aagcttcatg atgaagaacc ttcagccatc tcactcaagc  49680
aacttcagcc aaaagccgct tcatcctaga agaccttcgg cgccgaagca tagacccaac  49740
```

```
agtagcccct ttcgcggtgc tagatcgttt ttcgtaacga gcttgatccg tgaaaaaagt  49800
ctcttaagct tcggggagcc gaaggtccaa aaaacacctt ccctgagctc gttgtcgaga  49860
aacgatttag tttcccagcg cgtagcggtc ccaccttgca gagttactgt ttgatctctg  49920
tggtccacct tgcagtgaat gcgagcgggt gcccgcctgg tgcaaaaatc ctggcgcttc  49980
gccttcctac ctgcaatact atataaacag atgagtaggt gtgaagttac cacaacattc  50040
attgctattt gcactgtttt gctgccaaaa tttttaacca ccgccgaagc ttaactctcg  50100
gaatcgaacg aagctccagt ttgaagcctg cttcgtcaga agaaaaaact tgggaggaaa  50160
aaagtattag atttttacaa attcagaatt aaatggccag agtgcgttct accgctaggg  50220
ttgagcgtga ggggggcgaa actgaagatt cggagtctgt tcccatctcc gaagcgatgc  50280
agaggtccgg gctggtaact tcggaaaaga ttcccagtga tgatgcaaaa caggcagaac  50340
aagcagttgc cgaagcggaa ggagaagata ttgaggaaac tgatcccgaa gacgattatc  50400
ggattgccat gccaagcaag cccagtcact tggacttcgg aaagtctact gtttcgaagg  50460
ctgatctctc caaaatggta aagtcgggct tttttaatga gaatcagaag aagctattac  50520
gcttcggggg agaggagact accccaaagc cagagaagga tgaaattgtc attttcaaga  50580
gctttctaaa ggctggacta aggttccccc tacatgggat tattgcagag gtactgaaga  50640
ggtttggtgt ctactttcat cagctgactc ccaacgctat tgttagactt agcgtttata  50700
tctgggccct ccgaaaccaa gcggtggagc cgtttgcgga cagcttctgt cgagttcacg  50760
aactgcacta tcagacaaag gctagaaaag atggattgca tgacaatttt ggttgctata  50820
atttcgctta ccggaaaacc acaaagtttc ctgtaatcag ctaccgaagc aaatgggcag  50880
cgggctggaa gtcgaagtgg ttctatgtca aggttgatga cgacaaggag aagcttgtgc  50940
aaagtccact tgaactaatc ttcggagaaa cccgcccccca ttgcaacatg acaccggaag  51000
gtcctactca aaaagcaatg gatgaattca gaattatcgc agagcatatc agtacaagag  51060
acctggttca ggagtttttg gctttcaagg tttttcctag tttaaaagaa tgggaaatgc  51120
cgaagccaaa gggggaaaag aaagaaggtg aacttgtgcg tttaccttac tatttcaagt  51180
ttaagaaata ctttaaaaca ccttgccaag agtggctgga tacaattgaa gtaatgtgta  51240
atgaaatact tggcaactac tccaaaaaag aagatcaatt gatgactgcg gccttcggca  51300
cccgtccgaa gcgaagactg aatcgagtgc tggatgcctt gggttttgaa taccctgact  51360
atgaaaatct gaacaaaggt gccggaggcc agaaaagaaa aaggataact gaagccttaa  51420
atgaagatga aaaagaacca ccaaaaaaga aaattccgaa gaagaggaaa gcgtcttctc  51480
cgaagcgaaa aatatccgac gaggaagaaa ccctcgcatc accctctgcc actgatgtgg  51540
aaacaatttt gaaggtaatg actgaatccc tgcctgcgaa gctaagtcca ttggggcctc  51600
aactgacaat gtttttttcag aaggaaaagg agtccgaaaa aatggagaaa acgactaaag  51660
taaagagaca gaggatcatc ggtgtgacag aggtaattga caagacaccg ccaagagctt  51720
cagctcagaa gacaccagcg gctgaggaaa ggacagatat tgaaatcaca ccttcggagg  51780
tcgcggctgc cgaagctgcc tcagctgaag atttgaacct ggagagcaca atcgaacata  51840
ttgacaaaat attgttagac atggctgcag aagaagctac caccgccgcc gaagaggcca  51900
ctgccgcagc gtcgggaaaa aggaaggaaa ttgtagatga aacttcagaa aacgaagcct  51960
tcatgtttca aaatttagtt ggagaaaaat tgtcagaacc cgaaatagaa gagcttaaag  52020
agtatgccaa atcttgcggg tacaaaccag gagcactcct cttcggaggt attgatgatg  52080
agaaattaga ttgtatccga aaccaaactg gagccaaagt tattggtact ctgtcaaaga  52140
```

```
gtatcggttt tccgaagcta gaaatggaca ttagccgcta ccgacgacaa catatcgttg  52200
gtagtttatt ttattccaat ttcaaggtga actacttttc ccttttattg tctttaataa  52260
taaaaacatg tctaacaaag gttgttttcg tgcagagtat gctgttgagc aaagccttga  52320
aaatgcagca agattctgaa gacaagaaac acgaagctat aattgaaaat ttagaaaaca  52380
aaataaagga gcaatcagat gctatcgaga aaaagaactt tgagctccag gcaaccgaag  52440
gtttattggc ggaagccgaa gcaaaaataa cagaactgaa cacgaagctt ctccgccaat  52500
ctgagcagtt tgaccaagaa aaacaagaac ttaatacaaa acttgaagcc gaagctcaac  52560
aaaattcaga tttgaaaaaa ctattggcgg gccttcaaga aaaatgtttg gaatttggca  52620
acagatgcat tcaacgacta agaaaaattt ttcactcagt tggagccagc agtgagaaat  52680
tcaccccctc agctgaagat ttatcgaaga ccttcgaaca tattgagggt gaaattgacg  52740
agctcgacga agttatagct gggcacggtg acttctgtgc ctgggtagct tctcggggca  52800
ctgctgcagc cttcctaaaa gctggctgcg atcacggaaa gattgtcaat aggcccaatt  52860
tcactttatc accatcaatc ctagatgaca ctcctgatct cgcccgaagt atttccaata  52920
gatttgtgaa aatgatatgg acaaaaggcg ggcgagaaaa ggctggagac gaagctcgga  52980
gtcattttga accagtaaga aatcatacct tgtgcttacc tcttccttca agctcaattt  53040
tgacttacaa caacttaatt catataggat gacgaagctg aagccgatga ttgaaaagaa  53100
cgacgccgaa gctaaggtcc cccgaagatt aagtagtaga ctgtagatga acttaggaaa  53160
cttttgagat aacttttgta aatgtaacta aacttgtgct taatgaattc tgttcatacc  53220
ttggattatg ctcttaccct tccattaatg tatgtgaggt gctttgttgt ggacgaaatt  53280
atcttttttg agccaaaggc gaaaaaacac cttcccttct tttcgtacac agcgaagcat  53340
agaaaacaat atttcccttt cttccgaagc tctccttttt gcacgcgaag aagctcttct  53400
cttgtaccga agcaattact tatgccatga tgatgattat cctacatatg cctggatgaa  53460
tgtttatgaa tgcaaatgct atgatgtaat gtgatgtgca aatgaatgtc caaacacata  53520
tccgaagcta tactctcagc cattattttc ttagaaacaa tcacacatca gctctgcatt  53580
cccttaggaa cgactttgga gcttcttcgc cttttacttt cggcggaatc agcgttgact  53640
ttttcgctgt aagctctgca ttccctgagg aacgactttg gagcttcttc gccttttact  53700
tttggcggaa tcagcgttga cttttcgttg taagctctgc attcccttag gaacgacttt  53760
ggagcttctt cgccttttac ttttctgcac tcgatggtgc attctcagct tttacattta  53820
catctttggg agattttact cttataaaac taaaaaagga aattacatgc gatggcccca  53880
ttaaaaacct ttctccccct ttagaaagga aaagggtgcc atgaaaaaga aaaaacataa  53940
aaaagttaca tcaagttaca cataatatcg ccgaagctca tccgcattcc aagatctagg  54000
aatgtcgtta ccgtccatat ccttcaatct gtatgaaccg ggtcttgacg aagatactac  54060
taagaaaggt ccctcccatt tcaactgcaa cttgcccact gtgtctgggt tggccactct  54120
ccgaagcacc aaatgtcctg gctcaatatt ctttagccga acctttctat ctcgccattt  54180
gattgtttcg gcttgatatt tattgatatt ttccacagct tgaagcctaa tcccttctaa  54240
agcatctttt tccacagaat aagcatcttc agaacctgat tctgccgaag ctactactct  54300
tattgatcca gttttagctt cctccggagt tattgcttcg tcaccgaata ataacttgaa  54360
tggagtaaag cctgtagacc ttgatgttgt tgtgttgtgg ctccacacca ctttggttaa  54420
ctgatctggc cactttcccc taggttgatt gaagattaac ttcattattc ctgtcattat  54480
```

```
aatgtcattg tgaaagttgc ctagaggggg gggggtgaat aggcaagcta aaacgttttc  54540
aacaaaaact agaagcaaac tgggtaaaac tgaattgatc tcgaaattca cctagttaac  54600
tttggaaatg agatgttcta aatgatccac agggttcaaa gtagtagatc tgagaagggc  54660
acttctcaaa atccacacaa caaaaagata tgaacaaatc ttccacggaa gggtgagaga  54720
acgaaaaaca caaacaaaca caatgaataa gaacacaaga gacacaagat ttatcccgag  54780
gttcggtcac accaccaagg tgccctactt cctcgttgag gcgcccacaa agagtcgggt  54840
ctctttcaac cctaatcctc cctttgccga ccacaaaggt caagcccaca caataatctt  54900
tgctcaaacg agcgggtaat acaaactttc ttgtggtctt ccacaagatt tggagactca  54960
caagagacac ctagtcgtct aggagctaga agctccaaga gtaatgaatc cacaaagaac  55020
tcgatgtagt accaaagctc gaatgaagaa gagcaagaga gatttagaga tggagcacaa  55080
aaaccgcagc tctcaagctc actcaaagat ttctctccaa agatttgaaa tgggagaggc  55140
aagagatgtg tgagagagag tgggaggtgt ttcttgggtt agaaatggag ttcaaatcgt  55200
gctcactgct ttggggagag aggtaggagg tagtatatat aggtggagct caaaactagc  55260
cgttgggcag atttttctgc ctgagaccgg ttgaacctcc ccccagggcg gttgaacctc  55320
ccctggcagg cctggcagcc tgtctgccag tctgactggc agactgacgc gcagactgac  55380
cgcagactag tcaaagttga ccaaaaccag ttgaaccgcc caggggggc ggttgaaccg  55440
cccctgacag ctcctggcga cctgtttgcc agtctgactg gcagactgca gatcagaggt  55500
cagaggggtc agagaccagc tgaactgccc ctcaggacca gttcaaccgg tcttgaccag  55560
agagtgagaa aaccccagct caactgcccg gaggcaagtt cagctggtgt atggtcaaag  55620
aggttcacag ctgaagttga gttcagctga agttcagccc agctgaaaag ctcagctgca  55680
gctgaagaag ctcaactcag ctgaagttca gctcagctga aaagctcagc tgtagctgaa  55740
gaagctcagc tcagctgaag tccagctcag ctgaaaagct cagctgcagc tgaaggagct  55800
cagctcagct gaagtccagc tcagctgaaa agctcagctg cagctgaaca agttcagctg  55860
cttttcagca agaacactct aggtttctca aacctaacca tggtcaacca tagaacgata  55920
aagagatttt tgcttttcat aaatagcttt tgaatagaga ggtttgagct ttggcaaaca  55980
ccaaccttct tttggatcc ccctttatag tacgacgatt cctatactca agttaaataa  56040
aataaaatga agtaaactcc ttgagtcatt ggtgtctcat gtgtgatttc tccatggcat  56100
tgcttcataa ggatcacaaa catctttgtc tcaccttttg aagcaaactc aaatcaaacc  56160
ctgtgacttg taccatatca ccttatatga gttcaaatca tggcttcaag tcaccttact  56220
gatgcatcaa catgttgtaa ctcttcatag ctgattagtt catcgactta gtgcaagtac  56280
tctcttcttc accttagcca tggtacctcg gtctacaagc cgtcgcttgg ccttcacctt  56340
cgcttagttc ctcgaagccc tttccttgct atcttcaccc tatcaagcca ttcttgagtc  56400
acatcctatt gagcatccat taagagaatc atttcttcaa tattgtgaac cttgcttgaa  56460
tgtcttctag atataactat taagattaat caagctttag tttgattctc atatattcat  56520
atatggacta atagtaatat ggtcaagcca attcacgatt cctcatatct tattcacttt  56580
ggcttgacca atcctcttaa tcacttcaac ctctattatg atcatattta tgcatagtga  56640
tttctcagga cttgtccata tattcaaacc aatatagaga ccatattata tccatttgca  56700
ttgtctcact ggttatttca ccttgtgttg aaccttgttc actgatcatt atacactatt  56760
caagtatgtt catcatactg aatttcctgt tcaacactta gcaaacttgt tagaccttta  56820
aatgtgttgt tatccaaatc accaaaactc acaaaaggga tgaatgcact ttcaatctcc  56880
```

```
ccctttttgg tgattgatga caacacattt aaagcttaca taagatttga taaataagat  56940
tttgaatcct atgatatagt ttcctccccc taaacatgtg catttcagaa aataacactt  57000
ttgtactcaa atgccaaaag cacatattta ggtcaaagta tagacaactt atatcatact  57060
attcataggg tgcagtgtgt cataaaataa acgtgatgct catgacatgg aatgcactta  57120
tcaactttct tcatcttatg tttttcttat gattccccct tttgttaatt atttctcccc  57180
ttttctaaaa taaagataag ctttaatgca aaatttctcc ccctttgtca taaatctcca  57240
aaaaggttac aaagaatata aagggtagaa attatgattt aagcaagatg tgaacacact  57300
atcatgaaag ggatccttag atggcacaaa ggtaatggat aagtgtcata agtgatgtac  57360
ctttgcgttt taccttttca aggggtttcc agacttgtgt tggatttaga attcatttgc  57420
aagctcttgt tggcataatt gtgacatagg tccaagatat caaatgaaga ttgtcatact  57480
aactgaaaga taaatcttga tacctggagt ctagatgtca cctagcattt tcttatcaca  57540
acaagaggca acatgaaaat tgcacaaata tggattatgc aactagtgat catgtatgaa  57600
aaatatcaat tgaaaaacac caattgatac aatttgatag ataaatagat cactaatagc  57660
atattacact aagttctcct caagttttag tgcacacata tatatgtatt caattgatac  57720
ctattgagag tacttatttg caatttaaag taccattggc ataaaaaagt atcatatgaa  57780
tataatcata caacataagg aacatgtgca ctatttaatc aattaagttc tagaaggaga  57840
atctataagt tatgctactt cagatatttg taataaaaaa agatgtgata catatttacc  57900
aattttagat gacgttggag tagcatatac aggagaaact cattctctta tgaaatgtat  57960
agaagataca tttattggag caaagaatct ttgataccca tcaaaatttg cagtggaagc  58020
gattgtcttt gcccgaagat tcctttctaa ttcgagacta cacacataat agacttggaa  58080
atgaagttag tctcaaagat tcaaattata gactattctc cccctaaatg tgtgcataca  58140
agtgatgaat acttgtttag cttatgcact tggacttgtg aggccagggg attaagtcct  58200
acaatttgaa ccttggtaca aataaagtat gaaaatgtga aattgtacca atttaaggaa  58260
ttactcataa ttaaaaggta tattaataga catgatatgc aatattttaa gtcaagattc  58320
ttgagaagtt agcatgtttg actcatacct cactaagatg acttaagact aacttatgat  58380
atcaccacaa gaggtattaa tcaaatatct agagattctt taatcgtcac cacaagtgca  58440
accttatgat gtgacttaag atattgcata tacatgcaca cactagcatg taagagccta  58500
gatacacaaa tgtaatacaa tagttcatgg agtgacacac ctttgttcta cgccacatgg  58560
tctccattat aatcatgaat ttccatctta gcttttgata ggattgacat ttcaaagaga  58620
aactcatcct cttcaaacga tcaagagaaa ctcattttct tgataggttc aagagaaact  58680
cattttcatt tctatggaac cattcatcct catttgaagc tctccaaggt gtgagactac  58740
acaacatgaa cttgaaagaa atcattagtc tcacaagata taggctaaac tctccctcaa  58800
tttgtgcatg caagagtaca caaagtacac ttatgcacat taacaatgtg aggttaaagg  58860
agatgtttgt actatatctt ggcttaacat aacatgcttt atatagatga tgaaaattaa  58920
accaattgaa gatttaagaa ctgaaagtat atcaattgaa atcctgaagg gtaaagcatg  58980
ctaatatgaa cctcaaacct cataatgaag gatatcatat aaatatgtca ctacatcttc  59040
attatttggt tgacaaaaaa ataactccct tcttgaatca ctgtgatctc ttttctcttt  59100
acgatttcat ccaaccaagt gatcttgaac ttctttcatc ttttcttgat tcgatcatac  59160
ttgatatgag atcaattgaa actcaatgat tgaaacaacc aagactctta tatccgtaga  59220
```

```
ttttaaatcc atcttgaaaa cacttggaag gaccttattg aaacacttag aaaagagagc  59280
attagaaaaa caagggaggg tttcacaaat gataatcctt atatgtggat ggagaatgaa  59340
tcatcattct tgaaacccaa aggatagat taaattcctt taaactagtg cacacatata  59400
gttgatctca aagttatatg cactgttgaa cattttatat tgcaaggaaa ttaacctata  59460
ctatggtaca tcccactaag gatagaatac taaaacaact gaaggagagg aagttttcat  59520
accttggcct cttatcaact tcatcttact ttagttgaat aatatccttt aagcttgtga  59580
tttatccaat ttaaaacaag caccatctct taacatagat tttctatgga taaactcagc  59640
acaagagatg gaattagtag cacaagcact agtttcttat ttagcaaccc tttatatgtg  59700
gaaggcaagc gagttgctaa aatagagaaa cctcataata tggactaaat ttccttgaac  59760
cctcatgcac aatatatttt gaatgacatg gataaatatgc atggttgttc aatgaagtct  59820
aaaagggctg acttaatcca tattatggta agtgtctaat aaagaagaat caaatccaaa  59880
ttaactagat agagaatacg tcacataatt ttggattgtt caccatatga taatattcat  59940
tcatcttcca attagacctt tatttcataa tcaacaactg atgtatatcc tcaagtgctt  60000
cttttccctt agtggctaca caagtcacaa aagagataag atttgaaaat aatttgcact  60060
tgagattcag ttgttaccac ccttgctact atctccaaat atgatttata cattcattat  60120
cgagcatcca acttgatcca ttgaaggaat gatcctgcaa aacaagttta agcttcatat  60180
cttggtgccc aatttgaatt gggtcctttg agattagtag gaagagcctt gagtacccac  60240
acaatcctta ttgtgacctt tctctttgtg taggcaccca aatatacttg acaaccatct  60300
tacatggttt caagtcaata tttaatcaca cagataaaag ctagagttaa gaataggagc  60360
cttttctcct tttcttgata catcattatg ttgccttctt gatgatgaac ctagcttgac  60420
cttgggtgca cctagcttat caaggttagt cgcacaagca ttcatatcat aaagacaagt  60480
tatgcatgga atttacaact tagtgatcca attcaatgtg aagcatatgg atatcgattg  60540
aagtagattt ctaaaatatc aaaatatggg ttttcaaaat ttagagagta tggatcacta  60600
attgtacctt ttacagttta aaaatcatat ccatgttagt gcatatgtat gtgatgaata  60660
tcaacaaaaa gattcttatg cacttttaga attaacgata aggaaatttt aaactgcatc  60720
aagagtagct atttagaaaa caaagattac aatccatatg aatgagatac aaatttacca  60780
ttttggattg tcttagtata gcttactcaa gagaaactta ttctctatga cacaagatat  60840
ataatgttct cccactagat atgtgcatca agtatttgaa tgacttgcca catgcacttt  60900
caattcagtt aagagtctca tgaggagtac attacatatc atggtcaagg catgacaaat  60960
ttgcaatgaa ttaacttatc cttaagaata cttaccacca agtagagcgt accatttgtt  61020
ataccaattt gaaagatctt actatctgtg gtggtgtcat cgtagtattc ttcttttcat  61080
catttgtgga gacttccttc tttagcttgt tatctctttt ccttttaata ctagttgaaa  61140
aagaactttg aaaagagata ttagtagtac aaggaagtat ttaatgaatg gtgatcttta  61200
gatatgaatt gcacacaaat catcatttat gaggcataaa gacataaatt aaattccttt  61260
taaattaatg cacatggagc agtgaattca caatatgcac taatttacaa atttaagcca  61320
aaaggaattt aacctttata ttgacatttc ttttcataga atatattatt accaattgaa  61380
agaatgccac ttggaaggaa ctactattga tcaactacca attgaagcaa tttgttccat  61440
acctttgcct tgagcattcc taatctttct tttaggtgaa gattaacctt ttaaagcttg  61500
tgattttacc aattgaaaga gcacaatctc tacttatgaa tttccatgaa atatcttaaa  61560
agagattgta ttagtaacac aagcaatagt ttcctattta gcaacctcta gtatatgaat  61620
```

```
gacaagaagg ttactaaaac aaggaaactt catgatatga actaaattac ccttacaagc  61680
atcatgcata acatcaatta aaaaaacgaa agtagcatga ttatttaatt aagtttacat  61740
ggcaagttta attcatagca tggtgagtga ttaatgtaga agactcaaaa ccaatttaaa  61800
caagaatgaa tacttcacat agtattggtt cgatcttctt tgaatgttga atggcacact  61860
ccatttggga aacacattct catgttgtga aactacataa atcacttaga taaaaacatt  61920
agtctcacaa ctctagtcat atagagaatt tccctttttgg taagtgcttt aagaatttga  61980
atttcttact tagcactcta ttcatttaag aacatgggat aatcctcttt atgtctaggt  62040
catggcaata atacgataat caatttgaaa tatgccacaa gatacataca accaatttaa  62100
agcatgtaga ttgtcataat ataaaaatat gaacgtgcaa tctaccatat aattagatcc  62160
tttccaaagc aaggtaaaat cttttaagtt cattctcaag tgcttcattt ttcctatgtg  62220
gctacaaaag acacaaagga atatactaat taaaagcaat gtgcacttaa gaattaattg  62280
ttaccatcct ttggatatca cttggttgta ggcctttttgc ttgattccca caaaggttaa  62340
tccttattcc ctacaacaca agttcttggt agagatgaat atgaagttag tgatataaca  62400
actcaattca tctttgggtc aatcttaaag gatatacaat gtaagattga tagcttgaga  62460
taagaattga gttaaaccgc tcaagcaccc ccaaagcttc atatcatctg tgggtacctg  62520
caaaacttat caagtacatt ttggtaccca tctttggatg ggtccatcaa ggttagccaa  62580
taaggactta ggcacccaaa tagccttggt cctagaatgt ggtgaactca tcacctttct  62640
agcacaagag tcaaatttgg gtctcctaag catatttgaa tgtattgaca agttaggctt  62700
aggagtttta ccctttggac aaaccttgaa tagatgacct ttttcacggc aattgtagca  62760
aatgcgatgc ttgtccttgc aatgcatttg ccttttgctt tcatcctttt tgatggtcat  62820
ctttcttgat cgtgcaaggt cttgattctt catgtggggg catgaatcaa tttcatggcc  62880
tttctccttg catccatagc acctcctatc gcttctcttt gatctttctt tgttgaagca  62940
cataggtaca ttgttagagc aaatcatatg agcattaatt ttctcaccat ggatttttct  63000
catgcccttc ttggaaagtt tggttttctt ttgaaggggt tttgtgcatg ctacggttgt  63060
ccccttctca agctttttca ccatattatc acggttatct tgagaaggtt gagcatgaca  63120
ctttcccttc aaacgagtta agctccttct tagcattcca acttcttcct tgagctcttt  63180
attttcttgt gtgatagaaa tatcactaat tcctgaaatt tctagctcaa tggaagattg  63240
gctttcttga gagcaacatt tgttagcaca tgataatata gtttctactt gagtacatgt  63300
gcatatgtga ggttggtatg atttcaaatt agttaacaca acctcatgag ccatttctaa  63360
catgatatgt gaatccataa atttattatg atagcacaca agcatatcat gtttttcttg  63420
caaagctaga ttttcaatat ttagcctttc tatcgtgttc ttgagcatag tatttttcttt  63480
ttctaattga gcaacgcaag ataaagcatt tgaagtacta gtttgctcaa ttgaaatctt  63540
ttcatacctt tggaccaaat catcatgaga gcactttagc ttctcatgct ctttggtcaa  63600
cttctccaag tctttgattt tttcgatgag gatatcttct tgcttatgaa gcatttcctt  63660
ttgttcttcc gctcttttca taagtttgag caagctcatc cggttcttct tacttagttg  63720
agcgaagaat ttttgaagat catcctcatc ttcactatca ctttcatgct cctcctcatc  63780
ctcactttcg ctttcactgt cactctcatt agcaacaaag cacatatgag aagtggattt  63840
gaaagacgaa ccttgtgaag aggtggattc atcgtttggt ctccatcgat cattttcttc  63900
ttcttcaata atgttcttcg cctcatcttc cttcattttg aggaacatcc tttcggcgat  63960
```

```
tctcatggca agatctattg ccctaggatc aacatctgca ccaaaagata aagtcgaggc  64020
aacctcaact ttttcaagct tagaagcact ttcgtttctt agtccccccg acatgatctt  64080
tcctcacgcg gttaagcgtt agaacgagga ttaggctctg ataccaattg aaagttgcct  64140
agaggggggg tgaataggca agttaaaact ttttcaacaa aaactagaag caaactgggt  64200
aaaactgaat tgatctcgaa attcacccag ttaactttgg aaatgagatg ttctaaatga  64260
tccacagggt tcaaagtagt agatctgaga agggcacttc tcaaaatcca cacaacaaaa  64320
agatatgaac aaatcttcca cggaagggtg agagaacgaa aaacacaaac aaacacaatg  64380
aataagaaca caagagacac aagatttatc ccgaggttcg gtcacaccac caaggtgccc  64440
tacttcctcg ttgaggcgcc cacaaagagc cgggtctctt tcaaccctaa tcctcccttt  64500
gccgaccaca aaggtcaagc ccacacaata atctttgctc aaacgagcgg gtaatacaaa  64560
ctttcttgtg gtcttccaca agatttggag actcacaaga gacacctagt cgtctaggag  64620
ctagaagctc caagagtaat gaatccacaa agaactcgat gtagtaccaa agctcgaatg  64680
aagaagagca agagagattt agagatggag cacaaaaacc gcagctctca agctcactca  64740
aagatttctc tccaaagatt tgaaatggga gaggcaagag atgtgtgaga gagagtggga  64800
ggtgtttctt gggttagaaa tggagttcaa atcgtgctca ctgctttggg gagagaggta  64860
ggaggtagta tatataggtg gagctcaaaa ctagccgttg agcagatttt tctgcctgag  64920
accggttgaa cctcccccca gggcggttga acctcccctg gcaggcctgg cagcctgtct  64980
gccagtctga ctggcagact gacgcgcaga ctgaccgcag actggtcaaa gttgaccaaa  65040
accagttgaa ccgcccaggg ggggtggttg aaccgcccct gacagctcct ggcgacctgt  65100
ttgccagtct gactagcaga ctgcagatca gaggtcagag gggtcagaga ccagctgaac  65160
tgcccctcag gaccagttca accggtcttg accagagagt ttaggagaga aaaccccagc  65220
tcaactgccc ggaggcaagt tcagctggtg tatggtcaaa gaggttcaca gctgaagttg  65280
agttcagctg aagttcagcc cagctgaaaa gctcagctgc agctgaagaa gctcaactca  65340
gctgaagttc agctcagctg tagctgaaga agctcagctc agctgaagtc cagctcagct  65400
gaaaagctca gctgcagctg aaggagctca gctcagctga agtccagctc agctgaaaag  65460
ctcagctgca gctgaacaag ttcagctgct tttcagcaag aacactctag gtttctcaaa  65520
cctaaccatg gtcaaccata gaacgataaa gagatttttg cttttcataa atagcttttg  65580
aatagagagg tttgagcttt ggcaaacacc aaccttcttt ttggatcccc ctttatagta  65640
cgacgattcc tatactcaag ttaaataaaa taaaatgaag taaactcctt gagtcattgg  65700
tgtctcatgt gtgatttctc catggcattg cttcataagg atcacaaaca tctttgtctc  65760
accttttgaa gcaaactcaa atcaaaccct gtgacttgta ccatatcacc ttatatgagt  65820
tcaaatcatg gcttcaagtc accttactga tgcatcaaca tgttgtaact cttcatagct  65880
gattagttca tcgacttagt gcaagtactc tcttcttcac cttagccatg gtacctcggt  65940
ctacaagccg tcgcttggcc ttcaccttcg cttagttcct cgaagccctt tcccttgcta  66000
tcttcaccct atcaagccat tcttgaagtc acatcctatt gagcatccat taagagaatc  66060
atttctttca atattgtgaa cccttgcttg aaatgtcttc tagatataaa ctattaagat  66120
taatcaagct ttagtttgat tctcatatat tcatatatgg actaaatagt aaatatggtc  66180
aagccaattc acgattcctc atatcttatt cactttggct tgaccaatcc tcttaatcac  66240
ttcaacctct attatgatca tatttatgca tagtgatttc tcaggacttg tccatatatt  66300
caaaccaata tagagaccat attatatcca tttgcattgt ctcactggtt atttcacctt  66360
```

```
gtgttgaacc ttgttcactg atcattatac actattcaag tatgttcatc atactgaatt  66420
tcctgttcaa cacttagcaa acttgttaga cctttaaatg tgttgttatc caaatcacca  66480
aaactcacaa aagggatgaa tgcactttca cattggctct ttcaacgagc ccatttgact  66540
ccggatgcct gactgatgca aaatggatct tcgtaccaat ttgatcacag aaatccctaa  66600
aagcttcgga gtcgaactgt gttccattat ccacagtgat ggtctttggt accccgaaac  66660
gacaaacaat attctgccag aaaaactttt gaatggtggc cgaagttatt gtggctaaag  66720
gctttgcctc aatccattta gaaaaatatt ccacagccac cacaacatat cttaagttcc  66780
cttggaccgg tggtaatgga cccaacaagt caaggcccca cctttgcaat ggccagatgg  66840
gttgtatgag ttgtgttaaa gacgaaggtt gtttttgatc tcttgcacat ttctgacaac  66900
cttcgcactt ttgaactaat tccgctgcat ccgaagctgc cttcggccaa taaaaccctt  66960
gacggaaaac ttttccaagt aacggcctag atccaatgtg agatccacac aggcctgcat  67020
gtatttcttt catcaactct atgccttcgg ttctagataa acacttgagc aatggagcac  67080
aaactccatg cttgtacaac tccccttcta tcatgacata tggacgagct cttgcctcta  67140
tcctcctgtt ataagtttcg tcatctgaaa ggaatttacc ctgaagataa gagatgattt  67200
cagttctcca atcttcgcta taaacaggag atatattgag gactgctctt tcaaggagtt  67260
ccactgaagg tgcctttatt gttcgaagaa cacatccgaa ggtaaaggca gcccctgtgg  67320
ctgctgactt agctagcaaa tcagcatgtt cattttgtcc tcgagggata ttcttgacag  67380
aaaatccttc gaaggaagct tcaattcttc gaaccatgtc tagatatttt tcaagcttcg  67440
gatctttaac cttgcaactc ttgtcgatat gacccgaaca ccacctgaga atcagtttta  67500
agaatggccc ttctgaaaaa aaaaaaactt ttagcttccg aagacccaaa agcagggctt  67560
cgtactcggt aaatattgtt tgtacaactg aaatcgagtc ttgccgcata acaagtttta  67620
acttgggatg gcgaaaccaa cacagcagct gctcctgccc cgaaggttcc ccaagaccca  67680
ccgcaaaaca ctgtccacac ttcggcatct ttatttgttt cttcatcctg agcccctggc  67740
gtccagtcaa caatgaagtc tgctaacgcc tgggactgga tcgaagatct atgcacataa  67800
tcaatgcaaa attcattgag ctctgcagcc ccattttcca atccgcccag tagcttctct  67860
atttctcata atatccttca acggctgcga agaaggaaca acaatattgt atgcttgaaa  67920
gtagtgccga agcttcctgg atgccatcaa aacagcatat aataccttct ctaattctgt  67980
gtagtttttc tttgatatac taagaacttc agatacaaag tacattggga cctgcttctt  68040
gacttggcca tcaagcttct cctgaacaag tgctgcactt accgctgagt gcgaagctgc  68100
cacatataat aacaaaggag cccctggcgt tggtggagtt aatgttgtta aatctatcag  68160
atattgcttc agttcctcga aggctttttg ttggcttggt ccccattgaa agacttcggc  68220
tgatttcagc acttcgaaga atggtaaatt tctttctgct gatctagcta taaatctatt  68280
aagagatgcc aacctccctg ttaatctttg gacccccttt tttgtagttg gtggctccat  68340
tcgaagtata gcttcaattt tacttggatt agcttcaatt ccctttgttg ataccaagca  68400
tccaagaaat tttcccttct tcactccgaa gacacatttt tccgggttca attttaaacc  68460
agcttgtctg aaactggcga aggtctcctg caaatcagca atatgatttt cctgttttgt  68520
gctttttaca atgatgtcat caacataagt tagcacattt ctgccgatct gagagtggag  68580
aaccttcgca gtcattctgc tgaaacttcc tccagcgttt tttagcccct caggcatccg  68640
aagatagcaa tatgtgccac ttggggttat gaagctagtc ttcggctcat cttccttctt  68700
```

```
catccagatt tggtggtagc ctgagtaaca gtctagcaga ctcatgagct ctgaagaagc  68760
tgctgcatca actaacgagt ctatccttgg caatgggaat tcatccttcg gacaagcctt  68820
gttaagatct gtaaaatcga tacacattcg ccacttgcca ttggcctttt ttaccataac  68880
agtgttagct agccattctg ggtactttac ttctctgata actcctgcac tgaggagcct  68940
tttgacttca ttacgagcac cttcggcctt atcatcagac attttccgaa gcctctgctt  69000
tctaggtctg aaggatgggt caacattgag cgagtgttca ataacatccc tatttactcc  69060
gcagagatca ttggctgacc atgcaaaaac atctttgttg ttgaacaaaa accttatcaa  69120
ggttttctcc tgttcttcgg ataattgaga gcccaacagc accttctgct ctgctatgtc  69180
ttcacataag agcatgggct tcggctgatc cgctgaagct gctttctccc ttctgaattt  69240
gtactgttca caagcttcag ctccatctat gttatggatt gcttttgagt cagtccagtt  69300
cccttcggcc cttctggcag cttcctgact tccatgaata gcgatgggtc cttgatccga  69360
aggtatcttc atgcaaagat aagcaggatg aagaattgct tcgaaagcat tgagggtgcc  69420
acgaccaata attgcattgt aagggtattc catgtcaaca atgtcaaata taacttgctc  69480
agttctagtg ttgttgatga acccgaaggt cactgacatg gtgatcttgc ccagtgctac  69540
aatctgcctt cctccgaagc cacagagagg atgtgtagca tcatgaatct tatcttctgg  69600
ctcttgcatt tgtctgaagg ccttagcaaa tatgatatca gctgcactgc ctgtgtcaac  69660
caagacatta tggaccagaa atcctttgat aacacaagag ataaccatgg catcattgtg  69720
tgggtaatcc ttgagttgaa ggtcctcttg ggagaaggta atagggatgt gagaccatct  69780
tgacttgatg aagggtcctt gcaccccaac atgctgtacc cttctctgtg cttccttctt  69840
ctgcttcttg ttggctggct ctgaacatga accgcctgtt atcgggagta gcagcttcgg  69900
agccgaagca gctccagctt gatcgttgaa cgaagccatc agctcaaaaa agtggaagtg  69960
agttcaccgg aggtgggcgc caatgttggg gacttgttct caaatgctat gaattaagaa  70020
caagacaaca taaaatgttg aatattaaca tccttcgtcc atgaaacaat attcccttga  70080
ggataatgaa ccatggacga aggttcatga agacataatt acgaaggtta gatctccgta  70140
atcatattct catataaaat aacataagat aaaggatatg aaaagataaa cgagtcatgc  70200
acaaatattt acttaatata ttaaattatt gaatacatta tacctctgcc ttggcaaaga  70260
ttggtttccg aaagatgcga ttacaatagc cagaatgcgt gaacagtaaa ggaatactgt  70320
tcactattta taggcacagg acacagcctg tgaggaatta caattatgcc cctcataaaa  70380
gtttacaaca ttgacccaga cctttatgga ctaaaaggtc attccatcct taagtcggtt  70440
tgtaataccg aagcttcatg atgaagaacc ttcggccatc tcactcaagc aacttcagcc  70500
aaaagccgct tcttcctaga agaccttcgg cgccgaagca tagacccaac aacaccattc  70560
attcgttcgt tcatgtccat atctcgtcat tcatgttcga ttggacaagc acattggttg  70620
ttgcatattg acaagtccgt cgtacctgaa tctttgttcg gttagggccc ccatcacaaa  70680
gaaccccaca tacgtcccgc acggcggcac gagcacgagc cccttcaccg acacggcgac  70740
accatcagtc caccggcacc gactactcag accgagcctc cctccactcc ggcacggcac  70800
acgccagcga accggtcggg gtttccatcc aatcccgtca cgcacgccga gccatggcga  70860
gaccaaacaa agcttcctcc cggcgtcccc gcacggcagg gggagagtat gcgatgtgac  70920
cgagatcgag agcgaccggg cgggagcccc atccgcatcc gcgggacagc aacgcgcgtc  70980
cgaacccgag ccggcgccac cgctacctgc gtgcgtcgcc cgccaccgcc agaccgccag  71040
agccaatcag ccaagtactc ccatgtaaca cccgaaatcc tgtgcttaga attataaatg  71100
```

```
tttttatagg aagttttgtg ataaaaggac ttctaataaa aatttccgtc ctctataaaa  71160
tataataata agcaagaatc tggtattcga agcatagatc taaaacctaa agctaggagt  71220
tgaaaccaca tataagagag agacttttaa actaactatt gtttctttta atcaaaacca  71280
tccctaaaaa gataattgaa ctaaaataat tcatgagaaa gattacatat taacatagcc  71340
gaagtaaata taactaaaga tgattattta tcttaagtgt gcattcaaag ataaaatttc  71400
cttaaaaaaa ataatatgtg tataatccat cattagagca tttatctaaa tggatacaaa  71460
taaataaaag aaataagtaa aaattatgca tcatgcttga cctttgggtg tgaattcttg  71520
tattcaaaat tgaatctaag attgaattat gaaaattgaa aactaaaatc agaaaagatc  71580
aaaagaaagg agaaaataaa aaggaaaaag caaaagaata atggaagcca gcgtctgggc  71640
ctatttttcg ctgcctcggc ccattcccca ctatcttcgc gcggcccatt ggctcccact  71700
gcgccgctcc tacaccgaca ggtgggaccc gcgctatcag acactgtgtc gcacgctggt  71760
tgcctggtgt ctccgactcg tggggccgga tcgtcagtct tgaaagggaa ttaggcttat  71820
acctagttcc taaataattt tggtggttga attgcccaac acaaatcttt ggactaacta  71880
gtttgctcta gtatatagat tatacaggtg taaaaggttc acactcagcc aataaaaaga  71940
ccaagttttg gattcaacaa ggagcaaagg ggcaaccgaa ggcacccctg gtctggcgca  72000
ccggactgtc cggtgcgcca ccgggacatg tccggtgcac cagggggact cagactcaaa  72060
ctcgccacct tcgggaattt ctagaggcga ctcggctaaa attcaccgga ctgtccggtg  72120
tacaccggac agtgtccggt gctccaaggg aggtcgtcct caggaactcg ccagcctcgg  72180
gttttcactc cagccgctcc gctataattc accggactgt ccggtgcatc tgcggagcaa  72240
cggctacttc aggcgccaac ggctacctgc tgcgcattta ttgcgcgcca gcgcgcgcag  72300
aggtcaggca cgcccatgct ggcgcaccgg acagtgaaca gtgcatgtcc ggtgcgccac  72360
cggacatcaa gcggggccca gaagtcagag ctccaacggt cagaatccaa cggcagagat  72420
gacgtggcag ggggcaccgg actgtccggt gtgcaccgga ctatccggtg tgccatcgaa  72480
cagacagctt ccaccaacgg tcatgtttgg tggttggggc tataaatacc ccaaccaccc  72540
caccattcat tgcatccaag tcttccactt ctcaacctct tacaagagct aggcattcaa  72600
ttctagacac acccaaagag atcaaatcct ctccaattcc atacaaagcc taagtgacta  72660
gtgagagtga tttgccgtgt tcatttgagc tcttgcgctt ggatcgcttt ctttctttct  72720
cacttgttct tgtgatcaac actcaattgt aatcaaggca agaggcacca attgtgtggt  72780
ggcccttgcg gggaagtttt gttcccgact ttgatttgag aagagaaagc tcactcggtc  72840
cacggaccgt ttgagagagg gaagggttga aagagacccg gcctttgtgg cctcctcaac  72900
ggggagtagg tttgagagaa ccaaacctcg gtaaaacaaa tcctcgtgtc tcacttcatt  72960
attcgcttgc gatttgtttt gcgccctctc tcgcggactc ttttatattt ctaacactaa  73020
cccggcttgt agttgtgttt atatttgtaa atttcagttt cgccctattc accccccccct  73080
ctaggcgact atcaattggt atcagagccc ggtgcttcat tagagcctaa ccgctcgaag  73140
tgatgtcggg agatcacgcc aagaaggaga tggagaccgg cgacaagccc actacaagtc  73200
aagggagcac ttcgtcggaa gagtcccaca ccaagaggaa ggagaagagg aaggtctcct  73260
ccaaagggaa ggagaaaaga ctttcttcgc accgcgaaga aaagaaggac tcctccaaag  73320
ggaaggagaa atcttcttcg catcacaaag agaagaaaga aaagtcctct tcccacaagc  73380
cgcatcggag tggtgacaag aagaagagga tgaggaaggt ggtctattac gagaccgaca  73440
```

```
cttcatggac atctacctcc ggctccgacg cggcgtccgt cacttctaaa cgccaagagc  73500
gtaagaagta tagtaagatt cccctacgct acccccgcat ttctaaacat acacctttac  73560
tttccgttcc attaggcaaa ccaccaactt ttaatggtga agattatgca atgtggagtg  73620
atttaatgcg atttcatcta acctcactcc acaaaagtat atgggatgtt gttgagtttg  73680
gtgtacaggt accatccata ggggatgaag actatgacac agatgaagtg gcccaaatcg  73740
agcacttcaa ctctcaagct acaacaatac tcctcgcctc tataagcaag gaggaatata  73800
acaaggtgca agggttgaaa agcgcaaaag agatttggga cctactcaag accgcgcacg  73860
agggtgatga actcaccaaa atcaccaagc gcgaaacgat cgagggggag ctcggtcgct  73920
ttcgtcttcg cccaggggag gagccacaag atatgtacaa ccggctcaag accttggtga  73980
atcaagtgcg caacctcggg agcaaaaagt gggatgacca cgaagtggtt aaggttattt  74040
taagagctct tattttcctt aaccccacac aagttcaatt aattcgtggt aatcctagat  74100
atccactaat gacccccgag gaagttatcg ggaattttgt gagctttgaa tgcatgatca  74160
aaggatcaaa gaagatcaac gagcttgacg aaccttccac atccgaggcg caaccggtgg  74220
ccttcaaggc aacggaggag aataaggagg agtctacacc aagtagacaa ccaattgacg  74280
cctccaagct cgataatgag gagatggctt taatcatcaa aagctttcgc caaatcctca  74340
agcaacggag ggggaaggac tacaaatccc gctccaagaa ggtttgctac aagtgtggta  74400
agcccggtca ttttattgca aaatgtccta tgtctagtga cagtgacagg ggcgacgaca  74460
agaagggaaa gaggagagaa aagaagaagt attacaagaa gaagggcggc gatgcccatg  74520
tttgtcggga gtgggactcc gacgaaagct caagcgactc ctccgacgac gaggacgccg  74580
ccaacatcgc cgtcaccaag ggacttctct tccccaacgt cggccacaag tgcctcatgg  74640
caaaggacgg caaaaagaag aaggttaact ctaaatcctc cacaaaatat gaatcctcta  74700
gtgatgacca tgctagtgat gaggaggata acttgcttac cctttttgcc aatcttaaca  74760
tggaacaaaa agaaaaatta aatgaattga ttagtgctat tcatgaaaag gatgaccttt  74820
tggattccca agaggatttt ctaattaaag aaaataagaa acatgttaag gttaaaaatg  74880
cttacgctct acaagttgaa aaatgtgaaa aattgtctag tgagctaagc acttgccgtg  74940
agatgattga caaccttaga aatgaaaatg ctagtttaaa tgctaaggtt gattctcatg  75000
tttgtaatgt ttcaattccc aatcctagag ataataatga tgatttggtt gctaggattg  75060
aagaattaaa catttctctt gctagcctta gattagagaa tgaaaatttg attgctaagg  75120
ctaaagattt tgatgtttgc aaagttacaa ttgccaatct tagagataag aatgatatac  75180
ttcgtgctaa gattgttgaa cttaattctt gcaaaccatc tacatctacc attgagcatg  75240
tcactatttg tactagatgt agaaatgttg atattgatgc tattcatgat catatggctt  75300
taattaaaca acaaaatgat catatagcaa aactagatgc taaaattgcc gagcacaacc  75360
tagagaatga gaaatttaaa tttgctcgta gcatgcttta taatgggaga cgccctggca  75420
tcaaggatgg cattggcttc caaaggggag acaatgtcaa acttaatgcc cctccaaaga  75480
acttatctaa ctttgttaag ggcaaggctc tcatgcctca ggataacgag ggttacattt  75540
tataccctgc cggctatctt gagagcaaaa ttaggaaaat tcattctagg aagtctcact  75600
ctggccctaa ctatgctttt atgtataagg gtgagacatc tagttctagg caaccaaccc  75660
gtgctaagtt gcctaagaag aaaatttcta atgcatcaaa tgaacatagc atttcattta  75720
agacttttga tgcatcctat gttttgacta acaaatccgg caaggtcgtt gccaagtttg  75780
ttgggggcaa acacaagggg tcaaagactt gtgtttgggt acccaaagtt cttgtttcta  75840
```

```
atgccaaagg acccaaaaca gtttgggtac ctaaagtcaa gaactaaatt tgttttatag  75900
gtttatgcat ccgggggctc aagttggata ctcgacagcg ggtgcacaaa ccatatgacc  75960
ggggagaaaa ggatgttctc ctcatatgag aaaaaccaag atccccaacg agcgatcaca  76020
ttcagggatg gaaatcaagg tttggtcaaa ggtttgggta aaattgctat atctcctgac  76080
cattccattt caaatgtttt cttgttgatt cattagatta caatttgctt tccgtatccc  76140
aattgtgtca aatgggctac aactgtctat ttactgatgt aggtgtcact gtctttagaa  76200
gaagtgatga ttcaatagca tttaagggag tgttagaggg tcagctatac ttggtagatt  76260
ttgataaagc tgaactcgac acttgcttag ttgctaagac taacttgggt tggctctggc  76320
accgccgact agcccatgtt ggaatgaaga atcttcacaa gcttctaaag ggagaacaca  76380
ttttgggact aaccaatgtt cattttgaga aagacaggat ttgtagcgca tgccaagccg  76440
ggaagcaagt tggcacccat catccacaca agaacattat gacaagtgac aggccactgg  76500
aactccttca catggatcta ttcggcccga tcgcttacat aagcatcggc gggagtaagt  76560
actgtctagt tattgtggat gatttttctc gcttcacttg ggtgttcttt ttgcaggaca  76620
aatctcaaac ccaagacacc ttaaagggat tcttgagacg ggctcaaaat gagttcggct  76680
taaggatcaa gaaaattaga agcgacaacg gaacggagtt caagaactct caaattgaag  76740
gctttcttga ggaggagggc atcaagcatg agttttcttc tccctacact ccacaacaaa  76800
atggtgtagt ggagaggaag aatcgaactc tattggacat ggcaagaacc atgcttgatg  76860
agtacaagac accggatcgg ttttgggccg aggcggtcaa caccgcctgc tacgccatta  76920
accggttata tcttcaccga atcctcaaga agacatctta tgaactccta acccggtaaa  76980
aagccaaatg tttcatattt tagagttttt ggtagcaaat gctttattct tgttaaaaga  77040
ggtagaaaat ctaaatttgc tcctaaaact gtagaaggct tttactagg atatgactca  77100
aacacaaggg catatagagt ctttaacaag tcctcaggac ttgttgaagt ttcttgtgat  77160
gttgtgtttg atgagactaa cggctctcaa gtagagcaag ttgatcttga tgagacaggt  77220
gaagaacagg ctccatgcat agcgctaagg aacatgtcca ttggggatgt gtgtcctaag  77280
gaatccgaag agcctccaca cgcacaagat caaccatcct cctccatgca agcatctcca  77340
ccaacccaag atgaggtcga ggctcaagat gttgaacaag aagatcaaga agatgagcca  77400
cctcaaaatg acggcaacga tcaagggggga gatgcaaatg atcaagaaaa ggaggatgag  77460
caagaaccaa ggccgccaca tccaagagtc caccaagcaa tccaacgaga tcaccccgtc  77520
gacaccatcc tcggcgacat tcataagggg gtaaccactc gatctcgggt tgcacatttt  77580
tgtgaacatt actcttttgt ttcctctatt gagccacaca gggtagagga agcactccaa  77640
gatgcggatt gggtgatggc gatgcaagag gagctcaaca acttcacaag gaatgaggta  77700
tggcatttag ttccatgtcc taatcaaaat gttgtaggaa ccaaatgggt cttccgcaac  77760
aagcaagacg agcatggtgt ggtgacaagg aacaaagctc gactcgtggc caaggggtat  77820
tcacaagtcg aaggtttgga ttttggtgaa acctatgcac ccgtagctag gcttgaatct  77880
attcgcatat tattggccta tgatacttac catggcttca agctctatca aatggacgtg  77940
aagagtgcct tcctcaatgg accaatcaag gaggaggtct atgttgagca acctcccggc  78000
tttgaagaca gtgagtatcc taatcatgtt tataggctct ctaaggcgct ttatgggctc  78060
aagcaagccc caagagcatg gtatgaatgc cttagagatt tcctcattgc aaatggcttc  78120
aaagtcggca aagccgatcc tacactcttt actaaaactc ttgaaaatga cttgtttgta  78180
```

```
tgccaaattt atgttgatga tattatattt gggtctacta acaagtctac atgtgaagag  78240
tttagtaggg atcatgacac agaaattcga gatgtctatg atgggggagt tgaagtactt  78300
cttaggtttt caagtgaagc aactccaaga gggcaccttc atcagccaaa cgaagtacac  78360
tcaagacatt ctaaacaagt ttgggatgaa ggatgccaag cccatcaaga cacccatggg  78420
aacaaatggg catctcgacc tcgacacggg aggtaagtcc gtggatcaaa aggtataccg  78480
gtcgatgatt ggttcattgc tctacttatg tgcatctcga ccggacatta tgctttccgt  78540
atgcatgtgt gcaagattcc aagccgaccc taaggaatca caccttacgg ccgtgaaacg  78600
aatcttgaga tatttagctt acactcctaa gtttgggctt tggtaccctc ggggatccac  78660
atttgatttg attggttatt cggatgccga ttgggcgggg tgtaagatta ataggaagag  78720
cacatcgggg acttgccagt tcttgggaag atccttggtg tcttgggctt caaagaagca  78780
aaattcggta gctctttcta ccgccgaagc cgaatatatt gccgcaggcc attgatgcgc  78840
gcaattactt tggatgaggc aaaccctgcg ggactacggt tacaaattaa ccaaagtccc  78900
tttgctatgt gataatgaga gtgcaatcaa aatggccgac aatcccgtcg agcacagccg  78960
cactaaacac atagccattc ggtatcattt tcttagggat caccaacaaa agggggatat  79020
cgagatttca tacattaaca ctaaagatca attagccgat atctttacca agcctctcga  79080
tgaacaatct tttaccagac ttaggcatga gcttaatatt cttgattcta ggaatttctt  79140
tttgctaaac ttgcacacat tgctcataaa tatacctttg atcatgtctc tcttatatat  79200
gctatgaata atgtgctttc aagtgtattt caaaccaagt cataggtata ttgaaaggga  79260
attggagtct tcggcgaaga caaaggcttc cactccactc tactactcat ccttcgccgt  79320
cactccgagc atctctccaa ctttggtata atcatcactc ctatgtttca tttgccaaag  79380
gggacaaaat agtcattaaa gggctctaat gattccgttt ttggcgattt atgccaaagg  79440
gggagaaaat atgagcccaa agcaaaagga ccgcaccacc accctaattt taaacatatg  79500
attttcaatt ggttgaaaat ttcaaaattt gtatctcttt gtgttctaaa agggagcatg  79560
tagtatatgt agtattttca aaacttgata tctcaaaacc ctcttgaaca ctaagaggag  79620
aatttatttg agggggagtt ttgtttagtc aaaggaatgg catttgaaac agggggagaa  79680
aatttcaaat cttgaaaatg ctttgcaact cttattcatt tacctttgac tatttgcaaa  79740
agaaccttga aaagaattta caaaagaatt ttgcaaaaac aaaacatgtg gtgcaagcgt  79800
ggtccaaaat gatatataag aaacaatcca tgcatatctt gtaagtatta atattggctc  79860
aattccaagc aacctttgca cttacatttt gcaaactagt tcaattatgc acttttgaat  79920
ttgctttggt ttgtgttggc atcaatcacc aaaaaggggg agattgaaag ggaattaggc  79980
ttatacctag ttcctaaata attttggtgg ttgaattgcc caacacaaat ctttggacta  80040
actagtttgc tctagtatat agattataca ggtgtaaaag gttcacactc agccaataaa  80100
aagaccaagt tttggattca acaaggagca aaggggcaac ccgaaaggca cccctggtct  80160
ggcgcaccgg actgtccggt gcgccaccgg acatgtccgg tgcaccaggg ggactcagac  80220
tcaaactcgc caccttcggg aatttctaga ggcgactcgg ctaaaattca ccggactgtc  80280
cggtgtacac ccggacagtg tccggtgctc caagggaggt cgtcctcagg aactcgccag  80340
cctcgggttt tcactccagc cgctccgcta taattcaccg aactgtccga tgtgcaccgg  80400
agggggcggt gcatctgcgg agcaacggct acttcaggcg ccaacggcta cctgctgcgc  80460
atttattgcg caccagcgcg cgcagaggtc aggcacgccc atgctggcgc accggacagt  80520
gaacagtgca tgtccggtgc gccaccggac atcaagcggg gcccagaagt gtaacgcccc  80580
```

gaattttgca gttgaatttt ttcttttctt tactcgccaa aattcgggcg ttaccttttc 80640
cttttctttt ttcccttcgc taaaccttga ccttttccaa agttctagcg ggattcggtt 80700
tggatttccc gtgtaagaaa aaccctaaat actttatgtt gtttgatgca ccatgccgaa 80760
ccttgcattt cttttgattg ctttgaaagt gcaattgcat tcatgtagaa agatcggatt 80820
tcgaaaatgt ggagaggatc ttttctttct tttttctccc tctcttttc tctcctcttt 80880 ttctctctct cccgcgccgt gggccgaccc cggccggccc aggcccctgc gcgccccccc 80940
tcttgggcct ggaagggcca gccgccccccc cctctttccc ttattcccta accctctccc 81000
tctcccccct cattttctcc ctcgccaccg aatccgccgc ccctaccccc tacccgcccc 81060
ctgccctaga ttggcgggcc gccccctgcc gccgggcgcc cctcgccgtc gatccccgac 81120
accggtgagc cccccctcc tccctctctc cctcaacctt ctctcccctt tcctccctcc 81180
ccttcccctc gccgcttggc cccatggccg gtttggccgc ccgccccacc ccgccgggtc 81240
ggccgctcgg cccccccgcg ccctgccccg cgcccctgcg cgcccagcgg ttcggccgcc 81300 ccgccccccct gctcggccgg ctcggccgcc ccctgcgccg cccccccccc ccccgccagc 81360
tcggccgccc gccgccggtt caaccggccg gctcagcggc tcagccgccc ggtcagcccc 81420
ggccgcgccc gcgcccgcgc cccgcctagg gccggttcaa ccgccctagg gccggttcaa 81480
cccccccccc cttctgtttt ttttattttt ttattttatt ttatttactt tctgtgatca 81540
taattactgt attttaagta ggctaatcac tgttcatgct atgggaaaat aggaagttta 81600
atttaaaatt ccgttatgtt attgattcac gtagctaatt gtttaccctg tgcaatgttg 81660
atcaactaaa agtgattagg tttccatcag tatatataaa tatatataac agaattattt 81720
tgttaaaaac caattgtgtc attagtgcat aagatttaac cccctgcgag acctttcccc 81780
gtttctttct aaccataaca aatgcgttat cgaatgtcat acttgatgca tattcgcttt 81840
atttgttatc ttgtatggtg tactgttctt ttgtattaaa tatgtggatg tatgtatgta 81900
tgtttgcgct cgcatagaga acgatccggt cgaagagccc gaggaattcg caggagaagc 81960
ccctgagcag caatcggttg gtggaggcaa gtgtcctttg acctatctct gtcctattca 82020
ttctttaatt cacctcccgc attacacatt tatacctaag gatcgactag cttttgttat 82080
ccatgtcctt gtttacctat ttgggtcgga ttattactac ttagtctgat gctattgctc 82140
aactctaatc aatgaacatg atgtgattat ctatgatacg ctgttttccc ttctcttatt 82200
atgatgttgt acttgtggta ttcaaggggg ctcgagcggt ttctcgagtg cctctccgta 82260
aggacctgtt ctatggatga ccgcccggga aaacagtgca accatgaggg tggaatgggg 82320
tgcccttagc tgaataatta gaggatccgg gatgtagttc acttagccgt cgtgccgtca 82380
atggggctcg gtgtatgcgg ctcgctctgc caagtttggg ttcgcccctt ggggaggagt 82440
gcggtgcatt taggaaacct aacgggtggc tacagccccg gggaatcttt gtaaaggcta 82500
cgtagtgaaa ccctgcctat tcaccttggt agtgtttaag ggtttgatcg gcccgaggca 82560
agagggaatc acggcttgtg ggtaaagtgc acaacctctg cagagtgtta tgaaactgat 82620
atatcagccg tgctcacggt tatgagcggc caagggagct ccagagatta gtgatacttg 82680
atcagagata ttttggtaca ggtggcaatg agattgatgg ttctggttat gattatggta 82740
ttggtaagtg gtattctttc cgtttggaaa ggatacattg ggttaataac ttgggttaat 82800
gttaaaacct ggctttctac tagtaagtaa taacctgacc aactaaaagc aactgcttga 82860
ctgatcccca cataaagcta gtccactaca gccaaacagg atacttgctg agtatgttga 82920

```
tgtgtactca cccttgctct acacaccaac cccccccccc cccaggttgt cagcattgca  82980
accactgctc aggcgaagat gaagctgtgg aaggagactt ccagaaattc caagattacg  83040
acgagttcta ggtgtgggtt agcggcaacc cccagtcggc tgcctgtgaa ggccgcgtta  83100
tctacgtttc ttttccgcac tttgatttat tgtaagaact atatggacgt ctcagacgta  83160
tgatgtaata gactattttc ccttattaat actattttga cttttgtgtg attatgtcca  83220
tattatgtac ctgccgcctt ctaataactg atcctggcac gtacatgggt gcccccttc  83280
ctctaaaacc gggtgtgaca taagtggtat cagagccgtg ctgactgtag gaccgctaac  83340
ctagagtaga atggtcgttc taaggattat agacctctgt ctcttccttg actttgatat  83400
cccttcaaaa gttggtccta ccgaccaaac ctatgttcta ctatatacta taccttgcta  83460
aaaatcatgt tttattctaa tccttcattt acttatgatt cattacttgc tggtcatatt  83520
aattctgttc tcaccctttt gcttgcgatg tcttttgtag atggctcgac ttagacacac  83580
tgcacgaaag tcagtcatcc ccttcttacc ctcccgcctt gctgagcgtc cgcttcgccg  83640
tcccgtggcc ggacagtcca gccacttgga gagactacac caccgcctgc gtgaggagca  83700
ggaacgtcga cgacaggagc agcagagctc ttccctctcg ctccaccagg agatagagtc  83760
tgtgaggagc tgctcccctg tgcttcctct ggagccgccc cctgcatcac cactgggcgc  83820
cccagcttct ggagtagctg ctggaggaga cccagacgac ggagatggcg atgacagctc  83880
gagccacgac accgacttct ctgctaatct tgagccggaa ggatgggttg ctcgacccat  83940
cactcgcgac gctgctcgcg ggtgtcactt ccatgatgcg ctcgacaccc tgctacgtcg  84000
ggcatttgac cggcatactt ggtccgtcga gtatcgctgt gtggtctacc agcatagtcg  84060
cggggtctac ccggaccgct gggaggcaac ttgcttggtg cgctgcccgg aggacagtct  84120
ccagggtgca gaggcctgtt cagagcacta ttctatctct gagcgggact cagctgaggc  84180
agccatgcaa gatgctgcac ggcgtgcgct ttcgcactac tgctcggttt tcggtggggc  84240
agctgacggt cttgacctga agtattaccc ccgccgttca tctggcagca caggaggcgt  84300
gattgtctca cccgtcggtg agggcaatcc taggttgagc agcacagtca acctagccgc  84360
cgtgctaaac acggagctgg accatgcatt agacgagctg agtagggctc gtgctgagat  84420
cgccctgctg cgggctgagc gtgcggaacg tcgttttctg gacggtggtt cccccgctcc  84480
cgttgggact cagcacccgt accgctcacc tcagcgtgga caccagtctt atggcaatcc  84540
cgcctgcaag accaagataa acctagaacc atagatcgtt agagttggat cttgtaatta  84600
atacgaaata aatatataca tggaagcttc agtcttagcg ttagtctcgg tcttagttag  84660
ttttagttag acagggtagt ttgctatatc ctgtgcattt atgtttgtca tgatgaacta  84720
tgtttggttt ggatctttgt aatgattgtc accagagtgt gggtatcccc tgcattttgg  84780
tttacatact atgtcaataa agttagttat atagttggga aacccattat tctcctttcc  84840
tctttatctg agaagctgtg tggtctgtgt tggagatcag tgaagatgct catctgttca  84900
gtgctgttgg agaattctat actcttttct tatgctgcaa gctttgccag atcagttctg  84960
atgtgtggtt gcgttctgca gatgtcagag aacaggcgta gaggaggaag gcgtgctcag  85020
caggagcgag ccgctccgca ggatgaggtg ccccagcagc agcacctgcc gcccccgccc  85080
ccgatgtcga ttgagcagat gtttctgatg cagactcagg cagttcaagc catcggtcag  85140
actctggccg ccattcagca gcagcagcag cagcaacagc agcaagcacc accccagcct  85200
cagatgcctc agatgcctag agacaagcgt gctgaattca tgagaggtca tccaccaacg  85260
ttcgctcact cttctgaccc catggatgct gaagattggc tgcgcactgt ggagcgggag  85320
```

```
ttgcataccg ctcagtgcga tgaccgggag aaagtcttgt atggtccccg tctgttgaga  85380
ggagcagccc aatcatggtg ggagtcttac ctcgccaccc atgccaaccc cgacaccatc  85440
acctgggaag aattcagagg tagctttcgt cagtaccatg tgcctgcagg tctgatgaca  85500
gtgaagaagg aggagttcct ggcccttaag caagggtcat cgtctgtcag tgagtatcga  85560
gacaggtttc tgcaattgtc tcgctatgct cctgaagatg tcaacactga cgccaagcga  85620
cagtaccgtt ttctgggagg cttggtcgac cctctgcagt atcagctgat gaaccacacc  85680
ttcccgacat tccagcacct gattgacaga gcaatcatga cagaaaggaa gcgtaaggag  85740
atggaagatc gtaagcgcaa gatcagtgga ccccagcctg gaagcagcag ccgtccccgt  85800
ttctcaggca atcaacctca gcagttcagg cagaaccagc gtccacctca gcagcatcag  85860
cagcgtcagc agtatcagca gttccaaagg cagtatcctc agcatcagta ccagaaccgt  85920
cagagcaatc agtcaggagg tcagtttcaa aagcagaatc agcaagcacc tcgtcttcct  85980
gccccagcaa atcagcagaa cagtcaggca gcaccagctc aggttggaaa cagggcatgt  86040
ttccactgtg gagagcaagg ccattgggtg atgcaatgtc cgaagaaggc agcccagcag  86100
cagtcaggcc ccaatgcccc agcaaagcag aatgtgtctc agcctggagc aggcaatcgc  86160
tctcagcagc gctataatca tggaagattg aatcacttgg aggctgaagc agttcaggag  86220
acccccggca tgacagtagg tatgttccca gtcgattccc atattgcaga agtgttattt  86280
gatactggag caacacattc tttcattact gcatcatggg tagaagcaca taatcttcca  86340
attactacca tgtcaacccc tattcaaatt gactcagccg gtggtagaat tcgagctgat  86400
agcatttgtt taaatgtaag tgtggaaata agggggatag cgtttcccgc caaccttata  86460
gtaatgggta ctcagggaat agatgtcatc ctagggatga attggttaga taagtatcag  86520
gcagttatca gttgtgataa aaggacaatc aagttggtgt ccccactagg agaggaagtg  86580
gtgaccgggt tagtcccgcc tgagccaaag aaaggaagtt gttatcagat ggctgtcgat  86640
agcagtgaag cagacccaat tgagagtatc aaggttgtgt ctgaattccc agatgtgttt  86700
ccaaaggatt taccgggtat gccaccagag cggaaagttg aatttgctat agagcttctt  86760
cctggaaccg cccctatctt caagagagct tacagaatat ctggaccaga gttggatgag  86820
cttaagaagc aaattgatga gctgtcagag aaaggttaca tccggccaag cacctcgcct  86880
tgggccgccc ctgtcttgtt cgtagaaaag aaagatggta ctaagaggat gtgcatcgat  86940
tatcgagctt tgaatgaggt cacgatcaag aacaagtatc ctttgcccag aatagaagat  87000
ctgttcgacc agttgagagg agccagtgtg ttctccaaga tcgatctgag gtcaggttat  87060
catcagctca ggatccgacc ttcggacatt ccgaagacgg cattcattac caagtatggt  87120
ttatatgagt tcacagtgat gtcttttggt ttgaccaatg cgccagcatt cttcatgaac  87180
ttgatgaaca gtgtattcat ggattatctt gataagttcg tggtggtatt cattgatgac  87240
attctggttt attctcaaag tgaagaagag catgcggatc atttgaggat ggtgttgcag  87300
agattgcgag agcaccagtt gtattgcaaa gttgagcaag tgtgagttct ggatcagtga  87360
agtccctgtt cttgaggtca cattatcaac aaagaaagga ttggctgtgg atcccgaaga  87420
aagtggcaga catttctaaa actggaaagc gccaacggat gctcgaggaa atcaagagct  87480
ttcattggga atggccggga tattatcggc gattcattga agggttttcg aagattgcga  87540
agccaatgac agcgttgcta ggcaacaagg ttgagttcaa gtggacccag aaatgccaag  87600
aggcctttga agcgctgaaa gagaagttga ctacagcgcc cgtcctagtc ttgcccgatg  87660
```

```
tgcacaagcc cttctctgtg tactgtgatg cttgttacac aggtttggga tgtgtgttga  87720
tgcaagaggg aagagttgtg gcttactcgt cccgacagct gaaggttcat gagaagaatt  87780
acccaatcca tgatctagag ttggcagcag tggttcacgc actgaagtca tggaggcact  87840
atctgtatgg acagaaatgt gatgtttaca cagaccacaa gagtctgaag tacatattca  87900
ctcagtcaga attgaacatg aggcaacgaa gatggttaga attgatcaaa gactatgagt  87960
tggagattca ttaccatcca ggcaaagcaa acgtagtggc agatgctctg agcagaaaga  88020
gtcaagtcaa tctgatggtt gctcgcccga tgccttatga gttggccaag gagtttgaca  88080
ggttgagtct cggatttctg aacaattcgc gaggagtcac agttgaattg gaacctacct  88140
tggagcgcga aaccaaagaa gcgcagaaaa atgatgagaa gatcagtgag atccggcgac  88200
tgattctaga tggtaaaggc aaagattttc gagaagatgc ggaaggcgtg atatggttca  88260
aagaccgctt gtgtgttccc aatgtccagt ctattcggga gttgattctt aaggaagctc  88320
atgagacagc ttattcgatt caccctggca gtgagaagat gtatcaggat ctgaagaaga  88380
aattctggtg gtacggaatg aaaagagaaa tcgcagagca tgtggctatg tgcgatagtt  88440
gtcaaagaat taaggcagaa caccagagac cagctggatt gttgcaaccg ttgcagatcc  88500
ctcagtggaa atgggatgaa attggtatgg atttcatagt cggattgcct cgcacccgag  88560
ccggctacga ttccatttgg gtagtagtgg accgcttgac caagtcagcc cacttcatac  88620
ctgtcaagac caactacaac agtgcagtat tggcagaatt gtatatgtct cggatcgttt  88680
gtcttcatgg tgtgccaaag aagatagtgt cagatagagg aacgcagttc acctctcatt  88740
tctggcagca gttgcatgaa gccttgggca cgcatctgaa tttcagttca gcttatcacc  88800
cgcagacaga tggtcagact gaaagaacca atcaaattct tgaagatatg ttgagagcct  88860
gtgcgttgca agatcagtcc ggatgggaca agcgattgcc ttatgcagag ttttcctata  88920
acaacagtta tcaggccagt ttgaagatgt caccgtttca agcgctgtat ggaaggagtt  88980
gcagaactcc gttgcaatgg gatcagcctg gagagaagca ggtgtttggg ccagatattt  89040
tgcttgaagc cgaagagaac atcaagatgg tccgagagaa tctgaagata gcgcaatcaa  89100
ggcagcgaag ctatgcagac acaagaagaa gagagctgag tttcgaagtc ggagactttg  89160
tttatctgaa agtgtcaccg atcagaggag tcagaaggtt cggagtgaaa ggcaagctag  89220
caccccgcta cattggtccg tatcaaattc tctcaaagcg tggagaagtg gcttatcagc  89280
tcagtttgcc agagagtttg tctgctgtgc ataatgtctt tcatgtgtct cagttgaaga  89340
agtgcttgcg tgtgccggaa gagcagttgc cagtggaagg tctggaagtc caggaggact  89400
tgacctatgt tgagaagcca gctcagatcc ttgaggttgc agatagagtc acccgaagga  89460
agaccgtcag aatgtgcaaa gtcagatgga gtcaccactc tgaggaagaa gcaacctggg  89520
agcgtgaaga tgatctgatg gccaagtacc cggagctctt tgctagccag ccctgaatct  89580
cgagggcgag attcttttaa gggggatagg tttgtaacgc cccgaatttt gcagttgaat  89640
tttttctttc tttactcgcc aaaattcggg cgttaccttt tccttttctt ttttcccttc  89700
gctaaacctt gaccttttcc aaagttctag cgggattcgg tttggatttc ccgtgtaaga  89760
aaaaccctat attctttatg ttgtttgatg caccatgccg aaccttgcat tttgttcatt  89820
ctttgaaagt gcaattgcat tcatgtagaa agatcggatt cacgaatctc tagatcgnnn  89880
nnnnnnnnnn nnnnnnnnnn nnnnnnnnnn nnnnnnnnnn nnnnnnnnnn nnnnnnnnnn  89940
nnnnnnnnnn nnnnnnnnnn nnnnnnnnnn nnnnnnntcc ggtaggaatc ctatcttatg  90000
tggtggagcg gccctgccga cctgcatctt ggatgcttga gggcaatgca ttcagtagaa  90060
```

```
gattcggatc gaagtggggg gagatctttc tctctatttt ccccctccat ttctctcctc  90120
tttttgctct tcacccgcgc cgtgggacgg aaccccggtc gaccaggtcc atgggcgccc  90180
ccccttaga gcctggaagg cccagccgcc cccccctct ttcccttatt ccctaacctc  90240
tccctctccg ctcatttctc cctcccccac ctaaggcggc ggccctaccc cctaacccgc  90300
ccccctgtcc taggttggcg cgccgccccc tgccgccggg cgccccttgc cgttgaatcc  90360
cgacaacccg ggaggccccc cctcctccct ctcttcctcc tccctctttt ccctctcctc  90420
cctcccctttt ccctcgccgc ttggccccaa ggccggtttg gccgcccgcc ccaccccgcc  90480
gggttggccg cttgggcgcc ccgcgccctg ccccgcgccc ctgcgcgccc agcggtttgg  90540
ccgccccgcc cccctgcttg gccgggttgg ccgccccctg cgccgccccc cccccccccc  90600
cccgccagct cggccgcccg ccgccggttc aaccggccgg ctcagcggct cagccgcccg  90660
gtcagccccg gccgcgcccg cgcccgcgcc ccgcctaggg ccggttcaac cgccctaggg  90720
ccggttcaac cgcccccccc ccttctgttt tttttatttt tttattttat tttatttact  90780
ttctgtgatc ataattactg tattttaagt aggctaatca ctgttcatgc tatgggaaaa  90840
taggaagttt aatttaaaat ttcgttatgt tattgattca cgtagctaat tgtttaccct  90900
gtgcaatgtt gatcaactaa aagtgattag gtttccatca gtatatataa atatatataa  90960
cagaattatt ttgttaaaaa ccaattgtgt cattagtgca taagatttaa cccccctgcga  91020
gacctttccc cgtttctttc taaccataac aaatgcgtta tcgaatgtca tacttgatgc  91080
atattcgctt tatttgttat cttgtatggt gtactgttct tttgtattaa atatgtggat  91140
gtatgtatgt atgtttgcgc tcgcatagag aacgatccgg tcgaagagcc cgaggaattc  91200
gcaggagaag cccctgagca gcaatcggtt ggtggaggca agtgtccttt gacctatctc  91260
tgtcctattc attctttaat tcacctcccg cattacacat ttatacctaa ggatcgacta  91320
gcttttgtta tccatgtcct tgtttaccta tttgggtcgg attattacta cttagtctga  91380
tgctattgct caactctaat caatgaacat gatgtgatta tctatgatac gctgttttcc  91440
cttctcttat tatgatgttg tacttgtggt attcaagggg gctcgagcgg tttctcgagt  91500
gcctctccgt aaggacctgt tctatggatg accgcccggg aaaacagtgc aaccatgagg  91560
gtggaatggg gtgcccttag ctgaataatt agaggatctg ggatgtagtt cacttagccg  91620
tcgtgccgtc aatggggctc ggtgtatgcg gctcgctctg ccaagtttgg gttcgcccct  91680
tggggaggag tgcggtgcat ttaggaaacc taacgggtgg ctacagcccc ggggaatctt  91740
tgtaaaggct acgtagtgaa accctgccta ttcaccttgg tagtgtttaa gggtttgatc  91800
ggcccgaggc aagagggaat cacggcttgt gggtaaagtg cacaacctct gcagagtgtt  91860
atgaaactga tatatcagcc gtgctcacgg ttatgagcgg ccaagggagc tccagagatt  91920
agtgatactt gatcagagat attttggtac aggtggcaat gagattgatg gttctggtta  91980
tgattatggt attggtaagt ggtattcttt ccgtttggaa aggatacatt gggttaataa  92040
cttgggttaa tgttaaaacc tggctttcta ctagtaagta ataacctgac caactaaaag  92100
caactgcttg actgatcccc acataaagct agtccactac agccaaacag gatacttgct  92160
gagtatgttg atgtgtactc acccttgctc tacacaccaa accccccccc cccaggttgt  92220
cagcattgca accactgctc aggcgaagat gaagctgtgg aaggagactt ccaggagttc  92280
caagattacg acgagttcta ggtgtgggtt agcggcaacc cccagtcggc tgcctgtgaa  92340
ggccgcgtta tctacgtttc ttttccgcac tttgatttat tgtaagaact atatggacgt  92400
```

```
ctcagacgta tgatgtaatc gactattttc ccttattaat actattttga gcactgtgtg  92460
atgatgtcca tattatgtaa ctgctgtgta cgtgaataac tgatcctggc acgtacatgg  92520
ttcgcattcg gtttgccttc taaaaccggg tgtgacaaga agtcagagct ccaacggtca  92580
gaatccaacg gcagagatga cgtggcaggg ggcaccggac tgtctggtgt gcaccggact  92640
gtccggtgtg ccatcgaaca gacaacttcc accaacggtc atgtttggtg gttggggcta  92700
taaatacccc aaccacccca ccattcattg catccaagtc ttccacttct caacctctta  92760
caagagctag gcattcaatt ctagacacac ccaaagagat caaatcctct ccaattccat  92820
acaaagccta agtgactagt gagagtgatt tgccgtgttc atttgagctc ttgcgcttgg  92880
atcgctttct ttctttctca cttgttcttg tgatcaacac tcaattgtaa tcaaggcaag  92940
aggcaccaat tgtgtggtgg cccttgcggg gaagttttgt tcccggcttt gatttgagaa  93000
gagaaagctc attcggtccg cggaccgttt gagagaggga agggttgaaa gagacccggc  93060
ctttgtggcc tcctcaacgg ggagtaggtt tgagagaacc gaacctcggt aaaacaaatc  93120
ctcgtgtctc acttcattat tcgcttgcga tttgttttgc gccctctctc gcggactctt  93180
ttatatttct aacactaacc cggcttgtag ttgtgtttat atttgtaaat ttcagtttcg  93240
ccctattcac cccccctcta ggcgactatc aagtctcgtc actcacctca cgtgaactcc  93300
aacggaaaca ccgcacatat cggcctgaac agaatcccct cccagctccc gatcggggcg  93360
gacctaactg aatcgaccga tttctgggca cgattacggg gagcgggtca aatccgggca  93420
atactgcatg cgaatctgtc cttggcggca ctgacttgtg ggctccatct gtcgtaatca  93480
tcctcaacag agaagaagcg aaacggatgg cgcggtggcc gggattccta tgccggtcat  93540
ttcgcgctgg ctcggactcc tctgatccgg acccttggcc ctgtcatcta tatatattga  93600
gcaccaaagc tatcggatgg agctgggcgc aatcgagtag gcaggagggc ggtgtaggag  93660
agcagagaga tgagagagga accgccgtgg gggattctgt aatccatcgc ggtcgcaccc  93720
tcgaagaccc tccaggtgat tctctggtat ctgctgggtg cgtggcgggc ttggcgttcg  93780
agaatggcgg cctgcaccgc cgggattgcc ctatcaccat cggaacaggt cgtcatccgt  93840
cgtgcgccgt gaatagctga atctgctccg cggtcgctgg caagaccctc cccaaaggtt  93900
tgttttctcc ttcttcatgc gtagctcaag tcgaagccag gtttcatgga cttgcgcgtt  93960
ggtgtggtgg tgctccggcg cgtcgcggcc aggatgggtg gggcgccgtc atgtctggtg  94020
gcctggtgga agaaaacacc tctgccgttg atcggatact taacggccag gattctgaga  94080
aacgtaccgc tttggtgggt tgggatccag accgtagatc tcgtggttgg cggctgtgat  94140
tataaacgtt ataccettcg tccaaatcgt acgcgggccg tcgatcctgg aacgttcagt  94200
cgtgcggctg gcatcgttgt ttaaaatctc caccctcgat cgcccatctc acgatcacca  94260
gtgagtaccg gttcggaagg gtactcgatc taatctgggc cgtgcgagtt tgatcggacg  94320
actcaggatt gaagttaccc tttcgggtgc gaaattattc aaaagaaccc ctcgacttgt  94380
tctgattcaa tccgccatcc tcggattggg tgaattcata tgcctgagtc cctggtagag  94440
atcaaaatag tgtccgaagc ccaaatatga tatctggaat aataaaaccc ctttaagaaa  94500
tgaattttaa tattgaaagt taatcctaaa acttcataaa ttcataactt ctccgtttaa  94560
accccgaatt gacccgttcc agttgcgtta ggttcgtata aatattcact acgtagttat  94620
agcattggtt ataccatatc tcatgctttt ataattagat atttatttaa cccatgttta  94680
gtagattaac ctctctaaat caaagttaat ctgtttaaca ttatagtttg gctaaaatat  94740
gatccctaat tatattataa tttaacataa ggttgaacta attatttatt tagattattt  94800
```

```
tatcacatga tctattaaat caacataagg tctagtttta acggcttaaa ttgcatgggt  94860
cttctgaaaa ccataccttt tcaaccatga ccccgaattt agcggttctc gaacccacga  94920
tctcgtagca tcgcgtagac cgttattatt cagtttgtac ttatggttgg tgtgatgtta  94980
attttgtcta taccatgttt gtatgtattg ctacgtttaa cagtgaggtt acgagtcacc  95040
tgaagatcat cctggtacct ggaatctcga gtcccaggca agttgtgccc ttgatcactt  95100
ctttttaccc agccatgttc tgattaatca taatgatctg cataggttaa ttttgatggg  95160
acccaatagg ttaccctagt ttgattatct ttataccttg ttaccactaa actttctggg  95220
tagtacttgc tagtgctata tgtggttttg ggtatggaga tatattattc atgattacac  95280
ttttgttatc agttgttatt tgttgttcat gataagatca ttatgttaat tggaacatgg  95340
agaaccaccc gggaaaacag tgctaccaca agggaggaat gggacccctt ggctgattaa  95400
ttaggaaagc tagtggaaga ctaccttacc cgaaaggggc aagggcagta ggggagtggt  95460
cagtgtaggg aggccctcgg gaggattttg ctgcgatggc ggtcctgcaa gggattcctg  95520
cattggagct tcctataaac tgtagcgggt tttctgaagc tagtggaact ttgtaaaggc  95580
ctcgtagtgt taccctgcct cacctcctcg gtagaggtgt atgggaagtc gcgatccctt  95640
ggcagatggg taacatgact tgtgggtaaa gatgcgcaac ctatgcagag tgtaaaactg  95700
gtatactagc cgtgctcacg gtcatgagca gctcggaccc tcacatgatt aatttatgga  95760
acttaaattc aatttgtcat atgcattgca tcgcaggtga tgttgttact tctgttctac  95820
tatttaattg ggttggtatt tacttatact tagtaattgc taataaaatt ttgaccaact  95880
ttaaaagcaa tgctcaactc taaccatcct ctttggtaag ccttacactt cacatgagct  95940
cccacctttg gcgagttcat gcacattatt ccccacaact tgttgagcta tgaacgtatg  96000
tgagctcact cttgctgtct cacaccccc acaggtcaag aacaggtacc acaggatgag  96060
gctcttggag gatgcttcga tgtgttcgtg agaggtctag gccgtcgtct cccagtcaac  96120
tttgggttgc tggaccgttg tctccttata atgtaattat ttattttgta tagaactcct  96180
gttatatata aagatgtgac attcgatcct gtgccactat acatcatatg tgtgagactt  96240
gatcccagca tacctggtgt ttatgttcgt gcccgggtct tggtgcccta aaacctgggt  96300
gtgacatccc accgcgcaac tgcttccgtc ctctgccacc ggggcacgcc gaaagctcgc  96360
ctcgcaagcg cgcggccgcg ccagcacacc acgcctcgct tcgtttaccc gttgcttgcc  96420
gccgaatcga ccacgctggc gaccaggcca gcgccatcgc atcgtccccg gaccgctccg  96480
gtcgcgcccg ccaggcctcg gggctcgggt agaccaccac caaaacagaa ccttccctcc  96540
ggaccgaaac cgccgcttcc cctccccgct ctttctgtga ggagggaagc gaggcggatg  96600
ccgaggcgac ggggctcgcg caccgcactc gtgtgcccgc cgcccgggga ccaggcgacg  96660
tggtgactgg tgaggtgagg caagcgcgcg gttttaaatt ccccgcacgt ccttctcgcc  96720
gtagttttca gtccggaggt acatcaaggg aggaacaaac gtgagggctg cctgcctccg  96780
gacatgggct ccagcttcaa gtaccgagct ggcctctgcc tcatcgtcgc cgtcgtgctg  96840
atttgggtca tatccgcgga ggtcacgcag gtgaggtgtg gtgtggatcc tttgatcttg  96900
gtgcgtgttc ggtgttcctc tgttcacttg tttattttta ttggagcctc ttggatcttg  96960
gcttggcctt tgggacgcat gttggcctat tggtacgttt tgtgcgtaaa tgctctgtgc  97020
ctatcagatt gtatttgttg ggacgacctg ggggtgttgc tctgcatcta gatttttaaa  97080
cgttacgcgc agggttgcct gtgatagaaa atttttccca ggggaaggtt atgcatctgc  97140
```

caccactctg ccttaaaaag aacatctggc atcattctga atccagccga ggcttcacca 97200
ctggacttta tttatttaca ccataaaaag gcaaagaaaa gtcaaattct tttgtcttct 97260
actgtatact tttggagctg cctgcatgca tgctcttatg gacacccgtc aaatctgctg 97320
ttaatggttt aacgacttgt acctgcctgt cgtcagtcct cggtgcttag cttgttcatg 97380
taaactatgc taaagcataa tcatgcatgt ggttgttgtc acagttcttc tgtggttgat 97440
tgagggtggt tgcgatatgt ttgatcacct acaatacaca aacatgatta aagaagatac 97500
cgatggtaga atcaggggat actggtagta caatttcgtc actctcatga ctgcaaaaca 97560
cctcaacttc tagttcttga ttctttttaa aaaaatatat atttgtagtg tccatattgt 97620
gaaatatatc aattttcatt ttgtaactaa atttcttgtg caggggatat tcacaaagta 97680
caaacatcct tttgcagtta cttacttggg ggcctccctt atggtcatat acctcccttt 97740
gtcatttcta aaggattctg gaaacaccag tgcttcataa attgcaagca aaacttcctt 97800
tggtggtggt gccccttga agaatgacga atttcggaag actttagtgc taaattgcac 97860
tgatgtgagc attcctgtag tgaaagagac aaaaccactc atatatggaa tcactgaaat 97920
gaatgatggt gttttgaagg acaagcaact ttcgactaag gagattgcaa cttatggatt 97980
gtatctttgc cccttatggt ttgtgacaga ggtaatttta caatggcttt gcatgttaat 98040
ttgcaattcc aggggacttg aaatgttcat gtgaataact tttgacattt gtttctcaaa 98100
aactactgat atatgtttca gaaagcctaa atttcaatcg taaaagcaat actttgatag 98160
gtaaaggtaa ctcatttttc tcttacgctg aatgaatgca gtatttatcg aatgcagcgc 98220
ttgcaagaac tagtgttgcc agtaccaccg tactgtcttc aacttcaggg ctcttcactc 98280
ttttcattgg tgttttactt ggccaagact ccataagtgc ttcgaaagtt attgctgttt 98340
tcattagcat ggctggcgtt gtaatgacaa ctatgggaca gacttgggca tctgatgaat 98400
cagaagtagg caaatctggg tgagttgttt attactaggc ctttactctt ttatactctg 98460
ataatcacat tggacttaat ttaatgttct tgtaattttt ttggtcctgc gtacaactag 98520
tagttttcag ttagttggct tgcctggttt tttgggttaa aaaacaactc aaaacttgag 98580
tgttttattt ctatatttgc atgacttgat agtgatgaac atgaacaaaa acgaatttca 98640
attctgagat tggaatttcg ttcctatttt caactgcatt tccttgctac tgatacataa 98700
gctttacaat tgcagggcta cacaaaggac tcttctaggt gatatgtttg gttttatgtc 98760
ggcaatcgcg tatggtctat ttactggtag gttggtttgc tttgctttat ttgcagtgga 98820
gctctatgaa ttcggcccct aattgtttcg atattgtttc agtgctgctt aaaaaatttt 98880
gtggggagga aggagaaaag gttgatgtcc aaaaactgtt tggttatctt ggacttttta 98940
cccttgttgc tctctggtgg attggtattt tttgtttccc ttttcgaaat taatataaca 99000
ggagtataca atttcgtaat tttatgatcgt attctggtat ttcttaattg tgcatgcctt 99060
tcatggttat tttatgtaaa aaaaaatatg gttattgtgt tcatatttca gtctggccat 99120
taaccgcact aggcattgag ccaaagtttt cgatgcctca ctctgctaaa gtggatgaag 99180
tggtggtggc aaatagccta attggaagtg tactatcaga ttacttctgg tatgtgttaa 99240
agaaggctga tatcttttta tattaccaga ccactctatt attacttgca tactcggggt 99300
aattgtgaca ggctgactgt ggaacttatg gccagggccc tttctgttgt ttggactact 99360
cccttggtgg ccacgctagg catgtctctc acaattccac tggcgatggt tgcggatatg 99420
atcattcacg gccgtcacta ttcagcagtg tatattcttt gttctgtcca ggtgcgagta 99480
tccaacagtt tagtattttt ttaaaaaaaa ctagaattat agaaaaatat ctactatatc 99540

```
ttacggcagt aaccaatatg aatgctacgt gttcctgttc agcattctag ctcactgttg  99600
agtacatttg tcattctgtt tgaccatgtg agctttgttc ctttgcaggt attttcaggc  99660
tttgtcatcg cgagccttgc agatcggctt tcacgttctc tagggctatt atagtttcat  99720
aaaacgaagc aggttcttgt tagagtgtac atctggaagt ttaaaggtcg ggttggttag  99780
acaaaatact tgaggaaaca cgggttggga tttgggaaat gccagtaatt cgtttccctt  99840
ttgctccttt aaacatagga gcggtgaatt ttgccgcggc gaatagtaaa ggccagcaga  99900
cgaagaagaa accgtatatt gtagcaaccc tttgcaactg tatattctcc tactacaaat  99960
tgagcgacag tgtaaactgc cgtcgttctg gccttgtcga tccgtgtcga ttgcaaattt 100020
gcaaatgtca cttttatatc cttgtcgatc cgtgttcatg gcaattgcgc gagttaacaa 100080
agaatgaatg ggcaaaaaaa aaaaaaaaaa aaaaaaaaac ggagctacaa attgcagcga 100140
attgaatggg caagttgtca tactcctatg caaagtgtgc gacaatgcaa actgaaaagt 100200
gaaaatgact tactgcacaa gcaacgtcaa attcaaagtg tacatgctac tagcagctta 100260
gcgagcaact gaagttctca tagtcgccat gtcggagcga gatgcgatag acggcgaagg 100320
cggcactctg tccggggtcg cgcagcagcg gcgtggtgac cctgtcgacc tcgaccacct 100380
caaaaccatg ctcccgcagc acgtccatgc agtccagcac gctgtcccgc acctcgctcg 100440
ccgcccaccc cgcggtgccg ccgccgccct cgtccgtcca ccacataccc cgcagcgtgg 100500
ccgccatcgc cggcatgtcc tcgggatcgt agaagacgtc ggacaagagc acgacgccca 100560
ccctcccgtc gccgtcgtcg agcgggagca ggtcgcccca gcggagctcg cgcacgcggg 100620
cccgcgcggc gctgaggccg ttggcgtccg cgttggccct gaggcccggc agcagcgcgg 100680
ccacgtccgt gagcacgcag cgcgcggcgc cgaggcaggc cacggcggcg atgcccggga 100740
gccccgtgcc ggcgccgagc tccacgacgg tggcgccacg gaggcggcgc ctggcgcggg 100800
ggtccgcggc gaggtgcgcg gccaggacca gggacgactc ccacagccag gagccggtga 100860
ggacgcggcc cgtggccggg tcgctcgtgc cgtcgcgctc caccaccgcc agcgcgcgcc 100920
cggccacggc tacgtgcagg acctgcgggc acagcgcgtc cattcccgtt cccgcgcgcg 100980
gctggcttct ccctacgacc tacgtgccgg cctcgtcgtc ttaattatct ggtcgttgcc 101040
gccggagcct ctgctggaat ttctctgtcg ttgccggtgg caggttagcg acgggacact 101100
tgcggcgtca atataattgt ttgcgcgatg gcggtttggt cgtgcattgt agttggttga 101160
tgtcgtccat gcttactgac cgactgaata tgttcgttaa ccttttcttt tggtcagcgg 101220
ccagcgggtg gtggttggtt cgaacaaaat ccttgggccg attgggcgct aaagcttggg 101280
gccggagccc tccgtcagtg gccagcccat gggcgacatc tcggataaag attgacgaat 101340
cacaagaaga aagggaatgg tacaaaaaaa aataggaggc cgtatgaatg cttgcacttg 101400
cacagttgaa agtgcttaga ttagttatat tatcgtttat acgcttgctc taggtttaga 101460
caatatttcc attgattaga aaatctcata ccacttaatg tttgtgtgca ccatatctgt 101520
actcgaagag tcttatagtg agatcacacc aaccatattt gtggtgtgac cccacctcac 101580
acagagaaaa cgaggcacat aactgtttgg ccaaaggcta agacgatggg gaacaattca 101640
aaagagacca tctaggatac caacttacat gtggaaaaga cctaaaggct atatagttat 101700
ccgatcggaa gcttggcgct tgcaagactc cccaacaagg agtatgcaaa agtttgcact 101760
cttctcaata ccttaaaggt atcagagttc tcgacataac tctaactcaa ttaagatttg 101820
atactttatt tattgcttac ctaggttatg tgtttatttc atagtttagc ttgctaggct 101880
```

agcgacaata ttgaaaccta tattgtataa ttttttgtga tagaaatagc aacacatctg 101940
ataaaattat agctacatat ctagatagat taattacttt ctggcctaag tttcgactac 102000
atggaaatta gaggccttag tgtaaaaatt gagttttaag tggcataatt cgcacctctg 102060
tgttaggcgt cacggtctct ttaatggtat tgcactaaat aactcaactg tcatattttt 102120
gtgttgccct gatctgttgg ctcttggact cttggttaat tggttggttt taggaatttt 102180
ggttgaagtg cttggttggt ttctgttctt gccttctaag ttctgatccg tgaagcgtga 102240
atgaatctgt gaaactgtaa actatgcgat cgtgaagaac tgaagatgtt catatattgt 102300
acagatatgc aatgtgctag atcactgttg atttgttgaa tatgtgacga tcaatgaata 102360
tattagctcg ccacaacaac aaattaaaac taaagcaaca cttgcaatcg cgcgcgtgcc 102420
tggacaagca gcagctcaca tcacatgcat gcgtgtgtga cgatatgtgt ccaggtgagg 102480
caagcgcgtg cgtgtagttg accacgtacg agacggtgcg tgtgcgtgcg cgtgaccagc 102540
actccagcag ccatgtatgc atcgacctct tgccaggcag tagcagcgac gaagagccga 102600
gccgagccgg ccgacacgca cgcgctgcat gcatgcaggt ggccgaagac gtcaaacgtc 102660
atggcgggcg ccagcggtgc gtacgtaccg tgctttccaa tcaagcaaga gcatgcagca 102720
tgcatcgtcc actcgtcgtc gccggagctc cggcagaaca cgggacagct agcggcgccc 102780
gcccaggagg acacgggacg cgcgcccgcc ggccgccgcg tggcgaggct ggacggcgtc 102840
cggggaccta gtactagttg agcacgtacg gctgcatata tgaggacgaa ccgagcgagg 102900
ctgtctggcg ttgttgcaag cggcgcagct gatggcccga ccccggaagc aacaccttcc 102960
tcttctcctc acgcaagagc gcggcctgcc ccctttgtgg ccgtacgacg tggccggccg 103020
ggcgttacca tccgctagta cgcacaccga gtcgtggagg ccatcacgct acgcttgctc 103080
agtgttcctc tatcgtgttc gtacggggta cgtgcgtaca cgcgccatgg gcgggccagt 103140
gacggaagac acacatgata ggtagggcta gaaaagatgc gtgatgcagc agcagcacac 103200
cacgcgggtc gtcgtcgtct ctctcgcgtt cgcgttgtag cagccacacc acaccacacc 103260
acagtctgca actctgcatg gacgtacggg gtgcaaataa ggttttgcga gagcagaaaa 103320
gacccatgtc atcctgtgca gcagtgtgct gagcgactgc gaggcttagg cgcttagccg 103380
agcctgcggg atgcgccgat ccgtccagag gactccactc caggtccggt acccatccat 103440
ccgtcgcggg cgggccgtca accccttttgg cttttaatgc atttaatgca gcccttttgt 103500
cccttaaaaa gctaccacca gccgctcgat cccgcatttg gtcttggcca cgctcgctag 103560
ctcccttgct tgcttacttt gctcagctag ctagctagcg agagggccag agagcttcgc 103620
catggcggcg tcccactcgc ccaaggtcgc gagggaggtc gccgccgcca cctgcgccgt 103680
cgacgccaac accacgttcg tgcaggccga cccggccacg ttccgcgcgc tcgtgcagaa 103740
gctcacgggc gccgcgacgg acgatgcggc agcggcggcg gcggtgaccg tcgcgcacgc 103800
gccaccgccc ccgccgaggc ggcccaagct ccaggagagg cggcgcgcgg cgccggccag 103860
gctggagctg gagctggcgc ggccgcagcc ggcgtcgccg tccccgtcgt cgtcgttctt 103920
ctactaccac caccaccacg ctcacggcgc ccacgcccac caccactgcc acgggcccat 103980
gcattcgccg gtctcgccca tggacgccta catagcgctg gcggtctccg cgtcgccgtc 104040
gctgtcgtcg tcctcgtcca tgtcgccgca ctcgtcgtcg tgcggcggcg gcggggccgt 104100
ggtggtgata agcagggagg aggaggagga gcgggaggag aaggccatcg cgtccaaggg 104160
cttctacctg cacgcgtcgc ccaggggcgg cgacgaccag cccaagcttc tgccgctgtt 104220
ccccgtacgt ccactcaaat caactccggc gagctgaggg ctgaggctag ctagctagcc 104280

```
gtgtgcgttg accactgcac aaacatgcgt ttccggtaat tccagtgatg taaccgcgcg 104340
tctatatatt tgcgctagaa gaactagatg atgatgatcc atggatagat gatgcgacgt 104400
cgtacgcttg ttaattaatt tttagctagg cctttactgc tttatagtta gtagatggct 104460
aattaatcat ctgaatgtaa tgacgcgcgt ggcgtgaatg aagtgtgtct cccgtacgtc 104520
ttatgtgtgg tgtggtgtgg gtcatgtgtt ccactagagc aggcaggtca actcttgatc 104580
ctgcaatgga acccccatcg aactgcatca agcaggcaaa gctgtttgaa ggtttatcta 104640
taacgcgttc cacgcacgta ggctagtact ccctccgttt ctttttattt gtcgctggat 104700
agtgcaaaat tacactatcc agcgacaaat aaaaagaaaa cggagggagt acgtagctgc 104760
aatgtgggcg ggcgacatct gcagaacgtt gtcatctaca ggagaggaat atgtgtgtgg 104820
gaagtgggag gtagccacca cagggccgtc acgggctcac gggcgccatg ccgcctccgt 104880
ggctagctgc ggcagagcgc agacgatgga tcgcagagct catcatctgc tgatggctgc 104940
ctcacatgat ttgtacgcgt tggccgggaa cgtatgtatg tatgtatccc tagcttgaga 105000
actgcgctga gacgaacgag atcatccccg gttagctaaa gcatgattgg gagagcccgc 105060
cgccgcgcac acgtgcgaca ctggctgccc aagcaaagcg aattgaattc gaagccagcc 105120
ggggcaagcg atacaaaacg aacgccttgc ctccgacatc tctcaagtcc ccaacccaac 105180
gggatcnnnn nnnnnnnnnn nnnnnnnnnn nnnnnnnnnn nnnnnnnnnn nnnnnnnnnn 105240
nnnnnnnnnn nnnnnnnnnn nnnnnnnnnn nnnnnnnnnn nnnnnnccct tctttggcga 105300
tctgaagcaa taataaatag ataacaaaag tgtaatcatg aataatgtat ctccataccc 105360
aaaaccacat atagcactag catgtactac ccaaaaattt agtagtaaaa tcagtggtga 105420
aacaaggtat aaagatagcc aaatctaggg taacctattg ggtcccatca aaattaacct 105480
atgcagatca ttatgattaa taagaacatg aatgggtaaa agaagtgatc aagggcacaa 105540
cttgccttcc acgagctcct gctcagcagt ctctaccagc tgaacctcag gatcctctgt 105600
agcttgctcg tctactcgca tcaatacaat acatacatgg tatagcaaaa attaacatta 105660
caccaaacat gtaaataaaa tgcacagtaa taatctagac cctaaaatga gattatagga 105720
actggaatta ttaattttgg agttatatat tttaagttat gaatttccaa aggttttatg 105780
catttaatat agggttaagt gagaaataaa ttttaacgtg tatttcatgt aaaaacagtg 105840
gtactatttg atagagaata atattacaaa attataggaa ctggaatggt ccaatttgga 105900
gttcatatgc attttctaca aattaaacaa gtttctgcat ttaaatatgt actaaaacca 105960
ttttctaaag gattttcctg gttttattaa ttatctggac tgggcctcaa ttacagaaat 106020
gcgcaggggc taaacaataa aaattcccga gacacagagg gtaactcaag tgactgcggg 106080
ttgattctta agtttttcta gggtctcttc tgcgaactgg caaagtgaag ggtatcggc 106140
catgatgggc catcggatca gacccgaacg acccagatta ggtacgtgca cttaagtgat 106200
cagtctgcaa cgcgatccct tggatcggga tcctacggcc catagccaat ccgtgggttg 106260
gaacgcagaa ccaaatctac ccgtttgttc ccaaaccaac ggttccgatt taaagaaatt 106320
catcaccgcg ccagcactaa tctcaagcgc ccaaccagaa tccaacggcc cagcaccgac 106380
aaatccccac cattcatctc ccactccacg gatcaccggc tgtcttcttc ctccccacgc 106440
ccatctaccc cttttctctc tcttcatggt tgtatgctcg cctgaagccc ccccatggtg 106500
acgagtaccc cagagaccgg ggcccacgat tgacaggcaa taactaccgc agaccgcagt 106560
agctaggcgc gggttatgcg ttatgagact cacagggagg ttaacgcacc ggaacccgga 106620
```

tggtgtcggg gaagatggcc gtcggcggac ttgcggtgga gcgcggatcc ttcgcctccc 106680
gcccggcgac ccacacgatc aacgtcgcac ggctctgctt ctctgacacc acccgagatt 106740
ctagaaatcg cggaagccta aacgcgccac gacccttctc ctcgcttcac tcggctcgta 106800
aaaataccag caccagggat cctgatttat atcgactaca tggagccaat ccgaggaggg 106860
catgggcgca acagctgcgg ccgaatcggc cggactgttg acggagtctg gcggcgcgcg 106920
gtaaaaatcc gccgtctgtt agcgcacgcg cgattcgcgt gaggagaaga acaggagcac 106980
gcacctgacg tgtgggcctc aatggtcatc tccacgcgat aaggaagggc gagcgcgaga 107040
gaggccgagt ggtgggtccc agagaccagt gtcaccagcg aagacgggct gcgcggtgca 107100
aatcaaagat gggccgattt ggtagctgta gcccatttag gttcgacttc ttttctcttt 107160
ttctctgatt ttcttcttct cctattttca attcccaatt tgaatttcaa gtatgacttt 107220
gaatttgtac tcaaattaaa aatagatttt aatcatacca gtatggttaa gtttgtttat 107280
ttgtaaattt tgttttatat tttatattat ctctttcttt ctccttttc ctcaaatcct 107340
cttctcattg tcattttatt taattcatat tattattgct tttaatgcac aaacaaaaat 107400
ccaatatgat gcaatggttt atttgtgtct tattaaggat ctactctttt tttacatgag 107460
tggtcacatg taatgataac tagagacaca catacatata taaaggaaac aatttctcct 107520
tttattcttc cttacaaagt gggtattaca agggagaaca cgtgatgggt ttgactaacg 107580
tgcaattcga aaaagataga ccttgtgcag cttgtcaagc aggtaaacaa gtgggaggag 107640
cgcatcacag caagaatgtg atgaccactt caagacctct tgagctgcta catatggacc 107700
tcttcggacc cgtcgcctat ctaagcatag gaggaagtaa gtacggtcta gttattgttg 107760
atgacttttc ccgcttcact tgggtattct ttttgcagga taagactgaa acccaaggga 107820
ccctcaagcg cttcctaagg agagctcaaa atgagtttga gctcaaggtg aagaagataa 107880
ggagcgacaa cgggtccgaa ttcaagaacc ttcaagtgga ggagtctctt gaggaggaag 107940
gggtcaagca cgagttctcc gctccctaca caccacaaca aaatggtgtg gtagagagga 108000
agaataggac gctcatcgat atggcgagga cgatgcttgg agagttcaag acccccgagt 108060
gtttttggtc ggaagccgtg aacacggctt gccacgccat caacagggtc taccttcatc 108120
gcctcctcaa gaagacgtcg tacgagctac taaccggtaa caaacccaat gtatcatact 108180
ttcgagtatt tgggagtaaa tgctacattc tagtgaagaa gggtaggaat tccaaatttg 108240
ctcccaaagc cgtagaaggg tttttgttag gttatgactc aaatacaaag gcgtatagag 108300
tcttcaacaa atcatcgggt ttggttgaag tctctagcga cgttgtattt gatgagacta 108360
atggctctcc aagagagcaa gttgttgatc ttgatgatgt agatgaagaa gacgttccaa 108420
cggccgcaat acgcaccatg gcgattggag aggtgcggcc acaggaacaa aatgagtgag 108480
atcaaccttc ttcctcaact atggtgcatc cccaactca agacgatgaa caggttcatc 108540
aacaggaggc gtgtgatcaa gggggagcac aagatgatca tgtgatggag gaagaagcac 108600
aaccggcacc tccaacccaa gttcgagcga tgattcaaag ggatcatccc gtcgaccaaa 108660
ttctgggtga tattagcaag ggagtactac tcgatctcga ttagtaattt ttgggggcat 108720
actcttgtct ctttctatga actttcaggt agaaaggctt gctagaatcc ggactgggtg 108780
gtggggcatg cagagagagt ctcacaactt cannnnnnnn nnnnnnnnnn nnnnnnnnnn 108840
nnnnnnnnnn nnnnnnnnnn nnnnnnnnnn nnnnnnnnnn nnnnnnnnnn nnnnnnnnnn 108900
nnnnnnnnnn nnctttactt cttatgttca gcttgattcg taaccttcat aaacatctaa 108960
agggagaaca tgtgataggt aaaacaaatg taaccttcga aaaagataga ccttgtgcag 109020
cttgtcaagc aggtaaacag gtgggaaggt ctcataccaa aaatgtgatg accacatcaa 109080
gacctttgga gttgcttcat atggaccttt tcggacccgt cgcctatcta agcataggag 109140
gaagtaagta tggtcttgtt atcgttgatg acttttcccg cttcacttgg gtattctttt 109200
tgcaggataa aacagaaacc caagggaccc tcaagcgctt cctaaggaga gctcaaaatg 109260
agtttgagct caaagtgaag aagataagga gcgacaacgg gtcagagttc aagaaccttc 109320
aagtagaaga gtatcttgag gaggaaggaa tcaagcacga gttctccgct ccctacacac 109380
cacagcaaaa tggtgtagta gagaggaaga acaggactct cattgacatg gcgaggacga 109440
tgcttggaga gttcaagacc cccgagcggt tttgatcgga agccgtgaac acggcttgcc 109500
acgccataaa ccgggtctac cttcatcgcc tcctcaagaa gacttcatac gaactcctaa 109560
ccggtaacaa acccaatgtg tcttactttt gtgtatttgg gagcaaatgt tatattctag 109620
tgaagaaagg tagaaattct aagtttgctc ccaaagctgt agaagggttt ttgttaggtt 109680
atgactcaaa tacaaaggcg tatagggtct tcaacaaatc atcgggtttg gttgaagtct 109740
ctagcgacgt tgtatttgat gagactaatg gctctccaag agagcaagtt gttgatcttg 109800
atgatgtaga tgaagaagac gttccaacgg ccgcaatacg caccatggcg attggagagg 109860
tgcggccaca ggaacaaaat gagtgagatc aaccttcttc ctcaactatg gtgcatcccc 109920
caactcaaga cgatgaacag gttcatcaac aggaggcgtg tgatcaaggg ggagcacaag 109980
atgatcatgt gatggaggaa gaagcacaac cggcacctcc aacccaagtt cgagcgatga 110040
ttcaaaggga tcatcccgtc gaccaaattc tgggtgatat tagcaaggga gtaactactc 110100
gatctcgatt agttaatttt tgtgagcatt actcctttgt ctcttctatt gagcctttca 110160
gggtagaaga ggccttgcta gatccggact gggtgttggc catgcaagag gagctcaaca 110220
acttcaagag gaatgaagtt tggacactgg tgcctcgtcc taagcaaaat gttgtgggaa 110280
ccaagtgggt gttccgcaac aaacaagacg agcacggggt ggtgacaagg aacaaggctc 110340
gacttgtggc aaaaggttat gcccaagtcg caggtttgga ctttgaggag acttttgctc 110400
ctgtggctag gctagagtcc attcgtatct tgctagcata tgccgctcac cattctttca 110460
ggttgttcca aatggatgtg aagagcgctt tcctcaacga gccaatcaag gaggaggtgt 110520
acgtggagca accccctggc ttcgaggatg aacggtaccc cgaccacgtg tgtaagctct 110580
ctaaggcgct ctatggactt aagcaaaccc caagagcatg gtatgaatgc cttagagact 110640
ttctaattgc taatgctttc aaggttggga aagccgatcc aactcttttc actaagactt 110700
gtgacggtga tctttttgtg tgccaaattt atgtcgatga cataatattt ggttctacta 110760
ataaaaagtc ttgtgaagag tttagcaggg tgatgacgca gaaattcgag atgtcgatga 110820
tgggcgagtt gaactacttc cttgggttcc aagtgaagca actcaaggat ggcaccttca 110880
tctctcaaac gaagtacacg caagacttgc tgaagcggtt tgggatgaag gacaccaagc 110940
ccgcaaagac tccgatgggg accgatggac acaccgacct caacaaagga ggtaagtccg 111000
ttgatcaaaa ggcataccgg tcaatgatag ggtctttact ttatttatgt gctagtagac 111060
tggatattat gcttagcgta tgcatgtgtg caaggtttca atccgatcct aaggagtgtc 111120
acttagtggc agtgaagcga atccttagat atttagtcgc tacgccttgc ttcgggctct 111180
ggtatccaaa ggggtctacc tttgacttga ttggatattc agattccgac tatgctggat 111240
gtaaggttga taggaagagt acatcgggga cgtgccaatt cttaggaagg tccctgatgt 111300
catggaactc taagaaacaa acttccgttg ccctatccac cgctgaggcc gagtatgttg 111360
ccgcaggaca gtgttgcgcg caactacttt ggatgaggca aaccctcagg gactttggct 111420
acaatctgag caaagtccca ctcctatgtg ataatgagag tgctatccgc atggcggaaa 111480
atcctgttga acacaaccgc acaaagcaca tagacatccg gcatcacttt ttgagagacc 111540
accagcaaaa gggggatatc gaagtgtttc atgttagcac tgagaaccag ctagccgata 111600
tctttaccaa gcctctagat gagaagacct tttgcaggct gcgtagtgag ctaaatgtct 111660
tagattcgcg gaacttggat tgatttatag catacatgtg tttatgcctt tgatcatatt 111720
ccctatgcat tttgttgctt agttatggtg ctcaagttgt acaaacactc cctggacctc 111780
acaagtccat tgcaaagtga tgcacatatt taggggggaga tgtgttacaa cttgatcctt 111840
tgagactaac catgtgcttg agtttgctga tttaatctca aagaaggatt gaaaggaaaa 111900
aggtggactt ggaccatgaa agacttccac tgcactccga tgagagggta acttattcca 111960
agttcatctc atgtactctt attgcctttg catttttatt gaagattttg gtgaggcaat 112020
ggggttcaag ggccaagatt aatcccattt tggtgcttga tgccaaaggg ggagaaaata 112080
aaggccaaag cgataaatgg atcagctacc acttgagaga ttttgaaaat agtagaatag 112140
agcttttggt ttgtcaaaac tcttttattg tctctcttgt cagaaagttg gtttcttgtg 112200
gggagaagtt gttgattatg gaaaaaaggg agtttttgaa atcttgaatc aatttctctt 112260
ggaatgactc tatttatgtc ttaacatgtg tgtttgactt agagatagaa atttgagttt 112320
gatttgcaaa aacaaaccaa gtggtggcaa agaatgatcc atatatgcca aaactgattc 112380
aaaacaaatt tgagttttat ttgaagtgat tttgcacttg ttctacttgc tttatgttat 112440
gttggcataa atcaccaaaa agggggagat tgaaagggaa atgtgccctt gggccatttc 112500
taaatatttt ggtgattgag tgccaacgca agtgcttttg agttgatctg tgtaaaatgg 112560
tggacaaagt acaaatcaag gataaaggta tgtttctcag acttagtaca ttgttttaga 112620
gactaatgta ttgtgtctaa gtgctggaaa caggaaaaat cgaattggaa ttgtcttgcc 112680
tcgagcagcc aagactctgc tcagtctggg agcaccggac tgtccggtgg tgcaccggac 112740
agtgtccggt gtgtcaggct ggctcgagcg aactggccgc tctcgggaat tcaccggcga 112800
cgtacggcta taattcaccg gactgtccgg tgtgcaccgg actgtccggt gagccaacgg 112860
tcggccgggc caacggtcgg ccgcgcgatc tgcgcgggac acgtggctga gccaacggct 112920
agaagggggc atcggactgt ccggtgtgca ccggacatgt ccggtgcgcc aacggctctc 112980
tggctgccaa cggtcggctg cgccatttaa ggaaagaaat cgggcaccgg acagtgtccg 113040
gtgtgcaccg gactgtccgg tgtgccagtc gacagaaggc aagatcagcc ttcatagaat 113100
gctctcaacg gctactagct gccttggggc tataaaaggg acccctaggc gcatggagga 113160
gtacatcaag tatactcaaa gcaatcctaa gcatcgagac ttcgattcca cgcatttgtt 113220
tctttgtgat agcatctaga gctctagttg agttgtaaac tcattgggtt gtgttgcgag 113280
ctcttgttgc gacttgtgtg cgtgttgttg ctctgatttc tgagtcttgt gtgcgttgct 113340
catccatccc ttactccgtg tttctttgtg atcatctaag tgtaagggcg agaggctcca 113400
aagtgtggag attcctcgca aacgggatat agtaaagcaa gcaaaacacc gtggtattca 113460
agtgggtctt tggaccgctt gagaggggtt gattgcaacc ctcgtccgtt gggacgccac 113520
aacgtggagt aggcaagcgt tggtcttggt cgaaccacgg gataaaccac tgtgtcatct 113580
ctatgattgt tctcttgtgg ttattgtgtt tttgctaaga cttctctcta gccatttggt 113640
gattattgtg ctaacactta accaagtttt gtggcttaag ttttaagttt tacaggatca 113700
cctattcacc ccccctctag gtgctctcac tcactcttta tttgcccgcg atttgttttc 113760
caccctctct ctcggacttg tttctatttc taacgctaac ctggcttgta gttgtgctta 113820
agtttataaa tttcagattt gccctattca cccccctcta ggtgactttc aattggtatt 113880
agagccccgt gcttcattag agcctaaccg ctcgaagtga tgtcgggagc atccgccaag 113940
agggagatcg ggaccggcga gaagcccgcc acaagccatg ggaaggctcc atatggagag 114000
tccgccaaca agatgaaggg ctcccattca cacgataagt cgcgtcggag cggtgacaag 114060
aagaagaaga tgaggaaggt ggtctactac gagaccgact cttcgtcacc atctacctcc 114120
ggctccgaca cgccgtccat cacttctaag cgccatgagc gcaagaagtt tagtaagatt 114180
cccctatgct atcctcacat ttctaagcat actccattac tttccgtccc attaggcaaa 114240
ccaccgacat ttgacggtga agattattct aggtggagtg atatgatgat atatcaccta 114300
acctcactcc acaaatgcat atgggatgct gttgagtttg gtgtacaggt accattcgta 114360
taggtaccat gatgaggacg aggtggccaa atcgtgcact tcaactccaa gccaccacta 114420
tactcctcgc atctctaagt cgagaggagt ataacaaggt gcaagggtta aaaagcgcca 114480
aggagttttg ggacgttctc aagaccgcgc acgaaggaga tgagttgacc aaaatcacca 114540
agcgggagac gatcgaggga gagctcggtc gcttccggct tcgccaaggg gaggagccac 114600
aagacatgta caaccgcttg aagaccttgg taaaccaagt gcgcaacctc gggagcacca 114660
aatgggatga ccatgagatg gtcaaggtta ttctaagatc cctcgttttt cttaatccca 114720
cacaagttca attaattcgt ggtaatccta gatatacact aatgtctccc gaaaaagtaa 114780
taggaaactt tgtgagcttt gagttgatga tcaaaggctc aaagaaaatc atggagctag 114840
atggcccctc cacgcccgaa gcacaaccgg acgcattcaa tgcaatggag gagaagaagg 114900
aggagtctac atcaagtaga caacccattg acgcctctaa gcttgacaac gaggaaatgg 114960
cgctcatcat caagagcttc cgccaaatcc tcaaacaaag gaaggggaaa gattacaagc 115020
cctgttccaa gaaggtgtgc tacaagtgtg gtaagcccgt tcatttcatt gctaaatgtc 115080
cattatctag tgatagtgac aggagcgacg acaagaaggg aaagaggaga gaaaagaaga 115140
gatactataa gaagaagggc ggcgatgccc atgtgtgccg cgaatgggat tccgacgaga 115200
gctcctccga ctcctcctcc gacgaggacg ctgccaacat cgccgtcacc aagggcctcc 115260
tcttccccaa cgtcggccac aagtgcctca tggcaaagga cgacaaaagg aagaaggtaa 115320
aatcaagatc ctccactaaa tatgaaacct ctagtgatga ggataattat agtgatgaag 115380
aggataattt gcgcaccctt tttgccaacc taaacatgca acaaagggaa aaactaaatg 115440
aattaattag tgctattcat gagaaggatg atctcttgga ctctcaagtg gacttcctaa 115500
ttaaagaaaa caagaagcat gttaaggtta agaatgctta tgctctagaa gtagaaaaat 115560
gtgaaaaatt atctagtgag ctaagcactt gtcatgatat tattgccaac cttagaaatg 115620
aaaatgctaa attaatttgc taaggttgat tctaatgtta gtaatgtttc aattcccaat 115680
cttaaaaatg ataatattaa tttgcttgct aagattgaag aattgaatgt ctctcttgct 115740
agccttagaa atgataatga aaaattaatt gctaaggcta cagaattaga tgtttgcaat 115800
gctttaattt ccgatcttag agataacaat gatattttgc gtgctaagat tgttgaactt 115860
aattcttgca aaccccctac atctaccatt gagcatgtta ctatttgcac taggtgtaga 115920
gatgttaaca ttgatgctat tcatgatcac atagctttaa ttaaacaaca aaatgatcat 115980
ataacaaaat tagatgctaa aattgctgag catgacttag aaaatgaaaa ttttaaattt 116040
gctagaagca tgctctatag tgggagacgc cctggcatca aggatggcat tggcttccaa 116100

```
aagggagaaa tgtcaaactt agtgcccctc ctaaaagatt atctaacttt gttaaaggca 116160
aaactcccat gcctcaggat aacgagggtt acattttgta ccctgccggt taacccgaga 116220
gcaaaattag gagaattcac tctaggaagt ctcactctgg ccttaatcat gcttttatgt 116280
ataagggtga gacatctagc tctaggcaat caacccatgc aaaattgcct aagaagaaaa 116340
ctcctattgc atcaaatgat tctaacattt catttaaaac ttttgatgca tcttatgtgc 116400
taaccaacaa atcaggcaag gtagttgcca agtatgttgg ggacaaacac aagagctcca 116460
agacttgtgt ttgggtaccc aaagttcttg tatctaatgt caaaggaccc aaaaccgttt 116520
gggtacctaa aatcaagaac taaacttgtt ttgtaggttt atgcatccgg gggctcaagt 116580
tggatcattg atagcgggtg cacaaaccat atgacagggg agaagaaaat gttctcctcc 116640
tatgagaaaa ccaagatccc caacgagcta tcacattcgg agatgtaaat caaggtttgg 116700
ttaaaggatt gggtaaaata gctatatcac ctgaccattg catttcaaat gtttttcttg 116760
tagattcttt agattataac ttgctttcag tttcgcaatt atgtaaaatg ggttacaact 116820
gtctttttac ggatacaggt gttactgtct ttagaagaag tgatgattca atagcattta 116880
agggagtgtt agatggtcag ctatacttag tagattttga tagagctgaa ctcaacactt 116940
gcttaattgc taaggctaac aaggactggc tctggcatca ccgactagca catgttggaa 117000
tgaagaatct tcacaaactt ctaaagggag aacacatttt gggactaaca aatgttcatt 117060
ttgagaaaga caaagatttg tagcgcatgt caggcaggaa agcaagttgg tgttcatcat 117120
ccacacaaga acatcatgtc aactgacagg ccactcgagc tcctacacat ggatctattc 117180
gacccgattg cttacataag catcggcggg agtaagtatt gtctagttat tgtggatgac 117240
cattctcgct tcacttgggt gttctttttg caggaaaatc tcatacccaa gagatcttaa 117300
agagattctt gagacgggct caaaatgagt tcggcttgat gatcaagaaa ataagaagcg 117360
acaacgggac ggagttcaag aactcacaaa tcgaaggctt ccttgaggag gagggcatca 117420
agcatgagtt ctcctctccc cacacgacac aacaaaatgg tgtagtggag aggaagaatc 117480
gaactctatt ggatatggca agaaccatgc ttgatgagta caagacttcg gatcggtttt 117540
gggccgaggc ggtcaacacg gcttgctaca ccatcaaccg gttatatcta cactgaatcc 117600
tcaagaagac atcatacgaa ctcctaaccg gtaaaaagcc caatgtttca tattttagag 117660
tctttggtag caaatgcttt attcttgtta aaagaggtag aaaatctaaa tttgctccta 117720
agactgtaga aggcttttta ctaggttatg attcaaacac aagggcattt atagtcttta 117780
acaagtcctc tggattagtt gaagtctctt gtgacattgt gtttgataag agtaacggct 117840
ctcaagtaga gcaagttgat cttgatgagc taggtgatga agaggcttcg tgcgtcgagc 117900
taaggaacat gtccattggg gacgtgtgtc ctaaggaatc cgaagagcct ccaaatacac 117960
aagatcaacc atcttcctcc atacaagcat ctccaccaac tcaagatgag gatgaggctc 118020
aaaatgatga aggagaagat caagaagttg agctacctca agaggaaagc aatgatcaag 118080
ggggagatgc ccatgatcaa gttgaggaag atgaacaagt tccaaaaccg ccacacccaa 118140
aagtccacca agcaattcaa cgagatcacc ccgtgaacac catcctcggc gacattcaaa 118200
agggggtaac tacttgatct cgtgttgctc atttctgtga acattactct tttgttttct 118260
ctattgagcc acacagggta gaggaagcac ttcaagattc ggattgggtg gtggcaatgc 118320
aagaggagct aaacaatttc acaaggaatg aggcatgaca tttagttcca cgtcctaacc 118380
aaaatgttgt aggaaccaag tgggttttcc gcaacaagca agacgagcat ggtgtggtga 118440
caaggaacaa agcccgactt atggccaagg ggtattcaca agtcgaaggt ttggatttcg 118500
```

```
gtgaaaccta tgcacccgta gctacgcttg aatcaattcg cattttactt gcctatgcta 118560
cttaccatgg cttcaagctt tatcaaatgg acgtgaaaag tgtcttcctc aatggaccaa 118620
tcaaggagga agtctatgtt gagcaacctc ccgactttga agatagtgag taccctaatc 118680
acgtatataa actctctaag gcgctttatg ggctcaagca agccccaaga gcatggtatg 118740
aatgcctaag agattttctt atcactaatg gcttcaaagt cggaaaggca aatcctactt 118800
tatttactaa aactcttgac aatgatttgt ttgtatgcca aaatttatgt tgatgatatt 118860
atatttgggt ctactaacga atctacatgt gaggaattta gtaggatcat gacacagaaa 118920
ttcgagatgt cgatgatggg ggagttgaag tacttcttag gatttcaagt gaagcaactc 118980
caagagggca ccttcattag ccaaacgaag tatattcaag acattctaaa caagtttgga 119040
atgaaggatg ccaaacccat caagacaccc atgggaacaa atgggcatct cgacctcgac 119100
acgggaggta aatccgtagt tcaaaaggta taccggtcga tgataagttc tttactctat 119160
ttatgtgctt cacgaccgga tattatgctt tccgtatgca tgtgtgcaag attccaagcc 119220
gaccctaann nnnnnnnnnn nnnnnnnnnn nnnnnnnnnn nnnnnnnnnn nnnnnnnnnn 119280
nnnnnnnnnn nnnnnnnnnn nnnnnnnnnn nnnnnnnnnn nnnnnnnntc aaaatgcttt 119340
gtttgtgttg catcatcaca aaagggagat gaaagggata gcctacactt ttctatgatt 119400
tgtgctgaat gcccacacaa ataatgacta ctagctgctc tagtctatga gttctacagt 119460
gccaaagtca caataagcca ataaaaagac caagaaaggg ttcaaacaaa gagagcaaaa 119520
gacatcccaa atggtaccct ggtctggcgc accggactgt ccggtgtgcc accggacagt 119580
gtctggtgca ccaccggaca gtgtccggtg caccagggaa ctcgaagctg aacttgccac 119640
cttcgggaaa atgggagacc gctccgctat aatttaacgg actgtccggt gagtcaccgg 119700
acagtgtccg gtgcacaccg gactgtccgg tgtgccagcg gagcaacgac tacttcgcgc 119760
gcatcggtcg actgcaaccg cattaaatgc gctacaatgc gcgccagagt cagagcacgc 119820
gcaggagacg caccagacag tctacatgac ctatccggtg caccaccaga cagcccagag 119880
gccccaccaa tcagagctcc aacggtcgaa ccctaacgac cggatgacgt ggctggcaca 119940
ccggacagtg tccggtggcg caccggactg tccggtggag caccggactg tccggtgcgc 120000
catgcgacag cagccttcca acgaccactt tgtggtggtt ggggttataa ataccccaa 120060
ccacccccac attcaatggc atctaagttt tccaccttca acacattaca agagctatag 120120
cattcaattc tagacacaac taaagagatc aaatcctctc ccaagtccgg aatcactcca 120180
aatcaaatag tgactagaga gagcgacatt tgtgttcatt tgagctcttg cgcttggatt 120240
gcttcttttc tttctcattc tttcttgtga taaactcaat tgtaaccgat gcaagagaca 120300
ccaattgtgt ggtggtcctt gcggggactt tgcgtcccgt ttgattgaga agagaagctc 120360
actcggtcta agtgaccgtt tgagagaggg aaaagggttg aaagaaatcc agtctttgtg 120420
accacctcaa cggggagtag gtttgcaaga accgaacctc ggtaaaacaa atcatcgtgt 120480
ctcactcttt atttgcccgc gatttgtttt ccaccctctc tctcggactc gtttctattt 120540
ataacgctaa cccggcttgt agttgtgctt aagtttataa atttcagatt cgccctattc 120600
acccccctcta tgcgactttt aattttaatc tatgttttta ccgtgaaagg cttgctttga 120660
tttttctttt tcatagacct agcttatgtg ggaattttaa tctatgtttt tatggttaaa 120720
ggcttacatt gatcaatcct ttcgtagacc tcactcacgt ggaatttttt agcactgaat 120780
ctgtgttttt taagatatgt aatcattatt ctatataatg ataaacaatt tcctacaata 120840
```

cagttttgct atatcaaagc cagtgatgtc aggcgccgct gtagtgccaa ctgagcagta 120900
gtattgctgt agtatccaac caattacatg ccatatgaaa ttgttccatt tgaaaatttt 120960
gtcttcaaat acagtgacat ggtactctcg cattttggtc ggagcaaaac tagtagtgga 121020
gctgaactaa aaacacatat ttacaaatcc aaaaataaac gatacaccac aaaaaacctc 121080
acagcagcca acgattctac ttactatcac tcagtctcat tgaacaatat ttaaccgacg 121140
aaaatccaac aatagcactc catataggca gcaaataacc tagaggtaac ccagttttag 121200
gattatttac ctaacaccgg gtcaattaag attgctactg atcatcctgt tgtggatgct 121260
tctaaaatct gaatctgcgg gttccactgt cttcagaaag tgcagaacaa agtccacacc 121320
gagcaacctg ctggtccaac agccagccat gtaagggctt gttcgattta aggtagattg 121380
agagaaattt gaggggttct ctaaggtgtc actgaatgcg tactaggctg aagaacagca 121440
ttaacagttc agtagtttaa caatacggca tattgcaggt attgctgctc acaaaactga 121500
tgaagtgcta gttgaaccaa aatcctatga tgaggcaagg cagttcagtg aacgggaagc 121560
acaagccatg gattcggagt tttctgaact ctttggaaaa tcttggacac ttgtgcctcc 121620
agataacggt taaaccacgt aacccatgac tctatattta aattacccat caatattagg 121680
aagaaataca ctatagctaa agtacgtagg ccttaatttg tatctaatta ccaatgacct 121740
cctattgtaa taaataatag acataactca gttttcattc tattattgta gaaaatcgaa 121800
taccactcag atctacatct aaatcgagta ttaacatctt ctactacaat aaaattgttt 121860
agatcactat agaccatata tatgtttcta cattgcctac ttatatcaac attaatacat 121920
taaaatttaa ttaaagtaaa tgtgcacatc gtgccaatat aaatgggcaa taaatatata 121980
tgttatgttg cataagataa aattgtttcc ataacaacta tttctatata taggttgtta 122040
gtttagattt acttagatat tttaagtgag tttttgacac atctatattg atagtatagc 122100
cataattgca tatatgattc cctaattaag tggaagtgag aactgtgggt gatcattgat 122160
ggatctattt ttcaagctct ttaatattac tttaaaggaa aaggtcagcc attttaaggc 122220
ttgactatta aaaaaatcaa ggttagttgt gctaccacat tgatcctaga tctcacctca 122280
agctctatga cttatcttga atgatattat gcgtgttact aacaatttct tatgctattg 122340
tagtatttat gaatgtactg acgacttaaa atccttgttc tagagaagtg taaaaacaag 122400
agttaactaa acattcaata aacacacgag tttttaactt aacttgagat aataagaata 122460
aattttataa aatcaaaaat tgattcatga ctatatgatg cgacaagagc caccttagtt 122520
agcgatagga ttcaaattaa ttgcatgttt caaactatag agagatataa tgcaaaagga 122580
aaaaatgaat attgatgaga agacataaaa tccagtcctt tgcaaaaaaa gattaataat 122640
tacatgtaca tatagactct aaagtatcta ttatgtgtat tacgttagat gataaataaa 122700
tactatattt tgggaatgtt ccaaacctcc caagataatt attagttaga taacaagttg 122760
ttagctagtt ttaactggac tggagcagct aacaaataat agcttttgag aggtataact 122820
aacaattaga tggtccatta cctaatcgat ccgaacctct aagctaattt ttgttgataa 122880
ctatatatta gttttagagg tctgtaatag agtcttaata taaattatcc aaacaataac 122940
tagtgcttat atcctacaat tttaaaccgc gtgagagtac atgttgatga actagtgata 123000
ttaattaatg tatcataaat attaatagtt ttatatatat ttttaggcaa aattaaatat 123060
gggtgacttc tcgagaaaaa taaggacaac agttaaaaag aagagacgaa ggagtatttg 123120
acatgtgtgt gtacgtagca ggggtagcat atgaaccgac caatttcagc caacgtttaa 123180
gtacgcatcg ctcaccttgt ctccttccgt tgcccttgat gacttggagc atctctagcc 123240
agctagcatg gtactcaaac agtgccggta cgcataatgt atagtactat gtagacactg 123300
acagacacac ggcaggtact acatgtacaa gcgtatgcta tacgcttggg tgtgtgcatg 123360
aaaaactgct agcatatact ctctccgtct ttttttattt attttttatt tatcgcagtt 123420
tagtttaaaa ttaaattaga gaaggacaaa tatctaaaag gagagttatt acttattagt 123480
gtgtgtatat atatatatat atatatatat atatatatat atatatatat accagtaaaa 123540
acattcggcc gacaagatcc acccatatta tattcatgct cacacctaca gcacacggcg 123600
gagcgacacg agcaattcat ctcctgccgc cacgccacgc cgtgaggaac agtgaagtag 123660
atagacgagc aaattaagcg cgcgggcatt atctagcaac ttttcttcct gcgcgcgatg 123720
gagcattatc tagcaacttt tcttcctgcg cgcgagctgt gcgcacagtg gccgcacttg 123780
ccggcaatgt agccatccat ccacatagta tgaagatgac ggcgtggggt acggtctcgt 123840
cccatccggc gaggaaggta accgccggtc ggcctccccc gggtcgtctt ctcttctccc 123900
acagttattg cagtgcccga attagaaaca aggtttacac gagcgcgaga cccacacgta 123960
tcgaagacag tagcagctca gcagacgaca gtgcagcagg ccatcatcgt gcgtgcagca 124020
gcgagtgatg caacatgaga ccaaacaaaa tgagctgcga tgttgacacc ccatgccacc 124080
attcatcggt gcttgccaat ggtgattggt gagtgaatgc agaagggggg gagagagaac 124140
aaaaagcggc aaaaggacgc actgcctgac gcgacgccta gtcgcctacc aaagcactcg 124200
tcttcttccc ggaaactcct catttacagc aggggggcag caggcccatc catcctcgga 124260
tccatgtctc acccaatcaa gaacacagag aatggaaaag ggaaagaaag ggggaggggg 124320
tgtaaatcgg tggatcgacg agccgtttgc ccttgggtca aatgatggac cttcgccgtg 124380
gaatacgatc gaaggacgaa cgcccagtcc tggttcttgg tctacgtggg cctggccagc 124440
gaatggaacc cattcttctg gacccagccg gccgggcttt gcgtcgtact cgtaacaacg 124500
tagggatgga atcgtgatga tgctgcagct gcggtcgcgg cggcggccgg tactggcggc 124560
gggcacgggt gcggcggcgg cggccagctc gtgccgccgc cgttgttcct ggcgccgtgg 124620
agcctctgct gctgctgctg atgctgcagc tgcggaggcc agtgcccgcc tccgccgccg 124680
atcgccaggg aaaggcctcc cgccgcggtc cccggatcgc cgttgctcag gagctgccgc 124740
gatttgcatt gcacagaaca aacaaagcgt cagccagtta gctcggtacg tagtcggtac 124800
ccacttgcgg atgcctgggg ctgtacggcg gcaggtgggg ttgcatcatg catggcggcg 124860
ctcgcgtcga gctggagctg ccatgccacc cggtggttga aacgtgacaa gcttgctttt 124920
attaagcaag attttaaacg cacacctcgt ttgattcaga gaacgctgaa cgcgggcggg 124980
accaaaccaa aacggatacc tttgccttgg tgctccgacg tgcggccgtc tgccagtcga 125040
tgtcgaacgc catggggacg cgctggtccg aggacttgtc gtcgccgccg ccgccgccgc 125100
cgccgtcaag gctgcccctt ttgttccccg ccgagcttcc cagcgacagg tccaggttgt 125160
gctcgtcgcc ggcggcgccg cccgtcgccg ctgcatgcac ggcgaaacag cggaccgtcg 125220
tcagagattg cttcctgtcc atataggttg tagcaaaccg ccgcacagcg acgagggggg 125280
tgatcgttgc agagcgcggg cggggataga cgaacccgcc ggcgcgacct cctcctcggc 125340
gtaaatgctg ggatcgaagt ttgtcaccgc gtccttgccg ttgcacttga tggccgcgcg 125400
gtcgtacgcc ctgcgcgcgc gcgcacagag agagagaaag ggagagagac acggggcatc 125460
catcagtcag tttcgcggcc cagggggtag cggggctccg agaaccgccg ccaggcgagc 125520
acacagtgcg gtccaattat tttacctggc ggcttcctcc tcggtgtcga acaggcccaa 125580
gtagacgtac ctgcagtgca gcgacacaga ccggaagtga cagccatgaa tgaataatgt 125640
gaggcgcaac gacaaagaaa ggatgggctg atgccgatgc agatacaggg accagggatg 125700
gggagggatt gggaagagga agacatgaag tggttgggca agaagggaag gaaggcgagg 125760
agaagggaga tggacggacg accggcatac ttcttgccga ggaactggcc catgcgcgcc 125820
tcccaccgcc cgcacttgtg gagcgtcacg cccctgtact tggagctgcc ccgggggaac 125880
cccgtgctct gccgccggag cacgtgaacg aactcctcct tgctcaggtg gcacatctgc 125940
tggtagacca agacgtggat tagatagacg agaaaaaatt actatatata ttgttgctat 126000
atgctaccta gtatagcgca gttgtataat aaataaatca cctgcttcat gtcgtcttgg 126060
taatcctcca agctgaaatt gatgtcggcc tccacgccgc ggaacttgat cgccgctcga 126120
tcgtacgccc tgaggttggc gggagaacca gacaggcaga gattacaatt tggcggcgaa 126180
cccccgctgt tattggcgga gaacttggca tgggagtgag gagagccaat acgaatcgaa 126240
tgaaacagac agtaggcttt tattaccgag cagccgcatg ggcggtgtca aatccgcctg 126300
caagtcgcca caagccattt ttgtgaggag tcccgagtcc ggaaccaaaa acgcctcgga 126360
ttgggcggta tctatcgtct tccaagcatg gatgcgtatg gaatggatgg actcatggac 126420
gtgcaagaaa cttacccaga tagacctgct tgccgcaatc cctgcattgc cacaagcaca 126480
agcagagagc atggggatgt gagagagaga gagaggcagg ggacggggac acacagaggg 126540
agaggaggag gaagagagag agagagagag agcatggcct gcctattggc atcgtaagaa 126600
taacttggat aagatgtggc tacgaaaggc aaaagcagga gaggcgagaa atgccaaaac 126660
aagaggaatc caattccaat ccaacagcga acgccctccc cccctccctc gcgagctgag 126720
ctgctgcctg ctccgtctct ctccctcgag tgaggaaagg gcggcggcaa cggcaacgga 126780
gtcgggagta cgggactact caccatatgt gcgactccca ccgccccgtc cggcggtaga 126840
acgtgacgcc gcggtactgc gagctgcgcg accgcggccc gcgccggctc ttcttgccag 126900
ccgccgcctg caccgcagcg gggccgccgg ccggcgcggc ggcccggcgg agccagcccg 126960
cgcgcgcgtt cgacgagccg ggcgccgcgc cgatggtggc cgccggggcc aggacgaaga 127020
actggcgcgt gacgacggcg gcggcggcgg agtcgtcgtc gggtatgtcg actagcgcgg 127080
ccgccgacga gaaggacgcg ccggagtcgt cggcagatgg ggacggcggg gcagcctcgg 127140
cggccggcga gtcgttaagg tcccacatgg ctaggaggct aggcgctggt cttcctctct 127200
tgctggtacg acgagtacga tgcttgtgtg tgcctgtgca caccctcctc tgctcggtct 127260
ccttcttgcc tcgcactaca actcgggtga tgtgaagagg gagaggaccc cagccaaaag 127320
caggcgctgt tgccttgttg gggcatgcaa gtactttctc ttttgctatc cccttggcaa 127380
agactcttcc aacctaggag agcagaggag gccaaaagca cccgcccgcc cgcccgcgga 127440
taggctcagc tgcttgcgct gtgtgccaag gttgccgcgg ctgcaagttg ccactagttc 127500
cgggcaggac agagtggaat gagcgacgcc gagggggcgg cgtcgggcgt cggccaacag 127560
gcaccagtca tcacaaatcc atcagcactt agcagcacct catcacaaat cctacgtact 127620
ctttttttatc gcgggcgggc atagcaacaa cctataacgc tcgttcctcg tcaaagcgac 127680
cagaccggcc tgccgccgtt gtagttttcg tttggataat tggactggat ccgatacgca 127740
gagtcgcaga cacaacggcc ccgttggccg ttgggagtgc tggatccgcg ccttctcctt 127800
ttggggtgcg gcacagggtg ggtaggggac ggtttgctca gcagagtgtc agagtccaga 127860
gtcagcctat ttttactgtt actgcaccgt cgtatcgtct ctctgccatg gcggcagccg 127920
gagccacatg tggatgaggt cacctgctgc tgttggtggc ggctatcctc tgcattatcc 127980
aacgtatgcg actgctctat ttttcttccc tcgccgtcct cggcaggagg atcgagcgcg 128040
cgacaatctc ttttttgctc tgatcgggac cagtgatctt ttcccggtcc caggtaatta 128100
ggccaggcta tttccggaca cagtctttac ccgaacgtat cggaaataat agcaatttag 128160
agattaataa taatacaaaa aacagtagca tgtttcatat atgtataact aaggttgaca 128220
acatactcta aattttacgc tataaatttc acaaatcgta ttaggatcgg gctttcacat 128280
attagattag gattaggatc gatctctatt tttatttatt tttaaactat aaattattta 128340
gagctcttac aaattatgaa agaacatttg gatcacgatc tattatcata tctacgtata 128400
attcaacagc aaatcaaatc atatactagt gctagtgaca aaataaatat atgcatgcac 128460
ttttttatag tgcgggttgt cgacactaaa aacaacaacg caagagtaga cgtagaagac 128520
cggtgatgat gacgatgtcg gcatagagaa agcaaaccaa caacgagccg ttcgtaatga 128580
cagttcctaa aaacctgatg tgatccctac ccgtgcagtt aggagacgta ggcaagtcaa 128640
agcggccacc agacgctttg gtgcgtgggg taccttggct tgcattgcat accggcaggc 128700
acatagtttc caacccgtcc tcatcggaag caggacgcgg cggccaccaa cactagtaca 128760
acagtggctc gtagccgtag tcctatcttg cacgtacgat gtacaggagc caggaggggt 128820
ggtaattggt atacatgccg cgcgcgatac catgtgtatc gtcgctcgct gctcttcgct 128880
ctgtgctgtg aactaaaagt ttcagtgaac tggttctcgt ctcgatcacg gcacgaccag 128940
cacctgttct atcaaatcta tcgagtatct agtatctgtc agctgtctgt ctgcctctcc 129000
ctttcattct ctgcagtgtt gtgaacttgt gatcaagcga gctgggcagt atttcccccc 129060
ccccctacc ccacccgccc ctagctctgt tcaggacctg cattgtaatt tgtaaatgcc 129120
tgcctccgag ctgttgtttt cactcaactc gctcaaaaag gttgtaacgc ctcaaaatcc 129180
tatgttggta ttaaagtaaa attgtccaag aatgttgaat taaaataact ttcaaaattt 129240
tgtttctgat aaattttttta ataaaagtat ccctatatga ttttagctat tcctttatgc 129300
aatgaatata tattgtctct aaaatatttt atacactagg agcgctattg tctctacata 129360
accatttttt ttgtatgaat tgcatattga ataataaaat accttatata tataatgttg 129420
cattgcatgc tgaatatttt gatttgttgc atttaaaatt aaatttgaag tttgaacttt 129480
attggaaatt ggaaagcagg aaataggaaa ttaaaacatc aaataaaaag aaaaaaggaa 129540
aaagagtgta atacccactt tgtaataaaa atctaaaagg agagattata ttcctttata 129600
tacatgtgtg tcatctatat ctatcatttc atgtgaacac ctcacttcca caaataaata 129660
attaaataaa aacactcaaa taaatcatgc atcatgctag gattttcttt tgtgtgcata 129720
ttgtgacaaa ataaaataaa aatgtgacaa gaaaaatatt aaagtccaaa aagggaattt 129780
agaatctaaa agaaatccta gaaagggaag gaaagaaaat tttatgtgat aaaaaaatgt 129840
aaaataaata aataaaatat tattgctata ctagtgcttt aatgtgacac ctgactcagg 129900
ggtagagctc aaaagcagat tcaaatccaa atttgaattc aaaatattta tgaataagag 129960
gatagaaaat aaaagaaagg agaggggact acctgcgctc tgggccgaat ttcttctgtg 130020
atcggcccat caggcaaatg cgcacagccc aaaagaacgg attagaccgt gtgccgaccg 130080
gtgggccgtt ggtgccagcc tcttccctct gcgccgatgg tgggggccac attccagatg 130140
cgcgtgctgt ggcgacttgc aggcgggccc aggttgtcag ttccttcccc ttcgccgtaa 130200
cagaactcgc gttctctacg ccgcatgact atcacttccg ccgagacctc gcacgcgcca 130260
catcttgatc ccaggaccgc tctggattct attgcagaga tctcgccgtc accgccgcgg 130320
gtatcggatg gtcgttacat cgtgtgccga cttatgcgga ttggcctggg cgcataagta 130380
gcgcgccgct cggtatcttg gcccaccaaa tgaacccctg cctcgcacca cagttgattg 130440
tgtagcctcg tcggtgggag aactccgctg ccgccgaaga aagctcgacc catagccagt 130500
actagagaga gaaagacgtg cgccaccggg cggattaacg ggtttccgcg gtcacctgag 130560
taggggagtg ggtgcggcat ctgtcgccgt tgggcaccgc acccgtgcct ccgtccccgc 130620
ctgcttgcag tgaccccgcg cacctccatg acgcaactcg tgcgtgcccg ctcctgtcac 130680
tcgcggtcgg gttgccgcgg ctccccattg ccgtgcaggg cggggccaaa ctcgacggtg 130740
ccctcgtcgt ttgggggcct gcatggttac tcgggggctt ggtccacggc gggcataacc 130800
aatcgccgga gttgggcgtc gtcgccggtc cgcatcgcgt tgcgagcagc gtcgccatcg 130860
ctgcggtgta ggaagaaggg gctgccatcg ccatggacaa agcactgggc cgcagccgaa 130920
gaacttcatc tgcgctaggg cttcacagca ccgtgacccg cgcttcgtcg tcggccatcc 130980
cctgcctcct tcaacggtga gaattccccc tcctccgagt caacggggcc gagtcgcttg 131040
ctgttggtgg agtcttgcgt attccaggag aaggtagcgg cataaggtag aagagggagt 131100
tgtggctgtc agattgatga cgggcggcct agattacccc ttcattcctt agtcgtgggc 131160
cgttagatcg tgatccaaca cgcgtgatta gttgccagct catgcctttt tggttgccgt 131220
tggatctgga tccgaggctc cacatggcgt accccttcgt tgtgttaagt tggcggccgt 131280
gggatgaaaa tctaacggct cagggtgcat gcgcatactg ctgccgaccc atcttacaaa 131340
agagccctaa tgtcgttaat aaataacccg cagtccacgt agttgggctc tgagtcttag 131400
gaaaacttac accgagaccc ctgaacttct ctgtattagt gcgcccagtc cagagagcca 131460
gaaaaatcag aaaacaaata tagaattgga tttttaatgt agaaataaat gctagaattg 131520
gtttaattca tagaaaattc atgtgtagtc caaattaatc catttcagtt tctataattt 131580
tgtaataatg ttgtttatca ccctgtgtct ctgttttaag atgaaaatgg tattaaaatt 131640
tatttcttaa ttaacctcgt atcaaataca taaaacctta ggaaattcat atatcctccg 131700
ttttaacttc aatttgatcc gttcaagttg cgttagtctc gtagcaaggc gtatatcatt 131760
attacgcagt atattcttat gtttggtgtg atgttaattt tgtctatacc atgtttgttt 131820
gtattgctac gactagcagt gaggtcacga ggatttgaag aatcaccctg gtaactggaa 131880
tctcaagtgt caggcaagtt gtgcccttga ccacttttta cccaataatg ttctctaatt 131940
atcattcact cgtgcatagg ttaattttga tgggacccaa taggacaccc tagatttgtt 132000
tatctcatta ccttgtttac ccctgaatca cttgggtagt ttgctattgc tttacatggt 132060
tttgggataa tcaattatta tatctatgtt ccaattattc ttgttattct atttatgttc 132120
atgtcaagtt cattaatgtt aattggaaca tagagcttaa cttgagaaac acgtgccacc 132180
acaagggttt aatgggacgc ccttggctga ctaattagga aagctagtgg aagactacct 132240
tacccgaaag gggcaagggc agtaggggag tggtcagtgt agggaggtcc ttggttgatt 132300
ttgctgcgat ggcggtcaga caagaacctt gcattggaac ttcttataaa ctgtagcggg 132360
ttttcggaag ctagtggaac tttgtaaagg cctcgtagtg ttgccctgcc gcgcttccta 132420
ggtagaggtg tatgggattc gcgactcctg gcagatggtt agcatgactt gtgggtaaag 132480
ggtacnnnnn nnnnnnnnnn nnnnnnnnnn nnnnnnnnnn nnnnnnnnnn nnnnnnnnnn 132540
nnnnnnnnnn nnnnnnnnnn nnnnnnnnnn nnnnnnnnnn nnnnncaata ggacccccta 132600
gatttgtttg cttcattacc tttgtttacc cctgaatcac ttgggtagtt tgctattgct 132660
ttacatggtt tgggataatc aattattata tctatgttcc aattattctt gttattctat 132720
ttatgttcat gtcaagttca ttaatgttaa ttggaacata gagcttaact tgagaaacac 132780
gtgccaccac aagggtttaa tgggacgccc ttggctgact aattaggaaa gctagtggaa 132840
gactacctta cccgaaaggg gcaagggcag taggggagtg gtcagtgtag ggaggtcctt 132900
ggttgatttt gctgcgatgg cggtcagaca agaaccttgc attggaactt cttataaact 132960
gtagcgggtt ttcggaagct agtggaactt tgtaaaggcc tcgtagtgtt gccctgccgc 133020
gcttcctagg tagaggtgta tgggattcgc gaccccttgg cagatgggta gcatgacttg 133080
tgggtaaagg gtacaacctc tgcagagtgt aaaactagta tactagccgt gctcgcggtc 133140
atgagcggct caggactctc tgatgtttaa attatggaac ttaaattcaa ttttgtcatt 133200
tgcattgcat gggtctatta ttaattttgt tcaattactt tatctaaggt ttggtattca 133260
cttatactta gtaactgcta ataaaatttt gaccaactac ttaaaagcaa tgctcagctt 133320
taacccctat cattgattag ccttacacat cacatgacct cacacctttg tgagtttatg 133380
tccaccggtt ccccacaact tgttgagcta tgatcatgtg tgagctcacc cttctgtctc 133440
acaccccccc acaggagaag agcaggtggt tcaggaggag ccgcctaaca ctgaggagtt 133500
cgatctgatc taggtggcgt ttcccagtcg acattggcgc cgacgatcct tagttcgttt 133560
tacttttatc ttttatttg taataagtct tccgctatgt aataaatact ctgatgtttt 133620
atgacattta tctctataca ctctgttatt atatatgttg tcttcttggc gcatgtatga 133680
gatgcacccg gctttgttcc ttaaagccgg gtgtgacaga agtggtatca gaggaaatgt 133740
tgactgtagg acgaaaccta gatagaaatg gacaaaaccc ttcactactt accttactct 133800
gattctttct acacttatct tgattctgtc tcaccttcta ctgttctact ctgatcattc 133860 ttacctttc tactcttagt caagatggat ttcacacctt ggaatcccta cccctatgac 133920
atttttaaga ggtaggaagc ctaagacaaa attaaactat ttctttataa aatgttggtt 133980
gattgttctg atgatcaatg cctgatttgc ttctttgatt gatgnnnnnn nnnnnnnnnn 134040
nnnnnnnnnn nnnnnnnnnn nnnnnnnnnn nnnnnnnnnn nnnnnnnnnn nnnnnnnnnn 134100
nnnnnnnnnn nnnnnnnnnn nnnnagaatc tagagatttc gtcttttcac atctggaggt 134160
aaactgtgat cctctatcca aaatgatctt cttcggtaca tcgtgtggag acacaatccg 134220
agccatatat aactctacca attgagatac cttataagta gtcttgacca gaatggaatg 134280
agtcactttg gtaaatttat ccataataac ccatatagaa tcatatcctc tcggggtgcg 134340
aggcaatcca gtaatgaagt ccttaccaat ttcttcccct tccacttggg tatcttcagt 134400
ggatgtaata gtccagctgg tctttggtgt taggccttaa ctctttgaca cccatcgcac 134460
atagccacat gtgcagccac atctctcttc aatccatacc accagtattt ctgcttcaat 134520
tcctgataca tcttggtact accaggatga atagaataat ccaagttatg ggcttccttt 134580
agaatagtct tacgaaggct ttcaatacca ggaacacata tcctgccctt gaaccatatt 134640
gtgtcttgtt catcttccgt aaattccgga cctctacctt tcgtaataag atccttgatc 134700
tcttgtatct tagcatcacc aatctgtcgt tctgtggatt tcttgctcca aggtaggttc 134760
cacatcaata atgactcctt aagcgtgagc atctatcccc aggttaagtc tcctgaaatc 134820
ctcaacaatc tcatcgggta gctgggcaac aatagctgaa tgaacatgct cctttcgact 134880
caaggcatct gcaaccaaat ttgccttgcc caggtgatag tgaatctcca aatcataatc 134940
cttaataagc tccaaccaac ggcgttgcct aaggttgaga tccttctgag tgaatataaa 135000
ctcttatgat ccgtatatac ttggcacttg gtccccatga tataatgtct ccatatctta 135060
agcgcatgca caacggctgc caattccaag tcgtgagtgg ggtagttcaa ttcatgtctc 135120
cgtaactgat gagacgcata ggcaatcaca tgtccttcct gcatgagcac acatcctaag 135180
ccttggccac atgcatcaca atagatatca aatcctttct gtaggtctgg cataaccaat 135240
actggtggtg acatcaatct cttcttcaat tgatcaaagc tgtcttggca cttctcgtcc 135300
cacttaaatt ctctgtcctt ctccagaagc gaggtcgtag gcttagcaat cttagaaaat 135360
ccttcaataa atctccgata atatcctact agtctcaaga aactctgaat ctcagtaact 135420
gtagtgggta ctctccactc cattatctcc ttaaccttag taggatccat tgatattcct 135480
ccattagaaa taatatgacc aataaatggc acctcgccaa tccaaaactc gcacttgcta 135540
aacttggcat atagctggtt atctcgtagc ttctgtagca ccatcctcag atgttcctcg 135600
tgatcactat cactcttgga atagataaga atatcgtcga tgaaaaccac gacgaatcta 135660
tccaaatcat gaacacatta tcctttagat ccataaagta ggctagtgca ttagttagtc 135720
cagacgacat aacggtgaac tcatataaac catatcgggt caaggaattc gtcttgggaa 135780
tatccgatgg cctaatattc atttgatggt aacccgatcg aagatcaatc ttcgagaata 135840
ctcttgcacc tctcacctga ttaaataaat cttcaatgtg gggtaatgga tacttgttct 135900
tcatagtgac accattaagg gacctttaat ccacacacat cccttgcaat ccatctttct 135960
tctgtacaaa caaaaccgat gctctccaag gtgaagactc ggacgaatgt acccagcctc 136020
ttgtaattcc gttaattgct tcttaagttc ctttagttct tctacggaca tcctgtatgg 136080
ccgtttagaa ataggagtcg tcccaggtaa gagatcaatg accaactcaa catccatatc 136140
tggtggcacc cctaataact cctctggaaa gacatccgga agatctctaa ctgcacggat 136200
gttgtcaccc acaaacttct catcttctaa gaatgttgtt agactaatgg tggtagttac 136260
tgcaattcca acttcaaata tttctccttt ggaactggtg agttctatgg ttcccttagc 136320
acagtgtata aactgtcttt gcctttctta accatgaaat accaaggatc acgcctatag 136380
tgctctcttc taacactata ggggtagccc atctgcgtta gaaacatagg gtgcgaaagg 136440
aagaattgta gacaaggcga gtaattaaga ggaatattac tacgggggat ttattagcta 136500
agtagattag tgtgtcacct actaacgcta atacattacc ttatggtggt acatgctaag 136560
atgcccgtct atactatttc aatcaatcaa agaagcaaat caggcattga tcatcagaac 136620
aatcaaccaa catttttaat aaagaaaata gttttaattt tgtcttaggc ttcctacctc 136680
ttaaaaatgt catagggggta gggattccaa ggtgtgaaat ccatcttgac taagagtaga 136740
aaaggtaaga atgatcagag tagaacagta gaaggtgaga cagaatcaag ataagtgtag 136800
aaagaatcag agtaaggtaa gtagtgaagg gttttgtcca tttctatcta ggtttcgtcc 136860
tacagtcaac atttcctctg ataccacttc tgtcacaccc ggctttaagg aacaaagccg 136920
ggtgcatctc atacatgcgc caagaagaca acatatataa taacagagtg tatagagata 136980
aatgtcataa aacatcagag tatttattac atagcggaag acttattaca aaataaaaga 137040
taaaagtaaa acgaactaag gatcgtcggc gccaatgtcg actgggaaac gccacctaga 137100
tcagatcgaa ctcctcagtg ttaggcggct cctcctgaac cacctgctct tctcctgtgg 137160
gggggtgtga gacagcaagg gtgagctcac acatgatcat agctcaacaa gttgtgggga 137220
accggtggac ataaactcac aaaggtgtga ggtcatgtga tgtgtaaggc taatcaatga 137280
taggggttaa agctgagcat tgcttttaag tagttggtca aaattttatt agcagttact 137340
aagtataagt gaataccaaa ccttagataa agtaattgaa caaaattaat aatagaccca 137400
tgcaatgcaa atgacaaaat tgaatttaag ttccataatt taaacatcag agagtcctga 137460

```
gccgctcatg accgcgagca cggctagtat actagtttta cactctgcag aggttgtacc 137520
ctttacccac aagtcatgct acccatctgc caaggggtca cgaatcccat acacctctac 137580
ctaggaagcg cggcagggca acactacgag gcctttacaa agttccacta gcttccgaaa 137640
acccgctaca gtttataaga agttccaatg cagggttctt gtctgaccgc catcgcagca 137700
aaatcaacca aggacctccc tacactgacc actcccctac tgcccttgcc cctttcgggt 137760
aaggtagtct tccactagct ttcctaatta gtcagccaag ggcgtcccat taaacccttg 137820
tggtggcacg tgtttctcaa gttaagctct atgttccaat taacattaat gaacttgaca 137880
tgaacataaa tagaataaca agaataattg gaacatagat ataataattg attatcccaa 137940
aaccatgtaa agcaatagca aactacccaa gtgattcagg ggtaaacaag gtaatgagat 138000
aaacaaatct agggtgtcct attgggtccc atcaaaatta acctatgcac gagtgaatga 138060
taattagaga acattattgg gtaaaaagtg gtcaagggca caacttgcct ggcacttgag 138120
attccagtta ccagggtgat tcttcaaatc ctcgtgacct cactgctagt cgtagcaata 138180
caaacaaaca tggtatagac aaaattaaca tcacaccaaa cataagaata tactgcgtaa 138240
taatgatata cgcgttgcta cgagactaac gcaacttgaa cggatcaaat tgaagttaaa 138300
acggaggata tatgaatttc ctaaggtttt atgtatttga tacgaggtta attaagaaat 138360
aaattttaat accattttca tgttaaaaca gagacacagg gtgataaaca acattattac 138420
aaaattatag aaactgaaat ggattaattt ggactacaca tgaattttct atgaattaaa 138480
ccaattctag catttatttc tacattaaaa atccaattct atatttgttt tctgattttt 138540
ctggctctct ggactgggcg cactaataca gagaagttca ggggtctcgg tgtaagtttt 138600
cctaagactc agagcccaac tacgtggact gcgggttatt tattaacgac attagggctc 138660
ttttgtaaga tgggtcggca gcagtatgcg catgcaccct gagccgttag attttcatcc 138720
cacggccgca acttaacaca acgaaggggt acgccatgtg gagcctcgga tccagatcca 138780
acggcaacca aaaaggcatg agctggcaac taatcacgcg tgttggatca cgatctaacg 138840
gcccacgact aaggaatgaa ggggtaatct aggccgcccg tcatcaatct gacagccaca 138900
accccctctt ctaccttatg ccgctacctt ctcctggaat acgcaagact ccaccaacag 138960
caagcgactc ggccccgttg actcggagga gggggaattc tcaccgttga aggaggcagg 139020
ggatggccga cgacgaagcg cgggtcacgg tgctgtgaag ccctagcgca gatgaagttc 139080
ttcggctgcg gcccagtgct ttgtccatgg cgatggcagc cccttcttcc tacaccgcag 139140
cgatggcgac gctgctcgca acgcgatgcg gaccggcgac gacgcccaac tccggcgatt 139200
ggttatgccc gccgtggacc aagcccccga gtaaccatgc aggcccccaa acgacgaggg 139260
caccgtcgag tttggccccg ccctgcacgg caatggggag ccgcggcaac ccgaccgcga 139320
gtgacaggag cgggcacgca cgagttgcgt catggaggtg cgcggggtca ctgcaagcag 139380
gtggggacgg aggcacgggt gcggtgccca acggcgacag atgccgcacc cactccccta 139440
ctcaggtgac cgcggaaacc cgttaatccg cccggtggcg cacgtctttc tctctctagt 139500
actggctatg ggtcgagctt tcttcggcgg cagcggagtt ctcccaccga cgaggctaca 139560
caatcaactg tggtgcgagg caggggttca tttggtgggc caagataccg agcggcgcgc 139620
tacttatgcg cccaggccaa tccgcataag tcggcacacg atgtaacgac catccgatac 139680
ccgcggcggt gacggcgaga tctctgcaat agaatccaga gcggtcctgg gatcaagacg 139740
tggcgcgtgc gaggtctcgg cggaagtgat agtcatgcgg cgtagagaac gcgagttctg 139800
```

ttacggtgaa ggggaaggaa ctgacaacct gggcccgcct gcaagtcgcc acagcacgcg 139860
catctggaat gtggccccca ccatcggcgc agagggaaga ggctggcacc aacggcccac 139920
cggtcggcac acggtctaat ccgttctttt gggctgtgcg catttgcctg atgggccgat 139980
cacagaagaa attcggccca gagcgcaggt agtccccctc tcctttcttt tattttctat 140040
cctcttattc ataaatattt tgaattcaaa tttggatttg aatctgcttt tgagctctac 140100
ccctgagtca ggtgtcacat taaagcacta gtatagcaat aatattttat ttatttattt 140160
tacatttttt atcacataaa attttctttc cttccctttc taggatttct tttagattct 140220
aaattccctt tttggacttt aatatttttc ttgtcacatt tttattttat tttgtcacaa 140280
tatgcacaca aaagaaaatc ctagcatgat gcatgattta tttgagtgtt tttatttaat 140340
tatttatttg tggaagtgag gtgttcacat gaaatgatag atatagatga cacacatgta 140400
tataaaggaa tataatctct ccttttagat ttttattaca aagtgggtat tacaaatcct 140460
acccccctta acaagaatct cgtcctcgag atttaggaag gactaggaaa aagatgggga 140520
aaaatctatg tgaaactctt cttctctttc ccatgatgct tcatcttctc catggtgact 140580
ccattgcact ttgcacattt ttatcacctt attccttgta agtcgagtaa aagtgtcaag 140640
aatcttgatc ggataccccg tgtaagtcaa atcatcctga acactgagct cttccattgg 140700
taactgttcc tcaaggacac ggagacactt cttaagttga gacacgtaaa ttacattata 140760
cacatcagat atattatcag gtagctcgag ttgataggcc atctctccaa ctcgcctaaa 140820
aactcagaat ggtccaataa agtgagggaa caatttgccc ttaactttaa atctcctcat 140880
tccacgaagt ggtgacactt tgaggtacac atgatcacct tcctcaaact ccagtggtct 140940
tcttctatta tcagcgtagc tcttttgcct ggtctgagct accctcaaat tctcccgaat 141000
tatacggact tgttcctctg cttcttgaat aagttcaggc ccaaagaaat gtcttcctct 141060
agtctggtcc aaaaatagag gtgtcctgca tttcctgcca tacagagcct cgtacggtga 141120
catcttcaga ctagcctgat agctattatt atatgaaaac tcagcataag gtagactctt 141180
gtcacaacta ctaccatgct gaagggcgca agctctcaac atgtcttcca atacttgatt 141240
agccctttta gtttgtccat cagtctgagg ttggtaagcc aaactagaat tcaacttcgc 141300
atccatattc tcatgaaaac ttttccaaaa tctggaggta aactgtgatc ctctatccaa 141360
aatgatcttc ttcggtacat cgtgtggaga cacaatccga gccatatata actctaccaa 141420
ttgagatacc ttataagtag tcttgaccag aatggaatga gtcactttgg taaatttatc 141480
cataataacc catatagaat catatcctct cggggtgcga ggcaatccag taatgaagtc 141540
cttaccaatt tcttcccctt ccacttgggt atcttcagtg gatgtaatag tccagctggt 141600
ctttggtgtt aggccttaac tctttgacac ccatcgcaca tagccacatg tgcagccaca 141660
tctctcttca atccatacca ccagtatttc tgcttcaatt cctgatacat cttggtacta 141720
ccaggatgaa tagaataatc caagttatgg gcttccttta gaatagtctt acgaaggctt 141780
tcaataccag gaacacatat cctgcccttg aaccatattg tgtcttgttc atcttccgta 141840
aattccggac ctctaccttt cgtaataaga tccttgatct cttgtatctt agcatcacca 141900
atctgtcgtt ctgtggattt cttgctccaa ggtaggttcc acatcaataa tgactcctta 141960
agcgtgagca tctatcccca ggttaagtct cctgaaatcc tcaacaatct catcgggtag 142020
ctgggcaaca atagctgaat gaacatgctc ctttcgactc aaggcatctg caaccaaatt 142080
tgccttgccc gggtgatagt gaatctccaa atcataatcc ttaataagct ccaaccaacg 142140
gtgttgccta aggttgagat ccttctgagt gaatataaac tcttatgatc cgtatatact 142200
tggcacttgg tccccatgat ataatgtctc catatcttaa gcgcatgcac acggctggca 142260
attccaagtc gtgagtgggg tagttcaatt catgtctccg taactgatga gacgcatagg 142320
caatcacatg tccttcctgc atgagcacac atcctaagcc ttggccacat gcatcacaat 142380
agatatcaaa tcctttctgt aggtctggca taaccaatac tggtggtgac atcaatctct 142440
tcttcaattg atcaaagctg tcttggcact tctcgtccca cttaaattct ctgtccttct 142500
ccagaagcga ggtcgtaggc ttagcaatct tagaaaatcc ttcaataaat ctccgataat 142560
atcctactag tctcaagaaa ctctgaatct cagtaactgt agtgggtact ctccactcca 142620
ttatctcctt aaccttagta ggatccattg atattcctcc attagaaata atatgaccaa 142680
taaatggcac ctcgccaatc caaaactcgc acttgctaaa cttggcatat agctggttat 142740
ctcgtagctt ctgtagcacc atcctcagat gttcctcgtg atcactatca ctcttggaat 142800
agataagaat atcgtcgatg aaaaccacga cgaatctatc caaatcatga acacattatc 142860
ctttagatcc ataaagtagg ctagtgcatt agttagtcca aacgacataa cggtgaactc 142920
atataaacca tatcgggtca aggaattcgt cttgggaata tccgatggcc taatattcat 142980
ttgatggtaa cccgatcgaa gatcaatctt cgagaatact cttgcacctc tcacctgatt 143040
aaataaatct tcaatgtggg gtaatggata cttgttcttc atagtgacac cattaaggga 143100
cctttaatcc acacacatcc cttgcaatcc atctttcttc tgtacaaaca aaaccgatgc 143160
tctccaaggt gaagactcgg acgaatgtac ccagcctctt gtaattccgt taattgcttc 143220
ttaagttcct ttagttcttc tacggacatc ctgtatggcc gtttagaaat aggagtcgtc 143280
ccaggtaaga gatcaatgac caactcaaca tccatatctg gtggcacccc taataactcc 143340
tctggaaaga catccggaag atctctaact gcacggatgt tgtcacccac aaacttctca 143400
tcttctaaga atgttgttag actgatggtg gtagttactg caattccaac ttcaaatatt 143460
tctcctttgg aactggtgag ttctatggtt cccttagcac agtgtataaa ctgtctttgc 143520
ctttcttaac catgaaatac caaggatcac gcctatagtg ctctcttcta acactatagg 143580
ggtagcccat ctgcgttaga aacatagggt gcgaaaggaa gaattgtaga caaggcgagt 143640
aattaagagg aatattacta cgggggattt attagctaag tagattagtg tgtcacctac 143700
taacgctaat acattacctt atggtggtac atgctaagat gcccgtctat actatttcaa 143760
tcaatcaaag aagcaaatca ggcattgatc atcagaacaa tcaaccaaca tttttaataa 143820
agaaaatagt tttaattttg tcttaggctt cctacctctt aaaaatgtca taggggtagg 143880
gattccaagg tgtgaaatcc atcttgacta agagtagaaa aggtaagaat gatcagagta 143940
gaacagtaga aggtgagaca gaatcaagat aagtgtagaa agaatcagag taaggtaagt 144000
agtgaagggt tttgtccatt tctatctagg tttcgtccta cagtcaacat ttcctctgat 144060
accacttctg tcacacccgg ctttaaggaa caaagccggg tgcatctcat acatgcgcca 144120
agaagacaac atatataata acagagtgta tagagataaa tgtcataaaa cattagagta 144180
tttattacat agcggaagac ttattacaaa ataaaagata aaagtaaaac gaactaagga 144240
tcgtcggcgc caatgtcgac tgggaaacgc cacctagatc agatcgaact cctcagtgtt 144300
aggcggctcc tcctgaacca cctgctcttc tcctgtgggg ggggtgtgag acagaagggt 144360
gagctcacac atgatcatag ctcaacaagt tgtggggaac cggtggacat aaactcacaa 144420
aggtgtgagg tcatgtgatg tgtaggctat tcatgatagg ggttaagctg agcattgctt 144480
ttaagtagtg gtcaaatttt attatgcagg tactaagtan nnnnnnnnnn nnnnnnnnnn 144540
nnnnnnnnnn nnnnnnnnnn nnnnnnnnnn nnnnnnnnnn nnnnnnnnnn nnnnnnnnnn 144600
nnnnnnnnnn nnnnnnnnng gtttgggagt tgaagaatca gcttgattcg ttctctacct 144660
aggatacgcg gcagggcaac actactcgtt ctttacaagt tccactagct tccgaaaacc 144720
cgctacgtta agaagttcca atgcagggtt cttgtctgac cgccatcgca gcaaaatcaa 144780
ccaaggacct ccctacactg accactcccc tactgccctt gccccttcg ggtaaggtag 144840 tcttccacta gctttcctaa ttagtcagcc aagggcgtcc cattaaaccc ttgtggtggc 144900
acgtgtttct caagttaagc tctatgttcc aattaacatt aatgaacttg acatgaacat 144960
aaatagaata acaagaataa ttggaacata gatataataa ttgattatcc caaaaccatg 145020
taaagcaata gcaaactacc caagtgattc aggggtaaac aaggtaatga gataaacaaa 145080
tctagggtgt cctattgggt cccatcaaaa ttaacctatg cacgagtgaa tgataattag 145140
agaacattat tgggtaaaaa gtggtcaagg gcacaacttg cctgacactt gagattccag 145200
ttaccagggt gattcttcaa atcctcgtga cctcactgct agtcgtagca atataaacaa 145260
acatggtata gacaaaatta acatcacacc aaacataaga atatactgcg taataatgat 145320
atacgcgttg ctacgagact aacgcaactt gaacggatca aattgaagtt aaaacggagg 145380
atatatgaat ttcctaaggt tttatgtatt tgatacgagg ttaattaaga aataaatttt 145440
aataccattt tcatgttaaa acagagacac agggtgataa acaacattat tacaaaatta 145500
tagaaactga aatggattaa tttggactac acatgaattt tctatgaatt aaaccaattc 145560
tagcatttat ttctacatta aaaatccaat tctatatttg ttttctgatt tttctggctc 145620
tctggactgg gcgcactaat acagagaagt tcaggggtct cggtgtaagt tttcctaaga 145680
ctcagagccc aactacgtgg actgcgggtt atttattaac gacattaggg ctcttttgta 145740
agatgggtcg gcagcagtat gcgcatgcac cctgagccgt tagattttca tcccacggcc 145800
gcaacttaac acaacgaagg ggtacgccat gtggagcctc ggatcgagat ccaacggcaa 145860
ccaaaaaggc atgagctggc aactaatcac gcgtgttgga tcacgatcta acggcccacg 145920
actaaggaat gaaggggtaa tctaggccgc ccgtcatcaa tctgacagcc acaaccccct 145980
cttctacctt atgccgctac cttctcctgg aatacgcaag actccaccaa cagcaagcga 146040
ctcggccccg ttgactcgga ggagggggaa ttctcaccgt tgaaggaggc aggggatggc 146100
cgacgacgaa gcgcgggtca cggtgctgtg aagccctagc gcagatgaag ttcttcggct 146160
gcggcccagt gctttgtcca tggcgatggc agccccttct ccctacaccg cagcgatggc 146220
gacgctgctc gcaacgcgat gcggaccggc gacgacgccc aactccggcg attggttatg 146280
cccgccgtgg accaagcccc cgagtaacca tgcaggcccc caaacgacga gggcaccgtc 146340
gagtttggcc ccgccctgca cggcaatggg gagccgcggc aacccgaccg cgagtgacag 146400
gagcgggcac gcacgagttg cgtcatggag gtgcgcgggg tcactgcaag caggcgggga 146460
cggaggcacg ggtgcggtgc ccaacggcga cagatgccgc acccactccc ctactcaggt 146520
gaccgcggaa acccgttaat ccgcccggtg gcgcacgtct ttctctctct agtactggct 146580
atgggtcgag ctttcttcgg cggcagcgga gttctcccac cgacgaggct acacaatcaa 146640
ctgtggtgcg aggcaggggt tcatttggtg ggccaagata ccgagcggcg cgctacttat 146700
gcgcctaggc caatccgcat aagtcggcac acgatgtaac gaccatccga tacccgcggc 146760
ggtgacggcg agatctctgc aatagaatcc agagcggtcc tgggatcaag acgtggcgcg 146820
tgcgaggtct cggcggaagt gatagtcatg cggcgtagag aacatgagtt ctgttacggc 146880
gaaggggaag gaactgacaa cctgggcccg cctgcaagtc gccacagcac gcgcatctgg 146940
aatgtggccc ccaccatcgg cgcagaggga agaggctggc accaacggcc caccggtcgg 147000
cacacggtgt aatccgtttt tttgggctgt gcgcatttgc ctgatgggcc gatcacaaac 147060
gaatcaagct gattcatcag acgtccaaan nnnnnnnnnn nnnnnnnnnn nnnnnnnnnn 147120
nnnnnnnnnn nnnnnnnnnn nnnnnnnnnn nnnnnnnnnn nnnnnnnnnn nnnnnnnnnn 147180
nnnnnnnnna ttcccaacct taggaaagta attgacaaaa ttattaatag acccatgcaa 147240
tgcaaatgac aaaatgaatt aagttccata attaaacatc agagagtcct gagccgctca 147300
tgaccgcgag cacggctagt atactagttt tacactctgc agaggttgta ccctttaccc 147360
acaaagtcat gctacccatc tgccaagggg tcgcgaatcc catacacctc acctaggaag 147420
cgcggcaggg caacactacg aggcctttac aaagttccac tagcttccga aaacccgcta 147480
cagtttataa gaagttccaa tgcaaggttc ttgtctgacc gccatcgcag caaaaacaac 147540
caaggacctc cctacactga ccactcccct actgcccttg cccctttcgg gtaaggtagt 147600
cttccactag ctaaaaataa ttagtcagcc aagggcgtcc cattaaaccc ttgtggtggc 147660
acgtgtttct caagttaagc tctatgttcc aattaacatt aatgaacttg acatgaacat 147720
aaatagaata acaagaataa ttggaacata gatataataa ttgattatcc caaaaccatg 147780
taaagcaata gcaaactacc caagtgattc aggggtaaac aaggtaatga gataaacaaa 147840
tctagggtgt cctattgggt cccatcaaaa ttaacctatg cacgagtgaa tgataattag 147900
agaacattat tgggtaaaaa gtggtcaagg gcacaacttg cctgacactt gagattccag 147960
ttaccagggt gattcttcaa atcctcgtga cctcactgct agtcgtagca atacaaacaa 148020
acatggtata gacaaaatta acatcacacc aaacataaga atatactgcg taataatgat 148080
atacgcgttg ctacgagact aacgcaactt gaacggatca aattgaagtt aaaacggagg 148140
atatatgaat ttcctaaggt tttatgtatt tgatacgagg ttaattaaga aataaatttt 148200
aataccattt tcatgttaaa acagagacac agggtgataa acaacattat tacaaaatta 148260
tagaaactga aatggattaa tttggactac acatgaattt tctatgaatt aaaccaattc 148320
tagcatttat ttctacatta aaaatccaat tctatatttg ttttctgatt tttctggctc 148380
tctggactgg gcgcactaat acagagaagt tcaggggtct cggtgtaagt tttcctaaga 148440
ctcagagccc aactacgtgg actgcgggtt atttattaac gacattaggg ctcttttgta 148500
agatgggtcg gcagcagtat gcgcatgcac cctgagccgt tagattttca tcccacggcc 148560
gcaacttaac acaacgaagg ggtacgccat gtggagcctc ggatccagat ccaacggcaa 148620
ccaaaaaggc atgagctggc aactaatcac gtgtgttgga tcacgatcta acggcccacg 148680
actaaggaat gaaggggtaa tctaggccgc ccgtcatcaa tctgacagcc acaacccccct 148740 cttctacctt atgccgctac cttctcctgg aatacgcaag actccaccaa cagcaagcga 148800
ctcggccctg ttgactcgga ggaggggaat tctcaccgtt gaaggaggca ggggatggcc 148860
gacgacgaag cgcgggtcac ggtgctgtga agccctagcg cagatgaagt tcttcggctg 148920
cggcccagtg ctttgtccat ggcgatggca gccccttctt cctacaccgc agcgatggcg 148980
acgctgctcg caacgcgatg cggaccggcg acgatgccca actccggcga ttggttatgc 149040
ccgccgtgga ccaagccccc gagtaaccat gcaggccccc aaacgacgag ggcaccgtcg 149100
agtttggccc cgccctgcac ggcaatgggg agccgcggca acccgaccgc gagtgacagg 149160
agcgggcacg cacgagttgc gtcatggagg tgcgcggggt cactgcaagc aggcggggac 149220
ggaggcacgg gtgcggtgcc caacggcgac agatgccgca cccactcccc tactcaggtg 149280

-continued accgcggaaa cccgttaatc cgcccggtgg cgcacgtctt tctctctcta gtactggcta 149340
tgggtcgagc tttcttcggc ggcagcggag ttctcccacc gacgaggcta cacaatcaac 149400
tgtggtgcga ggcaggggtt catttggtgg gccaagatac cgagcggcgc gctacttatg 149460
cgcccaggcc aatccgcata agtcggcaca cgatgtaacg accatccgat acccgcggcg 149520
gtgacggcga gatctctgca atagaatcca gagcggtcct gggatcaaga cgtggcgcgt 149580
gcgaggtctc ggcggaagtg atagtcatgc ggcgtagaga acgcgagttc tgttacggcg 149640
aaggggaagg aactgacaac ctgggcccgc ctgcaagtcg ccacagcacg cgcatctgga 149700
atgtggcccc caccatcggc gcagagggaa gaggctggca ccaacggccc accggtcggc 149760
acacggtcta atccgttctt ttgggctgtg cgcatttgcc tgatgggccg atcacagaag 149820
aaattcggcc cagagcgcag gtagtccccc tctcctttct tttattttct atcctcttat 149880
tcataaatat tttgaattca aatttggatt tgaatatgct tttgagctct acccctgagt 149940
caggtgtcac attaaagcac tagtatagca ataatatttt atttatttat tttacatttt 150000
tttatcacat aaaatttttct ttccttccct ttctaggatt tcttttagat tctaaattcc 150060
ctttttggac tttaatattt ttcttgtcac atttttattt tattttgtca caatatgcac 150120
acaaaagaaa atcctagcat gatgcatgat ttatttgagt gtttttattt aattatttat 150180
ttgtggaagt gaggtgttca catgaaatga tagatataga tgacacacat gtatataaag 150240
gaatataatc tctcctttta gatttttatt acaaagtggg tattacaaat cctacccccc 150300
ttaacaagaa tctcgtcctc gagatttagg aaggactagg aaaaagatgg gggaaaatct 150360
atgtgaaact cttcttctct ttcccatgat gcttcatctt ctccatggtg actccattgc 150420
actttgcaca tttttatcac cttattcctt gtaagtcgag taaaagtgtc aagaatcttg 150480
atcggatacc ccgtgtaagt caaatcatcc tgaacactga gctcttccat tggtaactgt 150540
tcctcaagga cacggagaca cttcttaagt tgagacacgt aaattacatt atacacatca 150600
gatatattat caggtagctc gagttgatag gccatctctc caactcgcct aaaaactcat 150660
aatggtccaa taaagtgagg gaacaatttg cccttaactt taaatctcct cattccacga 150720
agtggtgaca ctttgaggta cacatgatca ccttcctcaa actccagtgg tcttcttcta 150780
ttatcagcgt agctcttttg cctggtctga gctaccctca aattctcccg aattatacgg 150840
acttgttcct ctgcttcttg aataagttca ggcccaaaga aatgtcttcc tctagtctgg 150900
tccaaaaata gaggtgtcct gcatttcctg ccatacagag cctcgtacgg tgacatcttc 150960
agactagcct gatagctatt attatatgaa aactcagcat aaggtagact cttgtcacaa 151020
ctactaccat gctgaagggc gcaagctctc aacatgtctt ccaatacttg attagccctt 151080
ttagtttgtc catcagtctg aggttggtaa gccaaactag aattcaactt cgcatccata 151140
ttctcatgaa aacttttcca aaatctagag gtaaactgtg atcctctatc caaaatgatc 151200
ttcttcggta catcgtgtgg agacacaatc cgagccatat ataactctac caattgagat 151260
accttataag tagtcttgac cagaatggaa tgagtcactt tggtaaattt atccataata 151320
acccatatag aatcatatcc tctcggggtg cgaggcaatc cagtaatgaa gtccttacca 151380
atttcttccc cttccacttg ggtatcttca gtggatgtaa tagtccagct ggtctttggt 151440
gttaggcctt aactctttga cacccatcgc acatagccac atgtgcagcc acatctctct 151500
tcaatccata ccaccagtat ttctgcttca attcctgata catcttggta ctaccaggat 151560
gaatagaata atccaagtta tgggcttcct ttagaatagt cttacgaaag ctttcaatac 151620
cagaaacact atcctgccct tgaaccatat tgggtcttgg ttcatcttcc gtaaattccg 151680

```
gacctcttcc tttttcaata agatccttga tttctcttgt atcttagcat caccaatctg 151740
tcggnnnnnn nnnnnnnnnn nnnnnnnnnn nnnnnnnnnn nnnnnnnnnn nnnnnnnnnn 151800
nnnnnnnnnn nnnnnnnnnn nnnnnnnnnn nnnnnnnnnn nnnntccgat tctagagaat 151860
tcgtctcctt tctgtaggtc tgttcatacc aatactggtg gtgaacaaac acatcttcaa 151920
ttgatcaaag ctgtcttggc acttcccgac ccacttaaat tctctgtcct tctccagaag 151980
cgaggtcgta ggcttagcaa tcttagaaaa tccttcaata aatctccgat aatatcctac 152040
tagtctcaag aaactctgaa tctcagtaac tgtagtgggt actctccact ccattatctc 152100
cttaacctta gtaggatcca ttgatattcc tccattagaa ataatatgac caataaatgg 152160
cacctcgcca atccaaaact cgcacttgct aaacttggca tatagctggt tatctcgtag 152220
cttctgtagc accatcctca gatgttcctc gtgatcacta tcactcttgg aatagataag 152280
aatatcgtcg atgaaaacca cgacgaatct atccaaatca tgaacacatt atcctttaga 152340
tccataaagt aggctagtgc attagttagt ccaaacgaca taacggtgaa ctcatataaa 152400
ccatatcggg tcaaggaatt cgtcttggga atatccgatg gcctaatatt catttgatgg 152460
taacccgatc gaagatcaat cttcgagaat actcttgcac ctctcacctg attaaataaa 152520
tcttcaatgt ggggtaatgg atacttgttc ttcatagtga caccattaag ggacctttaa 152580
tccacacaca tcccttgcaa tccatctttc ttctgtacaa acaaaaccga tgctctccaa 152640
ggtgaagact cggacaaatg tacccagcct cttgtaattc cgttaattgc ttcttaagtt 152700
cctttagttc ttctacggac atcctgtatg gccgtttaga aataggagtc gtcccaggta 152760
agagatcaat gaccaactca acatccatat ctggtggcac ccctaataac tcctctggaa 152820
agacatccgg aagatctcta actgcacgga tgttgtcacc cacaaacttc tcatcttcta 152880
agaatgttgt tagactgatg gtggtagtta ctgcaattcc aacttcaaat atttctcctt 152940
tggaactggt gagttctatg gttcccttag cacagtgtat aaactgtctt tgcctttctt 153000
aaccatgaaa taccaaggat cacgcctata gtgctctctt ctaacactat aggggtagcc 153060
catctgcgtt agaaacatag ggtgcgaaag gaagaattgt agacaaggcg agtaattaag 153120
aggaatatta ctacggggga tttattagct aagtagatta gtgtgtcacc tactaacgct 153180
aatacattac cttatggtgg tacatgctaa gatgcccgtc tatactattt caatcaatca 153240
aagaagcaaa tcaggcattg atcatcagaa caatcaacca acatttttaa taaagaaaat 153300
agttttaatt ttgtcttagg cttcctacct cttaaaaatg tcataggggt agtgtcggtg 153360
ttttgggtcc gaccgcacac ccggggttgc ccctcaaggt gtttttagga gtaggacggt 153420
gtcgacgact gtagcaaaat ggttcgtgcc gatcgcacga gggacaatgg acaagattta 153480
caggttcggg ccgcttagaa acgcgtaaca ccctacgtcc tggtgagtat atgagcgtgg 153540
ttacaaaagg attctctgga tagagggcgc agagagtttt tgtgggtggc taagtggagc 153600
agagtcgatc catctgaagg ggtgccccct aggccttata tattcggccg tggagcatta 153660
catgtgatac gataacaaca agtagctgaa agatagtgaa cttcttgagc ttatccttac 153720
gtaacctccg ccgacttatc ctcgcatggc tccgttgcat gggggcttca gcgcgggaaa 153780
gtcgggtctc tgtttgtgat tcattcgttc gacgttgtgg gccgcctgtg tttgcactaa 153840
tcagtcccac gtcttcttta ttttaacggc tgtctttccc taggcccacg aaagaatgac 153900
cttacgaatt attgggccct tgggcctttc gtgaggcctt ttacttcttt agtggacccg 153960
ggggatatct atcccccaca agcccccgat ctttgggttg atttggaggt aatcaactta 154020
```

aagatccaag gtccaaaaat gactccctgc tgttttctct tgctctgatc acttgttcga 154080
ccaaagttta gttttgtgcc tgtgccttag aaatcggcat tttggattat aagattctgg 154140
acttccttgg gtgcaccgaa ggtgcaccca atgggtgtag cccccgacct ttgagtagat 154200
tttagaagat aatctactcg aaggtcttct ccgaagattt tctccattcg cgctcctgca 154260
tctcagttga ggattgatct ttccaatctt gttctacgcc ttagaggtcg gcactatatt 154320
gatttagaat gataatccat ggggtgcacc gaaggtgcac ccaatgggtg tagcccccga 154380
ccttcaagtg gatttttgag gataatccac tcgaaggtct tccttctgtg tccttttgct 154440
gaaaattatc ctttctgctt gtaaaaaatt ggcatgatgt catccgcgct atgtcatcaa 154500
ttttatgctt cagaggtcag catgtatttt gtcttttgca gccgagttcg caatccatcc 154560
atatctcgct aggtagtgta atttatttgc tctgtgactg attggacatt tgatggacgt 154620
tctctgtcta gtcttcaagt catttctgtc gaccatattt tgcactctac tggctatatt 154680
tggcttccct ctaactcttg ttgatatctc atttttgtct tgaggtattc actgcatgcc 154740
ctgcacggat gtgaccgttt gaaaaatata ctgataattc ctgggcgtcc cccccccaat 154800
gggtgtgggc aagggacggc ttggtacgct gagtgtttta gcctggttgc ctctgagtag 154860
taatgcgatg ggacggctag tgtaatcata tcctttgcgc tgttgactgg agtcccaatg 154920
ggtgtagagt tgcatgaaac ggcgtccgct gtctgacgtg tcttcgggtg ggtggaagtg 154980
cttattgaat gtctttcgac tgttcagtga ccgcggttag aagtgagcgg ttgcctttcc 155040
cttctataaa taacccttt gcttctctgg tttcttcaca tctcttcgct gctccttact 155100
gcctcttccc tttcttctct cccaaaactt taaccatggg caagaacaac aagcgcaagc 155160
gcgagtcgac tcctccatcg gaggagtttg gtgactcaga atactcggag gaggagttct 155220
cctccgagcc tgaggggtct ccggctcccg tctctccccc ggcgtcgtcc gatgactcgg 155280
acgactccca ggggatagcc gcggaggtct ggacatatat ccgggccgtc gagcgcgccg 155340
ggctcgaagg ctcggatgag tcggagtgct cctcggatga ggaggactcg gacggcggcg 155400
acgagggtga agacgacgac gacgacgacg acgacgacga cgacgacgac ggcggctggg 155460
gtggcggcga cggcagcagg gacagcacca agggcagcag caggggcagc accaagggcg 155520
gcggcggcgg cagcagggac agcaccaagg gcagcagcag gggcagcacc aaaggcggcg 155580
gcggcggcag gggcaggggc agggccagtg gctagacgcc actggtcttc ttagatatta 155640
gtatagttta gtatagctag aataatgtag tagtaattag tgtagtttag tagtagtggt 155700
aatgtaaagt agaattaggg aagtaccaac tcataaagag ttggtttgta agttcgtcaa 155760
cttcccttta atgaagtata tcgttttatc cctctttttt gatgacttgc cactgctttt 155820
gctgaatgct gaactggttc tttttgatat agtagaaaca gcgccgagcg atgtgaagat 155880
tgacatcagc gttttagaag tagcactgag caatcgaaca caagaccagc gttttagagg 155940
caatgccgaa tgatagaagg tcggcatcgg cattttagaa gtaatgccaa gcgacaaaat 156000
acggggtcgg ctttttagaa ataacgccga gtgatagaat atcggcgtca gcattttaga 156060
agtaatgctg agcgtttgaa cacgtggtcg gcgttttaga ggcagcgcca agtgatttga 156120
aggtcggcgt cggcatttta gaagtaatgc cgagcgattg aacacggggt cggtgtttta 156180
gaggcagcgc cgagtgattg aaggtcggcg tcggcatttt agaagtaatg ccgagcgatt 156240
gaacacgtgg tcggcgtttt agaggcagcg ccgagtgatt gaaggtcggc gtcggcattt 156300
tagaagtaat gccgagcgat tgaacacgtg gtcggcgttt tagaggcagc gccgagtgat 156360
ttgaaggtcg gcgtcggcat tttagaagta atgccgagcg attgaacacg tggtcggcgt 156420

```
tttagaggca gcgccgagtg atttgaaggt cggcgtcggc attttagaag taatgccgag 156480
cgattgaaca cgtggtcggc gttttagagg cagcgccgag tgatagccag cttctcaagt 156540
tactttgagg aaaatggccg agtgatgagg tggcacatcg gctttcttgg aaataactgt 156600
tagatatcca cgtagcatgc tgggatttcg gagatgaccg ccgggtgatg actgggcact 156660
tttgaaaagg tatctggctc aagaatatcc cttaagagtc gcgctttcag ccgcctttgc 156720
tttccgtgcc ctagttcttg catttccgca tctgagtctt ctctgccact cgcctcctgc 156780
tctgtttcgc cagcgagaag caagatggcg cccaagagga agaccgcgaa ctcgtctgct 156840
gcagtgatcc ccgccatcga tcccaacagt cagttgccct tcgcaggtaa ccatatgtct 156900
gtgatttctg aagttgagct tctccgcctt gtttccatcg ggttctcccc tccacgggaa 156960
ctctgttctt ggcgctcttg ccatgggact actgtcccaa ccgaagatac ccacgagtca 157020
gtggtttaca ctcctttcct tcttcgcggc ctcggccttc ccatatctcc ttttttccgt 157080
ggcatccttg atttttatca catcaacctg actcacttga accctaactc cattctccaa 157140
atttctattt tcgttcacct ttgcgaagct tatcttggcg tgctgccgca ttttggctta 157200
tggaagtatc tgtatcactg ccgtcctggg atggccgggg ggcaacatca attggtcgga 157260
ggtgccagct tagagatgcg tcgggggcgg aagactgagt atctcgagat accccttaaa 157320
gacagcatta aaggttggcg tctggagtgg tttataatgg ataattatgg aaattctctc 157380
ccttcccgct cgggaagaca ggcagacgtt cgtactccga gttggactga atctcccacg 157440
gaccaagaag tagccgaagc gggcgtgttg cttactgaag ttggattact gaaagagaga 157500
ggtctgactg ccgaagccgt ggtcacagat tttgtgttca aaaacattca gccgctgaaa 157560
gacagggcct atccggcata tctttaccga gggctggccg actcaacccg agttactaat 157620
aggagaattc cttctgtgga tttggtgagc cggcttgaaa tgatcctcag gggtaaagtt 157680
tcgaacgttg gagctccagt ggcatactcg gcttggaacc taccttcttc tcaagccttc 157740
actctttttg tgtccaatcc acccgtgata gatagcaatt tgggtcttag agtgcgaccc 157800
tctgctgaag aggtccgttc tttagttgct tcgctcgggg atatacctga tgatgaacgg 157860
cagatttatt ttgaagtgcc tctgaaccct agtgatgcag acataaatga catgctcgat 157920
ctgctagctg tggattcatc tgatactgct cctgatggta cattggcagt ggtgcccctt 157980
ccagaggttg atgcgacctt ggactcctcg aaacctgtca gtactcgccc gaggcgccct 158040
agccgaacca gtcagcccga gccttctgct gatgagcaga agaagaaaag gagacgcctc 158100
cggcgagtgt ccagttttga cgaggatacc agcaccttag ctcctgctat cgaagaaatg 158160
tctgcaactg gcctagctga cattgatccc aatgggtgtg ctccgcctgc tgctgacccc 158220
aatgagggtg ttgtttgtgc tgttgctgtg gaagacgagg aggaagagaa tgaaactcca 158280
ttgactcgga aaaacagtcg gcagttcgtc gctagcggcg gtagtagtgg ggttccttct 158340
cctgccttgt ctgctcttat tggtctgcaa gaactgtcta tggccaattt tgatcaagct 158400
ctagaggata tggtccctga gaacttgttg ttggaacctg cagacgttga tgcaacagaa 158460
acttgtgcgg gcgtgccaga tgctggattg aggtcgtccc gtgcctcgtc gaccttagag 158520
cacgatctcg agggccggaa tgatgacttg gatcgtcctg atcctgcgga ggtagctgaa 158580
ggcccgtcga ccttagaggt ggtcacggca gagagcttgg atcctttgaa tagtgctgac 158640
atgtgcccag cccccgaggg tgtcgccggg gaggactcag ctcaggtgag gagcgtaggc 158700
cactacccag cccccgaggg tgttgccggg ggtgatccgg ctcaagtggg cagtgccaac 158760
```

cttgacccag cccccgaggg tgcccgagca gggtctcctt cctgcacttc tatggacgtt 158820
cacgtgggtt cacctccaca ctctggcggc atggtggtgg ctcaaactcc agatcagggg 158880
gtcgctttag agggcagcat ccccactggt ctggtgttag gctctgctga atgtactgag 158940
ctcgttcctg ctggtctact gcaaactgct tcgggtggtg gtctgacacc tgattatcag 159000
ctgatttctc ctgacttggg gatcccttcg ttcttttcca acctccaggt gctgtgccgt 159060
gctttaattt gatctctatg ttgcatgaat tgctgtcatt atgctcatct gttcttctcg 159120
tcaggctttg gtgaatggat tggccagtca actgaaatca cagggtgctt ctaccccaga 159180
agtggcgtca tctctcgagc gttggaatcc agtgttgctt catcgtcgtg tatctgagtt 159240
ggaggccacc aatgctggtc agtgtccttt cttcttcttc tttattcttg cccgtaggtt 159300
gttttacctt ctgacctcat tttgtttgaa tacttcttga tagggatgac tcggcagatc 159360
aaagttcttg aagaaaaaca ttctcaagat caagctgaaa tgactcgacg atgcgctgac 159420
ttcgaggaga agtattctca aagtcagatc gagttgagtc aggtctctgc ggctttggat 159480
gatgctaacg ctctgagttc ttctcttcat gtccagctta actctgagaa ggtagcttac 159540
gaacctgcgc ttcgccttat catgctcttg gattctgaat gagtttgatt tttgattttt 159600
gcttgtagga agaaaaacgt atccttgctg cttctcgcga caacttggac agattgtacc 159660
gagattccag tagctcgctg accatcttgg agaggagcca ccgctttacg atggaggagc 159720
ttgacaatca gcgtcgtcaa ctgcaagaat cttcggacga agtggcccgc cttacacagt 159780
tgctatcagc aaaggatgcc accatcaagg aactccgagc ttccaagaaa accattgccc 159840
gggagttaga aactgctcag caggttgtta aagttgctga agaagctgct gtcactttca 159900
aagctcagcg cgataaggcc ctggacaagg ccattcgggc gggacgaatc ttgatgagaa 159960
gacctggcgt ggttgtcccc gaggatataa gagccgacgt ggttgctgcc cctgattcct 160020
cgaatcgccc ttcttcgtca gtcgttcctg agagagacat tggaaaataa agaaacagtt 160080
cgcgtgctct gagcgcgcag ttagcatgag caagcattca tttagaggac atcagcttat 160140
cattcgaatg ttatgatttc tttcttatcg tatcagaatt tattagtttg caaatttgtg 160200
gtaatgctac atgataatta tgaagtttgt ttgtgggata tggaagtcat cccctgaact 160260
tcataagcgc gagtatgcta taccggttta agccgtcaat gacttttagc cggtaacttc 160320
cgttagtagg gtttagtgat cgccctaggt aaagtaagcg taagcatgtt gcaccgcctt 160380
aagtcgttgc cgacttaagt cgattgttcc gtttgtaggg catagtggtc accccgagtt 160440
aagtaagcgt gagcatgttg caccgcctta agtcgttgcc gacttaagtc gattgctccg 160500
tttgtagggc atagtggtca ccccgagtta agtaagcgtg agcatgttgc accgccttaa 160560
gtcgttgccg acttaagtcg attgctccgt ttgtagggca tagtggtcac cccgagttaa 160620
gtaagcgtga gcatgttgca ccgccttaag tcgttgccga cttaagtcga ttgctccgtt 160680
tgtagggcat agtggtcacc ccgagttaag taagcgtgag catgttgcac cgccttaagt 160740
cgttgccgac ttaagtcgat tgctccgttt gtagggcata gtggtcaccc cgagttaagt 160800
aagcgtgagc atgttgcacc gccttaagtc gttgccgact taagtcgatt gctccgtttg 160860
tagggcatag tggtcacccc gagttaagta agaatgcaag tcaatcataa acgaaccgag 160920
tgtccttgaa atctatcttt attgatgaca tatttccact ttacagagta catggccgcc 160980
ccggctgttt tgaagtacag ctaggggtaa aactttctga ggtgctctat gttccaagag 161040
ttcccaactt ccgtgccatc catttgggtg aggcgatatg atccgggacg agtgacttct 161100
gctactatga aaggtccttc ccataagggt gataacttgt gccgtccctc ccccgttaga 161160
attcggcgga ggacgaggtc tcccttcgaa aagaaacgtt gccgcacagc tttgtcgtgg 161220
tagcgcctta gagtctgctg gtatcgtgcc gattgaatca ctgcattcag tcgttcttcc 161280
tcaagtacgt caatatcctc cagcctagtg gcttcggctt ctgctatgct ttcgaaaatc 161340
aatcttggcg ccccaaactt gagatcagca ggtagcactg cctccgaccc atagaccatg 161400
aagaaaggag tgtttccatg cagggctcgg ctaggttggg ttctcaagct ccaaacaaca 161460
taaggcaatt ctcttatcca ttttcctgcg aatttttcat ttttatcaaa gacccttttt 161520
ctaagtgcct ccaatatcat tccgttggct cgctcaacct gcccgttggc tctcggatgg 161580
gctacagatg catacttgat ctgaatgctt ttttgctcgc agaagtcaaa gaattctgaa 161640
ctggtaaagt tggatcccaa gtcagtgatg atactgtttg gtatcccaaa tctgaatatt 161700
atgctttgta tgaattccac ggctttagca gaggtcaaag aggcaatggg ctggaactct 161760
atccacttag tgaatttgtc aattgccacc aatacatggg tgtatcctcc ttgagccttc 161820
ttgaaaggtc caatcatatc caatccccag catgcgaaag gccaagttac tggtatggtt 161880
tgtagctgct gcgctggcat gtgctgttgc ttcgacaggt attggcaagc ttcgcatctc 161940
tgaactaact cggctgcatc attcttcgcc gtcggccaat agaatcctga cctgaaaacc 162000
ttcccgacta atgttctgga tgctgcatgt attccgcact gccctgcatg gacttcctcc 162060
agaagttgct tcccggtgga cgggagaaca cacttcatga ggacgcctga cgcgcccctc 162120
cggtataata cctccccaat gagtgtatag tgagctgatt gtctggcaat gcgctctgct 162180
gagttcttgt catctggctc ttcttcattc tttatatact taataatcgg ttgcctccag 162240
tcatcagagt ctgactcggg ttggtctatg atgttgcact cttctatttg atccgtcgag 162300
atgctcggct gaaggatttc ttgcacgaag accccgggcg ggacttgagt ccgaccggat 162360
ccgagcttgg acaatacatc agccgccgtg ttccgatctc tttctatatg atggaactcc 162420
aggccttcga atttatcttc tagctttcgg acggtggcgc agtatcttcc cattgaatca 162480
cttgaacaat cccattcctt gtttatctga ctgatgacta ccagagaatc cccgtacacc 162540
atcagcctct tgacacccag cgatatggcg atgtttaatc cgtgtatcaa agcttcatat 162600
tcggctgcgt tgttagaggc cgggaatagc aattggagag cgtacttaag gtgttcgcct 162660
ccaggtgcag tgaagagaat tcctgctcct gctccctgca gcttcagcga gccatcaaaa 162720
tacattcgcc atacttctgc ggtttctgga ttatccggca cttgctgttc tgtccactct 162780
gatacgaagt cgaccagtgc ttgagttttg atggcagtgc gaggtcggaa ctcgatatca 162840
tgggacccca actcgcaagc ccacttggct attcggccaa tggcttcctt gttgtgaaga 162900
atgtccccta ttggaaaacc agtaactact atgactttgt ggtcgtcaaa gtagtggcgc 162960
agcttgcggg cagttagaag tactgcatat aatagcttct aaacttgagg atactttttc 163020
ttcgatgggc ctagaacctc actgatgaaa tagacgggat gttgtaccgg gtaggcatgc 163080
ccttcttcca ctcgctcgac taccaacgca gtgcttacca cgtgagtcgt gcaagagata 163140
tataacagca gatcttcagc cggctgagtc ggcgtagctc gccggggcgg tttcaatact 163200
ggcggcgttg tgaggaattt cttcagtgcg tctagagctt cctgtgcctc tgaagtccat 163260
tgaaacttat ccaccttctt cagcagttta taaaatggca gaccttttc tcccagcctg 163320 gatatgaatc tgctcagggc tgccatacat ccagtgagtc gctgaacctt cttttgtgat 163380
cgaggagctt ccatcttcat gatagcttca atcttatctg gattagcctc aattccccgg 163440
tggctgacga taaatccgag caactttcct gctggtaccc cgaaaacgca tttttcagga 163500
ttgagcttcc atctatatct tctcaagctg ttgaaaacca gctgtaaatc ttcgatgaag 163560
ttttctggat tctcagtttt gatcaccacg tcgtctaagt aagcctccac acgcttgccc 163620
cagtgatcgg ctaagcatgt ttgaatagcc ctctgataag tcgctccagc gtttttgagg 163680
ccgaacggca tggaggtata acagaaagca ccaaacgggg tgatgaacgc cgtttttttcc 163740
tcgtcttctt ttgccaaact aatctgatga tacccggaat agcaatctaa gaaagacagc 163800
atcgaacatc cagcggtgga atccaccacc tgatctatcc tcgggagccc gaagggatcc 163860
ttcggacagt gtttgttgag atcagtatag tcgacgcaca tgcgccaatc cactttattc 163920
tttttgagta caagaacagg gttggctaac cactcggggt gcaatacttc tctaataaat 163980
ccggccgcga ccaagcgggc taactcggca cgaatggctt ctctcttgtc gggcgtgaaa 164040
cgacgcagct tttgccggat cggcctcgcc tggggataga ccttcaattt gtgctcggcc 164100
agttctcttg ggactcccgg catatccgca ggttgccatg cgaatacgtc tcggttatct 164160
tgcaggaact ggacgagcgc gcttttctat ttgtcactca aactggagct gatgatggcc 164220
gtcttgcgct catcagcgaa ccccaggttg atccgcttgg tgtcttcagt cggccgcata 164280
gaggtcacgg cctgagcttc gtttgccggc acggcgaggt cttcatcagg cttagagttc 164340
gccggtgtag aaggaatcgc tgatggcttg gtggtgaggg ctgcttggat ggccactcgg 164400
aaacattctg cggcgccttg gaagtcggcg cgcacagtta tgattcctcg tggtcctggc 164460
atcttcagta tcatgtacgt gtagtgtggg atggccatga acttggccag ccctggcctc 164520
ccgatgatgg cgttgtaccc gcagtcgaag ttcgccacct cgaacctcag gaactcggtt 164580
ctgtaattat ccggagtccc gaaggtgacc ggcatgtaga tgtggcccag cggatactcc 164640
ccttccgtcg gcacgatgcc gaagaaagga gtgtctgact cgtggagctc tttgaggtga 164700
actcccaagc cttgaagcgt acgggggaag gtgacgttga tgctgctccc cccgtccact 164760
agcaccttct tcactcggct ctctcggatc accggatcga cgaggagcgg gtatttgcct 164820
gggtggtcga agttgagcca ttgatcctcc cgagtgaatg tgattgggtg ctccgaccac 164880
cggtacgggg cgggagggcc ggtggtcgcc accagtatct ggcggtcgtt gagcttttgt 164940
tgtctcttgt tctcctgcga cccatgtccg ccgaagatga cgttgacctc cctgtcaacg 165000
cgcgggaaag ctcctcctcc cccctcctcc ggctgatggg gctgtcgtgg ttcatctggt 165060
cctcctctcg gcggaggagg tggtagaggt tggaagggtc ggccatgccc gacggagtgc 165120
ttgaagtccc ggcagttgcg gagagtgtgg cgcatatcct tgtggtacgg gcactgggcg 165180
tcgaggatgt cgtccagcgt gcgttcgcct ccacgaggtc ctcctcgggc gcgagaggcg 165240
ggtggtccga cggcgtgtac ctcttcgcga ggcctcttct cccagcgctt gtcgggcggc 165300
tggttcgcgt cgcgtcgtgg taccgccggt gcgggctttg ctcctccgat gaggtcctgg 165360
gcccgctcgt cagcggtgat gtagaggtcg gcttcccgga acagctcctc ggaggtagtc 165420
ggcgcctttt gcagtatggc tcggacgaaa gctgagtcgt tagatcctct gtagaagtcc 165480
tcgattacgg ccgcctccgt gacctcgggg atgcggtttc tcatggtctg gaacctttta 165540
aggtatgacc tgagagtctc atccccccgg cgcttgatgg atttgaggtc ccatggttgc 165600
gctggcttgt cggagagaga ctggaagttg gcggtgaaac gtcgactgaa gtctccccag 165660
tcgtcgatgc agtgtcgggg tagatgtcgt agccactgca gcgcgtcttg cccgaggacg 165720
atgggcagat acgcagtcat gacgtcctcg gatgccccag cggcccgagc agcggtggtg 165780
tagacggcta accagccccc cggatcctgc ttaggttcat atttgtcgac attggatacc 165840
ttgaagttgg gaggccattg gatggcccta aggcgcggag taagggcgga tactccgcac 165900
gtgtcttcct gtcgtcgagg atgtcgtctg tcccggggag gggagtggcg gtggtggctc 165960
ctcgaccgtc cccgggtggt tccaccagtt gaagctgttg ccgactcagt tcgggtggcc 166020
tggctttggg tcgggaagcc atgatctcga tcatactcct ctcgacggcg aatttcgttc 166080
tcgtgccgcc gttcgcgcga agcattgata gagcttcgcg cgtctcggcg actgttgatg 166140
gcgtgtcgca gatcgttcgg cggatgagcg agcggtagaa gatggttggc tgcctgagtg 166200
aacaggcgcc ggtatccctc ggcgtcgggg gtccgaggaa gtccgtcagc tatccgggcc 166260
agaacgcctc cgacttcgct cggcgtattc atggctcggg cgaagtcggg gttcaggttg 166320
cgcccgaaga gcggattctc gcgtcgttgc cttgcatctt gctcggcttg ctcctgagtt 166380
cgacggcgat ctcgtcgtcg ggagttcctt cgttccctga agacgcgttc ttccggagtt 166440
tctcctatct ctgagacctc gtctcgcgag acaggttgct ccggatcctg ttctccagct 166500
gcgtgatgtc gtcgaacgtt cctgcgccga ttccttcgtc ggcgggattc tcgctgaggc 166560
ggttcttctc caggcgcggt cggttcatcg tcggagacgg cgggtgattc tgctctcccg 166620
atgaagagga tgtcggggta gaacggtatt gctgccgcgg cgactttctt tccattctcc 166680
tttgaagtcg gaggaacggg aagaacgacc ggcctctccc tgatctcctt ccttctcatg 166740
atctgtgtcc attctttcgt cggggaagta gacagcggag tcttccgggt cagcgagctt 166800
ctcgctccag cctccccgga gacgatcttt tcccgaagaa ccggaagtag cgtctttcca 166860
gcattttcgg agtttgttgg tggagacttc tgttccggca gatccgcgag gcggtgtaga 166920
attccttctt catccgccac ggaggagatt gtcccgaagc agaatgtgga tccgggacgc 166980
atggtgatct tgctgtggaa ggtgacggcc attgagctag cttggatcgt cgacacaccc 167040
cctacctggc gcgccagcta tcggtgtttt gggtccgacc gcacacccgg ggttgcccct 167100
caaggtgttt ttaggagtag gacggtgtcg acgactgtag caaaatggtt cgtgccgatc 167160
gcacgaggga caatggacaa gatttacagg ttcgggccgc ttagaaacgc gtaacaccct 167220
acgtcctggt gagtatatga gcgtggttac aaaaggattc tctggataga gggcgcagag 167280
agtttttgtg ggtggctaag tggagcagag tcgatccatc tgaaggggtg ccccctaggc 167340
cttatatact cggccgtgga gcattacatg tgatacgata acaacaagta gctgaaagat 167400
agtgaacttc ttgagcttat ccttacgtaa cctccgccga cttatcctcg catggctccg 167460
ttgcatgggg gcttcagcgc gggaaagtcg ggtctctgtt tgtgattcat tcgttcgacg 167520
ttgtgggccg cctgtgtttg cactaatcag tcccacgtct tctttatttt aacggctgtc 167580
tttccctagg cccacgaaag aatgacctta cgaattattg ggcccttggg cctttcgtga 167640
ggccttttac ttctttagtg gacccggggg atatctatcc cccacaggta gggattccaa 167700
ggtgtgaaat ccatcttgac taagagtaga aaaggtaaga atgatcagag tagaacagta 167760
gaaggtgaga cagaatcaag ataagtgtag aaagaatcag agtaaggtaa gtagtgaagg 167820
gttttgtcca tttctatcta ggtttcgtcc tacagtcaac atttcctctg ataccacttc 167880
tgtcacaccc ggctttaagg aacaaagccg ggtgcatctc atacatgcgc caagaagaca 167940
acatatataa taacagagtg tatagagata aatgtcataa aacatcagag tatttattac 168000
atagcggaag acttattaca aaataaaaga taaaagtaaa acgaactaag gatcgtcggc 168060
gccaatgtcg actgggaaat gccacctaga tcagatcgaa ctcctcagtg ttaggcggct 168120
cctcctgaac cacctgctct tctcctgtgg gggggtgtga gacagcaagg gtgagctcac 168180
acatgatcat agctcaacaa gttgtgggga accggtggac ataaactcac aaaggtgtga 168240
ggtcatgtga tgtgtaaggc taatcaatga taggggttaa agctgagcat tgcttttaag 168300
tagttggtca aaattttatt tagcagttac taaagtataa gtgaatacca aaaccttaga 168360
taaagtaatt gaacaaaaat taataataga ccccatgcaa tgcaaatgac aaaattgaat 168420
ttaagttcca taatttaaaa catcagagag tcctgagccg ctcatgaccg cgagcacggc 168480
tagtatacta gttttacact ctgcagaggt tgtacccttt acccacaagt catgctaccc 168540
atctgccaag gggtcacgaa tcccatacac ctctacctag gaagcgcggc agggcaacac 168600
tacgaggcct ttacaaagtt ccactagctt ccgaaaaccc gctacagttt ataagaagtt 168660
ccaatgcagg gttcttgtct gaccgccatc gcagcaaaat caaccaagga cctccctaca 168720
ctgaccactc ccctactgcc cttgcccctt tcgggtaagg tagtcttcca ctagctttcc 168780
taattagtca gccaagggcg tcccattaaa cccttgtggt ggcacgtgtt tctcaagtta 168840
agctctatgt tccaattaac attaatgaac ttgacatgaa cataaataga ataacaagaa 168900
taattggaac atagatataa taattgatta tcccaaaacc atgtaaagca atagcaaact 168960
acccaagtga ttcaggggta aacaaggtaa tgagataaac aaatctaggg tgtcctattg 169020
ggtcccatca aaattaacct atgcacgagt gaatgataat tagagaacat tattgggtaa 169080
aaagtggtca agggcacaac ttgcctggca ctagagattc cagttaccag ggtgattctt 169140
caaatcctcg tgacctcact gctagtcgta gcaatacaaa caaacatggt atagacaaaa 169200
ttaacatcac accaaacata agaatatact gcgtaataat gatatacgcg ttgctacgag 169260
actaacgcaa cttgaacgga tcaaattgaa gttaaaacgg aggatatatg aatttcctaa 169320
ggttttatgt atttgatacg aggttaatta agaaataaat tttaatacca ttttcatgtt 169380
aaaacagaga cacagggtga taaacaacat tattacaaaa ttatagaaac taaaatggat 169440
taatttggac tacacatgaa tttttttttt ttttaaccaa ttctagcatt tatttctaca 169500
ttaaaaatcc aacgaatcaa gctgattcat caaaggtacc aaatnnnnnn nnnnnnnnnn 169560
nnnnnnnnnn nnnnnnnnnn nnnnnnnnnn nnnnnnnnnn nnnnnnnnnn nnnnnnnnnn 169620
nnnnnnnnnn nnnnnnnnnn nnnntaactt aatgaacttg acatgaacat aaaaaagaat 169680
accaagaata attgaaacat agatataata attgattatc ccaaaaccat gtaaagcaat 169740
agcaaactac ccaagtgatt caggggtaaa caaaggtaat gagataaaca aatctagggt 169800
gtcctattgg tcccatcaaa attaacctat gcacgagtga atgataatta gagaacatta 169860
ttgggtaaaa aagtggtcaa gggcacaact tgcctggcac ttgagattcc agttaccagg 169920
gtgattcttc aaatcctcgt gacctcactg ctagtcgtag caatacaaac aaacatggta 169980
tagacaaaat taacatcaca ccaaacataa gaatatactg cgtaataatg atatacgcgt 170040
tgctacgaga ctaacgcaac ttgaacggat caaattgaag ttaaaacgga ggatatatga 170100
atttcctaag gttttatgta tttgatacga ggttaattaa gaaataaatt ttaataccat 170160
tttcatgtta aaacagagac acagggtgat aaacaacatt attacaaaat tatagaaact 170220
gaaatggatt aatttggact acacatgaat tttctatgaa ttaaaccaat tctagcattt 170280
atttctacat taaaaatcca attctatatt tgttttctga tttttctggc tctctggact 170340
gggcacacta atacagagaa gttcaggggt ctcggtgtaa gttttcctaa gactcagagc 170400
ccaactacgt ggactgcggg ttatttatta acgacattag ggctcttttg taagatgggt 170460
cggcagcagt atgcgcatgc accctgagcc gttagatttt catcccacgg ccgcaactta 170520
acacaacgaa ggggtacgcc atgtggagcc tcggatccag atccaacggc aaccaaaaag 170580
gcatgagctg gcaactaatc acgcgtgttg gatcacgatc taacggccca cgactaagga 170640
atgaaggggt aatctaggcc gcccgtcatc aatctgacag ccacaacccc ctcttctacc 170700
ttatgccgct accttctcct ggaatacgca agactccacc aacagcaagc gactcggccc 170760
tgttgactcg gaggagggga attctcaccg ttgaagagca gggatgccga cgacgaagcg 170820
cgggtcacgg tgctgtgaag ccctagcgca gaatgaagtt ccttcgggct nnnnnnnnnn 170880
nnnnnnnnnn nnnnnnnnnn nnnnnnnnnn nnnnnnnnnn nnnnnnnnnn nnnnnnnnnn 170940
nnnnnnnnnn nnnnnnnnnn nnnnnnnnnn tccacataag gtcggctcca agaggtaacg 171000
accatacgat aacccgcggc gggaacggcg agatctttag caaatagaat tccaggagcg 171060
gatcctggga tcaaagacgt gagcttgatt cgttctcggc ggaagtgata gtcatgcggc 171120
gtagagaacg cgagttctgt tacggcgaag gggaaggaac tgacaacctg ggcccgcctg 171180
caagtcgcca cagcacgcgc atctggaatg tggcccccac catcggcgca gagggaagag 171240
gctggcacca acggcccacc ggtcggcaca cggtctaatc cgttcttttg ggctgtgcgc 171300
atttgcctga tgggccgatc acagaagaaa ttcggcccag agcgcaggta gtccccctct 171360
cctttctttt attttctatc ctcttattca taaatatttt gaattcaaat ttggatttga 171420
atctgctttt gagctctacc cctgagtcag gtgtcacatt aaagcactag tatagcaata 171480
atattttatt tatttatttt acattttttt atcacataaa attttctttc cttccctttc 171540
taggatttct tttagattct aaattcccttt tttggacttt aatatttttc ttgtcacatt 171600
tttattttat tttgtcacaa tatgcacaca aaagaaaatc ctagcatgat gcatgattta 171660
tttgagtgtt tttatttaat tatttatttg tggaagtgag gtgttcacat gaaatgatag 171720
atatagatga cacacatgta tataaaggaa tataatctct ccttttagat ttttattaca 171780
aagtgggtat tacaaatcct accccccctta acaagaatct cgtcctcgag atttaggaag 171840
gactaggaaa aagatgggga aaaatctatg tgaaactctt cttctctttc ccatgatgct 171900
tcatcttctc catggtgact ccattgcact ttgcacattt ttatcacctt attccttgta 171960
agtcgagtaa aagtgtcaag aatcttgatc ggataccccg tgtaagtcaa atcatcctga 172020
acactgagct cttccattgg taactgttcc tcaaggacac ggagacactt cttaagttga 172080
gacacgtaaa ttacattata cacatcagat atattatcag gtagctcgag ttgataggcc 172140
atctctccaa ctcgcctaaa aactcataat ggtccaataa agtgagggaa caatttgccc 172200
ttaactttaa atctcctcat tccacgaagt ggtgacactt tgaggtacac atgatcacct 172260
tcctcaaact ccagtggtct tcttctatta tcagcgtagc tcttttgcct ggtctgagct 172320
accctcaaat tctcccgaat tatacggact tgttcctctg cttcttgaat aagttcaggc 172380
ccaaagaaat gtcttcctct agtctggtcc aaaaatagag gtgtcctgca tttcctgcca 172440
tacagagcct cgtacggtga catcttcaga ctagcctgat agctattatt atatgaaaac 172500
tcagcataag gtagactctt gtcacaacta ctaccatgct gaagggcgca agctctcaac 172560
atgtcttcca atacttgatt agccctttta gtttgtccat cagtctgagg ttggtaagcc 172620
aaaactagaa ttcaacttcg catccatatt ctcatgaaaa ctttttccaa aatctggagg 172680
taaactgtga ttcctctatc caaaatgatc ttcttcgggt acatcgtgtg ggagacacaa 172740
tccgagccat atattaactc taccaatttg agatacttta tagtagtctt gaccagaaat 172800
ggaatgaagt cactttggta attttatcca taataaccca a 172841

<210> SEQ ID NO 71
<211> LENGTH: 172841
<212> TYPE: DNA

<213> ORGANISM: Zea mays
<220> FEATURE:
<221> NAME/KEY: misc_feature
<222> LOCATION: (1872)..(1971)
<223> OTHER INFORMATION: n is a, c, g, or t
<220> FEATURE:
<221> NAME/KEY: misc_feature
<222> LOCATION: (3198)..(3297)
<223> OTHER INFORMATION: n is a, c, g, or t
<220> FEATURE:
<221> NAME/KEY: misc_feature
<222> LOCATION: (20998)..(21097)
<223> OTHER INFORMATION: n is a, c, g, or t
<220> FEATURE:
<221> NAME/KEY: misc_feature
<222> LOCATION: (25653)..(25752)
<223> OTHER INFORMATION: n is a, c, g, or t
<220> FEATURE:
<221> NAME/KEY: misc_feature
<222> LOCATION: (28223)..(28322)
<223> OTHER INFORMATION: n is a, c, g, or t
<220> FEATURE:
<221> NAME/KEY: misc_feature
<222> LOCATION: (38718)..(38817)
<223> OTHER INFORMATION: n is a, c, g, or t
<220> FEATURE:
<221> NAME/KEY: misc_feature
<222> LOCATION: (40257)..(40356)
<223> OTHER INFORMATION: n is a, c, g, or t
<220> FEATURE:
<221> NAME/KEY: misc_feature
<222> LOCATION: (53514)..(53613)
<223> OTHER INFORMATION: n is a, c, g, or t
<220> FEATURE:
<221> NAME/KEY: misc_feature
<222> LOCATION: (63930)..(64029)
<223> OTHER INFORMATION: n is a, c, g, or t
<220> FEATURE:
<221> NAME/KEY: misc_feature
<222> LOCATION: (67556)..(67655)
<223> OTHER INFORMATION: n is a, c, g, or t
<220> FEATURE:
<221> NAME/KEY: misc_feature
<222> LOCATION: (82865)..(82964)
<223> OTHER INFORMATION: n is a, c, g, or t
<220> FEATURE:
<221> NAME/KEY: misc_feature
<222> LOCATION: (137615)..(137714)
<223> OTHER INFORMATION: n is a, c, g, or t
<220> FEATURE:
<221> NAME/KEY: misc_feature
<222> LOCATION: (161457)..(161556)
<223> OTHER INFORMATION: n is a, c, g, or t
<220> FEATURE:
<221> NAME/KEY: misc_feature
<222> LOCATION: (162928)..(163027)
<223> OTHER INFORMATION: n is a, c, g, or t
<220> FEATURE:
<221> NAME/KEY: misc_feature
<222> LOCATION: (164025)..(164124)
<223> OTHER INFORMATION: n is a, c, g, or t
<220> FEATURE:
<221> NAME/KEY: misc_feature
<222> LOCATION: (171319)..(171418)
<223> OTHER INFORMATION: n is a, c, g, or t

<400> SEQUENCE: 71
ttgggttatt atggataaaa ttaccaaagt gacttcattc catttctggt caagactact 60
ataaagtatc tcaaattggt agagttaata tatggctcgg attgtgtctc ccacacgatg 120
tacccgaaga agatcatttt ggatagagga atcacagttt acctccagat tttggaaaaa 180
gttttcatga gaatatggat gcgaagttga attctagttt tggcttacca acctcagact 240
gatggacaaa ctaaaagggc taatcaagta ttggaagaca tgttgagagc ttgcgcccctt 300 cagcatggta gtagttgtga caagagtcta ccttatgctg agttttcata taataatagc 360

```
tatcaggcta gtctgaagat gtcaccgtac gaggctctgt atggcaggaa atgcaggaca    420
cctctatttt tggaccagac tagaggaaga catttctttg ggcctgaact tattcaagaa    480
gcagaggaac aagtccgtat aattcgggag aatttgaggg tagctcagac caggcaaaag    540
agctacgctg ataatagaag aagaccactg gagtttgagg aaggtgatca tgtgtacctc    600
aaagtgtcac cacttcgtgg aatgaggaga tttaaagtta agggcaaatt gttccctcac    660
tttattggac cattatgagt ttttaggcga gttggagaga tggcctatca actcgagcta    720
cctgataata tatctgatgt gtataatgta atttacgtgt ctcaacttaa gaagtgtctc    780
cgtgtccttg aggaacagtt accaatggaa gagctcagtg ttcaggatga tttgacttac    840
acggggtatc cgatcaagat tcttgacact tttactcgac ttacaaggaa taaggtgata    900
aaaatgtgca aagtgcaatg gagtcaccat ggagaagatg aagcatcatg ggaaagagaa    960
gaagagtttc acatagattt ttccccatct tttcctagt ccttcctaaa tctcgaggac    1020
gagattcttg ttaagggggg taggatttgt aatacccact ttgtaataaa aatctaaaag   1080
gagagattat attcctttat atacatgtgt gtcatctata tctatcattt catgtgaaca   1140
cctcacttcc acaaataaat aattaaataa aaacactcaa ataaatcatg catcatgcta   1200
ggattttctt ttgtgtgcat attgtgacaa aataaaataa aaatgtgaca agaaaaatat   1260
taaagtccaa aaagggaatt tagaatctaa aagaaatcct agaaagggaa ggaaagaaaa   1320
ttttatgtga taaaaaaatg taaaataaat aaataaaata ttattgctat actagtgctt   1380
taatgtgaca cctgactcag gggtagagct caaaagcaga ttcaaatcca aatttgaatt   1440
caaaatattt atgaataaga ggatagaaaa taaaagaaag gagaggggga ctacctgcgc   1500
tctgggccga atttcttctg tgatcggccc atcaggcaaa tgcgcacagc ccaaaagaac   1560
ggattagacc gtgtgccgac cggtgggccg ttggtgccag cctcttccct ctgcgccgat   1620
ggtgggggcc acattccaga tgcgcgtgct gtggcgactt gcaggcgggc ccaggttgtc   1680
agttccttcc ccttcgccgt aacagaactc gcgttctcta cgccgcatga ctatcacttc   1740
cgccgagaac gaatcaagct cacgtctttg atcccaggat ccgctcctgg aattctattt   1800
gctaaagatc tcgccgttcc cgccgcgggt tatcgtatgg tcgttacctc ttggagccga   1860
ccttatgtgg annnnnnnnn nnnnnnnnnn nnnnnnnnnn nnnnnnnnnn nnnnnnnnnn   1920
nnnnnnnnnn nnnnnnnnnn nnnnnnnnnn nnnnnnnnnn nnnnnnnnnn nagcccgaag   1980
gaacttcatt ctgcgctagg gcttcacagc accgtgaccc gcgcttcgtc gtcggcatcc   2040
ctgctcttca acggtgagaa ttcccctcct ccgagtcaac agggccgagt cgcttgctgt   2100
tggtggagtc ttgcgtattc caggagaagg tagcggcata aggtagaaga gggggttgtg   2160
gctgtcagat tgatgacggg cggcctagat taccccttca ttccttagtc gtgggccgtt   2220
agatcgtgat ccaacacgcg tgattagttg ccagctcatg cctttttggt tgccgttgga   2280
tctggatccg aggctccaca tggcgtaccc cttcgttgtg ttaagttgcg gccgtgggat   2340
gaaaatctaa cggctcaggg tgcatgcgca tactgctgcc gacccatctt acaaaagagc   2400
cctaatgtcg ttaataaata acccgcagtc cacgtagttg ggctctgagt cttaggaaaa   2460
cttacaccga gacccctgaa cttctctgta ttagtgtgcc cagtccagag agccagaaaa   2520
atcagaaaac aaatatagaa ttggattttt aatgtagaaa taaatgctag aattggttta   2580
attcatagaa aattcatgtg tagtccaaat taatccattt cagtttctat aattttgtaa   2640
taatgttgtt tatcaccctg tgtctctgtt ttaacatgaa aatggtatta aaatttattt   2700
```

```
cttaattaac ctcgtatcaa atacataaaa ccttaggaaa ttcatatatc ctccgtttta   2760
acttcaattt gatccgttca agttgcgtta gtctcgtagc aacgcgtata tcattattac   2820
gcagtatatt cttatgtttg gtgtgatgtt aattttgtct ataccatgtt tgtttgtatt   2880
gctacgacta gcagtgaggt cacgaggatt tgaagaatca ccctggtaac tggaatctca   2940
agtgccaggc aagttgtgcc cttgaccact tttttaccca ataatgttct ctaattatca   3000
ttcactcgtg cataggttaa ttttgatggg accaatagga caccctagat ttgtttatct   3060
cattaccttt gtttacccct gaatcacttg ggtagtttgc tattgcttta catggttttg   3120
ggataatcaa ttattatatc tatgtttcaa ttattcttgg tattcttttt tatgttcatg   3180
tcaagttcat taagttannn nnnnnnnnnn nnnnnnnnnn nnnnnnnnnn nnnnnnnnnn   3240
nnnnnnnnnn nnnnnnnnnn nnnnnnnnnn nnnnnnnnnn nnnnnnnnnn nnnnnnnatt   3300
tggtaccttt gatgaatcag cttgattcgt tggattttta atgtagaaat aaatgctaga   3360
attggttaaa aaaaaaaaaa attcatgtgt agtccaaatt aatccatttt agtttctata   3420
attttgtaat aatgttgttt atcaccctgt gtctctgttt taacatgaaa atggtattaa   3480
aatttatttc ttaattaacc tcgtatcaaa tacataaaac cttaggaaat tcatatatcc   3540
tccgttttaa cttcaatttg atccgttcaa gttgcgttag tctcgtagca acgcgtatat   3600
cattattacg cagtatattc ttatgtttgg tgtgatgtta attttgtcta taccatgttt   3660
gtttgtattg ctacgactag cagtgaggtc acgaggattt gaagaatcac cctggtaact   3720
ggaatctcta gtgccaggca agttgtgccc ttgaccactt tttacccaat aatgttctct   3780
aattatcatt cactcgtgca taggttaatt ttgatgggac ccaataggac accctagatt   3840
tgtttatctc attaccttgt ttacccctga atcacttggg tagtttgcta ttgctttaca   3900
tggttttggg ataatcaatt attatatcta tgttccaatt attcttgtta ttctatttat   3960
gttcatgtca agttcattaa tgttaattgg aacatagagc ttaacttgag aaacacgtgc   4020
caccacaagg gtttaatggg acgcccttgg ctgactaatt aggaaagcta gtggaagact   4080
accttacccg aaaggggcaa gggcagtagg ggagtggtca gtgtagggag gtccttggtt   4140
gattttgctg cgatggcggt cagacaagaa ccctgcattg gaacttctta taaactgtag   4200
cgggttttcg gaagctagtg gaactttgta aaggcctcgt agtgttgccc tgccgcgctt   4260
cctaggtaga ggtgtatggg attcgtgacc ccttggcaga tgggtagcat gacttgtggg   4320
taaagggtac aacctctgca gagtgtaaaa ctagtatact agccgtgctc gcggtcatga   4380
gcggctcagg actctctgat gttttaaatt atggaactta aattcaattt tgtcatttgc   4440
attgcatggg gtctattatt aatttttgtt caattacttt atctaaggtt ttggtattca   4500
cttatacttt agtaactgct aaataaaatt ttgaccaact acttaaaagc aatgctcagc   4560
tttaacccct atcattgatt agccttacac atcacatgac ctcacacctt tgtgagttta   4620
tgtccaccgg ttccccacaa cttgttgagc tatgatcatg tgtgagctca cccttgctgt   4680
ctcacacccc cccacaggag aagagcaggt ggttcaggag gagccgccta acactgagga   4740
gttcgatctg atctaggtgg catttcccag tcgacattgg cgccgacgat ccttagttcg   4800
ttttactttt atcttttatt ttgtaataag tcttccgcta tgtaataaat actctgatgt   4860
tttatgacat ttatctctat acactctgtt attatatatg ttgtcttctt ggcgcatgta   4920
tgagatgcac ccggctttgt tccttaaagc cgggtgtgac agaagtggta tcagaggaaa   4980
tgttgactgt aggacgaaac ctagatagaa atggacaaaa cccttcacta cttaccttac   5040
tctgattctt tctacactta tcttgattct gtctcacctt ctactgttct actctgatca   5100
```

```
ttcttacctt ttctactctt agtcaagatg gatttcacac cttggaatcc ctacctgtgg   5160
gggatagata tcccccgggt ccactaaaga agtaaaaggc ctcacgaaag gcccaagggc   5220
ccaataattc gtaaggtcat tctttcgtgg gcctagggaa agacagccgt taaaataaag   5280
aagacgtggg actgattagt gcaaacacag gcggcccaca acgtcgaacg aatgaatcac   5340
aaacagagac ccgactttcc cgcgctgaag cccccatgca acggagccat gcgaggataa   5400
gtcggcggag gttacgtaag gataagctca agaagttcac tatctttcag ctacttgttg   5460
ttatcgtatc acatgtaatg ctccacggcc gagtatataa ggcctagggg gcaccccttc   5520
agatggatcg actctgctcc acttagccac ccacaaaaac tctctgcgcc ctctatccag   5580
agaatccttt tgtaaccacg ctcatatact caccaggacg tagggtgtta cgcgtttcta   5640
agcggcccga acctgtaaat cttgtccatt gtccctcgtg cgatcggcac gaaccatttt   5700
gctacagtcg tcgacaccgt cctactccta aaaacacctt gaggggcaac cccgggtgtg   5760
cggtcggacc caaaacaccg atagctggcg cgccaggtag gggtgtgtc gacgatccaa   5820
gctagctcaa tggccgtcac cttccacagc aagatcacca tgcgtcccgg atccacattc   5880
tgcttcggga caatctcctc cgtggcggat gaagaaggaa ttctacaccg cctcgcggat   5940
ctgccggaac agaagtctcc accaacaaac tccgaaaatg ctggaaagac gctacttccg   6000
gttcttcggg aaaagatcgt ctccggggag gctggagcga gaagctcgct gacccggaag   6060
actccgctgt ctacttcccc gacgaaagaa tggacacaga tcatgagaag gaaggagatc   6120
agggagaggc cggtcgttct tcccgttcct ccgacttcaa aggagaatgg aaagaaagtc   6180
gccgcggcag caataccgtt ctaccccgac atcctcttca tcgggagagc agaatcaccc   6240
gccgtctccg acgatgaacc gaccgcgcct ggagaagaac cgcctcagcg agaatcccgc   6300
cgacgaagga atcggcgcag gaacgttcga cgacatcacg cagctggaga acaggatccg   6360
gagcaacctg tctcgcgaga cgaggtctca gagataggag aaactccgga agaacgcgtc   6420
ttcagggaac gaaggaactc ccgacgacga gatcgccgtc gaactcagga gcaagccgag   6480
caagatgcaa ggcaacgacg cgagaatccg ctcttcgggc gcaacctgaa ccccgacttc   6540
gcccgagcca tgaatacgcc gagcgaagtc ggaggcgttc tggcccggat agctgacgga   6600
cttcctcgga cccccgacgc cgagggatac cggcgcctgt tcactcaggc agccaaccat   6660
cttctaccgc tcgctcatcc gccgaacgat ctgcgacacg ccatcaacag tcgccgagac   6720
gcgcgaagct ctatcaatgc ttcgcgcgaa cggcggcacg agaacgaaat tcgccgtcga   6780
gaggagtatg atcgagatca tggcttcccg acccaaagcc aggccacccg aactgagtcg   6840
gcaacagctt caactggtgg aaccacccgg ggacggtcga ggagccacca ccgccactcc   6900
cctccccggg acagacgaca tcctcgacga caggaagaca cgtgcggagt atccgccctt   6960
actccgcgcc ttagggccat ccaatggcct cccaacttca aggtatccaa tgtcgacaaa   7020
tatgaaccta agcaggatcc ggggggctgg ttagccgtct acaccaccgc tgctcgggcc   7080
gctggggcat ccgaggacgt catgactgcg tatctgccca tcgtcctcgg gcaagacgcg   7140
ctgcagtggc tacgacatct accccgacac tgcatcgacg actggggaga cttcagtcga   7200
cgtttcaccg ccaacttcca gtctctctcc gacaagccag cgcaaccatg ggacctcaaa   7260
tccatcaagc gccgggggga tgagactctc aggtcatacc ttaaaaggtt ccagaccatg   7320
agaaaccgca tccccgaggt cacggaggcg gccgtaatcg aggacttcta cagaggatct   7380
aacgactcag ctttcgtccg agccatactg caaaaggcgc cgactacctc cgaggagctg   7440
```

```
ttccgggaag ccgacctcta catcaccgct gacgagcggg cccaggacct catcggagga   7500
gcaaagcccg caccggcggt accacgacgc gacgcgaacc agccgcccga caagcgctgg   7560
gagaagaggc ctcgcgaaga ggtacacgcc gtcggaccac ccgcctctcg cgcccgagga   7620
ggacctcgtg gaggcgaacg cacgctggac gacatcctcg acgcccagtg cccgtaccac   7680
aaggatatgc gccacactct ccgcaactgc cgggacttca agcactccgt cgggcatggc   7740
cgacccttcc aacctctacc acctcctccg ccgagaggag gaccagatga accacgacag   7800
ccccatcagc cggaggaggg gggaggagga gctttcccgc gcgttgacag ggaggtcaac   7860
gtcatcttcg gcggacatgg gtcgcaggag aacaagagac aacaaaagct caacgaccgc   7920
cagatactgg tggcgaccac cggccctccc gccccgtacc ggtggtcgga gcacccaatc   7980
acattcactc gggaggatca atggctcaac ttcgaccacc caggcaaata cccgctcctc   8040
gtcgatccgg tgatccgaga gagccgagtg aagaaggtgc tagtggacgg ggggagcagc   8100
atcaacgtca ccttccccg tacgcttcaa ggcttgggag ttcacctcaa agagctccac   8160
gagtcagaca ctcctttctt cggcatcgtg ccgacggaag gggagtatcc gctgggccac   8220
atctacatgc cggtcacctt cgggactccg gataattaca gaaccgagtt cctgaggttc   8280
gaggtggcga acttcgactg cgggtacaac gccatcatcg ggaggccagg gctggccaag   8340
ttcatggcca tcccacacta cacgtacatg atactgaaga tgccaggacc acgaggaatc   8400
ataactgtgc gcgccgactt ccaaggcgcc gcagaatgtt tccgagtggc catccaagca   8460
gccctcacca ccaagccatc agcgattcct tctacaccgg cgaactctaa gcctgatgaa   8520
gacctcgccg tgccggcaaa cgaagctcag gccgtgacct ctatgcggcc gactgaagac   8580
accaagcgga tcaacctggg gttcgctgat gagcgcaaga cggccatcat cagctccagt   8640
ttgagtgaca aatagaaaag cgcgctcgtc cagttcctgc aagataaccg agacgtattc   8700
gcatggcaac ctgcggatat gccgggagtc ccaagagaac tggccgagca caaattgaag   8760
gtctatcccc aggcgaggcc gatccggcaa aagctgcgtc gtttcacgcc cgacaagaga   8820
gaagccattc gtgccgagtt agcccgcttg gtcgcggccg gatttattag agaagtattg   8880
caccccgagt ggttagccaa ccctgttctt gtactcaaaa agaataaagt ggattggcgc   8940
atgtgcgtcg actatactga tctcaacaaa cactgtccga aggatccctt cgggctcccg   9000
aggatagatc aggtggtgga ttccaccgct ggatgttcga tgctgtcttt cttagattgc   9060
tattccgggt atcatcagat tagtttggca aaagaagacg aggaaaaaac ggcgttcatc   9120
accccgtttg gtgctttctg ttatacctcc atgccgttcg gcctcaaaaa cgctggagcg   9180
acttatcaga gggctattca aacatgctta gccgatcact ggggcaagcg tgtggaggct   9240
tacttagacg acgtggtgat caaaactgag aatccagaaa acttcatcga agatttacag   9300
ctggttttca acagcttgag aagatataga tggaagctca atcctgaaaa atgcgttttc   9360
ggggtaccag caggaaagtt gctcggattt atcgtcagcc accggggaat tgaggctaat   9420
ccagataaga ttgaagctat catgaagatg gaagctcctc gatcacaaaa gaaggttcag   9480
cgactcactg gatgtatggc agccctgagc agattcatat ccaggctggg agaaaaaggt   9540
ctgccatttt ataaactgct gaagaaggtg gataagtttc aatggacttc agaggcacag   9600
gaagctctag acgcactgaa gaaattcctc acaacgccgc cagtattgaa accgccccgg   9660
cgagctacgc cgactcagcc ggctgaagat ctgctgttat atatctcttg cacgactcac   9720
gtggtaagca ctgcgttggt agtcgagcga gtggaagaag ggcatgccta cccggtacaa   9780
catcccgtct atttcatcag tgaggttcta ggcccatcga agaaaaagta tcctcaagtt   9840
```

```
tagaagctat tatatgcagt acttctaact gcccgcaagc tgcgccacta ctttgacgac   9900
cacaaagtca tagtagttac tggttttcca ataggggaca ttcttcacaa caaggaagcc   9960
attggccgaa tagccaagtg ggcttgcgag ttggggtccc atgatatcga gttccgacct  10020
cgcactgcca tcaaaactca agcactggtc gacttcgtat cagagtggac agaacagcaa  10080
gtgccggata atccagaaac cgcagaagta tggcgaatgt attttgatgg ctcgctgaag  10140
ctgcagggag caggagcagg aattctcttc actgcacctg gaggcgaaca ccttaagtac  10200
gctctccaat tgctattccc ggcctctaac aacgcagccg aatatgaagc tttgatacac  10260
ggattaaaca tcgccatatc gctgggtgtc aagaggctga tggtgtacgg ggattctctg  10320
gtagtcatca gtcagataaa caaggaatgg gattgttcaa gtgattcaat gggaagatac  10380
tgcgccaccg tccgaaagct agaagataaa ttcgaaggcc tggagttcca tcatatagaa  10440
agagatcgga acacggcggc tgatgtattg tccaagctcg gatccggtcg gactcaagtc  10500
ccgcccgggg tcttcgtgca agaaatcctt cagccgagca tctcgacgga tcaaatagaa  10560
gagtgcaaca tcatagacca acccgagtca gactctgatg actggaggca accgattatt  10620
aagtatataa agaatgaaga agagccagat gacaagaact cagcagagcg cattgccaga  10680
caatcagctc actatacact cattggggag gtattatacc ggagggggcgc gtcaggcgtc  10740
ctcatgaagt gtgttctccc gtccaccggg aagcaacttc tggaggaagt ccatgcaggg  10800
cagtgcggaa tacatgcagc atccagaaca ttagtcggga aggttttcag gtcaggattc  10860
tattggccga cggcgaagaa tgatgcagcc gagttagttc agagatgcga agcttgccaa  10920
tacctgtcga agcaacagca catgccagcg cagcagctac aaaccatacc agtaacttgg  10980
cctttcgcat gctggggatt ggatatgatt ggacctttca agaaggctca aggaggatac  11040
acccatgtat tggtggcaat tgacaaattc actaagtgga tagagttcca gcccattgcc  11100
tctttgacct ctgctaaagc cgtggaattc atacaaagca taatattcag atttgggata  11160
ccaaacagta tcatcactga cttgggatcc aactttacca gttcagaatt ctttgacttc  11220
tgcgagcaaa aaagcattca gatcaagtat gcatctgtag cccatccgag agccaacggg  11280
caggttgagc gagccaacgg aatgatattg gaggcactta gaaaaagggt ctttgataaa  11340
aatgaaaaat tcgcaggaaa atggataaga gaattgcctt atgttgtttg gagcttgaga  11400
acccaaccta gccgagccct gcatggaaac actcctttct tcatggtcta tgggtcggag  11460
gcagtgctac ctgctgatct caagtttggg gcgccaagat tgattttcga aagcatagca  11520
gaagccgaag ccactaggct ggaggatatt gacgtacttg aggaagaacg actgaatgca  11580
gtgattcaat cggcacgata ccagcagact ctaaggcgct accacgacaa agctgtgcgg  11640
caacgtttct tttcgaaggg agacctcgtc ctccgccgaa ttctaacggg ggagggacgg  11700
cacaagttat caccccttatg ggaaggacct ttcatagtag cagaagtcac tcgtcccgga  11760
tcatatcgcc tcacccaaat ggatggcacg gaagttggga actcttggaa catagagcac  11820
ctcagaaagt tttacccccta gctgtacttc aaaacagccg gggcggccat gtactctgta  11880
aagtggaaat atgtcatcaa taaagataga tttcaaggac actcggttcg tttatgattg  11940
acttgcattc ttacttaact cggggtgacc actatgccct acaaacggag caatcgactt  12000
aagtcggcaa cgacttaagg cggtgcaaca tgctcacgct tacttaactc ggggtgacca  12060
ctatgcccta caaacggagc aatcgactta agtcggcaac gacttaaggc ggtgcaacat  12120
gctcacgctt acttaactcg ggtgaccac tatgccctac aaacggagca atcgacttaa  12180
```

```
gtcggcaacg acttaaggcg gtgcaacatg ctcacgctta cttaactcgg ggtgaccact  12240
atgccctaca aacggagcaa tcgacttaag tcggcaacga cttaaggcgg tgcaacatgc  12300
tcacgcttac ttaactcggg gtgaccacta tgccctacaa acggagcaat cgacttaagt  12360
cggcaacgac ttaaggcggt gcaacatgct cacgcttact taactcgggg tgaccactat  12420
gccctacaaa cggaacaatc gacttaagtc ggcaacgact taaggcggtg caacatgctt  12480
acgcttactt tacctagggc gatcactaaa ccctactaac ggaagttacc ggctaaaagt  12540
cattgacggc ttaaaccggt atagcatact cgcgcttatg aagttcaggg gatgacttcc  12600
atatcccaca aacaaacttc ataattatca tgtagcatta ccacaaattt gcaaactaat  12660
aaattctgat acgataagaa agaaatcata acattcgaat gataagctga tgtcctctaa  12720
atgaatgctt gctcatgcta actgcgcgct cagagcacgc gaactgtttc tttattttcc  12780
aatgtctctc tcaggaacga ctgacgaaga agggcgattc gaggaatcag gggcagcaac  12840
cacgtcggct cttatatcct cggggacaac cacgccaggt cttctcatca agattcgtcc  12900
cgcccgaatg gccttgtcca gggccttatc gcgctgagct ttgaaagtga cagcagcttc  12960
ttcagcaact ttaacaacct gctgagcagt ttctaactcc cgggcaatgg ttttcttgga  13020
agctcggagt tccttgatgg tggcatcctt tgctgatagc aactgtgtaa ggcgggccac  13080
ttcgtccgaa gattcttgca gttgacgacg ctgattgtca agctcctcca tcgtaaagcg  13140
gtggctcctc tccaagatgg tcagcgagct actggaatct cggtacaatc tgtccaagtt  13200
gtcgcgagaa gcagcaagga tacgtttttc ttcctacaag caaaaatcaa aaatcaaact  13260
cattcagaat ccaagagcat gataaggcga agcgcaggtt cgtaagctac cttctcagag  13320
ttaagctgga catgaagaga agaactcaga gcgttagcat catccaaagc cgcagagacc  13380
tgactcaact cgatctgact ttgagaatac ttctcctcga agtcagcgca tcgtcgagtc  13440
atttcagctt gatcttgaga atgtttttct tcaagaactt tgatctgccg agtcatccct  13500
atcaagaagt attcaaacaa aatgaggtca gaaggtaaaa caacctacgg gcaagaataa  13560
agaagaagaa gaaaggacac tgaccagcat tggtggcctc caactcagat acacgacgat  13620
gaagcaacac tggattccaa cgctcgagag atgacgccac ttctggggta gaagcaccct  13680
gtgatttcag ttgactggcc aatccattca ccaaagcctg acgagaagaa cagatgagca  13740
taatgacagc aattcatgca acatagagat caaattaaag cacggcacag cacctggagg  13800
ttggaaaaga acgaagggat ccccaagtca ggagaaatca gctgataatc aggtgtcaga  13860
ccaccacccg aagcagtttg cagtagacca gcaggaacga gctcagtaca ttcagcagag  13920
cctaacacca gaccagtggg gatgctgccc tctaaagcga ccccctgatc tggagtttga  13980
gccaccacca tgccgccaga gtgtggaggt gaacccacgt gaacgtccat agaagtgcag  14040
gaaggagacc ctgctcgggc accctcgggg gctgggtcaa ggttggcact gcccacttga  14100
gccggatcac ccccggcaac accctcgggg gctgggtagt ggcctacgct cctcacctga  14160
gctgagtcct ccccggcgac accctcgggg gctgggcaca tgtcagcact attcaaagga  14220
tccaagctct ctgccgtgac cacctctaag gtcgacgggc cttcagctac ctccgcagga  14280
tcaggacgat ccaagtcatc attccggccc tcgagatcgt gctctaaggt cgacgaggca  14340
cgggacgacc tcaatccagc atctggcacg cccgcacaag tttctgttgc atcaacgtct  14400
gcaggttcca acaacaagtt ctcagggacc atatcctcta gagcttgatc aaaattggcc  14460
atagacagtt cttgcagacc aataagagca gacaaggcag gagaaggaac cccactacta  14520
ccgccgctag cgacgaactg ccgactgttt ttccgagtca atggagtttc attctcttcc  14580
```

```
tcctcgtctt ccacagcaac agcacaaaca acaccctcat tggggtcagc agcaggcgga  14640
gcacacccat tgggatcaat gtcagctagg ccagttgcag acatttcttc gatagcagga  14700
gctaaggtgc tggtatcctc gtcaaaactg gacactcgcc ggaggcgtct cctttcttc  14760
ttctgctcat cagcagaagg ctcgggctga ctggttcggc tagggcgcct cgggcgagta  14820
ctgacaggtt tcgaggagtc caaggtcgca tcaacctctg gaaggggcac cactgccaat  14880
gtaccatcag gagcagtatc agatgaatcc acagctagca gatcgagcat gtcatttatg  14940
tctgcatcac tagggttcag aggcacttca aaataaatct gccgttcatc atcaggtata  15000
tccccgagcg aagcaactaa agaacggacc tcttcagcag agggtcgcac tctaagaccc  15060
aaattgctat ctatcacggg tggattggac acaaaaagag tgaaggcttg agaagaaggt  15120
aggttccaag ccgagtatgc cactggagct ccaacgttcg aaactttacc cctgaggatc  15180
atttcaagcc ggctcaccaa atccacagaa ggaattctcc tattagtaac tcgggttgag  15240
tcggccagcc ctcggtaaag atatgccgga taggccctgt ctttcagcgg ctgaatgttt  15300
ttgaacacaa aatctgtgac cacggcttcg gcagtcagac ctctctcttt cagtaatcca  15360
acttcagtaa gcaacacgcc cgcttcggct acttcttggt ccgtgggaga ttcagtccaa  15420
ctcggagtac gaacgtctgc ctgtcttccc gagcgggaag ggagagaatt tccataatta  15480
tccattataa accactccag acgccaacct ttaatgctgt ctttaagggg tatctcgaga  15540
tactcagtct tccgcccccg acgcatctct aagctggcac ctccgaccaa ttgatgttgc  15600
cccccggcca tcccaggacg gcagtgatac agatacttcc ataagccaaa atgcggcagc  15660
acgccaagat aagcttcgca aaggtgaacg aaaatagaaa tttggagaat ggagttaggg  15720
ttcaagtgag tcaggttgat gtgataaaaa tcaaggatgc cacggaaaaa aggagatatg  15780
ggaaggccga ggccgcgaag aaggaaagga gtgtaaacca ctgactcgtg ggtatcttcg  15840
gttgggacag tagtcccatg gcaagagcgc caagaacaga gttcccgtgg agggagaacc  15900
ccgatggaaa caaggcggag aagctcaact tcagaaatca cagacatatg gttacctgcg  15960
aagggcaact gactgttggg atcgatggcg gggatcactg cagcagacga gttcgcggtc  16020
ttcctcttgg gcgccatctt gcttctcgct ggcgaaacag agcaggaggc gagtggcaga  16080
gaagactcag atgcggaaat gcaagaacta gggcacggaa agcaaaggcg gctgaaagcg  16140
cgactcttaa gggatattct tgagccagat accttttcaa aagtgcccag tcatcacccg  16200
gcggtcatct ccgaaatccc agcatgctac gtggatatct aacagttatt tccaagaaag  16260
ccgatgtgcc acctcatcac tcggccattt tcctcaaagt aacttgagaa gctggctatc  16320
actcggcgct gcctctaaaa cgccgaccac gtgttcaatc gctcggcatt acttctaaaa  16380
tgccgacgcc gaccttcaaa tcactcggcg ctgcctctaa aacgccgacc acgtgttcaa  16440
tcgctcggca ttacttctaa aatgccgacg ccgaccttca aatcactcgg cgctgcctct  16500
aaaacgccga ccacgtgttc aatcgctcgg cattacttct aaaatgccga cgccgacctt  16560
caatcactcg gcgctgcctc taaaacgccg accacgtgtt caatcgctcg gcattacttc  16620
taaaatgccg acgccgacct tcaatcactc ggcgctgcct ctaaaacacc gaccccgtgt  16680
tcaatcgctc ggcattactt ctaaaatgcc gacgccgacc ttcaaatcac ttggcgctgc  16740
ctctaaaacg ccgaccacgt gttcaaacgc tcagcattac ttctaaaatg ctgacgccga  16800
tattctatca ctcggcgtta tttctaaaaa gccgaccccg tattttgtcg cttggcatta  16860
cttctaaaat gccgatgccg accttctatc attcggcatt gcctctaaaa cgctggtctt  16920
```

```
gtgttcgatt gctcagtgct acttctaaaa cgctgatgtc aatcttcaca tcgctcggcg  16980
ctgtttctac tatatcaaaa agaaccagtt cagcattcag caaaagcagt ggcaagtcat  17040
caaaaagagg ggataaaacg atatacttca ttaaagggaa gttgacgaac ttacaaacca  17100
actctttatg agttggtact tccctaattc tactttacat taccactact actaaactac  17160
actaattact actacattat tctagctata ctaaactata ctaatatcta agaagaccag  17220
tggcgtctag ccactggccc tgcccctgcc cctgccgccg ccgccgcctt tggtgctgcc  17280
cctgctgctg cccttggtgc tgtccctgct gccgccgccg ccgcccttgg tgctgcccct  17340
gctgctgccc ttggtgctgt ccctgctgcc gtcgccgcca ccccagccgc cgtcgtcgtc  17400
gtcgtcgtcg tcgtcgtcgt cgtcgtcgtc ttcaccctcg tcgccgccgt ccgagtcctc  17460
ctcatccgag gagcactccg actcatccga gccttcgagc ccggcgcgct cgacggcccg  17520
gatatatgtc cagacctccg cggctatccc ctgggagtcg tccgagtcat cggacgacgc  17580
cgggggagag acgggagccg gagacccctc aggctcggag gagaactcct cctccgagta  17640
ttctgagtca ccaaactcct ccgatggagg agtcgactcg cgcttgcgct tgttgttctt  17700
gcccatggtt aaagttttgg gagagaagaa agggaagagg cagtaaggag cagcgaagag  17760
atgtgaagaa accagagaag caaaggggtt atttatagaa gggaaaggca accgctcact  17820
tctaaccgcg gtcactgaac agtcgaaaga cattcaataa gcacttccac ccacccgaag  17880
acacgtcaga cagcggacgc cgtttcatgc aactctacac ccattgggac tccagtcaac  17940
agcgcaaagg atatgattac actagccgtc ccatcgcatt actactcaga ggcaaccagg  18000
ctaaaacact cagcgtacca agccgtccct tgcccacacc cattgggggg gggacgccca  18060
ggaattatca gtatattttt caaacggtca catccgtgca gggcatgcag tgaatacctc  18120
aagacaaaaa tgagatatca acaagagtta gagggaagcc aaatatagcc agtagagtgc  18180
aaaatatggt cgacagaaat gacttgaaga ctagacagag aacgtccatc aaatgtccaa  18240
tcagtcacag agcaaataaa ttacactacc tagcgagata tggatggatt gcgaactcgg  18300
ctgcaaaaga caaaatacat gctgacctct gaagcataaa attgatgaca tagcgcggat  18360
gacatcatgc caattttttta caagcagaaa ggataatttt cagcaaaagg acacagaagg  18420
aagaccttcg agtggattat cctcaaaaat ccacttgaag gtcgggggct acacccattg  18480
ggtgcacctt cggtgcaccc catggattat cattctaaat caatatagtg ccgacctcta  18540
aggcgtagaa caagattgga aagatcaatc ctcaactgag atgcaggagc gcgaatggag  18600
aaaatcttcg gagaagacct tcgagtagat tatcttctaa aatctactca aaggtcgggg  18660
gctacaccca ttgggtgcac cttcggtgca cccaaggaag tccagaatct tataatccaa  18720
aatgccgatt tctaaggcac aggcacaaaa ctaaactttg gtcgaacaag tgatcagagc  18780
aagagaaaac agcagggagt catttttgga ccttggatct ttaagttgat tacctccaaa  18840
tcaacccaaa gatcgggggc ttgtggggga tagatatccc ccgggtccac taaagaagta  18900
aaaggcctca cgaaaggccc aagggcccaa taattcgtaa ggtcattctt tcgtgggcct  18960
agggaaagac agccgttaaa ataaagaaga cgtgggactg attagtgcaa acacaggcgg  19020
cccacaacgt cgaacgaatg aatcacaaac agagacccga ctttcccgcg ctgaagcccc  19080
catgcaacgg agccatgcga ggataagtcg gcggaggtta cgtaaggata agctcaagaa  19140
gttcactatc tttcagctac ttgttgttat cgtatcacat gtaatgctcc acggccgaat  19200
atataaggcc tagggggcac cccttcagat ggatcgactc tgctccactt agccacccac  19260
aaaaactctc tgcgccctct atccagagaa tccttttgta accacgctca tatactcacc  19320
```

```
aggacgtagg gtgttacgcg tttctaagcg gcccgaacct gtaaatcttg tccattgtcc  19380
ctcgtgcgat cggcacgaac cattttgcta cagtcgtcga caccgtccta ctcctaaaaa  19440
caccttgagg ggcaaccccg ggtgtgcggt cggacccaaa acaccgacac taccccatg  19500
acatttttaa gaggtaggaa gcctaagaca aaattaaaac tattttcttt attaaaaatg  19560
ttggttgatt gttctgatga tcaatgcctg atttgcttct ttgattgatt gaaatagtat  19620
agacgggcat cttagcatgt accaccataa ggtaatgtat tagcgttagt aggtgacaca  19680
ctaatctact tagctaataa atcccccgta gtaatattcc tcttaattac tcgccttgtc  19740
tacaattctt cctttcgcac cctatgtttc taacgcagat gggctacccc tatagtgtta  19800
gaagagagca ctataggcgt gatccttggt atttcatggt taagaaaggc aaagacagtt  19860
tatacactgt gctaagggaa ccatagaact caccagttcc aaaggagaaa tatttgaagt  19920
tggaattgca gtaactacca ccatcagtct aacaacattc ttagaagatg agaagtttgt  19980
gggtgacaac atccgtgcag ttagagatct tccggatgtc tttccagagg agttattagg  20040
ggtgccacca gatatggatg ttgagttggt cattgatctc ttacctggga cgactcctat  20100
ttctaaacgg ccatacagga tgtccgtaga agaactaaag gaacttaaga agcaattaac  20160
ggaattacaa gaggctgggt acatttgtcc gagtcttcac cttggagagc atcggttttg  20220
tttgtacaga agaaagatgg attgcaaggg atgtgtgtgg attaaaggtc ccttaatggt  20280
gtcactatga agaacaagta tccattaccc cacattgaag atttatttaa tcaggtgaga  20340
ggtgcaagag tattctcgaa gattgatctt cgatcgggtt accatcaaat gaatattagg  20400
ccatcggata ttcccaagac gaattccttg acccgatatg gtttatatga gttcaccgtt  20460
atgtcgtttg gactaactaa tgcactagcc tactttatgg atctaaagga taatgtgttc  20520
atgatttgga tagattcgtc gtggttttca tcgacgatat tcttatctat tccaagagtg  20580
atagtgatca cgaggaacat ctgaggatgg tgctacagaa gctacgagat aaccagctat  20640
atgccaagtt tagcaagtgc gagttttgga ttggcgaggt gccatttatt ggtcatatta  20700
tttctaatgg aggaatatca atggatccta ctaaggttaa ggagataatg gagtggagag  20760
tacccactac agttactgag attcagagtt tcttgagact agtaggatat tatcggagat  20820
ttattgaagg attttctaag attgctaagc ctacgacctc gcttctggag aaggacagag  20880
aatttaagtg ggtcgggaag tgccaagaca gctttgatca attgaagatg tgtttgttca  20940
ccaccagtat tggtatgaac agacctacag aaaggagacg aattctctag aatcggannn  21000
nnnnnnnnnn nnnnnnnnnn nnnnnnnnnn nnnnnnnnnn nnnnnnnnnn nnnnnnnnnn  21060
nnnnnnnnnn nnnnnnnnnn nnnnnnnnnn nnnnnnnccg acagattggt gatgctaaga  21120
tacaagagaa atcaaggatc ttattgaaaa aggaagaggt ccggaattta cggaagatga  21180
accaagaccc aatatggttc aagggcagga tagtgtttct ggtattgaaa gctttcgtaa  21240
gactattcta aaggaagccc ataacttgga ttattctatt catcctggta gtaccaagat  21300
gtatcaggaa ttgaagcaga aatactggtg gtatggattg aagagagatg tggctgcaca  21360
tgtggctatg tgcgatgggt gtcaaagagt taaggcctaa caccaaagac cagctggact  21420
attacatcca ctgaagatac ccaagtggaa ggggaagaaa ttggtaagga cttcattact  21480
ggattgcctc gcaccccgag aggatatgat tctatatggg ttattatgga taaatttacc  21540
aaagtgactc attccattct ggtcaagact acttataagg tatctcaatt ggtagagtta  21600
tatatggctc ggattgtgtc tccacacgat gtaccgaaga agatcatttt ggatagagga  21660
```

```
tcacagttta cctctagatt ttggaaaagt tttcatgaga atatggatgc gaagttgaat  21720
tctagtttgg cttaccaacc tcagactgat ggacaaacta aaagggctaa tcaagtattg  21780
gaagacatgt tgagagcttg cgcccttcag catggtagta gttgtgacaa gagtctacct  21840
tatgctgagt tttcatataa taatagctat caggctagtc tgaagatgtc accgtacgag  21900
gctctgtatg gcaggaaatg caggacacct ctatttttgg accagactag aggaagacat  21960
ttctttgggc ctgaacttat tcaagaagca gaggaacaag tccgtataat tcgggagaat  22020
ttgagggtag ctcagaccag gcaaaagagc tacgctgata atagaagaag accactggag  22080
tttgaggaag gtgatcatgt gtacctcaaa gtgtcaccac ttcgtggaat gaggagattt  22140
aaagttaagg gcaaattgtt ccctcacttt attggaccat tatgagtttt taggcgagtt  22200
ggagagatgg cctatcaact cgagctacct gataatatat ctgatgtgta taatgtaatt  22260
tacgtgtctc aacttaagaa gtgtctccgt gtccttgagg aacagttacc aatggaagag  22320
ctcagtgttc aggatgattt gacttacacg ggtatccga tcaagattct tgacactttt  22380
actcgactta caaggaataa ggtgataaaa atgtgcaaag tgcaatggag tcaccatgga  22440
gaagatgaag catcatggga aagagaagaa gagtttcaca tagattttcc cccatctttt  22500
tcctagtcct tcctaaatct cgaggacgag attcttgtta aggggggtag gatttgtaat  22560
acccactttg taataaaaat ctaaaaggag agattatatt cctttatata catgtgtgtc  22620
atctatatct atcatttcat gtgaacacct cacttccaca aataaataat taaataaaaa  22680
cactcaaata aatcatgcat catgctagga ttttcttttg tgtgcatatt gtgacaaaat  22740
aaaataaaaa tgtgacaaga aaaatattaa agtccaaaaa gggaatttag aatctaaaag  22800
aaatcctaga aagggaagga aagaaaattt tatgtgataa aaaaatgtaa aataaataaa  22860
taaaatatta ttgctatact agtgctttaa tgtgacacct gactcagggg tagagctcaa  22920
aagcatattc aaatccaaat ttgaattcaa aatatttatg aataagagga tagaaaataa  22980
aagaaaggag agggggacta cctgcgctct gggccgaatt tcttctgtga tcggcccatc  23040
aggcaaatgc gcacagccca aaagaacgga ttagaccgtg tgccgaccgg tgggccgttg  23100
gtgccagcct cttccctctg cgccgatggt gggggccaca ttccagatgc gcgtgctgtg  23160
gcgacttgca ggcgggccca ggttgtcagt tccttcccct tcgccgtaac agaactcgcg  23220
ttctctacgc cgcatgacta tcacttccgc cgagacctcg cacgcgccac gtcttgatcc  23280
caggaccgct ctggattcta ttgcagagat ctcgccgtca ccgccgcggg tatcggatgg  23340
tcgttacatc gtgtgccgac ttatgcggat tggcctgggc gcataagtag cgcgccgctc  23400
ggtatcttgg cccaccaaat gaacccctgc ctcgcaccac agttgattgt gtagcctcgt  23460
cggtgggaga actccgctgc cgccgaagaa agctcgaccc atagccagta ctagagagag  23520
aaagacgtgc gccaccgggc ggattaacgg gtttccgcgg tcacctgagt aggggagtgg  23580
gtgcggcatc tgtcgccgtt gggcaccgca cccgtgcctc cgtccccgcc tgcttgcagt  23640
gaccccgcgc acctccatga cgcaactcgt gcgtgcccgc tcctgtcact cgcggtcggg  23700
ttgccgcggc tccccattgc cgtgcagggc ggggccaaac tcgacggtgc cctcgtcgtt  23760
tgggggcctg catggttact cgggggcttg gtccacggcg ggcataacca atcgccggag  23820
ttgggcatcg tcgccggtcc gcatcgcgtt gcgagcagcg tcgccatcgc tgcggtgtag  23880
gaagaagggg ctgccatcgc catggacaaa gcactgggcc gcagccgaag aacttcatct  23940
gcgctagggc ttcacagcac cgtgacccgc gcttcgtcgt cggccatccc ctgcctcctt  24000
caacggtgag aattcccctc ctccgagtca acagggccga gtcgcttgct gttggtggag  24060
```

```
tcttgcgtat tccaggagaa ggtagcggca taaggtagaa gagggggttg tggctgtcag  24120
attgatgacg ggcggcctag attacccctt cattccttag tcgtgggccg ttagatcgtg  24180
atccaacaca cgtgattagt tgccagctca tgccttttg gttgccgttg gatctggatc  24240
cgaggctcca catggcgtac cccttcgttg tgttaagttg cggccgtggg atgaaaatct  24300
aacggctcag ggtgcatgcg catactgctg ccgacccatc ttacaaaaga gccctaatgt  24360
cgttaataaa taacccgcag tccacgtagt tgggctctga gtcttaggaa aacttacacc  24420
gagacccctg aacttctctg tattagtgcg cccagtccag agagccagaa aaatcagaaa  24480
acaaatatag aattggattt ttaatgtaga aataaatgct agaattggtt taattcatag  24540
aaaattcatg tgtagtccaa attaatccat ttcagtttct ataattttgt aataatgttg  24600
tttatcaccc tgtgtctctg ttttaacatg aaaatggtat taaaatttat ttcttaatta  24660
acctcgtatc aaatacataa aaccttagga aattcatata tcctccgttt taacttcaat  24720
ttgatccgtt caagttgcgt tagtctcgta gcaacgcgta tatcattatt acgcagtata  24780
ttcttatgtt tggtgtgatg ttaattttgt ctataccatg tttgtttgta ttgctacgac  24840
tagcagtgag gtcacgagga tttgaagaat caccctggta actggaatct caagtgtcag  24900
gcaagttgtg cccttgacca ctttttaccc aataatgttc tctaattatc attcactcgt  24960
gcataggtta attttgatgg gacccaatag gacaccctag atttgtttat ctcattacct  25020
tgtttacccc tgaatcactt gggtagtttg ctattgcttt acatggtttt gggataatca  25080
attattatat ctatgttcca attattcttg ttattctatt tatgttcatg tcaagttcat  25140
taatgttaat tggaacatag agcttaactt gagaaacacg tgccaccaca agggtttaat  25200
gggacgccct tggctgacta attattttta gctagtggaa gactacctta cccgaaaggg  25260
gcaagggcag taggggagtg gtcagtgtag ggaggtcctt ggttgttttt gctgcgatgg  25320
cggtcagaca agaaccttgc attggaactt cttataaact gtagcgggtt ttcggaagct  25380
agtggaactt tgtaaaggcc tcgtagtgtt gccctgccgc gcttcctagg tgaggtgtat  25440
gggattcgcg accccttggc agatgggtag catgactttg tgggtaaagg gtacaacctc  25500
tgcagagtgt aaaactagta tactagccgt gctcgcggtc atgagcggct caggactctc  25560
tgatgtttaa ttatggaact taattcattt tgtcatttgc attgcatggg tctattaata  25620
attttgtcaa ttactttcct aaggttggga atnnnnnnnn nnnnnnnnnn nnnnnnnnnn  25680
nnnnnnnnnn nnnnnnnnnn nnnnnnnnnn nnnnnnnnnn nnnnnnnnnn nnnnnnnnnn  25740
nnnnnnnnnn nntttggacg tctgatgaat cagcttgatt cgtttgtgat cggcccatca  25800
ggcaaatgcg cacagcccaa aaaaacggat tacaccgtgt gccgaccggt gggccgttgg  25860
tgccagcctc ttccctctgc gccgatggtg ggggccacat tccagatgcg cgtgctgtgg  25920
cgacttgcag gcgggcccag gttgtcagtt ccttcccctt cgccgtaaca gaactcatgt  25980
tctctacgcc gcatgactat cacttccgcc gagacctcgc acgcgccacg tcttgatccc  26040
aggaccgctc tggattctat tgcagagatc tcgccgtcac cgccgcgggt atcggatggt  26100
cgttacatcg tgtgccgact tatgcggatt ggcctaggcg cataagtagc gcgccgctcg  26160
gtatcttggc ccaccaaatg aacccctgcc tcgcaccaca gttgattgtg tagcctcgtc  26220
ggtgggagaa ctccgctgcc gccgaagaaa gctcgaccca tagccagtac tagagagaga  26280
aagacgtgcg ccaccgggcg gattaacggg tttccgcggt cacctgagta ggggagtggg  26340
tgcggcatct gtcgccgttg ggcaccgcac ccgtgcctcc gtccccgcct gcttgcagtg  26400
```

```
accccgcgca cctccatgac gcaactcgtg cgtgcccgct cctgtcactc gcggtcgggt  26460
tgccgcggct ccccattgcc gtgcagggcg gggccaaact cgacggtgcc ctcgtcgttt  26520
gggggcctgc atggttactc gggggcttgg tccacggcgg gcataaccaa tcgccggagt  26580
tgggcgtcgt cgccggtccg catcgcgttg cgagcagcgt cgccatcgct gcggtgtagg  26640
gagaaggggc tgccatcgcc atggacaaag cactgggccg cagccgaaga acttcatctg  26700
cgctagggct tcacagcacc gtgacccgcg cttcgtcgtc ggccatcccc tgcctccttc  26760
aacggtgaga attccccctc ctccgagtca acggggccga gtcgcttgct gttggtggag  26820
tcttgcgtat tccaggagaa ggtagcggca taaggtagaa gagggggttg tggctgtcag  26880
attgatgacg ggcggcctag attacccctt cattccttag tcgtgggccg ttagatcgtg  26940
atccaacacg cgtgattagt tgccagctca tgccttttttg gttgccgttg gatctcgatc  27000
cgaggctcca catggcgtac cccttcgttg tgttaagttg cggccgtggg atgaaaatct  27060
aacggctcag ggtgcatgcg catactgctg ccgacccatc ttacaaaaga gccctaatgt  27120
cgttaataaa taacccgcag tccacgtagt tgggctctga gtcttaggaa aacttacacc  27180
gagacccctg aacttctctg tattagtgcg cccagtccag agagccagaa aaatcagaaa  27240
acaaatatag aattggattt ttaatgtaga aataaatgct agaattggtt taattcatag  27300
aaaattcatg tgtagtccaa attaatccat ttcagtttct ataattttgt aataatgttg  27360
tttatcaccc tgtgtctctg ttttaacatg aaaatggtat taaaatttat ttcttaatta  27420
acctcgtatc aaatacataa aaccttagga aattcatata tcctccgttt taacttcaat  27480
ttgatccgtt caagttgcgt tagtctcgta gcaacgcgta tatcattatt acgcagtata  27540
ttcttatgtt tggtgtgatg ttaattttgt ctataccatg tttgtttata ttgctacgac  27600
tagcagtgag gtcacgagga tttgaagaat caccctggta actggaatct caagtgtcag  27660
gcaagttgtg cccttgacca ctttttaccc aataatgttc tctaattatc attcactcgt  27720
gcataggtta attttgatgg gacccaatag gacaccctag atttgtttat ctcattacct  27780
tgtttacccc tgaatcactt gggtagtttg ctattgcttt acatggtttt gggataatca  27840
attattatat ctatgttcca attattcttg ttattctatt tatgttcatg tcaagttcat  27900
taatgttaat tggaacatag agcttaactt gagaaacacg tgccaccaca agggtttaat  27960
gggacgccct tggctgacta attaggaaag ctagtggaag actaccttac ccgaaagggg  28020
caagggcagt aggggagtgg tcagtgtagg gaggtccttg gttgattttg ctgcgatggc  28080
ggtcagacaa gaaccctgca ttggaacttc ttaacgtagc gggttttcgg aagctagtgg  28140
aacttgtaaa gaacgagtag tgttgccctg ccgcgtatcc taggtagaga acgaatcaag  28200
ctgattcttc aactcccaaa ccnnnnnnnn nnnnnnnnnn nnnnnnnnnn nnnnnnnnnn  28260
nnnnnnnnnn nnnnnnnnnn nnnnnnnnnn nnnnnnnnnn nnnnnnnnnn nnnnnnnnnn  28320
nntacttagt acctgcataa taaaatttga ccactactta aaagcaatgc tcagcttaac  28380
ccctatcatg aatagcctac acatcacatg acctcacacc tttgtgagtt tatgtccacc  28440
ggttccccac aacttgttga gctatgatca tgtgtgagct cacccttctg tctcacaccc  28500
cccccacagg agaagagcag gtggttcagg aggagccgcc taacactgag gagttcgatc  28560
tgatctaggt ggcgtttccc agtcgacatt ggcgccgacg atccttagtt cgttttactt  28620
ttatctttta ttttgtaata agtcttccgc tatgtaataa atactctaat gttttatgac  28680
atttatctct atacactctg ttattatata tgttgtcttc ttggcgcatg tatgagatgc  28740
acccggcttt gttccttaaa gccgggtgtg acagaagtgg tatcagagga aatgttgact  28800
```

```
gtaggacgaa acctagatag aaatggacaa aacccttcac tacttacctt actctgattc  28860
tttctacact tatcttgatt ctgtctcacc ttctactgtt ctactctgat cattcttacc  28920
ttttctactc ttagtcaaga tggatttcac accttggaat ccctacccct atgacatttt  28980
taagaggtag gaagcctaag acaaaattaa aactattttc tttattaaaa atgttggttg  29040
attgttctga tgatcaatgc ctgatttgct tctttgattg attgaaatag tatagacggg  29100
catcttagca tgtaccacca taaggtaatg tattagcgtt agtaggtgac acactaatct  29160
acttagctaa taaatccccc gtagtaatat tcctcttaat tactcgcctt gtctacaatt  29220
cttcctttcg caccctatgt ttctaacgca gatgggctac ccctatagtg ttagaagaga  29280
gcactatagg cgtgatcctt ggtatttcat ggttaagaaa ggcaaagaca gtttatacac  29340
tgtgctaagg gaaccataga actcaccagt tccaaaggag aaatatttga agttggaatt  29400
gcagtaacta ccaccatcag tctaacaaca ttcttagaag atgagaagtt tgtgggtgac  29460
aacatccgtg cagttagaga tcttccggat gtctttccag aggagttatt aggggtgcca  29520
ccagatatgg atgttgagtt ggtcattgat ctcttacctg ggacgactcc tatttctaaa  29580
cggccataca ggatgtccgt agaagaacta aaggaactta agaagcaatt aacggaatta  29640
caagaggctg ggtacattcg tccgagtctt caccttggag agcatcggtt ttgtttgtac  29700
agaagaaaga tggattgcaa gggatgtgtg tggattaaag gtcccttaat ggtgtcacta  29760
tgaagaacaa gtatccatta ccccacattg aagatttatt taatcaggtg agaggtgcaa  29820
gagtattctc gaagattgat cttcgatcgg gttaccatca aatgaatatt aggccatcgg  29880
atattcccaa gacgaattcc ttgacccgat atggtttata tgagttcacc gttatgtcgt  29940
ttggactaac taatgcacta gcctacttta tggatctaaa ggataatgtg ttcatgattt  30000
ggatagattc gtcgtggttt tcatcgacga tattcttatc tattccaaga gtgatagtga  30060
tcacgaggaa catctgagga tggtgctaca gaagctacga gataaccagc tatatgccaa  30120
gtttagcaag tgcgagtttt ggattggcga ggtgccattt attggtcata ttatttctaa  30180
tggaggaata tcaatggatc ctactaaggt taaggagata atggagtgga gagtacccac  30240
tacagttact gagattcaga gtttcttgag actagtagga tattatcgga gatttattga  30300
aggattttct aagattgcta agcctacgac ctcgcttctg gagaaggaca gagaatttaa  30360
gtgggacgag aagtgccaag acagctttga tcaattgaag aagagattga tgtcaccacc  30420
agtattggtt atgccagacc tacagaaagg atttgatatc tattgtgatg catgtggcca  30480
aggcttagga tgtgtgctca tgcaggaagg acatgtgatt gcctatgcgt ctcatcagtt  30540
acggagacat gaattgaact accccactca cgacttggaa ttgccagccg tgtgcatgcg  30600
cttaagatat ggagacatta tatcatgggg accaagtgcc aagtatatac ggatcataag  30660
agtttatatt cactcagaag gatctcaacc ttaggcaaca ccgttggttg gagcttatta  30720
aggattatga tttggagatt cactatcacc cgggcaaggc aaatttggtt gcagatgcct  30780
tgagtcgaaa ggagcatgtt cattcagcta ttgttgccca gctacccgat gagattgttg  30840
aggatttcag gagacttaac ctggggatag atgctcacgc ttaaggagtc attattgatg  30900
tggaacctac cttggagcaa gaaatccaca gaacgacaga ttggtgatgc taagatacaa  30960
gagatcaagg atcttattac gaaaggtaga ggtccggaat ttacggaaga tgaacaagac  31020
acaatatggt tcaagggcag gatatgtgtt cctggtattg aaagccttcg taagactatt  31080
ctaaaggaag cccataactt ggattattct attcatcctg gtagtaccaa gatgtatcag  31140
```

```
gaattgaagc agaaatactg gtggtatgga ttgaagagag atgtggctgc acatgtggct  31200
atgtgcgatg ggtgtcaaag agttaaggcc taacaccaaa gaccagctgg actattacat  31260
ccactgaaga tacccaagtg gaaggggaag aaattggtaa ggacttcatt actggattgc  31320
ctcgcacccc gagaggatat gattctatat gggttattat ggataaattt accaaagtga  31380
ctcattccat tctggtcaag actacttata aggtatctca attggtagag ttatatatgg  31440
ctcggattgt gtctccacac gatgtaccga agaagatcat tttggataga ggatcacagt  31500
ttacctccag attttggaaa agttttcatg agaatatgga tgcgaagttg aattctagtt  31560
tggcttacca acctcagact gatggacaaa ctaaaagggc taatcaagta ttggaagaca  31620
tgttgagagc ttgcgccctt cagcatggta gtagttgtga caagagtcta ccttatgctg  31680
agttttcata taataatagc tatcaggcta gtctgaagat gtcaccgtac gaggctctgt  31740
atggcaggaa atgcaggaca cctctatttt tggaccagac tagaggaaga catttctttg  31800
ggcctgaact tattcaagaa gcagaggaac aagtccgtat aattcgggag aatttgaggg  31860
tagctcagac caggcaaaag agctacgctg ataatagaag aagaccactg gagtttgagg  31920
aaggtgatca tgtgtacctc aaagtgtcac cacttcgtgg aatgaggaga tttaaagtta  31980
agggcaaatt gttccctcac tttattggac cattctgagt ttttaggcga gttggagaga  32040
tggcctatca actcgagcta cctgataata tatctgatgt gtataatgta atttacgtgt  32100
ctcaacttaa gaagtgtctc cgtgtccttg aggaacagtt accaatggaa gagctcagtg  32160
ttcaggatga tttgacttac acggggtatc cgatcaagat tcttgacact tttactcgac  32220
ttacaaggaa taaggtgata aaaatgtgca aagtgcaatg gagtcaccat ggagaagatg  32280
aagcatcatg ggaaagagaa gaagagtttc acatagattt ttccccatct ttttcctagt  32340
ccttcctaaa tctcgaggac gagattcttg ttaagggggg taggatttgt aatacccact  32400
ttgtaataaa aatctaaaag gagagattat attcctttat atacatgtgt gtcatctata  32460
tctatcattt catgtgaaca cctcacttcc acaaataaat aattaaataa aaacactcaa  32520
ataaatcatg catcatgcta ggattttctt ttgtgtgcat attgtgacaa aataaaataa  32580
aaatgtgaca agaaaaatat taaagtccaa aaagggaatt tagaatctaa aagaaatcct  32640
agaaagggaa ggaaagaaaa ttttatgtga taaaaaatgt aaaataaata aataaaatat  32700
tattgctata ctagtgcttt aatgtgacac ctgactcagg ggtagagctc aaaagcagat  32760
tcaaatccaa atttgaattc aaaatattta tgaataagag gatagaaaat aaaagaaagg  32820
agagggggac tacctgcgct ctgggccgaa tttcttctgt gatcggccca tcaggcaaat  32880
gcgcacagcc caaaagaacg gattagaccg tgtgccgacc ggtgggccgt tggtgccagc  32940
ctcttccctc tgcgccgatg gtgggggcca cattccagat gcgcgtgctg tggcgacttg  33000
caggcgggcc caggttgtca gttccttccc cttcaccgta acagaactcg cgttctctac  33060
gccgcatgac tatcacttcc gccgagacct cgcacgcgcc acgtcttgat cccaggaccg  33120
ctctggattc tattgcagag atctcgccgt caccgccgcg ggtatcggat ggtcgttaca  33180
tcgtgtgccg acttatgcgg attggcctgg gcgcataagt agcgcgccgc tcggtatctt  33240
ggcccaccaa atgaacccct gcctcgcacc acagttgatt gtgtagcctc gtcggtggga  33300
gaactccgct gccgccgaag aaagctcgac ccatagccag tactagagag agaaagacgt  33360
gcgccaccgg gcggattaac gggtttccgc ggtcacctga gtaggggagt gggtgcggca  33420
tctgtcgccg ttgggcaccg cacccgtgcc tccgtcccca cctgcttgca gtgaccccgc  33480
gcacctccat gacgcaactc gtgcgtgccc gctcctgtca ctcgcggtcg ggttgccgcg  33540
```

```
gctccccatt gccgtgcagg gcggggccaa actcgacggt gccctcgtcg tttgggggcc  33600
tgcatggtta ctcgggggct tggtccacgg cgggcataac caatcgccgg agttgggcgt  33660
cgtcgccggt ccgcatcgcg ttgcgagcag cgtcgccatc gctgcggtgt aggaagaagg  33720
ggctgccatc gccatggaca aagcactggg ccgcagccga agaacttcat ctgcgctagg  33780
gcttcacagc accgtgaccc gcgcttcgtc gtcggccatc ccctgcctcc ttcaacggtg  33840
agaattcccc ctcctccgag tcaacggggc cgagtcgctt gctgttggtg gagtcttgcg  33900
tattccagga gaaggtagcg gcataaggta gaagaggggg ttgtggctgt cagattgatg  33960
acgggcggcc tagattaccc cttcattcct tagtcgtggg ccgttagatc gtgatccaac  34020
acgcgtgatt agttgccagc tcatgccttt ttggttgccg ttggatctgg atccgaggct  34080
ccacatggcg taccccttcg ttgtgttaag ttgcggccgt gggatgaaaa tctaacggct  34140
cagggtgcat gcgcatactg ctgccgaccc atcttacaaa agagccctaa tgtcgttaat  34200
aaataacccg cagtccacgt agttgggctc tgagtcttag gaaaacttac accgagaccc  34260
ctgaacttct ctgtattagt gcgcccagtc cagagagcca gaaaaatcag aaaacaaata  34320
tagaattgga tttttaatgt agaaataaat gctagaattg gtttaattca tagaaaattc  34380
atgtgtagtc caaattaatc catttcagtt tctataattt tgtaataatg ttgtttatca  34440
ccctgtgtct ctgttttaac atgaaaatgg tattaaaatt tatttcttaa ttaacctcgt  34500
atcaaataca taaaacctta ggaaattcat atatcctccg ttttaacttc aatttgatcc  34560
gttcaagttg cgttagtctc gtagcaacgc gtatatcatt attacgcagt atattcttat  34620
gtttggtgtg atgttaattt tgtctatacc atgtttgttt gtattgctac gactagcagt  34680
gaggtcacga ggatttgaag aatcaccctg gtaactggaa tctcaagtgc caggcaagtt  34740
gtgcccttga ccacttttta cccaataatg ttctctaatt atcattcact cgtgcatagg  34800
ttaattttga tgggacccaa taggacaccc tagatttgtt tatctcatta ccttgtttac  34860
ccctgaatca cttgggtagt ttgctattgc tttacatggt tttgggataa tcaattatta  34920
tatctatgtt ccaattattc ttgttattct atttatgttc atgtcaagtt cattaatgtt  34980
aattggaaca tagagcttaa cttgagaaac acgtgccacc acaagggttt aatgggacgc  35040
ccttggctga ctaattagga aagctagtgg aagactacct tacccgaaag gggcaagggc  35100
agtaggggag tggtcagtgt agggaggtcc ttggttgatt ttgctgcgat ggcggtcaga  35160
caagaaccct gcattggaac ttcttataaa ctgtagcggg ttttcggaag ctagtggaac  35220
tttgtaaagg cctcgtagtg ttgccctgcc gcgcttccta ggtagaggtg tatgggattc  35280
gtgacccctt ggcagatggg tagcatgact tgtgggtaaa gggtacaacc tctgcagagt  35340
gtaaaactag tatactagcc gtgctcgcgg tcatgagcgg ctcaggactc tctgatgttt  35400
aaattatgga acttaaattc aattttgtca tttgcattgc atgggtctat tattaatttt  35460
gttcaattac tttatctaag gtttggtatt cacttatact tagtaactgc taataaaatt  35520
ttgaccaact acttaaaagc aatgctcagc tttaacccct atcattgatt agccttacac  35580
atcacatgac ctcacacctt tgtgagttta tgtccaccgg ttccccacaa cttgttgagc  35640
tatgatcatg tgtgagctca cccttgctgt ctcacacccc cccacaggag aagagcaggt  35700
ggttcaggag gagccgccta acactgagga gttcgatctg atctaggtgg cgtttcccag  35760
tcgacattgg cgccgacgat ccttagttcg ttttactttt atcttttatt ttgtaataag  35820
tcttccgcta tgtaataaat actctgatgt tttatgacat ttatctctat acactctgtt  35880
```

```
attatatatg ttgtcttctt ggcgcatgta tgagatgcac ccggctttgt tccttaaagc  35940
cgggtgtgac agaagtggta tcagaggaaa tgttgactgt aggacgaaac ctagatagaa  36000
atggacaaaa cccttcacta cttaccttac tctgattctt tctacactta tcttgattct  36060
gtctcacctt ctactgttct actctgatca ttcttacctt ttctactctt agtcaagatg  36120
gatttcacac cttggaatcc ctacccctat gacattttta agaggtagga agcctaagac  36180
aaaattaaaa ctattttctt tattaaaaat gttggttgat tgttctgatg atcaatgcct  36240
gatttgcttc tttgattgat tgaaatagta tagacgggca tcttagcatg taccaccata  36300
aggtaatgta ttagcgttag taggtgacac actaatctac ttagctaata aatcccccgt  36360
agtaatattc ctcttaatta ctcgccttgt ctacaattct tcctttcgca ccctatgttt  36420
ctaacgcaga tgggctaccc ctatagtgtt agaagagagc actataggcg tgatccttgg  36480
tatttcatgg ttaagaaagg caaagacagt ttatacactg tgctaaggga accatagaac  36540
tcaccagttc caaaggagaa atatttgaag ttggaattgc agtaactacc accattagtc  36600
taacaacatt cttagaagat gagaagtttg tgggtgacaa catccgtgca gttagagatc  36660
ttccggatgt ctttccagag gagttattag gggtgccacc agatatggat gttgagttgg  36720
tcattgatct cttacctggg acgactccta tttctaaacg gccatacagg atgtccgtag  36780
aagaactaaa ggaacttaag aagcaattaa cggaattaca agaggctggg tacattcgtc  36840
cgagtcttca ccttggagag catcggtttt gtttgtacag aagaaagatg gattgcaagg  36900
gatgtgtgtg gattaaaggt cccttaatgg tgtcactatg aagaacaagt atccattacc  36960
ccacattgaa gatttattta atcaggtgag aggtgcaaga gtattctcga agattgatct  37020
tcgatcgggt taccatcaaa tgaatattag gccatcggat attcccaaga cgaattcctt  37080
gacccgatat ggtttatatg agttcaccgt tatgtcgtct ggactaacta atgcactagc  37140
ctactttatg gatctaaagg ataatgtgtt catgatttgg atagattcgt cgtggttttc  37200
atcgacgata ttcttatcta ttccaagagt gatagtgatc acgaggaaca tctgaggatg  37260
gtgctacaga agctacgaga taaccagcta tatgccaagt ttagcaagtg cgagttttgg  37320
attggcgagg tgccatttat tggtcatatt atttctaatg gaggaatatc aatggatcct  37380
actaaggtta aggagataat ggagtggaga gtacccacta cagttactga gattcagagt  37440
ttcttgagac tagtaggata ttatcggaga tttattgaag gattttctaa gattgctaag  37500
cctacgacct cgcttctgga gaaggacaga gaatttaagt gggacgagaa gtgccaagac  37560
agctttgatc aattgaagaa gagattgatg tcaccaccag tattggttat gccagaccta  37620
cagaaaggat ttgatatcta ttgtgatgca tgtggccaag gcttaggatg tgtgctcatg  37680
caggaaggac atgtgattgc ctatgcgtct catcagttac ggagacatga attgaactac  37740
cccactcacg acttggaatt ggcagccgtt gtgcatgcgc ttaagatatg gagacattat  37800
atcatgggga ccaagtgcca agtatatacg gatcataaga gtttatattc actcagaagg  37860
atctcaacct taggcaacgc cgttggttgg agcttattaa ggattatgat ttggagattc  37920
actatcacct gggcaaggca aatttggttg cagatgcctt gagtcgaaag gagcatgttc  37980
attcagctat tgttgcccag ctacccgatg agattgttga ggatttcagg agacttaacc  38040
tggggataga tgctcacgct taaggagtca ttattgatgt ggaacctacc ttggagcaag  38100
aaatccacag aacgacagat tggtgatgct aagatacaag agatcaagga tcttattacg  38160
aaaggtagag gtccggaatt tacggaagat gaacaagaca caatatggtt caagggcagg  38220
atatgtgttc ctggtattga aagccttcgt aagactattc taaaggaagc ccataacttg  38280
```

```
gattattcta ttcatcctgg tagtaccaag atgtatcagg aattgaagca gaaatactgg  38340
tggtatggat tgaagagaga tgtggctgca catgtggcta tgtgcgatgg gtgtcaaaga  38400
gttaaggcct aacaccaaag accagctgga ctattacatc cactgaagat acccaagtgg  38460
aaggggaaga aattggtaag gacttcatta ctggattgcc tcgcaccccg agaggatatg  38520
attctatatg ggttattatg gataaattta ccaaagtgac tcattccatt ctggtcaaga  38580
ctacttataa ggtatctcaa ttggtagagt tatatatggc tcggattgtg tctccacacg  38640
atgtaccgaa gaagatcatt ttggatagag gatcacagtt tacctccaga tgtgaaaaga  38700
cgaaatctct agattctnnn nnnnnnnnnn nnnnnnnnnn nnnnnnnnnn nnnnnnnnnn  38760
nnnnnnnnnn nnnnnnnnnn nnnnnnnnnn nnnnnnnnnn nnnnnnnnnn nnnnnnncat  38820
caatcaaaga agcaaatcag gcattgatca tcagaacaat caaccaacat tttataaaga  38880
aatagtttaa ttttgtctta ggcttcctac ctcttaaaaa tgtcataggg gtagggattc  38940
caaggtgtga aatccatctt gactaagagt agaaaaggta agaatgatca gagtagaaca  39000
gtagaaggtg agacagaatc aagataagtg tagaaagaat cagagtaagg taagtagtga  39060
agggttttgt ccatttctat ctaggtttcg tcctacagtc aacatttcct ctgataccac  39120
ttctgtcaca cccggcttta aggaacaaag ccgggtgcat ctcatacatg cgccaagaag  39180
acaacatata taataacaga gtgtatagag ataaatgtca taaaacatca gagtatttat  39240
tacatagcgg aagacttatt acaaaataaa agataaaagt aaaacgaact aaggatcgtc  39300
ggcgccaatg tcgactggga aacgccacct agatcagatc gaactcctca gtgttaggcg  39360
gctcctcctg aaccacctgc tcttctcctg tggggggtg tgagacagaa gggtgagctc  39420
acacatgatc atagctcaac aagttgtggg gaaccggtgg acataaactc acaaaggtgt  39480
gaggtcatgt gatgtgtaag gctaatcaat gataggggtt aaagctgagc attgctttta  39540
agtagttggt caaaatttta ttagcagtta ctaagtataa gtgaatacca aaccttagat  39600
aaagtaattg aacaaaatta ataatagacc catgcaatgc aaatgacaaa attgaattta  39660
agttccataa tttaaacatc agagagtcct gagccgctca tgaccgcgag cacggctagt  39720
atactagttt tacactctgc agaggttgta ccctttaccc acaagtcatg ctacccatct  39780
gccaaggggt cgcgaatccc atacacctct acctaggaag cgcggcaggg caacactacg  39840
aggcctttac aaagttccac tagcttccga aaacccgcta cagtttataa gaagttccaa  39900
tgcaaggttc ttgtctgacc gccatcgcag caaaatcaac caaggacctc cctacactga  39960
ccactcccct actgcccttg cccctttcgg gtaaggtagt cttccactag ctttcctaat  40020
tagtcagcca agggcgtccc attaaaccct tgtggtggca cgtgtttctc aagttaagct  40080
ctatgttcca attaacatta atgaacttga catgaacata aatagaataa caagaataat  40140
tggaacatag atataataat tgattatccc aaaccatgta aagcaatagc aaactaccca  40200
agtgattcag gggtaaacaa aggtaatgaa gcaaacaaat ctagggggtc ctattgnnnn  40260
nnnnnnnnnn nnnnnnnnnn nnnnnnnnnn nnnnnnnnnn nnnnnnnnnn nnnnnnnnnn  40320
nnnnnnnnnn nnnnnnnnnn nnnnnnnnnn nnnnnngtac cctttaccca caagtcatgc  40380
taaccatctg ccaggagtcg cgaatcccat acacctctac ctaggaagcg cggcagggca  40440
acactacgag gcctttacaa agttccacta gcttccgaaa acccgctaca gtttataaga  40500
agttccaatg caaggttctt gtctgaccgc catcgcagca aatcaacca aggacctccc  40560
tacactgacc actcccctac tgcccttgcc cctttcgggt aaggtagtct tccactagct  40620
```

```
ttcctaatta gtcagccaag ggcgtcccat taaacccttg tggtggcacg tgtttctcaa  40680
gttaagctct atgttccaat taacattaat gaacttgaca tgaacataaa tagaataaca  40740
agaataattg gaacatagat ataataattg attatcccaa aaccatgtaa agcaatagca  40800
aactacccaa gtgattcagg ggtaaacaag gtaatgagat aaacaaatct agggtgtcct  40860
attgggtccc atcaaaatta acctatgcac gagtgaatga taattagaga acattattgg  40920
gtaaaaagtg gtcaagggca caacttgcct gacacttgag attccagtta ccagggtgat  40980
tcttcaaatc ctcgtgacct cactgctagt cgtagcaata caaacaaaca tggtatagac  41040
aaaattaaca tcacaccaaa cataagaata tactgcgtaa taatgatata cgccttgcta  41100
cgagactaac gcaacttgaa cggatcaaat tgaagttaaa acggaggata tatgaatttc  41160
ctaaggtttt atgtatttga tacgaggtta attaagaaat aaattttaat accattttca  41220
tcttaaaaca gagacacagg gtgataaaca acattattac aaaattatag aaactgaaat  41280
ggattaattt ggactacaca tgaattttct atgaattaaa ccaattctag catttatttc  41340
tacattaaaa atccaattct atatttgttt tctgattttt ctggctctct ggactgggcg  41400
cactaataca gagaagttca ggggtctcgg tgtaagtttt cctaagactc agagcccaac  41460
tacgtggact gcgggttatt tattaacgac attagggctc ttttgtaaga tgggtcggca  41520
gcagtatgcg catgcaccct gagccgttag attttcatcc cacggccgcc aacttaacac  41580
aacgaagggg tacgccatgt ggagcctcgg atccagatcc aacggcaacc aaaaaggcat  41640
gagctggcaa ctaatcacgc gtgttggatc acgatctaac ggcccacgac taaggaatga  41700
aggggtaatc taggccgccc gtcatcaatc tgacagccac aactccctct tctaccttat  41760
gccgctacct tctcctggaa tacgcaagac tccaccaaca gcaagcgact cggccccgtt  41820
gactcggagg agggggaatt ctcaccgttg aaggaggcag gggatggccg acgacgaagc  41880
gcgggtcacg gtgctgtgaa gccctagcgc agatgaagtt cttcggctgc ggcccagtgc  41940
tttgtccatg gcgatggcag ccccttcttc ctacaccgca gcgatggcga cgctgctcgc  42000
aacgcgatgc ggaccggcga cgacgcccaa ctccggcgat tggttatgcc cgccgtggac  42060
caagccccg agtaaccatg caggccccca aacgacgagg gcaccgtcga gtttggcccc  42120
gccctgcacg gcaatgggga gccgcggcaa cccgaccgcg agtgacagga gcgggcacgc  42180
acgagttgcg tcatggaggt gcgcggggtc actgcaagca ggcggggacg gaggcacggg  42240
tgcggtgccc aacggcgaca gatgccgcac ccactcccct actcaggtga ccgcggaaac  42300
ccgttaatcc gcccggtggc gcacgtcttt ctctctctag tactggctat gggtcgagct  42360
ttcttcggcg gcagcggagt tctcccaccg acgaggctac acaatcaact gtggtgcgag  42420
gcaggggttc atttggtggg ccaagatacc gagcggcgcg ctacttatgc gcccaggcca  42480
atccgcataa gtcggcacac gatgtaacga ccatccgata cccgcggcgg tgacggcgag  42540
atctctgcaa tagaatccag agcggtcctg ggatcaagat gtggcgcgtg cgaggtctcg  42600
gcggaagtga tagtcatgcg gcgtagagaa cgcgagttct gttacggcga aggggaagga  42660
actgacaacc tgggcccgcc tgcaagtcgc cacagcacgc gcatctggaa tgtggccccc  42720
accatcggcg cagagggaag aggctggcac caacggccca ccggtcggca cacggtctaa  42780
tccgttcttt tgggctgtgc gcatttgcct gatgggccga tcacagaaga aattcggccc  42840
agagcgcagg tagtcccctc tcctttcttt tattttctat cctcttattc ataaatattt  42900
tgaattcaaa tttggatttg aatctgcttt tgagctctac ccctgagtca ggtgtcacat  42960
taaagcacta gtatagcaat aatattttat ttatttattt tacatttttt tatcacataa  43020
```

```
aattttcttt ccttcccttt ctaggatttc ttttagattc taaattccct ttttggactt  43080
taatattttt cttgtcacat ttttatttta ttttgtcaca atatgcacac aaaagaaaat  43140
cctagcatga tgcatgattt atttgagtgt ttttatttaa ttatttattt gtggaagtga  43200
ggtgttcaca tgaaatgata gatatagatg acacacatgt atataaagga atataatctc  43260
tccttttaga tttttattac aaagtgggta ttacactctt tttccttttt tctttttatt  43320
tgatgtttta atttcctatt tcctgctttc caatttccaa taaagttcaa acttcaaatt  43380
taattttaaa tgcaacaaat caaaatattc agcatgcaat gcaacattat atatataagg  43440
tattttatta ttcaatatgc aattcataca aaaaaaatgg ttatgtagag acaatagcgc  43500
tcctagtgta taaaatattt tagagacaat atatattcat tgcataaagg aatagctaaa  43560
atcatatagg gatactttta ttaaaaaatt tatcagaaac aaaattttga aagttatttt  43620
aattcaacat tcttggacaa ttttacttta ataccaacat aggattttga ggcgttacaa  43680
ccttttttgag cgagttgagt gaaaacaaca gctcggaggc aggcatttac aaattacaat  43740
gcaggtcctg aacagagcta ggggcgggtg gggtaggggg gggggggaaa tactgcccag  43800
ctcgcttgat cacaagttca caacactgca gagaatgaaa gggagaggca gacagacagc  43860
tgacagatac tagatactcg atagatttga tagaacaggt gctggtcgtg ccgtgatcga  43920
gacgagaacc agttcactga aacttttagt tcacagcaca gagcgaagag cagcgagcga  43980
cgatacacat ggtatcgcgc gcggcatgta taccaattac cacccctcct ggctcctgta  44040
catcgtacgt gcaagatagg actacggcta cgagccactg ttgtactagt gttggtggcc  44100
gccgcgtcct gcttccgatg aggacgggtt ggaaactatg tgcctgccgg tatgcaatgc  44160
aagccaaggt accccacgca ccaaagcgtc tggtggccgc tttgacttgc ctacgtctcc  44220
taactgcacg ggtagggatc acatcaggtt tttaggaact gtcattacga acggctcgtt  44280
gttggtttgc tttctctatg ccgacatcgt catcatcacc ggtcttctac gtctactctt  44340
gcgttgttgt ttttagtgtc gacaacccgc actataaaaa agtgcatgca tatatttatt  44400
ttgtcactag cactagtata tgatttgatt tgctgttgaa ttatacgtag atatgataat  44460
agatcgtgat ccaaatgttc tttcataatt tgtaagagct ctaaataatt tatagtttaa  44520
aaataaataa aaatagagat cgatcctaat cctaatctaa tatgtgaaag cccgatccta  44580
atacgatttg tgaaatttat agcgtaaaat ttagagtatg ttgtcaacct tagttataca  44640
tatatgaaac atgctactgt tttttgtatt attattaatc tctaaattgc tattatttcc  44700
gatacgttcg ggtaaagact gtgtccggaa atagcctggc ctaattacct gggaccggga  44760
aaagatcact ggtcccgatc agagcaaaaa agagattgtc gcgcgctcga tcctcctgcc  44820
gaggacggcg agggaagaaa aatagagcag tcgcatacgt tggataatgc agaggatagc  44880
cgccaccaac agcagcaggt gacctcatcc acatgtggct ccggctgccg ccatggcaga  44940
gagacgatac gacggtgcag taacagtaaa aataggctga ctctggactc tgacactctg  45000
ctgagcaaac cgtcccctac ccaccctgtg ccgcacccca aaaggagaag gcgcggatcc  45060
agcactccca acggccaacg gggccgttgt gtctgcgact ctgcgtatcg gatccagtcc  45120
aattatccaa acgaaaacta caacggcggc aggccggtct ggtcgctttg acgaggaacg  45180
agcgttatag gttgttgcta tgcccgcccg cgataaaaaa gagtacgtag gatttgtgat  45240
gaggtgctgc taagtgctga tggatttgtg atgactggtg cctgttggcc gacgcccgac  45300
gccgcccccct cggcgtcgct cattccactc tgtcctgccc ggaactagtg gcaacttgca  45360
```

gccgcggcaa ccttggcaca cagcgcaagc agctgagcct atccgcgggc gggcgggcgg 45420
gtgcttttgg cctcctctgc tctcctaggt tggaagagtc tttgccaagg ggatagcaaa 45480
agagaaagta cttgcatgcc ccaacaaggc aacagcgcct gcttttggct ggggtcctct 45540
ccctcttcac atcacccgag ttgtagtgcg aggcaagaag gagaccgagc agaggagggt 45600
gtgcacaggc acacacaagc atcgtactcg tcgtaccagc aagagaggaa gaccagcgcc 45660
tagcctccta gccatgtggg accttaacga ctcgccggcc gccgaggctg ccccgccgtc 45720
cccatctgcc gacgactccg gcgcgtcctt ctcgtcggcg gccgcgctag tcgacatacc 45780
cgacgacgac tccgccgccg ccgccgtcgt cacgcgccag ttcttcgtcc tggccccggc 45840
ggccaccatc ggcgcggcgc ccggctcgtc gaacgcgcgc gcgggctggc tccgccgggc 45900
cgccgcgccg gccggcggcc ccgctgcggt gcaggcggcg gctggcaaga agagccggcg 45960
cgggccgcgg tcgcgcagct cgcagtaccg cggcgtcacg ttctaccgcc ggacggggcg 46020
gtgggagtcg cacatatggt gagtagtccc gtactcccga ctccgttgcc gttgccgccg 46080
ccctttcctc actcgaggga gagagacgga gcaggcagca gctcagctcg cgagggaggg 46140
ggggagggcg ttcgctgttg gattggaatt ggattcctct tgttttggca tttctcgcct 46200
ctcctgcttt tgcctttcgt agccacatct tatccaagtt attcttacga tgccaatagg 46260
caggccatgc tctctctctc tctctctctt cctcctcctc tccctctgtg tgtccccgtc 46320
ccctgcctct ctctctctct cacatcccca tgctctctgc ttgtgcttgt ggcaatgcag 46380
ggattgcggc aagcaggtct atctgggtaa gtttcttgca cgtccatgag tccatccatt 46440
ccatacgcat ccatgcttgg aagacgatag ataccgccca atccgaggcg tttttggttc 46500
cggactcggg actcctcaca aaaatggctt gtggcgactt gcaggcggat ttgacaccgc 46560
ccatgcggct gctcggtaat aaaagcctac tgtctgtttc attcgattcg tattggctct 46620
cctcactccc atgccaagtt ctccgccaat aacagcgggg gttcgccgcc aaattgtaat 46680
ctctgcctgt ctggttctcc cgccaacctc agggcgtacg atcgagcggc gatcaagttc 46740
cgcggcgtgg aggccgacat caatttcagc ttggaggatt accaagacga catgaagcag 46800
gtgatttatt tattatacaa ctgcgctata ctaggtagca tatagcaaca atatatatag 46860
taattttttc tcgtctatct aatccacgtc ttggtctacc agcagatgtg ccacctgagc 46920
aaggaggagt tcgttcacgt gctccggcgg cagagcacgg ggttcccccg gggcagctcc 46980
aagtacaggg gcgtgacgct ccacaagtgc gggcggtggg aggcgcgcat gggccagttc 47040
ctcggcaaga agtatgccgg tcgtccgtcc atctcccttc tcctcgcctt ccttcccttc 47100
ttgcccaacc acttcatgtc ttcctcttcc caatccctcc ccatccctgg tccctgtatc 47160
tgcatcggca tcagcccatc ctttctttgt cgttgcgcct cacattattc attcatggct 47220
gtcacttccg gtctgtgtcg ctgcactgca ggtacgtcta cttgggcctg ttcgacaccg 47280
aggaggaagc cgccaggtaa aataattgga ccgcactgtg tgctcgcctg gcggcggttc 47340
tcggagcccc gctaccccct gggccgcgaa actgactgat ggatgccccg tgtctctctc 47400
cctttctctc tctctgtgcg cgcgcgcgca gggcgtacga ccgcgcggcc atcaagtgca 47460
acggcaagga cgcggtgaca aacttcgatc ccagcattta cgccgaggag gaggtcgcgc 47520
cggcgggttc gtctatcccc gcccgcgctc tgcaacgatc acccccctcg tcgctgtgcg 47580
gcggtttgct acaacctata tggacaggaa gcaatctctg acgacggtcc gctgtttcgc 47640
cgtgcatgca gcggcgacgg gcggcgccgc cggcgacgag cacaacctgg acctgtcgct 47700
gggaagctcg gcggggaaca aaaggggcag ccttgacggc ggcggcggcg gcggcggcga 47760
cgacaagtcc tcggaccagc gcgtccccat ggcgttcgac atcgactggc agacggccgc 47820
acgtcggagc accaaggcaa aggtatccgt tttggtttgg tcccgcccgc gttcagcgtt 47880
ctctgaatca aacgaggtgt gcgtttaaaa tcttgcttaa taaaagcaag cttgtcacgt 47940
ttcaaccacc gggtggcatg gcagctccag ctcgacgcga gcgccgccat gcatgatgca 48000
accccacctg ccgccgtaca gccccaggca tccgcaagtg ggtaccgact acgtaccgag 48060
ctaactggct gacgctttgt ttgttctgtg caatgcaaat cgcggcagct cctgagcaac 48120
ggcgatccgg ggaccgcggc gggaggcctt tccctggcga tcggcggcgg aggcgggcac 48180
tggcctccgc agctgcagca tcagcagcag cagcagaggc tccacggcgc caggaacaac 48240
ggcggcggca cgagctggcc gccgccgccg cacccgtgcc cgccgccagt accggccgcc 48300
gccgcgaccg cagctgcagc atcatcacga ttccatccct acgttgttac gagtacgacg 48360
caaagcccgg ccggctgggt ccagaagaat gggttccatt cgctggccag gcccacgtag 48420
accaagaacc aggactgggc gttcgtcctt cgatcgtatt ccacggcgaa ggtccatcat 48480
ttgacccaag ggcaaacggc tcgtcgatcc accgatttac accccctccc cctttctttc 48540
ccttttccat tctctgtgtt cttgattggg tgagacatgg atccgaggat ggatgggcct 48600
gctgcccccc tgctgtaaat gaggagtttc cgggaagaag acgagtgctt tggtaggcga 48660
ctaggcgtcg cgtcaggcag tgcgtccttt tgccgctttt tgttctctct cccccccttc 48720
tgcattcact caccaatcac cattggcaag caccgatgaa tggtggcatg ggtgtcaac 48780
atcgcagctc attttgtttg gtctcatgtt gcatcactcg ctgctgcacg cacgatgatg 48840
gcctgctgca ctgtcgtctg ctgagctgct actgtcttcg atacgtgtgg gtctcgcgct 48900
cgtgtaaacc ttgtttctaa ttcgggcact gcaataactg tgggagaaga gaagacgacc 48960
cgggggaggc cgaccggcgg ttaccttcct cgccggatgg gacgagaccg taccccacgc 49020
cgtcatcttc atactatgtg gatggatggc tacattgccg gcaagtgcgg ccactgtgcg 49080
cacagctcgc gcgcaggaag aaaagttgct agataatgct ccatcgcgcg caggaagaaa 49140
agttgctaga taatgcccgc gcgcttaatt tgctcgtcta tctacttcac tgttcctcac 49200
ggcgtggcgt ggcggcagga gatgaattgc tcgtgtcgct ccgccgtgtg ctgtaggtgt 49260
gagcatgaat ataatatggg tggatcttgt cggccgaatg tttttactgg tatatatata 49320
tatatatata tatatatata tatatatata tatatacaca cactaataag taataactct 49380
ccttttagat atttgtcctt ctctaattta attttaaact aaactgcgat aaataaaaaa 49440
taaataaaaa aagacggaga gagtatatgc tagcagtttt tcatgcacac acccaagcgt 49500
atagcatacg cttgtacatg tagtacctgc cgtgtgtctg tcagtgtcta catagtacta 49560
tacattatgc gtaccggcac tgtttgagta ccatgctagc tggctagaga tgctccaagt 49620
catcaagggc aacggaagga gacaaggtga gcgatgcgta cttaaacgtt ggctgaaatt 49680
ggtcggttca tatgctaccc ctgctacgta cacacacatg tcaaatactc cttcgtctct 49740
tctttttaac tgttgtcctt atttttctcg agaagtcacc catatttaat tttgcctaaa 49800
aatatatata aaactattaa tatttatgat acattaatta atatcactag ttcatcaaca 49860
tgtactctca cgcggtttaa aattgtagga tataagcact agttattgtt tggataattt 49920
atattaagac tctattacag acctctaaaa ctaatatata gttatcaaca aaaattagct 49980
tagaggttcg gatcgattag gtaatggacc atctaattgt tagttatacc tctcaaaagc 50040
tattatttgt tagctgctcc agtccagtta aaactagcta acaacttgtt atctaactaa 50100

```
taattatctt gggaggtttg gaacattccc aaaatatagt atttatttat catctaacgt  50160
aatacacata atagatactt tagagtctat atgtacatgt aattattaat cttttttgc  50220
aaaggactgg attttatgtc ttctcatcaa tattcatttt ttccttttgc attatatctc  50280
tctatagttt gaaacatgca attaatttga atcctatcgc taactaaggt ggctcttgtc  50340
gcatcatata gtcatgaatc aatttttgat tttataaaat ttattcttat tatctcaagt  50400
taagttaaaa actcgtgtgt ttattgaatg tttagttaac tcttgttttt acacttctct  50460
agaacaagga ttttaagtcg tcagtacatt cataaatact acaatagcat aagaaattgt  50520
tagtaacacg cataatatca ttcaagataa gtcatagagc ttgaggtgag atctaggatc  50580
aatgtggtag cacaactaac cttgattttt ttaatagtca agccttaaaa tggctgacct  50640
tttcctttaa agtaatatta aagagcttga aaaatagatc catcaatgat cacccacagt  50700
tctcacttcc acttaattag ggaatcatat atgcaattat ggctatacta tcaatataga  50760
tgtgtcaaaa actcacttaa aatatctaag taaatctaaa ctaacaacct atatatagaa  50820
atagttgtta tggaaacaat tttatcttat gcaacataac atatatattt attgcccatt  50880
tatattggca cgatgtgcac atttacttta attaaatttt aatgtattaa tgttgatata  50940
agtaggcaat gtagaaacat atatatggtc tatagtgatc taaacaattt tattgtagta  51000
gaagatgtta atactcgatt tagatgtaga tctgagtggt attcgatttt ctacaataat  51060
agaatgaaaa ctgagttatg tctattattt attacaatag gaggtcattg gtaattagat  51120
acaaattaag gcctacgtac tttagctata gtgtatttct tcctaatatt gatgggtaat  51180
ttaaatatag agtcatgggt tacgtggttt aaccgttatc tggaggcaca agtgtccaag  51240
attttccaaa gagttcagaa aactccgaat ccatggcttg tgcttcccgt tcactgaact  51300
gccttgcctc atcataggat tttggttcaa ctagcacttc atcagttttg tgagcagcaa  51360
tacctgcaat atgccgtatt gttaaactac tgaactgtta atgctgttct tcagcctagt  51420
acgcattcag tgacacctta gagaacccct caaatttctc tcaatctacc ttaaatcgaa  51480
caagccctta catggctggc tgttggacca gcaggttgct cggtgtggac tttgttctgc  51540
actttctgaa gacagtggaa cccgcagatt cagattttag aagcatccac aacaggatga  51600
tcagtagcaa tcttaattga cccggtgtta ggtaaataat cctaaaactg ggttacctct  51660
aggttatttg ctgcctatat ggagtgctat tgttggattt tcgtcggtta aatattgttc  51720
aatgagactg agtgatagta agtagaatcg ttggctgctg tgaggttttt tgtggtgtat  51780
cgtttatttt tggatttgta aatatgtgtt tttagttcag ctccactact agttttgctc  51840
cgaccaaaat gcgagagtac catgtcactg tatttgaaga caaaattttc aaatggaaca  51900
atttcatatg gcatgtaatt ggttggatac tacagcaata ctactgctca gttggcacta  51960
cagcggcgcc tgacatcact ggctttgata tagcaaaact gtattgtagg aaattgttta  52020
tcattatata gaataatgat tacatatctt aaaaaacaca gattcagtgc taaaaaattc  52080
cacgtgagtg aggtctacga aaggattgat caatgtaagc ctttaaccat aaaaacatag  52140
attaaaattc ccacataagc taggtctatg aaaaagaaaa atcaaagcaa gcctttcacg  52200
gtaaaaacat agattaaaat taaaagtcgc atagaggggg tgaatagggc gaatctgaaa  52260
tttataaact taagcacaac tacaagccgg gttagcgtta taaatagaaa cgagtccgag  52320
agagagggtg gaaaacaaat cgcgggcaaa taaagagtga gacacgatga tttgttttac  52380
cgaggttcgg ttcttgcaaa cctactcccc gttgaggtgg tcacaaagac tggatttctt  52440
tcaacccttt tccctctctc aaacggtcac ttagaccgag tgagcttctc ttctcaatca  52500
```

```
aacgggacgc aaagtccccg caaggaccac cacacaattg gtgtctcttg catcggttac  52560

aattgagttt atcacaagaa agaatgagaa agaaaagaag caatccaagc gcaagagctc  52620

aaatgaacac aaatgtcgct ctctctagtc actatttgat ttggagtgat tccggacttg  52680

ggagaggatt tgatctcttt agttgtgtct agaattgaat gctatagctc ttgtaatgtg  52740

ttgaaggtgg aaaacttaga tgccattgaa tgtgggggtg gttgggggta tttataaccc  52800

caaccaccac aaagtggtcg ttggaaggct gctgtcgcat ggcgcaccgg acagtccggt  52860

gctccaccgg acagtccggt gcgccaccgg acactgtccg gtgtgccagc cacgtcatcc  52920

ggtcgttagg gttcgaccgt tggagctctg attggtgggg cctctgggct gtctggtggt  52980

gcaccggata ggtcatgtag actgtctggt gcgtctcctg cgcgtgctct gactctggcg  53040

cgcattgtag cgcatttaat gcggttgcag tcgaccgatg cgcgcgaagt agtcgttgct  53100

ccgctggcac accggacagt ccggtgtgca ccggacactg tccggtgact caccggacag  53160

tccgttaaat tatagcggag cggtctccca ttttcccgaa ggtggcaagt tcagcttcga  53220

gttccctggt gcaccggaca ctgtccggtg gtgcaccaga cactgtccgg tggcacaccg  53280

gacagtccgg tgcgccagac cagggtacca tttgggatgt cttttgctct ctttgtttga  53340

accctttctt ggtcttttta ttggcttatt gtgactttgg cactgtagaa ctcatagact  53400

agagcagcta gtagtcatta tttgtgtggg cattcagcac aaatcataga aaagtgtagg  53460

ctatcccttt catctcccct ttgtgatgat gcaacacaaa caaagcattt tgannnnnnn  53520

nnnnnnnnnn nnnnnnnnnn nnnnnnnnnn nnnnnnnnnn nnnnnnnnnn nnnnnnnnnn  53580

nnnnnnnnnn nnnnnnnnnn nnnnnnnnnn nnnttagggt cggcttggaa tcttgcacac  53640

atgcatacgg aaagcataat atccggtcgt gaagcacata aatagagtaa agaacttatc  53700

atcgaccggt ataccttttg aactacggat ttacctcccg tgtcgaggtc gagatgccca  53760

tttgttccca tgggtgtctt gatgggtttg gcatccttca ttccaaactt gtttagaatg  53820

tcttgaatat acttcgtttg gctaatgaag gtgccctctt ggagttgctt cacttgaaat  53880

cctaagaagt acttcaactc ccccatcatc gacatctcga atttctgtgt catgatccta  53940

ctaaattcct cacatgtaga ttcgttagta gacccaaata taatatcatc aacataaatt  54000

ttggcataca aacaaatcat tgtcaagagt tttagtaaat aaagtaggat ttgcctttcc  54060

gactttgaag ccattagtga taagaaaatc tcttaggcat tcataccatg ctcttggggc  54120

ttgcttgagc ccataaagcg ccttagagag tttatatacg tgattagggt actcactatc  54180

ttcaaagtcg ggaggttgct caacatagac ttcctccttg attggtccat tgaggaagac  54240

acttttcacg tccatttgat aaagcttgaa gccatggtaa gtagcatagg caagtaaaat  54300

gcgaattgat tcaagcgtag ctacgggtgc ataggtttca ccgaaatcca aaccttcgac  54360

ttgtgaatac cccttggcca taagtcgggc tttgttcctt gtcaccacac catgctcgtc  54420

ttgcttgttg cggaaaaccc acttggttcc tacaacattt tggttaggac gtggaactaa  54480

atgtcatgcc tcattccttg tgaaattgtt tagctcctct tgcattgcca ccacccaatc  54540

cgaatcttga agtgcttcct ctaccctgtg tggctcaata gagaaaacaa aagagtaatg  54600

ttcacagaaa tgagcaacac gagatcaagt agttaccccc ttttgaatgt cgccgaggat  54660

ggtgttcacg gggtgatctc gttgaattgc ttggtggact tttgggtgtg gcggttttgg  54720

aacttgttca tcttcctcaa cttgatcatg ggcatctccc ccttgatcat tgctttcctc  54780

ttgaggtagc tcaacttctt gatcttctcc ttcatcattt tgagcctcat cctcatcttg  54840
```

-continued

```
agttggtgga gatgcttgta tggaggaaga tggttgatct tgtgtatttg gaggctcttc  54900
ggattcctta ggacacacgt ccccaatgga catgttcctt agctcgacgc acgaagcctc  54960
ttcatcacct agctcatcaa gatcaacttg ctctacttga gagccgttac tcttatcaaa  55020
cacaatgtca caagagactt caactaatcc agaggacttg ttaaagacta taaatgccct  55080
tgtgtttgaa tcataaccta gtaaaaagcc ttctacagtc ttaggagcaa atttagattt  55140
tctacctctt ttaacaagaa taaagcattt gctaccaaag actctaaaat atgaaacatt  55200
gggcttttta ccggttagga gttcgtatga tgtcttcttg aggattcagt gtagatataa  55260
ccggttgatg gtgtagcaag ccgtgttgac cgcctcggcc caaaaccgat ccgaagtctt  55320
gtactcatca agcatggttc ttgccatatc caatagagtt cgattcttcc tctccactac  55380
accattttgt tgtgtcgtgt ggggagagga gaactcatgc ttgatgccct cctcctcaag  55440
gaagccttcg atttgtgagt tcttgaactc cgtcccgttg tcgcttctta ttttcttgat  55500
catcaagccg aactcatttt gagcccgtct caagaatctc tttaagatct cttgggtatg  55560
agattttcct gcaaaaagaa cacccaagtg aagcgagaat ggtcatccac aataactaga  55620
caatacttac tcccgccgat gcttatgtaa gcaatcgggt cgaatagatc catgtgtagg  55680
agctcgagtg gcctgtcagt tgacatgatg ttcttgtgtg gatgatgaac accaacttgc  55740
tttcctgcct gacatgcgct acaaatcttt gtctttctca aaatgaacat ttgttagtcc  55800
caaaatgtgt tctcccttta gaagtttgtg aagattcttc attccaacat gtgctagtcg  55860
gtgatgccag agccagtcct tgttagcctt agcaattaag caagtgttga gttcagctct  55920
atcaaaatct actaagtata gctgaccatc taacactccc ttaaatgcta ttgaatcatc  55980
acttcttcta aagacagtaa cacctgtatc cgtaaaaaga cagttgtaac ccattttaca  56040
taattgcgaa actgaaagca agttataatc taaagaatct acaagaaaaa catttgaaat  56100
gcaatggtca ggtgatatag ctattttacc caatccttta accaaacctt gatttacatc  56160
tccgaatgtg atagctcgtt ggggatcttg gttttctcat aggaggagaa cattttcttc  56220
tcccctgtca tatggtttgt gcacccgcta tcaatgatcc aacttgagcc cccggatgca  56280
taaacctaca aaacaagttt agttcttgat tttaggtacc caaacggttt tgggtccttt  56340
gacattagat acaagaactt tgggtaccca aacacaagtc ttggagctct tgtgtttgtc  56400
cccaacatac ttggcaacta ccttgcctga tttgttggtt agcacataag atgcatcaaa  56460
agttttaaat gaaatgttag aatcatttga tgcaatagga gttttcttct taggcaattt  56520
tgcatgggtt gattgcctag agctagatgt ctcaccctta tacataaaag catgattaag  56580
gccagagtga gacttcctag agtgaattct cctaattttg ctctcgggtt aaccggcagg  56640
gtacaaaatg taaccctcgt tatcctgagg catgggagtt ttgcctttaa caaagttaga  56700
taatctttta ggaggggcac taagtttgac atttctccct tttggaagcc aatgccatcc  56760
ttgatgccag ggcgtctccc actatagagc atgcttctag caaatttaaa attttcattt  56820
tctaagtcat gctcagcaat tttagcatct aattttgtta tatgatcatt ttgttgttta  56880
attaaagcta tgtgatcatg aatagcatca atgttaacat ctctacacct agtgcaaata  56940
gtaacatgct caatggtaga tgtagggggt ttgcaagaat taagttcaac aatcttagca  57000
cgcaaaatat cattgttatc tctaagatcg gaaattaaag cattgcaaac atctaattct  57060
gtagccttag caattaattt ttcattatca tttctaaggc tagcaagaga gacattcaat  57120
tcttcaatct tagcaagcaa attaatatta tcatttttaa gattgggaat tgaaacatta  57180
ctaacattag aatcaacctt agcaaattaa tttagcattt tcatttctaa ggttggcaat  57240
```

```
aatatcatga caagtgctta gctcactaga taatttttca catttttcta cttctagagc  57300
ataagcattc ttaaccttaa catgcttctt gttttcttta attaggaagt ccacttgaga  57360
gtccaagaga tcatccttct catgaatagc actaattaat tcatttagtt tttccctttg  57420
ttgcatgttt aggttggcaa aaagggtgcg caaattatcc tcttcatcac tataattatc  57480
ctcatcacta gaggtttcat atttagtgga ggatcttgat tttaccttct tccttttgtc  57540
gtcctttgcc atgaggcact tgtggccgac gttggggaag aggaggccct tggtgacggc  57600
gatgttggca gcgtcctcgt cggaggagga gtcggaggag ctctcgtcgg aatcccattc  57660
gcggcacaca tgggcatcgc cgcccttctt cttatagtat ctcttctttt ctctcctctt  57720
tcccttcttg tcgtcgctcc tgtcactatc actagataat ggacatttag caatgaaatg  57780
aacgggctta ccacacttgt agcacacctt cttggaacag ggcttgtaat ctttcccctt  57840
cctttgtttg aggatttggc ggaagctctt gatgatgagc gccatttcct cgttgtcaag  57900
cttagaggcg tcaatgggtt gtctacttga tgtagactcc tccttcttct cctccattgc  57960
attgaatgcg tccggttgtg cttcgggcgt ggaggggcca tctagctcca tgattttctt  58020
tgagcctttg atcatcaact caaagctcac aaagtttcct attacttttt cgggagacat  58080
tagtgtatat ctaggattac cacgaattaa ttgaacttgt gtgggattaa gaaaaacgag  58140
ggatcttaga ataaccttga ccatctcatg gtcatcccat ttggtgctcc cgaggttgcg  58200
cacttggttt accaaggtct tcaagcggtt gtacatgtct tgtggctcct cccccttggcg  58260
aagccggaag cgaccgagct ctccctcgat cgtctcccgc ttggtgattt tggtcaactc  58320
atctccttcg tgcgcggtct tgagaacgtc ccaaaactcc ttggcgcttt ttaacccttg  58380
caccttgtta tactcctctc gacttagaga tgcgaggagt atagtggtgg cttggagttg  58440
aagtgcacga tttggccacc tcgtcctcat catggtacct atacgaatgg tacctgtaca  58500
ccaaactcaa cagcatccca tatgcatttg tggagtgagg ttaggtgata tatcatcata  58560
tcactccacc tagaataatc ttcaccgtca aatgtcggtg gtttgcctaa tgggacggaa  58620
agtaatggag tatgcttaga aatgtgagga tagcataggg gaatcttact aaacttcttg  58680
cgctcatggc gcttagaagt gatggacggc gtgtcggagc cggaggtaga tggtgacgaa  58740
gagtcggtct cgtagtagac caccttcctc atcttcttct tcttgtcacc gctccgacgc  58800
gacttatcgt gtgaatggga gcccttcatc ttgttggcgg actctccata tggagccttc  58860
ccatggcttg tggcgggctt ctcgccggtc ccgatctccc tcttggcgga tgctcccgac  58920
atcacttcga gcggttaggc tctaatgaag cacggggctc taataccaat tgaaagtcac  58980
ctagaggggg gtgaataggg caaatctgaa atttataaac ttaagcacaa ctacaagcca  59040
ggttagcgtt agaaatagaa acaagtccga gagagagggt ggaaaacaaa tcgcgggcaa  59100
ataaagagtg agtgagagca cctagagggg gggtgaatag gtgatcctgt aaaacttaaa  59160
acttaagcca caaaacttgg ttaagtgtta gcacaataat caccaaatgg ctagagagaa  59220
gtcttagcaa aaacacaata accacaagag aacaatcata gagatgacac agtggtttat  59280
cccgtggttc gaccaagacc aacgcttgcc tactccacgt tgtggcgtcc caacggacga  59340
gggttgcaat caacccctct caagcggtcc aaagacccac ttgaatacca cggtgttttg  59400
cttgctttac tatatcccgt ttgcgaggaa tctccacact ttggagcctc tcgcccttac  59460
acttagatga tcacaaagaa acacggagta agggatggat gagcaacgca cacaagactc  59520
agaaatcaga gcaacaacac gcacacaagt cgcaacaaga gctcgcaaca caacccaatg  59580
```

```
agtttacaac tcaactagag ctctagatgc tatcacaaag aaacaaatgc gtggaatcga  59640
agtctcgatg cttaggattg ctttgagtat acttgatgta ctcctccatg cgcctagggg  59700
tccctttat agccccaagg cagctagtag ccgttgagag cattctatga aggctgatct  59760
tgccttctgt cgactggcac accggacagt ccggtgcaca ccggacactg tccggtgccc  59820
gatttctttc cttaaatggc gcagccgacc gttggcagcc agagagccgt tggcgcaccg  59880
gacatgtccg gtgcacaccg gacagtccga tgccccttc tagccgttgg ctcagccacg  59940
tgtcccgcgc agatcgcgcg gccgaccgtt ggcccggccg accgttggct caccggacag  60000
tccggtgcac accggacagt ccggtgaatt atagccgtac gtcgccggtg aattcccgag  60060
agcggccagt tcgctcgagc cagcctgaca caccggacac tgtccggtgc accaccggac  60120
agtccggtgc tcccagactg agcagagtct tggctgctcg aggcaagaca attccaattc  60180
gatttttcct gtttccagca cttagacaca atacattagt ctctaaaaca atgtactaag  60240
tctgagaaac ataccttat ccttgatttg tactttgtcc accattttac acagatcaac  60300
tcaaaagcac ttgcgttggc actcaatcac caaaatattt agaaatggcc caagggcaca  60360
tttccctttc aatctccccc tttttggtga tttatgccaa cataacataa agcaagtaga  60420
acaagtgcaa aatcacttca aataaaactc aaatttgttt tgaatcagtt ttggcatata  60480
tggatcattc tttgccacca cttggtttgt ttttgcaaat caaactcaaa tttctatctc  60540
taagtcaaac acacatgtta agacataaat agagtcattc caagagaaat tgattcaaga  60600
tttcaaaaac tcccttttt ccataatcaa caacttctcc ccacaagaaa ccaactttct  60660
gacaagagag acaataaaag agttttgaca aaccaaaagc tctattctac tattttcaaa  60720
atctctcaag tggtagctga tccatttatc gctttggcct ttattttctc cccctttggc  60780
atcaagcacc aaaatgggat taatcttggc ccttgaaccc cattgcctca ccaaaatctt  60840
caataaaaat gcaaaggcaa taagagtaca tgagatgaac ttggaataag ttaccctctc  60900
atcggagtgc agtggaagtc tttcatggtc caagtccacc tttttccttt caatccttct  60960
ttgagattaa atcagcaaac tcaagcacat ggttagtctc aaaggatcaa gttgtaacac  61020
atctcccct aaatatgtgc atcactttgc aatggacttg tgaggtccag ggagtgtttg  61080
tacaacttga gcaccataac taagcaacaa aatgcatagg gaatatgatc aaaggcataa  61140
acacatgtat gctataaatc aatccaagtt ccgcgaatct aagacattta gctcactacg  61200
cagcctgcaa aaggtcttct catctagagg cttggtaaag atatcggcta gctggttctc  61260
agtgctaaca tgaaacactt cgatatcccc cttttgctgg tggtctctca aaaagtgatg  61320
ccggatgtct atgtgctttg tgcggttgtg ttcaacagga ttttccgcca tgcggatagc  61380
actctcatta tcacatagga gtgggacttt gctcagattg tagccaaagt ccctgagggt  61440
ttgcctcatc caaagtagtt gcgcgcaaca ctgtcctgcg gcaacatact cggcctcagc  61500
ggtggatagg gcaacggaag tttgtttctt agagttccat gacatcaggg accttcctaa  61560
gaattggcac gtccccgatg tactcttcct atcaacctta catccagcat agtcggaatc  61620
tgaatatcca atcaagtcaa aggtagaccc ctttggatac cagagcccga agcaaggcgt  61680
agcgactaaa tatctaagga ttcgcttcac tgccactaag tgacactcct taggatcgga  61740
ttgaaacctt gcacacatgc atacgctaag cataaatatcc agtctactag cacataaata  61800
aagtaaagac cctatcattg accggtatgc cttttgatca acggacttac ctcctttgtt  61860
gaggtcggtg tgtccatcgg tccccatcgg agtctttgcg ggcttggtgt ccttcatccc  61920
aaaccgcttc agcaagtctt gcgtgtactt cgtttgagag atgaaggtgc catccttgag  61980
```

```
ttgcttcact tggaacccaa ggaagtagtt caactcgccc atcatcgaca tctcgaattt  62040
ctgcgtcatc accctgctaa actcttcaca agacttttta ttagtagaac caaatattat  62100
gtcatcgaca taaatttggc acacaaaaag atcaccgtca caagtcttag tgaaaagagt  62160
tggatcggct ttcccaacct tgaaagcatt agcaattaga aagtctctaa ggcattcata  62220
ccatgctctt ggggtttgct taagtccata gagcgcctta gagagcttac acacgtggtc  62280
ggggtaccgt tcatcctcga agccaggggg ttgctccacg tacacctcct ccttgattgg  62340
ctcgttgagg aaagcgctct tcacatccat ttggaacaac ctgaaagaat ggtgagcggc  62400
atatgctagc aagatacgaa tggactctag cctagccaca ggagcaaaag tctcctcaaa  62460
gtccaaacct gcgacttggg cataaccttt tgccacaagt cgagccttgt tccttgtcac  62520
caccccgtgc tcgtcttgtt tgttgcggaa cacccacttg gttcccacaa cattttgctt  62580
aggacgaggc accagtgtcc aaacttcatt cctcttgaag ttgttgagct cctcttgcat  62640
ggccaacacc cagtccggat ctagcaaggc ctcttctacc ctgaaaggct caatagaaga  62700
gacaaaggag taatgctcac aaaaattaac taatcgagat cgagtagtta ctcccttgct  62760
aatatcaccc agaatttggt cgacgggatg atccctttga atcatcgctc gaacttgggt  62820
tggaggtgcc ggttgtgctt cttcctccat cacatgatca tcttgtgctc cccctgatc  62880
acacgcctcc tgttgatgaa cctgttcatc gtcttgagtt gggggatgca ccatagttga  62940
ggaagaaggt tgatctcact cattttgttc ctgtggccgc acctctccaa tcgccatggt  63000
gcgtattgcg gccgttggaa cgtcttcttc atctacatca tcaagatcaa caacttgctc  63060
tcttggagag ccattagtct catcaaatac aacgtcgcta gagacttcaa ccaaacccga  63120
tgatttgttg aagaccctat acgcctttgt atttgagtca taacctaaca aaaacccttc  63180
tacagctttg ggagcaaact tagaatttct acctttcttc actagaatat aacatttgct  63240
cccaaataca caaaagtaag acacattggg tttgttaccg gttaggagtt cgtatgaagt  63300
cttcttgagg aggcgatgaa ggtagacccg gtttatggcg tggcaagccg tgttcacggc  63360
ttccgatcaa aaccgctcgg gggtcttgaa ctctccaagc atcgtcctcg ccatgtcaat  63420
gagagtcctg ttcttcctct ctactacacc attttgctgt ggtgtgtagg gagcggagaa  63480
ctcgtgcttg attccttcct cctcaagata ctcttctact tgaaggttct tgaactctga  63540
cccgttgtcg ctccttatct tcttcacttt gagctcaaac tcattttgag ctctccttag  63600
gaagcgcttg agggtccctt gggtttctgt tttatcctgc aaaaagaata cccaagtgaa  63660
gcgggaaaag tcatcaacga taacaagacc atacttactt cctcctatgc ttagataggc  63720
gacgggtccg aaaaggtcca tatgaagcaa ctccaaaggt cttgatgtgg tcatcacatt  63780
tttggtatga gaccttccca cctgtttacc tgcttgacaa gctgcacaag gtctatcttt  63840
ttcgaaggtt acatttgttt tacctatcac atgttctccc tttagatgtt tatgaaggtt  63900
acgaatcaag ctgaacataa gaagtaaagn nnnnnnnnnn nnnnnnnnnn nnnnnnnnnn  63960
nnnnnnnnnn nnnnnnnnnn nnnnnnnnnn nnnnnnnnnn nnnnnnnnnn nnnnnnnnnn  64020
nnnnnnnnnt gaagttgtga gactctctct gcatgcccca ccacccagtc cggattctag  64080
caagcctttc tacctgaaag ttcatagaaa gagacaagag tatgccccca aaaattacta  64140
atcgagatcg agtagtactc ccttgctaat atcacccaga atttggtcga cgggatgatc  64200
cctttgaatc atcgctcgaa cttgggttgg aggtgccggt tgtgcttctt cctccatcac  64260
atgatcatct tgtgctcccc cttgatcaca cgcctcctgt tgatgaacct gttcatcgtc  64320
```

```
ttgagttggg ggatgcacca tagttgagga agaaggttga tctcactcat tttgttcctg  64380
tggccgcacc tctccaatcg ccatggtgcg tattgcggcc gttggaacgt cttcttcatc  64440
tacatcatca agatcaacaa cttgctctct tggagagcca ttagtctcat caaatacaac  64500
gtcgctagag acttcaacca aacccgatga tttgttgaag actctatacg cctttgtatt  64560
tgagtcataa cctaacaaaa acccttctac ggctttggga gcaaatttgg aattcctacc  64620
cttcttcact agaatgtagc atttactccc aaatactcga aagtatgata cattgggttt  64680
gttaccggtt agtagctcgt acgacgtctt cttgaggagg cgatgaaggt agaccctgtt  64740
gatggcgtgg caagccgtgt tcacggcttc cgaccaaaaa cactcggggg tcttgaactc  64800
tccaagcatc gtcctcgcca tatcgatgag cgtcctattc ttcctctcta ccacaccatt  64860
ttgttgtggt gtgtagggag cggagaactc gtgcttgacc ccttcctcct caagagactc  64920
ctccacttga aggttcttga attcggaccc gttgtcgctc cttatcttct tcaccttgag  64980
ctcaaactca ttttgagctc tccttaggaa gcgcttgagg gtcccttggg tttcagtctt  65040
atcctgcaaa aagaataccc aagtgaagcg ggaaaagtca tcaacaataa ctagaccgta  65100
cttacttcct cctatgctta gataggcgac gggtccgaag aggtccatat gtagcagctc  65160
aagaggtctt gaagtggtca tcacattctt gctgtgatgc gctcctccca cttgtttacc  65220
tgcttgacaa gctgcacaag gtctatcttt ttcgaattgc acgttagtca aacccatcac  65280
gtgttctccc ttgtaatacc cactttgtaa ggaagaataa aaggagaaat tgtttccttt  65340
atatatgtat gtgtgtctct agttatcatt acatgtgacc actcatgtaa aaaaagagta  65400
gatccttaat aagacacaaa taaaccattg catcatattg gatttttgtt tgtgcattaa  65460
aagcaataat aatatgaatt aaataaaatg acaatgagaa gaggatttga ggaaaaagga  65520
gaaagaaaga gataatataa aatataaaac aaaatttaca aataaacaaa cttaaccata  65580
ctggtatgat taaaatctat ttttaatttg agtacaaatt caaagtcata cttgaaattc  65640
aaattgggaa ttgaaaatag gagaagaaga aaatcagaga aaaagagaaa agaagtcgaa  65700
cctaaatggg ctacagctac caaatcggcc catctttgat ttgcaccgcg cagcccgtct  65760
tcgctggtga cactggtctc tgggacccac cactcggcct ctctcgcgct cgcccttcct  65820
tatcgcgtgg agatgaccat tgaggcccac acgtcaggtg cgtgctcctg ttcttctcct  65880
cacgcgaatc gcgcgtgcgc taacagacgg cggattttta ccgcgcgccg ccagactccg  65940
tcaacagtcc ggccgattcg gccgcagctg ttgcgcccat gccctcctcg gattggctcc  66000
atgtagtcga tataaatcag gatccctggt gctggtattt ttacgagccg agtgaagcga  66060
ggagaagggt cgtggcgcgt ttaggcttcc gcgatttcta gaatctcggg tggtgtcaga  66120
gaagcagagc cgtgcgacgt tgatcgtgtg ggtcgccggg cgggaggcga aggatccgcg  66180
ctccaccgca agtccgccga cggccatctt ccccgacacc atccgggttc cggtgcgtta  66240
acctccctgt gagtctcata acgcataacc cgcgcctagc tactgcggtc tgcggtagtt  66300
attgcctgtc aatcgtgggc cccggtctct ggggtactcg tcaccatggg ggggcttcag  66360
gcgagcatac aaccatgaag agagagaaaa ggggtagatg ggcgtgggga ggaagaagac  66420
agccggtgat ccgtggagtg ggagatgaat ggtggggatt tgtcggtgct gggccgttgg  66480
attctggttg ggcgcttgag attagtgctg gcgcggtgat gaatttcttt aaatcggaac  66540
cgttggtttg ggaacaaacg ggtagatttg gttctgcgtt ccaacccacg gattggctat  66600
gggccgtagg atcccgatcc aagggatcgc gttgcagact gatcacttaa gtgcacgtac  66660
ctaatctggg tcgttcgggt ctgatccgat ggcccatcat ggccgatacc ccttcacttt  66720
```

```
gccagttcgc agaagagacc ctagaaaaac ttaagaatca acccgcagtc acttgagtta  66780
ccctctgtgt ctcgggaatt tttattgttt agcccctgcg catttctgta attgaggccc  66840
agtccagata attaataaaa ccaggaaaat cctttagaaa atggttttag tacatattta  66900
aatgcagaaa cttgtttaat ttgtagaaaa tgcatatgaa ctccaaattg gaccattcca  66960
gttcctataa ttttgtaata ttattctcta tcaaatagta ccactgtttt tacatgaaat  67020
acacgttaaa atttatttct cacttaaccc tatattaaat gcataaaacc tttggaaatt  67080
cataacttaa aatatataac tccaaaatta ataattccag ttcctataat ctcattttag  67140
ggtctagatt attactgtgc attttattta catgtttggt gtaatgttaa tttttgctat  67200
accatgtatg tattgtattg atgcgagtag acgagcaagc tacagaggat cctgaggttc  67260
agctggtaga gactgctgag caggagctcg tggaaggcaa gttgtgccct tgatcacttc  67320
ttttacccat tcatgttctt attaatcata atgatctgca taggttaatt ttgatgggac  67380
ccaataggtt accctagatt tggctatctt tataccttgt ttcaccactg attttactac  67440
taaatttttg ggtagtacat gctagtgcta tatgtggttt tgggtatgga gatacattat  67500
tcatgattac actttttgtta tctatttatt attgcttcag atcgccaaag aagggnnnnn  67560
nnnnnnnnnn nnnnnnnnnn nnnnnnnnnn nnnnnnnnnn nnnnnnnnnn nnnnnnnnnn  67620
nnnnnnnnnn nnnnnnnnnn nnnnnnnnnn nnnnngatcc cgttgggttg gggacttgag  67680
agatgtcgga ggcaaggcgt tcgttttgta tcgcttgccc cggctggctt cgaattcaat  67740
tcgctttgct tgggcagcca gtgtcgcacg tgtgcgcggc ggcgggctct cccaatcatg  67800
ctttagctaa ccggggatga tctcgttcgt ctcagcgcag ttctcaagct agggatacat  67860
acatacatac gttcccggcc aacgcgtaca aatcatgtga ggcagccatc agcagatgat  67920
gagctctgcg atccatcgtc tgcgctctgc cgcagctagc cacggaggcg gcatggcgcc  67980
cgtgagcccg tgacggccct gtggtggcta cctcccactt cccacacaca tattcctctc  68040
ctgtagatga caacgttctg cagatgtcgc ccgcccacat tgcagctacg tactccctcc  68100
gttttctttt tatttgtcgc tggatagtgt aattttgcac tatccagcga caaataaaaa  68160
gaaacggagg gagtactagc ctacgtgcgt ggaacgcgtt atagataaac cttcaaacag  68220
ctttgcctgc ttgatgcagt tcgatggggg ttccattgca ggatcaagag ttgacctgcc  68280
tgctctagtg gaacacatga cccacaccac accacacata agacgtacgg gagacacact  68340
tcattcacgc cacgcgcgtc attacattca gatgattaat tagccatcta ctaactataa  68400
agcagtaaag gcctagctaa aaattaatta acaagcgtac gacgtcgcat catctatcca  68460
tggatcatca tcatctagtt cttctagcgc aaatatatag acgcgcggtt acatcactgg  68520
aattaccgga aacgcatgtt tgtgcagtgg tcaacgcaca cggctagcta gctagcctca  68580
gccctcagct cgccggagtt gatttgagtg gacgtacggg gaacagcggc agaagcttgg  68640
gctggtcgtc gccgcccctg ggcgacgcgt gcaggtagaa gcccttggac gcgatggcct  68700
tctcctcccg ctcctcctcc tcctccctgc ttatcaccac cacggccccg ccgccgccgc  68760
acgacgacga gtgcggcgac atggacgagg acgacgacag cgacggcgac gcggagaccg  68820
ccagcgctat gtaggcgtcc atgggcgaga ccggcgaatg catgggcccg tggcagtggt  68880
ggtgggcgtg ggcgccgtga gcgtggtggt ggtggtagta gaagaacgac gacgacgggg  68940
acggcgacgc cggctgcggc cgcgccagct ccagctccag cctggccggc gccgcgcgcc  69000
gcctctcctg gagcttgggc cgcctcggcg ggggcggtgg cgcgtgcgcg acggtcaccg  69060
```

```
ccgccgccgc tgccgcatcg tccgtcgcgg cgcccgtgag cttctgcacg agcgcgcgga  69120
acgtggccgg gtcggcctgc acgaacgtgg tgttggcgtc gacggcgcag gtggcggcgg  69180
cgacctccct cgcgaccttg ggcgagtggg acgccgccat ggcgaagctc tctggccctc  69240
tcgctagcta gctagctgag caaagtaagc aagcaaggga gctagcgagc gtggccaaga  69300
ccaaatgcgg gatcgagcgg ctggtggtag ctttttaagg gacaaaaggg ctgcattaaa  69360
tgcattaaaa gccaaagggg ttgacggccc gcccgcgacg gatggatggg taccggacct  69420
ggagtggagt cctctggacg gatcggcgca tcccgcaggc tcggctaagc gcctaagcct  69480
cgcagtcgct cagcacactg ctgcacagga tgacatgggt cttttctgct ctcgcaaaac  69540
cttatttgca ccccgtacgt ccatgcagag ttgcagactg tggtgtggtg tggtgtggct  69600
gctacaacgc gaacgcgaga gagacgacga cgacccgcgt ggtgtgctgc tgctgcatca  69660
cgcatctttt ctagccctac ctatcatgtg tgtcttccgt cactggcccg cccatggcgc  69720
gtgtacgcac gtaccccgta cgaacacgat agaggaacac tgagcaagcg tagcgtgatg  69780
gcctccacga ctcggtgtgc gtactagcgg atggtaacgc ccggccggcc acgtcgtacg  69840
gccacaaagg gggcaggccg cgctcttgcg tgaggagaag aggaaggtgt tgcttccggg  69900
gtcgggccat cagctgcgcc gcttgcaaca acgccagaca gcctcgctcg gttcgtcctc  69960
atatatgcag ccgtacgtgc tcaactagta ctaggtcccc ggacgccgtc cagcctcgcc  70020
acgcggcggc cggcgggcgc gcgtcccgtg tcctcctggg cgggcgccgc tagctgtccc  70080
gtgttctgcc ggagctccgg cgacgacgag tggacgatgc atgctgcatg ctcttgcttg  70140
attggaaagc acggtacgta cgcaccgctg gcgcccgcca tgacgtttga cgtcttcggc  70200
cacctgcatg catgcagcgc gtgcgtgtcg gccggctcgg ctcggctctt cgtcgctgct  70260
actgcctggc aagaggtcga tgcatacatg gctgctggag tgctggtcac gcgcacgcac  70320
acgcaccgtc tcgtacgtgg tcaactacac gcacgcgctt gcctcacctg gacacatatc  70380
gtcacacacg catgcatgtg atgtgagctg ctgcttgtcc aggcacgcgc gcgattgcaa  70440
gtgttgcttt agttttaatt tgttgttgtg gcgagctaat atattcattg atcgtcacat  70500
attcaacaaa tcaacagtga tctagcacat tgcatatctg tacaatatat gaacatcttc  70560
agttcttcac gatcgcatag tttacagttt cacagattca ttcacgcttc acggatcaga  70620
acttagaagg caagaacaga aaccaaccaa gcacttcaac caaaattcct aaaaccaacc  70680
aattaaccaa gagtccaaga gccaacagat cagggcaaca caaaaatatg acagttgagt  70740
tatttagtgc aataccatta aagagaccgt gacgcctaac acagaggtgc gaattatgcc  70800
acttaaaact caatttttac actaaggcct ctaatttcca tgtagtcgaa acttaggcca  70860
gaaagtaatt aatctatcta gatatgtagc tataatttta tcagatgtgt tgctatttct  70920
atcacaaaaa attatacaat ataggtttca atattgtcgc tagcctagca agctaaacta  70980
tgaaataaac acataaccta ggtaagcaat aaataaagta tcaaatctta attgagttag  71040
agttatgtcg agaactctga tacctttaag gtattgagaa gagtgcaaac ttttgcatac  71100
tccttgttgg ggagtcttgc aagcgccaag cttccgatcg gataactata tagcctttag  71160
gtcttttcca catgtaagtt ggtatcctag atggtctctt ttgaattgtt ccccatcgtc  71220
ttagcctttg gccaaacagt tatgtgcctc gttttctctg tgtgaggtgg ggtcacacca  71280
caaatatggt tggtgtgatc tcactataag actcttcgag tacagatatg gtgcacacaa  71340
acattaagtg gtatgagatt ttctaatcaa tggaaatatt gtctaaacct agagcaagcg  71400
tataaacgat aatataacta atctaagcac tttcaactgt gcaagtgcaa gcattcatac  71460
```

```
ggcctcctat tttttttgt accattccct ttcttcttgt gattcgtcaa tctttatccg 71520
agatgtcgcc catgggctgg ccactgacgg agggctccgg ccccaagctt tagcgcccaa 71580
tcggcccaag gattttgttc gaaccaacca ccacccgctg gccgctgacc aaaagaaaag 71640
gttaacgaac atattcagtc ggtcagtaag catggacgac atcaaccaac tacaatgcac 71700
gaccaaaccg ccatcgcgca aacaattata ttgacgccgc aagtgtcccg tcgctaacct 71760
gccaccggca acgacagaga aattccagca gaggctccgg cggcaacgac cagataatta 71820
agacgacgag gccggcacgt aggtcgtagg gagaagccag ccgcgcgcgg gaacgggaat 71880
ggacgcgctg tgcccgcagg tcctgcacgt agccgtggcc gggcgcgcgc tggcggtggt 71940
ggagcgcgac ggcacgagcg acccggccac gggccgcgtc ctcaccggct cctggctgtg 72000
ggagtcgtcc ctggtcctgg ccgcgcacct cgccgcggac cccgcgcca ggcgccgcct 72060
ccgtggcgcc accgtcgtgg agctcggcgc cggcacgggg ctcccgggca tcgccgccgt 72120
ggcctgcctc ggcgccgcgc gctgcgtgct cacggacgtg gccgcgctgc tgccgggcct 72180
cagggccaac gcggacgcca acggcctcag cgccgcgcgg gcccgcgtgc gcgagctccg 72240
ctggggcgac ctgctcccgc tcgacgacgg cgacgggagg gtgggcgtcg tgctcttgtc 72300
cgacgtcttc tacgatcccg aggacatgcc ggcgatggcg gccacgctgc ggggtatgtg 72360
gtggacggac gagggcggcg gcggcaccgc ggggtgggcg gcgagcgagg tgcgggacag 72420
cgtgctggac tgcatggacg tgctgcggga gcatggtttt gaggtggtcg aggtcgacag 72480
ggtcaccacg ccgctgctgc gcgacccgg acagagtgcc gccttcgccg tctatcgcat 72540
ctcgctccga catggcgact atgagaactt cagttgctcg ctaagctgct agtagcatgt 72600
acactttgaa tttgacgttg cttgtgcagt aagtcatttt cacttttcag tttgcattgt 72660
cgcacacttt gcataggagt atgacaactt gcccattcaa ttcgctgcaa tttgtagctc 72720
cgtttttttt tttttttttt ttttttttgc ccattcattc tttgttaact cgcgcaattg 72780
ccatgaacac ggatcgacaa ggatataaaa gtgacatttg caaatttgca atcgacacgg 72840
atcgacaagg ccagaacgac ggcagtttac actgtcgctc aatttgtagt aggagaatat 72900
acagttgcaa agggttgcta caatatacgg tttcttcttc gtctgctggc ctttactatt 72960
cgccgcggca aaattcaccg ctcctatgtt taaaggagca aaagggaaac gaattactgg 73020
catttcccaa atcccaaccc gtgtttcctc aagtattttg tctaaccaac ccgaccttta 73080
aacttccaga tgtacactct aacaagaacc tgcttcgttt tatgaaacta taatagccct 73140
agagaacgtg aaagccgatc tgcaaggctc gcgatgacaa agcctgaaaa tacctgcaaa 73200
ggaacaaagc tcacatggtc aaacagaatg acaaatgtac tcaacagtga gctagaatgc 73260
tgaacaggaa cacgtagcat tcatattggt tactgccgta agatatagta gatatttttc 73320
tataattcta gttttttta aaaaaatact aaactgttgg atactcgcac ctggacagaa 73380
caaagaatat acactgctga atagtgacgg ccgtgaatga tcatatccgc aaccatcgcc 73440
agtggaattg tgagagacat gcctagcgtg gccaccaagg gagtagtcca aacaacagaa 73500
agggccctgg ccataagttc cacagtcagc ctgtcacaat taccccgagt atgcaagtaa 73560
taatagagtg gtctggtaat ataaaaagat atcagccttc tttaacacat accagaagta 73620
atctgatagt acacttccaa ttaggctatt tgccaccacc acttcatcca ctttagcaga 73680
gtgaggcatc gaaaactttg gctcaatgcc tagtgcggtt aatggccaga ctgaaatatg 73740
aacacaataa ccatattttt ttttacataa aataaccatg aaaggcatgc acaattaaga 73800
```

```
aataccagaa tacgatcata aattacgaaa ttgtatactc ctgttatatt aatttcgaaa  73860
agggaaacaa aaaataccaa tccaccagag agcaacaagg gtaaaaagtc caagataacc  73920
aaacagtttt tggacatcaa ccttttctcc ttcctcccca caaaattttt taagcagcac  73980
tgaaacaata tcgaaacaat taggggccga attcatagag ctccactgca aataaagcaa  74040
agcaaaccaa cctaccagta aatagaccat acgcgattgc cgacataaaa ccaaacatat  74100
cacctagaag agtcctttgt gtagccctgc aattgtaaag cttatgtatc agtagcaagg  74160
aaatgcagtt gaaaatagga acgaaattcc aatctcagaa ttgaaattcg tttttgttca  74220
tgttcatcac tatcaagtca tgcaaatata gaaataaaac actcaagttt tgagttgttt  74280
tttaacccaa aaaaccaggc aagccaacta actgaaaact actagttgta cgcaggacca  74340
aaaaaattac aagaacatta aattaagtcc aatgtgatta tcagagtata aaagagtaaa  74400
ggcctagtaa taaacaactc acccagattt gcctacttct gattcatcag atgcccaagt  74460
ctgtcccata gttgtcatta caacgccagc catgctaatg aaaacagcaa taactttcga  74520
agcacttatg gagtcttggc caagtaaaac accaatgaaa agagtgaaga gccctgaagt  74580
tgaagacagt acggtggtac tggcaacact agttcttgca agcgctgcat tcgataaata  74640
ctgcattcat tcagcgtaag agaaaaatga gttaccttta cctatcaaag tattgctttt  74700
acgattgaaa tttaggcttt ctgaaacata tatcagtagt ttttgagaaa caaatgtcaa  74760
aagttattca catgaacatt tcaagtcccc tggaattgca aattaacatg caaagccatt  74820
gtaaaattac ctctgtcaca aaccataagg ggcaaagata caatccataa gttgcaatct  74880
ccttagtcga aagttgcttg tccttcaaaa caccatcatt catttcagtg attccatata  74940
tgagtggttt tgtctctttc actacaggaa tgctcacatc agtgcaattt agcactaaag  75000
tcttccgaaa ttcgtcattc ttcaaagggg caccaccacc aaaggaagtt ttgcttgcaa  75060
tttatgaagc actggtgttt ccagaatcct ttagaaatga caaagggagg tatatgacca  75120
taagggaggc ccccaagtaa gtaactgcaa aaggatgttt gtactttgtg aatatcccct  75180
gcacaagaaa tttagttaca aaatgaaaat tgatatattt cacaatatgg acactacaaa  75240
tatatatttt tttaaaaaga atcaagaact agaagttgag gtgttttgca gtcatgagag  75300
tgacgaaatt gtactaccag tatcccctga ttctaccatc ggtatcttct ttaatcatgt  75360
ttgtgtattg taggtgatca aacatatcgc aaccaccctc aatcaaccac agaagaactg  75420
tgacaacaac cacatgcatg attatgcttt agcatagttt acatgaacaa gctaagcacc  75480
gaggactgac gacaggcagg tacaagtcgt taaaccatta acagcagatt tgacgggtgt  75540
ccataagagc atgcatgcag gcagctccaa aagtatacag tagaagacaa aagaatttga  75600
cttttctttg ccttttttatg gtgtaaataa ataaagtcca gtggtgaagc ctcggctgga  75660
ttcagaatga tgccagatgt tctttttaag gcagagtggt ggcagatgca taaccttccc  75720
ctgggaaaaa ttttctatca caggcaaccc tgcgcgtaac gtttaaaaat ctagatgcag  75780
agcaacaccc ccaggtcgtc ccaacaaata caatctgata ggcacagagc atttacgcac  75840
aaaacgtacc aataggccaa catgcgtccc aaaggccaag ccaagatcca agaggctcca  75900
ataaaaataa acaagtgaac agaggaacac cgaacacgca ccaagatcaa aggatccaca  75960
ccacacctca cctgcgtgac ctccgcggat atgacccaaa tcagcacgac ggcgacgatg  76020
aggcagaggc cagctcggta cttgaagctg gagcccatgt ccggaggcag gcagccctca  76080
cgtttgttcc tcccttgatg tacctccgga ctgaaaacta cggcgagaag gacgtgcggg  76140
gaatttaaaa ccgcgcgctt gcctcacctc accagtcacc acgtcgcctg gtccccgggc  76200
```

```
ggcgggcaca cgagtgcggt gcgcgagccc cgtcgcctcg gcatccgcct cgcttccctc  76260
ctcacagaaa gagcggggag gggaagcggc ggtttcggtc cggagggaag gttctgtttt  76320
ggtggtggtc tacccgagcc ccgaggcctg gcgggcgcga ccggagcggt ccggggacga  76380
tgcgatggcg ctggcctggt cgccagcgtg gtcgattcgg cggcaagcaa cgggtaaacg  76440
aagcgaggcg tggtgtgctg gcgcggccgc gcgcttgcga ggcgagcttt cggcgtgccc  76500
cggtggcaga ggacggaagc agttgcgcgg tgggatgtca cacccaggtt ttagggcacc  76560
aagacccggg cacgaacata aacaccaggt atgctgggat caagtctcac acatatgatg  76620
tatagtggca caggatcgaa tgtcacatct ttatatataa caggagttct atacaaaata  76680
aataattaca ttataaggag acaacggtcc agcaacccaa agttgactgg gagacgacgg  76740
cctagacctc tcacgaacac atcgaagcat cctccaagag cctcatcctg tggtacctgt  76800
tcttgacctg tggggggtgt gagacagcaa gagtgagctc acatacgttc atagctcaac  76860
aagttgtggg gaataatgtg catgaactcg ccaaaggtgg gagctcatgt gaagtgtaag  76920
gcttaccaaa gaggatggtt agagttgagc attgctttta aagttggtca aaattttatt  76980
agcaattact aagtataagt aaataccaac ccaattaaat agtagaacag aagtaacaac  77040
atcacctgcg atgcaatgca tatgacaaat tgaatttaag ttccataaat taatcatgtg  77100
agggtccgag ctgctcatga ccgtgagcac ggctagtata ccagttttac actctgcata  77160
ggttgcgcat ctttacccac aagtcatgtt acccatctgc caagggatcg cgacttccca  77220
tacacctcta ccgaggaggt gaggcagggt aacactacga ggcctttaca aagttccact  77280
agcttcagaa aacccgctac agtttatagg aagctccaat gcaggaatcc cttgcaggac  77340
cgccatcgca gcaaaatcct cccgagggcc tccctacact gaccactccc ctactgccct  77400
tgccccttc gggtaaggta gtcttccact agctttccta attaatcagc caaggggtcc  77460
cattcctccc ttgtggtagc actgttttcc cgggtggttc tccatgttcc aattaacata  77520
atgatcttat catgaacaac aaataacaac tgataacaaa agtgtaatca tgaataatat  77580
atctccatac ccaaaaccac atatagcact agcaagtact acccagaaag tttagtggta  77640
acaaggtata aagataatca aactagggta acctattggg tcccatcaaa attaacctat  77700
gcagatcatt atgattaatc agaacatggc tgggtaaaaa gaagtgatca agggcacaac  77760
ttgcctggga ctcgagattc caggtaccag gatgatcttc aggtgactcg taacctcact  77820
gttaaacgta gcaatacata caaacatggt atagacaaaa ttaacatcac accaaccata  77880
agtacaaact gaataataac ggtctacgcg atgctacgag atcgtgggtt cgagaaccgc  77940
taaattcggg gtcatggttg aaaaggtatg gttttcagaa gacccatgca atttaagccg  78000
ttaaaactag accttatgtt gatttaatag atcatgtgat aaaataatct aaataaataa  78060
ttagttcaac cttatgttaa attataatat aattagggat catattttag ccaaactata  78120
atgttaaaca gattaacttt gatttagaga ggttaatcta ctaaacatgg gttaaataaa  78180
tatctaatta taaaagcatg agatatggta taaccaatgc tataactacg tagtgaatat  78240
ttatacgaac ctaacgcaac tggaacgggt caattcgggg tttaaacgga gaagttatga  78300
atttatgaag ttttaggatt aactttcaat attaaaattc atttcttaaa ggggttttat  78360
tattccagat atcatatttg ggcttcggac actattttga tctctaccag ggactcaggc  78420
atatgaattc acccaatccg aggatggcgg attgaatcag aacaagtcga ggggttcttt  78480
tgaataattt cgcacccgaa agggtaactt caatcctgag tcgtccgatc aaactcgcac  78540
```

```
ggcccagatt agatcgagta cccttccgaa ccggtactca ctggtgatcg tgagatgggc  78600
gatcgagggt ggagatttta aacaacgatg ccagccgcac gactgaacgt tccaggatcg  78660
acggcccgcg tacgatttgg acgaagggta taacgtttat aatcacagcc gccaaccacg  78720
agatctacgg tctggatccc aacccaccaa agcggtacgt ttctcagaat cctggccgtt  78780
aagtatccga tcaacggcag aggtgttttc ttccaccagg ccaccagaca tgacggcgcc  78840
ccacccatcc tggccgcgac gcgccggagc accaccacac caacgcgcaa gtccatgaaa  78900
cctggcttcg acttgagcta cgcatgaaga aggagaaaac aaacctttgg ggagggtctt  78960
gccagcgacc gcggagcaga ttcagctatt cacggcgcac gacggatgac gacctgttcc  79020
gatggtgata gggcaatccc ggcggtgcag gccgccattc tcgaacgcca agcccgccac  79080
gcacccagca gataccagag aatcacctgg agggtcttcg agggtgcgac cgcgatggat  79140
tacagaatcc cccacggcgg ttcctctctc atctctctgc tctcctacac cgccctcctg  79200
cctactcgat tgcgcccagc tccatccgat agctttggtg ctcaatatat atagatgaca  79260
gggccaaggg tccggatcag aggagtccga gccagcgcga aatgaccggc ataggaatcc  79320
cggccaccgc gccatccgtt tcgcttcttc tctgttgagg atgattacga cagatggagc  79380
ccacaagtca gtgccgccaa ggacagattc gcatgcagta ttgcccggat ttgacccgct  79440
ccccgtaatc gtgcccagaa atcggtcgat tcagttaggt ccgccccgat cgggagctgg  79500
gaggggattc tgttcaggcc gatatgtgcg gtgtttccgt tggagttcac gtgaggtgag  79560
tgacgagact tgatagtcgc ctagaggggg ggtgaatagg gcgaaactga aatttacaaa  79620
tataaacaca actacaagcc gggttagtgt tagaaatata aaagagtccg cgagagaggg  79680
cgcaaaacaa atcgcaagcg aataatgaag tgagacacga ggatttgttt taccgaggtt  79740
cggttctctc aaacctactc cccgttgagg aggccacaaa ggccgggtct ctttcaaccc  79800
ttccctctct caaacggtcc gcggaccgaa tgagctttct cttctcaaat caaagccggg  79860
aacaaaactt ccccgcaagg gccaccacac aattggtgcc tcttgccttg attacaattg  79920
agtgttgatc acaagaacaa gtgagaaaga aagaaagcga tccaagcgca agagctcaaa  79980
tgaacacggc aaatcactct cactagtcac ttaggctttg tatggaattg gagaggattt  80040
gatctctttg ggtgtgtcta gaattgaatg cctagctctt gtaagaggtt gagaagtgga  80100
agacttggat gcaatgaatg gtggggtggt tggggtattt atagccccaa ccaccaaaca  80160
tgaccgttgg tggaagttgt ctgttcgatg gcacaccgga cagtccggtg cacaccagac  80220
agtccggtgc cccctgccac gtcatctctg ccgttggatt ctgaccgttg gagctctgac  80280
ttcttgtcac acccggtttt agaaggcaaa ccgaatgcga accatgtacg tgccaggatc  80340
agttattcac gtacacagca gttacataat atggacatca tcacacagtg ctcaaaatag  80400
tattaataag ggaaaatagt cgattacatc atacgtctga gacgtccata tagttcttac  80460
aataaatcaa agtgcggaaa agaaacgtag ataacgcggc cttcacaggc agccgactgg  80520
gggttgccgc taacccacac ctagaactcg tcgtaatctt ggaactcctg gaagtctcct  80580
tccacagctt catcttcgcc tgagcagtgg ttgcaatgct gacaacctgg gggggggggg  80640
tttggtgtgt agagcaaggg tgagtacaca tcaacatact cagcaagtat cctgtttggc  80700
tgtagtggac tagctttatg tggggatcag tcaagcagtt gcttttagtt ggtcaggtta  80760
ttacttacta gtagaaagcc aggttttaac attaacccaa gttattaacc caatgtatcc  80820
tttccaaacg gaaagaatac cacttaccaa taccataatc ataaccagaa ccatcaatct  80880
cattgccacc tgtaccaaaa tatctctgat caagtatcac taatctctgg agctcccttg  80940
```

```
gccgctcata accgtgagca cggctgatat atcagtttca taacactctg cagaggttgt  81000
gcactttacc cacaagccgt gattccctct tgcctcgggc cgatcaaacc cttaaacact  81060
accaaggtga ataggcaggg tttcactacg tagcctttac aaagattccc cggggctgta  81120
gccacccgtt aggtttccta aatgcaccgc actcctcccc aaggggcgaa cccaaacttg  81180
gcagagcgag ccgcatacac cgagccccat tgacggcacg acggctaagt gaactacatc  81240
ccagatcctc taattattca gctaagggca ccccattcca ccctcatggt tgcactgttt  81300
tcccgggcgg tcatccatag aacaggtcct tacggagagg cactcgagaa accgctcgag  81360
ccccccttgaa taccacaagt acaacatcat aataagagaa gggaaaacag cgtatcatag  81420
ataatcacat catgttcatt gattagagtt gagcaatagc atcagactaa gtagtaataa  81480
tccgacccaa ataggtaaac aaggacatgg ataacaaaag ctagtcgatc cttaggtata  81540
aatgtgtaat gcgggaggtg aattaaagaa tgaataggac agagataggt caaaggacac  81600
ttgcctccac caaccgattg ctgctcaggg gcttctcctg cgaattcctc gggctcttcg  81660
accggatcgt tctctatgcg agcgcaaaca tacatacata catccacata tttaatacaa  81720
aagaacagta caccatacaa gataacaaat aaagcgaata tgcatcaagt atgacattcg  81780
ataacgcatt tgttatggtt agaaagaaac ggggaaaggt ctcgcagggg gttaaatctt  81840
atgcactaat gacacaattg gtttttaaca aaataattct gttatatata tttatatata  81900
ctgatggaaa cctaatcact tttagttgat caacattgca cagggtaaac aattagctac  81960
gtgaatcaat aacataacga aattttaaat taaacttcct attttcccat agcatgaaca  82020
gtgattagcc tacttaaaat acagtaatta tgatcacaga aagtaaataa aataaaataa  82080
aaaaataaaa aaaacagaag gggggggggc ggttgaaccg gccctagggc ggttgaaccg  82140
gccctaggcg gggcgcgggc gcgggcgcgg ccggggctga ccgggcggct gagccgctga  82200
gccggccggt tgaaccggcg gcgggcggcc gagctggcgg gggggggggg ggggggcggc  82260
gcagggggcg gccaacccgg ccaagcaggg gggcggggcg gccaaaccgc tgggcgcgca  82320
ggggcgcggg gcagggcgcg gggcgcccaa gcggccaacc cggcggggtg gggcgggcgg  82380
ccaaaccggc cttggggcca agcggcgagg gaaaggggag ggaggagagg gaaaagaggg  82440
aggaggaaga gagggaggag ggggggcctc ccgggttgtc gggattcaac ggcaaggggc  82500
gcccggcggc agggggcggc gcgccaacct aggacagggg ggcgggttag ggggtagggc  82560
cgccgcctta ggtgggggag ggagaaatga gcggagaggg agaggttagg gaataaggga  82620
aagagggggg gggcggctgg gccttccagg ctctaaaggg ggggcgccca tggacctggt  82680
cgaccggggt tccgtcccac ggcgcgggtg aagagcaaaa agaggagaga aatggagggg  82740
gaaaatagag agaaagatct ccccccactt cgatccgaat cttctactga atgcattgcc  82800
ctcaagcatc caagatgcag gtcggcaggg ccgctccacc acataagata ggattcctac  82860
cggannnnnn nnnnnnnnnn nnnnnnnnnn nnnnnnnnnn nnnnnnnnnn nnnnnnnnnn  82920
nnnnnnnnnn nnnnnnnnnn nnnnnnnnnn nnnnnnnnnn nnnncgatct agagattcgt  82980
gaatccgatc tttctacatg aatgcaattg cactttcaaa gaatgaacaa aatgcaaggt  83040
tcggcatggt gcatcaaaca acataaagaa tatagggttt ttcttacacg ggaaatccaa  83100
accgaatccc gctagaactt tggaaaaggt caaggtttag cgaagggaaa aaagaaaagg  83160
aaaaggtaac gcccgaattt tggcgagtaa agaaagaaaa aattcaactg caaaattcgg  83220
ggcgttacaa acctatcccc cttaaaagaa tctcgccctc gagattcagg gctggctagc  83280
```

```
aaagagctcc gggtacttgg ccatcagatc atcttcacgc tcccaggttg cttcttcctc  83340
agagtggtga ctccatctga ctttgcacat tctgacggtc ttccttcggg tgactctatc  83400
tgcaacctca aggatctgag ctggcttctc aacataggtc aagtcctcct ggacttccag  83460
accttccact ggcaactgct cttccggcac acgcaagcac ttcttcaact gagacacatg  83520
aaagacatta tgcacagcag acaaactctc tggcaaactg agctgataag ccacttctcc  83580
acgctttgag agaatttgat acggaccaat gtagcggggt gctagcttgc ctttcactcc  83640
gaaccttctg actcctctga tcggtgacac tttcagataa acaaagtctc cgacttcgaa  83700
actcagctct cttcttcttg tgtctgcata gcttcgctgc cttgattgcg ctatcttcag  83760
attctctcgg accatcttga tgttctcttc ggcttcaagc aaaatatctg gcccaaacac  83820
ctgcttctct ccaggctgat cccattgcaa cggagttctg caactccttc catacagcgc  83880
ttgaaacggt gacatcttca aactggcctg ataactgttg ttataggaaa actctgcata  83940
aggcaatcgc ttgtcccatc cggactgatc ttgcaacgca caggctctca acatatcttc  84000
aagaatttga ttggttcttt cagtctgacc atctgtctgc gggtgataag ctgaactgaa  84060
attcagatgc gtgcccaagg cttcatgcaa ctgctgccag aaatgagagg tgaactgcgt  84120
tcctctatct gacactatct tctttggcac accatgaaga caaacgatcc gagacatata  84180
caattctgcc aatactgcac tgttgtagtt ggtcttgaca ggtatgaagt gggctgactt  84240
ggtcaagcgg tccactacta cccaaatgga atcgtagccg gctcgggtgc gaggcaatcc  84300
gactatgaaa tccataccaa tttcatccca tttccactga gggatctgca acggttgcaa  84360
caatccagct ggtctctggt gttctgcctt aattctttga caactatcgc acatagccac  84420
atgctctgcg atttctcttt tcattccgta ccaccagaat ttcttcttca gatcctgata  84480
catcttctca ctgccagggt gaatcgaata agctgtctca tgagcttcct taagaatcaa  84540
ctcccgaata gactggacat tgggaacaca caagcggtct ttgaaccata tcacgccttc  84600
cgcatcttct cgaaaatctt tgcctttacc atctagaatc agtcgccgga tctcactgat  84660
cttctcatca tttttctgcg cttctttggt ttcgcgctcc aaggtaggtt ccaattcaac  84720
tgtgactcct cgcgaattgt tcagaaatcc gagactcaac ctgtcaaact ccttggccaa  84780
ctcataaggc atcgggcgag caaccatcag attgacttga ctctttctgc tcagagcatc  84840
tgccactacg tttgctttgc ctggatggta atgaatctcc aactcatagt ctttgatcaa  84900
ttctaaccat cttcgttgcc tcatgttcaa ttctgactga gtgaatatgt acttcagact  84960
cttgtggtct gtgtaaacat cacatttctg tccatacaga tagtgcctcc atgacttcag  85020
tgcgtgaacc actgctgcca actctagatc atggattggg taattcttct catgaacctt  85080
cagctgtcgg gacgagtaag ccacaactct tccctcttgc atcaacacac atcccaaacc  85140
tgtgtaacaa gcatcacagt acacagagaa gggcttgtgc acatcgggca agactaggac  85200
gggcgctgta gtcaacttct ctttcagcgc ttcaaaggcc tcttggcatt tctgggtcca  85260
cttgaactca accttgttgc ctagcaacgc tgtcattggc ttcgcaatct tcgaaaaccc  85320
ttcaatgaat cgccgataat atcccggcca ttcccaatga aagctcttga tttcctcgag  85380
catccgttgg cgctttccag ttttagaaat gtctgccact ttcttcggga tccacagcca  85440
atcctttctt tgttgataat gtgacctcaa gaacagggac ttcactgatc cagaactcac  85500
acttgctcaa ctttgcaata caactggtgc tctcgcaatc tctgcaacac catcctcaaa  85560
tgatccgcat gctcttcttc actttgagaa taaaccagaa tgtcatcaat gaataccacc  85620
acgaacttat caagataatc catgaataca ctgttcatca agttcatgaa gaatgctggc  85680
```

```
gcattggtca aaccaaaaga catcactgtg aactcatata aaccatactt ggtaatgaat  85740
gccgtcttcg gaatgtccga aggtcggatc ctgagctgat gataacctga cctcagatcg  85800
atcttggaga acacactggc tcctctcaac tggtcgaaca gatcttctat tctgggcaaa  85860
ggatacttgt tcttgatcgt gacctcattc aaagctcgat aatcgatgca catcctctta  85920
gtaccatctt tcttttctac gaacaagaca ggggcggccc aaggcgaggt gcttggccgg  85980
atgtaacctt tctctgacag ctcatcaatt tgcttcttaa gctcatccaa ctctggtcca  86040
gatattctgt aagctctctt gaagataggg gcggttccag gaagaagctc tatagcaaat  86100
tcaactttcc gctctggtgg catacccggt aaatcctttg gaaacacatc tgggaattca  86160
gacacaacct tgatactctc aattgggtct gcttcactgc tatcgacagc catctgataa  86220
caacttcctt tctttggctc aggcgggact aacccggtca ccacttcctc tcctagtggg  86280
gacaccaact tgattgtcct tttatcacaa ctgataactg cctgatactt atctaaccaa  86340
ttcatcccta ggatgacatc tattccctga gtacccatta ctataaggtt ggcgggaaac  86400
gctatccccc ttatttccac acttacattt aaacaaatgc tatcagctcg aattctacca  86460
ccggctgagt caatttgaat aggggttgac atggtagtaa ttggaagatt atgtgcttct  86520
acccatgatg cagtaatgaa agaatgtgtt gctccagtat caaataacac ttctgcaata  86580
tgggaatcga ctgggaacat acctactgtc atgccggggg tctcctgaac tgcttcagcc  86640
tccaagtgat tcaatcttcc atgattatag cgctgctgag agcgattgcc tgctccaggc  86700
tgagacacat tctgctttgc tggggcattg gggcctgact gctgctgggc tgccttcttc  86760
ggacattgca tcacccaatg gccttgctct ccacagtgga aacatgccct gtttccaacc  86820
tgagctggtg ctgcctgact gttctgctga tttgctgggg caggaagacg aggtgcttgc  86880
tgattctgct tttgaaactg acctcctgac tgattgctct gacggttctg gtactgatgc  86940
tgaggatact gcctttggaa ctgctgatac tgctgacgct gctgatgctg ctgaggtgga  87000
cgctggttct gcctgaactg ctgaggttga ttgcctgaga aacggggacg gctgctgctt  87060
ccaggctggg gtccactgat cttgcgctta cgatcttcca tctccttacg cttcctttct  87120
gtcatgattg ctctgtcaat caggtgctgg aatgtcggga aggtgtggtt catcagctga  87180
tactgcagag ggtcgaccaa gcctcccaga aaacggtact gtcgcttggc gtcagtgttg  87240
acatcttcag gagcatagcg agacaattgc agaaacctgt ctcgatactc actgacagac  87300
gatgaccctt gcttaagggc caggaactcc tccttcttca ctgtcatcag acctgcaggc  87360
acatggtact gacgaaagct acctctgaat tcttcccagg tgatggtgtc ggggttggca  87420
tgggtggcga ggtaagactc ccaccatgat tgggctgctc ctctcaacag acggggacca  87480
tacaagactt tctcccggtc atcgcactga gcggtatgca actcccgctc cacagtgcgc  87540
agccaatctt cagcatccat ggggtcagaa gagtgagcga acgttggtgg atgacctctc  87600
atgaattcag cacgcttgtc tctaggcatc tgaggcatct gaggctgggg tggtgcttgc  87660
tgctgttgct gctgctgctg ctgctgaatg gcggccagag tctgaccgat ggcttgaact  87720
gcctgagtct gcatcagaaa catctgctca atcgacatcg gggcggggg cggcaggtgc  87780
tgctgctggg gcacctcatc ctgcggagcg gctcgctcct gctgagcacg ccttcctcct  87840
ctacgcctgt tctctgacat ctgcagaacg caaccacaca tcagaactga tctggcaaag  87900
cttgcagcat aagaaaagag tatagaattc tccaacagca ctgaacagat gagcatcttc  87960
actgatctcc aacacagacc acacagcttc tcagataaag aggaaaggag aataatgggt  88020
```

```
ttcccaacta tataactaac tttattgaca tagtatgtaa accaaaatgc aggggatacc  88080
cacactctgg tgacaatcat tacaaagatc caaaccaaac atagttcatc atgacaaaca  88140
taaatgcaca ggatatagca aactaccctg tctaactaaa actaactaag accgagacta  88200
acgctaagac tgaagcttcc atgtatatat ttatttcgta ttaattacaa gatccaactc  88260
taacgatcta tggttctagg tttatcttgg tcttgcaggc gggattgcca taagactggt  88320
gtccacgctg aggtgagcgg tacgggtgct gagtcccaac gggagcgggg gaaccaccgt  88380
ccagaaaacg acgttccgca cgctcagccc gcagcagggc gatctcagca cgagccctac  88440
tcagctcgtc taatgcatgg tccagctccg tgtttagcac ggcggctagg ttgactgtgc  88500
tgctcaacct aggattgccc tcaccgacgg gtgagacaat cacgcctcct gtgctgccag  88560
atgaacggcg gggtaatac ttcaggtcaa gaccgtcagc tgccccaccg aaaaccgagc  88620
agtagtgcga aagcgcacgc cgtgcagcat cttgcatggc tgcctcagct gagtcccgct  88680
cagagataga atagtgctct gaacaggcct ctgcaccctg gagactgtcc tccgggcagc  88740
gcaccaagca agttgcctcc cagcggtccg ggtagacccc gcgactatgc tggtagacca  88800
cacagcgata ctcgacggac caagtatgcc ggtcaaatgc ccgacgtagc agggtgtcga  88860
gcgcatcatg gaagtgacac ccgcgagcag cgtcgcgagt gatgggtcga gcaacccatc  88920
cttccggctc aagattagca gagaagtcgg tgtcgtggct cgagctgtca tcgccatctc  88980
cgtcgtctgg gtctcctcca gcagctactc cagaagctgg ggcgcccagt ggtgatgcag  89040
ggggcggctc cagaggaagc acaggggagc agctcctcac agactctatc tcctggtgga  89100
gcgagaggga agagctctgc tgctcctgtc gtcgacgttc ctgctcctca cgcaggcggt  89160
ggtgtagtct ctccaagtgg ctggactgtc cggccacggg acggcgaagc ggacgctcag  89220
caaggcggga gggtaagaag gggatgactg actttcgtgc agtgtgtcta agtcgagcca  89280
tctacaaaag acatcgcaag caaaagggtg agaacagaat taatatgacc agcaagtaat  89340
gaatcataag taaatgaagg attagaataa aacatgattt ttagcaaggt atagtatata  89400
gtagaacata ggtttggtcg gtaggaccaa cttttgaagg gatatcaaag tcaaggaaga  89460
gacagaggtc tataatcctt agaacgacca ttctactcta ggttagcggt cctacagtca  89520
gcacggctct gataccactt atgtcacacc cggttttaga ggaaaggggg cacccatgta  89580
cgtgccagga tcagttatta gaaggcggca ggtacataat atggacataa tcacacaaaa  89640
gtcaaaatag tattaataag ggaaaatagt ctattacatc atacgtctga gacgtccata  89700
tagttcttac aataaatcaa agtgcggaaa agaaacgtag ataacgcggc cttcacaggc  89760
agccgactgg gggttgccgc taacccacac ctagaactcg tcgtaatctt ggaatttctg  89820
gaagtctcct tccacagctt catcttcgcc tgagcagtgg ttgcaatgct gacaacctgg  89880
gggggggggg ggttggtgtg tagagcaagg gtgagtacac atcaacatac tcagcaagta  89940
tcctgtttgg ctgtagtgga ctagctttat gtggggatca gtcaagcagt tgcttttagt  90000
tggtcaggtt attacttact agtagaaagc caggttttaa cattaaccca agttattaac  90060
ccaatgtatc ctttccaaac ggaaagaata ccacttacca ataccataat cataaccaga  90120
accatcaatc tcattgccac ctgtaccaaa atatctctga tcaagtatca ctaatctctg  90180
gagctccctt ggccgctcat aaccgtgagc acggctgata tatcagtttc ataacactct  90240
gcagaggttg tgcactttac ccacaagccg tgattccctc ttgcctcggg ccgatcaaac  90300
ccttaaacac taccaaggtg aataggcagg gtttcactac gtagccttta caaagattcc  90360
ccggggctgt agccacccgt taggtttcct aaatgcaccg cactcctccc caaggggcga  90420
```

```
acccaaactt ggcagagcga gccgcataca ccgagcccca ttgacggcac gacggctaag  90480
tgaactacat cccggatcct ctaattattc agctaagggc accccattcc accctcatgg  90540
ttgcactgtt ttcccgggcg gtcatccata gaacaggtcc ttacggagag gcactcgaga  90600
aaccgctcga gccccccttga ataccacaag tacaacatca taataagaga agggaaaaca  90660
gcgtatcata gataatcaca tcatgttcat tgattagagt tgagcaatag catcagacta  90720
agtagtaata atccgaccca aataggtaaa caaggacatg gataacaaaa gctagtcgat  90780
ccttaggtat aaatgtgtaa tgcgggaggt gaattaaaga atgaatagga cagagatagg  90840
tcaaaggaca cttgcctcca ccaaccgatt gctgctcagg ggcttctcct gcgaattcct  90900
cgggctcttc gaccggatcg ttctctatgc gagcgcaaac atacatacat acatccacat  90960
atttaataca aaagaacagt acaccataca agataacaaa taaagcgaat atgcatcaag  91020
tatgacattc gataacgcat ttgttatggt tagaaagaaa cggggaaagg tctcgcaggg  91080
ggttaaatct tatgcactaa tgacacaatt ggtttttaac aaaataattc tgttatatat  91140
atttatatat actgatggaa acctaatcac ttttagttga tcaacattgc acagggtaaa  91200
caattagcta cgtgaatcaa taacataacg gaattttaaa ttaaacttcc tattttccca  91260
tagcatgaac agtgattagc ctacttaaaa tacagtaatt atgatcacag aaagtaaata  91320
aaataaaata aaaaaataaa aaaaacagaa gggggggggg gttgaaccgg ccctagggcg  91380
gttgaaccgg ccctaggcgg ggcgcgggcg cgggcgcggc cggggctgac cgggcggctg  91440
agccgctgag ccggccggtt gaaccggcgg cgggcggccg agctggcggg gggggggggg  91500
gcggcgcagg gggcggccga gccggccgag caggggggcg gggcggccga accgctgggc  91560
gcgcaggggc gcggggcagg gcgcgggggg gccgagcggc cgacccggcg gggtggggcg  91620
ggcggccaaa ccggccatgg ggccaagcgg cgaggggaag gggagggagg aaaggggaga  91680
gaaggttgag ggagagaggg aggaggggggg ggctcaccgg tgtcggggat cgacggcgag  91740
gggcgcccgg cggcaggggg cggcccgcca atctagggca gggggcgggt agggggtagg  91800
ggcggcggat tcggtggcga gggagaaaat gaggggggag agggagaggg ttagggaata  91860
agggaaagag gggggggcgg ctggcccttc caggcccaag aggggggcg cgcaggggcc  91920
tgggccggcc ggggtcggcc cacggcgcgg gagagagaga aaaagaggag agaaaaagag  91980
agggagaaaa aagaaagaaa agatcctctc cacattttcg aaatccgatc tttctacatg  92040
aatgcaattg cactttcaaa gcaatcaaaa gaaatgcaag gttcggcatg gtgcatcaaa  92100
caacataaag tatttagggt ttttcttaca cgggaaatcc aaaccgaatc ccgctagaac  92160
tttggaaaag gtcaaggttt agcgaaggga aaaaagaaaa ggaaaaggta acgcccgaat  92220
tttggcgagt aaagaaaaga aaaaattcaa ctgcaaaatt cggggcgtta cacttctggg  92280
ccccgcttga tgtccggtgg cgcaccggac atgcactgtt cactgtccgg tgcgccagca  92340
tgggcgtgcc tgacctctgc gcgcgctggt gcgcaataaa tgcgcagcag gtagccgttg  92400
gcgcctgaag tagccgttgc tccgcagatg caccgccccc tccggtgcac atcggacagt  92460
tcggtgaatt atagcggagc ggctggagtg aaaacccgag gctggcgagt tcctgaggac  92520
gacctccctt ggagcaccgg acactgtccg ggtgtacacc ggacagtccg gtgaatttta  92580
gccgagtcgc ctctagaaat tcccgaaggt ggcgagtttg agtctgagtc cccctggtgc  92640
accggacatg tccggtggcg caccggacag tccggtgcgc cagaccaggg gtgcctttcg  92700
ggttgcccct ttgctccttg ttgaatccaa aacttggtct ttttattggc tgagtgtgaa  92760
```

cctttacac ctgtataatc tatatactag agcaaactag ttagtccaaa gatttgtgtt 92820
gggcaattca accaccaaaa ttatttagga actaggtata agcctaattc cctttcaatc 92880
tccccctttt tggtgattga tgccaacaca aaccaaagca aattcaaaag tgcataattg 92940
aactagtttg caaaatgtaa gtgcaaaggt tgcttggaat tgagccaata ttaatactta 93000
caagatatgc atggattgtt tcttatatat cattttggac cacgcttgca ccacatgttt 93060
tgtttttgca aaattctttt gtaaattctt ttcaaggttc ttttgcaaat agtcaaaggt 93120
aaatgaataa gagttgcaaa gcattttcaa gatttgaaat tttctccccc tgtttcaaat 93180
gccattcctt tgactaaaca aaactccccc tcaaataaat tctcctctta gtgttcaaga 93240
gggttttgag atatcaagtt ttgaaaatac tacatatact acatgctccc ttttagaaca 93300
caaagagata caaattttga aattttcaac caattgaaaa tcatatgttt aaaattaggg 93360
tggtggtgcg gtccttttgc tttgggctca tattttctcc ccctttggca taaatcgcca 93420
aaaacggaat cattagagcc ctttaatgac tattttgtcc cctttggcaa atgaaacata 93480
ggagtgatga ttataccaaa gttggagaga tgctcggagt gacggcgaag gatgagtagt 93540
agagtggagt ggaagccttt gtcttcgccg aagactccaa ttccctttca atatacctat 93600
gacttggttt gaaatacact tgaaagcaca ttattcatag catatataag agagacatga 93660
tcaaaggtat atttatgagc aatgtgtgca agtttagcaa aaagaaattc ctagaatcaa 93720
gaatattaag ctcatgccta agtctggtaa aagattgttc atcgagaggc ttggtaaaga 93780
tatcggctaa ttgatcttta gtgttaatgt atgaaatctc gatatccccc ttttgttggt 93840
gatccctaag aaaatgatac cgaatggcta tgtgtttagt gcggctgtgc tcgacgggat 93900
tgtcggccat tttgattgca ctctcattat cacatagcaa agggactttg gttaatttgt 93960
aaccgtagtc ccgcagggtt tgcctcatcc aaagtaattg cgcgcatcaa tggcctgcgg 94020
caatatattc ggcttcggcg gtagaaagag ctaccgaatt ttgcttcttt gaagcccaag 94080
acaccaagga tcttcccaag aactggcaag tccccgatgt gctcttccta ttaatcttac 94140
accccgccca atcggcatcc gaataaccaa tcaaatcaaa tgtggatccc cgagggtacc 94200
aaagcccaaa cttaggagtg taagctaaat atctcaagat tcgtttcacg gccgtaaggt 94260
gtgattcctt agggtcggct tggaatcttg cacacatgca tacggaaagc ataatgtccg 94320
gtcgagatgc acataagtag agcaatgaac caatcatcga ccggtatacc ttttgatcca 94380
cggacttacc tcccgtgtcg aggtcgagat gcccatttgt tcccatgggt gtcttgatgg 94440
gcttggcatc cttcatccca aacttgttta gaatgtcttg agtgtacttc gtttggctga 94500
tgaaggtgcc ctcttggagt tgcttcactt gaaaacctaa gaagtacttc aactccccca 94560
tcatagacat ctcgaatttc tgtgtcatga tccctactaa actcttcaca tgtagacttg 94620
ttagtagacc caaatataat atcatcaaca taaatttggc atacaaacaa gtcattttca 94680
agagttttag taaagagtgt aggatcggct ttgccgactt tgaagccatt tgcaatgagg 94740
aaatctctaa ggcattcata ccatgctctt ggggcttgct tgagcccata aagcgcctta 94800
gagagcctat aaacatgatt aggatactca ctgtcttcaa agccgggagg ttgctcaaca 94860
tagacctcct ccttgattgg tccattgagg aaggcactct tcacgtccat ttgatagagc 94920
ttgaagccat ggtaagtatc ataggccaat aatatgcgaa tagattcaag cctagctacg 94980
ggtgcatagg tttcaccaaa atccaaacct tcgacttgtg aataccccctt ggccacgagt 95040 cgagctttgt tccttgtcac cacaccatgc tcgtcttgct tgttgcggaa gacccatttg 95100
gttcctacaa cattttgatt aggacatgga actaaatgcc atacctcatt ccttgtgaag 95160
ttgttgagct cctcttgcat cgccatcacc caatccgcat cttggagtgc ttcctctacc 95220
ctgtgtggct caatagagga aacaaaagag taatgttcac aaaaatgtgc aacccgagat 95280
cgagtggtta ccccttatg aatgtcgccg aggatggtgt cgacggggtg atctcgttgg 95340
attgcttggt ggactcttgg atgtggcggc cttggttctt gctcatcctc cttttcttga 95400
tcatttgcat ctccccttg atcgttgccg tcattttgag gtggctcatc ttcttgatct 95460
tcttgttcaa catcttgagc ctcgacctca tcttgggttg gtggagatgc ttgcatggag 95520
gaggatggtt gatcttgtgc gtgtggaggc tcttcggatt ccttaggaca cacatcccca 95580
atggacatgt tccttagcgc tatgcatgga gcctgttctt cacctgtctc atcaagatca 95640
acttgctcta cttgagagcc gttagtctca tcaaacacaa catcacaaga aacttcaaca 95700
agtcctgagg acttgttaaa gactctatat gcccttgtgt ttgagtcata tcctagtaaa 95760
aagccttcta cagttttagg agcaaattta gattttctac ctcttttaac aagaataaag 95820
catttgctac caaaaactct aaaatatgaa acatttggct ttttaccggg ttaggagttc 95880
ataagatgtc ttcttgagga ttcggtgaag atataaccgg ttaatggcgt agcaggcggt 95940
gttgaccgcc tcggcccaaa accgatccgg tgtcttgtac tcatcaagca tggttcttgc 96000
catgtccaat agagttcgat tcttcctctc cactacacca ttttgttgtg gagtgtaggg 96060
agaagaaaac tcatgcttga tgccctcctc ctcaagaaag ccttcaattt gagagttctt 96120
gaactccgtt ccgttgtcgc ttctaatttt cttgatcctt aagccgaact cattttgagc 96180
ccgtctcaag aatcccttta aggtgtcttg ggtttgagat ttgtcctgca aaaagaacac 96240
ccaagtgaag cgagaaaaat catccacaat aactagacag tacttactcc cgccgatgct 96300
tatgtaagcg atcgggccga atagatccat gtgaaggagt tccagtggcc tgtcacttgt 96360
cataatgttc ttgtgtggat gatgggtgcc aacttgcttc ccggcttggc atgcgctaca 96420
aatcctgtct ttctcaaaat gaacattggt tagtcccaaa atgtgttctc cctttagaag 96480
cttgtgaaga ttcttcattc caacatgggc tagtcggcgg tgccagagcc aacccaagtt 96540
agtcttagca actaagcaag tgtcgagttc agctttatca aaatctacca agtatagctg 96600
accctctaac actcccttaa atgctattga atcatcactt cttctaaaga cagtgacacc 96660
tacatcagta aatagacagt tgtagcccat ttgacacaat tgggatacgg aaagcaaatt 96720
gtaatctaat gaatcaacaa gaaaacattt gaaatggaat ggtcaggaga tatagcaatt 96780
ttacccaaac ctttgaccaa accttgattt ccatccctga atgtgatcgc tcgttgggga 96840
tcttggtttt tctcatatga ggagaacatc cttttctccc cggtcatatg gtttgtgcac 96900
ccgctgtcga gtatccaact tgagcccccg gatgcataaa cctataaaac aaatttagtt 96960
cttgacttta ggtacccaaa ctgttttggg tcctttggca ttagaaacaa gaactttggg 97020
tacccaaaca caagtctttg accccttgtg tttgccccca acaaacttgg caacgacctt 97080
gccggatttg ttagtcaaaa cataggatgc atcaaaagtc ttaaatgaaa tgctatgttc 97140
atttgatgca ttagaaattt tcttcttagg caacttagca cgggttggtt gcctagaact 97200
agatgtctca ccccttataca taaaagcata gttagggcca gagtgagact tcctagaatg 97260
aattttccta attttgctct caagatagcc ggcagggtat aaaatgtaac cctcgttatc 97320
ctgaggcatg agagccttgc ccttaacaaa gttagataag ttctttggag gggcattaag 97380
tttgacattg tctcccccttt ggaagccaat gccatccttg atgccagggc gtctcccatt 97440
ataaagcatg ctacgagcaa atttaaattt ctcattctct aggttgtgct cggcaatttt 97500
agcatctagt tttgctatat gatcattttg ttgtttaatt aaagccatat gatcatgaat 97560
agcatcaata tcaacatttc tacatctagt acaaatagtg acatgctcaa tggtagatgt 97620
agatggtttg caagaattaa gttcaacaat cttagcacga agtatatcat tcttatctct 97680
aagattggca attgtaactt tgcaaacatc aaaatcttta gccttagcaa tcaaattttc 97740
attctctaat ctaaggctag caagagaaat gtttaattct tcaatcctag caaccaaatc 97800
atcattatta tctctaggat tgggaattga aacattacaa acatgagaat caaccttagc 97860
atttaaacta gcattttcat ttctaaggtt gtcaatcatc tcacggcaag tgcttagctc 97920
actagacaat ttttcacatt tttcaacttg tagagcgtaa gcatttttaa ccttaacatg 97980
tttcttattt tctttaatta gaaaatcctc ttgggaatcc aaaaggtcat ccttttcatg 98040
aatagcacta atcaattcat ttaatttttc tttttgttcc atgttaagat tggcaaaaag 98100
ggtaagcaag ttatcctcct catcactagc atggtcatca ctagaggatt catattttgt 98160
ggaggattta gagttaacct tcttcttttt gccgtccttt gccatgaggc acttgtggcc 98220
gacgttgggg aagagaagtc ccttggtgac ggcgatgttg gcggcgtcct cgtcgtcgga 98280
ggagtcgctt gagctttcgt cggagtccca ctcccgacaa acatgggcat cgccgcccctt 98340
cttcttgtaa tacttcttct tttctctcct ctttcccttc ttgtcgtcgc ccctgtcact 98400
gtcactagac ataggacatt ttgcaataaa atgaccgggc ttaccacact tgtagcaaac 98460
cttcttggag cgggatttgt agtccttccc cctccgttgc ttgaggattt ggcgaaagct 98520
tttgatgatt aaagccatct cctcattatc gagcttggag gcgtcaattg gttgtctact 98580
tggtgtagac tcctccttat tctcctccgt tgccttgaag gccaccggtt gcgcctcgga 98640
tgtggaaggt tcgtcaagct cgttgatctt ctttgatcct ttgatcatgc attcaaagct 98700
cacaaaattc ccgataactt cctcgggggt cattagtgga tatctaggat taccacgaat 98760
taattgaact tgtgtggggt taaggaaaat aagagctctt aaaataacct taaccacttc 98820
gtggtcatcc cactttttgc tcccgaggtt gcgcacttga ttcaccaagg tcttgagccg 98880
gttgtacata tcttgtggct cctcccctgg gcgaagacga aagcgaccga gctccccctc 98940
gatcgtttcg cgcttggtga ttttggtgag ttcatcaccc tcgtgcgcgg tcttgagtag 99000
gtcccaaatc tcttttgcgc ttttcaaccc ttgcaccttg ttatattcct ccttgcttat 99060
agaggcgagg agtattgttg tagcttgaga gttgaagtgc tcgatttggg ccacttcatc 99120
tgtgtcatag tcttcatccc ctatggatgg tacctgtaca ccaaactcaa caacatccca 99180
tatacttttg tggagtgagg ttagatgaaa tcgcattaaa tcactccaca ttgcataatc 99240
ttcaccatta aaagttggtg gtttgcctaa tggaacggaa agtaaaggtg tatgtttaga 99300
aatgcggggg tagcgtaggg gaatcttact atacttctta cgctcttggc gtttagaagt 99360
gacggacgcc gcgtcggagc cggaggtaga tgtccatgaa gtgtcggtct cgtaatagac 99420
caccttcctc atcctcttct tcttgtcacc actccgatgc ggcttgtggg aagaggactt 99480
ttctttcttc tctttgtgat gcgaagaaga tttctccttc cctttggagg agtccttctt 99540
ttcttcgcgg tgcgaagaaa gtcttttctc cttccctttg gaggagacct tcctcttctc 99600
cttcctcttg gtgtgggact cttccgacga agtgctccct tgacttgtag tgggcttgtc 99660
gccggtctcc atctccttct tggcgtgatc tcccgacatc acttcgagcg gttaggctct 99720
aatgaagcac cgggctctga taccaattga tagtcgccta gaggggggggg tgaatagggc 99780
gaaactgaaa tttacaaata taaacacaac tacaagccgg gttagtgtta gaaatataaa 99840
agagtccgcg agagagggcg caaaacaaat cgcaagcgaa taatgaagtg agacacgagg 99900

```
atttgtttta ccgaggtttg gttctctcaa acctactccc cgttgaggag gccacaaagg  99960
ccgggtctct ttcaaccctt ccctctctca aacggtccgt ggaccgagtg agctttctct 100020
tctcaaatca aagtcgggaa caaaacttcc ccgcaagggc caccacacaa ttggtgcctc 100080
ttgccttgat tacaattgag tgttgatcac aagaacaagt gagaaagaaa gaaagcgatc 100140
caagcgcaag agctcaaatg aacacggcaa atcactctca ctagtcactt aggctttgta 100200
tggaattgga gaggatttga tctctttggg tgtgtctaga attgaatgcc tagctcttgt 100260
aagaggttga gaagtggaag acttggatgc aatgaatggt ggggtggttg gggtatttat 100320
agccccaacc accaaacatg accgttggtg gaagctgtct gttcgatggc acaccggata 100380
gtccggtgca caccggacag tccggtgccc cctgccacgt catctctgcc gttggattct 100440
gaccgttgga gctctgactt ctgggccccg cttgatgtcc ggtggcgcac cggacatgca 100500
ctgttcactg tccggtgcgc cagcatgggc gtgcctgacc tctgcgcgcg ctggcgcgca 100560
ataaatgcgc agcaggtagc cgttggcgcc tgaagtagcc gttgctccgc agatgcaccg 100620
gacagtccgg tgaattatag cggagcggct ggagtgaaaa cccgaggctg gcgagttcct 100680
gaggacgacc tcccttggag caccggacac tgtccggtgt acaccggaca gtccggtgaa 100740
ttttagccga gtcgcctcta gaaattcccg aaggtggcga gtttgagtct gagtcccccct 100800
ggtgcaccgg acatgtcccg gtggcgcacc ggacagtccg gtgcgccaga ccaggggtgc 100860
cttcggttgc ccctttgctc cttgttgaat ccaaaacttg gtctttttat tggctgagtg 100920
tgaacctttt acacctgtat aatctatata ctagagcaaa ctagttagtc caaagatttg 100980
tgttgggcaa ttcaaccacc aaaattattt aggaactagg tataagccta attccctttc 101040
aagactgacg atccggcccc acgagtcgga gacaccaggc aaccagcgtg cgacacagtg 101100
tctgatagcg cgggtcccac ctgtcggtgt aggagcggcg cagtgggagc caatgggccg 101160
cgcgaagata gtggggaatg ggccgaggca gcgaaaaata ggcccagacg ctggcttcca 101220
ttattctttt gctttttcct ttttattttc tcctttcttt tgatcttttc tgattttagt 101280
tttcaatttt cataattcaa tcttagattc aattttgaat acaagaattc acacccaaag 101340
gtcaagcatg atgcataatt tttacttatt tcttttattt atttgtatcc atttagataa 101400
atgctctaat gatggattat acacatatta tttttttaa ggaaatttta tctttgaatg 101460
cacacttaag ataaataatc atctttagtt atatttactt cggctatgtt aatatgtaat 101520
ctttctcatg aattatttta gttcaattat ctttttaggg atggttttga ttaaaagaaa 101580
caatagttag tttaaaagtc tctctcttat atgtggtttc aactcctagc tttaggtttt 101640
agatctatgc ttcgaatacc agattcttgc ttattattat attttataga ggacggaaat 101700
ttttattaga agtcctttta tcacaaaact tcctataaaa acatttataa ttctaagcac 101760
aggatttcgg gtgttacatg ggagtacttg gctgattggc tctggcggtc tggcggtggc 101820
gggcgacgca cgcaggtagc ggtggcgccg gctcgggttc ggacgcgcgt tgctgtcccg 101880
cggatgcgga tggggctccc gcccggtcgc tctcgatctc ggtcacatcg catactctcc 101940
ccctgccgtg cggggacgcc gggaggaagc tttgtttggt ctcgccatgg ctcggcgtgc 102000
gtgacgggat tggatggaaa ccccgaccgg ttcgctggcg tgtgccgtgc cggagtggag 102060
ggaggctcgg tctgagtagt cggtgccggt ggactgatgg tgtcgccgtg tcggtgaagg 102120
ggctcgtgct cgtgccgccg tgcgggacgt atgtggggtt ctttgtgatg gggggcccctaa 102180
ccgaacaaag attcaggtac gacggacttg tcaatatgca acaaccaatg tgcttgtcca 102240
```

```
atcgaacatg aatgacgaga tatggacatg aacgaacgaa tgaatggtgt tgttgggtct 102300
atgcttcggc gccgaaggtc ttctaggaag aagcggcttt tggctgaagt tgcttgagtg 102360
agatggccga aggttcttca tcatgaagct tcggtattac aaaccgactt aaggatggaa 102420
tgacctttta gtccataaag gtctgggtca atgttgtaaa cttttatgag gggcataatt 102480
gtaattcctc acaggctgtg tcctgtgcct ataaatagtg aacagtattc ctttactgtt 102540
cacgcattct ggctattgta atcgcatctt tcggaaacca atctttgcca aggcagaggt 102600
ataatgtatt caataattta atatattaag taaatatttg tgcatgactc gtttatcttt 102660
tcatatcctt tatcttatgt tattttatat gagaatatga ttacggagat ctaaccttcg 102720
taattatgtc ttcatgaacc ttcgtccatg gttcattatc ctcaagggaa tattgtttca 102780
tggacgaagg atgttaatat tcaacatttt atgttgtctt gttcttaatt catagcattt 102840
gagaacaagt ccccaacatt ggcgcccacc tccggtgaac tcacttccac ttttttgagc 102900
tgatggcttc gttcaacgat caagctggag ctgcttcggc tccgaagctg ctactcccga 102960
taacaggcgg ttcatgttca gagccagcca acaagaagca gaagaaggaa gcacagagaa 103020
gggtacagca tgttggggtg caaggaccct tcatcaagtc aagatggtct cacatcccta 103080
ttaccttctc ccaagaggac cttcaactca aggattaccc acacaatgat gccatggtta 103140
tctcttgtgt tatcaaagga tttctggtcc ataatgtctt ggttgacaca ggcagtgcag 103200
ctgatatcat atttgctaag gccttcagac aaatgcaaga gccagaagat aagattcatg 103260
atgctacaca tcctctctgt ggcttcggag gaaggcagat tgtagcactg ggcaagatca 103320
ccatgtcagt gaccttcggg ttcatcaaca acactagaac tgagcaagtt atatttgaca 103380
ttgttgacat ggaataccct tacaatgcaa ttattggtcg tggcaccctc aatgctttcg 103440
aagcaattct tcatcctgct tatctttgca tgaagatacc ttcggatcaa ggacccatcg 103500
ctattcatgg aagtcaggaa gctgccagaa gggccgaagg gaactggact gactcaaaag 103560
caatccataa catagatgga gctgaagctt gtgaacagta caaattcaga agggagaaag 103620
cagcttcagc ggatcagccg aagcccatgc tcttatgtga agacatagca gagcagaagg 103680
tgctgttggg ctctcaatta tccgaagaac aggagaaaac cttgataagg tttttgttca 103740
acaacaaaga tgtttttgca tggtcagcca atgatctctg cggagtaaat agggatgtta 103800
ttgaacactc gctcaatgtt gacccatcct tcagacctag aaagcagagg cttcggaaaa 103860
tgtctgatga taaggccgaa ggtgctcgta atgaagtcaa aaggctcctc agtgcaggag 103920
ttatcagaga agtaaagtac ccagaatggc tagctaacac tgttatggta aaaaaggcca 103980
atggcaagtg gcgaatgtgt atcgatttta cagatcttaa caaggcttgt ccgaaggatg 104040
aattcccatt gccaaggata gactcgttag ttgatgcagc agcttcttca gagctcatga 104100
gtctgctaga ctgttactca ggctaccacc aaatctggat gaagaaggaa gatgagccga 104160
agactagctt cataacccca agtggcacat attgctatct tcggatgcct gaggggctaa 104220
aaaacgctgg aggaagtttc agcagaatga ctgcgaaggt tctccactct cagatcggca 104280
gaaatgtgct aacttatgtt gatgacatca ttgtaaaaag cacaaaacag gaaaatcata 104340
ttgctgattt gcaggagacc ttcgccagtt tcagacaagc tggtttaaaa ttgaacccgg 104400
aaaaatgtgt cttcggagtg aagaagggaa aatttcttgg atgcttggta tcaacaaagg 104460
gaattgaagc taatccaagt aaaattgaag ctatacttcg aatggagcca ccaactacaa 104520
aaaagggggt ccaaagatta acagggaggt tggcatctct taatagattt atagctagat 104580
cagcagaaag aaatttacca ttcttcgaag tgctgaaatc agccgaagtc tttcaatggg 104640
```

gaccaagcca acaaaaagcc ttcgaggaac tgaagcaata tctgatagat ttaacaacat 104700
taactccacc aacgccaggg gctcctttgt tattatatgt ggcagcttcg cactcagcgg 104760
taagtgcagc acttgttcag gagaagcttg atggccaagt caagaagcag gtcccaatgt 104820
actttgtatc tgaagttctt agtatatcaa agaaaaacta cacagaatta gagaaggtat 104880
tatatgctgt tttgatggca tccaggaagc ttcggcacta ctttcaagca tacaatattg 104940
ttgttccttc ttcgcagccg ttgaaggata ttatgagaaa tagagaagct actgggcgga 105000
ttggaaaatg gggctgcaga gctcaatgaa ttttgcattg attatgtgca tagatcttcg 105060
atccagtccc aggcgttagc agacttcatt gttgactgga cgccaggggc tcaggatgaa 105120
gaaacaaata aagatgccga agtgtggaca gtgttttgcg gtgggtcttg ggaaccttc 105180
ggggcaggag cagctgctgt gttggtttcg ccatcccaag ttaaaacttg ttatgcggca 105240
agactcgatt tcagttgtac aaacaatatt taccgagtac gaagccctgc ttttgggtct 105300
tcggaagcta aaagtttttt tttttcaga agggccattc ttaaaactga ttctcaggtg 105360
gtgttcgggt catatcgaca agagttgcaa ggttaaagat ccgaagcttg aaaaatatct 105420
agacatggtt cgaagaattg aagcttcctt cgaaggattt tctgtcaaga atatccctcg 105480
aggacaaaat gaacatgctg atttgctagc taagtcagca gccacagggg ctgcctttac 105540
cttcggatgt gttcttcgaa caataaaggc accttcagtg gaactccttg aaagagcagt 105600
cctcaatata tctcctgttt atagcgaaga ttggagaact gaaatcatct cttatcttca 105660
gggtaaattc ctttcagatg acgaaactta taacaggagg atagaggcaa gagctcgtcc 105720
atatgtcatg atagaagggg agttgtacaa gcatggagtt tgtgctccat tgctcaagtg 105780
tttatctaga accgaaggca tagagttgat gaaagaaata catgcaggcc tgtgtggatc 105840
tcacattgga tctaggccgt tacttggaaa agttttccgt caagggtttt attggccgaa 105900
ggcagcttcg gatgcagcgg aattagttca aaagtgcgaa ggttgtcaga aatgtgcaag 105960
agatcaaaaa caaccttcgt ctttaacaca actcatacaa cccatctggc cattgcaaag 106020
gtggggcctt gacttgttgg gtccattacc accggtccaa gggaacttaa gatatgttgt 106080
ggtggctgtg gaatattttt ctaaatggat tgaggcaaag cctttagcca caataacttc 106140
ggccaccatt caaaagtttt tctggcagaa tattgtttgt cgtttcgggg taccaaagac 106200
catcactgtg gataatggaa cacagttcga ctccgaagct tttagggatt tctgtgatca 106260
aattggtacg aagatccatt ttgcatcagt caggcatccg gagtcaaatg ggctcgttga 106320
aagagccaat gtgaaagtgc attcatccct tttgtgagtt ttggtgattt ggataacaac 106380
acatttaaag gtctaacaag tttgctaagt gttgaacagg aaattcagta tgatgaacat 106440
acttgaatag tgtataatga tcagtgaaca aggttcaaca caaggtgaaa taaccagtga 106500
gacaatgcaa atggatataa tatggtctct atattggttt gaatatatgg acaagtcctg 106560
agaaatcact atgcataaat atgatcataa tagaggttga agtgattaag aggattggtc 106620
aagccaaagt gaataagata tgaggaatcg tgaattggct tgaccatatt tactatttag 106680
tccatatatg aatatatgag aatcaaacta aagcttgatt aatcttaata gtttatatct 106740
agaagacatt tcaagcaagg gttcacaata ttgaaagaaa tgattctctt aatggatgct 106800
caataggatg tgacttcaag aatggcttga tagggtgaag atagcaaggg aaagggcttc 106860
gaggaactaa gcgaaggtga aggccaagcg acggcttgta gaccgaggta ccatggctaa 106920
ggtgaagaag agagtacttg cactaagtcg atgaactaat cagctatgaa gagttacaac 106980
atgttgatgc atcagtaagg tgacttgaag ccatgatttg aactcatata aggtgatatg 107040
gtacaagtca cagggtttga tttgagtttg cttcaaaagg tgagacaaag atgtttgtga 107100
tccttatgaa gcaatgccat ggagaaatca cacatgagac accaatgact caaggagttt 107160
acttcatttt attttattta acttgagtat aggaatcgtc gtactataaa gggggatcca 107220
aaaagaaggt tggtgtttgc caaagctcaa acctctctat tcaaaagcta tttatgaaaa 107280
gcaaaaatct ctttatcgtt ctatggttga ccatggttag gtttgagaaa cctagagtgt 107340
tcttgctgaa aagcagctga acttgttcag ctgcagctga gcttttcagc tgagctggac 107400
ttcagctgag ctgagctcct tcagctgcag ctgagctttt cagctgagct ggacttcagc 107460
tgagctgagc ttcttcagct acagctgagc tgaacttcag ctgagttgag cttcttcagc 107520
tgcagctgag cttttcagct gggctgaact tcagctgaac tcaacttcag ctgtgaacct 107580
ctttgaccat acaccagctg aacttgcctc cgggcagttg agctggggtt ttctctccta 107640
aactctctgg tcaagaccgg ttgaactggt cctgaggggc agttcagctg gtctctgacc 107700
cctctgacct ctgatctgca gtctgctagt cagactggca aacaggtcgc caggagctgt 107760
caggggcggt tcaaccaccc cccctgggcg gttcaactgg ttttggtcaa ctttgaccag 107820
tctgcggtca gtctgcgcgt cagtctgcca gtcagactgg cagacaggct gccaggcctg 107880
ccaggggagg ttcaaccgcc ctggggggag gttcaaccgg tctcaggcag aaaaatctgc 107940
tcaacggcta gttttgagct ccacctatat atactacctc ctacctctct ccccaaagca 108000
gtgagcacga tttgaactcc atttctaacc caagaaacac ctcccactct ctctcacaca 108060
tctcttgcct ctcccatttc aaatctttgg agagaaatct ttgagtgagc ttgagagctg 108120
cggtttttgt gctccatctc taaatctctc ttgctcttct tcattcgagc tttggtacta 108180
catcgagttc tttgtggatt cattactctt ggagcttcta gctcctagac gactaggtgt 108240
ctcttgtgag tctccaaatc ttgtggaaga ccacaagaaa gtttgtatta cccgctcgtt 108300
tgagcaaaga ttattgtgtg ggcttgacct ttgtggtcgg caaagggagg attagggttg 108360
aaagagaccc ggctctttgt gggcgcctca acgaggaagt agggcacctt ggtggtgtga 108420
ccgaacctcg ggataaatct tgtgtctctt gtgttcttat tcattgtgtt tgtttgtgtt 108480
tttcgttctc tcacccttcc gtggaagatt tgttcatatc tttttgttgt gtggattttg 108540
agaagtgccc ttctcagatc tactactttg aaccctgtgg atcatttaga acatctcatt 108600
tccaaagtta actgggtgaa tttcgagatc aattcagttt tacccagttt gcttctagtt 108660
tttgttgaaa aagttttaac ttgcctattc acccccccctc taggcaactt tcaattggta 108720
tcagagccta atcctcgttc taacgcttaa ccgcgtgagg aaagatcatg tcggggggac 108780
taagaaacga aagtgcttct aagcttgaaa aagttgaggt tgcctcgact ttatcttttg 108840
gtgcagatgt tgatcctagg gcaatagatc ttgccatgag aatcgccgaa aggatgttcc 108900
tcaaaatgaa ggaagatgag gcgaagaaca ttattgaaga agaagaaaat gatcgatgga 108960
gaccaaacga tgaatccacc tcttcacaag gttcgtcttt caaatccact tctcatatgt 109020
gctttgttgc taatgagagt gacagtgaaa gcgaaagtga ggatgaggag gagcatgaaa 109080
gtgatagtga agatgaggat gatcttcaaa aattcttcgc tcaactaagt aagaagaacc 109140
ggatgagctt gctcaaactt atgaaaaagag cggaagaaca aaaggaaatg cttcataagc 109200
aagaagatat cctcatcgaa aaaatcaaag acttggagaa gttgaccaaa gagcatgaga 109260
agctaaagtg ctctcatgat gatttggtcc aaaggtatga aaagatttca attgagcaaa 109320
ctagtacttc aaatgcttta tcttgcgttg ctcaattaga aaaagaaaat actatgctca 109380
agaacacgat agaaaggcta aatattgaaa atctagcttt gcaagaaaaa catgatatgc 109440
ttgtgtgcta tcataataaa tttatggatt cacatatcat gttagaaatg gctcatgagg 109500
ttgtgttaac taatttgaaa tcataccaac ctcacatatg cacatgtact caagtagaaa 109560
ctatattatc atgtgctaac aaatgttgct ctcaagaaag ccaatcttcc attgagctag 109620
aaatttcagg aattagtgat atttctatca cacaagaaaa taaagagctc aaggaagaag 109680
ttggaatgct aagaaggagc ttaactcgtt tgaagggaaa gtgtcatgct caaccttctc 109740
aagataaccg tgataatatg gtgaaaaagc ttgagaaggg gacaaccgta gcatgcacaa 109800
aaccccttca aaagaaaacc aaactttcca agaagggcat gagaaaaatc catggtgaga 109860
aaattaatgc tcatatgatt tgctctaaca atgtacctat gtgcttcaac aaagaaagat 109920
caaagagaag cgataggagg tgctatggat gcaaggagaa aggccatgaa attgattcat 109980
gcccccacat gaagaatcaa gaccttgcac gatcaagaaa gatgaccatc aaaaaggatg 110040
aaagcaaaag gcaaatgcat tgcaaggaca agcatcgcat ttgctacaat tgccgtgaaa 110100
aaggtcatct attcaaggtt tgtccaaagg gtaaaactcc taagcctaac ttgtcaatac 110160
attcaaatat gcttaggaga cccaaatttg actcttgtgc tagaaaggtg atgagttcac 110220
cacattctag gaccaaggct atttgggtgc ctaagtcctt attggctaac cttgatggac 110280
ccatccaaag atgggtacca aaatgtactt gataagtttt gcaggtaccc acagatgata 110340
tgaagctttg ggggtgcttg agcggtttaa ctcaattctt atctcaagct atcaatctta 110400
cattgtatat cctttaagat tgacccaaag atgaattgag ttgttatatc actaacttca 110460
tattcatctc taccaagaac ttgtgttgta gggaataagg attaaccttt gtgggaatca 110520
agcaaaaggc ctacaaccaa gtgatatcca aaggatggta acaattaatt cttaagtgca 110580
cattgctttt aattagtata ttcctttgtg tcttttgtag ccacatagga aaaatgaagc 110640
acttgagaat gaacttaaaa gattttacct tgctttggaa aggatctaat tatatggtag 110700
attgcacgtt catattttta tattatgaca atctacatgc tttaaattgg ttgtatgtat 110760
cttgtggcat atttcaaatt gattatcgta ttattgccat gacctagaca taaagaggat 110820
tatcccatgt tcttaaatga atagagtgct aagtaagaaa ttcaaattct taaagcactt 110880
accaaaaggg aaattctcta tatgactaga gttgtgagac taatgttttt atctaagtga 110940
tttatgtagt ttcacaacat gagaatgtgt ttcccaaatg gagtgtgcca ttcaacattc 111000
aaagaagatc gaaccaatac tatgtgaagt attcattctt gtttaaattg gttttgagtc 111060
ttctacatta atcactcacc atgctatgaa ttaaacttgc catgtaaact taattaaata 111120
atcatgctac tttcgttttt ttaattgatg ttatgcatga tgcttgtaag ggtaatttag 111180
ttcatatcat gaagtttcct tgttttagta accttcttgt cattcatata ctagaggttg 111240
ctaaatagga aactattgct tgtgttacta atacaatctc ttttaagata tttcatggaa 111300
attcataagt agagattgtg ctctttcaat tggtaaaatc acaagcttta aaaggttaat 111360
cttcacctaa aagaaagatt aggaatgctc aaggcaaagg tatggaacaa attgcttcaa 111420
ttggtagttg atcaatagta gttccttcca agtggcattc tttcaattgg taataatata 111480
ttctatgaaa agaaatgtca atataaaggt taaattcctt ttggcttaaa tttgtaaatt 111540
agtgcatatt gtgaattcac tgctccatgt gcattaattt aaaaggaatt taatttatgt 111600
ctttatgcct cataaatgat gatttgtgtg caattcatat ctaaagatca ccattcatta 111660
aatacttcct tgtactacta atatctcttt tcaaagttct ttttcaacta gtattaaaag 111720

```
gaaaagagat aacaagctaa agaaggaagt ctccacaaat gatgaaaaga agaatactac 111780
gatgacacca ccacagatag taagatcttt caaattggta taacaaatgg tacgctctac 111840
ttggtggtaa gtattcttaa ggataagtta attcattgca aatttgtcat gccttgacca 111900
tgatatgtaa tgtactcctc atgagactct taactgaatt gaaagtgcat gtggcaagtc 111960
attcaaatac ttgatgcaca tatctagtgg gagaacatta tatatcttgt gtcatagaga 112020
ataagtttct cttgagtaag ctatactaag acaatccaaa atggtaaatt tgtatctcat 112080
tcatatggat tgtaatcttt gttttctaaa tagctactct tgatgcagtt taaaatttcc 112140
ttatcgttaa ttctaaaagt gcataagaat ctttttgttg atattcatca catacatatg 112200
cactaacatg gatatgattt ttaaactgta aaaggtacaa ttagtgatcc atactctcta 112260
aattttgaaa acccatattt tgatatttta gaaatctact tcaatcgata tccatatgct 112320
tcacattgaa ttggatcact aagttgtaaa ttccatgcat aacttgtctt tatgatatga 112380
atgcttgtgc gactaacctt gataagctag gtgcacccaa ggtcaagcta ggttcatcat 112440
caagaaggca acataatgat gtatcaagaa aaggagaaaa ggctcctatt cttaactcta 112500
gcttttatct gtgtgattaa atattgactt gaaaccatgt aagatggttg tcaagtatat 112560
ttgggtgcct acacaaagag aaaggtcaca ataaggattg tgtgggtact caaggctctt 112620
cctactaatc tcaaaggacc caattcaaat tgggcaccaa gatatgaagc ttaaacttgt 112680
tttgcaggat cattccttca atggatcaag ttggatgctc gataatgaat gtataaatca 112740
tatttggaga tagtagcaag ggtggtaaca actgaatctc aagtgcaaat tattttcaaa 112800
tcttatctct tttgtgactt gtgtagccac taagggaaaa gaagcacttg aggatataca 112860
tcagttgttg attatgaaat aaaggtctaa ttggaagatg aatgaatatt atcatatggt 112920
gaacaatcca aaattatgtg acgtattctc tatctagtta atttggattt gattcttctt 112980
tattagacac ttaccataat atggattaag tcagcccttt tagacttcat tgaacaacca 113040
tgcatattat ccatgtcatt caaaatatat tgtgcatgag ggttcaagga aatttagtcc 113100
atattatgag gtttctctat tttagcaact cgcttgcctt ccacatataa agggttgcta 113160
aataagaaac tagtgcttgt gctactaatt ccatctcttg tgctgagttt atccatagaa 113220
aatctatgtt aagagatggt gcttgtttta aattggataa atcacaagct taaaggatat 113280
tattcaacta aagtaagatg aagttgataa gaggccaagg tatgaaaact tcctctcctt 113340
cagttgtttt agtattctat ccttagtggg atgtaccata gtataggtta atttccttgc 113400
aatataaaat gttcaacagt gcatataact ttgagatcaa ctatatgtgt gcactagttt 113460
aaaggaattt aatctatcct tttgggtttc aagaatgatg attcattctc catccacata 113520
taaggattat catttgtgaa accctccctt gtttttctaa tgctctcttt tctaagtgtt 113580
tcaataaggt ccttccaagt gttttcaaga tggatttaaa atctacggat ataagagtct 113640
tggttgtttc aatcattgag tttcaattga tctcatatca agtatgatcg aatcaagaaa 113700
agatgaaaga agttcaagat cacttggttg gatgaaatcg taaagagaaa agagatcaca 113760
gtgattcaag aagggagtta ttttttgtc aaccaaataa tgaagatgta gtgacatatt 113820
tatatgatat ccttcattat gaggtttgag gttcatatta gcatgcttta cccttcagga 113880
tttcaattga tatactttca gttcttaaat cttcaattgg tttaattttc atcatctata 113940
taaagcatgt tatgttaagc caagatatag tacaaacatc tcctttaacc tcacattgtt 114000
aatgtgcata agtgtacttt gtgtactctt gcatgcacaa attgagggag agtttagcct 114060
atatcttgtg agactaatga tttctttcaa gttcatgttg tgtagtctca caccttggag 114120
```

```
agcttcaaat gaggatgaat ggttccatag aaatgaaaat gagtttctct tgaacctatc 114180
aagaaaatga gtttctcttg atcgtttgaa gaggatgagt ttctctttga aatgtcaatc 114240
ctatcaaaag ctaagatgga aattcatgat tataatggag accatgtggc gtagaacaaa 114300
ggtgtgtcac tccatgaact attgtattac atttgtgtat ctaggctctt acatgctagt 114360
gtgtgcatgt atatgcaata tcttaagtca catcataagg ttgcacttgt ggtgacgatt 114420
aaagaatctc tagatatttg attaatacct cttgtggtga tatcataagt tagtcttaag 114480
tcatcttagt gaggtatgag tcaaacatgc taacttctca agaatcttga cttaaaatat 114540
tgcatatcat gtctattaat ataccttta attatgagta attccttaaa ttggtacaat 114600
ttcacatttt catactttat ttgtaccaag gttcaaattg taggacttaa tcccctggcc 114660
tcacaagtcc aagtgcataa gctaaacaag tattcatcac ttgtatgcac acatttaggg 114720
ggagaatagt ctataatttg aatctttgag actaacttca tttccaagtc tattatgtgt 114780
gtagtctcga attagaaagg aatcttcggg caaagacaat cgcttccact gcaaattttg 114840
atgggtatca aagattcttt gctccaataa atgtatcttc tatacatttc ataagagaat 114900
gagtttctcc tgtatatgct actccaacgt catctaaaat tggtaaatat gtatcacatc 114960
tttttttatt acaaatatct gaagtagcat aacttataga ttctccttct agaacttaat 115020
tgattaaata gtgcacatgt tccttatgtt gtatgattat attcatatga tacttttta 115080
tgccaatggt actttaaatt gcaaataagt actctcaata ggtatcaatt gaatacatat 115140
atatgtgtgc actaaaactt gaggagaact tagtgtaata tgctattagt gatctattta 115200
tctatcaaat tgtatcaatt ggtgtttttc aattgatatt tttcatacat gatcactagt 115260
tgcataatcc atatttgtgc aattttcatg ttgcctcttg ttgtgataag aaaatgctag 115320
gtgacatcta gactccaggt atcaagattt atctttcagt tagtatgaca atcttcattt 115380
gatatcttgg acctatgtca caattatgcc aacaagagct tgcaaatgaa ttctaaatcc 115440
aacacaagtc tggaaacccc ttgaaaaggt aaaacgcaaa ggtacatcac ttatgacact 115500
tatccattac ctttgtgcca tctaaggatc cctttcatga tagtgtgttc acatcttgct 115560
taaatcataa tttctaccct ttatattctt tgtaaccttt ttggagattt atgacaaagg 115620
gggagaaatt ttgcattaaa gcttatcttt attttagaaa aggggagaaa taattaacaa 115680
aagggggaat cataagaaaa acataagatg aagaaagttg ataagtgcat tccatgtcat 115740
gagcatcacg tttattttat gacacactgc accctatgaa tagtatgata taagttgtct 115800
atactttgac ctaaatatgt gcttttggca tttgagtaca aaagtgttat tttctgaaat 115860
gcacatgttt agggggagga aactatatca taggattcaa aatcttattt atcaaatctt 115920
atgtaagctt taaatgtgtt gtcatcaatc accaaaaagg gggagattga aagtgcattc 115980
atccctttg tgagttttgg tgatttggat aacaacacat ttaaaggtct aacaagtttg 116040
ctaagtgttg aacaggaaat tcagtatgat gaacatactt gaatagtgta taatgatcag 116100
tgaacaaggt tcaacacaag gtgaaataac cagtgagaca atgcaaatgg atataatatg 116160
gtctctatat tggtttgaat atatggacaa gtcctgagaa atcactatgc ataaatatga 116220
tcataataga ggttgaagtg attaagagga ttggtcaagc caaagtgaat aagatatgag 116280
gaatcgtgaa ttggcttgac catattacta ttagtccata tatgaatata tgagaatcaa 116340
actaaagctt gattaatctt aatagttata tctagaagac attcaagcaa ggttcacaat 116400
attgaagaaa tgattctctt aatggatgct caataggatg tgactcaaga atggcttgat 116460
```

```
agggtgaaga tagcaaggaa agggcttcga ggaactaagc gaaggtgaag gccaagcgac 116520
ggcttgtaga ccgaggtacc atggctaagg tgaagaagag agtacttgca ctaagtcgat 116580
gaactaatca gctatgaaga gttacaacat gttgatgcat cagtaaggtg acttgaagcc 116640
atgatttgaa ctcatataag gtgatatggt acaagtcaca gggtttgatt tgagtttgct 116700
tcaaaaggtg agacaaagat gtttgtgatc cttatgaagc aatgccatgg agaaatcaca 116760
catgagacac caatgactca aggagtttac ttcattttat tttatttaac ttgagtatag 116820
gaatcgtcgt actataaagg gggatccaaa aagaaggttg gtgtttgcca aagctcaaac 116880
ctctctattc aaaagctatt tatgaaaagc aaaaatctct ttatcgttct atggttgacc 116940
atggttaggt ttgagaaacc tagagtgttc ttgctgaaaa gcagctgaac ttgttcagct 117000
gcagctgagc ttttcagctg agctggactt cagctgagct gagctccttc agctgcagct 117060
gagcttttca gctgagctgg acttcagctg agctgagctt cttcagctac agctgagctt 117120
ttcagctgag ctgaacttca gctgagttga gcttcttcag ctgcagctga gcttttcagc 117180
tgggctgaac ttcagctgaa ctcaacttca gctgtgaacc tctttgacca tacaccagct 117240
gaacttgcct ccgggcagtt gagctggggt tttctcactc tctggtcaag accggttgaa 117300
ctggtcctga ggggcagttc agctggtctc tgacccctct gacctctgat ctgcagtctg 117360
ccagtcagac tggcaaacag gtcgccagga gctgtcaggg gcggttcaac cgccccccct 117420
gggcggttca actggttttg gtcaactttg actagtctgc ggtcagtctg cgcgtcagtc 117480
tgccagtcag actggcagac aggctgccag gcctgccagg ggaggttcaa ccgccctggg 117540
gggaggttca accggtctca ggcagaaaaa tctgcccaac ggctagtttt gagctccacc 117600
tatatatact acctcctacc tctctcccca aagcagtgag cacgatttga actccatttc 117660
taacccaaga aacacctccc actctctctc acacatctct tgcctctccc atttcaaatc 117720
tttggagaga aatctttgag tgagcttgag agctgcggtt tttgtgctcc atctctaaat 117780
ctctcttgct cttcttcatt cgagctttgg tactacatcg agttctttgt ggattcatta 117840
ctcttggagc ttctagctcc tagacgacta ggtgtctctt gtgagtctcc aaatcttgtg 117900
gaagaccaca agaaagtttg tattacccgc tcgtttgagc aaagattatt gtgtgggctt 117960
gacctttgtg gtcggcaaag ggaggattag ggttgaaaga gacccgactc tttgtgggcg 118020
cctcaacgag gaagtagggc accttggtgg tgtgaccgaa cctcgggata aatcttgtgt 118080
ctcttgtgtt cttattcatt gtgtttgttt gtgtttttcg ttctctcacc cttccgtgga 118140
agatttgttc atatcttttt gttgtgtgga ttttgagaag tgcccttctc agatctacta 118200
ctttgaaccc tgtggatcat ttagaacatc tcatttccaa agttaactag gtgaatttcg 118260
agatcaattc agttttaccc agtttgcttc tagtttttgt tgaaaacgtt ttagcttgcc 118320
tattcacccc cccccctcta ggcaactttc acaatgacat tataatgaca ggaataatga 118380
agttaatctt caatcaacct aggggaaagt ggccagatca gttaaccaaa gtggtgtgga 118440
gccacaacac aacaacatca aggtctacag gctttactcc attcaagtta ttattcggtg 118500
acgaagcaat aactccggag gaagctaaaa ctggatcaat aagagtagta gcttcggcag 118560
aatcaggttc tgaagatgct tattctgtgg aaaaagatgc tttagaaggg attaggcttc 118620
aagctgtgga aaatatcaat aaatatcaag ccgaaacaat caaatggcga gatagaaagg 118680
ttcggctaaa gaatattgag ccaggacatt tggtgcttcg gagagtggcc aacccagaca 118740
cagtgggcaa gttgcagttg aaatgggagg gacctttctt agtagtatct tcgtcaagac 118800
ccggttcata cagattgaag gatatggacg gtaacgacat tcctagatct tggaatgcgg 118860
```

atgagcttcg gcgatattat gtgtaacttg atgtaacttt tttatgtttt ttctttttca 118920
tggcaccctt ttcctttcta aagggggaga aaggttttta atggggccat cgcatgtaat 118980
ttcctttttt agttttataa gagtaaaatc tcccaaagat gtaaatgtaa aagctgagaa 119040
tgcaccatcg agtgcagaaa agtaaaaggc gaagaagctc caaagtcgtt cctaagggaa 119100
tgcagagctt acaacgaaaa gtcaacgctg attccgccaa aagtaaaagg cgaagaagct 119160
ccaaagtcgt tcctcaggga atgcagagct tacagcgaaa aagtcaacgc tgattccgcc 119220
gaaagtaaaa ggcgaagaag ctccaaagtc gttcctaagg gaatgcagag ctgatgtgtg 119280
attgtttcta agaaaataat ggctgagagt atagcttcgg atatgtgttt ggacattcat 119340
ttgcacatca cattacatca tagcatttgc attcataaac attcatccag gcatatgtag 119400
gataatcatc atcatggcat aagtaattgc ttcggtacaa gagaagagct tcttcgcgtg 119460
caaaaaggag agcttcggaa gaaagggaaa tattgttttc tatgcttcgc tgtgtacgaa 119520
aagaagggaa ggtgtttttt cgcctttggc tcaaaaaaga taatttcgtc cacaacaaag 119580
cacctcacat acattaatgg aagggtaaga gcataatcca aggtatgaac agaattcatt 119640
aagcacaagt ttagttacat ttacaaaagt tatctcaaaa gtttcctaag ttcatctaca 119700
gtctactact taatcttcgg gggaccttag cttcggcgtc gttcttttca atcatcggct 119760
tcagcttcgt catcctatat gaattaagtt gttgtaagtc aaaattgagc ttgaaggaag 119820
aggtaagcac aaggtatgat ttcttactgg ttcaaaatga ctccgagctt cgtctccagc 119880
cttttctcgc ccgccttttg tccatatcat tttcacaaat ctattggaaa tacttcgggc 119940
gagatcagga gtgtcatcta ggattgatgg tgataaagtg aaattgggcc tattgacaat 120000
ctttccgtga tcgcagccag cttttaggaa ggctgcagca gtgccccgag aagctaccca 120060
ggcacagaag tcaccgtgcc cagctataac ttcgtcgagc tcgtcaattt caccctcaat 120120
atgttcgaag gtcttcgata aatcttcagc tgagggggtg aatttctcac tgctggctcc 120180
aactgagtga aaaatttttc ttagtcgttg aatgcatctg ttgccaaatt ccaaacattt 120240
ttcttgaagg cccgccaata gtttttttcaa atctgaattt tgttgagctt cggcttcaag 120300
ttttgtatta agttcttgtt tttcttggtc aaactgctca gattggcgga gaagcttcgt 120360
gttcagttct gttatttttg cttcggcttc cgccaataaa ccttcggttg cctggagctc 120420
aaagttcttt ttctcgatag catctgattg ctcctttatt ttgttttcta aattttcaat 120480
tatagcttcg tgtttcttgt cttcagaatc ttgctgcatt ttcaaggctt tgctcaacag 120540
catactctgc acgaaaacaa cctttgttag acatgttttt attattaaag acaataaaag 120600
ggaaaagtag ttcaccttga aattggaata aaataaacta ccaacgatat gttgtcgtcg 120660
gtagcggcta atgtccattt ctagcttcgg aaaaccgata ctctttgaca gagtaccaat 120720
aactttggct ccagtttggt ttcggataca atctaatttc tcatcatcaa tacctccgaa 120780
gaggagtgct cctggtttgt acccgcaaga tttggcatac tctttaagct cttctatttc 120840
gggttctgac aatttttctc caactaaatt ttgaaacatg aaggcttcgt tttctgaagt 120900
ttcatctaca atttccttcc tttttcccga cgctgcggca gtggcctctt cggcggcggt 120960
ggtagcttct tctgcagcca tgtctaacaa tattttgtca atatgttcga ttgtgctctc 121020
caggttcaaa tcttcagctg aggcagcttc ggcagccgcg acctccgaag gtgtgatttc 121080
aatatctgtc ctttcctcag ccgctggtgt cttctgagct gaagctcttg gcggtgtctt 121140
gtcaattacc tctgtcacac cgatgatcct ctgtctcttt actttagtcg ttttctccat 121200
tttttcggac tccttttcct tctgaaaaaa cattgtcagt tgaggcccca atggacttag 121260
cttcgcaggc agggattcag tcattacctt caaaattgtt tccacatcag tggcagaggg 121320
tgatgcgagg gtttcttcct cgtcggatat ttttcgcttc ggagaagacg ctttcctctt 121380
cttcggaatt ttcttttttg gtggttcttt ttcatcttca tttaaggctt cagttatcct 121440
ttttcttttc tggcctccgg cacctttgtt cagattttca tagtcagggt attcaaaacc 121500
caaggcatcc agcactcgat tcagtcttcg cttcggacgg gtgccgaagg ccgcagtcat 121560
caattgatct tctttttgg agtagttgcc aagtatttca ttacacatta cttcaattgt 121620
atccagccac tcttggcaag gtgttttaaa gtatttctta aacttgaaat agtaaggtaa 121680
acgcacaagt tcaccttctt tcttttcccc ctttggcttc ggcatttccc attcttttaa 121740
actaggaaaa accttgaaag ccaaaaactc ctgaaccagg tctcttgtac tgatatgctc 121800
tgcgataatt ctgaattcat ccattgcttt ttgagtagga ccttccggtg tcatgttgca 121860
atgggggcgg gtttctccga agattagttc aagtggactt tgcacaagct tctccttgtc 121920
gtcatcaacc ttgacataga accacttcga cttccagccc gctgcccatt tgcttcggta 121980
gctgattaca ggaaactttg tggttttccg gtaagcgaaa ttatagcaac caaaattgtc 122040
atgcaatcca tcttttctag cctttgtctg atagtgcagt tcgtgaactc gacagaagct 122100
gtccgcaaac ggctccaccg cttggtttcg gagggcccag atataaacgc taagtctaac 122160
aatagcgttg ggagtcagct gatgaaagta gacaccaaac ctcttcagta cctctgcaat 122220
aatcccatgt agggggaacc ttagtccagc ctttagaaag ctcttgaaaa tgacaatttc 122280
atccttctct ggctttgggg tagtctcctc tcccccgaag cgtaatagct tcttctgatt 122340
ctcattaaaa aagcccgact ttaccatttt ggagagatca gccttcgaaa cagtagactt 122400
tccgaagtcc aagtgactgg gcttgcttgg catggcaatc cgataatcgt cttcgggatc 122460
agtttcctca atatcttctc cttccgcttc ggcaactgct tgttctgcct gttttgcatc 122520
atcactggga atcttttccg aagttaccag cccggacctc tgcatcgctt cggagatggg 122580
aacagactcc gaatcttcag tttcgccccc ctcacgctca accctagcgg tagaacgcac 122640
tctggccatt taattctgaa tttgtaaaaa tctaatactt ttttcctccc aagtttttttc 122700
ttctgacgaa gcaggcttca aactggagct tcgttcgatt ccgagagtta agcttcggcg 122760
gtggttaaaa attttggcag caaaacagtg caaatagcaa tgaatgttgt ggtaacttca 122820
cacctactca tctgtttata tagtattgca ggtaggaagg cgaagcgcca ggatttttgc 122880
accaggcggg cacccgctcg cattcactgc aaggtggacc acagagatca aacagtaact 122940
ctgcaaggtg ggaccgctac gcgctgggaa actaaatcgt ttctcgacaa cgagctcagg 123000
gaaggtgttt tttggacctt cggctccccg aagcttaaga gactttttc acggatcaag 123060
ctcgttacga aaaacgatct agcaccgcga aaggggctac tgttgggtct atgcttcggc 123120
gccgaaggtc ttctaggatg aagcggcttt tggctgaagt tgcttgagtg agatggctga 123180
aggttcttca tcatgaagct tcggtattac aaaccgactt aaggatggaa tgacctttta 123240
gtccataaag gtctgggtca atgttgtaaa cttttatgag gggcataatt gtaattcctc 123300
acaggctgtg tcctgtgcct ataaatagtg aacagtattc ctttactgtt cacgcattct 123360
ggctattgta atcgcatctt tcggaaacca atctttgcca aggcagaggt ataattgtat 123420
tcaataattt aatatattaa gtaaatttaa tatttgtgca tgactcgttt atcttttcat 123480
atcctttatc ttatgttatt ttatatgaga atatgattac ggagatctaa ccttcgtaat 123540
tatgtcttca tgaaccttcg tccatggttc attatcctca agggaatatt gtttcatgga 123600

```
cgaaggatgt taatattcaa cattttatgt tgccttgttc ttaattcata gcatttgaga 123660
acaagtcccc aacaggtgtc taaccaacag gaattccacg gtttccagag aagacccatc 123720
ttcttaacgt gggcatgaga ctgtcctcag tggatcatgc taaataatct taccttaatt 123780
taaacataac ttagcaaact aacttgcagt ctagaaacaa aatataaaat atatatagcc 123840
actcgatata gatttcagtt gactgcaaca tatgtcatat gtgaaggcct tttattcaga 123900
aaacagcaaa aagagaagca tgccttgggc atgcgatttt tgttggtcat cctttatatt 123960
ctcatggata tggagatatg gtcaaggatg gaaataaaga attcatgagc atcctgttgc 124020
tcgtagcttg cgaggtttga tgatgcatgc tgccaccaac taaaaaaatc acaatggtac 124080
caataatcag aagaaattta gatacttcta ttcaagaggt agaaagaatc gataggtggc 124140
atactgtttt ctatgctcag tctcatagaa gaatagagaa attatgctaa tcatggaatt 124200
catatggtcc cgatatcctc aaacatgggg actgtaataa aatccatcta gcaaagacca 124260
agttccccag aatacctaca aactcatctg gccaactgtt acctgcactg aatttgctga 124320
tttgtgtgca ttttatcact ttttatatat ttttagacag tttaatggct gctaagcatg 124380
acagatgact taagccgtta ggcccaaata ggtcaacttg agagctcaaa tgggaacgta 124440
tctggtgctc aaaggggtac gatgttcata tgcatatttt aaatctggtg catccatcat 124500
gcattcaacg gcaccagcta attttacgaa aaactccttc catcatggga ggaaggtgga 124560
aggggtgctt cacaaaattg gtgctgctgt taaatgtaaa atagatgcac cagatttaaa 124620
atatgcacat gaacatcata accctttgaa caccagatac gttccttaac gctacatgtt 124680
cggtatggga tcagggatag gatgccatgt taccaaccaa ttgtcacgta ttgagatgtg 124740
tgactgttcc cccttttttc taatagcgtt acaataacat actctctccg tccaaaacta 124800
aaatttattt tagttaatta atatgtccac acaataatta atttatgtgt ctatatttac 124860
cattatctat tcgttttagc tcttgatttt tacgtctata tttaaaggta tgacgataaa 124920
tctagataga tatacaaaac acatacatta attactgcgt atatctattt aaagcctaaa 124980
acgaatttta attttaggca gagggtgtac attatttagt gattattttt ttagtccggc 125040
cagatcggtc atgatcaaat ctgaaccgaa cgaagaccaa tcggtccctg tcttcggagc 125100
cgaaaacttg taaaatgccc ttatagttac atatgctgaa atcttcgtgc cattccgcta 125160
cttctagaaa tggtcgtaga ttgtacagtc atccaagtcg ttgtagtata gtggtaagta 125220
tttccgcctg tcacgcggac gacccgggtt cgatccccgg caacggcgat ttttttatta 125280
tcactcggta ttctcgcttc aacttttgag acccgttgtt accgatccta ggccgcattt 125340
acttcagctt tttttgctcg gtgtagtgta tctgcatatt tcattgcatc agactttgaa 125400
tatacccatg tacatgtggt aatatatctc aaaaaactac tctcgctcgg tattctcgct 125460
tcaacttttg agacccgttg ttcccgatcc taggccgcat ttacttcagc tttttttgct 125520
cggtgtagtg tatctgcata tttcattgca tcagactttg aatataccca tgtacatgtg 125580
gtaatatatc tcaaaaaact actctcgctc ggtattctcg cttcaacttt tgagacccgt 125640
tgttcccgat cctaggccgc atttacttca gctttttttg ctcggtgtag tgtatctgca 125700
tatttcattg catcagactt tgaatatacc catgtacatg tggtaatata tctcaaaaac 125760
tactctcgct cggtattctc gcttcaactt ttgagacccg ttgttcccga tcctaggccg 125820
catttacttc agcttttttt gctcggtgta gtgtatctgc atatttcatt gcatcagact 125880
ttgaatatac ccatgtacat gtggtaatat atctcaaaaa actactctcg ctcggtattc 125940
```

```
tcgcttcaac ttttgagacc cgttgttccc gatcctaggc cgcatttact tcagcttttt 126000
ttgctcggtg tagtgtatct gcatatttca ttgcatcaga ctttgaatat acccatgtac 126060
atgtggtaat atatctcaaa aacctactct cgctcggtat tctcgcttca acttttgaga 126120
cccgttgttc ccgatcctag gccgcattta cttcagcttt ttttgctcgg tgtagtgtat 126180
ctgcatattt cattgcatca gactttgaat atacccatgt acatgtggta atatatctca 126240
aaaacctact ctcgctcggt attctcgctt caacttttga gacccgttgt tcccgatcct 126300
aggccgcatt tacttcagct ttttttgctc ggtgtagtgt atctgcatat ttcattgcat 126360
cagactttga atatacccat gtacatgtgg taatatatct caaaaaccta ctctcgctcg 126420
attcctagct caagtgctca accaccactg cctcttggca gcagagaatc ctagctcctc 126480
tcgcaacaac tccagcttct taataaaacc gccagtgaaa atgctatttt tactggtggt 126540
tgtttaagaa aaccgccagt gaaaatgcta tttccactgg tggttgttga ataaccgcca 126600
atggaaaatg acgattttca ctagccccta gcactgacgg cactgaaaaa cgccagtgaa 126660
aacagtttta ggactgtcac tatagttttt ctgtgtacta gtgagattca cgctaaaaaa 126720
atcacgtaca tgcatatata ctatcaggct cacgcgctac cctagtaggc tggtacaact 126780
atacaatatg tcaatctata cgcatttgct aaacatctga gaaccaaact ttgcacgcta 126840
tgtcacgatg acaaggcggc gctgcagagt gttagctttc agaaagaaca ggccttcttc 126900
aaccgagtat aagaatgtcc ttggcctccc tcaacctcgg cgtccacgac cgtaccagga 126960
ggcgcgttgt gcctgcatgt agaagcacga tgtgcggtta cactgagggt gcattaacca 127020
gattgcccgc gaaaaagctc aatgacgaca gttgattcag atcaaacatt agccagattg 127080
catcagtcat gtagaaatag tccctcgact ctcaaaactg tcatacacag gtgtttcact 127140
catttcactg tggtttgact acacttgacc ttctagttga cgcagacaag gcctcagggc 127200
caagcagaga gcgggccaag ctcatcacta attaccggtt gccactgtga gaaggctcag 127260
aggctgacaa gtggctgtca ctcgcgagct cgtgatgatt ggggacccca cacgggccag 127320
gacccggttg ccactgtgcg aaggctcaga ggctgacaag tagggctgac aatgggctgt 127380
aaattttgca ctataagatt taaggatcaa atcggattag gatcgggttt tatttctagt 127440
catttttgaa ctataattta tttagggcct tgacattttg tgaagaacca tatggatcac 127500
aatccattac caccttact gacaagtggc tgctggttca ttcagacaaa gcacacgata 127560
atcgtgccgt gctctagctt ttggaacaac tagctcgcct cggaaagcgt gccgaggatg 127620
ttaattaccg ggtgaattag tcaatcaatg tcaagggagg ggggcatttt gtcgtctgat 127680
gggacctcaa gcagtcgctc accgttggcc cgttgccgcg ccacttgtgt ttgttgagct 127740
tgcagttgca cctgcacact tgctctctcc tcacactcag ctctgcaccg cgaccgctcc 127800
gctcgccacg ccacgccacg gtctcgtgag gccggcgccc ggagccagcg ggccatgttc 127860
accgacggca tgtcgaggct ggcggtggcg gtgagcgtca cggtggcgtt cagcctggcc 127920
atcttcctca ccatcctagt gctcctcctc gcggacctca tctgcgcgca cctccggcgc 127980
cggcggctcc gcgccgaggc gtcctggtcg aagctcggcc tggcgctggc gacgccgccg 128040
tccccggcgc gcgacgccgc cgcgtcgtcg tcacgcgagg cgttcgccgg cacgccgccc 128100
ttctactacg cgcacggcgt cctgcacgcg cccagcacca aggacctcct cgtcgccatc 128160
cccaggctgg agggcgccgt gtggcggtgg tcgccgccgc cgccgtcgcg ctcgggctcg 128220
tcgggagcca cctcggcgtg cggcgacgcg ttcatgtgca tctccaaccc ggtgtacgac 128280
cgagggcaga ccgcggccgc cggcggtggg gagacgccgc cgttcgagac gccgggctcg 128340
```

tcgccgtacg gggtcacgga ggaggaggcg tgcgcgtacg acgagaagga tgccggcggg 128400
ttctcgccgc cgctgtcggc tatgaggaag ctcccgccgt tgggcgtcct ggccgcgtac 128460
cccccgccgg cgctgagctt cgccgatggc gggccgtcgc cgcaggcaac ggtgggcgac 128520
accaaccggg cctcctcctc ctcatcgtcc gcccactttt tctcttattg gtcgtcgaag 128580
taagagatca cttgtaccgt gcgcgaatgt agtaaagctc tgcagctcga tcccattcat 128640
caatcatcat cgttttggcc atttttcctc gttcagtcat atcatcatca tcatctgcta 128700
ttattgcaca ttccatctct aacgtctggg cgtgcggaaa ccagagcttt tggtcggtgt 128760
tttttcaaga aaggaaacta taaacagttg gtgaatagcg caccgtgtgc tgagttcttg 128820
catgcactct cagcaaccgg agcatcggta caaaaggcag aagggcctcg tcatgctcgt 128880
gctgtgatga ggcgtagagg ccgacatcgg ctcagtgggt cctgacatca aacccaagaa 128940
cactgttagg tgtttggttc cagaggccaa aatttaatac gttgtcacat tgaaagtttt 129000
aatctttatt ataaatatta aatgtaatct aattattatt tagtttttat ctatataatt 129060
agttttataa ttaaactacg tttgagaaaa cgtttcagac tgttgttgcc cacgcctcga 129120
cacactcgtt gtatactgga taacctttta tgcgtgatgt gtccacaagg aaacaatacg 129180
ccgttgctcc ttgccgttgt ttaggtggtg ttgcttgaga gacaggtttg atctggaagc 129240
gtttccatcc agtgtacaag aaccgtgggg gtcaggttag caaaagctgg tgtcttccaa 129300
aacagctcag cctctttaca agaaccgtgg gggtcaggtc agatttgctt gtggcatttg 129360
aaagaggctc aacaagatgg caagttggca atgtaaaaaa aaaaagatag ttgctaccag 129420
cgttttcatt catgtagaga cggttgatga ttctgagcta atttttcatt gtattcgacg 129480
cacttagggc tagtttggga gccacaaatc cgaaagaaaa ttgaattcca ttccagtttt 129540
gtggctccaa aactaacact tagggcttct ttggtcacaa gggaattgag acggattgag 129600
gagaaaatca actaatttttg tctttaatcc tatccaatcc ccttgtcacc aaacaagaca 129660
ttatcatgaa tcttttcact aatatggtct ggtttagtaa tagtagaatt aaaggagatt 129720
aagggcttat aaggttaggg agtccctttc tagttaaaat taaataagaa ggatttaatc 129780
ctcttcaatc tcctacgatc cttttgtaac caaacaaggc ccgagggggga aggaaagccc 129840 cttaattcct tccaaaccag tcataaagca agtgcatttc ccgcttagat catttgaata 129900
atcgtgattt agacatagat caattaatct aatatggatt gaccatatga taaagatatt 129960
tatgcggcaa cattctactg tagaagaatc aaatgaagaa cgtgttataa attgtagagt 130020
agataaatat cttggttcaa cataaaatta attttcatct ctcatcctaa tctaagatag 130080
ccttatatct aaacttttga aaaagcggtg gaatgtaaat tttcacgaca aatagtctat 130140
tttattaagt aaattccaat tcattattag atttggtgta gctctggccc tgtttactcg 130200
ctttcaaaaa aaaacagagg ttttatactt ttaaaaaaca aaacgtctac acgcaagaag 130260
cccataggcc atatagccca gacgtgtaat gagccatcgg gaagcagacg tgggcacgta 130320
gcccatgggc catggctcgt gcgtggatgc tggagcctgg aggcaagcaa cggccgagtc 130380
gggccgcaac ggaagcgccg gcagcgacag tctgcagtct gcgggcgccg ccttgagtgt 130440
gcacgctagc ctgcaatcac tgcatgacct tcccgcttcg actggcatgc tactagcaga 130500
ccgggctcgt gatgcaactt taacgtcggc ccaataagcg gctttcggga gcagagcaga 130560
gcagcggcac ggggccgtgg accgggggag caagctgcag ctcgaaccgc ccgccgtccg 130620
cagactgtta ctgttacatc gtcggtcacc gtctggactg tacgggacgg cacgggtccg 130680
ccgcgaatcc actccacggc agtggctgag tgcgacgggg ttggtggcca gagcagcaga 130740
gcgaggctgc tggtccaaag ggcctgcag gtgctgtgac atgctcggtg ggcgcgtggc 130800
cgaaagctga acggctgggt cgtcgaacga cccgcggtgg tcagttgcag cagtaattgc 130860
tcagttgacc cgttgtgtat gcatgcatgc atatgcgtgg gatcacgcac cgcggaaatg 130920
agcgggccca cccacagcca caggtaaagc gagattcccg tgacaggcgc tttcagatta 130980
gtagattaca gtgtgcttgc catcgcctgc attgcttggt ccaaaaggct cacgggaggg 131040
gcggagggag cagcaacata ccaaattttt ttttaaaaaa aaaacatacc aattttgtat 131100
gaagtcatgt gaacacaaac tttgtaccaa agtttttctt tgaaaaaaca taccaactta 131160
ataatgccta accattattc acgctaaaca gtcgcttagt agggtgaaac gattatttta 131220
atgggatgaa cggttgatta aaagaacccg ggtgtagtac cgtgtaccgc cgtgtgcaaa 131280
cggtgtgtta aatagactaa aactaaacga tgttttagac aaacagtgag tataagaaat 131340
atcagtatct tttaatatat aaatctgatt aactttttac cctgctgctc catgcgccgg 131400
cagaggcgct gtgttacagt gtgtgaagtt ctctcttttg acaagggttg ggtacggttc 131460
gaagtttgaa actggggtcg gtgggtccca gcagtcaggc actcaggcta cttgtgtaat 131520
aactgctgac acatgacttt tgcagacaat gctacagtgc tactaaaata gtctactccg 131580
tagaagaaat tgccatgcgg ctcgggagtc gggagtcaat gggtgaacca gaaactgtcc 131640
aacggcgaga cgccaaaatg cacgccctac actgtcctgt ccgtccgtcc acgcctcaca 131700
cggtacgcag cttttacgca ggcagcgcgc gtccatgtct gatgcagagc ctgacgtctc 131760
ctctcgccgg ccttcctgtg tcactatttg tatgagcgga gggagaagta gccggctacc 131820
tcgacggaaa accccagcag gatttctgga tgatgcttgg tggatgaaag gcaaggcacg 131880
taaagccatg catcatgcac cacctaaagt cttagcagta cgaagcagac gagacgaccg 131940
gtaagccaaa gcagaagaag aagataagca tgcgtgccct gttttataca cttgttgtgt 132000
tgatgctgag aggattcttg cctttcaatg gtattggtgg cacaccaaca caacactgcg 132060
ctcttgcatc gcattctagc cagccagtgc ccgctcgcct actgctctca ccttctttac 132120
gttcccgcta gggaagggaa tggcagatgg gcgcagcagc agcagcccat agctagcgcg 132180
tatccaccag ctagcaattt ttcttttgaa agaaaaaaaa acaatctttt ttaccaggca 132240
ggttacagcg tgcatctgtc agaatatgtt ggctcgttga gacggattaa taataagaga 132300
gtgagtttgt tgtcgacgtg tgtgtgtgtg tgtgtggggc caaatcacag tggacgcagg 132360
aggaatgatc cggtgcatat gcttttacag taatcactag ccagcaccaa caacaattat 132420
agagacaaat ccaaaccctc agccagctct ctgaagaact ggtcaaaagg taattaatat 132480
gcacaggcag cacactagca cagcacagag cggcagagga taacacagtg gtggagggcg 132540
ctactacaca ctattctgga taatatggga gagcaggaaa ccctttcgtc tgaacttact 132600
gaaacaagaa aatcaagaag aaaaaaaagg catccattca gtgattggtg agcgagcaga 132660
gcaggtgacg atcgaggtga ggtgaaagaa aaaagctggc accgcattta ggcgaggttc 132720
tttacgtaat ttagcccaaa gtggcaacaa cggggaaaaa aggtaaagac catggcggat 132780
cgccggcgca tccttccacc ggccgtatat tcgccccggc ccccggggtg gagggaggac 132840
ggacggacga ggagcacgag tcccggtcag aaaagcagcg aagcacgcgc cagatcgaca 132900
gcgcagcgca gcgcaggcat ccgcatcaac gggagcggag taggcctcgg gctcgggacg 132960
ttttacccga aaaccgcgcg aaaaaaacag cctctttgct tcatgagcgg cgtggctgac 133020
gagcagcgtc tttcctgttg attaattaga caaattccaa attaaattcc aaatataaat 133080

```
catgaccaaa tcagaagaac tgaaataaaa gccaaatcag atgatgcgta ctgattagac 133140
ttactgattg ttggcgcgcg ccaggatcag ctgggtcgac gatgtcagaa gatcacgagc 133200
agtcgcgtga agacgcttcc caaaaacctt attcgccctc tcccggtgca ggatctagaa 133260
gacgaagggt tccggagacc tgctctcctg atcgcagatg cacctctgcg gtcgggacga 133320
agggaactaa aaggcggctc agctatgaag agaggcgaaa gcgaactggg atctgggatt 133380
atttggaggc tggctgccgg gctcctttta tagggccgag tccgcgaccc cagtgcttat 133440
ccgcccacga aaatctcgca atcagttgag attttatagg gatcggttag gataagcgta 133500
acagccaaga aaccaaaaaa tcaaacggca aaaggtagcc gcgcccccgc aaggcgaggg 133560
gccggatttc ggcggaccat tcgcgcgcat gtcgtgcgcc cgcgcccttc gccccgcccc 133620
gccccgcccc ggcccggccc ggccaggcca ggcgaggcga gcgagcgcgc gcgcgcgtgt 133680
ggctctccac actctctcct ctcatccatg acttggtgag tgagtgtggc ttccatattt 133740
aagttagctc tactccacaa gagctagcaa tatggtgcta ttggttccac ctatcccttt 133800
gccatccact tatatgggct tttgagattt tcctgggatt tatttgaata acttaattgg 133860
gccaagccca taaatcctaa caatccccca ccagatctca aatgcccatc tgcagttttc 133920
gccactgttc actactgttt aatatactag tttttcagca gagactgtta agttgaactt 133980
ccgcctagaa ctccaagtta caccaaccca caacttggac aatggactat gccttgaatt 134040
gcaagttttg cgtgaatggg tttcacttga agtcatgact agtacttggc taccagtagt 134100
ccccttctcg ggtggagcat atacgtcgta ctccaaggtc tcttcatgag tttactagag 134160
atcacccaga tctcatagac tgcgacgtta gacagtctaa ctcatatagg tgtgttcttt 134220
caaagaatgt tctgcaggac aacatcttcg ctaatacaag ccaacagaac acattaaggc 134280
acaaagccaa cctgccttac agcatttgag agtattgcat ctttacttag agagggtcaa 134340
aagttactct cctcagttca ccaatggctt gttcttccca ggacctaatt cacgggatct 134400
ccgatcacat agactgggtt tccaccatgg caactttatt cgggtctcat acccatctct 134460
ctcgatgcga tttctatcac attacgtggt agtcccttgg taaaaggatc tgccagattt 134520
ttatctgttg aaatataagt cacacttata actccggagt ttctcaactt tctgacagac 134580
ttcaatcgtc ttttgacatg tcttgatgac tttccattat ccttagaact cgtcacttta 134640
gcaatcactg tctgattgtc acagttcata aggatagctg gtattggttt ctcaaccacc 134700
ggcaagtcca tcaagagttc acgcaaccat tctgcctcaa cggttgctgt gtcaagtgca 134760
gctagctcgg cttccatggt tgacctcgtc aaaatggtct gcttgcatga cctccatgat 134820
accgcacctc caccaatagt aaagacataa ccactggtgg cataaagctc gtctgcatca 134880
gatatccagt tcgaatcact atatccttca agtactgcat gctgaccaga atagtgaatt 134940
ccataactca ttgtaccttg caggtagcgc ataacccgct caagtgcatg ccaatgatca 135000
gtcccggggt ttgacatgaa cctactcaat ttgctcacag caaacgagat atcgggcctt 135060
gttgcaccag caagatacat gagtgaaccg acaatctgag agtatctcaa ttggtctaaa 135120
ccaattctct tgttctttcg cagtgtcaca ctgggatcat aaggagttgg agaaggtttg 135180
cactcagaga agccaaatcg cttcaaaacc ttttcaacat agtgagattg cgagagagta 135240
atcccaccat ctgccttaat cagcttgatg tttagaatca catcagcttc tcccagatct 135300
ttcatatcaa aactctttga tagaaaagac ttgacttcat tgatcacatc aatgtttgtg 135360
ccaaatatca atatatcatc aacatataag cacaatataa ctccttcgcc cccaccacag 135420
```

cgataatata cacacctgtc tgcctcatta atggcaaagc ctgcagacgt tagagtagtg 135480
tcaaacttct catgccactg ctttggtgct tgcttcagac catacaaaga tttcaataac 135540
ttgcacacct tgctttcttg accctttact acaaatccat caggctgttc catatagatt 135600
tcctcgtcca gctctccatt aagaaaagct gtctttacat ccatctgatg aacaaggaga 135660
ccatacgagg cagccaaaga aagtagtact cgaatagtgg tcattctagc aacaggtgag 135720
taagtatcaa agaagtcttc tccttctttc tgagtatagc ctttagccac aagcctagcc 135780
ttgtactttt caattgtacc atcaggcttg agcttctttt taaacaccca cttacaaccc 135840
acgggtttgc atccataggg tcgatcagtg acttcccacg taccatttga aagaatagag 135900
tccatctcat tatgaactgc ttctttccaa tcatctgcat ctggagatgc aaatgcttct 135960
gcaatggtag taggagtatc gtccacaagg tacacaatga aatcattacc aaaggatttt 136020
tcaacccttt gtctcttgct ccttttagga gcatcattgt catcctcctc taggacaatt 136080
tcatgtggct gttcaaaact ctcaataggt gtattatgtt caggaattat ctcagaagag 136140
tatctagaat tgctatgaat gtctttcatt ggaaatatat gctcaaagaa agtagcatca 136200
cgtgattcca taatagtatc aacatacaca tcaggaactt cagatttaac tactaaaaat 136260
ctatatgcta tgctacacga agcatatcca agaaagacac aatccactgt ccttggacca 136320
agcttgcgct ttttattaat tggtacattg actttcgcca tgcacccccca agtgcgcaag 136380
tatgaaagtg atggttttct cccaacccac ttctcataag ggttttctc ttctttgccc 136440
ataggaattc tattcagaac atgacatgaa gtcaggactg cctcccccca ccatgcctta 136500
gataaaccac aagtgtctaa catggcattc accaggtcag tcaacgtacg gtttttcctt 136560
tcagcaatcc cgtttgactc gggtgaatag ggaggagtcc tctcatgaat aatgccatgt 136620
tctgcacaga aatcatcaaa gactttggga aagaactcgc caccacgatc tgatctaaga 136680
cgtttgatct ttctctctag ttggttttca acctcagcct tatagatttt aaagtagtct 136740
aaagcctcat ctttagtttt tagcaagtat acatagcaaa atctagacgc atcatcaatc 136800
aatgtcatga agtatctctt accacctttt gtcaacacac cattcatctc acaaagatca 136860
gaatgtatga gttctagtgg tgccaggtgt ctctcctcag cagccttatg aggctttcga 136920
ggttgcttcg actgcacaca actatggcac ttagaacctt tgactatggt gatattcgga 136980
attaaactca tggttgcaag ccgagacata gagccaaaat taatatgaca caaacgagaa 137040
tgccaaatac tcgcaagatc atcaacattt gcacaaatat ggttcacaga cttattattg 137100
aaatctaaca aagaaaagcg gaacaagcct ccgcaatcat agcctttacc aataaattgt 137160
ccagacttgg acacaactaa cttattggac tctaaaacta ccttgaaccc atctctacat 137220
agaagggttc cgctaacgag attcttgtgt atagaaggga catgatgcac gttcttcagc 137280
tgcacgatct ttcccgaagt aaacttcaga tccaccgtgc cagtgccatg aacagaagca 137340
tgtgacccat tccccattag cacggaagaa tcccgggcgc cctgataaga agagaacaag 137400
ttgatgtcag aacacacatg aacattagca ccagtatcaa gccaccagct aggtgattga 137460
aatactgaga agatgaaagg taaattacca taccctttgt cttcctcatt gctagcgacc 137520
actgtgttga cattgccctt tttgccacgg cgatccgctc gatcgggaca atccttggca 137580
aaatgacccg cctcgccaca tccgaaacat gtcannnnnn nnnnnnnnnn nnnnnnnnnn 137640
nnnnnnnnnn nnnnnnnnnn nnnnnnnnnn nnnnnnnnnn nnnnnnnnnn nnnnnnnnnn 137700
nnnnnnnnnn nnnnctgcct ccccccacca tgcattagat aaaccacaag tgtctaacat 137760
ggcattcacc aggtcagtca acgtacggtt tttcctttca gcaatcccgt ttgactcggg 137820
tgaataggga ggagtcctct catgaataat gccatgttct gcacagaaat cgtcaaagac 137880
tttgggaaag aactcgccac cacgatctga tctaagacgt ttgatctttc tctctagttg 137940
gttttcaact tcagccttat agattttaaa gtagtctaaa gcctcatctt tagtttttag 138000
caagtataca tagcaaaatc tagacgcatc atcaatcaat gtcatgaagt atcttttacc 138060
accttttgtc aacacaccat tcatctcaca aagatcagaa tgtatgagtt ctagtggtgc 138120
caggtgtctc tcctcagcag ccttatgagg ctttcgaggt tgcttcgact gcacacaact 138180
atggcactta gaacctttga ctatggtgat attcggaatt aaactcatgg ttgcaagccg 138240
agacatagag ccaaaattaa tatgacacaa acgagaatgc caaatactcg caagatcatc 138300
aacattagca caaatatggt tcacagactt attattgaaa tctaacaaag aaaagcggaa 138360
caagcctccg caatcatagc ctttaccaat aaattgtcca gacttggaca caactaattt 138420
attggactct aaaactacct tgaacccatc tctacataga agggttccgc taacgagatt 138480
cttgtgtata gaagggacat gatgcacgtt cttcagctgc acgatctttc ccgaagtaaa 138540
cttcagatcc accgtgccag tgccatgaac agaagcatgt gacccattcc ccattagcac 138600
ggaagaatcc cgggcgccct gataagaaga gaacaagttg atgtcagaac acacatgaac 138660
attagcacca gtatcaagcc accagctagg tgattgaaat actgagaaga tgaaaggtaa 138720
attaccatac cctttgtctt cctcattgct agcgaccact gtgttgacat tgcccttttt 138780
gccacggcga tccgctcgat cgggacaatc cttggcaaaa tgacccgcct cgccacatgc 138840
gaaacatgtc aattcagcct tgttcttctt cttcttgaag ttggtagttt tgttgggctt 138900
gttagatttt ggctttcctt tgcccttgtt gtggttcttc tgaaccatgt tggcgctgga 138960
gtggccctcg cctcctttag atcccgtgtc cttagcccga gctttctcct caacatccag 139020
agacgctatc agattttcaa ctgatatctc ctgtctctta tgtttcagag ctgtggcgaa 139080
gttcctccat gtagaaggca actttgcaat aatgcatccg gccacaaatc ggtcaggaag 139140
gactatctta aggtggtcga gctccttggc tatacactgt atttcatgag cttgctctac 139200
aatagagcga ttatcaacca tcttataatc atgaaagctc tccatgatat acaggtcact 139260
gccagcatct gatgcaccat acttagtagt aagtgcatcc cacaactgtt tcccgtctgt 139320
gtactgcata ttcgcatcaa ccagacggtc aacaagggcg ctaagaacgg ctcccgtgaa 139380
catagtattg gcatggtcgt actctttctc ctgttcagga gtcagtggac cctcaggtct 139440
gcctttacta acatggaaga cattcatagc agtaagccag agcgtggcct tgacttgcca 139500
tctcttaaag tgcataccat taaacttttc tggcttcagc gcgtcggcaa aagcagccat 139560
agaaaaacta ggaaattgtc tacaataagg tttttggatt gttgattaat tagacaaatt 139620
ccaaattaaa ttccgaatat aaatcatgac caaatcagaa gaactgaaat aaaagccaaa 139680
tcagatgatg cgtactgatt agacttactg attgttggcg cgcgccagga tcagctgggt 139740
cgacgatgtc agaagatcac gagcagtcgc gtgaagacgc ttcccaaaaa ccttattcgc 139800
cctctcccgg tgcaggatct agaagacgaa gggttccaga gacctgctct cctgatcgca 139860
gatgcacctc tgcggtcggg acgaagggaa ctaaaaggcg gctcagctat gaagagaggc 139920
gaaagcgaac tgggatctgg gattatttgg aggctggctg ccgggctcct tttatagggc 139980
cgagtccgcg accccagtgc ttatccgccc acgaaaatct cgcaatcagt tgagatttta 140040
tagggatcgg ttaggataag cgtaacagcc aagaaaccaa aaaatcaaac ggcaaaaggt 140100
agccgcgccc ccgcaaggcg aggggccgga tttcggcgga ccattcgcgc gcatgtcgtg 140160

```
cgcccttcgc cccgccccgc cccgccccgg cccggcccgg cccggccagg cgagcgagcg 140220
cgcgcgcgcg tgtggctctc cacactctct cctctcatcc atgacttggt gagtgagtgt 140280
ggcttccata tttaagttag ctctactcca caagagctag caatatggtg ctattggttc 140340
cacctatccc tttgccatcc acttatatgg gcttttgaga ttttcctggg atttatttga 140400
ataacttaat tgggccaagc ccataaatcc taacatttcc gtgctgtttg tgcagttgaa 140460
cgcatgatcg acctcacacg tcgctggtgg gaacacgaaa ggaactgaag aaacgcagcg 140520
agaatggtgg tggtaccgta cgtacgtggt gggttcagac tgcctccgtg atcttctttc 140580
tttttgacct gttttctgct tgaacaaggc aagttatttt gtggtggcac ttgatgtgcg 140640
gtccacattt taagcatcgc cgcccgccag aatataagca cctgacaacc attgccctgg 140700
ggcaaccaaa gcccatacag cgcgcttgat tagttgccag gaaatgacgc ttgattagca 140760
ggtgaaaaaa caaaatcacc agaggctcca gcacagctca cgagttgatg catatataat 140820
gaatggcgcg cggcttgttc tgaaacaact cgctttcatg atttttttctc atgagctgac 140880
aaatgtgcag cagctagctg cacacgatcc aactaaacat actactacta ctatctcatg 140940
gcacttgggt tacacccgga ggtattcaat gcgaaggatg ctactccgag acaagaaaag 141000
aaaaagataa attcaatgcg atgcaaggga tgagctcatg agcatgagca tagcagccat 141060
catccatcct gatgctgcgc tgtccaagtg cagtgtatgc aaaggatgag agagagaagg 141120
ataggccttg ctgtcgtagt gctgctgctg caactgcaag gctccaaaac caaatgggtc 141180
aggcgcaggg aggtcatgtg aaagacaaca cgatacaggc ctctaacctt tggtccttca 141240
tgtgaggtca ggttattaat aaggtcatca gttattttat aacccaccct tcgttttaaa 141300
ctctagtcta cagaatatag cctgtagtat aaaacattgc tttatatgtt tttacacaag 141360
tccatctagt gatcttatac tcctgctaat tctaatgggg gcgcatttaa ggggttttta 141420
ttagtgggga ggaaaaggac ccttgcaaag gcctagaaga gagagagaga gtgagtgcct 141480
ggatgtgggg aagagggaga aataaataaa cccgaattca gccaaacctc tctctcccac 141540
ctcctgtcac caccaccaca cccctcctcc tcccctgtct ttctccctct ccctcttgac 141600
aaaatttcct ccacccattc tcttcctcct cttcttcccc accgactcca ccgatccacc 141660
tctttctatc tgaatttcct ctcgtcttgc ccaccgctcc atctgtctgt tgcctctctc 141720
tctcgcaacc aatcggttct tgtttcctcc gtctgctggg ttgattctct ctctcttcct 141780
ctccgtggag aggagaggat cgagaaacag gagacaggaa agaagagaaa tcagaacgga 141840
gcctgttctt ttgcctggat tgcggttctc gcgagttgtt cagaaactct gggccagttt 141900
ctggtacggt ttgttgcatc tctctgttaa actgcctttt tttgtatttc tagttatatc 141960
tcttgatttt gcatagcgaa acaatccctt gtttgttgtt tcaatccatg attccttcgc 142020
aaatatgcgt tttttttcct cgctgattcc ttcacgtttc aatccacagt acttgtacat 142080
ggagcggcct tggtacggct ctcgttaagc tgtcaataat tcttgtcttc cccgaagcaa 142140
aattcccaac ttccatgttt gaaaaaaaac actttttttct ttcgtttgct cgcggtacag 142200
agatagatgg atgtactggg cgtgttcttg gttcagttaa aaacctctta tctgctcccg 142260
tatttcgttt tcgtcatcgc agagggaatc gatccttctc ttggaaatag tggatggcta 142320
ctcccacctt ttccctttat atttttgctt cttttactgc gtccttttca ccttttgcaa 142380
aaccgatagg gaagggaaat aaatacaaaa gagaaaaaaa acattgtgag cgagcgtcca 142440
caggagcaac gggccccatc ctgcatgcgg tccatctgtt taggtcgcat gcattgtaca 142500
ttcaccgtgc tttgcttcac ccattaaaat gcatgcatca ccacagcttt ttgctcgcaa 142560
```

cagcaacccg aaccatcaag tttggtgcac gcgtacgcca caccaaatgc gcctaatgcc 142620
aagattccta cagtcggatt agttgccaat accctgatta gttgctgcct actacagtaa 142680
tgtgtgagag caaaacaggt gcagctgctt ccatagagta acaacccaga gtagaattac 142740
aatatttttg gagtgcagac aacagttcct tgtatgtaga gttgacatat tttggtggca 142800
aatgttgaag gaatagccta gataaagcgt agccccgttc tatatcccgt tcatttcagt 142860
ccttttcttg tgttccaata aagttggagc acagctctgt tgcccaaaat gtttgatgtg 142920
ttacttacaa ctggcaggtc ctttaaaata ctggaacgag gaaccatcag agatgctaag 142980
gcaacagacc aattgatgtt atctcgctac cctagtttgg atcatcacaa tgcaaggaca 143040
gaggaattct gtggagcatt ttgctgatgt ttttggattc gacattgcat ctagttcagg 143100
caaccctgtg atggatcagc agtcatattg gaacaatgtt cttggatcag tagaatcgca 143160
gaatcttcaa ggttatcaga tgaatcacag tgatgctgcc atgccatatg ggaatgagac 143220
acagcaagat ggtacatttc ttggtttctg ggaatcaggc gaagcaagtg caagtggcag 143280
ctctaacaat gccaaaacag agcatcttag tattggcggt ggtctgagga ttggtgaaag 143340
gcgactggta gctgacaatg gcatttctct ggatgtggat atcaacctta acgccaacgt 143400
taacgatcta tgtggtcaaa gttcaaatgt taactgtaca tctcagggcc ctgagcacta 143460
tggtggcggt gatcgtagtg ttgtaaattc tcagccaact gacctgagat tacacccata 143520
caggactttc ctactagatg cagagcaagc agattctttt actttgaacc ctagtgaaaa 143580
ccctttgtgt gatttttcac tgatgcaaga aagcattgac caaagacccg gtagttccct 143640
ggatggacgc cggctagcct gcaagagaaa aaatgttgaa ggacccaatg gccagagttc 143700
agcaggtgct agcactagtt tttcccacag gaacgacaat gctttccata acattgcttc 143760
ttcaagttac aatcctgcac ctatcagaaa tccgtcctca cccaattgct tgccggttcc 143820
aagttctatc gatgatcaac tcccacgata tggaactaat gcagggctct cagccggtac 143880
ctatgacctt aatggagggg tcaacaatgc tgggaattcg cagagaagtt tccgggcaag 143940
aattactacg tctcaacaga ttgctccctg tagtgtatgg ccctcttcaa atgctatcag 144000
acttcctaat tcatggaatc atcagccacc tcattttcaa agtgcatttg atgataccca 144060
ggaggttatt cctgtggtca gcagcctcaa cttgcaatac cagcatccag tgaatgtttc 144120
tagtgtgcca ccggctgcaa accgtttcac tggccatgga gcttcatcat cgagagctgg 144180
cagtttggag aacagaattc ttggtagtca agaggctcct acaaggaatg tggtgcctgc 144240
caactactct gatttagttc ccccgtctgt agtagacccg agacgtttgc tgccagaacc 144300
atctaattgg agttctgatg tccgaggcac tgcaatatca ggaagtattc ctcctgtatc 144360
aagagctaat aacagtgcaa ctgttaatcc gccagcagga ttcagtcacc aaaacctcac 144420
ccggcgccat cctcgaaatt tatcagaggt atttttttcc tccatttttc gcatttggtt 144480
ttctctattt ttggattttg gttttcagtt tgattgctca tcttcccacc aaaatatcaa 144540
gtgacgccat acttaaaatt tggtttgatc atcttctcga tttgatcttt tattttctta 144600
taggagattg gtcggctatc tggagcactt cgcggccatc aacccccacg cttaaggccg 144660
gggtttctgt tggagcgcca gggcgatggt gtttggggtg ttcctttatc aacaaggggt 144720
agagaaggaa gaaggttaat ggaggtaaga tgatcggttc tgttcaaaaa aatggttttt 144780
agcatccact tggaaacata aaagtccatc attattaggt gttttttgtg tggcagcaaa 144840
gattacacta aatcatcctc taatttatga atttatgctt gcaaaggccc cccttgtttt 144900
cagttatcct tgtcatcttt gtgtttgcct atctaagcaa attaccctat tctattccca 144960
caccaaattg gtagaactgc tctactcgaa atgctttatt tcattttgtt tgtgcacttc 145020
ataatcccta atttgatcta gcatgcttct tcatgcccct gcaactcttg aaatactgaa 145080
attttttat catttatttc cacatattat cacactgccg gttgttgtat cttttacttt 145140
ttttctaaga tattttcact agtattgtta tagagaaact tgaaccttaa tgatatgttt 145200
caccttatgt ttttatgcaa aatactgcac tattttatcc tttttgttcc ctagccttgc 145260
ttgttcttgc ttgcgttaac tactgtgacc atcatgtaaa ggtgcatggt tccttgtctt 145320
atgacaatcc aagtttactt gtcaacagat tcggaatgca cttgaaatga tccatagagg 145380
ggagaatgta aggcttgagg tcagtactag caatgtccat ctgagttttt ttaactctgt 145440
ttgctaccat tatatcgaca tgccactaaa ataaacaaaa gtaaaattgt tctttgtgga 145500
ttgttctttt tttttgctgg acgtggttaa gttatgattg gctggttagt acaatcgtac 145560
ttcagcataa tattgtgtta agcctgccag cctgtgttac cctgtaatta aaattccaat 145620
ttaaaatagc atggtaagaa aagaaaaaca tgactataat cgtaaacata ccatacctac 145680
agctgtcagc agaaaactaa ggactaatat caactaccgc ataagtttaa gcatataaca 145740
gaaacacaga tataagtgac aatgaattgc ctcctgtgat ctactgtagt ccaaaactac 145800
tatttgttag ttggtaggag gtttatattt aatttgctta aaattaatgg gtcaacatgt 145860
agcaaactag taatctgaaa gttcagtact tgtagataga aaatcatgaa tcccatgagt 145920
gtacagcacg aagaaaaaat aaaactgaat gaattcaaaa gttttgggtg cccttgagtt 145980
tttacctgct agtacttgat atatttcctt cttacgccaa atgtattctt gaacagtcta 146040
tcttctatgg cggtgttgac attcacgata gacacaggga catgcgcctt gacattgaca 146100
atatgtccta tgaggtttgt gttccttagt gaagcattac ctgcaccttt gcgaatctaa 146160
aatctaatct aagatggttg ccctactttc aggagctatt agcactcgag gaaagaatag 146220
gaaatgtcgg cactggcctc agcgaggaag ctgtgataag gttgctcaaa caaaggaaat 146280
tttcatcttg gacactaaaa gcatctttgg accctgaacc atgttgtatc tgccaggtat 146340
ttcatatact cccgagcatc tcagaatcat ggcttgttct tttgccgtag gtagatacac 146400
caatcgcatt gaatgattga attgggcatt caggtgtttt tggttcacat atttgtagcg 146460
tgaacggtaa tcggtaacgt taaaccatgt ttgtttaagt ccaaccgtaa tcgaatacca 146520
cactagaaat tgataccgtc ctattcaaac ttgttaccga tggtaatcga gtgtaaatca 146580
ttaccgttgc catttatgtt acatttcgtg aaccaaacgg cacctcagtt aggtcaccta 146640
ggccatcatc acgtgtacaa agcaatgcag cacttaacta aattggccca caaatattag 146700
aagggcaagt taagtctaaa agttgctaag cttgtctact tataccatct aggcctccaa 146760
tggagaatca taccctggta ggtctctgga tttctacaaa ttaacggttt gaaatggtag 146820
aactaagaat atttgtctca tcccttgaga tttccatgct attgatcttg gttcctagtg 146880
tctcaggaaa gaattacaat ccgactctag catgacttcc atcggatcac taaaaaagac 146940
tacttaggcc ttgttcgttt acatcggatt gtacccggaa tcgttccgat taatcaaagt 147000
ttatataaat tatagaagca atccggctcg gaattattcc gacccaccaa tccgacacaa 147060
acgaacaagc ccttaaggtg atagtgtaga ggactaggca taatgcgtgc gtttaatttg 147120
cacggaacct ttcagggaaa aaaatattta gttcagaggg ttggagggca agatgcctct 147180
cgggatacat atgtcagtac gagattacaa tgtcctaacg gccaaatata ctcaacactg 147240
ttaacctttt ttatagggtg gctaataaaa aataacatca actctggcaa caaaacctgt 147300
agcatagaac tgtctattta atcaggattt ccattgtcga tgtaaatcat gtacaccagt 147360
atctgttatc tgctgtgaat ttaattcctt tttgcctatg aacatgtccc agcgtcacct 147420
tatagagcaa tgaaattagc agttgaacga ggctaatata tatacctacc ttatgtcctt 147480
tttatccctg tccaggagga gtacgctgat ggagacgacc tcgggaagct ggactgcggg 147540
cacgacttcc acgctggctg catcaagcaa tggctggtgg tgaagaacgt gtgccccatc 147600
tgcaagagca ccgcattgaa gaagacctga aacccgaaca aaggctcgtg tcagagacat 147660
cccccatgtt tctatgttca ctcgatggtt cgcgagatca tttgccgatt cgtattgcta 147720
cgcttttttt tttttggtcg ggaaaatttt gccagccacc ttttggttaa tgtctttcct 147780
gcttgatgta gtgaatttgg actatgcctg atagttgtcc ttgacctgaa tcaggttggt 147840
gtgtgggtgt ttcatgtttg gttgctgtga tagctggtac gaacaatgta tttctgttat 147900
gcaagtaata gaaatgaagt ttctccggtc aaaaaaaaaa ggtggaggaa cgattcatat 147960
cgtacggaca ttctgatgat cattactagc tccgtagctc gaactgaaac agcatgtcac 148020
tgtactaaac tattttatgt gctggaactg aaacccgcct cgctgtcgtt gctccggacc 148080
ggaccacgtc gttcgcggta ctgctgccgg catgttcgcg cgctagcctc cgtcctccgc 148140
cttcgcgcgc cgcccatggc tcgcaggccc atggaaatct cgcacgcacg cacgacagct 148200
ggtcagctgc cagtcgcctt ggcatcgggg caagtgcctg cgccgttgag ctgctgctaa 148260
caaagctaca cagacggtac tttgtcatgc tcatatgcag cgctcgcata cagcgccgtt 148320
gaaacatgat gacgcgcgcc cgctaagact cccgtagtcc cgttgccttt gccttcactt 148380
cccttttccc tttccgatgt ggtgggtggc ctaacaacac ccacccaatt acccaaatcg 148440
ccccatgcaa atgcaacgcg agcatcaccg gcagcaggca ggggcactgc tcacccaccc 148500
tgaccctcgg cgaccgctat cccggttcgt taggcgttag cgactggcca cgatgagctg 148560
gcagtgggag gctggtccat gattgcaccc atgcagtcct cagctaactg gctgccggcc 148620
gcccggcgca cgaacgaagt gacgaggaag cgggccagcc gacctaacgc ggcggattcg 148680
cgcaccagcc gacagctaac tgcgttggta agccaagcca aggcgggggg cgatgccgac 148740
ggaacgaaac aactggatca tgccaaagcg ggcggcgggg ggagattagt ttatggtgca 148800
actcaggcgg caaagatatt aatcgctgtc aagcaaggcc gattcgaata atcatactgc 148860
tagtagtaga actagtagtg agagagggtg atgatgactt gtttttctta tcgctgttac 148920
agctgtcctt tttgacattt tggaaagacc gccgcttgtg gccgcctccc tccgtctccg 148980
cctgccctgc ccctgcctgc ccgcccgcca cgccgcccct gctgctgctg gcctgctgcc 149040
ttcgtgctta tccacaacgt acccaaaagg ccaaaaccct cgccgcaccg ccctcccgcc 149100
cgccgaccat ccggtcgtcg aggacggata ggataggata ggcaggcggc cgggtcagct 149160
ggatcgtcgt gtacgtacgt acgtacgtgg ggacggtcgg acggagacga caacggcatg 149220
ctgcgtcgtg ggattgggaa taaccgataa cggacgtcgt cgttgaacct cgccttgcgg 149280
tgcctgctgc tcagctctct cgctcgcttg tcactcggcg tcggagctct cggggctcgg 149340
cgcacggttc agatccgggt tcttgacgcg cccgctccac gcaggccgct gcggcttctg 149400
ctcctcttcc tcctgctgct cctccgcgtg cacccgcagc tgcggcaggt ggttgtggtg 149460
cctatggcgc tcgcggtggt gcggcggcgg gaccaccatg ccggtctgga gcgcgtccac 149520
gcgggacccc acctcgatgg ccttcttccg tatggacgcc gcggacagcg tgcagccgcc 149580
gccgccgccg gcggcggcgg cggccgggtc gcgcgcgtgc tcccccacgt ccacgccatc 149640
cgccagcccg aacgagggga tctcctcggg gaagttgagc cgcgccgacc gcccgcgcag 149700
gtagaacacg gccgtgtcgt aggcgcgcgc cgccgccacg gccgtggcgt aggaccccag 149760
ccagatgcgc gtgcgcttgt gcggctcccg gatctccgcc acccacttgc cccacttgcg 149820
catgcgcacg ccgcggtact gccgccgcgg ctgcgtctgc tggtgcgccg cccccagctg 149880
cggcgccgcc atcgccgcct gctccgcctc catcttcacc gccgcggccg ccagaggagc 149940
catggctgcg gctgcggcaa cagcggccgc agccgactcc tcgatggaag accggtactc 150000
gccctgcatc atcaacagct caagccgcaa gccgccgcct ttgctggctg ccgctgccgc 150060
ctccccctct ttctctctct ctctctctcc tgctgggggc tgtgcaggca ggcgcagcag 150120
cagtggtatc tgcagctgct tttggcggtg gcgtggtttt cttggcttcc cttccctgtc 150180
tctctgtttg ctgggcgagt atttgtattg ggattttgtg ggtcgaaggg gggatgagtt 150240
gggcggaagg cgtcgacgac accccctgta ctgtgctgtg ctgtttggaa gggagctctc 150300
accgccggca cacaaattgt taggtccacc ggctaacttg catccggtgc ccatccactg 150360
ccaacgggct aactatatat gactggttcc aaactgcggg tacgtatctc cggctatgtt 150420
gtattattct cttatatcga ccctaattat ctaccatagt catataacct tcgtcacctc 150480
ttatatatcg tagttatcta acgcacagtc ttcaatctca tcttacaatc atctcaacac 150540
cacgttaact tttcttttac gtacttatag ttgacataaa catattattt tatttaaata 150600
aaaatacatt tgattacata attaagcaaa taaaattaca taatccattt aaaatttaaa 150660
agtacatggc ttaaaccaaa aaaaaataca caattcgtta atataactat aaactactag 150720
tcctcctcct catcttcctc tcctacctcg tgcaccgatt ctttatattc taatttataa 150780
gttgctttat caatcttttt ttcatagcta acttatagtc ttttatcttg tcttccttca 150840
tatcagtaat aaaacgatct ggtagtttgt taaattacta ccacaaagca actccaatag 150900
ttctataaaa aaagagcttg ataaaatcat gtttagcaag ttacaaaata gctatccaaa 150960
gtaaaagtaa catagtctcc gatagctgct catatttagg gagtaattcg attttcaatc 151020
tagctttggc agccctgcac ctatcagatc aggctgacgg tagggttgga agcagaggat 151080
gtcgagggca gaagagaaaa aggccggtcg acatgacata tggaggagtg atggtccgct 151140
gacacaacct atgggacagt aaggtccaac ggtaaaggag aaacttatgc caaacgtgtt 151200
tgacctagct atatcactgt gctagaaagt ggaaaacgag cttgctatac cttgctacct 151260
cactgtgtgg aaaatggaaa aaataatcat gccagtgtga agaaattgac gtcaggtgca 151320
tttaaggagc tcctatcgag ttgccaaata tagagattat atagagttga cagcaactaa 151380
ctaattagca agtctattta gagaaccatt ttttctgttt aattattaaa tttaagacga 151440
tttagagagt tgtttagaga actattagag ttactctaag gagctctaac agcttgtcca 151500
taccttcttg gttagggacc ctactgtata acaacgagac aaagaaggaa aggtaatggt 151560
tgtggtagag aaatggcgag aggaaaaaga gattagtagg aaagaggggt ggggacgtac 151620
gtgtacatta gaatctgagc tacagaaatt ttgcgctgaa cctaggtagg tttctgccac 151680
gtagaatata aaaggtgaat tgatgtacac aggcctagct gtggacggag ccacggaagc 151740
gatcccgtga agaagcttac ctgttgggca cactggttaa ttgcgtcagc attggatggg 151800
tttacgaaca gcgacaattt acaatctaga aagaaaggtg aagacaataa tgtcaagaac 151860
caaattggcg tggatacgat acgagcatct ggttgtcaca atcacaacgc acccccaccc 151920
cacccgctcg ctctcctccc tgctcgtcac caacccatgt gcacacctgt cgcctcaccg 151980
ttgccctgct gaccctaaac gtttcgttca ctagttccca ggacagaatg cgtggcggat 152040
tgaccctaac gtggtgcgta cctctggcta cgtgtgttgg aggacggaat aatggcgtct 152100
gggcccggcg atgtttcttg gaatgatctg ggacgaggag tacgtgcttc cgtacggagc 152160
cgtcgtcgct ccactcagtc accacacaag taaaaacctg gtcgatgctg cgtggtttcg 152220
ccgtttgaaa cttttggttt ggattgaagc tacgcagtcc gcagccaaga ctactttttt 152280
ttttatgctg cgtggttttt ttaagtaaat aacgtggtcg cagcatgacg acgctcctga 152340
taattgcctt gccgccatgc tgtgcttttt taggtgggca gggcagatag gtgccgccac 152400
cgacccgggc gcgccgctcg cgtgcataat ttgctgcggg gggaatagct ggcccggctt 152460
tcctcctctc ctgcccgcga ctccaaaccc aaaaaatcat gcaaatctaa agccgagagc 152520
tgtcggtttc ctacgagaga cctgctgctc tgctctcgag acgccagggc atcgccagta 152580
gtacccaatc atcagcgcca gcaagcaagc aagcaagcgc gcggctcgtc gtcgtcggcg 152640
gcaggtcgta cgtacaccgg gcagtggggt tttggatcca gcggcggcag ggcagcacgg 152700
gggacggaca aacacgacgt gtcgctgggg cgcggtcggc cggcggggcc ttcacctcgc 152760
cctacctgga ccacatgcac gaggctcgag ctcgataggt ggacaataac gttgtagtcc 152820
tatagtacga gcggtgtatg tagctgtagg ctagctagcg gctagggcgc cggtagtggt 152880
gcctcaacgt cgatcgcgcc cccgagctat agcctgtgtg gtgcggcggt gccggccagt 152940
gcaaatagga ttgtccaact catcttcttc ttccttgctc gtttcatctc tccttcgcac 153000
tcggcgatgc cggccactac tgtagtcgcc acgtcctagc taatgttcct caagacatca 153060
acgcgcctag ctagctagct aattccctat ttttctgtcc cacgcagagt tttttttac 153120
ttggcacaac agtggcatct ggcacgtatg ggcagcatgt caacgatatt gatttcatcg 153180
cagtcaacag taccacccac tgtgcagccg tgcaggacaa agaaacgtca ctgtatccgc 153240
agacgaaagt agtacgggcc ggtagtactt ctctgttgga gattacacga gtggacaggg 153300
aaagagaaaa aaaaaacccc gtcactctga tcaactggta cggcgcaggt cagcagcgat 153360
ggtgtagtgg atggtggatg ccgggattgg aggtggtcat cggctcaccg ggtgctttgg 153420
ccgtcgtttg ttaggttcag ccggcggagg aggagagcga gacaaacagg gcacgggcac 153480
atgtccaggc gccgtacgtt tggtgcacgt accgatttgg ccaacccccc acaaccaacc 153540
gccgttgcgt tgcgtccatc ggcctcgctc gcaccggcac cgccgacatg aggtgggcgg 153600
gcgggcggct ccaggtccag gtggcgtcgt cggggtgatg cgcgccgacg tggagacgtg 153660
gccccttcct tcttctacgc aaaatccccc acccacccac ccacccccat ccatccacac 153720
ctcctcttcc taatccggac gcgggacgtc aatttgcttg ccagcagcga cggcatcggc 153780
cgcccgcctt gtatctaatc taaccccgta atcattcacg ctaacgacgc ccgtggcggg 153840
gttagcgtag gcagcggccc ggctggctgt ggctgtctct gtctgcttgg aagttggacc 153900
acggtgcggc gcgtaggggc ccggccagct ggtgctgtcg tctgcccgct cgcgtggtcg 153960
cgtttatttc tcggtcggcg cgggcaagcg ctcctctacc gggtccggat ccggacggta 154020
gctagagggc gcagttgctg caggtcggtg gccgagggcg ggcgagtcgt atacgtcgcg 154080
gagagctgga tcggagttgg gtgtgcaggt aggtaggtgt gcgcccgccc cagcagactt 154140
cagatatctg ggatgacgtg gggagttctg ttgggtccgt ccggcccgcc gtacgtagta 154200
cgccagctcg ctgcttgtct gtactagagt gaccagccga gctcgcgacg ggtactggat 154260
gccggtccgt accgtaccgg tggtaaacag cgcatgcagt gcatttcagc tagctagatc 154320
cagtactagt agttttaact atatattcgt cgtaccagat cagaggcata gctggtcccc 154380

```
gcctccccgg acaggtaaac tgcttccatc tgtttccatc ggaggcggcc ctggcgtggc 154440
agtggcactg gcactggctc tggctgcctc gccatgcaac gcaacgatta tacgtgtgcg 154500
cgtcgagctg catattctag ttgtaccggc aggcagttca agtgtcgaac gatctcagac 154560
accaaaccga gatccaagtg acggcgaacg gagctgcccc cgcctgccca gcccagacgg 154620
cctgcatagc tgccgccagg cccaggcgcg accggccgca gcgcgccgac aaggaaccat 154680
gctggctgac tagctcgatc gagcggagca tgcggaccat aaatggccaa atagactgtg 154740
cctaacgggg ccggtccgaa gcacgacccg tttaatagtg ctgggccaag ttcagcacga 154800
gaattgtact gtgcttgggc cgctgccttg gtccgcagtg cggcccggcc cggcccggca 154860
cgactatata ttttctattt tataaaatat agtatatata tttacatttt atatttgcta 154920
tttacaacaa atgtactaga gttctattga ttagtctctt ttagttaatg ttttcagcct 154980
tgtaaagaga ggtcgcgggt tcaaattctc actcacacac agtttttttt gctattttcc 155040
ttgatttaat tggagaacgt ggccagttaa cgggccggcc tggcacgact accatggcat 155100
gcgggccggc cgagcatggc ccgattatct atcgggccta acgggcccgt gctgggccgg 155160
gctgtgccac ccgtttgggc acctataatg ctgacaatgc aggttgatag tttcaaggag 155220
caatagctga gctagacaca cacacagttt tttgctattt tccttaattt aatgggagaa 155280
cgtgaccagt taacgggccg gctcagcacg actaccaggc cggcgtgccg tgcctgggcc 155340
gcggcacgcg ggccagccgg gcacggccca attattcgtc ggatctaacg ggcccgtgct 155400
gggccgggcc gggccatccg tttaggcacc tataatacgg acactgcagg ttgatagttc 155460
aaaggaggaa tagctgagct agccaagcca tgcatgtcca tgtccatggg gcctgtactg 155520
cgcgacgatg ctcctcagct gctgtctcgc tgcttgccct caggggcacg acgttatcag 155580
tagcctcggt ccgtgaagca gggagcgcga gcccttccac ggctacgacc tacgacctga 155640
actccgatcc gaataccaca ctgatcccaa cacatgtttt ccgttgatcg ctagaagcca 155700
ccgcccactc gcccaggcta tcttcagctt cgattccatg tgtcttctgc atgatgaaaa 155760
ggttgggccc ccgcccgcct ggatccgttt ccgtgcatga ttagatgcag tgcaggccct 155820
gaaaattgct gttttcttct gacaaatcgt cacaggcaca ggcggccggc cggccgcagt 155880
ccgctggtcg ccttgcgcag agatgccatg ccacgggctg gccggcgcgg ggaggggagg 155940
ggccggacgg gggaacgggc cccccatgac aagcctcctg cagtcctgtc gatatgatgt 156000
ggagcaaacc aggacagccg ccagcagatg aacgcagagt gggcagcact ctctttgtgt 156060
gtgtgtgtgt gtggtggcat cttgccgtct tgcatggatc catcatggtc ggtggctgga 156120
ccgtcggagg gcaccgcacc atagatagag gagcattgca ttcacgatat cacagaagag 156180
gctgcccagg ccggtggtaa agctaggtga cgaggaaaat gatgcatggc caagtgctgc 156240
agacagagag ggcgtgtttg cgaccctgtg cctgactagt tcggcccgtt caactggtcc 156300
aggctaagat tagtctgtcc cagcttccgc aacttactat atttgcgcat ttgtatcata 156360
tgagactcag agactggctc agacgagctg gtgtttgtca cccagtatgt agccgggtta 156420
gaagactaaa actacctaac cgtggaatcc ttgcgccacg accagccagg ctcccagaaa 156480
acggaccttc atctcgtttc tgtggagcca ggctgagaga ctaaacttgc acgcggacag 156540
ccaggctccc gatcaagtca ggccaacgca aatacgagaa ctgcagcctg agagcgcagc 156600
caggctgctg ggccatggcg gcaaacacac agagtcgtcc tcttacactc ggcactttcg 156660
gtgcaggtgc tgaggtgttg acccggcgaa cgagcgagcg aggcccctcc cgccgacgcg 156720
ggcaagcgat cgagaaaaaa gcctgaatcg agaacggttg gtgctgctgg tcgacgacca 156780
```

```
ctgtttcctt ttcctacgct acgactagcg tttggtgcat ggcagtacgc cagtacccgt 156840
gcgtgaccga cctggttttg tgctgattaa ggacttgttc gtttacgtcg gattggtggg 156900
tcggaacaat tccgaaccgg attgcttctc taatttatat aaactttgat taactggaac 156960
gattccggat gtaatccgat gtaaacgaaa agacctaagg ctgcgttcgt ttgtttagga 157020
ttggggcagg aatggttcca ggtgatcaaa acctatacaa attagataag cattcctggt 157080
tggattggtt ctaggtcacg attccggaac aaacgaacac accctaaggc cttcttcgtt 157140
tgtgtcggat tgtaactgaa atcgttccag caaatcaaag tttatataaa ttagagaagc 157200
aatccaatta gaaatctttt cgacccacac caatccggca caaacgaaca agacctaagt 157260
ctttgttctt ttgtaccaca ttgcataaaa aattatttca gttaattaaa gtttatataa 157320
attagataag cactaatctc aaacaaccga acggcaccta cggaagatag ggaaaagcgg 157380
tgtccggctc atgcctcccg tctactgttg gcctcatcaa gcctgtcgcc ctgcccggcc 157440
aagagaccga gaggactgct tcttgcttct tggagcgtga tatatcctct gatgggttgg 157500
gtgtgtaagt gtggtctgac tcgtgcgagc ctggtccact ggaaacaggc cgttccttac 157560
gtatatgtgc atgtaattag gagagatgtt tcaggcttaa gctgcagccg cgggtgcagc 157620
cttggcgccg tgtaagcagg caaccaaacg agagtcgcag catggtcaac acatacacag 157680
aggctgaatg ggcaggtgca gacgtccaat cacgcgacta gtgtttgctc ccctgcctgt 157740
cactagcagt gtggcttagt gctaggaata tgtgttagtt tttgtttggg ccagcacaca 157800
tgacctaaaa atagaagcgt aaaacacatc ccacaataaa ataatatgaa tcgaatgcgg 157860
gcctaggtcg ggccctatgt tctagcccat cggaacccga catcgatttt taaatttatt 157920
tgatttagta aggtacagaa tttatattgt tgtaacatag ctacaaactt taggaccgga 157980
attgaccatt atttctactc tttagacagg caacgaaacg actcaaactt ttcttttagg 158040
taggggtggg cacattttta ccttaaaccg aaccaaaacg aaatttcggt agttcggttc 158100
agtttcggtt ttttatatca gaagttcgtt ttttactgta taccgaaccg aaataccaaa 158160
aaaccaaaaa ccaaacttta tcaattctaa aatttgacta tttgattatg tgaactaaat 158220
gtgtgaatca attaaattgt tattcactta tttatatgtg atgtatgatg tatctctgaa 158280
tatttgtacc tatataattt ttacttttga aaattatgtg taatctatca tgtaaacttg 158340
ttgtatgtgt tgtcttagta taagtttggt attcggtttt taccaaaaac caaaaccaaa 158400
gtaagaaatc gaaactgaac ttctcgattt ttttatttta gagaaaacga tcgatttcta 158460
atgtctagaa aaatcaaagt tttttaaaac cgaaaatccg aacccaagtt taaaaaaacg 158520
aatgtccaac tctactttta tgtcttcttg gcccaagaca caatggactt gggcgggtcc 158580
ggttcggcct tcccagcact agtgtgctcc cggccttagg ctggtcgcag tcgcgagctg 158640
taaaagctcc cctaagattt tacagtggac gcgggagctg cagcggtaaa ctgtaccgat 158700
gactgcacat gtatagagga caccgaaaac tctatattca gcgcttgcac tctctcactc 158760
tatatacggg gctgtcggtg tggggcccag tgacagccgg tatgggtgcg gacaaccggt 158820
agttgagaag tgggaaaaag taatataata tgtggtagtt ggtatagagt tgagatatag 158880
agtaaacatg actgcagagg attgtggtat agagtagata atcttgctga cggggataaa 158940
atattctttt taaagtagaa atttagagta gtatgagtgc ggatagcctt acgaatatgg 159000
tacacggtac atacaggcta ggtggcggcc acggccgggg gcggtgtgta tgtgtatcgt 159060
catcatgctt tcgccgttac ctacgcggct acgcataggt aaaatatagg ctatgtttgg 159120
```

tttctttagt ctagagacta aagtttaatt agaagactaa agtttagtct ctaacatgtt 159180
tggttataga ggctaaaaat agtaagaata tattaaatga cttataagaa aactaaaatg 159240
acctttaaca ttctactact attagtacaa ttgaactaaa tgagtgataa atgtggaatt 159300
aatatggttt agtccctact aaagactaaa tcattttagt ttatatttaa tcctagtgtt 159360
tggcaaaaaa aggactaaat gagactaaaa actagaaact aatctttagt ccctctaacc 159420
aaacacccca tagtcggagt tatagaggaa aaaacatttt ttctgtattg tttaatataa 159480
aaacacatac tgtactagat aaagaaaaca catagtcttc cgttggtaat tgattgagtg 159540
agtttatttt tagaacaaat ggtcggaaat tatatgcacg acggtatgaa gtccgtgacc 159600
caaggggaat ggatcaggct tcccactttc ctagtccacg gcgcgtggtg cagtacagct 159660
acgggtgata gacaagtgac aacgatagtt attactatat atatacacga tactttagta 159720
ttcccggacg acaaaccatg tagaatgaat gatattgaac cgatttgaat acatagcaaa 159780
ttaaaaaata ttttaattta ttctaataca atttaattta tatggaattg aaataactga 159840
acaagacctt aatacagagc aagtaagtcg aaactagcat ggcatgacta tttggatttg 159900
ccgtgggtgg agatggctct ttatttgtag ccacagctgg ccactaggca atgccgtcaa 159960
ggccggcgtc aacaaaaata aaggtgatga tggacaatgt tgccttgtct tggttgggtc 160020
cctactgact aggacgtact gacaatgcag atgcaggctt gcagcgcaac tcgtaaactt 160080
tggataggaa taggagagaa tatatatccg taccgagaag aaaagttgtt agtacgtgat 160140
gaacagcgtc aacaggggca cgccgagccg tcctggtcct ggtccaggtc cagcccatgc 160200
ttcgtcctcc cgtgttctgt gcatcagaca cttgttgcag agtcagcatg tgcatccatg 160260
gctaccggta ctgaggtaca cgttgtaata gccatgttta atatctattg catgcgctcg 160320
cccccacgta cttctcgctc ctgcaccaac actcctgttt accgccacat tgactatata 160380
tcatgatagc gttaaaaacc ttatactcag acttaggagg tggaaaggag aaaatgggga 160440
agtgggccgc aggattagga gttgggccag aagggttctc tctttgtcac acccggcttt 160500
aaggaacaaa gccgggtgca tctcatacat gcgccaagaa gacaacatat ataataacag 160560
agtgtataga gataaatgtc ataaaacatc agagtattta ttacatagcg gaagacttat 160620
tacaaaataa aagataaaag taaaacgaac taaggatcgt cggcgccaat gtcgactggg 160680
aaacgccacc tagatcagat cgaactcctc agtgttaggc ggctcctcct gaaccacctg 160740
ctcttctcct gtgggggggt gtgagacagc aagggtgagc tcacacatga tcatagctca 160800
acaagttgtg gggaaccggt ggacataaac tcacaaaggt gtgaggtcat gtgatgtgta 160860
aggctaatca atgatagggg ttaaagctga gcattgcttt taagtagttg gtcaaaattt 160920
tattagcagt tactaagtat aagtgaatac caaaccttag ataaagtaat tgaacaaaat 160980
taataataga cccatgcaat gcaaatgaca aaattgaatt taagttccat aatttaaaca 161040
tcagagagtc ctgagccgct catgaccgcg agcacggcta gtatactagt tttacactct 161100
gcagaggttg taccctttac ccacaagtca tgctacccat ctgccaaggg gtcgtgaatc 161160
ccatacacct ctacctagga agcgcggcag ggcaacacta cgaggccttt acaaagttcc 161220
actagcttcc gaaaacccgc tacagtttat aagaagttcc aatgcagggt tcttgtctga 161280
ccgccatcgc agcaaaatca accaaggacc tccctacact gaccactccc ctactgccct 161340
tgcccctttc gggtaaggta gtcttccact agctttccta atttgtcttc caagggcgtc 161400
ccattaaacc cttgtggtgg cacgtgtacg aatcaagctg attcatcaga atcggannnn 161460
nnnnnnnnnn nnnnnnnnnn nnnnnnnnnn nnnnnnnnnn nnnnnnnnnn nnnnnnnnnn 161520
nnnnnnnnnn nnnnnnnnnn nnnnnnnnnn nnnnnnagaa tcctagagat ttcgtccacc 161580
cgaccgcgag tgacaggagc gggcacgcac gagttgcgaa aaaaaaatgc gcggggtcac 161640
tgcaagcagg cggggacgga aggcacgggt gcggtgccca acggcgacag atgccgcacc 161700
cactccccta ctcaggtgac cgcggaaacc cgttaatccg cccggtggcg cacgtctttc 161760
tctctctagt actggctatg ggtcgagctt tcttcggcgg cagcggagtt ctcccaccga 161820
cgaggctaca caatcaactg tggtgcgagg caggggttca tttggtgggc caagataccg 161880
agcggcgcgc tacttatgcg cccaggccaa tccgcataag tcggcacacg atgtaacgac 161940
catccgatac ccgcggcggt gacggcgaga tctctgcaat agaatccaga gcggtcctgg 162000
gctcggcgga agtgatagtc acgcggcgta gagaacgcga gttctgttac ggcgaagggg 162060
aaggaactga caacctgggc ccgcctgcaa gtcgccacag cacgcgcatc tggaatgtgg 162120
cccccaccat cggcgcagag ggaagaggct ggcaccaacg gcccaccggt cggcacacgg 162180
tctaatccgt tcttttgggc tgtgcgcatt tgcctggtgg gcctactggc caggaagact 162240
tcgcgcgtgc gcaccagtcg cagacaagtg gacccgtgtt gccagggtca tcttcccctg 162300
attgccgctg gcgtgaaacg ggtctccaaa gtcgccgccg ctttactcgc cgatgaatcg 162360
cgcgcgtagt tgtaacagcc gccgcgttga tcggaggatc aggtcgagat ttgccccctc 162420
aacctgggta caaagacccc gggcgcgtcg cgagaactgt tgaccacccc gagcgcgatc 162480
tctggcacgc ggaacccgcg cgtcgtcgcc taactccgcc gagttcagag ctaagccgcc 162540
gcaaccgcgc atgccacaat ctgcgctggc ccatgacctg accgaactct gcgcgtcgtg 162600
atcctcacct tctatatctg cggaccgacc ccctcctttc ctctcccttt ccccattgcc 162660
accgtgcgcc attgcgaaag aaagtagccg ccgtacttgt tcccagacca ccgcgccacc 162720
cgtggccgaa ttggagtgca gggagtttcg cctgacacca ctggagccgc tcatcacatc 162780
gctggacgag aagggcccct ggacctccat aattgctcga cggaggccgc ttctgccgcc 162840
aaaccccgtc gtcggctctt acatggctcc ccggtaagat tgccccccatt gagttcgtcg 162900
tatctccacg acgaatctcc tagatctnnn nnnnnnnnnn nnnnnnnnnn nnnnnnnnnn 162960
nnnnnnnnnn nnnnnnnnnn nnnnnnnnnn nnnnnnnnnn nnnnnnnnnn nnnnnnnnnn 163020
nnnnnnnatg aatctagaga ttcgtacctt atactcagac ttaggaggtg gaaggagaaa 163080
tggggaaggg gacacaggat taggagttgg gccagaaggg ttctctcttt gtcacacccg 163140
gctttaagga acaaagccgg gtgcatctca tacatgcgcc aagaagacaa catatataat 163200
aacagagtgt atagagataa atgtcataaa acatcagagt atttattaca tagcggaaga 163260
cttattacaa aataaaagat aaaagtaaaa cgaactaagg atcgtcggcg ccaatgtcga 163320
ctgggaaacg ccacctagat cagatcgaac tcctcagtgt taggcggctc ctcctgaacc 163380
acctgctctt ctcctgtggg ggggtgtgag acagcaaggg tgagctcaca catgatcata 163440
gctcaacaag ttgtggggaa ccggtggaca taaactcaca aaggtgtgag gtcatgtgat 163500
gtgtaaggct aatcaatgat aggggttaaa gctgagcatt gcttttaagt agttggtcaa 163560
aattttatta gcagttacta agtacaagtg aataccaaac cttagataaa gtaattgaac 163620
aaaattaata atagacccat gcaatgcaaa tgacaaaatt gaatttaagt tccataattt 163680
aaacatcaga gagtcctgag ccgctcatga ccgcgagcac ggctagtata ctagttttac 163740
actctgcaga ggttgtaccc tttacccaca agtcatgcta cccatctgcc aaggggtcgc 163800
gaatcccata cacctctacc taggaagcgc ggcagggcaa cactacgagg cctttacaaa 163860

```
gttccactag cttccgaaaa cccgctacag tttataagaa gttccaatgc agggttcttg 163920
gtctgaccgc catcgcagca aaatcaacca aggacctccc tacactgacc actcccctac 163980
tgcccttgcc cctttcgggt aaggtaacga atctctagat tagtnnnnnn nnnnnnnnnn 164040
nnnnnnnnnn nnnnnnnnnn nnnnnnnnnn nnnnnnnnnn nnnnnnnnnn nnnnnnnnnn 164100
nnnnnnnnnn nnnnnnnnnn nnnncatggg aagagaagga ggagcttcgc atagattttc 164160
ctcacctttt ccctcgttct tcctaaatct cgaggacgag attattttta agggggggtag 164220
gatttgtaac acccactttg taaaaataaa acctaagagt aaagattata ttccttcgca 164280
tatatgggtg tcatccctat gtagcatttc atgtggacat ctcacctaaa caaataaata 164340
attaacaaaa gacacctaaa taacctaagt gcatcatgtt ggcttttact tgtatgtgca 164400
tttaatgata acaataatca tatcaataga aatacaaagg tgtcccaaat tgggattcaa 164460
agacctcatt tacaatttaa aaaaatggaa ataacataaa agaacaagga aaagaaaggg 164520
atcaccttgt aaagaaaact atataaaaat aaatataact tttcaaattg gtactcttaa 164580
gttacaactt ttgtctgagt acaaattcac aacaaaaaaa tttgaattca aatagagatt 164640
taaaagataa aagaaaagga aaataaaaaa aaagaaaaaa aaagataaag cctacctggg 164700
ccgtggctac cccttttggc ccagtttcgc attacccctc cgcgcagccc aggcgggagc 164760
atggctgcgc tgctggctcc gctgacaacg tgggcctact ggccaggaag acttcgcgcg 164820
tgcgcaccag tcgcagacaa gtggacccgt gttgccaggg tcatcttccc ctgattgccg 164880
ctggcgtgaa acgggtctcc aaagtcgccg ccgctttact cgccgatgaa tcgcgcgcgt 164940
agttgtaaca gccgccgcgt tgatcggagg atcaggtcga gatttgcccc ctcaacctgg 165000
gtacaaagac cccgggcgcg tcgcgagaac tgttgaccac cccgagcgcg atctctggca 165060
cgcggaaccc gcgcgtcgtc gcctaactcc gccgagttca gagctaagcc gccgcaaccg 165120
cgcatgccac aatctgcgct ggcccatgac ctgaccgaac tctgcgcgtc gtgatcctca 165180
ccttctatat ctgcggaccg acccccctcct ttcctctccc tttccccatt gccaccgtgc 165240
gccattgcga aagaaagtag ccgccgtact tgttcccaga ccaccgcgcc acccgtggcc 165300
gaattggagt gcagggagtt tcgcctgaca ccactggagc cgctcatcac atcgctggac 165360
gagaagggcc cctggacctc cataattgct cgacggaggc cgctactgcc gccaaacccc 165420
gtcgtcggct ctctacaccg atcaaccacc ggtaagattg cccccattga gttcgtcgta 165480
atctccacta ccgattgctc atcaccgcgt tcggaatagc tcgccaaatc acagatccgt 165540
agttcgccgc cgtgctcaca tccgtaggat tagctgggcg gcgccgccgc gcatggtcag 165600
tgtgttggga acgatgaagt gctggtcgtt gatcccgggt tggttggtca ggattagatg 165660
agtgtgggga tcgctggtag ccgtcgaatg ccaatccagc gcatagtatt acataccatt 165720
tcgggtgtgg tcttgatcta atcaggaccc tcggtcgacg atcgggcggc tcgggttcga 165780
aggatacccc ttcggcgggt cggtttagcg attaggcccc tctgttttta gggaaatcac 165840
ccgcggtccg cacagtgttg ttcactgtgt cttaagaatc ttactctaag acccctgtag 165900
tttgcagaaa atgaggccca gtccatagtt ctttaaattc agttatttaa ttatagaaat 165960
tactttttaa tacaaaataa ttgctagaac tttgataatt catagaaaat acatatgaac 166020
ttcaaaataa tccattccac cttctaaatt tttgtaattt tattctttat cacctagagc 166080
ctctgttatg tcatgaaaac agtaagaaat ttatttatca cttaatccta tttaaagcac 166140
ataaaacctt tgaaaatcca taacttaaat tctataactc caaaaattat gattcctgtt 166200
cctagaattt tattttaatg tgtagattat tactgtgtat tttgtttata tgtttgatgt 166260
```

aatgttaatt tctctatatg cattgtgctt gtttgtattg tggcgagtag aagagcccgt 166320
gaccgaggac cctggtgagc agcaggttga agtagctgag caggagctca ttgaaggcaa 166380
gttgtgccct tgaccacttt ttacccaata atgttcttta atatcactta tccatgcata 166440
ggttaatttt gatgggaccc gataggtcac cctagattgt ttatctcatt accttgttta 166500
cccctgaatc acttgggtag tttgctattg ctttacatgg ttttgggata atcatttatt 166560
acctctatgt tccaattctt tttgttattc tatttatgtt catgttgaga tcattaatgt 166620
taattggaac atagagctta acttgagaac cacgtgccac cacaagggtt taatgggacg 166680
cccttggctg attaattagg aaagctagtg gaagactacc ttacccgaaa ggggcaaggg 166740
cagtagggga gtggtcaatg aagggaggtc cctggttgat tttgctgcga tggcggtcag 166800
ccaggaaccc tgcattggaa cttcctataa actgtagcgg gttttcggaa gctagtggaa 166860
ctttgtaaag gcctcgtagt gttgccctgc cgcgcttcct aggtagaggt gtatgggatt 166920
cgcgacccct tggcagatgg gtagcatgac ttgtgggtaa agggtacaac ctctgcagag 166980
tgtaaaactg gtatactagc cgagctcacg gtcatgagca gctcaggact ctctgatgtt 167040
taaattatgg aacttaaatt caattttgtc atttgcatat gcatgggttt attattaatt 167100
ttgttctatt actttattta aggtttggta tttacttaca cttagtaact gctaataaaa 167160
ttttgaccaa ctacttaaaa gcaatgctca gctttaacca ttctctttga taagccttac 167220
actccatgag ctctcacctt tggtgagttc atgtcacatt attccccaca acttgttgag 167280
cgatgatcat gtgtgagctc acccttgctg tctcacaccc cccccccaca ggagaagagc 167340
aggtggttca ggaggagcca caaggcgagg agtatgatct gatctaggtg gcgtttctca 167400
gttgacattg gcgccgacga tccttagttc gttttacttt tatcttttat tttttaata 167460 agtcttccgc tatgtaataa atactctgat gttttacgac atttatctct atacactctg 167520
ttattatata tgttgtcttc ttggcgcatg tatgagatgc acctggcttt gttccttaaa 167580
gccgggtgtg acagaagtgg tatcagagga aatgttgact gtaggacgaa acctagatag 167640
aaatggacag accctttcct acttacctta ctctgactca ttctatactc atctcatctt 167700
gatcttgtct caccttctat tgttctactc ttatcattct taccttttct actcctagac 167760
aagatggatt tcacaccttg gagtccctac ccctatgaca tttttaagag gtaggaagcc 167820
taagacaaaa ttaaaactat tttctttatt aaaaatgttg gttgattgtt ctgatgatca 167880
atgcctgatt tgcttctttg attgattgaa atagtataga cgggcatctt agcatgtacc 167940
accataaggt aatgtattag ctttagtggg tgacacacta atctacttag ctaataaatc 168000
ccccgtagta acattactcg taattacatg ccttgtctat aatcctttct ttcttaccct 168060
gtgttcctga cccaaatggg ctacccctat actgttagaa gagagcagta taggcttgat 168120
ccttggtatg tcatggttaa gaaaggcaaa ggcactttgt acattgtgct aagggaaccg 168180
tagcactcac cagttccaaa ggacaaagat ttgaagttga agttgcagta actaccacca 168240
tcagactagt ggcgttctta gtagatgaga agttgtgggt gacaacatcc gtgtggttag 168300
agattttccg gatgtctttc cagaggagtt accagggatg ccacccgata gagaagttga 168360
gtttgttatt gatctcttac ctggaaccgc ccctatttct aaatggccat acaagatgtc 168420
cgtagaagaa ctaaaaggaa cttaagaagc aattaacgga attacaagag gatgggtaca 168480
ttcgtccgag ttcttcacct tgtggagcac cagttctatt ttgtacagaa gaaagatgga 168540
tcgcaaggga tgtgcgtgga ttataggacc cttaacgatg tcactgtgaa ggacaagtgt 168600
ccattacccc gcattaagga tttatttaat cagatgagag gtgctagagt attctcgaag 168660
attgatctcc gatcgggtta ccatcagatg aggattagac catcggatat tcccaagacg 168720
gctttctcga ctcgatatgg attatatgag tttactgtta tgtcgtttgg attaaccaat 168780
gcaccagctt attttatgaa cttgatgaat aaggtgttta tggagtattt ggacagactc 168840
gtcgtagtat tcatcgacga tattcttatt tattccaaga gtgatagtga tcatgaggaa 168900
catctgagat tggtgctaca aaagctaaga gataatcaac tctacaccaa gtttaccaaa 168960
tgcgagtttt ggattggcga ggtgccattt cttggacata tcatttctga tggaggaata 169020
tcagtggatc ctgctaaagt taaggagata atggagtgga gagtacccac tacagtgact 169080
gagattcgga gtttcttggg attagcaggc tattatcgga gatttattga agggttctct 169140
aagattgcca agcctatgac ttcgcttttg gagaaaggaa aagaatttaa gtgggacgag 169200
aagtgtcaag acagctttga tctattgaag aagaggttaa tgtcgccacc agtattggtt 169260
atgccggacc tacagaaagg atttgatatc tattgcgatg catgtggcca aggcttagga 169320
tgtgtggtca tgcaggaagg acatgtgatt gcttatgctt ctcgacaatt acggagacat 169380
gaattgaact accccactca tgacttggaa ttggcagccg ttgtgcatgc acttaagatt 169440
tggagacatt acattatggg aatcaagtgt caagtataca cagatcataa gagtctgaag 169500
tatatattca ctcagaagga tctcaacctt aggcaacgcc gttggttgga gcttattaag 169560
gattatgatt tggagattca ctatcacccg agcaaggcaa atttggttgc agatgccttg 169620
agtcgaaagg agcatgttca ttcagctgtt gttgcccagc tacccgatga gattgttgag 169680
gatttcagga gacttaacct ggggatagtt gctcacactg aaggagttac tattgatgtg 169740
gaacctacct tggagcaaga aatccgtaaa ggacaaattg gtgatgctaa aatacgagag 169800
attaaggatc tgattactga aggtcgagtt ctggaattta cggaagatga gcaaggcact 169860
gtatggttca aggacaagat gtgtgttcct gatattgaaa gccttcgtga gactatattg 169920
aaggaggccc atgactcaaa ttattctatt catcctggta gtactaagat gtatcaggat 169980
ttgaagcgga agtattggtg gtatggattg aaaagagatg tggctgcaca tgtggctatg 170040
tgtgatgtat gtcaaagagt taaggctgaa caccagaggc cagttggact attgcaccca 170100
ctgaagatac ccgagtggaa gtgggaagag attggtatgg atttcattac tggattgcct 170160
cgcacccaga aggatatga tgctatatgg gtgattgtgg atagattgac taaagtggct 170220
cactttattc ctgtcaagac tacttataaa ggttctcagc tagcagagtt gtatatggct 170280
cggcttgtgt gtttacatgg agtaccaaag aagatcgtgt ctgatcgagg ttcgcagttt 170340
acctcaagat tttggagaag ctttcatgag aacatgagca cgaagttgaa ttttagtacg 170400
gcttatcacc ctcagactga tgaacagact gaaaggacta atcaagtttt ggaagatatg 170460
ttgagagcat gtgcccttca gcatgggagg aagtgcagga ctcctttgta ttgggatcag 170520
actggagaga gacagttctt tgggcctgaa ttgattcaag aagcagaaga acaagtccgt 170580
ataattcgag agaatttgag agtggctcaa accaggcaaa agagttatgc tgataataga 170640
aggaggccac tgtaatttga agaaggagat tatgtgtatc tcaaggtgtc accactgcgt 170700
ggaatgagga gattcaaagt taagggcaaa ttgtcccctc gctatattgg accattcttg 170760
atctttagga gagttggaga gatggcatac caacttgagt tacctgctag tctatcggat 170820
gtgcataatg tgtttcacgt atctcaactc aagaagtggc tccgtgtccc tgaggaacag 170880
ttaccaatgg aagagcttag tgttcagggt gatttaactt acacggaata cccgatcaag 170940
atttaggata ctttgactcg agttacaaga aataaggtgg taaagatgtg caaagtccaa 171000

```
tggagtcacc acggtgaaga tgaagcaact tgggaaagag aagaagagct tcgcatagat 171060
tttcctcacc ttttccctcg ttcttcctaa atctcgagga cgagattatt tttaaggggg 171120
gtaggatttg taacacccac tttgtaaaaa taaaacctaa gagtaaagat tatattcctt 171180
cgcatatatg ggtgtcatcc ctatgtagca tttcatgtgg acatctcacc taaacaaata 171240
aataattaac aaaagacacc taaataacct aagtgcatca tgttggcttt acttgtatgt 171300
gcattaatgt aaccaaacnn nnnnnnnnnn nnnnnnnnnn nnnnnnnnnn nnnnnnnnnn 171360
nnnnnnnnnn nnnnnnnnnn nnnnnnnnnn nnnnnnnnnn nnnnnnnnnn nnnnnnnncg 171420
aatctagaga ttcgtctaag ggtacaacct ctgcattagt gtaaaactgg tatactagcc 171480
gagctcacgg tcatgagcag ctcaggactc tctgatgttt aaattatgga acttaaattc 171540
aattttgtca tttgcatatg catgggttta ttattaattt tgttctatta ctttatttaa 171600
ggtttggtat ttacttacac ttagtaactg ctaataaaat tttgaccaac tacttaaaag 171660
caatgctcag ctttaaccat tctctttgat aagccttaca ctccatgagc tctcaccttt 171720
ggtgagttca tgtcacatta ttccccacaa cttgttgagc gatgatcatg tgtgagctca 171780
cccttgctgt ctcacacccc ccccacagga gaagagcagg tggttcagga ggagccacaa 171840
ggcgaggagt atgatctgat ctaggtggcg tttctcagtt gacattggcg ccgacgatcc 171900
ttagttcgtt ttacttttat cttttatttt tttaataagt cttccgctat gtaataaata 171960
ctctgatgtt ttacgacatt tatctctata cactctgtta ttatatatgt tgtcttcttg 172020
gcgcatgtat gagatgcacc tggctttgtt ccttaaagcc gggtgtgaca cggggtgcga 172080
ggcaatccag taatgaagtc cttaccaatt tcttcccctt ccacttgggt atcttcagtg 172140
gatgtaatag tccagctggt ctttggtgtt aggccttaac tctttgacac ccatcgcaca 172200
tagccacatg tgcagccaca tctctcttca atccatacca ccagtatttc tgcttcaatt 172260
cctgatacat cttggtacta ccaggatgaa tagaataatc caagttatgg gcttccttta 172320
gaatagtctt acgaaggctt tcaataccag gaacacatat cctgcccttg aaccatattg 172380
tgtcttgttc atcttccgta aattccggac ctctaccttt cgtaataaga tccttgatct 172440
cttgtatctt ggcatcacca atctgtcgtt ctgtggattt tcttgctcca aggtaggttc 172500
cacatcaata atgactcctt aagcgtgagc atctatcccc aggttaagtc tcctgaaatc 172560
ctcaacaatc tcatcgggta gctgggcaac aatagctgaa tgaacatgct cctttcgact 172620
caaaggcttc tgcaaccaaa tttgccttgc ccagtgatag tgaatctcca aatcattatc 172680
ccttaataag ctccaaccaa cggcgtgcct aaggttgaga tccttcctga gtgaatataa 172740
actcttatga tccgttatac ttggcacttg ttccccatga tataaagtct ccatatcttt 172800
aagcgcatgc ccaacggcct gccaattcca tagcatgaga g                      172841
```

CORN ELITE EVENT MZIR098

RELATED APPLICATION INFORMATION

This application is a national stage entry under 35 U.S.C. § 371 of International Application No. PCT/US2018/037189, filed 13 Jun. 2018, which claims the benefit of U.S. Provisional Application No. 62/519,993, filed 15 Jun. 2017, the disclosures of which are incorporated herein by reference in their entirety.

STATEMENT REGARDING ELECTRONIC SUBMISSION OF A SEQUENCE LISTING

A Sequence Listing in ASCII text format, submitted under 37 C.F.R. § 1.821, entitled "81336_ST25.txt", 510 KB (523,050 bytes) in size, generated on Jun. 14, 2017 and filed via EFS-Web is provided in lieu of a paper copy. This Sequence Listing is hereby incorporated by reference into the specification for its disclosures.

FIELD OF THE INVENTION

The invention relates generally to the field of plant molecular biology, plant transformation, and plant breeding. More specifically, the invention relates to insect resistant transgenic corn plants comprising a novel transgenic genotype and to methods of detecting the presence of the corn plant DNA in a sample and compositions thereof.

BACKGROUND

Plant pests are a major factor in the loss of the world's important agricultural crops. About $8 billion are lost every year in the U.S. alone due to infestations of non-mammalian pests including insects. Species of corn rootworm are considered the most destructive corn pests. Important rootworm pest species include *Diabrotica virgifera virgifera*, the western corn rootworm; *D. longicornis barberi*, the northern corn rootworm, *D. undecimpunctata howardi*, the southern corn rootworm, and *D. virgifera zeae*, the Mexican corn rootworm.

Corn rootworm is mainly controlled by intensive applications of chemical pesticides. Good corn rootworm control can thus be reached, but these chemicals can sometimes also affect beneficial organisms. Another problem resulting from the wide use of chemical pesticides is the appearance of resistant insect varieties. This has been partially alleviated by various resistance management practices, but there is an increasing need for alternative pest control strategies. One such alternative includes the expression of foreign genes encoding insecticidal proteins in transgenic plants. This approach has provided an efficient means of protection against selected insect pests, and transgenic plants expressing insecticidal toxins have been commercialized, allowing farmers to reduce applications of chemical insecticides.

*Bacillus thuringiensis* (Bt) Cry proteins (also called δ-endotoxins) are proteins that form a crystalline matrix in *Bacillus* that are known to possess insecticidal activity when ingested by certain insects. Genes coding for Cry proteins have been isolated and their expression in crop plants have been shown to provide another tool for the control of economically important insect pests. Such transgenic plants expressing the Cry proteins have been commercialized, allowing farmers to reduce or augment applications of chemical insect control agents. Coleopteran-active Cry proteins useful in transgenic plants include, for example, Cry3A, Cry3B and the Cry34/Cry35 complex.

Although the usage of transgenic plants expressing Cry proteins is another tool in the insect control toolbox, it is still susceptible to resistance breakdown. Insect pests that now have resistance against the Cry proteins expressed in certain transgenic plants are known. A strategy to reduce the chances of resistance breakdown is to "stack" transgenic traits with different modes of action against the same insect pest species in a single plant. Currently, transgenic traits are frequently stacked through breeding and subsequent screening to get multiple transgenic traits in a single commercial germplasm. These breeding and screening steps are required for every variety of germplasm into which introduction of these two traits is desirable. For many agronomically important crops, such as corn, these two traits need to be maintained as hybrids for dozens of germplasm varieties. Additionally, factors such as the genetic linkage of undesirable traits or genetic recombination may complicate the introduction of two traits from two distinct loci into a single germplasm variety. Therefore, it would be advantageous to create a nucleic acid molecule which carries multiple insecticidal traits and can be introduced at a single locus in the genome of the transgenic plant. Such a molecule is described in publication WO2016209360 (herein incorporated by reference). However, the creation of such a molecule for transgenic insertion into a crop plant does not predictably create a desirable transgenic event.

The expression of foreign genes in plants can be influenced by their chromosomal position, for example due to chromatin structure and/or the proximity of transcriptional regulation elements close to the integration site (See for example, Weising et al., 1988, "Foreign Genes in Plants," Ann. Rev. Genet. 22:421-477). A high-quality transgenic event is preferred to not be in a promoter or gene region of the genome. A high-quality transgenic event also must not have negative effects on the agronomic performance of the transgenic plant. Additionally, a high-quality transgenic event is the result of a single, intact, transgene insertion, with little or no transgene rearrangement, and without contamination by extraneous heterologous DNA, such as DNA from the backbone of a vector used during the transformation process. A high-quality transgenic event also is preferred to lack introduced ORFs, which potentially may be expressed in the transgenic plant.

Therefore, it is common to produce hundreds of different events and screen those events for a single event that has desired molecular qualities and transgene expression levels and patterns for commercial purposes. The identified event which satisfies all criteria required for a high-quality event which may be used for commercial purposes is considered an elite event. The elite event is characterized by its exact genomic location, as it is that location which is responsible for the molecular qualities, transgene expression levels, and agronomic performance of the event. This elite event is useful for introgressing its transgene into other genetic backgrounds by sexual outcrossing using conventional breeding methods. Progeny of such crosses maintain the transgene expression characteristics of the original transformant. This strategy may be used to generate an infinite number of hybrids and varieties comprising the elite event, and used to ensure reliable transgene expression in each variety and hybrid.

Because a particular elite event is characterized by its genomic location, it would be advantageous to be able to detect its presence in order to determine whether progeny of a sexual cross contain the elite event. In addition, a method for detecting a particular elite event would be helpful for complying with regulations requiring the pre-market approval and labeling of foods derived from recombinant crop plants, for example. It is possible to detect the presence of a transgene by any well-known nucleic acid detection method, including but not limited to thermal amplification (polymerase chain reaction (PCR)) using polynucleotide primers or DNA hybridization using nucleic acid probes. Typically, for the sake of simplicity and uniformity of reagents and methodologies for use in detecting a particular DNA construct that has been used for transforming various plant varieties, these detection methods generally focus on frequently used genetic elements, for example, promoters, terminators, and marker genes, because for many DNA constructs, the coding sequence region is interchangeable. As a result, such methods may not be useful for discriminating between constructs that differ only with reference to the coding sequence. In addition, such methods are not useful for discriminating between different events, particularly those produced using the same DNA construct. To solve this problem, the sequence of genomic DNA adjacent to the inserted heterologous DNA, the flanking sequence, needs to be known. In particular, the junction sequence between the flanking genomic sequence and the inserted transgene needs to be known.

SUMMARY

The present invention includes insect resistant and herbicide tolerant transgenic elite event MZIR098 corn, which has incorporated into its genome a transgene comprising the insecticidal trait mCry3A, disclosed in U.S. Pat. No. 7,030,295 (incorporated herein by reference), the insecticidal trait eCry3.1Ab, disclosed in U.S. Pat. No. 8,309,516 (herein incorporated by reference), and the herbicide tolerance trait phosphinothricin acetyltransferase (PAT) (U.S. Pat. Nos. 5,531,236, 5,646,024, 5,648,477, and 5,276,268, herein incorporated by reference). Elite event MZIR098 corn comprises the elite event MZIR098 junction sequences in its genome. The invention further includes novel isolated nucleic acid sequences, namely the junction sequences, which are unique to elite event MZIR098 and are useful for identifying the transgenic corn comprising elite event MZIR098 and for detecting nucleic acids from transgenic elite event MZIR098 corn in a biological sample. The present invention also includes kits comprising the reagents necessary for use in detecting these nucleic acids in a biological sample.

The invention is drawn to an elite event, designated MZIR098, comprising a novel transgenic genotype that comprises coding sequences for insect resistance genes mCry3A and eCry3.1Ab, and for herbicide tolerance gene PAT. These genes are useful in controlling insect pests, particularly *Diabrotica* spp. insect pests, and also confer herbicide tolerance, particularly to glutamine synthetase (GS) inhibitor herbicides, to plants comprising this event and progeny thereof. The invention also provides transgenic MZIR098 corn plants comprising the genotype of the invention, seed, cells, and tissues from transgenic corn plants comprising the genotype of the invention, and methods for producing a transgenic MZIR098 corn plant comprising the genotype of the invention by crossing a corn inbred comprising the MZIR098 genotype of the invention with itself or another corn line of a different genotype. The transgenic MZIR098 corn plants of the invention may have essentially all of the morphological and physiological characteristics of the corresponding isogenic non-transgenic corn plant in addition to those conferred upon the corn plant by the novel MZIR098 genotype of the invention. The invention also provides compositions and methods for detecting the presence of nucleic acids from elite event MZIR098 based on the DNA sequence of the recombinant expression cassettes inserted into the corn genome that resulted in the elite event MZIR098, and of genomic sequences flanking the insertion site. The elite event MZIR098 can be further characterized by analyzing gene expression levels or protein levels of mCry3A, eCry3.1Ab, and PAT, as well as by testing efficacy against GS inhibitor herbicides, such as glufosinate or bialaphos, or by testing for Corn Rootworm resistance.

According to one aspect, the invention provides an optionally isolated nucleic acid molecule comprising at least 10 contiguous nucleotides of a heterologous DNA sequence inserted into the corn plant genome of the elite event MZIR098 initial corn transformant and at least 10 contiguous nucleotides of a corn plant genome DNA flanking the point of insertion of a heterologous DNA sequence inserted into the corn plant genome of the elite event MZIR098 initial corn transformant. The optionally isolated nucleic acid molecule according to this aspect may comprise at least 20 or at least 50 contiguous nucleotides of a heterologous DNA sequence inserted into the corn plant genome of the elite event MZIR098 initial corn transformant and at least 20 or at least 50 contiguous nucleotides of a corn plant genome DNA flanking the point of insertion of a heterologous DNA sequence inserted into the corn plant genome of the elite event MZIR098 initial corn transformant.

According to another aspect, the invention provides a optionally isolated nucleic acid molecule comprising at least one junction sequence of elite event MZIR098 selected from the group consisting of SEQ ID NO: 1 and SEQ ID NO: 2, and complements thereof. A junction sequence spans the junction between the heterologous DNA comprising the expression cassettes inserted into the corn genome and DNA from the corn genome flanking the insertion site and is diagnostic for the elite event MZIR098.

According to another aspect, the invention provides an optionally isolated nucleic acid linking a heterologous DNA molecule to the corn plant genome in corn elite event MZIR098 comprising a sequence of from about 11 to about 20 contiguous nucleotides selected from the group consisting of SEQ ID NO: 1, SEQ ID NO: 2, and complements thereof.

According to another aspect, the invention provides an optionally isolated nucleic acid molecule comprising a nucleotide sequence selected from the group consisting of SEQ ID NO: 1, SEQ ID NO: 2, SEQ ID NO: 3, SEQ ID NO: 4, and complements thereof.

According to another aspect of the invention, an amplicon comprising a nucleic acid molecule of the invention is provided.

According to still another aspect of the invention, flanking sequence primers for detecting elite event MZIR098 are provided. Such flanking sequence primers comprise a preferably isolated nucleic acid sequence comprising at least 10-15 contiguous nucleotides from nucleotides 1-1076 as set forth in SEQ ID NO: 8 (designated herein as the 5' flanking sequence), or the complements thereof. In one embodiment of this aspect the flanking sequence primers are selected from the group consisting of SEQ ID NO: 10, 14, 15, 16, 38, 42, 65, and complements thereof.

In another aspect of the invention, the flanking sequences primers comprise a preferably isolated nucleic acid sequence comprising at least 10-15 contiguous nucleotides from nucleotides 1-1075 as set forth in SEQ ID NO: 9 (designated herein as the 3' flanking sequence), or the complements thereof. In one embodiment of this aspect the flanking sequence primers are selected from the group consisting of SEQ ID NO: 19, 20, 21, 36, 41, 45, 67, and complements thereof.

According to another aspect of the invention, primer pairs that are useful for nucleic acid amplification, for example, are provided. Such primer pairs comprise a first primer comprising a nucleotide sequence of at least 10-15 contiguous nucleotides in length which is or is complementary to one of the above-described genomic flanking sequences (SEQ ID NO: 8 or SEQ ID NO: 9) and a second primer comprising a nucleotide sequence of at least 10-15 contiguous nucleotides of heterologous DNA inserted into the elite event MZIR098 genome. The second primer preferably comprises a nucleotide sequence which is or is complementary to the insert sequence adjacent to the plant genomic flanking DNA sequence as set forth in SEQ ID NO: 7. In one embodiment of this aspect the insert sequence primers are selected from the group consisting of SEQ ID NO: 11, 17, 18, 22, 23, 24, 29, 31, 33, 34, 35, 37, 43, 46, 47, 48, 49, 50, and complements thereof.

According to another aspect of the invention, methods of detecting the presence of DNA corresponding to elite event MZIR098 in a biological sample are provided. Such methods comprise: (a) contacting the sample comprising DNA with a pair of primers that, when used in a nucleic acid amplification reaction with genomic DNA from corn elite event MZIR098; produces an amplicon that is diagnostic for corn elite event MZIR098; (b) performing a nucleic acid amplification reaction, thereby producing the amplicon; and (c) detecting the amplicon. In one embodiment of this aspect, the amplicon comprises a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, and complements thereof.

According to another aspect, the invention provides methods of detecting the presence of a DNA corresponding to the elite event MZIR098 in a biological sample. Such methods comprise: (a) contacting the sample comprising DNA with a probe that hybridizes under high stringency conditions with genomic DNA from corn elite event MZIR098 and does not hybridize under high stringency conditions with DNA of a control corn plant; (b) subjecting the sample and probe to high stringency hybridization conditions; and (c) detecting hybridization of the probe to the DNA. The detected hybridized DNA sequence includes at least one polynucleotide sequence comprising SEQ ID NO: 1, SEQ ID NO: 2, SEQ ID NO: 3, SEQ ID NO: 4, SEQ ID NO: 5, SEQ ID NO: 6, and complements thereof.

According to another aspect of the invention, a kit is provided for the detection of elite event MZIR098 nucleic acids in a biological sample. The kit includes at least one DNA sequence comprising a sufficient length of polynucleotides which is or is complementary to SEQ ID NO: 1, SEQ ID NO: 2, SEQ ID NO: 3, SEQ ID NO: 4, SEQ ID NO: 5 or SEQ ID NO: 6, wherein the DNA sequences are useful as primers or probes that hybridize to isolated DNA from elite event MZIR098, and which, upon amplification of or hybridization to a nucleic acid sequence in a sample followed by detection of the amplicon or hybridization to the target sequence, are diagnostic for the presence of nucleic acid sequences from corn elite event MZIR098 in the sample. The kit further includes other materials necessary to enable nucleic acid hybridization or amplification methods.

In another aspect, the invention provides a method of detecting corn elite event MZIR098 protein in a biological sample comprising: (a) extracting protein from a sample of corn elite event MZIR098 tissue; (b) assaying the extracted protein using an immunological method comprising antibody specific for the mCry3A, eCry3.1Ab, or PAT protein produced by the corn elite event MZIR098 event; and (c) detecting the binding of said antibody to the mCry3A, eCry3.1Ab, or PAT protein.

In another aspect, the invention provides a biological sample derived from an elite event MZIR098 corn plant, tissue, or seed, wherein the sample comprises a nucleic acid comprising a nucleotide sequence which is or is complementary to a sequence selected from the group consisting of SEQ ID NO: 1 and SEQ ID NO: 2, and wherein the sequence is detectable in the sample using a nucleic acid amplification or nucleic acid hybridization method. In one embodiment of this aspect, the sample is selected from the group consisting of corn flour, corn meal, corn syrup, corn oil, cornstarch, and cereals manufactured in whole or in part to contain corn by-products.

In another aspect, the invention provides an extract derived from an elite event MZIR098 corn plant, tissue, or seed comprising a nucleotide sequence which is or is complementary to a nucleotide sequence selected from the group consisting of SEQ ID NO: 1 and SEQ ID NO: 2. In one embodiment of this aspect, the sequence is detectable in the extract using a nucleic acid amplification or nucleic acid hybridization method. In another embodiment of this aspect, the sample is selected from the group consisting of corn flour, corn meal, corn syrup, corn oil, cornstarch, and cereals manufactured in whole or in part to contain corn by-products.

According to another aspect of the invention, corn plants and seeds comprising the nucleic acid molecules of the invention are provided. In one embodiment of the invention, a deposit of elite event MZIR098 corn seed was made to the American Type Culture Collection (ATCC) in accordance with the Budapest Treaty on May 1, 2017. The seed was tested on May 12, 2017 and found to be viable. An example of said seed is deposited as ATCC Accession No: PTA-124143.

According to another aspect, the invention provides a method for producing a corn plant with insect resistance and herbicide tolerance to GS inhibitor herbicides comprising: (a) sexually crossing a first parent corn plant with a second parent corn plant, wherein first or second parent corn plant comprises corn elite event MZIR098 DNA, thereby producing a plurality of first generation progeny plants; (b) selecting a first generation progeny plant that is resistant to at least corn rootworm infestation; (c) selfing the first generation progeny plant, thereby producing a plurality of second generation progeny plants; (d) selecting from the second generation progeny plants, a plant that has insect resistance and herbicide tolerance to GS inhibitor herbicides; wherein the second generation progeny plants comprise a nucleotide sequence selected from the group consisting of SEQ ID NO: 1, SEQ ID NO: 2, SEQ ID NO: 3 and SEQ ID NO: 4.

According to yet another aspect, the invention provides a method for producing corn seed comprising crossing a first parent corn plant with a second parent corn plant and harvesting the resultant first generation corn seed, wherein the first or second parent corn plant is an inbred corn plant of the invention.

According to another aspect, the invention provides a method of producing hybrid corn seeds comprising the steps of: (a) planting seeds of a first inbred corn line according to the invention and seeds of a second inbred corn line having a different genotype; (b) cultivating corn plants resulting from said planting until time of flowering; (c) emasculating flowers of corn plants of one of the corn inbred lines; (d) allowing pollination of the other inbred line to occur, and (e) harvesting the hybrid seed produced thereby.

According to another aspect of the invention, the invention provides a method of selecting corn plants and seeds comprising the nucleic acid molecules of elite event MZIR098 on chromosome 10. In one embodiment of the invention, polymorphic markers are used to select or track the sequences specific to the elite event MZIR098. The invention provides a method of selecting sequences specific to the elite event MZIR098 comprising the steps of: (a) detecting a polymorphic marker sequence; (b) designing an assay for the purposes of detecting the marker; (c) running the assay on corn nucleic acid sequences from many corn lines, and (d) selecting corn lines based upon the sequences with nucleotides specific to elite event MZIR098.

According to another aspect of the invention, the invention provides a method of determining the zygosity of a corn plant comprising elite event MZIR098 comprising (a) obtaining a DNA sample of genomic DNA from said corn plant; (b) producing a contacted sample by contacting said DNA sample with (i) a first event primer and a second event primer, wherein said first event primer specifically binds said transgene construct, said second event primer specifically binds said 5' corn genomic flanking DNA or said 3' corn genomic flanking DNA, and wherein said first event primer and said second event primer produce an event amplicon which is unique to event MZIR098, when subjected to quantitative PCR conditions, (ii) at least one native insertion site first primer and at least one native insertion site second primer, wherein the first primer is a forward primer and the second primer is a reverse primer, wherein a first primer and second primer function together to produce an amplicon from the native MZIR098 insertion site when elite event MZIR098 is not present in the genome, when subjected to quantitative PCR conditions, (iii) a fluorescent event probe that hybridizes with said event amplicon, (iv) a fluorescent native insertion site probe that hybridizes with said native insertion site amplicon; (c) subjecting said contacted sample to fluorescence-based endpoint quantitative PCR conditions; (d) quantitating said fluorescent event probe that hybridized to said event amplicon and quantitating said fluorescent native insertion site probe that hybridized to said native insertion site amplicon; (e) comparing amounts of hybridized fluorescent event probe to hybridized fluorescent native insertion site probe; and (f) determining zygosity of said corn plant comprising corn elite event MZIR098 by comparing fluorescence ratios of hybridized fluorescent event probe and hybridized fluorescent native insertion site probe. The event primer set and probe and native insertion site primer set and probe may be mixed with the same DNA sample, or they may be separate with different DNA samples derived from the same corn plant. There may be more than one forward native insertion site primer and/or more than one reverse native insertion site primer. The quantification of the fluorescence from the event probe and the fluorescence from the native insertion site probe may be sequentially or simultaneously. Zygosity determination may be made using data analysis software, such as SDS software on the ABI 7900HT, as described in Example 9 and shown in FIG. 2. The results indicate if the corn plant is homozygous for elite event MZIR098 (ie, has positive results for the event endpoint quantitative PCR but not for the native insertion site endpoint quantitative PCR), is heterozygous for elite event MZIR098 (ie, has a positive result for both the event and for the native insertion site endpoint quantitative PCRs) or is wild type (ie, has positive results for the native insertion site endpoint quantitative PCR but not for the event endpoint quantitative PCR).

According to another aspect of the invention, the invention provides a site on chromosome 10 for targeted integration of a heterologous nucleic acid. The invention provides a method of selecting sequences specific to the elite event MZIR098 for targeted integration comprising the steps of: (a) designing homologous sequences based on the insertion site or vector sequence; (b) using these homologous sequences at a target locus; (c) using a targeted endonuclease, such as a zinc finger nuclease, a meganuclease, a TALEN, or a Cas9 nuclease, to create a break in the target locus, and (d) inserting a heterologous donor molecule within nucleotides specific to elite event MZIR098. An example of this technique is demonstrated in Shukla et al. (Nature, 2009, 459: 437-441, herein incorporated by reference).

DESCRIPTION OF THE SEQUENCES IN THE SEQUENCE LISTING

SEQ ID NO: 1 is a nucleic acid sequence of the 5' genome-insert junction, unique to event MZIR098.

SEQ ID NO: 2 is a nucleic acid sequence of the 3' genome-insert junction, unique to event MZIR098

SEQ ID NO: 3 is a nucleic acid sequence of the 5' genome-insert junction, sequence, plus additional 5' flanking genomic sequence.

SEQ ID NO: 4 is a nucleic acid sequence of the 3' genome-insert junction, sequence, plus additional 3' flanking genomic sequence.

SEQ ID NO: 5 is a nucleic acid sequence of the transgene insertion plus the 5' and 3' junction sequences, unique to event MZIR098.

SEQ ID NO: 6 is a nucleic acid sequence of the transgene insertion plus the 5' and 3' junction sequences, unique to event MZIR098, plus additional 5' and 3' flanking genomic sequence.

SEQ ID NO: 7 is a nucleic acid sequence of the full-length transgene insertion of event MZIR098.

SEQ ID NO: 8 is a nucleic acid sequence of the 5' flanking genomic sequence of the MZIR098 transgene insertion SEQ ID NO: 9 is a nucleic acid sequence of the 3' flanking genomic sequence of the MZIR098 transgene insertion SEQ ID NO: 10-12 are primer and probe sequences useful for detection of the MZIR098 event SEQ ID NO: 13 is a nucleic acid sequence of an amplicon produced using primers represented by SEQ ID NO: 10-11.

SEQ ID NO: 14-52 are primer and probe sequences useful for elite event MZIR098 detection and transgene sequencing.

SEQ ID NO: 53 is a nucleic acid sequence of the eNOS-02 enhancer of the eCry3.1Ab expression cassette within the MZIR098 transgene.

SEQ ID NO: 54 is a nucleic acid sequence of the prCMP-04 promoter of the eCry3.1Ab expression cassette within the MZIR098 transgene.

SEQ ID NO: 55 is a nucleic acid sequence of the eCry3.1Ab coding sequence, which encodes for an engineered insecticidal protein, of the eCry3.1Ab expression cassette within the MZIR098 transgene.

SEQ ID NO: 56 is a nucleic acid sequence of the tNOS-05-01 terminator of the eCry3.1Ab expression cassette within the MZIR098 transgene.

SEQ ID NO: 57 is a nucleic acid sequence of the prUbi1-18 promoter of the mCry3A expression cassette within the MZIR098 transgene.

SEQ ID NO: 58 is a nucleic acid sequence of mCry3A coding sequence, which encodes for an engineered insecticidal protein, of the mCry3A expression cassette within the MZIR098 transgene.

SEQ ID NO: 59 is a nucleic acid sequence of the tNOS-20 terminator of the mCry3A expression cassette within the MZIR098 transgene.

SEQ ID NO: 60 is a nucleic acid sequence of the pr35S-04-01 promoter of the PAT expression cassette within the MZIR098 transgene.

SEQ ID NO: 61 is a nucleic acid sequence of the cPAT-08 coding sequence, which encodes for a PAT protein that confers tolerance to GS inhibitor herbicides, of the PAT expression cassette within the MZIR098 transgene.

SEQ ID NO: 62 is a nucleic acid sequence of the eCry3.1Ab expression cassette within the MZIR098 transgene.

SEQ ID NO: 63 is a nucleic acid sequence of the mCry3A expression cassette within the MZIR098 transgene.

SEQ ID NO: 64 is a nucleic acid sequence of the PAT expression cassette within the MZIR098 transgene.

SEQ ID NO: 65-69 are primer and probe sequences useful for the detection of the MZIR098 insertion site when MZIR098 is not present, also referred to as the native insertion site, in endpoint zygosity assays.

SEQ ID NO: 70 is AC204437.3 Chromosome 10 sequence, where N is any base "A", "T", "G" or "C". This sequence includes the chromosomal location of the MZIR098 insertion site.

SEQ ID NO: 71 is the reverse complement of SEQ ID NO: 70, AC204437.3 Chromosome 10 sequence, where N is any base "A", "T", "G" or "C".

BRIEF DESCRIPTION OF DRAWINGS

FIG. 2 is representative of data produced in Example 9.

DETAILED DESCRIPTION

Figure 1:
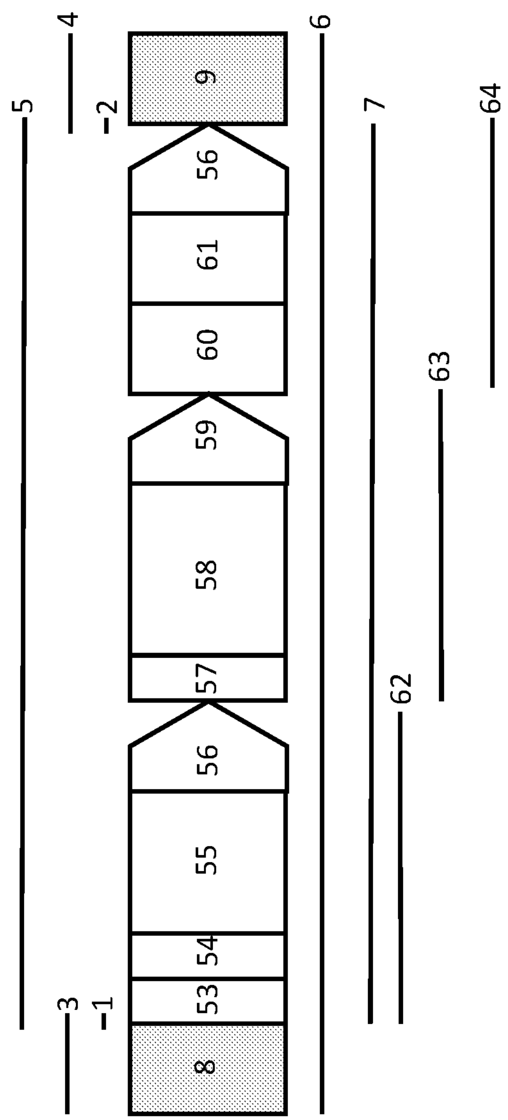
FIG. 1 (FIG. 1) is a graphical map illustrating the organization of the elements comprising the heterologous nucleic acid sequences inserted into the genome of corn to create elite event MZIR098 and sets forth the relative positions at which the inserted nucleic acid sequences are linked to corn genomic DNA sequences which flank the ends of the inserted heterologous DNA sequences, and also the positions of the junction sequences which comprise nucleic acid sequence of both the transgene and the flanking genomic sequence. Numbers indicate the graphical representation of sequences according to their Sequence Identification Number (SEQ ID NO). Therefore, "1" is a graphical representation of SEQ ID NO: 1, "2" represents SEQ ID NO: 2, "3" represents SEQ ID NO: 3, "4" represents SEQ ID NO: 4, "5" represents SEQ ID NO: 5, "6" represents SEQ ID NO: 6, "7" represents SEQ ID NO: 7, "8" represents SEQ ID NO: 8, "9" represents SEQ ID NO: 9, and numbers "53" through "64" represent SEQ ID NO: 53 through SEQ ID NO: 64, respectively. The gray regions for "8" and "9" indicate the flanking genomic sequence. The white regions for "53"-"61" indicate the transgene insertion.

The foregoing and other aspects of the invention will become more apparent from the following detailed description.

The following definitions and methods are provided to better define the invention and to guide those of ordinary skill in the art in the practice of the invention. Unless otherwise noted, terms used herein are to be understood according to conventional usage by those of ordinary skill in the relevant art. Definitions of common terms in molecular biology may also be found in Rieger et al., Glossary of Genetics: Classical and Molecular, $5^{th}$ edition, Springer-Verlag: New York, 1994.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

A "biological sample" is a plant, plant material or products comprising plant material. The term "plant" is intended to encompass corn (*Zea mays*) plant tissues, at any stage of maturity, as well as cells, tissues, organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. A biological sample may be crushed, non-viable material. A biological sample may be derived from a commodity product, such as a corn commodity product. Corn, also known as maize, is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups and dextrose for food use. Maize oil is recovered from maize germ, which is a by-product of both dry- and wet-milling industries.

A corn commodity product is typically derived from the grain, from the ear of the corn. Corn commodity products may also be derived from non-grain parts of the corn plant. A number of different industrial processes can be employed to extract or utilize these plant products, as are well known in the art. Corn commodity products include corn flour, corn meal, corn syrup, corn oil, corn starch, and cereals manufactured in whole or in part to contain corn by-products. Corn commodity products may be crushed, non-viable material derived from corn seeds but which are no longer capable of germination. Corn, including both grain and non-grain portions of the plant, is also used extensively as livestock feed, primarily for beef cattle, dairy cattle, hogs, and poultry. Industrial uses of maize, include production of ethanol, maize starch in the wet-milling industry and maize flour in the dry-milling industry. The industrial applications of maize starch and flour are based on functional properties, such as viscosity, film formation, adhesive properties and ability to suspend particles. The maize starch and flour have application in the paper and textile industries. Other industrial uses include applications in adhesives, building materials, foundry binders, laundry starches, explosives, oil-well muds, and other mining applications. Plant parts other than the grain of maize are also used in industry: for example, stalks and husks are made into paper and wallboard and cobs are used for fuel and to make charcoal.

A biological extract or “extract” may be derived from a biological sample or from a corn commodity product. A biological extract is from crushed biological material, and is no longer viable or capable of germination. It is understood that, in the context of the invention, such biological samples or extracts are tested for the presence of nucleic acids specific to corn elite event MZIR098, implying the presence of nucleic acids in the samples. Thus, the methods referred to herein for identifying elite event MZIR098 in biological samples or extracts relate to the identification in biological samples or extracts of nucleic acids which are from an elite event MZIR098 corn plant and are diagnostic for elite event MZIR098.

A “coding sequence” is a nucleic acid sequence that is transcribed into RNA such as mRNA, rRNA, tRNA, snRNA, sense RNA or antisense RNA. Preferably the RNA is then translated in an organism to produce a protein.

“Detection kit” as used herein refers to a kit used to detect the presence or absence of DNA from corn elite event MZIR098 plants in a sample comprising nucleic acid probes and primers of the invention, which hybridize specifically under high stringency conditions to a target DNA sequence, and other materials necessary to enable nucleic acid hybridization or amplification methods.

“Expression cassette” as used herein means a nucleic acid molecule capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as “inserted sequence” or “insertion sequence” when transformed into a plant.

A “gene” is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

“Gene of interest” refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The “gene of interest” may also be one that is transferred to plants for the production of commercially valuable enzymes or metabolites in the plant.

“Genotype” as used herein is the genetic material inherited from parent corn plants not all of which is necessarily expressed in the descendant corn plants. The MZIR098 genotype refers to the heterologous genetic material transformed into the genome of a plant as well as the genetic material flanking the inserted sequence.

“MZIR098-specific” refers to a nucleotide sequence which is suitable for discriminatively identifying elite event MZIR098 in plants, plant material, or in products such as, but not limited to, food or feed products (fresh or processed) comprising or derived from plant material.

“Insert DNA” or “insert sequence” refers to the heterologous DNA within the expression cassettes used to transform the plant material. Insert DNA is derived from a T-DNA, which is contained within a binary vector used in *Agrobacterium*-mediated transformation of a plant. “Flanking DNA” or “flanking sequence” can exist of either genomic DNA naturally present in an organism such as a plant, or foreign (heterologous) DNA introduced via the transformation process which is extraneous to the original insert DNA molecule, e.g. fragments associated with the transformation event. Flanking sequence as used herein refers to a sequence of at least 10 bp, at least 20 bp, at least 50 bp, at least 100 bp, at least 150 bp, at least 200 bp, at least 250 bp, at least 300 bp, at least 400 bp, at least 500 bp, at least 1000 bp, at least 2000 bp, at least 3000 bp, at least 4000 bp, and at least 5000 bp, which is located either immediately upstream of and contiguous with or immediately downstream of and contiguous with the original foreign insert DNA molecule. Transformation procedures leading to random integration of the foreign DNA will result in transformants containing different flanking regions characteristic of and likely unique to each transformant. When recombinant DNA is introduced into a plant through traditional crossing, its flanking sequences will generally not be changed. Transformants will also contain unique junctions between a piece of heterologous insert DNA and genomic DNA, or two pieces of genomic DNA, or two pieces of heterologous DNA. A “junction” is a point where two specific DNA fragments join. For example, a junction exists where insert DNA joins flanking DNA. A junction point also exists in a transformed organism where two DNA fragments join together in a manner that is modified from that found in the native organism. "Junction DNA" or "junction sequence" refers to DNA that comprises a junction point. Two junction sequences set forth in this disclosure are the junction point between the maize genomic DNA and the 5' end of the insert as set forth in SEQ ID NO: 1, and the junction point between the 3' end of the insert and maize genomic DNA as set forth in SEQ ID NO: 2. An event may be defined by its junction sequences. These junction sequences can be transmitted to progeny and introgressed into other germplasms via traditional crossing.

The term "event" refers to the original transformant that includes the heterologous DNA and/or progeny of said event. More generally, the term "event" refers to an artificial genetic locus or genotype that, as a result of genetic engineering such as transformation, carries a foreign inserted DNA or transgene comprising at least one copy of at least one gene of interest and also comprises flanking genomic sequence immediately adjacent to the inserted DNA that would be expected to be transferred to a progeny that receives the inserted DNA, including the transgene of interest, as a result of a sexual cross of one parental line which comprises the inserted DNA (e.g., the original transformant and progeny resulting from selfing) and a parental line that does not contain the inserted DNA. The event comprises the junction sequences and the foreign inserted DNA, which may be referred to as the transgene or the T-DNA insertion. The presence of an event in a cell may be identified genotypically by its junction sequences. At the genetic level, an event is part of the genetic makeup of a plant.

The term, for example, "event MZIR098 plant", "MZIR098 plant", "elite event MZIR098 plant", or "event MZIR098 corn" refers to a corn plant that comprises the MZIR098 event. An event MZIR098 plant may refer to progeny of the original transformant. The term "event MZIR098 plant" also refers to progeny produced by a sexual outcross between an event MZIR098 plant and another corn line. Even after repeated backcrossing to a recurrent parent, the inserted DNA, genomic flanking DNA, and junction sequences from the originally transformed plant are present in the progeny of the cross at the same chromosomal location. Similarly, an "MZIR098 seed" refers to a seed which comprises the MZIR098 event.

An "elite event" comprises all of the desirable characteristics of an event required for commercial utility. An elite event comprises one and only one complete copy of the transgene, with an absence of vector backbone sequence. The transgene is inserted at a desirable location in the genome, which, among other characteristics, allows easy introgression into desired commercial genetic backgrounds. The genomic location of the transgene of an elite event also allows for proper expression of the traits comprising the transgene. The expression of the traits of the transgene in an elite event is correct, appropriate, and stable spatially and temporally, both in heterozygous (or hemizygous) and homozygous conditions; is at a commercially acceptable level for a range of environmental conditions in which the plants carrying the event are likely to be exposed in normal agronomic use; and is stable through multiple generations of progeny. The transgene of the elite event also shows normal Mendelian segregation. An elite event has desirable agronomic characteristics, such as yield, vigor, fertility, and the like, which are not negatively impacted by the presence of the event in the genome of the plant. An elite event has a superior combination of efficacy, including herbicide tolerance and agronomic performance in broad genotype backgrounds and across multiple environmental locations. The status of an event as an elite event is confirmed by introgression of the elite event in different relevant genetic backgrounds and observing compliance with the criteria described above. An "elite event" may refer to a genetic locus comprising a foreign DNA as a transgene, which meets the above-described criteria. A plant, plant material or progeny such as seeds can comprise one or more elite events in its genome. The likelihood of having all of these characteristics in an event is small, such that an elite event is non-obvious and atypical of events recovered from the transformation process. An elite event may only be found by an extensive selection procedure.

Plants harboring elite event MZIR098 are characterized by their insect resistance, particularly to *Diabrotica* spp, as well as by their tolerance to GS inhibitors such as glufosinate or bialaphos. Corn plants comprising elite event MZIR098 are useful in controlling coleopteran insect pests including *Diabrotica virgifera virgifera*, the western corn rootworm, *D. virgifera zeae*, the Mexican corn rootworm, and *D. longicornis barberi*, the northern corn rootworm. Plants harboring elite event MZIR098 are also characterized by having agronomical characteristics that are comparable to commercially available varieties of corn, in the absence of herbicide application or insect pest pressure. Thus, plants comprising elite event MZIR098 can tolerate the application of GS inhibitor herbicides without negatively affecting the yield of said plants compared to isogenic lines lacking event MZIR098. Additionally, corn plants comprising elite event MZIR098 have no statistically significant difference in their disease susceptibility, or lodging compared to isogenic corn plants without the MZIR098 event. These characteristics make the elite event MZIR098 very useful for control *Diabrotica* spp. insect pests of corn, particularly western corn rootworm, as well as control of glyphosate-resistant weeds in corn fields. Because mCry3A and eCry3.1Ab provide two modes of action, elite event MZIR098 also can be used in IRM approaches to prevent or delay development of resistance to mCry3A or eCry3.1Ab in insect pests.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

The term "isolated" when used in relation to a nucleic acid refers to a nucleic acid sequence that is identified and separated from at least one contaminant nucleic acid with which it is ordinarily associated in its natural source. An isolated nucleic acid is present in a form or setting that is different from that in which it is found in nature. In contrast, a non-isolated nucleic acids such as DNA and RNA found in the state they exist in nature. An isolated nucleic acid may be in a transgenic plant or biological sample and still be considered "isolated".

"Operably-linked" refers to the association of nucleic acid sequences on a single nucleic acid fragment so that the function of one affects the function of the other. For example, a promoter is operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

The tools developed to identify an elite event or the plant or plant material comprising an elite event, or products which comprise plant material comprising the elite event, are based on the specific genomic characteristics of the elite event, such as, a specific restriction map of the genomic region comprising the inserted DNA, molecular markers, or the sequence of the flanking region(s) of the inserted DNA.

Once one or both of the flanking regions of the inserted DNA, or transgene, have been sequenced, primers and probes can be developed which specifically recognize this (these) sequence(s) in the nucleic acid (DNA or RNA) of a sample by way of a molecular biological technique. For instance, a PCR method can be developed to identify the elite event in biological samples (such as samples of plants, plant material or products comprising plant material). Such a PCR is based on at least two specific "primers", one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment" or discriminating amplicon) is amplified from a nucleic acid sample comprising the elite event. This means that only the targeted integration fragment, and no other sequence in the plant genome or foreign DNA, is amplified under optimized PCR conditions.

"Primers" as used herein are isolated nucleic acids that are annealed to a complementary target DNA strand by nucleic acid hybridization to form a hybrid between the primer and the target DNA strand, then extended along the target DNA strand by a polymerase, such as DNA polymerase. A primer pair comprises a "forward" primer and a "reverse" primer. Primer pairs or sets can be used for amplification of a nucleic acid molecule, for example, by the polymerase chain reaction (PCR) or other conventional nucleic-acid amplification methods.

PCR primers suitable for identification of elite corn event MZIR098 may be the following:

a) oligonucleotides ranging in length from 17 bp to about 200 bp, comprising a nucleotide sequence of at least 17 consecutive nucleotides, preferably 20 consecutive nucleotides, selected from DNA in the 5' flanking sequence (SEQ ID NO: 8), such that the primer recognizes the 5' flanking sequence; or b) oligonucleotides ranging in length from 17 bp to about 200 bp, comprising a nucleotide sequence of at least 17 consecutive nucleotides, preferably 20 consecutive nucleotides, selected from DNA in the 3' flanking sequence (SEQ ID NO: 9), such that the primer recognizes the 3' flanking sequence; or c) oligonucleotides ranging in length from 17 bp to about 200 bp, comprising a nucleotide sequence of at least 17 consecutive nucleotides, preferably 20 consecutive nucleotides, selected from the DNA in the transgene (SEQ ID NO: 7), such that the primer recognizes the transgene.

The primers may of course be longer than the mentioned 17 consecutive nucleotides, and may, e.g., be 20, 21, 22, 23, 24, 25, 30, 35, 50, 75, 100, 150, 200 bp long or even longer. The primers may entirely consist of nucleotide sequence selected from the mentioned nucleotide sequences of flanking sequences and transgene DNA sequences. However, the nucleotide sequence of the primers at their 5' end (i.e. outside of the 3'-located 17 consecutive nucleotides) is less critical. Thus, the 5' sequence of the primers may comprise or consist of a nucleotide sequence selected from the flanking sequences or foreign DNA, as appropriate, but may contain several (e.g., 1, 2, 5, or 10) mismatches. The 5' sequence of the primers may even entirely be a nucleotide sequence unrelated to the flanking sequences or foreign DNA, such as, e.g., a nucleotide sequence representing one or more restriction enzyme recognition sites. Such unrelated sequences or flanking DNA sequences with mismatches should preferably be not longer than 100, more preferably not longer than 50 or 25 nucleotides.

Moreover, suitable primers may comprise, consist or consist essentially of a nucleotide sequence spanning the junction region between the plant DNA derived sequences and the inserted DNA sequences (SEQ ID NO: 1 and 2). It will also be immediately clear to the skilled artisan that properly selected PCR primer pairs should also not comprise sequences complementary to each other.

Examples of suitable primers for detection or identification of elite event MZIR098 include SEQ ID NOs: 10, 11, 14 through 52, and complements thereof. Other examples of suitable oligonucleotide primers for the detection or identification of elite event MZIR098 comprise at least 10 contiguous nucleotides of SEQ ID NO: 7, 8, and 9, and complements thereof. A person of ordinary skill in the art will appreciate that for a primer set to be diagnostic for corn elite event MZIR098, the resulting amplicon must comprise SEQ ID NO: 1 or SEQ ID NO: 2.

A "probe" is an isolated nucleic acid to which is attached a conventional detectable label or reporter molecule, such as a radioactive isotope, ligand, chemiluminescent agent, or enzyme. Such a probe is complimentary to a strand of a target nucleic acid, in the case of the invention, to a strand of genomic DNA from corn elite event, MZIR098. The genomic DNA of elite event MZIR098 can be from a corn plant or from a sample that includes DNA from the event. Probes according to the invention include not only deoxyribonucleic or ribonucleic acids but also polyamides and other probe materials that bind specifically to a target DNA sequence and can be used to detect the presence of that target DNA sequence.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such primers and probes hybridize specifically to a target sequence under high stringency hybridization conditions. Primers and probes according to the invention may have complete sequence complementarity with the target sequence, although probes differing from the target sequence and which retain the ability to hybridize to target sequences may be designed by conventional methods.

"Stringent conditions" or "stringent hybridization conditions" include reference to conditions under which a probe will hybridize to its target sequence, to a detectably greater degree than to other sequences. Stringent conditions are target-sequence-dependent and will differ depending on the structure of the polynucleotide. By controlling the stringency of the hybridization and/or wash conditions, target sequences can be identified which are 100% complementary to the probe (homologous probing). Alternatively, stringency conditions can be adjusted to allow some mismatching in sequences so that lower degrees of similarity are detected (heterologous probing). Longer sequences hybridize specifically at higher temperatures. An extensive guide to the hybridization of nucleic acids is found in Tijssen (1993) *Laboratory Techniques in Biochemistry and Molecular Biology-Hybridization with Nucleic* Acid Probes, Part I, Chapter 2 "Overview of principles of hybridization and the strategy of nucleic acid probe assays", Elsevier: New York; and *Current Protocols in Molecular Biology*, Chapter 2, Ausubel et al., Eds., Greene Publishing and Wiley-Interscience: New York (1995), and also Sambrook et al. (2001) *Molecular Cloning: A Laboratory Manual* ($5^{th}$ Ed. Cols Spring Harbor Laboratory, Cold Spring Harbor, N.Y.).

Specificity is typically the function of post-hybridization washes, the critical factors being the ionic strength and temperature of the final wash solution. Generally, high stringency hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, under high stringency conditions a probe will hybridize to its target subsequence, but to no other sequences.

An example of high stringency hybridization conditions for hybridization of complementary nucleic acids which have more than 100 complementary residues on a filter in a Southern or northern blot is 50% formamide with 1 mg of heparin at 42° C., with the hybridization being carried out overnight. An example of very high stringency wash conditions is 0.15M NaCl at 72° C. for about 15 minutes. An example of high stringency wash conditions is a 0.2×SSC wash at 65° C. for 15 minutes (see, Sambrook, infra, for a description of SSC buffer).

Exemplary hybridization conditions for the invention include hybridization in 7% SDS, 0.25 M $NaPO_4$ pH 7.2 at 67° C. overnight, followed by two washings in 5% SDS, 0.20 M $NaPO_4$ pH7.2 at 65° C. for 30 minutes each wash, and two washings in 1% SDS, 0.20 M $NaPO_4$ pH7.2 at 65° C. for 30 minutes each wash. An exemplary medium stringency wash for a duplex of, e.g., more than 100 nucleotides, is 1×SSC at 45° C. for 15 minutes. An exemplary low stringency wash for a duplex of, e.g., more than 100 nucleotides, is 4-6×SSC at 40° C. for 15 minutes.

For probes of about 10 to 50 nucleotides, high stringency conditions typically involve salt concentrations of less than about 1.0 M Na ion, typically about 0.01 to 1.0 M Na ion concentration (or other salts) at pH 7.0 to 8.3, and the temperature is typically at least about 30° C. High stringency conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under high stringency conditions are still substantially identical if the proteins that they encode are substantially identical. This occurs, e.g., when a copy of a nucleic acid is created using the maximum codon degeneracy permitted by the genetic code.

The following are exemplary sets of hybridization/wash conditions that may be used to hybridize nucleotide sequences that are substantially identical to reference nucleotide sequences of the invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C. The sequences of the invention may be detected using all the above conditions. For the purposes of defining the invention, the high stringency conditions are used.

As used herein, "amplified DNA" or "amplicon" refers to the product of nucleic acid amplification of a target nucleic acid sequence that is part of a nucleic acid template. For example, to determine whether a com plant resulting from a sexual cross contains transgenic event genomic DNA from the corn plant of the invention, DNA extracted from the com plant tissue sample may be subjected to a nucleic acid amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the event DNA. Alternatively, the second primer may be derived from the flanking sequence. The amplicon is of a length and has a sequence that is also diagnostic for the event. The amplicon may range in length from the combined length of the primer pairs plus one nucleotide base pair to any length of amplicon producible by a DNA amplification protocol, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more polynucleotides, plus or minus any of the increments listed above. Alternatively, primer pairs can be derived from flanking sequence on both sides of the inserted DNA so as to produce an amplicon that includes the entire insert nucleotide sequence of the transgene as well as the sequence flanking the transgenic insert. A member of a primer pair derived from the flanking sequence may be located a distance from the inserted DNA sequence, this distance can range from one nucleotide base pair up to the limits of the amplification reaction, or about 20,000 bp. The use of the term “amplicon” specifically excludes primer dimers.

TaqMan (ThermoFisher Scientific, Waltham, Mass., USA) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Flybridization of the FRET probe results in cleavage and release of the fluorescent moiety away from the quenching moiety on the FRET probe. A fluorescent signal indicates the presence of the flanking/transgene insert sequence due to successful amplification and hybridization. This fluorescent signal can be quantified.

“Transformation” is a process for introducing heterologous nucleic acid into a host cell or organism. In particular, “transformation” means the stable integration of a DNA molecule into the genome of an organism of interest.

“Transformed/transgenic/recombinant” refer to a host organism such as a bacterium or a plant into which a heterologous nucleic acid molecule has been introduced. The nucleic acid molecule can be stably integrated into the genome of the host or the nucleic acid molecule can also be as an extrachromosomal molecule. Such an extrachromosomal molecule can be auto-replicating. Transformed cells, tissues, or plants are understood to encompass not only the end product of a transformation process, but also transgenic progeny thereof. A “non-transformed”, “non-transgenic”, or “non-recombinant” host refers to a wild-type organism, e.g., a bacterium or plant, which does not contain the heterologous nucleic acid molecule. As used herein, “transgenic” refers to a plant, plant cell, or multitude of structured or unstructured plant cells having integrated, via well known techniques of genetic manipulation and gene insertion, a nucleic acid representing a gene of interest into the plant genome, and typically into a chromosome of a cell nucleus, mitochondria or other organelle containing chromosomes, at a locus different to, or in a number of copies greater than, that normally present in the native plant or plant cell. Transgenic plants result from the manipulation and insertion of such nucleic acid sequences, as opposed to naturally occurring mutations, to produce a non-naturally occurring plant or a plant with a non-naturally occurring genotype. Techniques for transformation of plants and plant cells are well known in the art and may comprise for example electroporation, microinjection, *Agrobacterium*-mediated transformation, and ballistic transformation.

The nomenclature for DNA bases and amino acids as set forth in 37 C.F.R. § 1.822 is used herein.

This invention relates to a genetically improved line of corn that provides dual modes of action for control of corn rootworm (*Diabrotica* spp.) and tolerates herbicides containing a GS inhibitor, such as glufosinate-ammonium. The dual modes of action are provided by the presence of two insecticidal trait genes, namely mCry3A and eCry3.1Ab. Herbicide tolerance is provided by the presence of the herbicide tolerance trait gene PAT, which encodes a phosphinothricin acetyltransferase and is derived from *Streptomyces viridochromogenes*. The invention is particularly drawn to an elite transgenic corn event designated elite event MZIR098 comprising a novel genotype, as well as to compositions and methods for detecting nucleic acids from this event in a biological sample. The invention is further drawn to corn plants comprising the elite event MZIR098 genotype, to transgenic seed from the corn plants, and to methods for producing a corn plant comprising the elite event MZIR098 genotype by crossing a corn inbred comprising the elite event MZIR098 genotype with itself or another corn line. Corn plants comprising the elite event MZIR098 genotype of the invention are useful as part of insect pest management and as part of a weed control program because they possess herbicide tolerance to GS inhibitors.

The present invention embodies a novel genotype of corn, which is a result of the random insertion of a transgene in the genome of a corn plant by *Agrobacterium*-mediates transformation. It is recognized in the art that the genomic location of such an insertion cannot be predicted. The present invention encompasses the particular novel genotype and novel sequences, namely SEQ ID NO: 1, SEQ ID NO: 2, SEQ ID NO: 3, SEQ ID NO: 4, SEQ ID NO: 5, or SEQ ID NO: 6, and complements thereof, which are novel and diagnostic for elite event MZIR098. Furthermore, the present invention discloses a corn plant comprising elite event MZIR098, an example of which is deposited as ATCC Accession No: PTA-124143. A corn plant comprising elite event MZIR098 contains within its genome SEQ ID NO: 1, SEQ ID NO: 2, and SEQ ID NO: 5. Further, the present invention encompasses specific tools in the form of specific polynucleotide molecules that are capable of identifying the transgene insertion at its specific insertion site in the corn genome.

The present invention comprises a molecular stack comprising expression cassettes with mCry3A, eCry3.1Ab, and PAT coding sequences. The present invention possesses many advantages over a breeding stack which may comprise the same three traits. A plant comprising a breeding stack would comprise the three traits present as two or possibly single events, such that the genome of the plant has two or possibly three separate transgene insertions. The creation of such a plant technically can be complicated, as two parents each containing at least one copy of an event would need to be crossed, and the progeny would need to be screened for the presence of each trait. Additionally, because each event is present at a different genomic location, the resultant plant would need to be evaluated for agronomic and trait performance, to ensure that the presence of two or possibly three insertions in the genome had no deleterious effects. Additionally, the progeny of a plant comprising a breeding stack would need to be screened for the presence of each trait. Finally, such a procedure would need to be performed for every corn variety, or germplasm, into which the breeding stack was desired. The present invention solves these problems by having all traits as a molecular stack, so that they are singly inserted into the genome together. The molecular stack also provides greater stability in the expression of the traits in multiple germplasms, as the traits are inserted together at a single genomic locus and therefore have the same position effects regardless of the germplasm into which they have been introduced.

In one embodiment, the invention encompasses a transgenic corn seed of an elite event MZIR098 corn plant. An example of said seed being deposited as ATCC Accession No: PTA-124143. The transgenic seed, a transgenic plant, transgenic cell, and transgenic tissue of elite event MZIR098 comprises a nucleic acid molecule with at least 90%, 91%, 92%, 93%, 94%, 95%, 96%, 97%, 98%, 99%, or 100% identity to SEQ ID NO: 1, SEQ ID NO: 2, SEQ ID NO: 3, SEQ ID NO: 4, SEQ ID NO: 5, or SEQ ID NO: 6, and complements thereof. These sequences define a point of insertion of a heterologous DNA sequence inserted into the corn plant genome of corn elite event MZIR098. The invention further comprises a transgenic corn plant, transgenic seed, transgenic cell, and transgenic tissue of elite event MZIR098 capable of producing an elite event MZIR098 diagnostic amplicon, wherein said diagnostic amplicon hybridizes under stringent conditions to SEQ ID NO: 1, SEQ ID NO: 2, SEQ ID NO: 3, or SEQ ID NO: 4. The invention further comprises a transgenic insect resistant and herbicide tolerant plant, cell, seed, tissue, or progeny thereof, comprising: a DNA construct comprising three expression cassettes, wherein said first expression cassette in operable linkage comprises: (i) a NOS enhancer represented by SEQ ID NO: 53; (ii) a CMP promoter represented by SEQ ID NO: 54; (iv) an engineered insecticidal protein eCry3.1Ab coding sequence represented by SEQ ID NO: 55; and (v) a NOS transcriptional terminator represented by SEQ ID NO: 56; and wherein said second expression cassette in operable linkage comprises (i) a maize Ubi1 promoter represented by SEQ ID NO: 57; (ii) an engineered insecticidal protein mCry3A coding sequence represented by SEQ ID NO: 58; and (iii) a transcriptional terminator represented by SEQ ID NO: 59; and wherein said third expression cassette in operable linkage comprises (i) a CaMV 35S promoter represented by SEQ ID NO: 60; (ii) a PAT coding sequence represented by SEQ ID NO: 61; and (iii) a NOS transcriptional terminator represented by SEQ ID NO: 56, wherein the sequence overlapping the junction between the corn genomic DNA and the 5' flank of the construct comprises SEQ ID NO: 1 and the overlapping junction between the corn genomic DNA and the 3' flank of the construct comprises SEQ ID NO: 2, and wherein the DNA construct is present in the corn elite event MZIR098 deposited with American Type Culture Collection (ATCC) Accession No. PTA-124143.

In another embodiment, the invention encompasses a preferably isolated nucleic acid molecule comprising SEQ ID NO: 1, SEQ ID NO: 2, SEQ ID NO: 3, SEQ ID NO: 4, SEQ ID NO: 5, or SEQ ID NO: 6, and complements thereof. In another embodiment, the invention encompasses a optionally isolated nucleic acid molecule, wherein the nucleic acid molecule is comprised in a corn seed deposited as ATCC Accession No. PTA-124143. In another embodiment, the invention comprises an isolated nucleic acid molecule comprising: a) SEQ ID NO: 1; b) operably linked at the 3' end of said sequence of step (a) an expression cassette comprising SEQ ID NO: 62 (eNOS-02:prCMP-04:eCry3.1Ab:tNOS-05-01); c) operably linked at the 3' end of said cassette of step (b) and in the same orientation, an expression cassette comprising SEQ ID NO: 63 (prUbi1-18:mCry3A:tNOS-20); d) operably linked at the 3' end of said cassette of step (c) and in the same orientation, an expression cassette comprising SEQ ID NO: 64 (pr35S-04-01:cPAT-08:tNOS-05-01) and e) operably linked at the 3' end of said cassette of step (d) SEQ ID NO: 2.

In one embodiment, the invention encompasses a nucleic acid molecule, optionally isolated, comprising at least 10 or more (for example 15, 20, 25, or 50) contiguous nucleotides of a heterologous DNA sequence inserted into the corn plant genome of corn elite event MZIR098 and at least 10 or more (for example 15, 20, 25, or 50) contiguous nucleotides of a corn plant genome DNA flanking the point of insertion of a heterologous DNA sequence inserted into the corn plant genome of corn elite event MZIR098. Also included are nucleotide sequences that comprise 10 or more nucleotides of contiguous insert sequence from elite event MZIR098 and at least one nucleotide of flanking DNA from elite event MZIR098 adjacent to the insert sequence. Such nucleotide sequences are diagnostic for elite event MZIR098. Nucleic acid amplification of genomic DNA from the elite event MZIR098 may produce an amplicon comprising such diagnostic nucleotide sequences (namely, SEQ ID NO: 1, SEQ ID NO: 2, SEQ ID NO: 3, SEQ ID NO: 4, SEQ ID NO: 5, SEQ ID NO: 6 and the complements thereof).

In another embodiment, the invention encompasses a nucleic acid molecule, preferably isolated, comprising a nucleotide sequence which comprises at least one junction sequence of elite event MZIR098 selected from the group consisting of SEQ ID NO: 1, SEQ ID NO: 2, SEQ ID NO: 3, SEQ ID NO: 4, and complements thereof, wherein a junction sequence spans the junction between a heterologous expression cassette inserted into the corn genome and DNA from the corn genome flanking the insertion site and is diagnostic for the event. In a further embodiment, the invention comprises a nucleic acid molecule relating to the corn elite event MZIR098, characterized in that it consists of the sequence of SEQ ID NO: 1. In another embodiment, the invention comprises a nucleic acid molecule relating to the corn elite event MZIR098, characterized in that it consists of the sequence of SEQ ID NO: 2. In another embodiment, the invention comprises the use of SEQ ID NO: 1 or SEQ ID NO: 2 to identify corn elite event MZIR098 in a plant.

In another embodiment, the invention encompasses a nucleic acid molecule linking a heterologous DNA molecule to the corn plant genome in corn elite event MZIR098 comprising a sequence of from about 11 to about 20 contiguous nucleotides of a sequence selected from the group consisting of SEQ ID NO: 1, SEQ ID NO: 2, and the complements thereof.

In another embodiment, the invention encompasses a nucleic acid molecule, preferably isolated, comprising a nucleotide sequence selected from the group consisting of SEQ ID NO: 1, SEQ ID NO: 2, SEQ ID NO: 3, SEQ ID NO: 4, and complements thereof.

In another embodiment, the invention encompasses a nucleic acid molecule, comprising a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and the complements thereof. In a further embodiment, the invention encompasses the nucleic acid molecule described above wherein the molecule is within the genome of a transgenic organism, for example a transgenic maize plant. The invention also includes a genome comprising said nucleic acid molecule.

In another embodiment, the invention encompasses flanking sequence primers for detecting elite event MZIR098. Such flanking sequence primers comprise an isolated nucleic acid sequence comprising at least 10-15 contiguous nucleotides from SEQ ID NO: 8 (designated herein as the 5' flanking sequence), SEQ ID NO: 9 (designated herein as the 3' flanking sequence) or the complements thereof. In one aspect of this embodiment the flanking sequence primers are selected from the group consisting of SEQ ID NO: 10, SEQ ID NO: 14, SEQ ID NO: 15, SEQ ID NO: 16, SEQ ID NO: 38, SEQ ID NO: 42, SEQ ID NO: 65, SEQ ID NO: 19, SEQ ID NO: 20, SEQ ID NO: 21, SEQ ID NO: 36, SEQ ID NO: 41, SEQ ID NO: 45, SEQ ID NO: 67, and complements thereof. The flanking sequences can be extended to include additional chromosome 10 sequence, with specific emphasis on nucleotides comprised within SEQ ID NO: 70 or SEQ ID NO: 71, useful in detecting sequences associated with the corn elite event MZIR098. In the context of SEQ ID NO: 70 and SEQ ID NO: 71, an "N" is defined as any base "A", "T", "G", or "C". SEQ ID NO: 71 is the reverse complement of SEQ ID NO: 70.

In still another embodiment, the invention encompasses a pair of polynucleotide primers comprising a first polynucleotide primer and a second polynucleotide primer which function together in the presence of a corn elite event MZIR098 DNA template in a sample to produce an amplicon diagnostic for the corn elite event MZIR098. In some aspects of this embodiment, the first primer sequence is or is complementary to a corn plant genomic sequence flanking the point of insertion of a heterologous DNA sequence inserted into the corn plant genome of corn elite event MZIR098, and the second polynucleotide primer sequence is or is complementary to the heterologous DNA sequence inserted into the corn plant genome of the corn elite event MZIR098. Another embodiment of the invention is the use of these polynucleotide primers to identify corn elite event MZIR098 in a plant.

In one aspect of this embodiment the first polynucleotide primer comprises at least 10 contiguous nucleotides from position 1-1076 of SEQ ID NO: 8, or at least 10 contiguous nucleotides from position 1-1075 of SEQ ID NO: 9, or complements thereof. In a further aspect of this embodiment, the first polynucleotide primer comprises the nucleotide sequence set forth in SEQ ID NO: 10, SEQ ID NO: 14, SEQ ID NO: 15, SEQ ID NO: 16, SEQ ID NO: 38, SEQ ID NO: 42, SEQ ID NO: 65, or complements thereof. In yet another aspect of this embodiment, the second polynucleotide primer comprises at least 10 contiguous nucleotides of SEQ ID NO: 7, or the complements thereof. In still a further aspect of this embodiment, the second polynucleotide primer comprises the nucleotide sequence set forth in SEQ ID NO: 11, SEQ ID NO: 17, SEQ ID NO: 22 through 24, SEQ ID NO: 29, SEQ ID NO: 43, SEQ ID NO: 46 through 49, or the complements thereof.

In another aspect of this embodiment, the first polynucleotide primer comprises the nucleotide sequence of SEQ ID NO: 19, SEQ ID NO: 20, SEQ ID NO: 21, SEQ ID NO: 36, SEQ ID NO: 41, SEQ ID NO: 45, SEQ ID NO: 67, or complements thereof, and the second polynucleotide primer comprises the nucleotide sequence of SEQ ID NO: 18, SEQ ID NO: 31, SEQ ID NO: 33 through 35, SEQ ID NO: 37, SEQ ID NO: 50, or the complement thereof, such that the pair function together in the presence of a corn elite event MZIR098 DNA template in a sample to produce an amplicon diagnostic for the corn elite event MZIR098. In another aspect of this embodiment, the first polynucleotide primer comprises at least 10 contiguous nucleotides of SEQ ID NO: 7, or the complements thereof and the second polynucleotide primer comprises at least 10 contiguous nucleotides from position 1-1075 of SEQ ID NO: 9, or complements thereof, such that the pair function together in the presence of a corn elite event MZIR098 DNA template in a sample to produce an amplicon diagnostic for the corn elite event MZIR098. Another embodiment of the invention is the use of these polynucleotide primers to identify corn elite event MZIR098 in a plant.

In another aspect of this embodiment, the first polynucleotide primer comprises SEQ ID NO: 10, and the second polynucleotide primer comprises SEQ ID NO: 11, and the pair function together in the presence of a corn elite event MZIR098 DNA template in a sample to produce an amplicon diagnostic for the corn event MZIR098 which can be detected by a probe comprising SEQ ID NO: 12, as described in Example 2.

It is well within the skill in the art to obtain additional sequence further out into the genome sequence flanking either end of the inserted heterologous DNA sequences for use as a primer sequence that can be used in such primer pairs for amplifying sequences that are diagnostic for the elite event MZIR098. For the purposes of this disclosure, the phrase "further out into the genome sequence flanking either end of the inserted heterologous DNA sequences" refers specifically to a sequential movement away from the ends of the inserted heterologous DNA sequences, the points at which the inserted DNA sequences are adjacent to native genomic DNA sequence, and out into the genomic DNA of the particular chromosome into which the heterologous DNA sequences were inserted. Preferably, a primer sequence corresponding to or complementary to a part of the insert sequence should prime the transcriptional extension of a nascent strand of DNA or RNA toward the nearest flanking sequence junction. Consequently, a primer sequence corresponding to or complementary to a part of the genomic flanking sequence should prime the transcriptional extension of a nascent strand of DNA or RNA toward the nearest flanking sequence junction. A primer sequence can be, or can be complementary to, a heterologous DNA sequence inserted into the chromosome of the plant, or a genomic flanking sequence. One skilled in the art would readily recognize the benefit of whether a primer sequence would need to be, or would need to be complementary to, the sequence as set forth within the inserted heterologous DNA sequence or as set forth in SEQ ID NO: 1 or SEQ ID NO: 2 depending upon the nature of the product desired to be obtained through the use of the nested set of primers intended for use in amplifying a particular flanking sequence containing the junction between the genomic DNA sequence and the inserted heterologous DNA sequence. Further more, one skilled in the art would be able to design primers for a multitude of native corn genes for the purposes of designing a positive control. One such example is the corn Adh1 gene, where examples of suitable primers for producing an amplicon by nucleic acid amplification are well known in the art (see, for example, U.S. Pat. No. 8,466,346, incorporated by reference herein).

In another embodiment, the invention encompasses a method of detecting the presence of a nucleic acid molecule that is unique to event MZIR098 in a sample comprising corn nucleic acids, the method comprising: a) isolating a nucleic acid molecule from corn; b) combining the nucleic acid molecule with a pair of polynucleotide primers of the invention; c) performing a nucleic acid amplification reaction which results in an amplicon diagnostic for the corn elite event MZIR098; and d) detecting the amplicon.

In another embodiment, the invention encompasses a method of confirming the absence of a nucleic acid molecule that is unique to event MZIR098 in a sample comprising corn nucleic acids, the method comprising: a) isolating genomic DNA from corn; b) combining the nucleic acid molecule with a pair of polynucleotide primers of the invention and with a pair of polynucleotide primers to a corn native gene, for example to the corn Adh1 gene, as a positive control; c) performing a nucleic acid amplification reaction which results in no amplicon specific to elite event MZIR098 and results in an amplicon specific to the corn native gene positive control; and d) detecting an amplicon specific to the corn native gene positive control.

In another embodiment, the invention encompasses a method of detecting the presence of a nucleic acid molecule that is unique to event MZIR098 in a sample comprising corn nucleic acids, for example a biological sample, the method comprising: a) isolating a nucleic acid molecule from corn; b) combining the nucleic acid molecule with a pair of polynucleotide primers of the invention and with a polynucleotide probe comprising a nucleotide sequence of SEQ ID NO: 1, SEQ ID NO: 2, SEQ ID NO: 10 through 12, SEQ ID NO: 14 through SEQ ID NO: 52, or a complement thereof; c) performing a nucleic acid amplification reaction which results in an amplicon which can be detected by the probe; and d) detecting the probe. In a further embodiment, the invention encompasses a DNA molecule comprising the amplicon produced by the methods of the invention. In a preferred aspect of this embodiment, the amplicon comprises a nucleotide sequence selected from the group consisting of SEQ ID NO: 1, SEQ ID NO: 2, SEQ ID NO: 3, SEQ ID NO: 4, and complements thereof.

In another embodiment, the invention encompasses a method of detecting the presence of DNA corresponding to the corn elite event MZIR098 in a biological sample, wherein the method comprises: (a) contacting the sample comprising DNA with a probe that hybridizes under high stringency conditions with genomic DNA from corn elite event MZIR098 and does not hybridize under high stringency conditions with DNA of a control corn plant; (b) subjecting the sample and probe to high stringency hybridization conditions; and (c) detecting hybridization of the probe to the DNA. In one aspect of this embodiment the probe comprises a nucleotide sequence selected from the group consisting of SEQ ID NO: 1, SEQ ID NO: 2, SEQ ID NO: 3, SEQ ID NO: 4, and complements thereof.

In another embodiment, the invention encompasses a method of detecting the presence of a DNA corresponding to the corn elite event MZIR098 event in a biological sample, wherein the method comprises: (a) contacting the sample comprising DNA with a probe that hybridizes under high stringency conditions with genomic DNA from corn event corn elite event MZIR098 and does not hybridize under high stringency conditions with DNA of a control corn plant; (b) subjecting the sample and probe to high stringency hybridization conditions; and (c) detecting hybridization of the probe to the DNA. Detection can be by any means well known in the art including but not limited to fluorescent, chemiluminescent, radiological, immunological, or otherwise. In the case in which hybridization is intended to be used as a means for amplification of a particular sequence to produce an amplicon which is diagnostic for the corn elite event MZIR098 corn event, the production and detection by any means well known in the art of the amplicon is intended to be indicative of the intended hybridization to the target sequence where one probe or primer is utilized, or sequences where two or more probes or primers are utilized. The term "biological sample" is intended to comprise a sample that contains or is suspected of containing a nucleic acid comprising from between five and ten nucleotides either side of the point at which one or the other of the two terminal ends of the inserted heterologous DNA sequence contacts the genomic DNA sequence within the chromosome into which the heterologous DNA sequence was inserted, herein also known as the junction sequences. In addition, the junction sequence comprises as little as two nucleotides: those being the first nucleotide within the flanking genomic DNA adjacent to and covalently linked to the first nucleotide within the inserted heterologous DNA sequence.

In yet another embodiment, the invention encompasses a kit for detecting the presence of corn elite event MZIR098 nucleic acids in a biological sample, wherein the kit comprises at least one nucleic acid molecule of sufficient length of contiguous nucleotides homologous or complementary to a nucleotide sequence selected from the group consisting of SEQ ID NO: 1, SEQ ID NO: 2, SEQ ID NO: 3, and SEQ ID NO: 4, that functions as a DNA primer or probe specific for corn elite event MZIR098, and other materials necessary to enable nucleic acid hybridization or amplification. A variety of detection methods can be used including TaqMan (ThermoFisher Scientific), thermal amplification, ligase chain reaction, southern hybridization, ELISA methods, and colorimetric and fluorescent detection methods. In particular the invention provides for kits for detecting the presence of the target sequence, i.e., at least one of the junctions of the insert DNA with the genomic DNA of the corn plant in corn elite event MZIR098, in a sample containing genomic nucleic acid from event corn elite event MZIR098. The kit is comprised of at least one polynucleotide capable of binding to the target site or substantially adjacent to the target site and at least one means for detecting the binding of the polynucleotide to the target site. The detecting means can be fluorescent, chemiluminescent, colorimetric, or isotopic and can be coupled at least with immunological methods for detecting the binding. A kit is also envisioned which can detect the presence of the target site in a sample, i.e., at least one of the junctions of the insert DNA with the genomic DNA of the corn plant in corn elite event MZIR098, taking advantage of two or more polynucleotide sequences which together are capable of binding to nucleotide sequences adjacent to or within about 100 base pairs, or within about 200 base pairs, or within about 500 base pairs or within about 1000 base pairs of the target sequence and which can be extended toward each other to form an amplicon which contains at least the target site In another embodiment, the invention encompasses a method for detecting corn elite event MZIR098 protein in a biological sample, the method comprising: (a) extracting protein from a sample of corn elite event MZIR098 tissue; (b) assaying the extracted protein using an immunological method comprising antibody specific for the mCry3A, eCry3.1Ab, and/or PAT protein produced by the corn elite event MZIR098 event; and (c) detecting the binding of said antibody to the mCry3A, eCry3.1Ab, and/or PAT protein.

Another embodiment of the invention encompasses a corn plant, or parts thereof, comprising the genotype of the transgenic corn elite event MZIR098, wherein the genotype comprises the nucleotide sequence set forth in SEQ ID NO: 1, SEQ ID NO: 2, SEQ ID NO: 3, SEQ ID NO: 4, SEQ ID NO: 5, SEQ ID NO: 7, or the complements thereof. Said genotype is within the genome of a corn plant. In one aspect of this embodiment, the corn plant is from the inbred corn lines CG5NA58, CG5NA58A, CG3ND97, CG5NA01, CG5NF22, CG4NU15, CG00685, CG00526, CG00716, NP904, NP948, NP934, NP982, NP991, NP993, NP2010, NP2013, NP2015, NP2017, NP2029, NP2031, NP2034, NP2045, NP2052, NP2138, NP2151, NP2166, NP2161, NP2171, NP2174, NP2208, NP2213, NP2222, NP2275, NP2276, NP2316, BCTT609, AF031, H8431, 894, BUTT201, R327H, 2044BT, and 2070BT. One skilled in the art will recognize however, that the corn elite event MZIR098 genotype can be introgressed into any plant variety that can be bred with corn, including wild maize species, and thus the preferred inbred lines of this embodiment are not meant to be limiting.

In another embodiment, the invention encompasses a corn plant comprising at least a first and a second DNA sequence linked together to form a contiguous nucleotide sequence, wherein the first DNA sequence is within a junction sequence and comprises at least about 10-15 contiguous nucleotides selected from the group consisting of nucleotides SEQ ID NO: 1, SEQ ID NO: 2, SEQ ID NO: 3, SEQ ID NO: 4, SEQ ID NO: 10, and complements thereof, wherein the second DNA sequence is within the heterologous insert DNA sequence selected from the group consisting of SEQ ID NO: 11, SEQ ID NO: 17, SEQ ID NO: 18, SEQ ID NO: 22 through SEQ ID NO: 35, SEQ ID NO: 37, SEQ ID NO: 39, SEQ ID NO: 40, SEQ ID NO: 43, SEQ ID NO: 44, SEQ ID NO: 46 through SEQ ID NO: 52, and complements thereof. In another embodiment, the first sequence is a genomic flanking sequence upstream of the junction sequence, for example SEQ ID NOs: 10, 14, 15, 16, 19, 20, 21, 38, 41, 42, 45, 65, 67, or the complements thereof, and the second DNA sequence is within the heterologous insert DNA sequence selected from the group consisting of SEQ ID NO: 11, SEQ ID NO: 17, SEQ ID NO: 18, SEQ ID NO: 22 through SEQ ID NO: 35, SEQ ID NO: 37, SEQ ID NO: 39, SEQ ID NO: 40, SEQ ID NO: 43, SEQ ID NO: 44, SEQ ID NO: 46 through SEQ ID NO: 52, and complements thereof, and wherein the first and the second DNA sequences are useful as nucleotide primers or probes for detecting the presence of corn elite event MZIR098 nucleic acid sequences in a biological sample. In one aspect of this embodiment, a pair of nucleotide primers, one of which comprises the first nucleic acid sequences described above, and the other which comprises the second nucleic acid sequences described above, are used in a DNA amplification method to amplify a target DNA sequence from template DNA extracted from the corn plant and the corn plant is identifiable from other corn plants by the production of an amplicon corresponding to a DNA sequence comprising SEQ ID NO: 1 or SEQ ID NO: 2.

In one embodiment, the invention provides a corn plant, wherein the event corn elite event MZIR098 genotype confers upon the corn plant insect resistance, particular to the *Diabrotica* spp. insect pests, and tolerance to GS inhibitor herbicides. In one aspect of this embodiment, the genotype conferring insect resistance upon the corn plant comprises a mCry3A gene or an eCry3.1Ab gene. In another aspect of this embodiment, the genotype conferring upon the corn plant tolerance to GS inhibitor herbicides comprises a PAT gene.

In one embodiment, the invention provides a biological sample derived from an elite event MZIR098 corn plant, tissue, or seed, wherein the sample comprises a nucleotide sequence which is or is complementary to a sequence selected from the group consisting of SEQ ID NO: 1, SEQ ID NO: 2, SEQ ID NO: 3, SEQ ID NO: 4, SEQ ID NO: 5 and SEQ ID NO: 6, and wherein the sequence is detectable in the sample using a nucleic acid amplification or nucleic acid hybridization method. Thus, the genetic sequence functions a means of detection. In one aspect of this embodiment, the sample is selected from a corn commodity product, for example and not limited to corn flour, corn meal, corn syrup, corn oil, corn starch, and cereals manufactured in whole or in part to contain corn products. It is known in the art that a biological sample or extract may comprise proteins with biological activity. Therefore, in a further embodiment, the invention provides a biological sample derived from an elite event MZIR098 corn plant, tissue, or seed, wherein said biological sample comprises insecticidal proteins mCry3A and/or eCry3.1Ab, which continue to have insecticidal activity.

In another embodiment, the invention provides an extract derived from an elite event MZIR098 corn plant, tissue, or seed comprising a nucleotide sequence which is or is complementary to a nucleotide sequence selected from the group consisting of SEQ ID NO: 1, SEQ ID NO: 2, SEQ ID NO: 3, SEQ ID NO: 4, SEQ ID NO: 5, and SEQ ID NO: 6. An example of such seed is deposited at the ATCC under Accession No. PTA-124143. In one aspect of this embodiment, the sequence is detected in the extract using a nucleic acid amplification or nucleic acid hybridization method. In another aspect of this embodiment, the sample is selected from a corn commodity product, such as corn flour, corn syrup, corn oil, cornstarch, and cereals manufactured in whole or in part to contain corn products.

In another embodiment, the invention provides a method of producing a corn commodity product, comprising the steps of: a) obtaining transgenic elite event MZIR098 corn plant, cells or tissues thereof; and b) producing a corn commodity product from the said transgenic corn plant, cells, or tissue thereof, wherein the commodity product comprises protein concentrate, protein isolate, starch, meal, flour or oil therefrom.

In another embodiment, the invention provides a corn commodity product comprising a detectable amount of a DNA molecule unique for corn elite event MZIR098, wherein said molecule comprises SEQ ID NO: 1, SEQ ID NO: 2, SEQ ID NO: 3, SEQ ID NO: 4, SEQ ID NO: 5 or SEQ ID NO: 6. In a further embodiment, the invention provides a non-living plant material comprising a detectable amount of a nucleic acid molecule comprising SEQ ID NO: 1, SEQ ID NO: 2, SEQ ID NO: 3, SEQ ID NO: 4, SEQ ID NO: 5 or SEQ ID NO: 6, wherein the nucleic acid molecule is comprised in a corn seed deposited at the ATCC under the Accession No. PTA-124143.

In another embodiment, the invention provides a method for determining zygosity of a corn plant comprising a corn elite event MZIR098 of the invention, said method comprising: (a) obtaining a DNA sample of genomic DNA from said corn plant; (b) producing a contacted sample by contacting said DNA sample with (i) a first event primer and a second event primer, wherein said first event primer specifically binds said transgene construct, said second event primer specifically binds said 5' corn genomic flanking DNA or said 3' com genomic flanking DNA, and wherein said first event primer and said second event primer produce an event amplicon which is unique to event MZIR098, when subjected to quantitative PCR conditions, (ii) at least one native insertion site first primer and at least one native insertion site second primer, wherein the first primer is a forward primer and the second primer is a reverse primer, wherein a first and second primer function together when subjected to quantitative PCR conditions to produce an amplicon from the native MZIR098 insertion site when elite event MZIR098 is not present in the genome, (iii) a fluorescent event probe that hybridizes with said event amplicon, (iv) a fluorescent native insertion site probe that hybridizes with said native insertion site amplicon; (c) subjecting said contacted sample to fluorescence-based endpoint quantitative PCR conditions; (d) quantitating said fluorescent event probe that hybridized to said event amplicon and quantitating said fluorescent native insertion site probe that hybridized to said native insertion site amplicon; (e) comparing amounts of hybridized fluorescent event probe to hybridized fluorescent native insertion site probe; and (f) determining zygosity of said corn plant comprising corn elite event MZIR098 by comparing fluorescence ratios of hybridized fluorescent event probe and hybridized fluorescent native insertion site probe. The event primer set and probe and native insertion site primer set and probe may be mixed with the same DNA sample, or they may be separate with different DNA samples derived from the same corn plant. The native insertion primer set may comprise more than one forward native insertion site primer and/or more than one reverse native insertion site primer. The quantification of the fluorescence from the event probe and the fluorescence from the native insertion site probe may be sequentially or simultaneously. Zygosity determination may be made using data analysis software, such as SDS software on the ABI 7900HT, as described in Example 9 and shown in FIG. 2. The results indicate if the corn plant is homozygous for elite event MZIR098 (ie, has positive results for the event endpoint quantitative PCR but not for the native insertion site endpoint quantitative PCR), is heterozygous for elite event MZIR098 (ie, has a positive result for both the event and for the native insertion site endpoint quantitative PCRs) or is wild type (ie, has positive results for the native insertion site endpoint quantitative PCR but not for the event endpoint quantitative PCR).

It will be recognized that some sequence diversity will be found for the native insertion site, based on genetic diversity of the various corn germplasms into which elite event MZIR098 is introduced. Therefore, for successful zygosity determination in novel corn germplasms, a native insertion site primer set may need to be identified so that an amplicon is produced when elite event MZIR098 is not present in the genome, when subjected to quantitative PCF conditions. Multiple native insertion site primer sets and probes may be needed to properly determine the zygosity of event MZIR098 in a variety of corn germplams. Multiple native insertion site primer sets and/or probes may be included in a single reaction to produce a native insertion site amplicon that hybridizes with a native insertion site probe. Similarly, event primers which specifically bind to the 5' or 3' flanking sequence of the MZIR098 may need to be identified for successful zygosity determination in novel corn germplasms, as the 5' and/or 3' flanking sequences may be diverse among a variety of germplams. Again, multiple event primer sets may be included in a single reaction to produce an event amplicon unique to event MZIR098.

In a further embodiment of the method for determining zygosity described above, the event and/or native insertion site amplicon may consists of 50-200 nucleotides in length. In a preferred embodiment, the amplicon for the event and for the native insertion site is 50-150 nucleotides in length. In another embodiment, the first event primer comprises at least 10 contiguous nucleotides from position 1-8476 as set forth in SEQ ID NO: 7, or a complement thereof, and the second event primer comprises at least 10 contiguous nucleotides from position 1-1076 as set forth in SEQ ID NO: 8 or from position 1-1075 as set forth in SEQ ID NO: 9, or a complement thereof. In a further embodiment, the first event primer is selected from SEQ ID NO: 11, 17, 18, 22, 23, 24, 25, 26, 27, 28, 29, 30, 31, 32, 33, 34, 35, 37, 39, 40, 43, 44, 46, 47, 48, 49, 50, 51, 52, or a complement thereof. In another embodiment, the second event primer is selected from SEQ ID NO: 10, 14, 15, 16, 19, 20, 21, 36, 38, 41, 42, 45, 65, 67, or a complement thereof. In another embodiment, the first native insertion site primer comprises at least 10 contiguous nucleotides from position 1-1076 as set forth in SEQ ID NO: 8, or a complement thereof, and the second native insertion site primer comprises at least 10 contiguous nucleotides from position 1-1075 as set forth in SEQ ID NO: 9, or a complement thereof. In another embodiment, the first native insertion site primer is selected from SEQ ID NO: 10, 14, 15, 16, 38, 42, 65, or a complement thereof. In another embodiment, the second native insertion site primer is selected from SEQ ID NO: 19, 20, 21, 36, 41, 45, 67, or a complement thereof. In another embodiment, the fluorescent native insertion site probe comprises SEQ ID NO: 68 or SEQ ID NO: 69. It is recognized that there may be more than one first primer or second primer for the native insertion site primers.

In a further embodiment, the results of the method for determining zygosity described above are read directly in a plate reader. The present invention also encompasses a kit for performing the method of determining zygosity described above. The kit comprises all primers and probes needed for performing the zygosity assay on a DNA sample, including a first event primer, a second event primer, at least one native insertion site primer, at least one native insertion site reverse primer, an event probe, and a native insertion site probe. The kit may include more than one primer set/probe for the event, for the native insertion site, or both. The kit may also include more than one pair of primers, for example two forward primers and a single reverse primer, as described in Example 9.

In a further embodiment, the present invention encompasses a method of breeding a corn plant comprising herbicide tolerant corn elite event MZIR098 wherein the zygosity of a corn plant comprising corn elite event MZIR098 is determined by the method described above. The zygosity determination method may be used in a breeding program to determine the zygosity of the event MZIR098 in a segregating progeny population. Corn plants may then be selected which are homozygous for event MZIR098 based on the results of the zygosity determination method described above. Corn plants may also be discarded if they are found to be heterozygous for event MZIR098 based on the results of the zygosity determination method.

In yet another embodiment, the invention provides a method for producing a corn plant useful for control of insects and also tolerant to herbicides comprising: (a) sexually crossing a first parent corn plant with a second parent corn plant, wherein said first or second parent corn plant comprises corn elite event MZIR098, thereby producing a plurality of first generation progeny plants; (b) selecting a first generation progeny plant that has herbicide tolerance to GS inhibitors and/or insect resistance to *Diabrotica* spp, such as western corn rootworm; (c) selfing the first generation progeny plant, thereby producing a plurality of second generation progeny plants; and (d) selecting from the second generation progeny plants a plant that has herbicide tolerance to GS inhibitors and/or insect resistance to corn rootworm; wherein the second generation progeny plants comprise a nucleotide sequence selected from the group consisting of SEQ ID NO: 1, SEQ ID NO: 2, SEQ ID NO:3, SEQ ID NO: 4, SEQ ID NO: 5, and SEQ ID NO: 6.

In yet another embodiment, the invention provides a use of corn elite event MZIR098 to confer insect resistances and/or herbicide tolerance to a plant lacking said event. This usage may comprise, for example, sexually crossing a parent corn plant comprising event MZIR098 with a second parent corn plant which does not comprise event MZIR098 and selecting for progeny which comprise event MZIR098. The progeny may further be backcrossed to the second parent, optionally multiple times, or crossed with additional corn plants as part of a breeding program to produce at least one variety of corn comprising elite event MZIR098 which previously did not comprise said event.

In another embodiment, the invention provides a method of asexually propagating corn elite event MZIR098. Asexual propagation of a corn plant may be performed using methods well-known in the art, for example by anther culture or by microspore-derived plant tissue culture. in vitro plant regeneration may be performed by micropropagation, which involves the suppression of apical dominance resulting in the activation and multiplication of auxillary buds, or by somatic embryogenesis, where for example cotyledon containing embryos are formed from somatic cells. Asexual propagation and in vitro plant regeneration are needed for asexual reproduction. In a further embodiment, the invention provides a corn elite event MZIR098 produced by asexual propagation. The invention also provides use of a corn elite event MZIR098 plant, cells, or tissues to produce a corn elite event MZIR098 plant. This plant may be produced by asexual propagation.

In another embodiment, the invention provides a method of producing hybrid corn seeds comprising: (a) planting seeds of a first inbred corn line, an example of said seed deposited as ATCC accession No. PTA-124143, wherein said seed comprises a nucleotide sequence selected from the group consisting of SEQ ID NO: 1, SEQ ID NO: 2, SEQ ID NO:3, SEQ ID NO: 4, SEQ ID NO: 5, and SEQ ID NO: 6, and seeds of a second inbred line having a different genotype than the first inbred corn plant; (b) cultivating corn plants resulting from said planting until time of flowering and the production of flowers; (c) emasculating said flowers of plants of either the first or the second corn inbred line; (d) sexually crossing the two different inbred lines with each other by pollinating the non-emasculated plant with pollen of the emasculated plant; and (e) allowing hybrid seed to be produced and harvesting the hybrid seed produced thereby. In one aspect of this embodiment, the first inbred corn line provides the female parents. In another aspect of this embodiment, the first inbred corn line provides the male parents. The invention also encompasses the hybrid seed produced by the embodied method and hybrid plants grown from the seed.

In another embodiment, the invention provides a method of selecting markers associated with corn elite event MZIR098 comprising: (a) screening corn elite event MZIR098 chromosome 10 sequences, (b) comparing these with a non-transgenic NP2222 sequences, (c) comparing the sequences for the purpose of detecting sequence variations, (d) using these sequence variations as a means to develop markers associated with corn elite event MZIR098, (e) using the markers to screen lines, and (f) detecting marker confirming the presence of corn elite event MZIR098 sequences on chromosome 10. In a further embodiment, the invention provides a method of breeding a corn plant comprising herbicide tolerant elite event MZIR098 which is genetically linked to or a complement of a nucleic acid marker, wherein said marker is identified using SEQ ID NO: 1, SEQ ID NO: 2, SEQ ID NO: 10 through SEQ ID NO: 12, SEQ ID NO: 14 through SEQ ID NO: 52, SEQ ID NO: 65, SEQ ID NO: 67, or their complements. In another embodiment, the invention provides a method of marker assisted selection for herbicide tolerant corn elite event MZIR098 comprising: (a) isolating nucleic acid molecule(s), or preparing a nucleic acid sample, from corn; (b) combining the nucleic acid molecule(s) with a pair of polynucleotide primers and probes, selected from the group comprising SEQ ID NO: 1, SEQ ID NO: 2, SEQ ID NO: 10 through SEQ ID NO: 12, SEQ ID NO: 14 through SEQ ID NO: 52, SEQ ID NO: 65, SEQ ID NO: 67, or their complements; (c) performing a nucleic acid amplification reaction which results in an amplicon; (d) detecting the amplicon; and (e) selecting the plant for the purposes of breeding herbicide tolerant corn comprising corn elite event MZIR098.

In another embodiment, the invention comprises a transgenic corn plant, cells, or tissues comprising elite event MZIR098, characterized by the SEQ ID NO: 1, SEQ ID NO: 2, SEQ ID NO: 3, SEQ ID NO: 4, SEQ ID NO: 5, or SEQ ID NO: 6, wherein the transgenic corn plant, cells, or tissues are further defined as a progeny or derived from a progeny of any generation of a corn plant comprising elite event MZIR098. In a further embodiment, the transgenic corn plant, cells, or tissues are or are derived from a hybrid bred from at least one parent comprising elite event MZIR098.

One skilled in the art will recognize that the transgenic genotype of the invention can be introgressed by breeding into other corn lines comprising different transgenic genotypes. For example, a corn inbred comprising the transgenic genotype of the invention can be crossed with a corn inbred comprising the transgenic genotype of the lepidopteran resistant Bt11 event, which is known in the art, thus producing corn seed that comprises both the transgenic genotype of the invention and the Bt11 transgenic genotype. Examples of other transgenic events which can be crossed with an inbred of the invention include: the Enogen event 3272, the glyphosate tolerant/lepidopteran insect resistant MON802 event, the lepidopteran insect resistant event DBT418, the lepidopteran insect resistant event DAS-06275-8, the lepidopteran insect resistant event MIR162, the male sterile event MS3, the lepidopteran insect resistant event MON 80100, the lepidopteran insect resistant event 176, and the coleopteran insect resistant event MON863, all of which are known in the art. It will be further recognized that other combinations can be made with the transgenic genotype of the invention and thus these examples should not be viewed as limiting.

In another embodiment, the invention encompasses a process for producing corn elite event MZIR098 seed. This process comprises crossing a corn elite event MZIR098 of the invention with a second corn plant. The second corn plant may or may not comprise the MZIR098 event. In preferred embodiments, the second corn plant does not comprise the MZIR098 event. Following the crossing, or pollination event, the seed is allowed to develop and set in the maternal plant. The invention further comprises the corn elite event MZIR098 seed produced by the process described above, as well as the corn elite event MZIR098 plant produced by germinating the seed.

In another embodiment, the invention provides a process of introducing an additional trait into a corn elite event MZIR098 plant, comprising: (a) crossing a corn elite event MZIR098 plant grown from corn elite event MZIR098 seed, representative seed deposited under ATCC Accession Number PTA-124143, with another maize plant that comprises an additional trait to produce hybrid progeny plants, (b) selecting hybrid progeny plants that have the additional trait to produce selected hybrid progeny plants; (c) crossing the selected progeny plants with the corn elite event MZIR098 parental plants to produce backcross progeny plants; (d) selecting for backcross progeny plants that have the additional trait to produce selected backcross progeny plants; and (e) repeating steps (c) and (d) at least three or more times to produce backcross progeny plants that comprise the additional trait and corn elite event MZIR098. The invention further comprises a plant produced by the process described above.

In another embodiment, the invention provides a method for developing a corn elite event MZIR098 plant germplasm in a corn plant breeding program, comprising applying plant breeding techniques wherein said techniques comprise recurrent selection, backcrossing, pedigree breeding, marker enhanced selection, haploid/double haploid production, or transformation of a corn elite event MZIR098 plant, or its parts, wherein application of said techniques results in development of a second corn germplasm comprising elite event MZIR098.

In another embodiment, the invention provides a method of producing a corn elite event MZIR098 plant with doubled haploid chromosomes, the method comprising: (a) crossing the plant of claim 2 with an inducer maize plant to produce a progeny with haploid chromosomes; and (b) doubling the haploid chromosomes in the progeny to produce a corn elite event MZIR098 plant with doubled haploid chromosomes.

Breeding

Manipulations (such as mutation, further transfection, and further breeding) of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when (i) it is predominantly derived from the initial variety, or from a variety that is itself predominantly derived from the initial variety, while retaining the expression of the essential characteristics that result from the genotype or combination of genotypes of the initial variety;

(ii) it is clearly distinguishable from the initial variety; and (iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment.

The transgenic genotype of the invention can be introgressed in any corn inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Field crops are bred through techniques that take advantage of the plant's method of pollination. A plant is self-pollinated if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

Corn can be bred by both self-pollination and cross-pollination techniques. Corn has separate male and female flowers on the same plant, located on the tassel and the ear, respectively. Natural pollination occurs in corn when wind blows pollen from the tassels to the silks that protrude from the tops of the ears.

A reliable method of controlling male fertility in plants offers the opportunity for improved plant breeding. This is especially true for development of corn hybrids, which relies upon some sort of male sterility system. There are several options for controlling male fertility available to breeders, such as: manual or mechanical emasculation (or detasseling), cytoplasmic male sterility, genetic male sterility, gametocides and the like.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using one of many methods of conferring genetic male sterility in the art, each with its own benefits and drawbacks. These methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329,308 and PCT application PCT/CA90/00037 published as WO 90/08828).

Development of Corn Inbred Lines

The use of male sterile inbreds is but one factor in the production of corn hybrids. Plant breeding techniques known in the art and used in a corn plant breeding program include, but are not limited to, recurrent selection, backcrossing, pedigree breeding, restriction length polymorphism enhanced selection, marker assisted selection and transformation. The development of corn hybrids in a corn plant breeding program requires, in general, the development of homozygous inbred lines, the crossing of these lines, and the evaluation of the crosses. Pedigree breeding and recurrent selection breeding methods are used to develop inbred lines from breeding populations. Corn plant breeding programs combine the genetic backgrounds from two or more inbred lines or various other germplasm sources into breeding pools from which new inbred lines are developed by selfing and selection of desired phenotypes. The new inbreds are crossed with other inbred lines and the hybrids from these crosses are evaluated to determine which of those have commercial potential. Plant breeding and hybrid development, as practiced in a corn plant-breeding program, are expensive and time-consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1 \rightarrow F_2$; $F_2 \rightarrow F_3$; $F_3 \rightarrow F_4$; $F_4 \rightarrow F_{0.5}$; etc.

Recurrent selection breeding, backcrossing for example, can be used to improve an inbred line and a hybrid that is made using those inbreds. Backcrossing can be used to transfer a specific desirable trait from one inbred or source to an inbred that lacks that trait. This can be accomplished, for example, by first crossing a superior inbred (recurrent parent) to a donor inbred (non-recurrent parent), that carries the appropriate gene(s) for the trait in question. The progeny of this cross is then mated back to the superior recurrent parent followed by selection in the resultant progeny for the desired trait to be transferred from the non-recurrent parent. After five or more backcross generations with selection for the desired trait, the progeny will be homozygous for loci controlling the characteristic being transferred, but will be like the superior parent for essentially all other genes. The last backcross generation is then selfed to give pure breeding progeny for the gene(s) being transferred. A hybrid developed from inbreds containing the transferred gene(s) is essentially the same as a hybrid developed from the same inbreds without the transferred gene(s).

An inbred plant could also be produced by applying double haploid methods to the progeny of a cross between a corn plant comprising elite event MZIR098 and a different plant. Double haploid methods produce substantially homozygous plants without repeated backcrossing steps. The haploid/doubled haploid process of developing inbreds starts with the induction of a haploid by using, for example, KWS inducers lines, Krasnador inducers lines, stock six inducer lines (Coe, 1959, Am. Nat. 93:381-382). The haploid cell is then doubled, and the doubled haploid plant is produced. In some embodiments, the invention is a method of producing a corn plant with doubled haploid chromosomes derived from a corn elite event MZIR098, the method comprising: (a) crossing a plant, wherein said plant comprises elite event MZIR098, with an inducer maize plant to produce a progeny with haploid chromosomes; and (b) doubling the haploid chromosomes in the progeny to produce a maize plant with doubled haploid chromosomes. In some embodiments, the progeny may be for example a cell, seed, embryo or plant. In further embodiments, the maize plant with doubled haploid chromosomes produced by step (b) above is a maize inbred plant with the characteristics of corn elite event MZIR098. In other embodiments, the plant crossed with an inducer in step (a) is a hybrid maize plant produced by crossing a corn plant comprising elite event MZIR098 with a different plant.

For examples of the use of double hybrid methods, see Prasanna et al. (eds) Doubled Haploid Technology in Maize Breeding: Theory and Practice Mexico, D.F.: CIMMYT, Barnabus et al. "Colchicine, an efficient genome doubling agent for maize microsporescultured in anthero", Plant Cell Reports, 1999, 18: 858-862 or US patent publication 2003/0005479. Sometimes this doubled haploid can be used as an inbred but sometimes it is further self pollinated to finish the inbred development. Another breeding process is pedigree selection which uses the selection in an F2 population produced from a cross of two genotypes (often elite inbred lines), or selection of progeny of synthetic varieties, open pollinated, composite, or backcrossed populations. Pedigree selection is effective for highly heritable traits, such as a transgenic event, but other traits, such as yield, require replicated test crosses at a variety of stages for accurate selection.

Elite inbred lines, that is, pure breeding, homozygous inbred lines, can also be used as starting materials for breeding or source populations from which to develop other inbred lines. These inbred lines derived from elite inbred lines can be developed using the pedigree breeding and recurrent selection breeding methods described earlier. As an example, when backcross breeding is used to create these derived lines in a corn plant-breeding program, elite inbreds can be used as a parental line or starting material or source population and can serve as either the donor or recurrent parent.

Development of Corn Hybrids

A single cross corn hybrid results from the cross of two inbred lines, each of which has a genotype that complements the genotype of the other. The hybrid progeny of the first generation is designated $F_1$. In the development of commercial hybrids in a corn plant-breeding program, only the $F_1$ hybrid plants are sought. Preferred $F_1$ hybrids are more vigorous than their inbred parents. This hybrid vigor, or heterosis, can be manifested in many polygenic traits, including increased vegetative growth and increased yield.

The development of a corn hybrid in a corn plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrid progeny ($F_1$). During the inbreeding process in corn, the vigor of the lines decreases. Vigor is restored when two different inbred lines are crossed to produce the hybrid progeny ($F_1$). An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained. Much of the hybrid vigor exhibited by $F_1$ hybrids is lost in the next generation ($F_2$). Consequently, seed from hybrids is not used for planting stock.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed.

Once the seed is planted, it is possible to identify and select these self-pollinated plants. These self-pollinated plants will be genetically equivalent to the female inbred line used to produce the hybrid.

As is readily apparent to one skilled in the art, the foregoing are only some of the various ways by which the inbred of the invention can be obtained by those looking to introgress the transgenic genotype of the invention into other corn lines. Other means are available, and the above examples are illustrative only.

One skilled in the art will also recognize that transgenic corn seed comprising the transgenic genotype of the invention can be treated with various seed-treatment chemicals, including insecticides. In one embodiment, the invention comprises a method for protecting a corn elite event MZIR098 plant against feeding damage by one or more pests, said method comprising (a) providing a MZIR098 seed of the corn elite event MZIR098 plant; and (b) treating the MZIR098 plant with an insecticide. In preferred embodiments, the insecticide may comprise an active ingredient selected from the group consisting of thiamethoxam, lambda-cyhalothrin, and tefluthrin. For example, the transgenic corn seed of the invention can be treated with the commercial insecticide Cruiser®. The present invention also encompasses a corn elite event MZIR098 seed treated with an insecticide. In a further embodiment, the invention comprises a corn elite event MZIR098 seed treated with an insecticide which comprises an active ingredient selected from the group consisting of thiamethoxam, lambda-cyhalothrin, and tefluthrin. In another embodiment, the invention encompasses a corn elite event MZIR098 plant treated with an insecticide. In a preferred embodiment, the invention encompasses a corn elite event MZIR098 plant treated with an insecticide which comprises an active ingredient selected from the group consisting of thiamethoxam, lambda-cyhalothrin, and tefluthrin.

In another embodiment, the invention provides a method of controlling weeds, where an herbicide is applied to a field comprising corn elite event MZIR098 plants. In preferred embodiments, the herbicide is a GS inhibitor, such as glufosinate or bialaphos. Examples of commercially available herbicides comprising a GS inhibitor include Herbiace, Meiji Herbiace, Liberty®, Ignite®, Rely®, Finale®, and Basta®.

In another embodiment, the invention provides a method of controlling glyphosate-resistant weeds in an area comprising at least corn elite event MZIR098 plant, wherein said method comprises applying a GS inhibitor herbicide, such as glufosinate or bialaphos, to at least a portion of said area. The glyphosate-resistant weeds may be unwanted volunteer *Brassica* ssp, millet, switchgrass, maize, sorghum, wheat, oat, turf grass, pasture grass, *papaya*, flax, peppers, potato, sunflower, tomato, crucifers, soybean, common bean, lotus, grape, peach, cacao, cotton, rice, soybean, sugarcane, sugar beet, tobacco, barley, cassava, cucumber, watermelon, melon, orange, clementine, castor bean, or grapevine. In another embodiment, the invention provides a method of controlling weeds in an area under cultivation, said area comprising a plurality of corn elite event MZIR098 plants, said method comprising applying a GS inhibitor herbicide, such as glufosinate or bialaphos, over the top of the plants.

In another embodiment, the present invention provides a corn plant comprising elite event MZIR098, wherein the corn plant is useful for control of *Diabrotica* spp. insect pests. In further embodiments, the corn plant is useful for control of corn rootworm. Examples of corn rootworm species include western corn rootworm and northern corn rootworm. Another embodiment of the invention is a method of controlling insect pests, comprising planting a corn plant comprising elite event MZIR098 in a field. The field may comprise at least one MZIR098 corn plant, at least 50% MZIR098 corn plants, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% MZIR098 corn plants. The present invention also provides a use of a corn plant comprising elite event MZIR098 for controlling insect pests in a field. The insect pests may be *Diabrotica* spp. The insect pests may further be corn rootworm, for example western corn rootworm and northern corn rootworm.

Another embodiment of the invention is a recombinant sequence, which comprises a maize chromosomal target site located on chromosome 10 between SNP markers SYN23814 and PZE-110102022 and a heterologous nucleic acid. The maize chromosomal target site on chromosome 10 is also located between SNP markers PZE-110101785, PZE-110101800, and SYN23814 (all at the 5' flanking sequence) and SNP markers PZE-110102022, PZA02167.2, SYNGENTA16568, and SYN8530 (all at the 3' flanking sequence). The heterologous nucleic acid may be introduced at the maize chromosomal target site by targeted insertion. A further embodiment is a recombinant nucleic acid molecule of chromosome 10 comprising a heterologous nucleic acid sequence inserted on chromosome 10 set forth as nucleotide 1 to nucleotide 172,841 of SEQ ID NO: 70. A preferred embodiment is a recombinant nucleic acid molecule comprising a heterologous nucleic acid sequence inserted on chromosome 10 set forth as nucleotide 18,206 to 18,246 of SEQ ID NO: 70. Another embodiment is a recombinant nucleic acid molecule comprising a heterologous nucleic acid proximal at its 5' end to nucleotides 16,206 to 18,206 of SEQ ID NO: 70 and proximal at its 3' end to nucleotides 18,246 to 20,246 of SEQ ID NO: 70. In another embodiment, the present invention provides a corn genome having a heterologous nucleic acid inserted on chromosome 10 set forth as nucleotide 18,206 to 18,246 of SEQ ID NO: 70, wherein the heterologous nucleic acid comprises SEQ ID NO: 7. In a further embodiment, the present invention provides a corn genome having a heterologous nucleic acid inserted on chromosome 10 set forth as nucleotide 18,206 to 18,246 of SEQ ID NO: 70, wherein the heterologous nucleic acid comprises SEQ ID NO: 62, 63, and/or SEQ ID NO: 64.

Another embodiment of the invention is a method of making a transgenic maize plant comprising inserting a heterologous nucleic acid at a position on chromosome 10 set forth as nucleotide 1 to nucleotide 172,841 of SEQ ID NO: 70. A preferred embodiment is a method of making a transgenic maize plant, wherein the heterologous nucleic acid is inserted on chromosome 10 set forth as between nucleotide 18,206 to nucleotide 18,246 of SEQ ID NO: 70. A further embodiment is a method of making a transgenic maize plant comprising inserting a heterologous nucleic acid at a position on chromosome 10, wherein the heterologous nucleic acid is proximal at its 5' end to nucleotides 16,206 to 18,206 of SEQ ID NO: 70 and proximal at its 3' end to nucleotides 18,246 to 20,246 of SEQ ID NO: 70.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: *A Laboratory Manual, 3d Ed*, Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1. Transformation and Selection of the Elite Event MZIR098

The MZIR098 event was produced by *Agrobacterium*-mediated transformation of the inbred corn (*Zea mays*) line NP2222. Immature embryos were transformed essentially as described in Negrotto et al. (Plant Cell Reports 19: 798-803, 2000), incorporated herein by reference, using the T-DNA fragment from binary vector 17629 (PCT Application No. PCT/US16/29424, incorporated by reference herein). Vector 17629 contains a nucleotide sequence comprising eCry3.1Ab, mCry3A and PAT tandem expression cassettes as part of its T-DNA sequence. The first expression cassette comprises a NOS gene enhancer region, derived from the nopaline synthase (NOS) gene from *A. tumefaciens* (eNOS-02; SEQ ID NO: 38) operably linked to a Cestrum Yellow leaf curl virus promoter prCMP-04; SEQ ID NO: 39; US Patent Publication US20040086447), operably linked to an engineered Cry toxin eCry3.1Ab (SEQ ID NO: 40; International Publication No. WO 08/121633, published Oct. 9, 2008, herein incorporated by reference), operably linked at the 3' end to a terminator sequence derived from the nopaline synthase (NOS) gene from *A. tumefaciens* (tNOS-05-01; SEQ ID NO: 41). The second expression cassette comprises a constitutive corn promoter based on a ubiquitin gene (prUbi1-18; SEQ ID NO: 42; Christensen et al., 1992, *PMB* 18: 675-689), operably linked to a modified Cry toxin mCry3A (SEQ ID NO: 43; U.S. Pat. No. 7,030,295), operably linked at its 3' end to a terminator sequence derived from the NOS gene (tNOS-20; SEQ ID NO: 44). The third expression cassette comprises a CaMV 35S promoter (pr35S-04-01; SEQ ID NO: 45) operably linked to a PAT coding sequence (cPAT-08; SEQ ID NO: 46), operably linked at its 3' end to a terminator sequence derived from the NOS gene (NOS-05-01; SEQ ID NO: 41). The T-DNA sequence comprising these three expression cassettes is SEQ ID NO: 7.

Immature embryos were excised from 8-12 day old ears and rinsed with fresh medium in preparation for transformation. Embryos were mixed with the suspension of *Agrobacterium* cells harboring the binary vector 17629, vortexed for 30 seconds, and allowed to incubate for an additional 5 minutes. Excess *Agrobacterium* solution was aspirated and embryos were then moved to plates containing a non-selective culture medium. Embryos were co-cultured with the remaining *Agrobacterium* at 22° C. for 2-3 days in the dark. The PAT gene was used as a selectable marker during the transformation process (Negrotto et al. 2000). The embryos producing embryogenic calli were transferred to a series of cell culture selection media containing bialaphos as selection agent and cultured for 10-11 weeks in total. The selection media contained 200 mg/ml timentin and/or 10 ml/l PPM (Plant Preservative Mix) to ensure that the *Agrobacterium* was cleared from the transformed tissue.

Regenerated plantlets were tested by TaqMan PCR analysis (see Example 2) for the presence of the eCry3.1 Ab, mCry3A, and PAT genes, as well as for the absence of the antibiotic resistance spectinomycin (spec) gene, which is on the vector 17629 backbone. Plants positive for all transgenes, and negative for the spec gene, were transferred to the greenhouse for further propagation. Events then were analyzed a second time using TaqMan PCR analysis, this time to determine copy number of the transgenes. Single-copy events were then analyzed for transgenic proteins using ELISA (see Example 7). Event identified with good protein levels were then allowed to grow to maturity. The coding sequences of the transgenes in these transgenic events was verified, to identify events with mutations in the transgenic protein sequences. Finally, the remaining events were analyzed intactness of the T-DNA insert using the Fluidigm BioMark System (Fluidigm Corporation, San Francisco, Calif., USA), to determine if a full-length single copy of the T-DNA was inserted into the genome of the event. Events with good seed set, both as the product of selfing and from out-crossing, were finally identified.

TABLE 1

T0 Event Selection

| T0 Event Selection | Events | % |
|---|---|---|
| Embryos used in corn transformation | 42698 | |
| Primary any-copy events evaluated | 2043 | 100 |
| Events that passed 1° TaqMan and sent to greenhouse | 610 | 30 |
| Events selected for further work based on ELISA protein expression in leaves of one or both rootworm genes | 196 | 10 |
| Events selected based on 2° TaqMan confirmation | 173 | 8.47 |
| Events that passed herbicide tolerance screen based on leaf painting with glufosinate | 166 | 8.13 |

TABLE 1-continued

| T0 Event Selection | | |
|---|---|---|
| T0 Event Selection | Events | % |
| Events that passed CDS coding sequence verification to eliminate events with altered amino acid sequences in three trait genes (mCry3A, eCry3.1Ab, PAT) | 137 | 6.71 |
| Events for which sufficient T1 and F1 seed was obtained in greenhouse | 109 | 5.34 |
| Events planted in winter nursery, following additional event attrition based on Southern blot data | 92 | 4.50 |

As shown in Table 1, a large-scale corn transformation effort was undertaken in which over 42,000 embryos were transformed to generate 2,043 putative any-copy events. An any-copy event may contain multiple T-DNA insertions at multiple locations in the genome and/or whole or partial duplications and/or T-DNA rearrangements at a given insertion site. 610 of these were putatively determined by primary TaqMan analysis to have a single insertion, with no backbone contamination. Following ELISA expression analysis, 196 events were determined to have desirable levels of expression of all trait genes and selected for additional extensive molecular characterization. This molecular characterization included verification of coding sequences to eliminate events with altered protein coding sequences. This molecular characterization data together with greenhouse seed yield was used to select a total of 109 events. Molecular analysis by Southern blot for each of these events was performed. To advance, an event needed to be free of the 17629 vector backbone, contain one and only copy of the intact T-DNA insertion, and have no genetic rearrangements. The mCry3A and eCry3.1Ab coding sequences contain a long stretch (1400 bp) of 100% identity, so the possibility of rearrangement within the transgene or during insertion into the genome was high. These events were each evaluated by Southern analysis. Based on those results, 92 backbone-free, intact (no genetic rearrangement) single-copy events were selected for field trials.

The field trials typically comprised a hybrid line from each event tested, with at least 6 plants of each hybrid per plot, three replicates per location, and at least two locations evaluated. For the field trial, Western Corn Rootworm damage was assessed using the ISU (Iowa State University) 0-3 scale. All field trials included positive controls of transgenic event MIR604 (which comprises mCry3A, but not eCry3.1Ab), transgenic event 5323 (which comprises eCry3.1Ab, but not mCry3A), and transgenic hybrids which result from a cross from MIR604 and 5323. All field trials also included a negative control which was non-transgenic corn. Events were also evaluated for herbicide tolerance; they were sprayed with a 2× or a 4× the maximum labeled rate of Ignite® at the V4 maize developmental stage. Events were also evaluated for agronomic performance, including yield. Events which performed the best compared to the positive and negative controls were selected for advancement.

Following two years of field trial data, 35 events were selected based on trait and agronomic performance, using assays similar to those described above. After two additional field trials, 18 events were selected for further evaluation, and finally 12 events were evaluated in extensive event selection trials (see Example 8). These field trials included trait expression studies with field grown root samples harvested at V6 and V8 developmental stages. These samples were obtained from roots of plants (from each of the 12 events) which were part of active CRW field efficacy trials. Briefly, the roots were obtained, evaluated for CRW damage, lyophilized, ground, and 100 mg of the lyophilized root tissue was used for mCry3A and eCry3.1Ab ELISA assays performed similar to as described in Example 7. Root samples from transgenic MIR604 plants (expressing mCry3A) and from transgenic 5323 (expressing eCry3.1Ab) were also analyzed by ELISA as positive controls.

The 12 events were also subjected to flanking sequence recovery, so that the genomic location of the transgene insertion was identified and characterized. There are a number of criteria for a high-quality genomic insertion. Firstly, the transgene insertion cannot be in a genic region of the genome. Genic regions are understood to include 5'-untranslated regions (UTRs), exons, introns and 3'-UTRs. Additionally, the transgene insertion cannot be in a promoter region. Promoter regions are estimated to be 2 kilobases (kb) upstream of a gene. Additionally, a high-quality junction sequence does not comprise a "junction ORF", which is a putative Open Reading Frame (ORF) that crosses the T-DNA and genomic DNA junction. A junction ORF is initiated by an "ATG" nucleic acid sequence, which may be created as a result of the random insertion of the T-DNA into the genome, where genomic sequence breaks as well as small insertion, deletions, and/or rearrangements of nucleic acid sequence can occur. A junction ORF may comprise a sequence which could, if expressed, contain an amino acid sequence similar to amino acid sequences of known allergens. Therefore, junction ORFs are highly undesirable and cannot occur in a high quality genomic insertion, or in an elite transgenic event.

Of the 12 events selected for further study, 7 had the T-DNA insertion in a genic region or a promoter region. For another one, the RB could not be sequenced, suggesting a T-DNA rearrangement upon insertion. Of the remaining four candidate events (MZIR098, MZIR08G, MZIROAN, and MZIROBC), event 08G had mCry3A expression in the roots lower at the V8 growth stage compared to the MIR604 positive control, and eCry3.1Ab expression in roots lower than the event 5323 positive control for both the V4 and V8 growth stages. The remaining three events expressed mCry3A and eCry3.1Ab at least to the levels of the positive controls. However, only event MZIR098 surprisingly and unexpectedly expressed mCry3A to a level significantly higher than MIR604. Event MIR604 is an elite event, which was selected because it had the best mCry3A expression amongst its sister events, in addition to a high-quality genomic insertion and junction sequences and excellent agronomic performance. The finding that event MZIR098 has an even higher level of mCry3A protein, especially in the roots, where the CRW insect pest feeds on the corn plant, was unpredictable and unexpected.

Based on the combination of all of the trait efficacy trials, agronomic trials, molecular and genomic characterization, and protein levels of mCry3A and eCry3.1Ab in the roots, only one event was cleanly identified to have the potential to be an elite event. This event was MZIR098. Event MZIR098 plants were further evaluated for CRW efficacy, CRW high pressure agronomic equivalence testing, and agronomic performance in a number of different hybrid genetic backgrounds. Trials were performed in 40 locations for three years. Agronomic traits evaluated include yield, lodging, flowering, plant height, and disease pressure. The trials showed that event MIZ098 has excellent agronomic performance across multiple locations, for multiple growing seasons, under a variety of environmental pressures, and in multiple genetic backgrounds.

The superior performance of plants comprising the MZIR098 event is due to the intactness of the transgene itself and to the transgene insertion, at a specific location in the corn genome which supports high expression and thus high efficacy of the trait genes encoded on the transgene, and which further does not have any negative impact on plant performance. Additionally, the high agronomic performance and trait efficacy, with no negative effects, of all MZIR098 hybrids produced from multiple genetic backgrounds, further showcase the novelty of the MZIR098 event. Again, this is due to the exact genomic location of the transgene and characteristics of the transgene insertion, which are described by the nucleic acid sequence of the junction sequences (SEQ ID NO: 1 and SEQ ID NO: 2). Therefore, event MZIR098 was found to be an elite event, and it was selected as the lead event for commercial launch. FIG. 1 illustrates the transgene of MZIR098 inserted into the corn genome.

Example 2. Elite Event MZIR098 Detection by TaqMan PCR

A real-time, MZIR098-specific polymerase chain reaction (PCR) method was developed to detect and quantify MZIR098 deoxyribonucleic acid (DNA) extracted from seed, grain and other plant material samples. The method consists of a maize-specific PCR method as a reference and an event-specific PCR method for detection and quantification of MZIR098 maize DNA. This method can be used to determine the relative content of event MZIR098 maize DNA in proportion to total maize DNA in samples.

For specific detection of MZIR098 maize genomic DNA, two specific primers (SEQ ID NO: 10 and SEQ ID NO: 11) were used to amplify a 73-bp fragment of the region that spans the 5' insert-to-plant genome junction (SEQ ID NO: 13). A control primer set and probe, for example to an endogenous maize gene, may be used as a positive control. The amount of PCR product is determined during each cycle in real-time by measuring the fluorescence produced by an MZIR098-specific oligonucleotide probe labeled with 6-FAM™ as a reporter dye at its 5' end and BHQ®-1plus as a quencher at its 3' end (SEQ ID NO: 12). The primers and probe are shown in Table 2.

It is recognized that other primer combinations could be used to detect an MZIR098 junction sequences. For example, to detect the 5' junction sequence (SEQ ID NO: 1), a first primer may be selected from SEQ ID NOs: 10, 14, 15, 16, 38, 42, 65, or the complement thereof, and a second primer may be selected from SEQ ID NOs: 11, 17, 22, 23, 24, 25, 29, 43, 46, 47, 48, 49, or the complement thereof. A skilled person of the art would recognize that a first primer comprising a sequence from the 5' flanking sequence (SEQ ID NO: 8, or a complement thereof) and a second primer comprising a sequence from within the transgene (SEQ ID NO: 7, or a complement thereof) can function as a pair in a PCR reaction to produce an amplicon that comprises the 5' junction sequence (SEQ ID NO: 1), and this amplicon may be detected by a probe, for example. Similarly, to detect the 3' junction sequence (SEQ ID NO: 2), a first primer may be selected from SEQ ID NOs: 19, 20, 21, 36, 41, 45, 67, or the complement thereof, and a second primer may be selected from SEQ ID NOs: 18, 31, 33, 34, 35, 37, 50, 52 or a complement thereof. A skilled person of the art would recognize that a first primer comprising a sequence from the 3' flanking sequence (SEQ ID NO: 9, or a complement thereof) and a second primer comprising a sequence from within the transgene (SEQ ID NO: 7, or a complement thereof) can function as a pair in a PCR reaction to produce an amplicon that comprises the 3' junction sequence (SEQ ID NO: 2), and this amplicon may be detected by a probe, for example. It is important to note that these junction sequences are novel to the invention described herein. Therefore, it is only with the present disclosure that a skilled person would know the junction sequences which are novel and unique to event MZIR098, and also have motivation to detect them.

TaqMan analysis was essentially carried out as described in Ingham et al. (Biotechniques, 31:132-140, 2001) herein incorporated by reference. Briefly, genomic DNA was isolated from leaves of transgenic and non-transgenic corn plants using the Puregene® Genomic DNA Extraction kit (Gentra Systems, Minneapolis, Minn.) essentially according to the manufacturer's instruction, except all steps were conducted in 1.2 ml 96-well plates. The dried DNA pellet was resuspended in TE buffer (10 mM Tris-HCl, pH 8.0, 1 mM EDTA).

TaqMan PCR reactions were carried out in 96-well plates. For the endogenous corn gene control, primers and probes were designed specific to the *Zea mays* alcohol dehydrogenase (Adh) gene (Genbank accession no. AF044295). It will be recognized by the skilled person that other corn genes can be used as endogenous controls.

TABLE 2

Elite Event MZIR098 Detection by TaqMan PCR

| Primer/ probe name | Primer sequence 5' to 3' | SEQ ID NO: |
|---|---|---|
| Forward primer, targeting flanking sequence | ATCTCAGACACCAAACCGAGATC | 10 |
| Reverse primer, targeting transgene | ACACCGTTAGGCTAGTGCCAGT | 11 |
| Probe, targeting junction sequence | 6-FAM ™-CAAGTGACAGCGAAC GGAGCTGGTTT-BHQ ®-1plus | 12 |

The master mix for the event MZIR098-specific TaqMan PCR is shown in the table below:

TABLE 3

Detection of MZIR098 by TaqMan PCR

| Components | Final concentration |
|---|---|
| DNA (5-10 ng/μL) | 30 ng |
| JumpStart ™ Taq ReadyMix ™* | 1× |
| MZIR098 forward primer ( | 300 nM |
| MZIR098 reverse primer | 300 nM |
| MZIR098 probe | 100 nM |
| Adh forward primer | 300 nM |
| Adh reverse primer | 300 nM |
| Adh probe | 100 nM |
| Nuclease-free water | as needed |
| Total volume[a] | 6 uL |

*supplemented with Sulforhodamine 101 and 11 mM $MgCl_2$

PCR was performed in the ABI Prism 7700 instrument using the following amplification parameters: 10 min at 95° C., followed by 40 cycles of 15 s at 95° C. and 1 min at 60°

C. The PCR may be run on an ABI 7900HT, a GeneAmp PCR system 9700, or any other appropriate system. The data was analyzed using the SDS software on the ABI 7900HT. Results validated the above methodology, verifying it successfully identified the MZIR098 event in a biological sample derived from corn tissue, including seed, grain, and other plant material samples.

Example 3. Elite Event MZIR098 Detection by Southern Blot

An extensive genetic characterization of the T-DNA insert of elite event MZIR098 was performed by means of Southern blot analyses and nucleotide sequencing. The genetic stability of the insert was assessed both by Southern blot analyses and by examining the inheritance patterns of the transgenes over at least three generations of MZIR098 maize. Sequencing results confirmed the expected copy number of each of the functional elements in the T-DNA. In addition, the corn genomic sequences flanking the MZIR098 insert were identified and characterized. It was also determined that the MZIR098 insert did not disrupt the function of any known corn gene. These data collectively demonstrate that no deleterious changes occurred in the MZIR098 genome as a result of the T-DNA insertion, further demonstrating that MZIR098 is an elite event.

Southern blot analyses were performed to characterize the transgenic insert of MZIR098 maize by determining the number of vector 17629 T-DNA integration sites, the presence or absence of vector 17629 backbone sequence, and the addition of extraneous fragments of T-DNA. The MZIR098 corn generations used in Southern blot analysis included T2 (two samples, from ear 4 and ear 35), T3, T4, T5, and F1. The T2 through T5 generations were in the genetic background NP2222. The F1 generation was in the background NP2391/NP2222 and was representative of a commercial corn hybrid. Five generations of MZIR098 corn were included to demonstrate stability of the T-DNA insert over multiple generations. The control substances were nontransgenic, near-isogenic NP2222, NP2391, and NP2222/NP2391 corn. All material was grown in a greenhouse. Leaf tissue from seven plants were sampled, pooled, and subjected to DNA extraction. The genomic DNA used for Southern blot analyses was isolated from leaf tissue by a method modified from that described by Murray and Thompson (1980, Nucleic Acids Research, 8: 4321-4325).

The elements of the vector necessary for its replication and selection in different bacterial hosts are categorized as "vector backbone" (the region outside of the T-DNA). In the Southern blot analyses, the presence or absence of vector backbone was determined through the use of two backbone-specific probes that together covered every base pair of vector 17629 outside of the T-DNA. These elements were not expected to be transferred to the plant cell or integrate into the plant genome during T-DNA transfer.

Each Southern blot analysis was performed with genomic DNA extracted from MZIR098 corn and from nontransgenic, near-isogenic corn, which was used as a negative control to identify any endogenous corn DNA sequences that hybridized with the probes. To demonstrate the sensitivity of the analyses, each analysis also included two positive assay controls representing 1 copy and 1/7 copy per genome of a DNA fragment of known size in the corn genome. The positive assay controls were PCR-amplified fragments that corresponded to the two backbone-specific probes or to the T-DNA-specific probe used in characterization of the MZIR098 corn insert.

The positive assay controls for the T-DNA-specific probe and backbone-specific probes 1 and 2 were loaded in a well together with 7.5 μg of digested DNA from nontransgenic, near-isogenic NP2222/NP2391 corn, in order to more accurately reflect their migration speeds in the corn genome matrix. The positive assay control for T-DNA-specific probe was analyzed in the absence of nontransgenic corn genomic DNA, so that endogenous bands would not obscure the positive assay control.

Corn genomic DNA was analyzed via two restriction enzyme digestion strategies. In the first strategy, the genomic DNA was digested with an enzyme that cut within the MZIR098 insert and in the corn genome flanking the MZIR098 insert. This first strategy was used twice, with two different enzymes, to determine the number of vector 17629 T-DNA inserts within the MZIR098 corn genome and the presence or absence of extraneous DNA fragments of the insert in other regions of the MZIR098 corn genome. The enzymes used were HindIII and XcmI. In the second strategy, the genomic DNA was digested with restriction enzymes that cut within the insert to release DNA fragments of predictable size. This strategy was used to determine the number of copies of the T-DNA at each location within the MZIR098 corn genome, the intactness of the insert, and the presence or absence of any closely linked extraneous T-DNA fragments. The enzymes used were BmtI, HindIII, and XcmI. BmtI cleaves flanking sequences outside of the T-DNA insert. The probe used to detect the T-DNA insert comprised the full-length T-DNA (SEQ ID NO: 7).

Genomic DNA samples, at about 7.5 μg/lane, were cut with restriction enzymes and run overnight on an agarose gel in 1×TBE buffer at about 32 volts. Gels were photographed, washed, and blotted onto nylon membrane with 10×SSC as the transfer solution. They were linked to the membrane with UV light and pre-hybridized with calf thymus DNA at 65° C. The probes were labeled with radioactive Phosphorus 32. Probes were added and hybridized at 65° C., 3 hrs to overnight. Blots were washed several times and exposed in a phosphorimager cassette. Images were developed and scored.

No unexpected bands were detected by blots performed using either strategy, further supporting that the MZIR098 maize event is an elite event, comprising a fully-intact, single copy T-DNA, with no extraneous DNA fragments, either from the vector 17629 backbone or from partial secondary T-DNA insertions, detected. Additionally, the Southern blot analyses demonstrated that the hybridization bands specific to the MZIR098 insert were identical in all lanes containing genomic DNA extracted from MZIR098 corn plants of generation T2 (ear 4), T2 (ear 35), T3, T4, T5, or F1. These results support the conclusion that the MZIR098 insert is stably inherited from one generation to the next and that MZIR098 corn contains a single T-DNA insert.

Example 4: Mendelian Inheritance of the T-DNA Insert of Elite Event MZIR098

The purpose of this study was to confirm Mendelian inheritance ratios of eCry3.1Ab, mCry3A, and PAT-08 by determining their segregation ratios in three generations of MZIR098 maize backcrossed (BC) to a maize inbred. Prior to this study, hemizygous MZIR098 maize plants of the F2 generation were crossed with nontransgenic maize line NP2391. The resulting F1 generation was backcrossed to the nontransgenic recurrent parent (NP2391) to yield the BC1F1 generation. MZIR098 maize plants from the BC1F1 generation were backcrossed three more times to the nontransgenic recurrent parent (NP2391) to yield the BC2F1, BC3F1, and BC4F1 generations. Positive hemizygous segregants, as determined by glufosinate herbicide resistance and real-time PCR analysis, were utilized in each backcross. Individual plants from three generations of MZIR098 maize backcrossed (BC) to a maize inbred (the BC2F1, BC3F1, and BC4F1 generations) were tested for the presence of eCry3.1Ab, mCry3A, and PAT-08 by real-time polymerase chain reaction (PCR) analysis. The results from real-time PCR analysis were used to determine the segregation ratios of eCry3.1Ab, mCry3A, and PAT-08. The expected segregation ratio for each gene was 1:1 in each generation (i.e., 50% of the plants in each generation were expected to carry the gene). Chi-square analysis of this segregation data was performed to test the hypothesis that the MZIR098 event is inherited according to Mendelian principles, which is consistent with insertion into a chromosome within the maize nuclear genome.

The expected and observed segregation ratios are shown in Table 4. The genes eCry3.1Ab, mCry3A, and PAT-09 co-segregated (i.e., when one gene was present, the other two genes were also present). The critical value for rejection of the hypothesis of segregation according to Mendelian inheritance at $\alpha$=0.05 was 3.84. All of the chi-square values were less than 3.84 for each generation tested, indicating that eCry3.1Ab, mCry3A, and PAT-08 were inherited in a predictable manner, according to Mendelian principles. These results support the conclusion that the MZIR098 T-DNA insert integrated into a chromosome within the corn nuclear genome.

TABLE 4

Mendelian Inheritance of transgene of event MZIR098

| | $BC_2F_1$ | | $BC_3F_1$ | | $BC_4F_1$ | |
|---|---|---|---|---|---|---|
| Trait[a] | Observed | Expected | Observed | Expected | Observed | Expected |
| Positive | 85 | 93 | 69 | 70 | 75 | 74.5 |
| Negative | 101 | 93 | 71 | 70 | 74 | 74.5 |
| Total | 186 | 186 | 140 | 140 | 149 | 149 |
| $\chi^2$ | 1.38* | | 0.03* | | 0.01* | |

[a]The observed frequencies of eCry3.1Ab, mCry3A, and PAT-08 were identical; the three genes segregated as one locus.
*P < 0.05 ($\chi^2$ < 3.84).

Example 5: Analysis of Flanking DNA Sequence

Adaptor PCR was used for flanking sequence recovery, using a gene specific primer with homology to the target TDNA border sequences (as exemplified below) of vector 17629 combined with another primer with homology to the adaptor which was ligated to digested genomic DNA from a corn plant comprising event MZIR098. A primary adaptor PCR was followed by a secondary adaptor PCR (nested PCR), using a nested gene specific primer with homology to the target TDNA border sequence of vector 17629 combined with another nested primer with homology to the same adaptor.

The GenomeWalker™ Universal Kit (Clontech, Cat No. 638904) was used to recover the genome sequence flanking transgene insert of the event MZIR098. Restriction digestion was completed by combing 8 μl genomic DNA (20 to 100 ng/μl), 1 μl blunt restriction enzyme (PvuII, EcoRV or StuI in separate reactions) and 1 μl digestion buffer specific to selected enzyme, followed by incubating at 37° C. overnight. Ligation of digested genomic DNA to GenomeWalker Adaptor was completed by combining the restriction digestion product with 0.475 ul GenomeWalker Adaptor, 1.1 ul 10×T4 DNA ligase buffer and 0.125 ul T4 DNA ligase, followed by incubating at 16° C. overnight. The ligated products were heat-treated to inactivate the enzymes, and were used in primary adaptor PCR and secondary adaptor PCR for flanking sequence recovery. Primary PCR and secondary (nested) PCR were carried out with Sigma high fidelity enzyme (Sigma, Cat. No. D1313), using PCR parameters recommended by manufacturer for the GenomeWalker™ Universal Kit.

The 5' and 3' flanking sequences and junction sequences were confirmed using standard PCR procedures. The 5' flanking and junction sequence was confirmed using a first polynucleotide primer set forth in SEQ ID NO: 14 through SEQ ID NO: 16 combined with a second polynucleotide primer of SEQ ID NO: 17 (see Table 6 below). The 3' flanking and junction sequence were confirmed using a first polynucleotide primer set forth in SEQ ID NO: 19 through SEQ ID NO: 21 combined with a second polynucleotide primer of SEQ ID NO: 18 (see table below). It will be recognized by the skilled person that other primer sequences can be used to confirm the flanking and junction sequences.

TABLE 5

Primers used to confirm flanking and junction sequences

| Target Region | Primer Sequence | SEQ ID NO. |
|---|---|---|
| 5' FS | TCCGGACGGTAGCTAGAGG | 14 |
| 5' FS | CGTTTATTTCTCGGTCGGCG | 15 |
| 5' FS | TTACGTCGCGGAGAGATGGAT | 16 |
| TDNA_RB | GTGAGTGGACATTTCCCAAACTACCCT | 17 |
| TDNA_LB | CAAGGCCAGTTAGGCCAGTTA | 18 |
| 3' FS | GACATGGACATGCATGGGT | 19 |
| 3' FS | CCACACACACACACACAAAGAGAGT | 20 |
| 3' FS | GTGGCATCGTCTAGCGATCAAC | 21 |

Both 5' flanking sequence and 3' flanking sequence of the event MZIR098 were used to search maize genome databases. Identical matches to both flanking sequences were found on Chromosome 10 (MAIZE_REF_3_GENOME), and on a BAC clone, NCBI Accession No. AC204437.3. Using this information, it was determined that the heterologous DNA insertion of event MZIR098 displaced 39 nucleotides of maize genomic DNA, which lies between the 5' flanking sequence (upstream of the deleted sequence) and the 3' flanking sequence (downstream of the deleted sequence).

The event MZIR098 insert was found to be flanked on the right border (5' flanking sequence) by the corn genomic sequence shown in SEQ ID NO: 8 and flanked on the left border (3' flanking sequence) by the corn genomic sequence shown in SEQ ID NO: 9. The 5' junction sequence is set forth in SEQ ID NO: 1 and SEQ ID NO: 3. The 3' junction sequence is set forth in SEQ ID NO: 2 and SEQ ID NO: 4. The genomic integration site of the 17629 vector transgene in event MZIR098 is comprised within SEQ ID NO: 70 and its complement SEQ ID NO: 71. More specifically, the genomic integration site of event MZIR098 is between 18,206-18,246 of NCBI Accession No. AC204437.3 (SEQ ID NO: 70).

Example 6: T-DNA Insert Sequencing

The nucleotide sequence of the entire transgene DNA insert present in event MZIR098 was determined to demonstrate overall integrity of the insert, contiguousness of the functional elements and to detect any individual basepair changes. The event MZIR098 insert was PCR amplified from genomic DNA derived from individual plants as overlapping fragments to cover the entire TDNA insert which is linked to its 5' flanking sequence and 3' flanking sequence on each side.

TABLE 6

Primer sequence combinations used for overlapping PCR

| PCR Amplicon | SEQ ID NO. | Sequence |
|---|---|---|
| Amplicon-A | 14 | TCCGGACGGTAGCTAGAGG |
| | 17 | GTGAGTGGACATTTCCCAAACTACCCT |
| Amplicon-B | 15 | CGTTTATTTCTCGGTCGGCG |
| | 17 | GTGAGTGGACATTTCCCAAACTACCCT |
| Amplicon-C | 16 | TTACGTCGCGGAGAGATGGAT |
| | 17 | GTGAGTGGACATTTCCCAAACTACCCT |
| Amplicon-D | 22 | GTAGGCCGCTTCCCTAATTAGC |
| | 23 | CGCTGATGCCCTTCTGGATCAC |
| Amplicon-E | 24 | GTAGTTTGGGAAATGTCCACTCACCCGT |
| | 25 | ACCGGCAACAGGATTCAATCTTAAG |
| Amplicon-F | 26 | ACCAGATCGGCCTGAAGACC |
| | 27 | CAGAAGTAGAACTACCGGGCCCTAAC |
| Amplicon-G | 28 | GGATTCCTTTCCCACCGCT |
| | 29 | GCTGGGCCAGATGGTGTTCAG |
| Amplicon-H | 30 | GCCCTGCCTTCATACGCTATTTATT |
| | 31 | ACCGGCAACAGGATTCAATCTTAAG |
| Amplicon-I | 32 | CAGCACCAGCCAGATCACCTTCA |
| | 33 | CCACAACACCCTCAACCTCAGCA |
| Amplicon-J | 34 | ACAGTGAACTTTAGGACAGAGCCACAA |
| | 35 | CACATTGCGGATACGGCC |
| Amplicon-K | 36 | GACATGGACATGCATGGGT |
| | 18 | CAAGGCCAGTTAGGCCAGTTA |
| Amplicon-L | 20 | CCACACACACACACACAAAGAGAGT |
| | 18 | CAAGGCCAGTTAGGCCAGTTA |
| Amplicon-M | 21 | GTGGCATCGTCTAGCGATCAAC |
| | 18 | CAAGGCCAGTTAGGCCAGTTA |
| Amplicon-N | 37 | GACGTAAGGGATGACGCACAATCCCA |
| | 31 | ACCGGCAACAGGATTCAATCTTAAG |

PCR amplification was carried out using high fidelity enzyme (Sigma, Cat. No.D1313) with PCR parameters adjusted for different target regions. In one example, PCR was carried out using the following parameters: 30 sec at 96° C. for 1 cycle, followed by 35 cycles of 30 s at 94° C., 30 s at 60° C. and 3 min at 68 C, followed by 1 cycle of 7 min at 68° C. In another example, PCR was carried out using the following parameters: 5 min at 95° C. for 1 cycle, followed by 35 cycles of 30 s at 94° C., 30 s at 59° C. and 1 to 7 min at 68° C., followed by 1 cycle of 10 min at 68° C.

PCR product obtained from the overlapping PCR amplification was treated with EXO-SAP before sequencing using the following protocol: EXO-SAP master mix was prepared by combining Exonuclease I (USB, Cat No. 72073), Shrimp Alkaline Phosphatase (USB, Cat No. 70092Z) and EX-SAP buffer (20 mM Tris-HCl (pH8.0), 10 mM MgCl2) at 1:1:2. To each PCR product, 1/10 volume of EXO-SAP master mix was added. The reaction was carried out for 30 min at 37° C. followed by 20 min at 80° C. to inactivate the enzymes. Sequencing was carried out using the ABI3730XL DNA Analyzer with ABI BigDye® chemistry. The final consensus sequence was determined by combining the sequence data from different PCR amplicons to generate consensus sequence of the event MZIR098 insert (SEQ ID NO: 7) linked to its 5' genome sequence and 3' genome sequence at each side (SEQ ID NO: 8 and SEQ ID NO: 9). SEQ ID NO: 6 comprises the full-length T-DNA insertion with 100 bp of 5' and 3' flanking genomic sequences. c The consensus sequence data for the event MZIR098 insert demonstrates that the overall integrity of the insert and contiguousness of the functional elements within the insert as intended in pSYN17629 have been maintained. The nucleotide sequence analysis thus demonstrated that the MZIR098 insert contains a single copy of each of the functional elements (eCry3.1Ab, mCry3A, PAT-08, the eNOS-02 enhancer, the prCMP-04 promoter, the prUbi1-18 promoter, the pr35S-04 promoter, and the tNOS-05-01 and tNOS-20 terminators).

Example 7: Detection of Elite Event MZIR098 eCrv3.1Ab, mCrv3A, and PAT Proteins via ELISA The concentrations of eCry3.1Ab, mCry3A, and PAT in various MZIR098 corn tissues were quantified by enzyme-linked immunosorbent assay (ELISA) to establish an expression profile for these proteins as produced in MZIR098 corn. The tissues analyzed were leaves and roots at four growth stages (V6, R1, R6, and senescence), whole plants at three stages (V6, R1, and R6), kernels at two stages (R6 and senescence), and pollen (stage R1). The tissues were collected from MZIR098 corn and a nontransgenic, near-isogenic control corn grown concurrently according to local agronomic practices at four U.S. locations in 2013. The genotypes of the plants used in these studies were NP2391×NP2222(MZIR098) and NP2391×NP2222.

At each location, one plot was planted with MZIR098 corn, and one plot was planted with nontransgenic corn. Five replicate samples of each tissue type were collected from each plot for MZIR908; two replicate samples were collected for the nontransgenic control. For leaves, all the true leaves from one plant were collected per sample. For roots, the entire root ball excluding brace roots were collected per sample. For pollen, a pooled sample was collected from 10 to 15 tassels per plot. For whole plants, the entire plant including the root ball was collected per sample. For kernels, all the kernels from the primary ear of a single plant were collected per sample. All tissue samples except pollen were ground to a powder, and all samples were then lyophilized. The percent dry weight (DW) of each sample was determined from the sample fresh weight before and the sample dry weight after lyophilization.

Protein was extracted from representative aliquots of the lyophilized tissue samples at a ratio of 3 ml protein extraction buffer (PBST buffer) to approximately 30 mg of lyophilized tissue. The samples were homogenized, centrifuged, and the supernatant was collected. For pollen samples, ~25 mg lyophilized pollen was homogenized using a KLECO homogenizer. Borate extraction buffer was then added, the samples were incubated on ice for at least 20 minutes, centrifuged, and the supernatant was collected. Samples were diluted in ELISA diluent (PBS containing 1% BSA, 0.05% Tween-20).

eCry3.1Ab was quantified using rabbit anti-G6-Cry1Ab and an alkaline phosphatase-conjugated donkey anti-rabbit immunoglobin G following standard techniques. mCry3A was quantified using the QualiPlate™ ELISA kit for Modified Cry3A using standard methods. PAT was quantified using the QualiPlate™ ELISA Kit for LibertyLink® PAT/pat. The sample extracts were analyzed for each trait protein in duplicate or triplicate, and a standard curve was generated for each ELISA plate with known amounts of the corresponding reference protein. Concurrent analysis of tissues from the nontransgenic corn confirmed the absence of plant-matrix effects on the analysis methods. All protein concentrations were adjusted for extraction efficiency.

For glufosinate-treated MZIR098 maize, the eCry3.1Ab protein concentrations ranged from below limit of detection in pollen to 45.94 μg/g fresh weight in leaves (V6 stage). The arithmetic mean expression value for eCry3.1Ab protein in kernels (senescence) is 1.42±0.56 μg/g fresh weight. The mCry3A protein concentrations ranged from 0.72 μg/g fresh weight in roots (senescence) to 236.71 μg/g fresh weight in pollen. The arithmetic mean expression value for mCry3A protein in kernels (senescence) is 7.55±1.58 μg/g fresh weight. The PAT protein concentrations ranged from below limit of detection in pollen, roots and kernels (R6 and senescence), leaves (senescence), and whole plants (R6) to 1.75 μg/g fresh weight in leaves (V6).

For untreated MZIR098 maize, the eCry3.1Ab protein concentrations ranged from below limit of detection in pollen to 46.68 μg/g fresh weight in leaves (V6 stage). The arithmetic mean expression value for eCry3.1Ab protein in kernels (senescence) is 1.50±0.79 μg/g fresh weight. The mCry3A protein concentrations ranged from 0.53 μg/g fresh weight in roots (senescence) to 246.96 μg/g fresh weight in pollen. The arithmetic mean expression value for mCry3A protein in kernels (senescence) is 8.30±2.02 μg/g fresh weight. The PAT protein concentrations ranged from below limit of detection in pollen, leaves and roots and kernels (R6 and senescence), and whole plants (R6) to 1.85 μg/g fresh weight in leaves (V6).

Example 8: Insect Control Field Efficacy of Elite Event MZIR098

Field trials of 12 different transgenic events with positive and negative controls were planted in three locations. There were three replications of each event per location and each replication was planted in three 20 foot long rows, of which the center row was harvested for root expression studies and root damage ratings. For each replication, 10 plants were sampled. Field trials relied on natural populations of corn rootworm. When 80% of the larvae in the plots reach pupation, roots were dug at the V10 stage, washed to remove soil, and rated using the node injury scale of 0-3 (Oleson et al., 2005, J. Econ. Entomol. 98: 1-8). Following that analysis, about 50% of each root ball was cut into large pieces, frozen, ground and lyophilized, and 100 mg of the lyophilized root tissue was used for ELISA assays. The amounts of mCry3A and eCry3.1Ab protein present in the root samples from V6 and V8 plants from each of the 12 events were determined by ELISA as described in Example 7. Root samples from transgenic MIR604 plants (expressing mCry3A) and from transgenic 5323 (expressing eCry3.1Ab) were also analyzed by ELISA as positive controls.

The expression data and root damage ratings (RDR) were analyzed by one-way analysis of variance (ANOVA) using the SAS JMP statistical package (JMPSAS Institute 2010). The Student's pairwise t test was used for mean separation to distinguish treatment differences. Results from all the tests were considered statistically significant at P<0.05. Results for both the mCry3A and eCry3.1Ab protein levels in V6 and V8 roots and the CRW RDR are shown in Table 7 below.

TABLE 7

Average root protein levels and RDR in field trials

| | | mCry3A | | eCry3.1Ab | | |
|---|---|---|---|---|---|---|
| Event | n | V6 | V8 | V6 | V8 | RDR* |
| 5323 | 30 | n/a | 85.0 H-K | 516.8 C-E | 296.8 B-D | 0.04 B |
| 5323 × MIR604 | 30 | 294.5 D-F | 195.5 F-H | 470.2 D-F | 257.8 C-E | 0.04 B |
| MIR604 | 30 | 278.1 EF | 197.6 FG | n/a | 25.0 H | 0.10 B |
| MZIR098 | 30 | 352.5 C | 253.4 DE | 473.1 D-F | 294.8 B-D | 0.03 B |
| MZIR0A6 | 30 | 312.2 C-E | 310.5 BC | 539.9 CD | 364.1 A | 0.02 B |
| MZIR071 | 30 | 277.9 EF | 194.3 F-I | 679.4 A | 313.1 A-C | 0.03 B |
| MZIR07N | 30 | 258.1 F | 114.6 J | 661.1 AB | 163.7 G | 0.02 B |
| MIZR08A | 30 | 271.4 EF | 168.9 F-J | 555.3 CD | 299.7 B-D | 0.03 B |
| MZIR08G | 30 | 114.2 G | 42.4 K | 330.3 G | 53.1 H | 0.03 B |
| MZIR092 | 30 | 249.9 F | 152.7 G-J | 735.4 A | 295.6 B-D | 0.10 B |
| MZIR09W | 30 | 294.9 D-F | 203.7 F | 490.2 C-F | 231.2 E-G | 0.03 B |
| MZIR0AN | 30 | 259.9 F | 220.2 EF | 491.9 C-F | 238.8 D-F | 0.02 B |
| MZIR0B5 | 30 | 330.2 CD | 276.5 CD | 411.6 FG | 353.8 AB | 0.03 B |
| MZIR0AD | n/a | 279.0 EF | 146.0 IJ | 554.0 CD | 195.2 FG | n/a |
| MZIR0BC | 30 | 292.2 D-F | 203.3 F | 571.8 BC | 301.3 B-D | 0.03 B |
| Non Bt Control | 30 | 0.0 H | 0.0 K | 0.0 H | 0.0 H | 1.74 A |

*Average root damage ratings (RDR)

Means followed by the same letter within the same column are not statistically different among events (P < 0.05). Means were separated using Student's t test

Example 9: Zygosity Determination of Elite Event MZIR098 by End-Point TaqMan PCR This protocol describes a procedure for determination of zygosity status of event MZIR098 present in individual plants comprising elite event MZIR098. This method uses duplex end-point TaqMan PCR, where one reaction is specific for the event MZIR098 insertion and other is specific for the corresponding wild type allele sequence where the event MZIR098 transgenic DNA integrated. This wild type allele sequence may be referred to as the native insertion site. Because event MZIR098 is introgressed into a large number of corn germplasms, a primer/probe set for the native insertion site which is suitable for as many varieties as possible needed to be identified.

DNA samples from biological samples are prepared using methods known in the art. Primers/probe master mixes are prepared as 50× stocks, with primers at a concentration of 15 μM and the probe at a concentration of 5 μM. The following table (Table 8) indicates each reagent and amount for a 10 μL reaction:

TABLE 8

Zygosity Determination by End-Point TaqMan PCR

| Component | Volume Per Reaction |
|---|---|
| DNA sample (10-20 ng DNA/μL) | 3.0 μL |
| JumpStart ™ ReadyMix ™ (2×)[1] | 5.0 μL |

TABLE 8-continued

| Zygosity Determination by End-Point TaqMan PCR | |
|---|---|
| Component | Volume Per Reaction |
| 50× primers/probe master mix for MZIR098[2] | 0.2 μL |
| 50× primers/probe master mix for wild type allele[2] | 0.2 μL |
| Nuclease-free water | 1.6 μL |
| Total Volume | 10.0 μL |

[1]with $MgCl_2$ and Sulforhodamine 101 added

[2]Final concentration 300 nM (each primer) and 100 nM (each probe)

For Table 8, the sequences of the primers used for detection of event MZIR098 were 5'-ATCTCAGACACCAAACCGAGATC-3' (SEQ ID NO: 10) and 5'-ACACCGTTAGGCTAGTGCCAGT-3' (SEQ ID NO: 11). The sequence of the MZIR098 probe was 5'-CAAGTGACAGCGAACGGAGCTGGTTT-3' (SEQ ID NO: 12). For the native insertion site, the primer/probe set is designed against genomic sequences flanking the T-DNA insert. Alternatively, the primer/probe set for the native insertion site may include multiple primers and multiple probes. This design covers more varieties than a single primer-probe assay due to sequence differences amongst different corn varieties. In this example, two forward primers (5'-ACCAAACCGAGATCCAAGTGA-3'; SEQ ID NO: 65 and 5'-GCGCGTCGACCTGCAC-3', SEQ ID NO: 66), one reverse primer (5'-GCATGGTTCCTTGTCGGC-3'; SEQ ID NO: 67), and two native insertion site probes (5' CTAGTTGTACCTGCCCCCGCCTG-3'; SEQ ID NO: 68 and 5' AACGGAGCTGCCCCCGCC-3'; SEQ ID NO: 69) were used.

Figure 2:
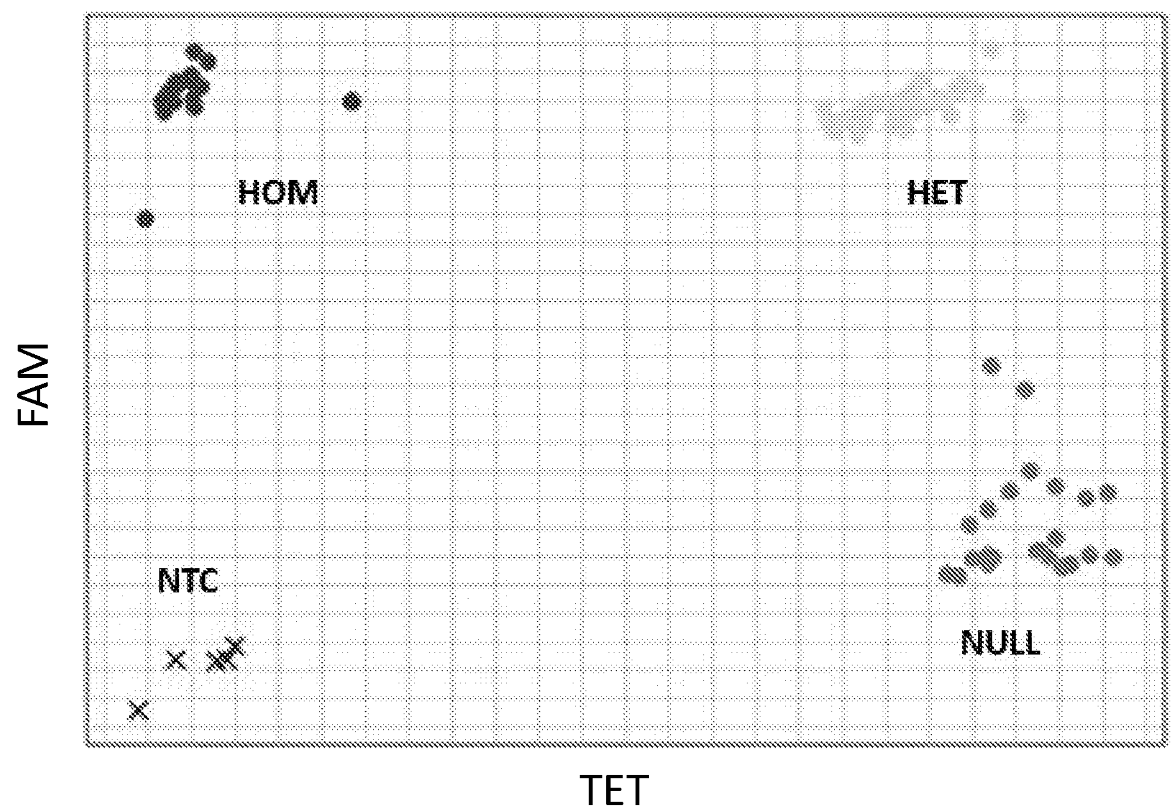
FIG. 2 (FIG. 2) is a plot of the intensities of the signals from FAM (Y axis) which is the signal from the Event Specific Allele (ESA), which is the transgene insertion, and TET (X axis) which is the signal from the native insertion allele (WT allele; genomic location of transgene, but no transgene present) assay. The points or dots are from the final read of each sample of about 90 samples, after 40 cycles of PCR. Clusters in the upper left quadrant are from homozygous plants (HOM) because no TET (WT allele) signal is present. Clusters in the lower right are from null plants (NULL) because no FAM (ESA) signal is present. The heterozygotes (HET) are located in between in the upper right, because they have signal from both assays. The quadrant position and the gaps in between the groupings, or clusters, that allow for zygosity calls to be made based on their position.

PCR was performed in the ABI 7900HT instrument using the following amplification parameters: 10 min at 95° C., followed by 40 cycles of 15 s at 95° C. and 1 min at 60° C. The PCR may be run on an ABI Prism 7700, a GeneAmp PCR system 9700, or any other appropriate system. The data was analyzed using the SDS software on the ABI 7900HT. Data analysis includes making calls (Hom, Het, Null) based on cluster positions, as shown in FIG. 2. Results indicate if the biological sample was taken from a corn plant which is "homozygous", or contains one copy of the MZIR098 event on each Chromosome 10, for a total of two copies of the MZIR098 event; "heterozygous", where the plant comprises event MZIR098 in one Chromosome 10 but the second Chromosome 10 does not have the event; or "null", where event MZIR098 is not present on either Chromosome 10 of the corn plant evaluated. Determining how many copies of event MZIR098 are present in a maize plant is useful for breeding purposes, so that the segregation of event MZIR908 in the resulting progeny of a cross may be determined.

Example 10: Use of Elite Event MZIR098 Insertion Site for Targeted Integration in Maize The elite event MZIR098 flanking sequences are disclosed in SEQ ID NO: 8 (5' flanking sequence) and SEQ ID NO: 9 (3' flanking sequence) and were used to search maize genome databases. Matches to both flanking sequences were found on a BAC clone of chromosome 10, CH201-411G1 (NCBI Accession No. AC204437.3; SEQ ID NO: 70). Using this information, it was determined that the elite event MZIR098 insertion is in the corn genome on chromosome 10 between nucleotides 18,206-18,246 of NCBI Accession No. AC204437.3 (SEQ ID NO: 70). Additionally, the flanking sequences were used to determine the physical position of the MZIR098 insertion site on the publicly available maize reference assembly of Maize B73, using Maize B73 Reference RefGen_v4 (AGPv4, August 2016). This reference assembly was created by the Arizona Genomics Institute. The assembly was for corn_v4 in Chado, and chromosome pseudo-assemblies of component BAC clones were guided by the physical map, also known as the maize accessioned golden path (AGP). SEQ ID NO: 8 (5' flanking) aligns to physical position 145,988,054-145,988,634 on chromosome 10, and the SEQ ID NO: 9 (3' flanking) aligns to 145,988,674-145,988,730 and 145,989,526-145,990,048 on chromosome 10. Fragmentation of SEQ ID NO: 9 may be due to genomic differences in corn varieties (the original event MZIR098 was into NP2222, and this alignment compares to variety B73) or to errors in the genomic sequencing or assembly of the current assembly of the B73 genome. Regardless, the MZIR098 insertion is at about 145,988,634-145,988,674 on chromosome 10 of B73, which is a relevant reference point for any corn variety genome. This location can be found on-line at the Maize Genetics and Genomics Database (maizegdb.org), using the Maize B73 RefGen_v4 (AGPv4, August 2016) data source.

Using publicly available data generated using the 50 k SNP Illumina Infinium chip (Illumina, San Diego, Calif.), molecular markers flanking the MZIR098 insertion site were identified. The 50 k SNP Illumina Infinium chip is an Illumina BeadChip array of 56,110 maize SNPs developed from B73 genes and initially validated on a variety of germplasm (Americas, Europe, and wild relatives; Ganal et al 2011, Plos One 6(12): e28334. doi:10.1371). Approximately 50% (28,156) of these SNP markers have been mapped onto the very high resolution IBM and LHRF mapping panels (Ganal et al 2011). Using the public Illumina Infinium maize 50 k SNP chip marker name, the MZIR098 insertion site is between markers SYN23814 and PZE110102022. More broadly, the MZIR098 insertion is between marker group These markers are described with respect to the positions of marker loci in the genome of the maize B73 variety (RefGen_v4, AGPv4, August 2016) at the Maize Genetics and Genomics Database internet resource (maizegdb.org).

Consistent agronomic performance of the corn elite event MZIR098 over several generations under field conditions suggests that these identified genomic regions around the corn elite event MZIR098 insertion site provide good genomic locations for the targeted integration of other transgenic genes of interest. Such targeted integration overcomes the problems with so-called "positions effects," where a transgene may insert into a transcriptionally silent region of the genome, or may disrupt the function or expression pattern of a native gene by insertion either into or in proximity to a native gene. Further advantages of such targeted integration include, but are not limited to, reducing the extremely large amount of resources required for the screening and testing of thousands of randomly inserted transgenic events before obtaining a transgenic plant that exhibits the desired level of transgene expression without also exhibiting abnormalities resulting from the inadvertent insertion of the transgene into an important locus in the host genome. Moreover, such targeted integration allows for stacking transgenes at a single genomic location, rendering introgression of the stacked traits into desirable germplasm significantly more efficient.

Using the above disclosed teaching, the skilled person is able to use methods well-known in the art to target transgenes to the same genomic insertion site as that of corn elite event MZIR098 or to a site in close proximity to the insertion site of corn elite event MZIR098. Site specific nucleases, including for example Zinc Finger Nucleases (ZFNs), meganucleases, Transcription Activator-Like Effector Nucelases (TALENS) and Clustered Regularly Interspaced Short Palindromic Repeats/CRISPR-associated nuclease (CRISPR/Cas) with an engineered crRNA/tracr RNA (for example as a single-guide RNA, or as modified crRNA and tracrRNA molecules which form a dual molecule guide), and methods of using this nucleases to target known genomic locations, such as the genomic insertion site of elite event MZIR098, are well-known in the art (see reviews by Bortesi and Fischer, 2015, Biotechnology Advances 33: 41-52; and by Chen and Gao, 2014, Plant Cell Rep 33: 575-583, and references within). Patent publication WO2016106121 (hereby incorporated by reference in its entirety) exemplifies using the insertion site of the corn event MIR604 for targeted insertion. This application is incorporated in its entirety herein. The MIR604 insertion site in untransformed corn is used as a site for targeted insertion for some examples. The MIR604 event is also used as a site for targeted insertion, to add additional transgenes. The disclosure of the present application, as well as the teachings known in the art and taught, for example, in the WO2016106121 publication provide sufficient disclosure for a position of ordinary skill in the art to perform targeted insertion at the genomic insertion site of elite event MZIR098, either the genomic location in the absence of the event, or the genomic location of the event itself with targeted integration into part of the MZIR098 transgene or proximal to the MZIR098 transgene.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the invention.

DEPOSIT

Applicants have made a deposit of corn seed of elite event MZIR098 disclosed above on May 1, 2017 in accordance with the Budapest Treaty at the American Type Culture Collection (ATCC), 10801 University Boulevard, Manassas, Va. 20110-2209 under ATCC Accession No. PTA-124143. The seed was tested on May 12, 2017 and found to be viable. The deposit will be maintained in the depositary for a period of 30 years, or 5 years after the last request, or the effective life of the patent, whichever is longer, and will be replaced as necessary during that period. Applicants impose no restrictions on the availability of the deposited material from the ATCC; however, applicants have no authority to waive any restrictions imposed by law on the transfer of biological material or its transportation in commerce.

All publications and published patent documents cited in this specification are incorporated herein by reference to the same extent as if each individual publication or patent document was specifically and individually indicated to be incorporated by reference.

What is claimed is:

1. A seed of a transgenic corn plant comprising elite event MZIR098, wherein representative seed of said plant have been deposited as ATCC Accession No. PTA-124143.

* * * * *